United States Patent
Ghosh et al.

(10) Patent No.: US 7,504,508 B2
(45) Date of Patent: *Mar. 17, 2009

(54) PGD2 RECEPTOR ANTAGONISTS FOR THE TREATMENT OF INFLAMMATORY DISEASES

(75) Inventors: Shomir Ghosh, Brookline, MA (US); Amy M. Elder, Arlington, MA (US); Kenneth G. Carson, Princeton, NJ (US); Kevin T. Sprott, Boston, MA (US); Sean J. Harrison, Belmont, MA (US); Frederick A. Hicks, Somerville, MA (US); Christelle C. Renou, Somerville, MA (US); Dominic Reynolds, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 446 days.

This patent is subject to a terminal disclaimer.

(21) Appl. No.: 11/101,208

(22) Filed: Apr. 7, 2005

(65) Prior Publication Data

US 2005/0256158 A1 Nov. 17, 2005

Related U.S. Application Data

(63) Continuation-in-part of application No. 10/678,872, filed on Oct. 3, 2003, now Pat. No. 7,211,672.

(60) Provisional application No. 60/560,410, filed on Apr. 7, 2004, provisional application No. 60/416,501, filed on Oct. 4, 2002.

(51) Int. Cl.
C07D 215/38 (2006.01)

(52) U.S. Cl. .......... 546/112; 546/152; 546/159

(58) Field of Classification Search .......... 546/112, 546/152, 159
See application file for complete search history.

(56) References Cited

U.S. PATENT DOCUMENTS

| | | | |
|---|---|---|---|
| 5,258,510 A | 11/1993 | Ogawa et al. | |
| 6,048,873 A | 4/2000 | Vasudevan et al. | |
| 6,147,089 A | 11/2000 | DeNinno et al. | |
| 6,197,786 B1 | 3/2001 | DeNinno et al. | |
| 6,291,677 B1 | 9/2001 | Vasudevan et al. | |
| 6,310,075 B1 | 10/2001 | DeNinno et al. | |
| 6,313,107 B1 | 11/2001 | Vasudevan et al. | |
| 6,313,142 B1 | 11/2001 | Damon et al. | |
| 6,362,198 B1 | 3/2002 | Goldstein et al. | |
| 6,362,199 B1 | 3/2002 | DiFabio | |
| 6,395,751 B1 | 5/2002 | DeNinno et al. | |
| 6,489,478 B1 | 12/2002 | DeNinno et al. | |
| 6,586,448 B1 | 7/2003 | DeNinno et al. | |
| 6,600,045 B2 | 7/2003 | Damon et al. | |
| 7,211,672 B2 * | 5/2007 | Ghosh et al. | 546/157 |
| 7,220,760 B2 * | 5/2007 | Awad et al. | 514/313 |

| | | |
|---|---|---|
| 2002/0022218 A1 | 2/2002 | Li et al. |

FOREIGN PATENT DOCUMENTS

| | | |
|---|---|---|
| EP | 0987251 A1 | 3/2000 |
| EP | 0992496 A1 | 4/2000 |
| EP | 1125929 A1 | 8/2001 |
| EP | 1221439 A1 | 7/2002 |
| JP | P200253557 A | 2/2002 |
| WO | WO 9105549 | 5/1991 |
| WO | WO 9401113 | 1/1994 |
| WO | WO 0006153 A1 | 2/2000 |
| WO | WO 0017165 A1 | 3/2000 |
| WO | WO 0017166 A1 | 3/2000 |
| WO | WO 0140190 A1 | 6/2001 |
| WO | WO 0149675 A1 | 7/2001 |
| WO | WO 0158875 A2 | 8/2001 |
| WO | WO 0176629 A1 | 10/2001 |
| WO | WO 0211710 A2 | 2/2002 |
| WO | WO 0218361 A2 | 3/2002 |
| WO | WO 0222585 A1 | 3/2002 |
| WO | WO 02058652 A1 | 8/2002 |

(Continued)

OTHER PUBLICATIONS

Zalukaev, CA 69:27206, abstract only of Trudy Problemnoi Laboratorii Khimii Vysokomolekulyarnykh Soedinenii, 1966, No. 4, pp. 5-16.*

(Continued)

*Primary Examiner*—D. Margaret Seaman

(57) ABSTRACT

Disclosed herein are compounds represented by Structural Formula (I) and (I-A):

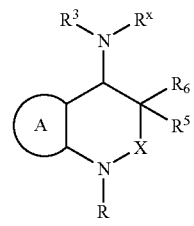

I

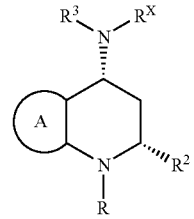

I-A

Also disclosed is the use of such compounds for inhibiting the G-protein coupled receptor referred to as chemoattractant receptor-homologous molecule expressed on Th2, or simply "CRTH2" for the treatment of inflammatory disorders. The variables in Structural Formula (I) and (I-A) are defined herein.

2 Claims, No Drawings

FOREIGN PATENT DOCUMENTS

| | | |
|---|---|---|
| WO | WO 02079165 A1 | 10/2002 |
| WO | WO 02088069 A2 | 11/2002 |
| WO | WO 03097042 A1 | 11/2003 |
| WO | WO 03097598 A1 | 11/2003 |
| WO | WO 03105849 A1 | 12/2003 |
| WO | WO 2004035543 A1 | 4/2004 |
| WO | WO 2004/052863 A1 | 6/2004 |
| WO | WO 2005/007094 A2 | 1/2005 |

OTHER PUBLICATIONS

Zalukaev, CA 67:53250, abstract only of Zhurnal Organicheskoi Khimii, vol 3(4), pp. 753-756, 1967.*

Zalukaev, CA 65:81601, abstract only of Zhurnal Obshchei Khimii, vol. 36(6), pp. 1052-1055, 1966.*

Zalukajevs, CA 59:54789, abstract only of Zhurnal Obshchei Khimii, vol. 33(6), pp. 1956-1958, 1963.*

Zalukaev, L.P., et al., "Bimolecular alkylidenearylamines. XI. New data on intermolecular donor-acceptor reactions in 4-anilino-2-methyl-1,2,3,4-tetrahydroquinolines," *Chemical Abstracts*, Accession No. 67:53250 (1967).

Zalukaev, L.P., et al., "Bimolecular alkylidene aryl amines. X. Intramolecular donor-acceptor interaction in 2-methyl-4-anilino-1,2,3,4-tetra-hydroquinoline," *Chemical Abstracts*, Accession No. 65:81601 (1966).

Funabashi, Masuo, et al., "Configuration and conformation of so-called bis(alkylidenearlyamines)," *Chemical Abstracts*, Accession No. 72:31075 (1969).

Zalukajevs, L., "Bimolecular alkylidenearylamines. II. Structure of the products of bromination of 1-benzoyl-2-methyl-4-anilino-1,2,3,4-tetrahydroquinoline," *Chemical Abstracts*, Accession No. 48:56687 (1951).

Zalukajevs, L., et al., "Bimolecular alkylidenearylamines. IX. Steric structure of 2-methyl-4-anilino-1,2,3,4-tetrahydroquinolines," *Chemical Abstracts*, Accession No. 62:22149 (1964).

Zalukajevs, L., et al., "Bimolecular alkylidenearylamines. VIII. Synthesis and bromination of 2-methyl-4-N-acetylanilino-1,2,3,4-tetrahydroquinoline," *Chemical Abstracts*, Accession No. 59:54789 (1963).

* cited by examiner

PGD2 RECEPTOR ANTAGONISTS FOR THE TREATMENT OF INFLAMMATORY DISEASES

PRIORITY INFORMATION

The present application claims priority under 35 U.S.C. § 119(e) to U.S. Provisional application No. 60/560,410, filed Apr. 7, 2004, entitled "PGD2 Receptor Antagonists for the Treatment of Inflammatory Diseases", and also claims priority under 35 U.S.C. § 120 and is a continuation-in-part of U.S. application Ser. No. 10/678,872 now U.S. Pat. No. 7,211,672, filed Oct. 3, 2003, entitled "PGD2 Receptor Antagonists for the Treatment of Inflammatory Diseases", which in turn claims priority to U.S. Provisional Application No. 60/416,501, filed Oct. 4, 2002, entitled "PGD2 Receptor Antagonists for the Treatment of Inflammatory Diseases", and the entire contents of each of these applications are hereby incorporated by reference.

BACKGROUND OF THE INVENTION

CRTH2 is a G protein-coupled chemoattractant receptor expressed on Th2 cells (Nagata et al., *J. Immunol.*, 1999, 162, 1278-1286), eosinophils, and basophils (Hirai et al., *J. Exp. Med.*, 2001, 193, 255-261). Prostaglandin D2 (PGD2) is a natural ligand for CRTH2, and is the major inflammatory mediator produced from mast cells. It has been shown that activation of CRTH2 by PGD2 induces migration and activation of Th2 cells (Hirai et al., *J. Exp. Med.* 2001, 193, 255-261; Gervais et al., *J. Allergy Clin. Immunol.* 2001, 108, 982-988) which in turn are involved in the orchestration of an allergic inflammatory response by directly or indirectly inducing migration, activation, priming and prolonged survival of effector cells, such as eosinophils and basophils (Sanz et al., *J. Immunol.* 1998, 160, 5637-5645; Pope et al., *J. Allergy Clin. Immunol.* 2001, 108, 594-601; Teran L. M., *Clin. Exp. Allergy* 1999, 29, 287-290). The role of PGD2 in the initiation and maintenance of allergic inflammation has also been demonstrated in mouse models of asthma by showing that overproduction of PGD2 in vivo by PGD2 synthase exacerbates airway inflammation (Fujitani et al., *J. Immunol.* 2002, 168, 443-449).

Accordingly, compounds which are modulators, preferably inhibitors, of the interaction between CRTH2 and PGD2 should be useful for the treatment of diseases and disorders that are mediated by CRTH2, PGD2, Th2 cells, eosinophils, and/or basophils. These diseases include but are not limited to allergic disorders, asthmatic disorders, and inflammatory disorders such as allergic rhinitis, allergic asthma, bronchoconstriction, atopic dermatitis and systemic inflammatory disorders.

DETAILED DESCRIPTION OF THE INVENTION

Compounds of this invention, and pharmaceutically acceptable compositions thereof, are effective as inhibitors of the interaction between CRTH2 and its natural ligand PGD2. Thus, compounds of the invention and pharmaceutical compositions thereof are useful for treating inflammatory disorders and/or disorders with an inflammatory component.

1. Description of Compounds of General Formula I (and Subsets Thereof)

In one embodiment, the present invention relates to a compound of formula I:

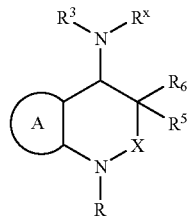

I or a pharmaceutically acceptable salt thereof, wherein:
Ring A is an optionally substituted monocyclic aromatic ring;
R is —$X_1$—$R^1$, wherein:
  $X_1$ is a bond, S(O), S(O)$_2$, C(O) or C(O)NH, provided that when $X_1$ is a bond, SO or SO$_2$, then $R^1$ is not H; and
  $R^1$ is H or an optionally substituted, cycloaliphatic group, aromatic group or non-aromatic heterocyclic group;
X is —C(O)— or —C($R^2$)$_2$—, wherein:
  each $R^2$ is independently —H, —$X_4$—$R^8$ or an optionally substituted, aliphatic group, cycloaliphatic group, aromatic group or a non-aromatic heterocyclic group;
$R^X$ is —$X_2$—$R^4$, wherein:
  $X_2$ is a bond, S(O), S(O)$_2$, C(O) or C(O)NH; and
  $R^4$ is —H, —$X_6$—$R^{10}$ or an optionally substituted, aliphatic group, cycloaliphatic group, aromatic group or non-aromatic heterocyclic group;
  provided that when $X_2$ is a bond, SO or SO$_2$, then $R^4$ is not H;
$R^3$ is an optionally substituted, cycloaliphatic group, aromatic group or non-aromatic heterocyclic group; or —NR$^X$R$^3$, taken together, is an optionally substituted non-aromatic nitrogen containing heterocyclic group;
$X_4$ and $X_6$ are each independently a straight or branched hydrocarbyl group optionally substituted with one or more groups selected from the group consisting of halo, —OH, =O, $C_1$-$C_3$ alkoxy, nitro and cyano;
$R^5$ and $R^6$ are each independently H or $C_1$-$C_3$ alkyl;
$R^8$ and $R^{10}$ are each independently H, —C(O)OR" or an optionally substituted, cycloaliphatic group, aromatic group or non-aromatic heterocyclic group;
R" is H or $R^{13}$; and
$R^{13}$ is $C_1$-$C_6$ alkyl or $C_3$-$C_8$ cycloalkyl.

In another embodiment, the present invention relates to a compound of formula I:

or a pharmaceutically acceptable salt thereof, wherein:
Ring A is an optionally substituted monocyclic aromatic ring;
R is —$X_1$—$R^1$;
$R^X$ is —$X_2$—$R^4$, and $R^3$ is an optionally substituted aromatic group; or —NR$^X$R$^3$, taken together, is an optionally substituted non-aromatic nitrogen containing heterocyclic group;
X is —C(O)— or —C($R^2$)$_2$—;
$X_1$ and $X_2$ are each independently a bond, S(O), S(O)$_2$, C(O) or C(O)NH;
$R^1$ is H or an optionally substituted, cycloaliphatic group, aromatic group or non-aromatic heterocyclic group;
  provided that when $X_1$ is a bond, SO or SO$_2$, then $R^1$ is not H;
each $R^2$ is independently H, —$X_4$—$R^8$ or an optionally substituted, aliphatic group, cycloaliphatic group, aromatic group or non-aromatic heterocyclic group;

R⁴ is H, —X₆—R¹⁰ or an optionally substituted, aliphatic group, cycloaliphatic group, aromatic group or non-aromatic heterocyclic group;

provided that when X₂ is a bond, SO or SO₂, then R⁴ is not H;

X₄ and X₆ are each independently a straight or branched hydrocarbyl group optionally substituted with one or more groups selected from the group consisting of halo, —OH, =O, C₁-C₃ alkoxy, nitro and cyano;

R⁵ and R⁶ are each independently H or C₁-C₃ alkyl; and

R⁸ and R¹⁰ are each independently H, —C(O)OR" or an optionally substituted, cycloaliphatic group, aromatic group or non-aromatic heterocyclic group;

R" is H or R¹³; and

R¹³ is C₁-C₆ alkyl or C₃-C₈ cycloalkyl.

In one embodiment, compounds of formula I include compounds other than: 2-Methyl-N-phenyl-N-[1,2,3,4-tetrahydro-2-methyl-1-(2-methyl-1-oxobutyl)-4-quinolinyl]-butamide; N-(1-Acetyl-1,2,3,4-tetrahydro-2-methyl-4-quinolinyl)-N-phenyl-heptamide; N-phenyl-N-[1,2,3,4-tetrahydro-2-methyl-1-(1-oxo-3-phenylpropyl)-4-quinolinyl]-benzenepropanamide; N-phenyl-N-[1,2,3,4-tetrahydro-2-methyl-1-(3-nitrobenzoyl)-4-quinolinyl]-hexanamide; N-[1,1'-biphenyl]-3-yl-N-[1,2,3,4-tetrahydro-1-(4-methoxybenzoyl)-2-methyl-4-quinolinyl]-acetamide; N-(1-benzoyl-1,2,3,4-tetrahydro-2-methyl-4-quinolinyl)-N-(4-nitrophenyl)-heptanamide; N-(1-benzoyl-1,2,3,4-tetrahydro-2-methyl-4-quinolinyl)-N-(4-methoxyphenyl)-2-methyl-propanamide; N-[1-(4-fluorobenzoyl)-1,2,3,4-tetrahydro-2-methyl-4-quinolinyl]-N-phenyl-butanamide; N-phenyl-N-[1,2,3,4-tetrahydro-1-(3-methoxybenzoyl)-2-methyl-4-quinolinyl]-pentanamide; 2-ethyl-N-[1-(2-ethyl-1-oxobutyl)-1,2,3,4-tetrahydro-2,8-dimethyl-4-quinolinyl]-N-(2-methylphenyl)-butanamide; N-[1-[(4-fluorophenyl)acetyl]-1,2,3,4-tetrahydro-2-methyl-4-quinolinyl]-N-phenyl-propanamide; N-phenyl-N-[1,2,3,4-tetrahydro-2-methyl-1-(4-nitrobenzoyl)-4-quinolinyl]-octanamide; N-cyclohexyl-4-[(cyclohexylamino)carbonyl]phenylamino]-3,4-dihydro-2-methyl-1(2H)-quinolinecarboxamide; N-[1-(4-ethylbenzoyl)-1,2,3,4-tetrahydro-2,8-dimethyl-4-quinolinyl]-N-(2-methylphenyl)-3-(4-nitrophenyl)-2-propenamide; 3-(4-methoxyphenyl)-N-phenyl-N-[1,2,3,4-tetrahydro-1-[3-(4-methoxyphenyl)-1-oxo-2-propenyl]-2-methyl-4-quinolinyl]-2-propenamide; 4-[(ethoxyoxoacetyl)phenylamino]-3,4-dihydro-2-methyl-∀-oxo-ethyl ester-1(2H)-quinolineacetic acid; N-[1-(3-cyclohexyl-1-oxopropyl)-1,2,3,4-tetrahydro-2-methyl-4-quinolinyl]-N-phenyl-cyclohexanepropanamide; 4-(acetylphenylamino)-3,4-dihydro-2-methyl-gamma-oxo-1(2H)-quinolinepentanoic acid; N-(1-benzoyl-1,2,3,4-tetrahydro-2-methyl-4-quinolinyl)-2,2-dimethyl-N-phenyl-propanamide; N-(1-benzoyl-6-bromo-1,2,3,4-tetrahydro-2-methyl-4-quinolinyl)-N-phenyl-pentanamide; N-[1-(2-furanylcarbonyl)-1,2,3,4-tetrahydro-2-methyl-4-quinolinyl]-N-phenyl-acetamide; 2-methyl-N-phenyl-N-[1,2,3,4-tetrahydro-1-(3-methoxybenzoyl)-2-methyl-4-quinolinyl]-propanamide; N-[1-[(1,3-dihydro-1,3-dioxo-2H-isoindol-2-yl)acetyl]-1,2,3,4-tetrahydro-2-methyl-4-quinolinyl]-N-phenyl-acetamide; 2,2,2-trifluoro-N-phenyl-N-[1,2,3,4-tetrahydro-1-(3-methoxybenzoyl)-2-methyl-4-quinolinyl]-acetamide; 2-ethyl-N-[1-(2-ethyl-1-oxobutyl)-1,2,3,4-tetrahydro-2-methyl-4-quinolinyl]-N-phenyl-butanamide; N-(1-benzoyl-1,2,3,4-tetrahydro-2-methyl-4-quinolinyl)-N-(3-methoxyphenyl)-acetamide; N-phenyl-N-[1,2,3,4-tetrahydro-2-methyl-1-(1-oxohexyl)-4-quinolinyl]-acetamide; N-(1-acetyl-1,2,3,4-tetrahydro-2-methyl-4-quinolinyl)-N-phenyl-2-thiophenecarboxamide; N-[1-(2-fluorobenzoyl)-1,2,3,4-tetrahydro-2-methyl-4-quinolinyl]-N-phenyl-hexanamide; N-phenyl-N-[1,2,3,4-tetrahydro-1-(4-methoxybenzoyl)-2-methyl-4-quinolinyl]-hexanamide; N-phenyl-N-[1,2,3,4-tetrahydro-1-(4-methoxybenzoyl)-2-methyl-4-quinolinyl]-hexanamide; N-[1-(cyclopropylcarbonyl)-1,2,3,4-tetrahydro-2-methyl-4-quinolinyl]-N-phenyl-cyclopropanecarboxamide; N-(1-benzoyl-1,2,3,4-tetrahydro-2-methyl-4-quinolinyl)-N-(4-methylphenyl)-acetamide; 2-methyl-N-phenyl-N-[1,2,3,4-tetrahydro-2-methyl-1-(2-methyl-1-oxopropyl)-4-quinolinyl]-propanamide; N-phenyl-N-[1,2,3,4-tetrahydro-1-(4-methoxybenzoyl)-2-methyl-4-quinolinyl]-2-thiophenecarboxamide; 1-(3,5-dinitrobenzoyl)-N-formyl-1,2,3,4-tetrahydro-2-methyl-N-phenyl-4-quinolinamine; N-[1-(4-chloro-3-nitrobenzoyl)-1,2,3,4-tetrahydro-2-methyl-4-quinolinyl]-N-phenyl-acetamide; N-phenyl-N-[1,2,3,4-tetrahydro-2-methyl-1-(3-nitrobenzoyl)-4-quinolinyl]-acetamide; N-phenyl-N-[1,2,3,4-tetrahydro-1-(3-methoxybenzoyl)-2-methyl-4-quinolinyl]-hexanamide; N-[1-(2-furanylcarbonyl)-1,2,3,4-tetrahydro-2-methyl-4-quinolinyl]-N-phenyl-2-furancarboxamide; N-phenyl-N-[1,2,3,4-tetrahydro-2-methyl-1-(1-oxopropyl)-4-quinolinyl]-acetamide; N-phenyl-N-[1,2,3,4-tetrahydro-1-[3-(4-methoxyphenyl)-1-oxo-2-propenyl]-2-methyl-4-quinolinyl]-acetamide; 3-(2-furanyl)-N-[1-[3-(2-furanyl)-1-oxo-2-propenyl]-1,2,3,4-tetrahydro-2-methyl-4-quinolinyl]-N-phenyl-2-propenamide; N-[1-[2-(1,3-dihydro-1,3-dioxo-2H-isoindol-2-yl)-1-oxo-3-phenylpropyl]-1,2,3,4-tetrahydro-2-methyl-4-quinolinyl]-N-phenyl-octanamide; N-[1-(3-chlorobenzoyl)-1,2,3,4-tetrahydro-2-methyl-4-quinolinyl]-N-phenyl-acetamide; Relative stereochemistry N-phenyl-N-[(2R,4S)-1,2,3,4-tetrahydro-2-methyl-1-(1-oxopropyl)-4-quinolinyl]-acetamide; Relative stereochemistry N-[(2R,4S)-1-benzoyl-1,2,3,4-tetrahydro-2-methyl-4-quinolinyl]-2-methyl-N-phenyl-propanamide; Relative stereochemistry N-[(2R,4S)-1-acetyl-1,2,3,4-tetrahydro-2-methyl-4-quinolinyl]-N-phenyl-hexanamide; Relative stereochemistry N-[(2R,4S)-1-acetyl-1,2,3,4-tetrahydro-2-methyl-4-quinolinyl]-N-phenyl-propanamide; Relative stereochemistry N-[(2R,4S)-1-acetyl-1,2,3,4-tetrahydro-2-methyl-4-quinolinyl]-N-phenyl-heptanamide; Relative stereochemistry N-[(2R,4S)-1-benzoyl-1,2,3,4-tetrahydro-2-methyl-4-quinolinyl]-2,2-dimethyl-N-phenyl-propanamide; N-[1-(3-fluorobenzoyl)-1,2,3,4-tetrahydro-2-methyl-4-quinolinyl]-N-phenyl-acetamide; N-[1-[4-(1,1-dimethylethyl)benzoyl]-1,2,3,4-tetrahydro-2-methyl-4-quinolinyl]-N-phenyl-acetamide; N-(1-acetyl-1,2,3,4-tetrahydro-2-methyl-4-quinolinyl)-2-methyl-N-phenyl-propanamide; 2,2,2-trifluoro-N-phenyl-N-[1,2,3,4-tetrahydro-2-methyl-1-(trifluoroacetyl)-4-quinolinyl]-acetamide; Relative stereochemistry N-[(2R,4S)-1-acetyl-1,2,3,4-tetrahydro-2-methyl-4-quinolinyl]-2,2-dimethyl-N-phenyl-propanamide; Relative stereochemistry N-[(2R,4S)-1-acetyl-1,2,3,4-tetrahydro-2-methyl-4-quinolinyl]-N-phenyl-butanamide; Relative stereochemistry N-[(2R,4S)-1-benzoyl-1,2,3,4-tetrahydro-2-methyl-4-quinolinyl]-N-phenyl-acetamide; Relative stereochemistry N-phenyl-N-[(2R,4S)-1,2,3,4-tetrahydro-2-methyl-1-(1-oxoheptyl)-4-quinolinyl]-acetamide; Relative stereochemistry N-phenyl-N-[(2R,4S)-1,2,3,4-tetrahydro-2-methyl-1-(1-oxohexyl)-4-quinolinyl]-acetamide; Relative stereochemistry N-[(2R,4S)-1-acetyl-1,2,3,4-tetrahydro-2-methyl-4-quinolinyl]-N-phenyl-pentanamide; N-phenyl-N-[1,2,3,4-tetrahydro-2-methyl-1-(1-oxo-3-phenyl-2-propenyl)-4-quinolinyl]-acetamide; Relative stereochemistry N-[(2R,4S)-1-benzoyl-1,2,3,4-tetrahydro-2-methyl-4-quinolinyl]-N-phenyl-heptanamide; Relative stereochemistry N-[(2R,4S)-1-acetyl-1,2,3,4-tetrahydro-2-methyl-4-quinolinyl]-N-phenyl-acetamide; Relative stereochemistry N-[(2R,4S)-1-benzoyl-1,2,3,4-tetrahydro-2-methyl-4-quinolinyl]-N-phenyl-pentanamide; N-phenyl-N-[1,2,3,4-tetrahydro-2-methyl-1-(tricyclo[3.3.1.13,7]dec-1-ylcarbonyl)-4-quinolinyl]-acetamide; N-phenyl-N-[1,2,3,4-tetrahydro-2-methyl-1-(1-oxopropyl)-4-quinolinyl]-propanamide; N-phenyl-N-[1,2,3,4-tetrahydro-2-methyl-1-(2-thienylcarbonyl)-4-quinolinyl]-acetamide; N-phenyl-N-[1,2,3,4-tetrahydro-1-(4-methoxybenzoyl)-2-methyl-4-quinolinyl]-2-furancarboxamide; N-phenyl-N-[1,2,3,4-tetrahydro-1-(4-methoxybenzoyl)-2-methyl-4-quinolinyl]-acetamide; N-[1-(3,5-dinitrobenzoyl)-1,2,3,4-tetrahydro-2-methyl-4-quinolinyl]-N-phenyl-acetamide; N-phenyl-N-[1,2,3,4-tetrahydro-2-methyl-1-(4-nitrobenzoyl)-4-quinolinyl]-acetamide; N-phenyl-N-[1,2,3,4-tetrahydro-1-(2-iodobenzoyl)-2-methyl-4-quinolinyl]-acetamide; N-phenyl-N-[1,2,3,4-tetrahydro-2-methyl-1-(2-methyl-1-oxopropyl)-4-quinolinyl]-acetamide; N-phenyl-N-[1,2,3,4-tetrahydro-2-methyl-1-[(4-methylphenyl)sulfonyl]-4-quinolinyl]-acetamide; N-phenyl-N-[1,2,3,4-tetrahydro-2-methyl-1-[(4-nitrophenyl)methyl]-4-quinolinyl]-acetamide; N-phenyl-N-[1,2,3,4-tetrahydro-1-(3-methoxybenzoyl)-2-methyl-4-quinolinyl]-acetamide; N-(1-acetyl-1,2,3,4-tetrahydro-2-methyl-4-quinolinyl)-N-phenyl-butanamide; N-phenyl-N-[1,2,3,4-tetrahydro-2-methyl-1-(1-oxobutyl)-4-quinolinyl]-acetamide; N-(1-benzoyl-1,2,3,4-tetrahydro-2-methyl-4-quinolinyl)-N-phenyl-hexanamide; N-(1-benzoyl-1,2,3,4-tetrahydro-2-methyl-4-quinolinyl)-N-phenyl-pentanamide; N-(1-benzoyl-1,2,3,4-tetrahydro-2-methyl-4-quinolinyl)-N-phenyl-propanamide; 1-benzoyl-1,2,3,4-tetrahydro-4-(N-phenylacetamido)quinaldine; N-(1-acetyl-6-bromo-1,2,3,4-tetrahydro-2-methyl-4-quinolinyl)-N-phenyl-acetamide; N-(1-acetyl-1,2,3,4-tetrahydro-2-methyl-6-nitro-4-quinolyl)-acetanilide; N-(1-acetyl-6-chloro-1,2,3,4-tetrahydro-2-methyl-4-quinolyl)-acetanilide; N-(1-acetyl-1,2,3,4-tetrahydro-2-methyl-4-quinolinyl)-N-phenyl-acetamide; N-(1-benzoyl-6-bromo-1,2,3,4-tetrahydro-2-methyl-4-quinolinyl)-N-phenyl-acetamide; N-(1-benzoyl-6-chloro-1,2,3,4-tetrahydro-2-methyl-4-quinolinyl)-N-phenyl-acetamide; N-(1-benzoyl-1,2,3,4-tetrahydro-2-methyl-4-quinolinyl)-N-phenyl-butanamide; N-phenyl-N-[1,2,3,4-tetrahydro-1-(3-fluorobenzoyl)-2-methyl-4-quinolinyl]-hexanamide. N-[1-(3-Chloro-benzoyl)-2-methyl-1,2,3,4-tetrahydro-quinolin-4-yl]-N-phenyl-acetamide; N-[1-(4-Fluoro-benzoyl)-2-methyl-6-nitro-1,2,3,4-tetrahydro-quinolin-4-yl]-N-phenyl-acetamide; Pentanoic acid (1-benzoyl-6-bromo-2-methyl-1,2,3,4-tetrahydro-quinolin-4-yl)-phenyl-amide; N-(1-Benzoyl-6-chloro-2-methyl-1,2,3,4-tetrahydro-quinolin-4-yl)-N-phenyl-acetamide; N-[6-Chloro-1-(4-fluoro-benzoyl)-2-methyl-1,2,3,4-tetrahydro-quinolin-4-yl]-N-phenyl-acetamide; N-[6-Bromo-1-(4-fluoro-benzoyl)-2-methyl-1,2,3,4-tetrahydro-quinolin-4-yl]-N-phenyl-acetamide; N-(1-Benzoyl-6-nitro-2-methyl-1,2,3,4-tetrahydro-quinolin-4-yl)-N-phenyl-acetamide; N-(1-Benzoyl-2-methyl-1,2,3,4-tetrahydro-quinolin-4-yl)-N-phenyl-butyramide; or N-[1-(3-Methoxy-benzoyl)-2-methyl-1,2,3,4-tetrahydro-quinolin-4-yl]-2,2-dimethyl-N-phenyl-propionamide.

In a preferred embodiment of the present invention, X is —CHR$^2$—, R$^2$ is —H, methyl or ethyl; R$^3$ is a substituted or unsubstituted aromatic group; R$^5$ and R$^6$ are —H; and the remainder of the variables in Structural Formula (I) are as defined above. More preferably, the compound is represented by a structural formula selected from Structural Formulas (II)-(VIII):

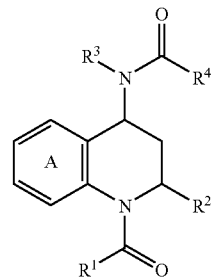
(II)

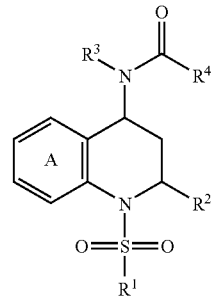
(III)

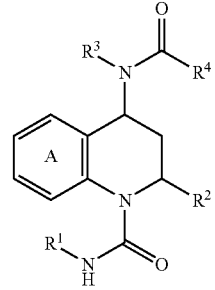
(IV)

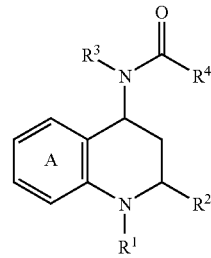
(V)

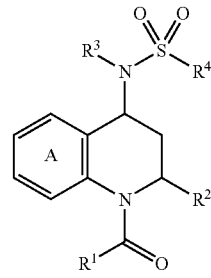
(VI)

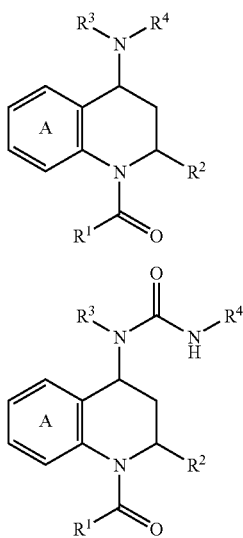

The variables in Structural Formulas (II)-(VIII) are as described above for Structural Formula (I). Preferred values for these variables are provided below.

Phenyl Ring A is a substituted or unsubstituted phenyl group. Unless otherwise indicated suitable substituents for Phenyl Ring A are provided in the section below describing suitable aryl ring substituents.

$R^1$ in Structural Formulas (II)-(IV) and (VI)-(VIII) is —H, optionally substituted, cycloaliphatic group, aromatic group or non-aromatic heterocyclic group, provided that $R^1$ in Structural Formulas (III) is not —H.

$R^2$ in Structural Formulas (II)-(VII) is —H, methyl or ethyl.

$R^3$ in Structural Formulas (II)-(VIII) is an optionally substituted phenyl group.

$R^4$ in Structural Formulas (II)-(VI) and (VII) is —H, —CH$_2$C(O)R$^{14}$, —CH$_2$R'5, —CH$_2$OR$^{14}$ or an optionally substituted C$_1$-C$_3$ alkyl group or an optionally substituted cycloalkyl group, aromatic group or non-aromatic heterocyclic group, provided that $R^4$ in Structural Formula (VI) is not —H; and $R^4$ in Structural Formulas (VII) is CH$_2$)$_n$—R$^{13a}$.

$R^{13a}$ is —H, —CH$_2$C(O)R$^{14}$, —CH$_2$R$^{15}$, —CH$_2$OR$^{14}$ or an optionally substituted C$_1$-C$_3$ alkyl group or an optionally substituted cycloalkyl group, aromatic group or non-aromatic heterocyclic group.

Each $R^{14}$ is independently an —H or an optionally substituted alkyl group, aromatic group, cycloalkyl group or non-aromatic heterocyclic group.

Each $R^{15}$ is independently an optionally aromatic group, cycloalkyl group or non-aromatic heterocyclic group.

n is 0, 1, 2 or 3.

More preferred values for $R^1$, $R^4$ and $R^{13a}$ in Structural Formulas (II)-(VIII) are $R^1$ and $R^{13a}$ are an optionally substituted, phenyl, pyridyl, furanyl, thiophenyl, isoxazolyl, imidazolyl, pyrazolyl, pyrrolyl, benzofuranyl, tetrazolyl, thiazolyl, benzyl, benzothiazolyl, benzoimidazolyl, benzotriazolyl, benzomorpholinyl, benzopyrazolyl, indolyl, —CH$_2$-(N-pyridyl), —CH$_2$-furanyl, —CH$_2$-thiophenyl, —CH$_2$-isoxazolyl, —CH$_2$-imidazolyl, —CH$_2$-pyrazolyl, —CH$_2$-pyrollyl, —CH$_2$-benzofuranyl, —CH$_2$-tetrazolyl, —CH$_2$-thiazolyl, —CH$_2$-tetrazolyl, —CH$_2$-benzothiazolyl, —CH$_2$-benzimidazolyl, —CH$_2$—O-phenyl, —CH$_2$C(O)-phenyl, naphthalimidyl, tetrahydrofuranyl, cyclohexyl, cyclopentyl or cyclopropyl group; and $R^4$ is C$_1$-C$_4$ alkyl, —CH$_2$OH, —CH$_2$OCH$_3$, —CH$_2$OCH$_2$CH$_3$, —CH$_2$CH$_2$OCH$_3$, —CH$_2$CH$_2$OCH$_2$CH$_3$ or an optionally substituted, phenyl, pyridyl, furanyl, thiophenyl, isoxazolyl, imidazolyl, pyrazolyl, pyrrolyl, benzofuranyl, tetrazolyl, benzyl, benzothiazolyl, benzoimidazolyl, benzotriazolyl, benzomorpholinyl, benzopyrazolyl, indolyl, —CH$_2$—(N-pyridyl), —CH$_2$-furanyl, —CH$_2$-thiophenyl, —CH$_2$-isoxazolyl, —CH$_2$-imidazolyl, —CH$_2$-pyrazolyl, —CH$_2$-pyrollyl, —CH$_2$-benzofuranyl, —CH$_2$-tetrazolyl, —CH$_2$-thiazolyl, —CH$_2$-tetrazolyl, —CH$_2$-benzothiazolyl, —CH$_2$-benzimidazolyl, —CH$_2$—O-phenyl, —CH$_2$C(O)-phenyl, naphthalimidyl, tetrahydrofuranyl, cyclohexyl, cyclopentyl or cyclopropyl group, wherein $R^1$, $R^4$ and $R^{13}$ are independently selected; and Ring A is optionally substituted at the five, six, seven and/or the eight position.

Even more preferably, the compounds in Structural Formulas (II)-(VIII) have one of the following features and preferably all of the following features: Phenyl Ring A is optionally substituted at the five, six, seven and/or eight position with $R^{11}$, wherein $R^{11}$ is selected from substituents provided in the section below describing suitable aryl ring substituents unless otherwise indicated herein.

$R^1$ is phenyl, thiophenyl, furanyl, pyridyl, oxazolyl, benzotriazole, pyrimidinyl, isoxazolyl or benzomorpholinyl, each group being optionally substituted with $R^{11}$; $R^3$ is [$R^{11}$]-phenyl; and $R^4$ is methyl, ethyl, propyl, iso-propyl, n-butyl, sec-butyl, tert-butyl, —CH$_2$OCH$_3$ or —CH$_2$OCH$_2$CH$_3$.

Especially preferred are compounds represented by Structural Formulas (II)-(VIII) wherein Phenyl Ring A is optionally substituted at the six and/or seven position with $R^{11}$; $R^1$ is thiophenyl, [$R^{11}$]-thiophenyl, oxazolyl, [$R^{11}$]-oxazolyl, pyridinyl, [$R^{11}$]-pyridinyl, benzotriazolyl, [$R^{11}$]-benzotriazolyl, benzomorpholinyl, [$R^{11}$]-benzomorpholinyl, phenyl or phenyl substituted with one to four groups selected from the group consisting of halo, —OR° and —N(R$^{11}$)$_2$, [R$^{11}$]-oxazolyl, oxazolyl and

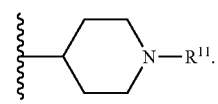

$R^3$ is phenyl substituted with one to four atoms or groups selected from the group consisting of Br, Cl, —CH$_3$, —N(R$^{16}$)$_2$, —NHC(O)OR", —S(O)$_2$CH$_3$, —S(O)$_2$N(R$^{16}$)$_2$ and —R$^{13}$C(O)N(R$^{16}$)$_2$, where R$^{16}$ is C$_1$-C$_6$ alkyl.

In third preferred embodiment, Ring A in Structural Formulas (I) is a monocyclic heteroaryl group such as thiophene, furan, pyridine, pyrazole, pyrrole, [2,3]pyrimidine, [3,4]pyrimidine, [4,5]pyrimidine, [5,6]pyrimidine, oxazole, isoxazole or 1,2,3-triazole, each group being optionally substituted with $R^{11}$. When Ring A has these values, then the compound preferably has at least one and preferably all of the following features: X is —CHR$^2$—, $R^2$ are —H, methyl or ethyl; $R^5$ and $R^6$ are —H; and $R^3$ is a substituted or unsubstituted phenyl group. When the compound has at least one or all of these features, then preferably $R^1$ and $R^4$ are independently —H, —CH$_2$C(O)R$^{14}$, —CH$_2$R$^{15}$ or —CH$_2$OR$^{14}$ or an optionally substituted alkyl group, cycloalkyl group, aromatic group or non-aromatic heterocyclic group; and $R^{14}$ and $R^{15}$ are as described above for Structural Formula (II).

When Ring A in Structural Formula (I) is a monocyclic heteroaryl, as described in the preceding paragraph, commonly selected values for $X_1$ and $X_2$ are as follows: $X_1$ and $X_2$ are both C(O); $X_1$ is $S(O)_2$ and $X_2$ is C(O); $X_1$ is C(O)NH and $X_2$ is C(O); $X_1$ is a bond and $X_2$ is C(O); and $X_2$ is C(O); $X_1$ is C(O) and $X_2$ is $S(O)_2$; $X_1$ is C(O) and; $X_1$ is C(O) and $X_2$ is a bond; or $X_1$ is C(O) and $X_2$ is C(O)NH. Alternatively, Phenyl Ring A in Structural Formulas (II)-(VIII) is replaced with one of the monocyclic aromatic groups described in the preceding paragraph and the remainder of the variables are as described above.

In a fourth preferred embodiment, $R^2$ in Structural Formulas (I)-(VIII) is —H, $C_1$-$C_4$ alkyl, halogentated $C_1$-$C_6$ alkyl, $C_3$-$C_8$ cycloalkyl, substituted $C_3$-$C_8$ cycloalkyl, phenyl, substituted phenyl, —C(O)O$R^{16}$, benzyl, substituted benzyl or —$(CH_2)_nO(CH_2)_m$; $R^{16}$ is $C_1$-$C_6$ alkyl; n and m are positive integers such n+m=6; and the remainder of the variables are as described above.

Also disclosed herein is a compound represented by Structural Formula (II) and methods of use thereof for inhibiting CRTH2 in a subject in need of treatment therefore and pharmaceutical compositions comprising the same, wherein $R^1$ has the value corresponding to any one of the compounds in Table 1-6 and $R^3$ and $R^4$ are as described above for Structural Formula (II).

Also disclosed herein is a compound represented by Structural Formula (II) and methods of use thereof for inhibiting CRTH2 in a subject in need of treatment therefore and pharmaceutical compositions comprising the same, wherein $R^3$ has the value corresponding to any one of the compounds in Table 1-6 and $R^1$ and $R^4$ are as described above for Structural Formula (II).

Also disclosed herein is a compound represented by Structural Formula (II) and methods of use thereof for inhibiting CRTH2 in a subject in need of treatment therefore and pharmaceutical compositions comprising the same, wherein $R^4$ has the value corresponding to any one of the compounds in Table 1-6 and $R^1$ and $R^3$ are as described above for Structural Formula (II).

Also disclosed herein is a compound represented by Structural Formula (III) and methods of use thereof for inhibiting CRTH2 in a subject in need of treatment therefore and pharmaceutical compositions comprising the same, wherein $R^3$ has the value corresponding to any one of the compounds in Table 1-6 and $R^1$ and $R^4$ are as described above for Structural Formula (III).

Also disclosed herein is a compound represented by Structural Formula (III) and methods of use thereof for inhibiting CRTH2 in a subject in need of treatment therefore and pharmaceutical compositions comprising the same, wherein $R^4$ has the value corresponding to any one of the compounds in Table 1-6 and $R^1$ and $R^3$ are as described above for Structural Formula (III).

Also disclosed herein is a compound represented by Structural Formula (III) and methods of use thereof for inhibiting CRTH2 in a subject in need of treatment therefore and pharmaceutical compositions comprising the same, wherein $R^1$ has the value corresponding to any one of the compounds in Table 1-6 and $R^3$ and $R^4$ are as described above for Structural Formula (III).

Also disclosed herein is a compound represented by Structural Formula (IV) and methods of use thereof for inhibiting CRTH2 in a subject in need of treatment therefore and pharmaceutical compositions comprising the same, wherein $R^3$ has the value corresponding to any one of the compounds in Table 1-6 and $R^1$ and $R^4$ are as described above for Structural Formula (IV).

Also disclosed herein is a compound represented by Structural Formula (IV) and methods of use thereof for inhibiting CRTH2, wherein $R^4$ has the value corresponding to any one of the compounds in Table 1-6 and $R^1$ and $R^3$ are as described above for Structural Formula (IV).

Also disclosed herein is a compound represented by Structural Formula (IV) and methods of use thereof for inhibiting CRTH2, wherein $R^1$ has the value corresponding to any one of the compounds in Table 1-6 and $R^3$ and $R^4$ are as described above for Structural Formula (IV).

Also disclosed herein is a compound represented by Structural Formula (V) and methods of use thereof for inhibiting CRTH2 in a subject in need of treatment therefore and pharmaceutical compositions comprising the same, wherein $R^3$ has the value corresponding to any one of the compounds in Table 1-6 and $R^1$ and $R^4$ are as described above for Structural Formula (V).

Also disclosed herein is a compound represented by Structural Formula (V) and methods of use thereof for inhibiting CRTH2 in a subject in need of treatment therefore and pharmaceutical compositions comprising the same, wherein $R^4$ has the value corresponding to any one of the compounds in Table 1-6 and $R^1$ and $R^3$ are as described above for Structural Formula (V).

Also disclosed herein is a compound represented by Structural Formula (V) and methods of use thereof for inhibiting CRTH2 in a subject in need of treatment therefore and pharmaceutical compositions comprising the same, wherein $R^1$ has the value corresponding to any one of the compounds in Table 1-6 and $R^3$ and $R^4$ are as described above for Structural Formula (V).

Also disclosed herein is a compound represented by Structural Formula (VI) and methods of use thereof for inhibiting CRTH2 in a subject in need of treatment therefore and pharmaceutical compositions comprising the same, wherein $R^3$ has the value corresponding to any one of the compounds in Table 1-6 and $R^1$ and $R^4$ are as described above for Structural Formula (VI).

Also disclosed herein is a compound represented by Structural Formula (VI) and methods of use thereof for inhibiting CRTH2 in a subject in need of treatment therefore and pharmaceutical compositions comprising the same, wherein $R^4$ has the value corresponding to any one of the compounds in Table 1-6 and $R^1$ and $R^3$ are as described above for Structural Formula (VI).

Also disclosed herein is a compound represented by Structural Formula (VI) and methods of use thereof for inhibiting CRTH2 in a subject in need of treatment therefore and pharmaceutical compositions comprising the same, wherein $R^1$ has the value corresponding to any one of the compounds in Table 1-6 and $R^3$ and $R^4$ are as described above for Structural Formula (VI).

Also disclosed herein is a compound represented by Structural Formula (VII) and methods of use thereof for inhibiting CRTH2 in a subject in need of treatment therefore and pharmaceutical compositions comprising the same, wherein $R^3$ has the value corresponding to any one of the compounds in Table 1-6 and $R^1$ and $R^4$ are as described above for Structural Formula (VII).

Also disclosed herein is a compound represented by Structural Formula (VII) and methods of use thereof for inhibiting CRTH2 in a subject in need of treatment therefore and pharmaceutical compositions comprising the same, wherein $R^4$ has the value corresponding to any one of the compounds in Table 1-6 and $R^1$ and $R^3$ are as described above for Structural Formula (VII).

Also disclosed herein is a compound represented by Structural Formula (VII) and methods of use thereof for inhibiting CRTH2 in a subject in need of treatment therefore and pharmaceutical compositions comprising the same, wherein $R^1$ has the value corresponding to any one of the compounds in Table 1-6 and $R^3$ and $R^4$ are as described above for Structural Formula (VII).

Also disclosed herein is a compound represented by Structural Formula (VIII) and methods of use thereof for inhibiting CRTH2 in a subject in need of treatment therefore and pharmaceutical compositions comprising the same, wherein $R^3$ has the value corresponding to any one of the compounds in Table 1-6 and $R^1$ and $R^4$ are as described above for Structural Formula (VIII).

Also disclosed herein is a compound represented by Structural Formula (VIII) and methods of use thereof for inhibiting CRTH2 in a subject in need of treatment therefore and pharmaceutical compositions comprising the same, wherein $R^4$ has the value corresponding to any one of the compounds in Table 1-6 and $R^1$ and $R^3$ are as described above for Structural Formula (VIII).

Also disclosed herein is a compound represented by Structural Formula (VIII) and methods of use thereof for inhibiting CRTH2 in a subject in need of treatment therefore and pharmaceutical compositions comprising the same, wherein $R^1$ has the value corresponding to any one of the compounds in Table 1-6 and $R^3$ and $R^4$ are as described above for Structural Formula (VIII).

Specific examples of compounds of general formula I are shown in the Exemplification Section herein.

It will be understood that the immediately following definitions and description apply to compounds of general formula I (and subsets thereof described above in this section 1 entitled "Description of Compounds of General Formula I (and subsets thereof)" As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001.

Many of the disclosed CRTH2 inhibitors contain one or more chiral centers. The presence of chiral centers in a molecule gives rise to stereoisomers. For example, a pair of optical isomers, referred to as "enantiomers", exist for every chiral center in a molecule; and a pair of diastereomers exist for every chiral center in a compound having two or more chiral centers. Even though Structural Formulas (I)-(VIII) do not explicitly depict stereochemistry, it is to be understood that these formulas encompass enantiomers free from the corresponding optical isomer, racemic mixtures, mixtures enriched in one enantiomer relative to its corresponding optical isomer, a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diastereomeric pairs in which one diastereomeric pair is enriched relative to the other diastereomeric pair(s).

A preferred diastereomeric pair is when $R^2$ and $NR^XR^3$ in Structural Formulas (I)-(VIII) are cis relative to one another. By way of example, the cis diastereomeric pair for the compound represented by Structural Formula (II) is shown below in Structural Formulas (IX) and (X):

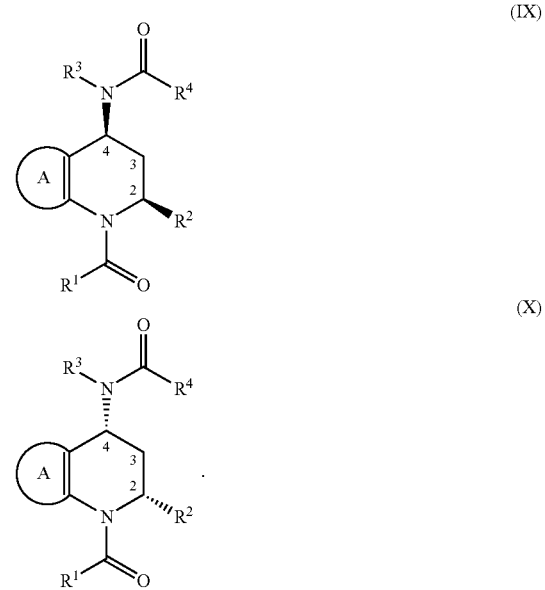

The preferred configuration for $R^2$ and $NR^XR^3$ (depicted by $N(R^3)(COR^4)$ in Structural Formulas (IX) and (X) is (2R,4S), as shown in Structural Formula (IX). Thus, Structural Formula (IX) represents a preferred optical isomer for the compound represented by Structural Formula (II). Similarly, the corresponding (2R,4S) optical isomer for the compounds represented by Structural Formulas (I) and (III)-(VIII) and Tables 1-6 are also specifically disclosed. The more preferred configuration for $R^2$ and —$NR^XR^3$ (depicted by $N(R^3)$ $(COR^4)$) in Structural Formulas (IX) and (X) is (2S,4R), as shown in Structural Formula (X). Thus, Structural Formula (X) represents a more preferred optical isomer for the compound represented by Structural Formulas (1) and (III)-(VIII) and in Tables 1-6.

As used herein, a structure depicting one optical isomer or a reference to one optical isomer is meant to include enantiomeric mixtures which are enriched with the depicted or referenced enantiomer relative to its optical isomer, for example, an enantiomeric excess of at least 50%, 75%, 90%, 95% 99% or 99.5%. As used herein, a structure depicting a diastereomeric pair or a reference to one diasteromeric pair is meant to include mixtures which are enriched with the depicted or referenced diastereomeric pair relative to other diastereomers or diastereomeric pair(s) for the compound, for example, a molar excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided in Scheme 1 and 2.

In certain instances compounds of the present invention may be associated in isolated form with solvent or water, as in a "solvate" or "hydrate". References to the disclosed compounds or structural formulas depicting the disclosed compounds are meant to include such solvates and hydrates.

The term "aliphatic" as used herein means straight-chain or branched hydrocarbons which are completely saturated or which contain one or more units of unsaturation, but which are not aromatic. An aliphatic group is typically $C_{1-8}$, more typically $C_{1-6}$. For example, suitable aliphatic groups include substituted or unsubstituted linear or branched alkyl, alkenyl, alkynyl groups and hybrids thereof. The terms "alkyl", "alkoxy", "hydroxyalkyl", "alkoxyalkylene", and "alkoxycarbonyl", used alone or as part of a larger moiety includes both straight and branched saturated chains containing one to eight carbon atoms. The terms "alkenyl" and alkynyl" used alone or as part of a larger moiety shall include both straight and branched chains containing two to eight carbon atoms and one or more double and/or triple bonds, respectively.

The term "cycloaliphatic" used alone or as part of a larger moiety shall include cyclic $C_3$-$C_{10}$ hydrocarbons which are completely saturated or which contain one or more units of unsaturation, but which are not aromatic. Cycloaliphatic groups are typically $C_{3-10}$, more typically $C_{3-7}$. A "cycloalkyl" is an cyclic aliphatic group that is completely saturated.

"Alkoxy" means (alkyl)-O—; "alkoxyalkylene" means (alkyl)-O-(alkylene) such as methoxymethylene ($CH_3OCH_2$); "hydroxyalkyl" means hydroxy substituted alkyl group; "alkoxy carbonyl means a carbonyl substituted with a carbonyl as in (alkyl)-O—C(O)—; and "aralkyl" mean alkyl substituted with an aromatic group. A "$C_1$-$C_4$ aralkyl group", for example, has a $C_1$-$C_4$ alkyl group substituted with an aromatic group.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR+ (as in N-substituted pyrrolidinyl).

The term "aromatic group" used alone or as part of a larger moiety as in "aralkyl", "aralkoxy", or "aryloxyalkyl", includes to carbocyclic aromatic ring groups and heteroaryl rings groups. The term "aromatic group" may be used interchangeably with the terms "aryl", "aryl ring" or "aromatic ring".

Carbocyclic aromatic ring groups have only carbon ring atoms and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (aliphatic or heterocyclic), such as in an indanyl, phthalimidyl, naphthimidyl, phenantriidinyl, or tetrahydronaphthyl, where the radical or point of attachment is on the aromatic ring.

The term "heteroaryl" or "heteroaromatic", used alone or as part of a larger moiety as in "heteroaralkyl" or "heteroarylalkoxy", refers to heteroaromatic ring groups having five to fourteen members, including monocyclic heteraromatic rings and polycyclic aromatic rings in which a monocyclic aromatic ring is fused to one or more other carbocyclic or heteroaromatic aromatic rings. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisazolyl. Also included within the scope of the term "heteroaryl", as it is used herein, is a group in which a heteroaryl ring is fused to one or more cycloaliphatic or non-aromatic heterocyclic groups where the radical or point of attachment is on the heteroaromatic ring. Examples include tetrahydroquinolinyl, tetrahydroisoquinolinyl, and pyrido[3,4-d]pyrimidinyl. The term "heteroaryl" may be interchangeably with the term "heteroaryl ring" or the term "heteroaromatic".

The term "non-aromatic heterocyclic ring", used alone or as part of a larger moiety as in "hetercyclylalkyl", refers to non-aromatic ring systems typically having five to fourteen members, preferably five to ten, in which one or more ring carbons, preferably one to four, are each replaced by a heteroatom such as N, O, or S. Examples of non-aromatic heterocyclic rings include 3-1H-benzimidazol-2-one, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrorolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, and benzothianyl.

A "hydrocarbyl group" is a polymethylene group, i.e., $—(CH_2)_n—$, wherein n is a positive integer. Preferably, n is an integer from 1 to 6, more preferably from 2 to 4 and more preferably from 2 to 3. A "substituted hydrocarbyl" is a hydrocarbyl group in which one or more methylene hydrogen atoms are replaced with a substituent. Suitable substituents are as described below for a substituted aliphatic group. Preferred substituents for the hydrocarbyl groups represented by $X_3$—$X_6$ are halo, —OH, =O, $C_1$-$C_3$ alkyl, $C_1$-$C_3$ alkoxy, nitro and cyano.

A hydrocarbyl group can be optionally interrupted by one or more functional groups. A hydrocarbyl is interrupted by a functional group when one of the internal methylenes is replaced with the functional group. Examples of suitable "interrupting functional groups" include —O—, —S—, —N($R^a$)—, —S(O)—, —SO$_2$—, —C(O)—, —OC(O)—, —N($R^a$)C(O)—, —C(O)N($R^a$)—, —SO$_2$N($R^a$)—, and —N($R^a$)SO$_2$—. $R^a$ is —H or a $C_1$-$C_3$ alkyl group.

An aromatic group (including Ring A, carbocyclic aromatic, heteroaryl, aralkyl, aralkoxy, aryloxyalkyl and heteroaralkyl and the like) group may contain one or more substituents. Examples of suitable substituents on an unsaturated carbon atom of an aromatic group include a halogen —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$—CN, —N(R')$_2$, —NR'CO$_2$R°, —NR'C(O)R°, —NR'NR'C(O)R°, —N(R')C(O)N(R')$_2$, —NR'NR'C(O)N(R')$_2$, —NR'NR'CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R')$_2$, —S(O)R°, —NR'SO$_2$N(R')$_2$, —NR'SO$_2$R°, —C(=S)N(R')$_2$, —(CH$_2$)$_y$N(R')$_2$, —C(=NH)—N(R')$_2$, —(CH$_2$)$_y$NHC(O)R°, —(CH$_2$)$_y$NHC(O)CH(V-R°)(R°). R' is R°, —CO$_2$R°, —SO$_2$R° or —C(O)R° and preferably hydrogen, C$_{1-6}$ aliphatic, CO$_2$R°, SO$_2$R° or C(O)R°. R° is hydrogen or substituted or unsubstituted aliphatic, cycloaliphatic, arpmatic, aralkyl or non-aromatic heterocyclic group, and preferably hydrogen, C$_{1-6}$ alkyl, phenyl (Ph), —CH$_2$ (Ph), aralkyl, non-aromatic heterocyclic group or heteroaryl; y is 0-6; and V is C$_1$-C$_6$ alkylene group. Examples of substituents on the aliphatic group or the phenyl ring of R° include amino, alkylamino, dialkylamino, aminocarbonyl, halogen, alkyl, aminoalkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocycle may contain one or more substituents. Examples of suitable substituents on the saturated carbon of an aliphatic group of a non-aromatic heterocycle include those listed above for the unsaturated carbon of an aromatic group and the following: =O, =S, =NNHR*, =NN(R*)$_2$, =NNHC(O)R*, =NNHCO$_2$(alkyl), =NNHSO$_2$ (alkyl), or =NR*. Each R* is independently selected from hydrogen, an unsubstituted aliphatic group or a substituted aliphatic group. Examples of substituents on the aliphatic group represented by R* include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the substitutable nitrogen of a heteroaryl or non-aromatic heterocyclic group include —R$^+$, —N(R$^+$)$_2$, —C(O)R$^+$, —CO$_2$R$^+$, —C(O)C(O)R$^+$, —C(O)CH$_2$ C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein R$^+$ is hydrogen, an aliphatic group, a substituted aliphatic group, phenyl (Ph), substituted Ph, —O(Ph), substituted —O(Ph), CH$_2$(Ph), or an unsubstituted heteroaryl or non-aromatic heterocyclic ring. Examples of substituents on the aliphatic group or the phenyl ring represented by R$^+$ include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

2. Description of Compounds of General Formula I-A (and Subsets Thereof)

Another embodiment of the present invention is a compound represented by Structural Formula I-A:

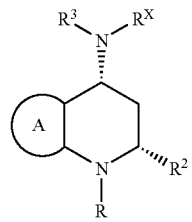

I-A or a pharmaceutically acceptable salt thereof, wherein:
Ring A is an optionally substituted monocyclic aromatic;
R is —X$_1$—R$^1$;
R$^X$ is —X$_2$—R$^4$;
X$_1$ and X$_2$ are each independently —S(O)$_2$—, —C(O)—, or —C(O)NH—;
R$^1$ is:
 A) an aromatic group or heteroaromatic group having 5-6 ring atoms, fused to a monocyclic non-aromatic heterocyclic ring or monocyclic aromatic or heteroaromatic ring wherein the non-aromatic heterocyclic ring, the aromatic ring, or the heteroaromatic ring are optionally substituted; or
 B) an aromatic group or heteroaromatic group having 5-6 ring atoms, substituted by:
  i) T$^1$-V-T-R$^Y$;
  ii) T$^1$-V-T-M-R$^Y$; or
  iii) V-R$^9$, wherein R$^9$ is an optionally substituted non-aromatic carbocyclic or heterocyclic group;
  and wherein the aromatic or heteroaromatic group having 5-6 ring atoms optionally is further substituted by 1-2 independently selected groups represented by R$^Z$;
 each R$^Z$ is independently selected from halogen, haloalkyl, R°, —OR°, —O(haloalkyl), —SR°, —NO$_2$, —CN, —N(R')$_2$, —NR'CO$_2$R°, —NR'C(O)R°, —NR'NR'C(O)R°, —N(R')C(O)N(R')$_2$, —NR'NR'C(O)N(R')$_2$, —NR'NR'CO$_2$R°, —C(O)C(O)R°, —C(O)CH$_2$C(O)R°, —CO$_2$R°, —C(O)R°, —C(O)N(R')$_2$, —OC(O)R°, —OC(O)N(R°)$_2$, —S(O)$_2$R°, —SO$_2$N(R')$_2$, —S(O)R°, —NR'SO$_2$N(R')$_2$, —NR'SO$_2$R°, —C(=S)N(R')$_2$, and —C(=NH)—N(R')$_2$;
 each R' is independently hydrogen, alkyl, —C(O)OR°, S(O)$_2$R°, or —C(O)R°;
 each R° is independently hydrogen or an alkyl group, non-aromatic heterocyclic group or aromatic group and the alkyl, non-aromatic heterocyclic group and aromatic group represented by R° is optionally substituted with one or more independently selected groups represented by R$^\#$;
 R$^\#$ is R$^+$, —OR$^+$, —O(haloalkyl), —SR$^+$, —NO$_2$, —CN, —N(R$^+$)$_2$, —NHCO$_2$R$^+$, —NHC(O)R$^+$, —NHNHC(O)R$^+$, —NHC(O)N(R$^+$)$_2$, —NHNHC(O)N(R$^+$)$_2$, —NHNHCO$_2$R$^+$, —C(O)C(O)R$^+$, —C(O)CH$_2$C(O)R$^+$, —CO$_2$R$^+$, —C(O)R$^+$, —C(O)N(R$^+$)$_2$, —OC(O)R$^+$, —OC(O)N(R$^+$)$_2$, —S(O)$_2$R$^+$, —SO$_2$N(R$^+$)$_2$, —S(O)R$^+$, —NHSO$_2$N(R$^+$)$_2$, —NHSO$_2$R$^+$, —C(=S)N(R$^+$)$_2$, or —C(=NH)—N(R$^+$)$_2$;
 R$^+$ is —H, a C$_1$-C$_3$ alkyl group, a monocyclic heteroaryl group, a non-aromatic heterocyclic group or a phenyl group optionally substituted with alkyl, haloalkyl, alkoxy, haloalkoxy, halo, —CN, —NO$_2$, amine, alkylamine or dialkylamine; or —N(R$^+$)$_2$ is a non-aromatic heterocyclic group, provided that non-aromatic heterocyclic groups represented by $R^+$ and $—N(R^+)_2$ that comprise a secondary ring amine are optionally acylated or alkylated;

V is a covalent bond, $—O—$, $—C(O)—$, $—N(R')—$, $—S—$, $—S(O)—$, $—C(O)NR^5—$, $—NR^5C(O)—$, $—S(O)_2NR^5—$, $—NR^5S(O)_2—$, or $—S(O)_2—$;

T is $C_{1-10}$ is a straight chain alkylene;

$T^1$ is a covalent bond, or a $C_{1-10}$ straight chain alkylene, wherein T and $T^1$ together contain no more than 10 carbon atoms, and wherein T and $T^1$ are optionally and independently substituted at any one or more substitutable carbon atoms with halide, alkyl, gem dialkyl, gem dihalo, haloalkyl, alkoxy, haloalkoxy, spiro cycloalkyl, optionally N-substituted nitrogen containing spiro non-aromatic heterocyclic group, O-containing spiro non-aromatic heterocyclic group, amine, alkylamine, dialkylamine, alkoxy, or hydroxyl;

M is an optionally substituted group selected from monocyclic aromatic, heteroaromatic, monocyclic non-aromatic carbocyclic, or heterocyclic group;

$R^Y$ is $—C(O)OR^5$, $—C(O)R^5$, $—OC(O)R^5$, $—C(O)N(R^5)_2$, $—NR^5C(O)R^5$, $—NR^5C(O)OR^5$, $—S(O)_2R^5$, $—S(O)_2COR^5$, $—S(O)_2N(R^5)_2$, $—NR^5S(O)_2R^5$, $—NR^5S(O)_2R^5$, $S(O)_2OR^5$, $—S(O)OR^5$, $—S(O)R^5$, $—SR^5$, $—C(O)NR^5S(O)_2R^5$, $—CN$, $—NR^5C(O)N(R^5)_2$, $—OC(O)N(R^5)_2$, $—N(R^5)_2$, $—OR^5$, an optionally substituted non-aromatic heterocyclic group or an optionally substituted heteroaryl group;

provided that T is $C_{2-10}$ when V is a covalent bond, and T is $C_{2-10}$ when V is $—O—$, $—S—$, or $—N(R')—$ and $R^Y$ is $—CN$, $—OH$, $—SH$, $—N(R^5)_2$ each $R^5$ is independently $—H$, alkyl, haloalkyl, hydroxyalkyl, carboxyalkyl, $—C(O)OCH_2C_6H_5$, $S(O)_2CH_3$, $—C(O)OH$, $—C(O)OMe$, $—C(O)OEt$, $C(O)NH_2$, benzyl, pyrrolidinyl, morpholinyl, or $—N(R^5)_2$ is a nitrogen-containing non-aromatic heterocyclic group;

$R^2$ is $C_{1-3}$ alkyl;

$R^3$ is an optionally substituted monocyclic or bicyclic group selected from aromatic, heteroaromatic, non-aromatic carbocyclic, or non-aromatic heterocyclic; and $R^4$ is optionally substituted $C_{1-6}$alkyl, $C_{1-4}$ hydroxyalkyl, or optionally substituted $C_{3-6}$cycloalkyl.

In one embodiment, compounds of formula I-A, or a pharmaceutically acceptable salt thereof, are provided, wherein:

Ring A is an optionally substituted monocyclic aromatic;

R is $—X_1—R^1$;

$R^X$ is $—X_2—R^4$;

$X_1$ and $X_2$ are each independently $—S(O)_2—$, $—C(O)—$, or $—C(O)NH—$;

$R^1$ is: A) an aromatic group or heteroaromatic group having 5-6 ring atoms, substituted by:
  i) $T^1$-V-T-$R^Y$;
  ii) $T^1$-V-T-M-$R^Y$; or
  iii) V-$R^9$ wherein $R^9$ is an optionally substituted non-aromatic carbocyclic or heterocyclic group;

and wherein the aromatic or heteroaromatic group represented by $R^1$ optionally is further substituted by 1-2 independently selected groups represented by $R^Z$; or B) an aromatic group or heteroaromatic group having 5-6 ring atoms, fused to a monocyclic non-aromatic heterocyclic ring or monocyclic aromatic ring wherein the non-aromatic heterocyclic ring or the aromatic ring are optionally substituted;

each $R^Z$ is independently selected from halogen, haloalkyl, $R°$, $—OR°$, $—O(haloalkyl)$, $—SR°$, $—NO_2$, $—CN$, $—N(R')_2$, $—NR'CO_2R°$, $—NR'C(O)R°$, $—NR'NR'C(O)R°$, $—N(R')C(O)N(R')_2$, $—NR'NR'C(O)N(R')_2$, $—NR'NR'CO_2R°$, $—C(O)C(O)R°$, $—C(O)CH_2C(O)R°$, $—CO_2R°$, $—C(O)R°$, $—C(O)N(R°)_2$, $—OC(O)R°$, $—OC(O)N(R°)_2$, $—S(O)_2R°$, $—SO_2N(R')_2$, $—S(O)R°$, $—NR'SO_2N(R')_2$, $—NR'SO_2R°$, $—C(=S)N(R')_2$, and $—C(=NH)—N(R')_2$;

each R is independently hydrogen, alkyl, $—C(O)OR°$, $S(O)_2R°$, or $—C(O)R°$;

each $R°$ is independently hydrogen or an alkyl group, non-aromatic heterocyclic group or aromatic group and the alkyl, non-aromatic heterocyclic group and aromatic group represented by $R°$ is optionally substituted with one or more independently selected groups represented by $R^\#$;

$R^\#$ is $R^+$, $—OR^+$, $—O(haloalkyl)$, $—SR^+$, $—NO_2$, $—CN$, $—N(R^+)_2$, $—NHCO_2R^+$, $—NHC(O)R^+$, $—NHNHC(O)R^+$, $—NHC(O)N(R^+)_2$, $—NHNHC(O)N(R^+)_2$, $—NHNHCO_2R^+$, $—C(O)C(O)R^+$, $—C(O)CH_2C(O)R^+$, $—CO_2R^+$, $—C(O)R^+$, $—C(O)N(R^+)_2$, $—OC(O)R^+$, $—OC(O)N(R^+)_2$, $—S(O)_2R^+$, $—SO_2N(R^+)_2$, $—S(O)R^+$, $—NHSO_2N(R^+)_2$, $—NHSO_2R^+$, $—C(=S)N(R^+)_2$, or $—C(=NH)—N(R^+)_2$;

$R^+$ is $—H$, a $C_1$-$C_3$ alkyl group, a monocyclic heteroaryl group, a non-aromatic heterocyclic group or a phenyl group optionally substituted with alkyl, haloalkyl, alkoxy, haloalkoxy, halo, $—CN$, $—NO_2$, amine, alkylamine or dialkylamine; or $—N(R^+)_2$ is a non-aromatic heterocyclic group, provided that non-aromatic heterocyclic groups represented by $R^+$ and $—N(R^+)_2$ that comprise a secondary ring amine are optionally acylated or alkylated;

$R^Y$ is $—C(O)OR^5$, $—C(O)R^5$, $—OC(O)R^5$, $—C(O)NR^5_2$, $—NR^5C(O)R^5$, $—NR^5C(O)OR^5$, $—S(O)_2R^5$, $—S(O)_2COR^5$, $—S(O)_2N(R^5)_2$, $—NR^5S(O)_2R^5$, $—NR^5S(O)_2R^5$, $S(O)_2OR^5$, $—S(O)OR^5$, $—S(O)R^5$, $—SR^5$, $—C(O)NR^5S(O)_2R^5$, $—CN$, $—NR^5C(O)N(R^5)_2$, $—OC(O)N(R^5)_2$, $—N(R^5)_2$, $—OR^5$, an optionally substituted non-aromatic heterocyclic group or an optionally substituted heteroaryl group;

V is a covalent bond, $—O—$, $—C(O)—$, $—N(R')—$, $—S—$, $—S(O)—$, $—C(O)NR^5—$, $—NR^5C(O)—$, $—S(O)_2NR^5—$, $—NR^5S(O)_2—$, or $—S(O)_2—$;

T is $C_{1-10}$ is a straight chain alkylene; provided that T is $C_{2-10}$ when V is a covalent bond, and T is $C_{2-10}$ when V is $—O—$, $—S—$, or $—N(R')—$ and $R^Y$ is $—CN$, $—OH$, $—SH$, $—N(R^5)_2$;

$T^1$ is a covalent bond, or a $C_{1-10}$ straight chain alkylene, wherein T and $T^1$ together contain no more than 10 carbon atoms, and wherein T and $T^1$ are optionally and independently substituted at any one or more substitutable carbon atoms with halide, alkyl, gem dialkyl, gem dihalo, haloalkyl, alkoxy, haloalkoxy, spiro cycloalkyl, optionally N-substituted nitrogen containing spiro non-aromatic heterocyclic group, amine, alkylamine, dialkylamine, or hydroxyl;

each $R^5$ is independently $—H$, alkyl, haloalkyl, hydroxyalkyl, carboxyalkyl, $—C(O)OCH_2C_6H_5$, $S(O)_2CH_3$, $—C(O)OH$, $—C(O)OMe$, $—C(O)OEt$, $C(O)NH_2$, benzyl, pyrrolidinyl, morpholinyl, or $—N(R^5)_2$ is a nitrogen-containing non-aromatic heterocyclic group;

M is an optionally substituted monocyclic aromatic, heteroaromatic or an optionally substituted monocyclic non-aromatic carbocyclic or heterocyclic group;

$R^2$ is $C_{1-3}$ alkyl;

$R^3$ is an optionally substituted aromatic group having 5-6 ring atoms; and $R^4$ is $C_{1-3}$ alkyl or $C_{1-3}$ hydroxyalkyl.

The sections below defining the terms "aromatic group", "heteroaromatic group", "non-aromatic carbocycle" and "non-aromatic heterocyclic group" provide specific examples of suitable values for M. Suitable substituents for aromatic rings represented by M are as defined for R'l; suitable substituents for carbocyclics and non-aromatics are as described in sections below defining suitable substituents for these two groups.

In certain aspects compounds of the invention are compounds other than one of the following compounds:

When $R^1$ is phenyl para substituted with V-T-$R^Y$, $R^2$ is methyl, $R^3$ is para chlorophenyl, $R^X$ is $C(O)CH_3$, $X_1$ is —C(O) and V is —O—, T-$R^Y$ is —$CH_2$—$CH_2$—$C(CH_3)_2$—$CONH_2$, —$CH_2$—$CH_2$—$C(CH_3)_2$—OH, —$CH_2$—$CH_2$—$CH_2$—$C(CH_3)_2$—OH, —$CH_2$—$CH_2$—$C(CH_3)_2$—COOH, —$CH_2$—C (spiro cyclopropyl)-$CH_2$—COOH, or —$CH_2$—$C(CH_3)_2$—COOH.

When $R^1$ is phenyl para substituted with V-T-$R^Y$, $R^2$ is methyl, $R^3$ is para chlorophenyl, $R^X$ is $C(O)CH_3$, $X_1$ is —C(O) and V is a covalent bond then, T-$R^Y$ is —$CH_2$—$CH_2$—COOH.

When $R^2$ is methyl, $R^3$ is para chlorophenyl, $R^X$ is $C(O)CH_3$, $X_1$ is C(O) and $R^1$ is phenyl para substituted with V-$R^9$ wherein $R^9$ is an optionally substituted non-aromatic heterocyclic group, V is a covalent bond $R^1$ is N-morpholinyl, N-ethoxycarbonyl-4-piperdinyl, N-acetyl-4-piperdinyl, N-ethoxycarbonyl-4-piperid-3-enyl, N-pyrrolidinyl, N-ethyl-N'-piperazinyl, N-acetyl-N'-piperazinyl, N-(2'-hydroxyacetyl)-N'-piperazinyl, N—($CH_2C(O)OH$-N'-piperazinyl, or N—($CH_2C(O)NH_2$)-N'-piperazinyl.

When $R^2$ is methyl, $R^3$ is para chlorophenyl, $R^X$ is $C(O)CH_3$, $X_1$ is C(O) and $R^1$ is phenyl para substituted with V-$R^9$ wherein $R^9$ is an optionally substituted non-aromatic heterocyclic group, V is —O—, $R^1$ is N-ethoxycarbonyl-4-piperdinyl or N-acetyl-4-piperdinyl.

When $R^2$ is methyl, $R^3$ is phenyl, $R^X$ is $C(O)CH_2CH_3$, $X_1$ is C(O) and $R^1$ is phenyl para substituted with a non-aromatic heterocyclic group, $R^1$ is N-acetyl-4-piperdinyl, or N-morpholinyl.

When $R^2$ is methyl, $R^3$ is para chlorophenyl, $R^X$ is $C(O)CH_3$, $X_1$ is C(O) and $R^1$ is phenyl fused to an optionally substituted non-aromatic heterocyclic group, $R^1$ tetrahydrofuranyl, or N'-methyl morpholinyl.

When $R^2$ is methyl, $R^3$ is para chlorophenyl, $R^X$ is $C(O)CH_3$, $X_1$ is C(O) and $R^1$ is pyridinyl para substituted with a non aromatic heterocyclic group, $R^1$ is N-morpholinyl.

When $R^2$ is methyl, $R^3$ is para chlorophenyl, $R^X$ is $C(O)CH_3$, $X_1$ is C(O) and $R^1$ is phenyl fused to an optionally substituted aromatic group, $R^1$ is N-isopropyl triazolyl, N-methyl triazolyl, N-isopropyl imidazolyl, 2, methyl N hydroxyethyl imidazolyl, 2, methyl N carboxymethyl imidazolyl, N carboxyethyl triazolyl N-isopropyl pyrazolyl.

When $R^2$ is methyl, $R^3$ is para chlorophenyl, $R^X$ is $C(O)CH_3$, $X_1$ is C(O) and $R^1$ is imidazolyl fused to an optionally substituted aromatic group, $R^1$ is phenyl.

When $R^2$ is methyl, $R^3$ is para chlorophenyl, $R^X$ is $C(O)CH_3$, $X_1$ is C(O) and $R^1$ is thiazolyl fused to an optionally substituted aromatic group, $R^1$ is phenyl.

In some embodiments compounds of the invention are compounds other than compounds disclosed in our U.S. patent application Ser. No. 10/678,872 filed Oct. 4, 2003 (the entire contents of which are incorporated herein by reference).

In other embodiments, compounds of the invention are compounds other than: (±)-Cis-N-[1-(1H-indole-2-carbonyl)-2-methyl-1,2,3,4-tetrahydro-quinolin-4-yl]-N-phenyl-propionamide; (±)-Cis-N-[1-(benzofuran-2-carbonyl)-2-methyl-1,2,3,4-tetrahydro-quinolin-4-yl]-N-phenyl-propionamide; (±)-Cis-{4-[2-methyl-4-(phenyl-propionyl-amino)-3,4-dihydro-2H-quinoline-1-carbonyl]-phenoxy}-acetic acid ethyl ester; (±)-Cis-{4-[2-Methyl-4-(phenyl-propionyl-amino)-3,4-dihydro-2H-quinoline-1-carbonyl]-phenoxy}-acetic acid; (±)-Cis-N-{2-methyl-1-[4-(2-morpholin-4-yl-ethoxy)-benzoyl]-1,2,3,4-tetrahydro-quinolin-4-yl}-N-phenyl-propionamide; (±)-Cis-N-[1-(4-carbamoylmethoxy-benzoyl)-2-methyl-1,2,3,4-tetrahydro-quinolin-4-yl]-N-phenyl-propionamide; (±)-Cis-N-{1-[4-(2-hydroxy-2-methyl-propoxy)-benzoyl]-2-methyl-1,2,3,4-tetrahydro-quinolin-4-yl}-N-phenyl-propionamide; (±)-Cis-N-[1-(4-dimethylcarbamoylmethoxy-benzoyl)-2-methyl-1,2,3,4-tetrahydro-quinolin-4-yl]-N-phenyl-propionamide; (±)-Cis-N-[1-(benzo[b]thiophene-3-carbonyl)-2-methyl-1,2,3,4-tetrahydro-quinolin-4-yl]-N-phenyl-acetamide; (±)-Cis-N-[1-(benzo[b]thiophene-2-carbonyl)-2-methyl-1,2,3,4-tetrahydro-quinolin-4-yl]-N-phenyl-propionamide; (±)-Cis-{4-[4-(acetyl-phenyl-amino)-2-methyl-3,4-dihydro-2H-quinoline-1-carbonyl]-phenylamino}-acetic acid; (±)-Cis-N-[1-(1-isopropyl-1H-benzotriazole-5-carbonyl)-2-methyl-1,2,3,4-tetrahydro-quinolin-4-yl]-N-phenyl-propionamide; (±)-Cis-4-{4-[2-methyl-4-(phenyl-propionyl-amino)-3,4-dihydro-2H-quinoline-1-carbonyl]-phenyl}-piperidine-1-carboxylic acid ethyl ester; (±)-Cis-N-[2-methyl-1-(4-piperidin-4-yl-benzoyl)-1,2,3,4-tetrahydro-quinolin-4-yl]-N-phenyl-propionamide; (±)-Cis-N-{1-[4-(1-acetyl-piperidin-4-yl)-benzoyl]-2-methyl-1,2,3,4-tetrahydro-quinolin-4-yl}-N-phenyl-propionamide; (±)-Cis-N-{1-[4-(1-ethyl-piperidin-4-yl)-benzoyl]-2-methyl-1,2,3,4-tetrahydro-quinolin-4-yl}-N-phenyl-propionamide; (±)-Cis-N-{2-methyl-1-[4-(4-methyl-piperazin-1-yl)-benzoyl]-1,2,3,4-tetrahydro-quinolin-4-yl}-N-phenyl-propionamide; (±)-Cis-N-[2-methyl-1-(4-methyl-3,4-dihydro-2H-benzo[1,4]oxazine-7-carbonyl)-1,2,3,4-tetrahydro-quinolin-4-yl]-N-phenyl-propionamide; (±)-Cis-N-[2-Methyl-1-(4-morpholin-4-yl-benzoyl)-1,2,3,4-tetrahydro-quinolin-4-yl]-N-phenyl-propionamide; (±)-Cis-N-[2-methyl-1-(4-pyrrolidin-1-yl-benzoyl)-1,2,3,4-tetrahydro-quinolin-4-yl]-N-phenyl-propionamide; (±)-Cis-2-{4-[4-(acetyl-phenyl-amino)-2-methyl-3,4-dihydro-2H-quinoline-1-carbonyl]-phenylamino}-propionic acid methyl ester; (±)-Cis-2-{4-[4-(acetyl-phenyl-amino)-2-methyl-3,4-dihydro-2H-quinoline-1-carbonyl]-phenylamino)-propionamide; (±)-Cis-N-[1-(2,3-dihydro-benzo [1,4]dioxine-6-carbonyl)-2-methyl-1,2,3,4-tetrahydro-quinolin-4-yl]-N-phenyl-propionamide; (±)-Cis-N-[1-(benzo[c]isoxazole-3-carbonyl)-2-methyl-1,2,3,4-tetrahydro-quinolin-4-yl]-N-phenyl-propionamide; (±)-Cis-4-(4-{4-[(4-chloro-phenyl)-propionyl-amino]-2-methyl-3,4-dihydro-2H-quinoline-1-carbonyl}-phenoxy-butyric acid ethyl ester; (±)-Cis-4-(4-{4-[(4-chloro-phenyl)-propionyl-amino]-2-methyl-3,4-dihydro-2H-quinoline-1-carbonyl}-phenoxy)-butyric acid; (±)-Cis-N-(4-chloro-phenyl)-N-{2-methyl-1-[4-(1H-tetrazol-5-ylmethoxy)-benzoyl]-1,2,3,4-tetrahydro-quinolin-4-yl}-propionamide; (±)-Cis-N-(4-chloro-phenyl)-N-{1-[4-(3-hydroxy-2,2-dimethylpropoxy)-benzoyl]-2-methyl-1,2,3,4-tetrahydro-quinolin-4-yl}-acetamide; (±)-Cis-3-(4-{4-[acetyl(4-chloro-phenyl)-amino]-2-methyl-3,4-dihydro-2H-quinoline-1-carbonyl}-phenoxy)-2,2-dimethyl-propionic acid methyl ester; (±)-Cis-N-(4-chloro-phenyl)-N-[1-(4-cyclopentyloxy-benzoyl)-2-methyl-1,2,3,4-tetrahydro-quinolin-4-yl]-acetamide; (±)-Cis-N-{1-[4-(4-Acetyl-piperazin-1-yl)-benzoyl]-2-methyl-1,2,3,4-tetrahydro-quinolin-4-yl}-N-(4-chloro-phenyl)-acetamide; (2S,4R)-N-(4-Chloro-phenyl)-N-[2-methyl-1-(4-morpholin-4-yl-benzoyl)-1,2,3,4-tetrahydro-quinolin-4-yl]-acetamide; (2S,4R)-4-(4-{4-[Acetyl-(4-chloro-phenyl)-amino]-2-methyl-3,4-dihydro-2H-quinoline-1-carbonyl}-phenoxy)-butyric acid; (2S,4R)-N-(4-Chloro-phenyl)-N-[2-methyl-1-(6-morpholin-4-yl-pyridine-3-carbonyl)-1,2,3,4-tetrahydro-quinolin-4-yl]-acetamide; (2S,4R)-4-(4-{4-[Acetyl-(4-chloro-phenyl)-amino]-2-methyl-3,4-dihydro-2H-quinoline-1-carbonyl}-phenoxy)-piperidine-1-carboxylic acid ethyl ester; (2S,4R)-N-(4-Chloro-phenyl)-N-(2-methyl-1-[4-(2-morpholin-4-yl-ethoxy)-benzoyl]-1,2,3,4-tetrahydro-quinolin-4-yl)-acetamide; (2S,4R)-(4-{4-[Acetyl-(4-chloro-phenyl)-amino]-2-methyl-3,4-dihydro-2H-quinoline-1-carbonyl}-phenoxy)-acetic acid; (2S,4R)-N-(4-Chloro-phenyl)-N-{2-methyl-1-[4-(1H-tetrazol-5-ylmethoxy)-benzoyl]-1,2,3,4-tetrahydro-quinolin-4-yl}-acetamide; (2S,4R)-N-{1-[4-(1-Acetyl-piperidin-4-yloxy)-benzoyl]-2-methyl-1,2,3,4-tetrahydro-quinolin-4-yl}-N-(4-chloro-phenyl)-acetamide; (2S,4R)-N-(4-Chloro-phenyl)-N-{2-methyl-1-[4-(pyridin-4-ylmethoxy)-benzoyl]-1,2,3,4-tetrahydro-quinolin-4-yl}-acetamide; (2S,4R)-4-(3-{4-[Acetyl-(4-chloro-phenyl)-amino]-2-methyl-3,4-dihydro-2H-quinoline-1-carbonyl}-phenoxy)-butyric acid; (2S, 4R)-4-(4-{4-[Acetyl-(4-chloro-phenyl)-amino]-2-methyl-3,4-dihydro-2H-quinoline-1-carbonyl}-phenyl)-piperidine-1-carboxylic acid ethyl ester; (2S,4R)-N-(4-Chloro-phenyl)-N-[2-methyl-1-(4-pyrrolidin-1-yl-benzoyl)-1,2,3,4-tetrahydro-quinolin-4-yl]-acetamide; (2S,4R)-N-(4-Chloro-phenyl)-N-[1-(1-isopropyl-1H-benzotriazole-5-carbonyl)-2-methyl-1,2,3,4-tetrahydro-quinolin-4-yl]-acetamide; (2S,4R)-3-(4-{4-[Acetyl-(4-chloro-phenyl)-amino]-2-methyl-3,4-dihydro-2H-quinoline-1-carbonyl}-phenyl)-propionic acid; (2S,4R)-3-(4-{4-[Acetyl-(4-chloro-phenyl)-amino]-2-methyl-3,4-dihydro-2H-quinoline-1-carbonyl}-phenyl)-acrylic acid; N-{(2S,4R)-1-[4-(1-acetylpiperidin-4-yl)benzoyl]-2-methyl-1,2,3,4-tetrahydroquinolin-4-yl}-N-phenylpropanamide; N-{(2R,4S)-1-[4-(1-acetylpiperidin-4-yl)benzoyl]-2-methyl-1,2,3,4-tetrahydroquinolin-4-yl}-N-phenylpropanamide; N-[(2S,4R)-2-methyl-1-(4-morpholin-4-ylbenzoyl)-1,2,3,4-tetrahydroquinolin-4-yl]-N-phenylpropanamide; N-[(2R,4S)-2-methyl-1-(4-morpholin-4-ylbenzoyl)-1,2,3,4-tetrahydroquinolin-4-yl]-N-phenylpropanamide; N-{(2S,4R)-1-[4-(1-acetylpiperidin-4-yl)benzoyl]-2-methyl-1,2,3,4-tetrahydroquinolin-4-yl}-N-phenylpropanamide; N-{(2R,4S)-1-[4-(1-acetylpiperidin-4-yl)benzoyl]-2-methyl-1,2,3,4-tetrahydroquinolin-4-yl}-N-phenylpropanamide; N-{(2S,4R)-1-[4-(1-acetylpiperidin-4-yl)benzoyl]-2-methyl-1,2,3,4-tetrahydroquinolin-4-yl}-N-(4-chlorophenyl)acetamide; (4-{[(2S,4R)-4-[acetyl(4-chlorophenyl)amino]-2-methyl-3,4-dihydroquinolin-1(2H)-yl]carbonyl}phenoxy)butanoic acid; N-{(2S,4R)-1-[4-(2-amino-2-oxoethoxy)benzoyl]-2-methyl-1,2,3,4-tetrahydroquinolin-4-yl}-N-(4-chlorophenyl)acetamide; Ethyl 4-(4-{[(2S,4R)-4-[acetyl(4-chlorophenyl)amino]-2-methyl-3,4-dihydroquinolin-1(2H)-yl]carbonyl}phenyl)-3,6-dihydropyridine-1(2H)-carboxylate; N-[(2S,4R)-1-(1,3-benzodioxol-5-ylcarbonyl)-2-methyl-1,2,3,4-tetrahydroquinolin-4-yl]-N-phenylacetamide; N-{(2S,4R)-2-methyl-1-[(3-methyl-1-benzofuran-2-yl)carbonyl]-1,2,3,4-tetrahydroquinolin-4-yl}-N-phenylacetamide; 4-(4-{[(2S,4R)-4-[acetyl(4-chlorophenyl)amino]-2-methyl-3,4-dihydroquinolin-1(2H)-yl]carbonyl}phenoxy)-N-ethylbutanamide; N-(4-Chlorophenyl)-N-[(2S,4R)-1-(3-ethyl-4-fluorobenzoyl)-2-methyl-1,2,3,4-tetrahydroquinolin-4-yl]acetamide; 4-(4-{[(2S,4R)-4-[Acetyl(4-chlorophenyl)amino]-2-methyl-3,4-dihydroquinolin-1(2H)-yl]carbonyl}phenoxy)-2,2-dimethylbutanamide; N-(4-chlorophenyl)-N-{(2S,4R)-2-methyl-1-[4-(4-oxo-4-pyrrolidin-1-ylbutoxy)benzoyl]-1,2,3,4-tetrahydroquinolin-4-yl}acetamide; 4-(4-{[(2S,4R)-4-[Acetyl-(4-chlorophenyl)amino]-2-methyl-3,4-dihydroquinolin-(2H)-yl]carbonyl}phenoxy)butanamide; 4-(4-{[(2S,4R)-4-[acetyl(4-chlorophenyl)amino]-2-methyl-3,4-dihydroquinolin-1(2H)-yl]carbonyl}phenoxy)-N-(methylsulfonyl)butanamide; Ethyl 4-(4-{[(2S,4R)-4-[acetyl(4-chlorophenyl)amino]-2-methyl-3,4-dihydroquinolin-1(2H)-yl]carbonyl}phenoxy)butanoate; 4-(4-{[(2S,4R)-4-[acetyl(4-chlorophenyl)amino]-2-methyl-3,4-dihydroquinolin-1(2H)-yl]carbonyl}phenoxy)-N-hydroxybutanamide; N-(4-chlorophenyl)-N-{(2S,4R)-1-[4-(3-cyanopropoxy)benzoyl]-2-methyl-1,2,3,4-tetrahydroquinolin-4-yl}acetamide; N-(4-chlorophenyl)-N-((2S,4R)-2-methyl 1-{4-[3-(1,2,4-oxadiazol-5-yl)propoxy]benzoyl}-1,2,3,4-tetrahydroquinolin-4-yl)acetamide; 3-(4-{[(2S,4R)-4-[acetyl(4-chlorophenyl)amino]-2-methyl-3,4-dihydroquinolin-1(2H)-yl]carbonyl}phenoxy)propanamide; N-{(2S,4R)-1-[4-(3-aminopropoxy)benzoyl]-2-methyl-1,2,3,4-tetrahydroquinolin-4-yl}-N-(4-chlorophenyl)acetamide; N-{(2S,4R)-1-[4-(2-amino-2-oxoethoxy)benzoyl]-2-methyl-1,2,3,4-tetrahydroquinolin-4-yl}-N-(4-chlorophenyl)acetamide; N-(4-chlorophenyl)-N-((2S,4R)-2-methyl-1-{4-[2-(methylamino)-2-oxoethoxy]benzoyl}-1,2,3,4-tetrahydroquinolin-4-yl)acetamide; 2-(4-{[(2S,4R)-4-[acetyl(4-chlorophenyl)amino]-2-methyl-3,4-dihydroquinolin-1(2H)-yl]carbonyl}phenoxy)-N,N-dimethylacetamide; N-(4-chlorophenyl)-N-{(2S,4R)-2-methyl-1-[4-(2-morpholin-4-yl-2-oxoethoxy)benzoyl]-1,2,3,4-tetrahydroquinolin-4-yl}acetamide; N-(4-chlorophenyl)-N-((2S,4R)-2-methyl-1-{4-[2-(2-oxopyrrolidin-1-yl)ethoxy]benzoyl}-1,2,3,4-tetrahydroquinolin-4-yl)acetamide; N-(4-chlorophenyl)-N-((2S,4R)-1-{4-[2-(1H-imidazol-1-yl)ethoxy]benzoyl}-2-methyl-1,2,3,4-tetrahydroquinolin-4-yl)acetamide; N-(4-chlorophenyl)-N-{(2S,4R)-2-methyl-1-[4-(2-pyrrolidin-1-ylethoxy)benzoyl]-1,2,3,4-tetrahydroquinolin-4-yl}acetamide; N-(4-chlorophenyl)-N-[(2S,4R)-1-(2,3-dihydro-1-benzofuran-5-ylcarbonyl)-2-methyl-1,2,3,4-tetrahydroquinolin-4-yl]acetamide; N-(4-Chlorophenyl)-N-{(2S,4R)-2-methyl-1-[4-(3-pyrrolidin-1-ylpropoxy)benzoyl]-1,2,3,4-tetrahydroquinolin-4-yl}acetamide; N-(4-chlorophenyl)-N-{(2S,4R)-2-methyl-1-[4-(3-morpholin-4-ylpropoxy)benzoyl]-1,2,3,4-tetrahydroquinolin-4-yl}acetamide; N-(4-chlorophenyl)-N-((2S,4R)-2-methyl-1-{4-[(4-oxopentyl)oxy]benzoyl}-1,2,3,4-tetrahydroquinolin-4-yl)acetamide; N-(4-Chlorophenyl)-N-{(2S,4R)-1-[4-(3-hydroxy-3-methylbutoxy)benzoyl]-2-methyl-1,2,3,4-tetrahydroquinolin-4-yl}acetamide; N-(4-Chlorophenyl)-N-((2S,4R)-1-{4-[(4-hydroxy-4-methylpentyl)oxy]benzoyl}-

2-methyl-1,2,3,4-tetrahydroquinolin-4-yl)acetamide; N-(4-chlorophenyl)-N-((2S,4R)-1-{4-[(1-ethylpiperidin-4-yl)methoxy]benzoyl}-2-methyl-1,2,3,4-tetrahydroquinolin-4-yl)acetamide; N-(4-chlorophenyl)-N-((2S,4R) 1-{4-[3-(1H-imidazol-1-yl)propoxy]benzoyl}-2-methyl-1,2,3,4-tetrahydroquinolin-4-yl)acetamide; (2S,4R)-N-(4-Chlorophenyl)-N-[2-methyl-1-(4-methyl-3,4-dihydro-2H-benzo[1,4]oxazine-7-carbonyl)-1,2,3,4-tetrahydroquinolin-4-yl]-acetamide; N-(4-chlorophenyl)-N-{(2S,4R)-2-methyl-1-[(4-methyl-3,4-dihydro-2H-1,4-benzoxazin-6-yl)carbonyl]-1,2,3,4-tetrahydroquinolin-4-yl}acetamide; N-(4-chlorophenyl)-N-{(2S,4R)-1-[4-(4-ethylpiperazin-1-yl)benzoyl]-2-methyl-1,2,3,4-tetrahydroquinolin-4-yl}acetamide; N-{(2S,4R)-1-[4-(4-acetylpiperazin-1-yl)benzoyl]-2-methyl-1,2,3,4-tetrahydroquinolin-4-yl}-N-(4-chlorophenyl)acetamide; N-(4-chlorophenyl)-N-{(2S,4R)-1-[4-(4-glycoloylpiperazin-1-yl)benzoyl]-2-methyl-1,2,3,4-tetrahydroquinolin-4-yl}acetamide; N-(4-chlorophenyl)-N-{(2S,4R)-2-methyl-1-[4-(3-morpholin-4-ylprop-1-yn-1-yl)benzoyl]-1,2,3,4-tetrahydroquinolin-4-yl}acetamide; 4-(4-{[(2S,4R)-4-[acetyl(4-chlorophenyl)amino]-2-methyl-3,4-dihydroquinolin-1(2H)-yl]carbonyl}phenyl)but-3-ynoic acid; N-[(2S,4R)-1-(1H-benzimidazol-2-ylcarbonyl)-2-methyl-1,2,3,4-tetrahydroquinolin-4-yl]-N-(4-chlorophenyl)acetamide; N-[(2S,4R)-1-(1,3-benzothiazol-2-ylcarbonyl)-2-methyl-1,2,3,4-tetrahydroquinolin-4-yl]-N-(4-chlorophenyl)acetamide; N-(4-chlorophenyl)-N-{(2S,4R)-2-methyl-1-[(1-methyl-1H-1,2,3-benzotriazol-5-yl)carbonyl]-1,2,3,4-tetrahydroquinolin-4-yl}acetamide; N-(4-chlorophenyl)-N-{(2S,4R)-1-[(1-isopropyl-1H-benzimidazol-5-yl)carbonyl]-2-methyl-1,2,3,4-tetrahydroquinolin-4-yl}acetamide; [4-(4-{[(2S,4R)-4-[acetyl(4-chlorophenyl)amino]-2-methyl-3,4-dihydroquinolin-1(2H)-yl]carbonyl}phenyl)piperazin-1-yl]acetic acid; N-((2S,4R)-1-{4-[4-(2-amino-2-oxoethyl)piperazin-1-yl]benzoyl}-2-methyl-1,2,3,4-tetrahydroquinolin-4-yl)-N-(4-chlorophenyl)acetamide; 3-(4-{[(2S,4R)-4-[acetyl(4-chlorophenyl)amino]-2-methyl-3,4-dihydroquinolin-1(2H)-yl]carbonyl}phenoxy)propanoic acid; 4-(4-{[(2S,4R)-4-[acetyl(4-chlorophenyl)amino]-2-methyl-3,4-dihydroquinolin-1(2H)-yl]carbonyl}phenoxy)-2,2-dimethylbutanoic acid; {1-[(4-{[(2S,4R)-4-[acetyl(4-chlorophenyl)amino]-2-methyl-3,4-dihydroquinolin-1(2H)-yl]carbonyl}phenoxy)methyl]cyclopropyl}acetic acid; (2E)-4-(4-{[(2S,4R)-4-[acetyl(4-chlorophenyl)amino]-2-methyl-3,4-dihydroquinolin-1(2H)-yl]carbonyl}phenoxy)but-2-enoic acid; 3-(4-{[(2S,4R)-4-[Acetyl-(4-chlorophenyl)amino]-2-methyl-3,4-dihydroquinolin-1(2H)-yl]carbonyl}phenoxy)-2,2-dimethylpropanoic acid; (2E)-4-(4-{[(2S,4R)-4-[acetyl(4-chlorophenyl)amino]-2-methyl-3,4-dihydroquinolin-1(2H)-yl]carbonyl}phenoxy)-2-methylbut-2-enoic acid; N-(4-chlorophenyl)-N-{(2S,4R)-2-methyl-1-[4-(3-{[(trifluoromethyl)sulfonyl]amino}propoxy)benzoyl]-1,2,3,4-tetrahydroquinolin-4-yl}acetamide; N-(4-chlorophenyl)-N-((2S,4R)-1-{[1-(2-hydroxyethyl)-2-methyl-1H-benzimidazol-5-yl]carbonyl}-2-methyl-1,2,3,4-tetrahydroquinolin-4-yl)acetamide; 5-{[(2S,4R)-4-[acetyl(4-chlorophenyl)amino]-2-methyl-3,4-dihydroquinolin-1(2H)-yl]carbonyl}-2-methyl-1H-benzimidazol-1-yl)acetic acid; 3-(5-{[(2S,4R)-4-[acetyl(4-chlorophenyl)amino]-2-methyl-3,4-dihydroquinolin-1(2H)-yl]carbonyl}-1H-1,2,3-benzotriazol-1-yl)propanoic acid; (2S,4R)-N-(4-Chlorophenyl)-N-[1-(1-isopropyl-1H-indazole-5-carbonyl)-2-methyl-1,2,3,4-tetrahydro-quinolin-4-yl]-acetamide; and (2S,4R)-N-(4-Chloro-phenyl)-N-(2-methyl-1-{4-[3-(1H-tetrazol-5-yl)-propoxy]-benzoyl}-1,2,3,4-tetrahydro-quinolin-4-yl)-acetamide.

The classes and subclasses described in more detail below and in the specification herein apply to each of the embodiments for compound I-A as described above.

In one embodiment, the present invention is a compound represented by Structural Formulas (II-A), (III-A) or (IV-A).

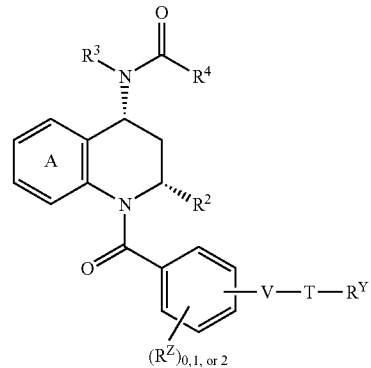

(II-A)

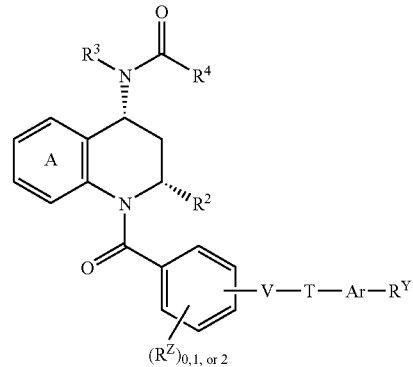

(III-A)

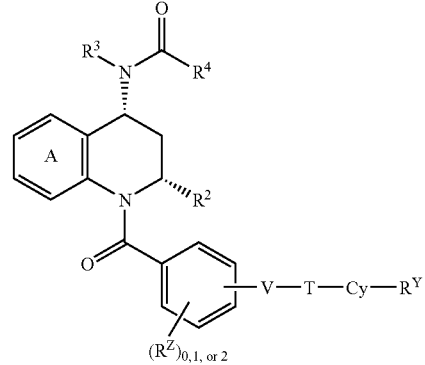

(IV-A)

Ar in Structural Formula (III-A) is a monocyclic aromatic ring. Cy in Structural Formula (IV) is a monocyclic non-aromatic carbocyclic or heterocyclic group. All other variables in Structural Formulas (II-A)-(IV-A) are as described for Structural Formula (I-A). Preferably, V in Structural Formulas (II-A)-(IV-A) is a covalent bond, —O—, or —N(R')—, and T in Structural Formulas (II-A)-(IV-A) is a $C_{1-6}$ straight chain alkylene optionally substituted at any one or more substitutable carbon atoms with halide, alkyl, gem dialkyl, gem dihalo, haloalkyl, spiro cycloalkyl, optionally N-substituted nitrogen containing spiro non-aromatic heterocyclic group, amine, alkylamine, dialkylamine, or hydroxyl.

Alternatively, in Structural Formula (I-A)-(IV-A) V is a covalent bond, —NR'- or —O—; and T is a $C_{1-10}$ straight chain alkylene (preferably $C_{1-5}$, more preferably $C_{1-3}$) optionally mono-substituted at any substitutable carbon atom with halide, alkyl, haloalkyl, amine, dialkylamine, or hydroxyl.

Preferably, $R^Y$ in Structural Formula (I-A) and (II-A) is —C(O)OR$^5$, —C(O)N(R$^5$)$_2$, —NR$^5$C(O)R$^5$, —NR$^5$C(O)OR$^5$, —S(O)$_2$N(R$^5$)$_2$, —NR$^5$S(O)$_2$R$^5$, —OR$^5$, —CN, —NR$^5$C(O)N(R$^5$)$_2$, —N(R$^5$)$_2$, an optionally substituted non-aromatic heterocyclic group represented by $R^7$, or an optionally substituted heteroaryl group represented by $R^8$. $R^7$ is an optionally substituted piperidinonyl, oxazolidinyl, oxazolidinonyl, thiazolidinyl, tetrahydrofuranyl, tetrahydropyranyl, thiazolidinyl, tetrahyrothiophene, morpholinyl, thiomorpholinyl, imidazolidinyl, imidazolidinonyl, dioxanyl, dioxolanyl, dithiolanyl, pyrrolidinyl, pyrrolidinonyl, piperazinyl, or piperidinyl. $R^8$ is an optionally substituted furanyl, tetrazolyl, oxazolyl, isoxazolyl, oxadiazolyl, pyrrolyl, pyrazolyl, pyridinyl, pyrimidyl, thiazolyl, thienyl, or imidazolyl, and all the remainder of the variables are as described in the previous paragraph.

More preferably, $R^Y$ in Structural Formula (I-A) and (II-A) is —C(O)OR$^5$, —C(O)N(R$^5$)$_2$, —NR$^5$C(O)R$^5$, —NR$^5$C(O)OR$^5$, —S(O)$_2$N(R$^5$)$_2$, —NR$^5$S(O)$_2$R$^5$, —NR$^5$C(O)N(R$^5$)$_2$, —OH, an optionally substituted non-aromatic heterocyclic group represented by $R^7$ or an optionally substituted heteroaryl group represented by $R^8$. $R^7$ is piperidinonyl, morpholinyl, imidazolidinonyl, pyrrolidinyl, pyrrolidinonyl, piperazinyl, or piperidinyl. $R^8$ is tetrazolyl, oxazolyl, oxadiazolyl, pyrrolyl, pyrazolyl, pyridinyl, or imidazolyl. $R^5$ is independently H or alkyl, or N(R$^5$)$_2$ is a nitrogen-containing non-aromatic heterocyclic group. V is a covalent bond, or —O—; and T is a $C_{1-5}$ straight chain alkylene optionally substituted at the carbon atom adjacent to $R^Y$ with halide, alkyl, gem dialkyl, gem dihalo, haloalkyl, spiro cycloalkyl, optionally N-substituted nitrogen containing spiro non-aromatic heterocyclic group, amine, dialkylamine, or hydroxyl.

More preferably, $R^1$ in Structural Formula (I-A)-(III-A) is a phenyl ring optionally substituted by at the meta and para positions (more preferably para) by V-T-R$^Y$ or V-T-M-R$^Y$. Even more preferably $R^Y$ is —C(O)OR$^5$, —C(O)N(R$^5$)$_2$, —OH, N-morpholinyl, 2-morpholinyl, 3-morpholinyl, N-substituted 2-morpholinyl, N-substituted 3-morpholinyl, N-imidazolidinyl, 2-imidazolidinyl, 4-imidazolidinyl, 5-imidazolidinyl, N-substituted 2-imidazolidinyl, N'-substituted N-imidazolidinyl, N-substituted 4-imidazolidinyl, N-substituted 5-imidazolidinyl, N-imidazolidinonyl, 4-imidazolidinonyl, 5-imidazolidinonyl, N-substituted 4-imidazolidinonyl, N-substituted 5-imidazolidinonyl, N-pyrrolidinyl, 2-pyrrolidinyl, 3-pyrrolidinyl, N-substituted 2-pyrrolidinyl, N-substituted 3-pyrrolidinyl, N-pyrrolidin-2-onyl, 3-pyrrolidin-2-onyl, 4-pyrrolidin-2-onyl, 5-pyrrolidin-2-onyl, N-substituted 3-pyrrolidin-2-only, N-substituted 4-pyrrolidin-2-only, N-substituted 5-pyrrolidin-2-onyl, N-pyrrolidin-3-onyl, 2-pyrrolidin-3-onyl, 4-pyrrolidin-3-onyl, 5-pyrrolidin-3-onyl, N-substituted 2-pyrrolidin-3-onyl N-substituted 4-pyrrolidin-3-onyl, N-substituted 5-pyrrolidin-3-onyl, N-piperidinyl, 2-piperidinyl, 3-piperidinyl, 4-piperidinyl, N-substituted 2-piperidinyl, N-substituted 3-piperidinyl, N-substituted 4-piperidinyl, N-piperidin-2-onyl, 3-piperidin-2-onyl, 4-piperidin-2-onyl, 5-piperidin-2-onyl, 6-piperidin-2-onyl, N-substituted 3-piperidin-2-onyl, N-substituted 4-piperidin-2-onyl, N-substituted 5-piperidin-2-onyl, N-substituted 6-piperidin-2-onyl, N-piperidin-3-onyl, 2-piperidin-3-onyl, 4-piperidin-3-onyl, 5-piperidin-3-onyl, 6-piperidin-3-onyl, N-substituted 2-piperidin-3-onyl, N-substituted 4-piperidin-3-onyl, N-substituted 5-piperidin-3-onyl, N-substituted 6-piperidin-3-onyl, N-piperidin-4-onyl, 2-piperidin-4-onyl, 3-piperidin-4-onyl, 5-piperidin-4-onyl, 6-piperidin-4-onyl, N-substituted 2-piperidin-4-onyl, N-substituted 3-piperidin-4-onyl, N-substituted 5-piperidin-4-onyl, N-substituted 6-piperidin-4-onyl, N-piperazinyl, 2-piperazinyl, N'-substituted N-piperazinyl, N-substituted 2-piperazinyl, furanyl, N-tetrazolyl, 5-tetrazolyl, N-substituted 5-tetrazolyl, 4-(1,2,3)oxadiazolyl, 5-(1,2,3)oxadiazolyl, 3-(1,2,4)oxadiazolyl, 5-(1,2,4)oxadiazolyl, 3-(1,2,5)oxadiazolyl, 4-(1,2,5)oxadiazolyl, 2-(1,3,4)oxadiazolyl, 5-(1,3,4)oxadiazolyl, N-pyrrolyl, 2-pyrrolyl, 3-pyrrolyl, N-substituted 2-pyrrolyl, N-substituted 3-pyrrolyl, N-pyrazolyl, 3-pyrazolyl, 4-pyrazolyl, 5-pyrazolyl, N-substituted 3-pyrazolyl, N-substituted 4-pyrazolyl, N-substituted 5-pyrazolyl, 2-pyridinyl, 3-pyridinyl, 4-pyridinyl, N-imidazolyl, 2-imidazolyl, 4-imidazolyl, 5-imidazolyl; N-substituted 2-imidazolyl, N-substituted 4-imidazolyl, or N-substituted 5-imidazolyl. V is —O—, and T is a $C_{1-3}$ straight chain alkylene substituted at the carbon adjacent to $R^Y$ with fluoro, methyl, gem dimethyl, gem difluoro fluoromethyl, spiro cyclopropyl, spiro cyclobutyl, optionally N-substituted spiro azetidinyl, optionally N-substituted spiro aziridinyl, optionally N-substituted sprio pyrrolidinyl, optionally N-substituted spiro piperidinyl, amine, methylamine, dimethylamine, or hydroxyl.

Still more preferably $R^Y$ is —C(O)OR$^5$, —C(O)N(R$^5$)$_2$, —OH, N-tetrazolyl, 5-tetrazolyl, N-substituted 5-tetrazolyl, N-imidazolyl, 2-imidazolyl, 4-imidazolyl, 5-imidazolyl; N-substituted 2-imidazolyl, N-substituted 4-imidazolyl, or N-substituted 5-imidazolyl. $R^5$ is —H, methyl, or ethyl. $R^1$ in Structural Formula (I-A)-(III-A) is a phenyl ring optionally substituted by at the para position by V-T-R$^Y$ or V-T-M-R$^Y$.

In another preferred embodiment, the present invention is a compound represented by Structural Formula (V-A):

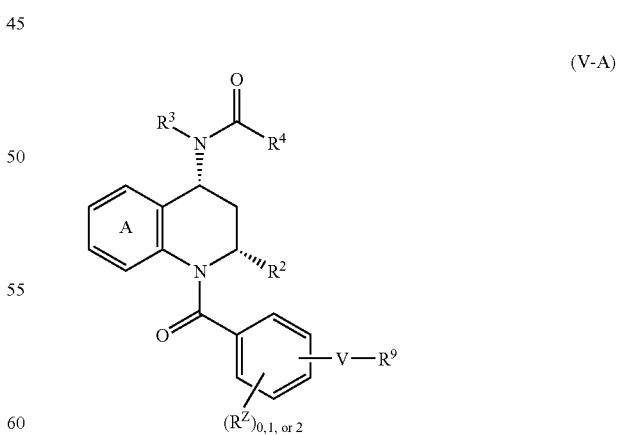

(V-A)

All variables in Structural Formula (V-A) are as described for Structural Formula (I-A). Preferably $R^9$ in Structural Formula (V-A) is an optionally substituted cyclohexanyl, oxazolidinyl, oxazolidinonyl, thiazolidinyl, tetrahydrofuranyl, tetrahydropyranyl, thiazolidinyl, tetrahydrothienyl, morpholinyl, thiomorpholinyl, imidazolidinyl, imidazolidinonyl, dioxanyl, dioxolanyl, dithiolanyl, pyrrolidinyl, pyrrolidinonyl, piperazinyl, isothiazolidinyl S,S, dioxide, piperidinyl, or 1,2,5-thiadiazolidine S,S-dioxide. In other embodiments, $R^9$ in Structural Formula (V-A) is an optionally substituted cyclohexanyl, oxazolidinyl, oxazolidinonyl, thiazolidinyl, tetrahydrofuranyl, tetrahydropyranyl, thiazolidinyl, tetrahydrothienyl, morpholinyl, thiomorpholinyl, imidazolidinyl, imidazolidinonyl, dioxanyl, dioxolanyl, dithiolanyl, pyrrolidinyl, pyrrolidinonyl, piperazinyl, isothiazolidinyl S,S, dioxide, or piperidinyl. $R^9$ is preferably meta or para to the carbon atom bonded to the carbonyl, more preferably para. V is preferably a covalent bond or —O—, more preferably a covalent bond.

More preferably, $R^9$ in Structural Formula (V-A) is oxazolidinyl, thiazolidinyl, tetrahydrofuranyl, morpholinyl, imidazolidinyl, imidazolidinonyl, pyrrolidinyl, pyrrolidinonyl, piperazinyl, or piperidinyl, each optionally substituted by alkyl, halide, haloalkyl, hydroxyalkyl, —C(O)O$R^{12}$, —C(O)$R^{12}$, —OC(O)$R^{12}$, —$R^{12}$C(O)O$R^{12}$, —C(O)N($R^{12}$)$_2$, —N$R^{12}$C(O)$R^{12}$, —N$R^{12}$C(O)O$R^{12}$, —S(O)$_2R^{12}$, —S(O)$_2$CO$R^{12}$, —S(O)$_2$N($R^{12}$)$_2$, —S(O)$_2$O$R^{12}$, —S(O)O$R^{12}$, —O$R^{12}$, —S$R^{12}$, —CN, —N$R^{12}$C(O)N($R^{12}$)$_2$, —OC(O)N($R^{12}$)$_2$, —(CH$_2$)$_n$CO$_2$H, —(CH$_2$)$_n$C(O)N$R^\circ$, —(CH$_2$)$_n$C(CH$_3$)$_2$CO$_2$H, —(CH$_2$)$_n$C(CH$_3$)$_2$C(O)N$R^\circ$ or —N($R^{12}$)$_2$, n is an integer from 1 to 4, and each $R^{12}$ is independently —H, alkyl, haloalkyl, or hydroxyalkyl; and all of the other variables are as described in the previous paragraph. Alternatively, for those groups represented by $R^9$ which have a substitutable ring nitrogen, the group is N-substituted with $T^2$-$R^{\gamma 1}$, which is defined below, and optionally substituted at one or more substitutable ring carbon atoms with one or more groups listed above in this paragraph.

More preferably, $R^9$ in Structural Formula (V-A) is N-morpholinyl, 2-morpholinyl, 3-morpholinyl, N-substituted 2-morpholinyl, N-substituted 3-morpholinyl, N-pyrrolidinyl, 2-pyrrolidinyl, 3-pyrrolidinyl, N-substituted 2-pyrrolidinyl, N-substituted 3-pyrrolidinyl, N-piperazinyl, 2-piperazinyl, N'-substituted N-piperazinyl, N-substituted 2-piperazinyl, N-piperidinyl, 2-piperidinyl, 3-piperidinyl, 4-piperidinyl, N-substituted 2-piperidinyl, N-substituted 3-piperidinyl, N-substituted 4-piperidinyl, each optionally substituted at any substitutable carbon atom by alkyl, halide, haloalkyl, hydroxyalkyl, —C(O)O$R^{12}$, —C(O)$R^{12}$, —OC(O)$R^{12}$, or —C(O)N($R^{12}$)$_2$, and wherein the N-substituents are alkyl, haloalkyl, hydroxyalkyl, —C(O)O$R^{12}$, —C(O)$R^{12}$, (CH$_2$)$_n$CO$_2$H, (CH$_2$)$_n$C(O)N$R^\circ$, (CH$_2$)$_n$C(CH$_3$)$_2$CO$_2$H, —(CH$_2$)$_n$C(CH$_3$)$_2$C(O)N$R^\circ$ or —C(O)N($R^{12}$)$_2$. For these groups represented by $R^9$ which have a substitutable ring N, one preferred N-substituent is $T^2$-$R^{\gamma 1}$, which is defined below.

Even more preferably, $R^9$ in Structural Formula (V-A) is N-piperidinyl, 2-piperidinyl, 3-piperidinyl, 4-piperidinyl, N-substituted 2-piperidinyl, N-substituted 3-piperidinyl, N-substituted 4-piperidinyl, N-piperazinyl, 2-piperazinyl, N'-substituted N-piperazinyl, or N-substituted 2-piperazinyl, and is optionally substituted by at any substitutable carbon atom by chloride, fluoride, bromide, methyl, ethyl, —C(O)O$R^{12}$, —OC(O)$R^{12}$, —C(O)$R^{12}$ or C(O)NH$_2$, and wherein the N-substituents are methyl, ethyl, —C(O)O$R^{12}$, —C(O)$R^{12}$, —(CH$_2$)$_n$CO$_2$H, —(CH$_2$)$_n$C(O)N$R^\circ$, —(CH$_2$)$_n$C(CH$_3$)$_2$CO$_2$H, —(CH$_2$)$_n$C(CH$_3$)$_2$C(O)N$R^\circ$, or —C(O)NH$_2$, and each $R^{12}$ is independently —H, methyl, or ethyl. For these groups represented by $R^9$ which have a substitutable ring N, one preferred N-substituent is $T^2$-$R^{\gamma 1}$, which is defined below.

In another preferred embodiment, the present invention is a compound represented by Structural Formula (VI-A):

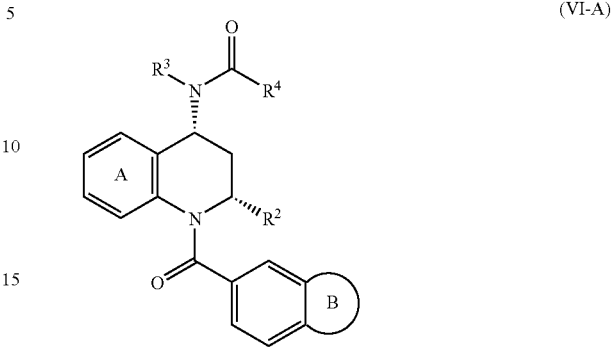

(VI-A)

B is an optionally substituted monocyclic non-aromatic heterocyclic ring represented by $R^{10}$, or a monocyclic aromatic ring (preferably heteroaromatic) represented by $R^{13}$; all other variables in Structural Formula (VI-A) are as described for Structural Formula (I-A).

Preferably, $R^{10}$ in Structural Formula (VI-A) is oxazolidinyl, oxazolidinonyl, dioxolanyl, thiazolidinyl, tetrahydrofuranyl, tetrahydropyranyl, tetrahydrothiopyranyl, tetrahydrothienyl, morpholinyl, thiomorpholinyl, imidazolidinyl, imidazolidinonyl, dioxanyl, dithiolanyl, pyrrolidinyl, piperazinyl, piperidinyl, piperidinyl, tetrahydrothienyl S,S dioxide, thiomorpholinyl S,S dioxide, tetrahydrothiopyranyl S,S dioxide, each of which are optionally substituted. $R^{13}$ is pyrazolyl, triazolyl, imidazolyl, furanyl, pyrrolyl, thienyl, cyclopentadienyl, and thienyl S,S dioxide, each of which are optionally substituted. All other variables in Structural Formula (VI-A) are as described in the previous paragraph.

Other examples of suitable values for $R^{10}$ include tetrahydrofuranyl, tetrahydropyranyl, morpholinyl, imidazolidinyl, imidazolidinonyl, pyrrolidinyl, piperazinyl, or piperidinyl each of which is optionally substituted at any substitutable carbon ring atom with alkyl, halide, haloalkyl, hydroxyalkyl, —C(O)O$R^{12}$, —C(O)$R^{12}$, —OC(O)$R^{12}$, —$R^{12}$C(O)O$R^{12}$—, —C(O)N($R^{12}$)$_2$, —N$R^{12}$C(O)$R^{12}$, —N$R^{12}$C(O)O$R^{12}$, —S(O)$_2R^{12}$, —S(O)$_2$CO$R^{12}$, —S(O)$_2$N($R^{12}$)$_2$, —S(O)$_2$O$R^{12}$, —S(O)O$R^{12}$, —O$R^{12}$, —S$R^{12}$, —CN, —N$R^{12}$C(O)N($R^{12}$)$_2$, —OC(O)N($R^{12}$)$_2$, —N($R^{12}$)$_2$, —(CH$_2$)$_{1-4}$CO$_2R^{12}$, —O(CH$_2$)$_{1-4}$CO$_2R^{12}$, —(CH$_2$)$_{1-4}$CON($R^{12}$)$_2$, —O(CH$_2$)$_{1-4}$CON($R^{12}$)$_2$, —(CH$_2$)$_{0-3}$(C(CH$_3$)$_2$)CO$_2R^{12}$, —O(CH$_2$)$_{0-3}$(C(CH$_3$)$_2$)CO$_2R^{12}$, —(CH$_2$)$_{0-3}$(C(CH$_3$)$_2$)CON($R^{12}$)$_2$, or —O(CH$_2$)$_{0-3}$(C(CH$_3$)$_2$)CON($R^{12}$)$_2$, and each of which is optionally substituted at any substitutable ring nitrogen: atom with alkyl, haloalkyl, hydroxyalkyl, —C(O)O$R^{12}$, —C(O)$R^{12}$, —$R^{12}$C(O)O$R^{12}$—, —C(O)N($R^{12}$)$_2$; and other examples of suitable values for $R^{13}$ include triazolyl, imidazolyl, furanyl, pyrrolyl, thienyl, each of which is optionally substituted at any substitutable ring carbon atom with alkyl, halide, haloalkyl, hydroxyalkyl, —C(O)O$R^{12}$, —C(O)$R^{12}$, —OC(O)$R^{12}$, —C(O)O$R^{12}$—, —C(O)N($R^{12}$)$_2$, —N$R^{12}$C(O)$R^{12}$, —N$R^{12}$C(O)O$R^{12}$, —S(O)$_2R^{12}$, —S(O)$_2$CO$R^{12}$, —S(O)$_2$N($R^{12}$)$_2$, —S(O)$_2$O$R^{12}$, —S(O)O$R^{12}$, —O$R^{12}$, —S$R^{12}$, —CN, —N$R^{12}$C(O)N($R^{12}$)$_2$, —OC(O)N($R^{12}$)$_2$, —N($R^{12}$)$_2$, —(CH$_2$)$_{1-4}$CO$_2R^{12}$, —O(CH$_2$)$_{1-4}$CO$_2R^{12}$, —(CH$_2$)$_{1-4}$CON($R^{12}$)$_2$, —O(CH$_2$)$_{1-4}$CON($R^{12}$)$_2$, —(CH$_2$)$_{0-3}$(C(CH$_3$)$_2$)CO$_2R^{12}$, —O(CH$_2$)$_{0-3}$(C(CH$_3$)$_2$)CO$_2R^{12}$, —(CH$_2$)$_{0-3}$(C(CH$_3$)$_2$)CON($R^{12}$)$_2$, or —O(CH$_2$)$_{0-3}$(C(CH$_3$)$_2$)CON($R^{12}$)$_2$, and each of which is optionally substituted at any substitutable ring nitrogen atom with alkyl haloalkyl, hydroxyalkyl, —C(O)OR$^{12}$, —C(O)R$^{12}$, —R$^{12}$C(O)OR$^{12}$, —S(O)$_2$R$^{12}$, S(O)$_2$N(R$^{12}$)$_2$, —C(O)N(R$^{12}$)$_2$. Each R$^{12}$ is independently H, alkyl, haloalkyl, or hydroxyalkyl.

Still other examples of suitable values for R$^{10}$ include tetrahydrofuranyl, tetrahydropyranyl, morpholinyl, imidazolidinyl, imidazolidinonyl, pyrrolidinyl, piperazinyl, or piperidinyl each of which is optionally substituted at any substitutable carbon ring atom with alkyl, halide, haloalkyl, hydroxyalkyl, —C(O)OR$^{12}$, —C(O)R$^{12}$, —OC(O)R$^{12}$, —R$^{12}$C(O)OR$^{12}$—, —C(O)N(R$^{12}$)$_2$, —NR$^{12}$C(O)R$^{12}$, —NR$^{12}$C(O)OR$^{12}$, —S(O)$_2$R$^{12}$, —S(O)$_2$COR$^{12}$, —S(O)$_2$N(R$^{12}$)$_2$, —S(O)$_2$OR$^{12}$, —S(O)OR$^{12}$, —OR$^{12}$, —SR$^{12}$, —CN, —NR$^{12}$C(O)N(R$^{12}$)$_2$, —OC(O)N(R$^{12}$)$_2$, or —N(R$^{12}$)$_2$, and each of which is optionally substituted at any substitutable ring nitrogen atom with alkyl haloalkyl, hydroxyalkyl, —C(O)OR$^{12}$, —C(O)R$^{12}$, —R$^{12}$C(O)OR$^{12}$—, —C(O)N(R$^{12}$)$_2$; and other examples of suitable values for R$^{13}$ include triazolyl, imidazolyl, furanyl, pyrrolyl, thienyl, each of which is optionally substituted at any substitutable ring carbon atom with alkyl, halide, haloalkyl, hydroxyalkyl, —C(O)OR$^{12}$, —C(O)R$^{12}$, —OC(O)R$^{12}$, —C(O)OR$^{12}$—, —C(O)N(R$^{12}$)$_2$, —NR$^{12}$C(O)R$^{12}$, —NR$^{12}$C(O)OR$^{12}$, —S(O)$_2$R$^{12}$, —S(O)$_2$COR$^{12}$, —S(O)$_2$N(R$^{12}$)$_2$, —S(O)$_2$OR$^{12}$, —S(O)OR$^{12}$, —OR$^{12}$, —SR$^{12}$, —CN, —NR$^{12}$C(O)N(R$^{12}$)$_2$, —OC(O)N(R$^{12}$)$_2$, or —N(R$^{12}$)$_2$, and each of which is optionally substituted at any substitutable ring nitrogen atom with alkyl haloalkyl, hydroxyalkyl, —C(O)OR$^{12}$, —C(O)R$^{12}$, —R$^{12}$C(O)OR$^{12}$, —S(O)$_2$R$^{12}$, S(O)$_2$N(R$^{12}$)$_2$, —C(O)N(R$^{12}$)$_2$. Each R$^{12}$ is independently H, alkyl, haloalkyl, or hydroxyalkyl.

Even more preferably, in Structural Formula (VI-A) R$^{10}$ is dioxolanyl, tetrahydrofuranyl, morpholinyl, each optionally substituted at any substitutable carbon atom by alkyl, halide, haloalkyl, hydroxyalkyl, —C(O)OR$^{12}$, —C(O)R$^{12}$, —OC(O)R$^{12}$, or —C(O)N(R$^{12}$)$_2$, or each optionally substituted at any substitutable nitrogen atom by alkyl, haloalkyl, hydroxyalkyl, —C(O)OR$^{12}$, —C(O)R$^{12}$, or —C(O)N(R$^{12}$)$_2$. R$^{13}$ is triazolyl, imidazolyl, or pyrrolyl each optionally substituted at any substitutable carbon atom by alkyl, halide, haloalkyl, hydroxyalkyl, —C(O)OR$^{12}$, —C(O)R$^{12}$, —OC(O)R$^{12}$, or —C(O)N(R$^{12}$)$_2$, and each optionally substituted at any substitutable nitrogen atom by alkyl, haloalkyl, hydroxyalkyl, C(O)OR$^{12}$, —C(O)R$^{12}$, —R$^{12}$C(O)OR$^{12}$, —S(O)$_2$R$^{12}$, S(O)$_2$N(R$^{12}$)$_2$, —C(O)N(R$^{12}$)$_2$.

Still more preferably, in Structural Formula (VI-A) R$^{10}$ is morpholinyl and is optionally N-substituted by methyl, ethyl, —C(O)OR$^{12}$, C(O)NH$_2$ or —C(O)R$^{12}$, R$^{13}$ is triazolyl and is optionally N-substituted by methyl, ethyl, —C(O)OR$^{12}$, C(O)NH$_2$ or —C(O)R$^{12}$, and each R$^{12}$ is independently —H, methyl, or ethyl.

In another preferred embodiment, in Structural Formula (VI-A) Ring B a monocyclic non-aromatic heterocycle or a monocyclic heteroaryl group comprising a ring nitrogen atom that is substituted with T$^2$-R$^{Y1}$. These monocyclic non-aromatic and heteroaryl groups are optionally further substituted. Preferably, the monocyclic non-aromatic heterocyclic ring is represented by R$^{10}$, Preferably, the monocyclic heteroaromatic ring is represented by R$^{13}$. Examples of suitable values for R$^{10}$ include oxazolidinyl, oxazolidinonyl, thiazolidinyl, morpholinyl, thiomorpholinyl, imidazolidinyl, imidazolidinonyl, pyrrolidinyl, piperazinyl, or piperidinyl, each of which is N-substituted with T$^2$-R$^{Y1}$ and optionally further substituted at any one or more ring carbon atoms by alkyl, halide, haloalkyl, hydroxyalkyl, —C(O)OR$^{12}$, —C(O)R$^{12}$, —OC(O)R$^{12}$, —R$^{12}$C(O)OR$^{12}$—, —C(O)N(R$^{12}$)$_2$, —NR$^{12}$C(O)R$^{12}$, —NR$^{12}$C(O)OR$^{12}$, —S(O)$_2$R$^{12}$, —S(O)$_2$COR$^{12}$, —S(O)$_2$N(R$^{12}$)$_2$, —S(O)$_2$OR$^{12}$, —S(O)OR$^{12}$, —OR$^{12}$, —SR$^{12}$, —CN, —NR$^{12}$C(O)N(R$^{12}$)$_2$, —OC(O)N(R$^{12}$)$_2$, —N(R$^{12}$)$_2$, —(CH$_2$)$_{1-4}$CO$_2$R$^{12}$, —O(CH$_2$)$_{1-4}$CO$_2$R$^{12}$, —(CH$_2$)$_{1-4}$CON(R$^{12}$)$_2$, —O(CH$_2$)$_{1-4}$CON(R$^{12}$)$_2$, —(CH$_2$)$_{0-3}$(C(CH$_3$)$_2$)CO$_2$R$^{12}$, —O(CH$_2$)$_{0-3}$(C(CH$_3$)$_2$)CO$_2$R$^{12}$, —(CH$_2$)$_{0-3}$(C(CH$_3$)$_2$)CON(R$^{12}$)$_2$, or —O(CH$_2$)$_{0-3}$(C(CH$_3$)$_2$)CON(R$^{12}$)$_2$.

Other examples of suitable values for R$^{10}$ include oxazolidinyl, oxazolidinonyl, thiazolidinyl, morpholinyl, thiomorpholinyl, imidazolidinyl, imidazolidinonyl, pyrrolidinyl, piperazinyl, or piperidinyl, each of which is N-substituted with T$^2$-R$^{Y1}$ and optionally further substituted at any one or more ring carbon atoms by alkyl, halide, haloalkyl, hydroxyalkyl, —C(O)OR$^{12}$, —C(O)R$^{12}$, —OC(O)R$^{12}$, —R$^{12}$C(O)OR$^{12}$, —C(O)N(R$^{12}$)$_2$, —NR$^{12}$C(O)R$^{12}$, —NR$^{12}$C(O)OR$^{12}$, —S(O)$_2$R$^{12}$, —S(O)$_2$COR$^{12}$, —S(O)$_2$N(R$^{12}$)$_2$, —S(O)$_2$OR$^{12}$, —S(O)OR$^{12}$, —OR$^{12}$, —SR$^{12}$, —CN, —NR$^{12}$C(O)N(R$^{12}$)$_2$, —OC(O)N(R$^{12}$)$_2$, or —N(R$^{12}$)$_2$.

Examples of suitable values for R$^{13}$ include pyrazolyl, triazolyl, imidazolyl, or pyrrolyl, each of which is N-substituted with T$^2$-R$^{Y1}$ and optionally further substituted at any one or more ring carbon atoms with alkyl, halide, haloalkyl, hydroxyalkyl, —C(O)OR$^{12}$, —C(O)R$^{12}$, —OC(O)R$^{12}$, —R$^{12}$C(O)OR$^{12}$—, —C(O)N(R$^{12}$)$_2$, —NR$^{12}$C(O)R$^{12}$, —NR$^{12}$C(O)OR$^{12}$, —S(O)$_2$R$^{12}$, —S(O)$_2$COR$^{12}$, —S(O)$_2$N(R$^{12}$)$_2$, —S(O)$_2$OR$^{12}$, —S(O)OR$^{12}$, —OR$^{12}$, —SR$^{12}$, —CN, —NR$^{12}$C(O)N(R$^{12}$)$_2$, —OC(O)N(R$^{12}$)$_2$, —N(R$^{12}$)$_2$, —(CH$_2$)$_{1-4}$CO$_2$R$^{12}$, —O(CH$_2$)$_{1-4}$CO$_2$R$^{12}$, —(CH$_2$)$_{1-4}$CON(R$^{12}$)$_2$, —O(CH$_2$)$_{1-4}$CON(R$^{12}$)$_2$, —(CH$_2$)$_{0-3}$(C(CH$_3$)$_2$)CO$_2$R$^{12}$, —O(CH$_2$)$_{0-3}$(C(CH$_3$)$_2$)CO$_2$R$^{12}$, —(CH$_2$)$_{0-3}$(C(CH$_3$)$_2$)CON(R$^{12}$)$_2$, or —O(CH$_2$)$_{0-3}$(C(CH$_3$)$_2$)CON(R$^{12}$)$_2$.

Other examples of suitable values for R$^{13}$ include pyrazolyl, triazolyl, imidazolyl, or pyrrolyl, each of which is N-substituted with T$^2$-R$^{Y1}$ and optionally further substituted at any one or more ring carbon atoms with alkyl, halide, haloalkyl, hydroxyalkyl, —C(O)OR$^{12}$, —C(O)R$^{12}$, —OC(O)R$^{12}$, —R$^{12}$C(O)OR$^{12}$—, —C(O)N(R$^{12}$)$_2$, —NR$^{12}$C(O)R$^{12}$, —NR$^{12}$C(O)OR$^{12}$, —S(O)$_2$R$^{12}$, —S(O)$_2$COR$^{12}$, —S(O)$_2$N(R$^{12}$)$_2$, —S(O)$_2$OR$^{12}$, —S(O)OR$^{12}$, —OR$^{12}$, —SR$^{12}$, —CN, —NR$^{12}$C(O)N(R$^{12}$)$_2$, —OC(O)N(R$^{12}$)$_2$, or —N(R$^{12}$)$_2$. Each R$^{12}$ is independently H, alkyl, haloalkyl, or hydroxyalkyl. All other variables are as described above for Structural Formula (VI-A).

Preferably, T$^2$ in Structural Formula (VI-A) is C$_{16}$ is a straight chain alkylene optionally substituted at any one or more substitutable carbon atoms with halide, alkyl, gem dialkyl, gem dihalo, haloalkyl, spiro cycloalkyl, optionally N-substituted nitrogen containing spiro non-aromatic heterocyclic group, amine, alkylamine, dialkylamine, or hydroxyl. R$^{Y1}$ is —C(O)OR$^5$, —C(O)N(R$^5$)$_2$, —NR$^5$C(O)R$^5$, —NR$^5$C(O)OR$^5$, —S(O)$_2$N(R$^5$)$_2$, —NR$^5$S(O)$_2$R$^5$, —OR$^5$, —CN, —NR$^5$C(O)N(R$^5$)$_2$, —N(R$^5$)$_2$, an optionally substituted non-aromatic heterocyclic group represented by R$^7$, or an optionally substituted heteroaryl group represented by R$^8$. R$^7$ is an optionally substituted piperidinonyl, oxazolidinyl, oxazolidinonyl, thiazolidinyl, tetrahydrofuranyl, tetrahydropyranyl, thiazolidinyl, tetrahyrothiophene, morpholinyl, thiomorpholinyl, imidazolidinyl, imidazolidinonyl, dioxanyl, dioxolanyl, dithiolanyl, pyrrolidinyl, pyrrolidinonyl, piperazinyl, or piperidinyl. R$^8$ is an optionally substituted furanyl, tetrazolyl, oxazolyl, isoxazolyl, oxadiazolyl, pyrrolyl, pyrazolyl, pyridinyl, pyrimidyl, thiazolyl, thienyl, or imidazolyl.

Other examples of suitable values for R$^{10}$ include morpholinyl, thiomorpholinyl, imidazolidinyl, imidazolidinonyl, pyrrolidinyl, piperazinyl, or piperidinyl each of which is N-substituted with T$^2$-R$^{Y1}$ and further optionally substituted at any substitutable carbon ring atom with alkyl, halide, haloalkyl, hydroxyalkyl, —C(O)OR$^{12}$, —C(O)R$^{12}$, —OC(O)R$^{12}$, —R$^{12}$C(O)OR$^{12}$—, —C(O)N(R$^{12}$)$_2$, —NR$^{12}$C(O)

$R^{12}$, —$NR^{12}C(O)OR^{12}$, —$S(O)_2R^{12}$, —$S(O)_2COR^{12}$, —$S(O)_2N(R^{12})_2$, —$S(O)_2OR^{12}$, —$S(O)OR^{12}$, —$OR^{12}$, —$SR^{12}$, —CN, —$NR^{12}C(O)N(R^{12})_2$, —$OC(O)N(R^{12})_2$, or —$N(R^{12})_2$. Other examples of suitable values for $R^{13}$ include triazolyl, imidazolyl, or pyrrolyl, each of which is N-substituted with $T^2$-$R^{Y1}$ and further optionally substituted at any substitutable ring carbon atom with alkyl, halide, haloalkyl, hydroxyalkyl, —$C(O)OR^{12}$, —$C(O)R^{12}$, —$OC(O)R^{12}$, —$R^{12}C(O)OR^{12}$—, —$C(O)N(R^{12})_2$, —$NR^{12}C(O)R^{12}$, —$NR^{12}C(O)OR^{12}$, —$S(O)_2R^{12}$, —$S(O)_2COR^{12}$, —$S(O)_2N(R^{12})_2$, —$S(O)_2OR^{12}$, —$S(O)OR^{12}$, —$OR^{12}$, —$SR^{12}$, —CN, —$NR^{12}C(O)N(R^{12})_2$, —$OC(O)N(R^{12})_2$, or —$N(R^{12})_2$. $R^{Y1}$ is —$C(O)OR^5$, —$C(O)N(R^5)_2$, —$NR^5C(O)R^5$, —$NR^5C(O)OR^5$, —$S(O)_2N(R^5)_2$, —$NR^5S(O)_2R^5$, —$NR^5C(O)N(R^5)_2$, —OH, an optionally substituted non-aromatic heterocyclic group represented by $R^7$ or an optionally substituted heteroaryl group represented by $R^8$. Each $R^5$ is independently H or alkyl, or $N(R^5)_2$ is a nitrogen-containing non-aromatic heterocyclic group. $R^7$ is piperidinonyl, morpholinyl, imidazolidinonyl, pyrrolidinyl, pyrrolidinonyl, piperazinyl, or piperidinyl. $R^8$ is tetrazolyl, oxazolyl, oxadiazolyl, pyrrolyl, pyrazolyl, pyridinyl, or imidazolyl. $T^2$ is a $C_{1-5}$ straight chain alkylene optionally substituted at the carbon atom adjacent to $R^Y$ with halide, alkyl, gem dialkyl, gem dihalo, haloalkyl, spiro cycloalkyl, optionally N-substituted nitrogen containing spiro non-aromatic heterocyclic group, amine, dialkylamine, or hydroxyl.

Preferably, other examples of suitable values for $R^{10}$ include morpholinyl, pyrrolidinyl, piperazinyl, or piperidinyl each of which is N-substituted with $T^2$-$R^{Y1}$ and further optionally substituted at any substitutable carbon atom by alkyl, halide, haloalkyl, hydroxyalkyl, —$C(O)OR^{12}$, —$C(O)R^{12}$, —$OC(O)R^{12}$. Other examples of suitable values for $R^{13}$ include imidazolyl, or pyrrolyl each of which is N-substituted with $T^2$-$R^{Y1}$ and further optionally substituted at any substitutable carbon atom by alkyl, halide, haloalkyl, hydroxyalkyl, —$C(O)OR^{12}$, —$C(O)R^{12}$, —$OC(O)R^{12}$, or —$C(O)N(R^{12})_2$, and each optionally substituted at any substitutable nitrogen atom by alkyl, haloalkyl, hydroxyalkyl, $C(O)OR^{12}$, —$C(O)R^{12}$, —$R^{12}C(O)OR^{12}$, —$S(O)_2R^{12}$, $S(O)_2N(R^{12})_2$, —$C(O)N(R^{12})_2$. $R^{Y1}$ is —$C(O)OR^5$, —$C(O)N(R^5)_2$, —OH, N-morpholinyl, 2-morpholinyl, 3-morpholinyl, N-substituted 2-morpholinyl, N-substituted 3-morpholinyl, N-imidazolidinyl, 2-imidazolidinyl, 4-imidazolidinyl, 5-imidazolidinyl, N-substituted 2-imidazolidinyl, N'-substituted N-imidazolidinyl, N-substituted 4-imidazolidinyl, N-substituted 5-imidazolidinyl, N-imidazolidinonyl, 4-imidazolidinonyl, 5-imidazolidinonyl, N-substituted 4-imidazolidinonyl, N-substituted 5-imidazolidinonyl, N-pyrrolidinyl, 2-pyrrolidinyl, 3-pyrrolidinyl, N-substituted 2-pyrrolidinyl, N-substituted 3-pyrrolidinyl, N-pyrrolidin-2-onyl, 3-pyrrolidin-2-onyl, 4-pyrrolidin-2-onyl, 5-pyrrolidin-2-onyl, N-substituted 3-pyrrolidin-2-only, N-substituted 4-pyrrolidin-2-only, N-substituted 5-pyrrolidin-2-onyl, N-pyrrolidin-3-onyl, 2-pyrrolidin-3-onyl, 4-pyrrolidin-3-onyl, 5-pyrrolidin-3-onyl, N-substituted 2-pyrrolidin-3-onyl N-substituted 4-pyrrolidin-3-onyl, N-substituted 5-pyrrolidin-3-onyl, N-piperidinyl, 2-piperidinyl, 3-piperidinyl, 4-piperidinyl, N-substituted 2-piperidinyl, N-substituted 3-piperidinyl, N-substituted 4-piperidinyl, N-piperidin-2-onyl, 3-piperidin-2-onyl, 4-piperidin-2-onyl, 5-piperidin-2-onyl, 6-piperidin-2-onyl, N-substituted 3-piperidin-2-onyl, N-substituted 4-piperidin-2-onyl, N-substituted 5-piperidin-2-onyl, N-substituted 6-piperidin-2-onyl, N-piperidin-3-onyl, 2-piperidin-3-onyl, 4-piperidin-3-onyl, 5-piperidin-3-onyl, 6-piperidin-3-onyl, N-substituted 2-piperidin-3-onyl, N-substituted 4-piperidin-3-onyl, N-substituted 5-piperidin-3-onyl, N-substituted 6-piperidin-3-onyl, N-piperidin-4-onyl, 2-piperidin-4-onyl, 3-piperidin-4-onyl, 5-piperidin-4-onyl, 6-piperidin-4-onyl, N-substituted 2-piperidin-4-onyl, N-substituted 3-piperidin-4-onyl, N-substituted 5-piperidin-4-onyl, N-substituted 6-piperidin-4-onyl, N-piperazinyl, 2-piperazinyl, N'-substituted N-piperazinyl, N-substituted 2-piperazinyl, furanyl, N-tetrazolyl, 5-tetrazolyl, N-substituted 5-tetrazolyl, 4-(1,2,3)oxadiazolyl, 5-(1,2,3)oxadiazolyl, 3-(1,2,4)oxadiazolyl, 5-(1,2,4)oxadiazolyl, 3-(1,2,5)oxadiazolyl, 4-(1,2,5)oxadiazolyl, 2-(1,3,4)oxadiazolyl, 5-(1,3,4)oxadiazolyl, N-pyrrolyl, 2-pyrrolyl, 3-pyrrolyl, N-substituted 2-pyrrolyl, N-substituted 3-pyrrolyl, N-pyrazolyl, 3-pyrazolyl, 4-pyrazolyl, 5-pyrazolyl, N-substituted 3-pyrazolyl, N-substituted 4-pyrazolyl, N-substituted 5-pyrazolyl, 2-pyridinyl, 3-pyridinyl, 4-pyridinyl, N-imidazolyl, 2-imidazolyl, 4-imidazolyl, 5-imidazolyl; N-substituted 2-imidazolyl, N-substituted 4-imidazolyl, or N-substituted 5-imidazolyl. $T^2$ is a $C_{1-3}$ straight chain alkylene substituted with fluoro, methyl, gem dimethyl, gem difluoro fluoromethyl, spiro cyclopropyl, spiro cyclobutyl, optionally N-substituted spiro azetidinyl, optionally N-substituted spiro aziridinyl, optionally N-substituted spiro pyrrolidinyl, optionally N-substituted spiro piperidinyl, amine, methylamine, dimethylamine, or hydroxyl.

More preferably, other examples of suitable values for $R^{10}$ include morpholinyl, N-substituted with $T^2$-$R^{Y1}$ and further optionally substituted at the carbon alpha to the nitrogen atom with methyl or gem dimethyl. Other examples of suitable values for $R^{13}$ include imidazolyl N-substituted with $T^2$-$R^{Y1}$ and further optionally substituted at the carbon alpha to the nitrogen atom with methyl or gem dimethyl. $R^{Y1}$ is —$C(O)OR^5$, —$C(O)N(R^5)_2$, —OH, N-tetrazolyl, 5-tetrazolyl, N-substituted 5-tetrazolyl, N-imidazolyl, 2-imidazolyl, 4-imidazolyl, 5-imidazolyl; N-substituted 2-imidazolyl, N-substituted 4-imidazolyl, or N-substituted 5-imidazolyl.

In one embodiment, in Structural Formula (VI-A) $R^1$ is an optionally substituted phenyl ring fused to the group represented by $R^{10}$ as represented by the following Structural Formulas:

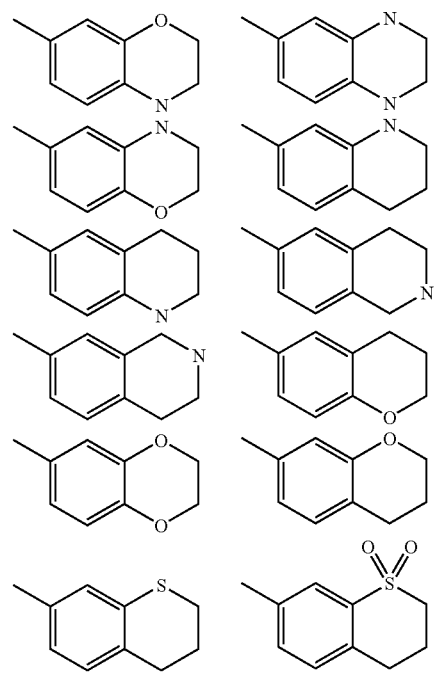

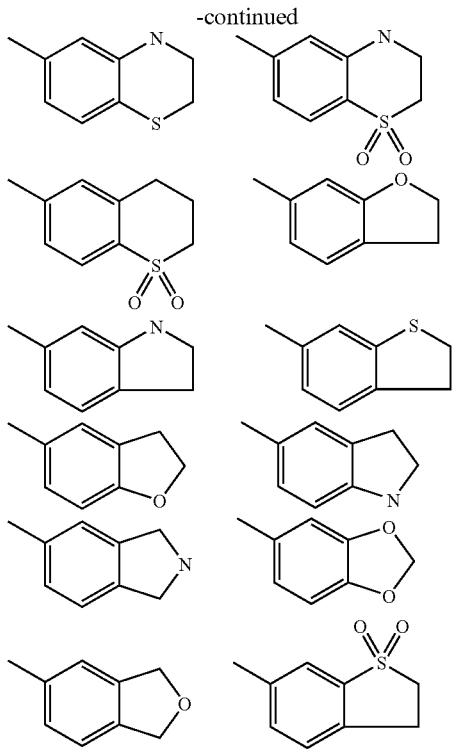

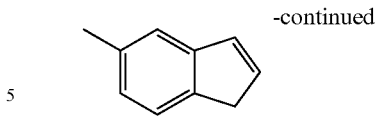

The Structural Formulas shown above for the fused bicyclic rings can be further optionally substituted at one or more substitutable carbon atoms or nitrogen atoms. Examples of suitable substituents as described above for the groups represented by $R^{10}$ and $R^{13}$. In a more specific embodiment, any one of the fused bicyclic ring systems shown above that have substitutable nitrogen atoms are N-substituted with $T^2$-$R^{Y1}$. $T^2$-$R^{Y1}$ is as described above.

As described above, Ring A (preferably phenyl ring A) in Structural Formulas (I-A)-(VI-A) is optionally substituted (preferably at the six and seven positions) with one or more groups represented by $R^{14}$; in Structural Formulas (I-A)-(V-A) $R^1$ is an aromatic group (preferably a phenyl ring) optionally substituted by 1-2 independently selected groups represented by $R^Z$; and in Structural Formulas (I-A)-(VI-A) $R^3$ is an aromatic group (preferably e.g., a phenyl ring) optionally substituted with one or more groups represented by $R^{11}$. Suitable values for $R^{14}$, $R^Z$, and $R^{11}$ are ones that do not substantially decrease the ability of the compound of the invention to inhibit CRTH2. Examples of suitable substituents are halogen, haloalkyl, $R°$, —$OR°$, —O(haloalkyl), —$SR°$, —$NO_2$, —CN, —N(R')$_2$, —NR'CO$_2$R°, —NR'C(O)R°, —NR'NR'C(O)R°, —N(R')C(O)N(R')$_2$, —NR'NR'C(O)N(R')$_2$, —NR'NR'CO$_2$R°, —C(O)C(O)R°, —C(O)CH$_2$C(O)R°, —CO$_2$R°, —C(O)R°, —C(O)N(R°)$_2$, —OC(O)R°, —OC(O)N(R')$_2$, —S(O)$_2$R°, —SO$_2$N(R')$_2$, —S(O)R°, —NR'SO$_2$N(R')$_2$, —NR'SO$_2$R°, —C(=S)N(R')$_2$, and —C(=NH)—N(R')$_2$. Additional values for $R^{11}$ include 3,4-methylene-dioxy and 3,4-ethylene-dioxy. In other embodiments, suitable substituents for $R^{11}$ also include halogen, haloalkyl, $R°$, —$OR°$, —O(haloalkyl), —$SR°$, 3,4-methylene-dioxy, 3,4-ethylene-dioxy, —$NO_2$—CN, —N(R')$_2$, —NR'CO$_2$R°, —NR'C(O)R°, —NR'NR'C(O)R°, —N(R')C(O)N(R')$_2$, —NR'NR'C(O)N(R')$_2$, —NR'NR'CO$_2$R°, —C(O)C(O)R°, —C(O)CH$_2$C(O)R°, —CO$_2$R°, —C(O)R°, —C(O)N(R°)$_2$, —OC(O)R°, —OC(O)N(R°)$_2$, —S(O)$_2$R°, —SO$_2$N(R')$_2$, —S(O)R°, —NR'SO$_2$N(R')$_2$, —NR'SO$_2$R°, —C(=S)N(R')$_2$, —O(CH$_2$)$_{1-4}$CO$_2$R°, —(CH$_2$)$_{1-4}$CO$_2$R°, —(CH$_2$)$_{1-4}$CON(R°)$_2$, —O(CH$_2$)$_{1-4}$CON(R°)$_2$, —(CH$_2$)$_{0-3}$(C(CH$_3$)$_2$)CO$_2$R°, —O(CH$_2$)$_{0-3}$(C(CH$_3$)$_2$)CO$_2$R°, —(CH$_2$)$_{0-3}$(C(CH$_3$)$_2$)CON(R')$_2$, —O(CH$_2$)$_{0-3}$(C(CH$_3$)$_2$)CON(R°)$_2$, or —C(=NH)—N(R')$_2$.

Each $R^1$ is independently hydrogen, alkyl, —C(O)OR°, S(O)$_2$R°, or —C(O)R°. Each $R°$ is independently hydrogen or an alkyl group, non-aromatic heterocyclic group or aromatic group and the alkyl, non-aromatic heterocyclic group and aromatic group represented by $R°$ is optionally substituted with one or more independently selected groups represented by $R^\#$. $R^\#$ is $R^+$, —$OR^+$, —O(haloalkyl), —$SR^+$, —$NO_2$, —CN, —N($R^+$)$_2$, —NHCO$_2$$R^+$, —NHC(O)$R^+$, —NHNHC(O)$R^+$, —NHC(O)N($R^+$)$_2$, —NHNHC(O)N($R^+$)$_2$, —NHNHCO$_2$$R^+$, —C(O)C(O)$R^+$, —C(O)CH$_2$C(O)$R^+$, —CO$_2$$R^+$, —C(O)$R^+$, —C(O)N($R^+$)$_2$, —OC(O)$R^+$, —OC(O)N($R^+$)$_2$, —S(O)$_2$$R^+$, —SO$_2$N($R^+$)$_2$, —S(O)$R^+$, —NHSO$_2$N($R^+$)$_2$, —NHSO$_2$$R^+$, —C(=S)N($R^+$)$_2$, or —C(=NH)—N($R^+$)$_2$. $R^+$ is —H, a $C_1$-$C_3$ alkyl group, a monocyclic heteroaryl group, a non-aromatic heterocyclic group or a phenyl group optionally substituted with alkyl, haloalkyl, alkoxy, haloalkoxy, halo, —CN, —NO$_2$, amine, alkylamine or dialkylamine; or —N($R^+$)$_2$ is a non-aromatic In one embodiment in Structural Formula (VI-A) $R^1$ is an optionally substituted phenyl ring fused to the group represented by $R^{13}$ as represented by the following Structural Formulas:

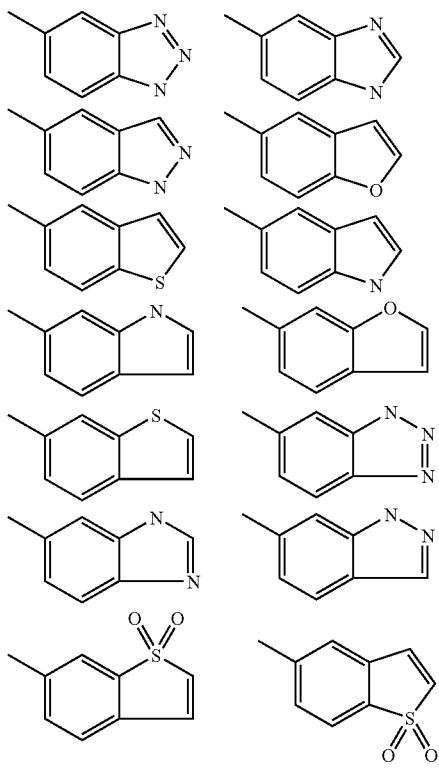

heterocyclic group, provided that non-aromatic heterocyclic groups represented by R+ and —N(R+)₂ that comprise a secondary ring amine are optionally acylated or alkylated.

Preferred values for $R^Z$ and $R^{11}$ are halogen, haloalkyl, —R°, —OR°, —O(haloalkyl), —CO₂R°, —C(O)R°, —NR'SO₂R°, —C(O)N(R°)₂, —OC(O)R°, and —OC(O)N(R°)₂. 3,4-methylene-dioxy and 3,4-ethylene-dioxy, and —N(R')₂ are also preferred values for $R^{11}$. Each R° is independently hydrogen, haloalkyl or an alkyl group, each $R^1$ is independently H or alkyl.

Preferably, $R^3$ is a phenyl ring optionally substituted at the meta or para positions with one or more groups represented by $R^{11}$. More preferred values for $R^{11}$ and $R^Z$ are halogen, haloalkyl, —R°, —OR°, and —O(haloalkyl). —NR'SO₂R° and —N(R')₂ are also preferred values for $R^{11}$.

More preferably, $R^3$ is a phenyl ring optionally substituted at the para position with $R^{11}$. $R^1$ is a phenyl ring optionally substituted at the meta position by $R^Z$. Even more preferred values for $R^Z$ and $R^{11}$ are chloride, fluoride, bromide, —OR°, or R°. —NR'SO₂R° and —N(R')₂ are also preferred values for R". Each R° is independently hydrogen, haloalkyl or a C₁₋₃ alkyl group. Each R' is independently hydrogen or a C₁₋₃ alkyl group.

$R^{14}$ is an optional substituent, preferably at the six an seven positions on phenyl ring A; preferred values are halogen R°, —OR°, —CO₂R°, —C(O)R°, —C(O)N(R°)₂, —CN, —OC(O)R°, (CH₂)ₙCO₂R°, O(CH₂)ₙCO₂R°, NHSO₂R°, NHC(O)N(R°)₂, (CH₂)ₙOH, O(CH₂)ₙOH, (CH₂)ₙC(O)N(R°)₂, or O(CH₂)ₙC(O)N(R°)₂. R° is hydrogen, haloalkyl or a C₁₋₃ alkyl group.

Another embodiment of the present invention, is a compound represented by Structural Formula (X-A):

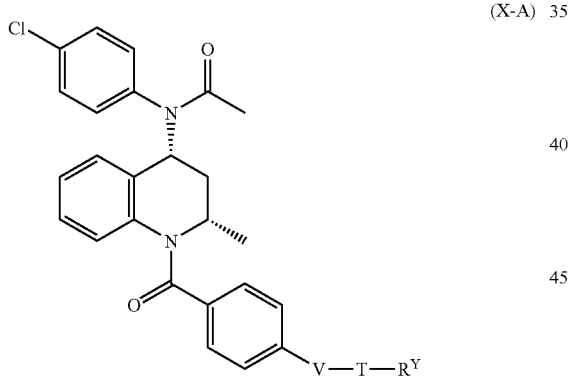

(X-A)

V is a covalent bond or —O—.
T is an unsubstituted straight chained C₁₋₁₀ alkylene.
$R^Y$ is —C(O)OR⁵, —C(O)R⁵, —OC(O)R⁵, —C(O)N(R⁵)₂, —NR⁵C(O)R⁵, —NR⁵C(O)OR⁵, —S(O)₂R⁵, —S(O)₂COR⁵, —S(O)₂N(R⁵)₂, —NR⁵S(O)₂, —NR⁵S(O)₂R⁵, S(O)₂OR⁵, —S(O)OR⁵, —SR⁵, —C(O)NR⁵S(O)₂R⁵, —CN, —NR⁵C(O)N(R⁵)₂, —OC(O)N(R⁵)₂, —N(R⁵)₂, —OR⁵, an optionally substituted non-aromatic heterocyclic group or an optionally substituted heteroaryl group.

In some embodiments, the compound of Structural Formula (X-A), excludes compounds where T-R$^Y$ is —CH₂R²⁰, —CH₂CH₂R²¹, or —(CH₂)₃R²². R²⁰ is —COOH, —C(O)NH₂, —C(O)NHCH₃, C(O)N(CH₃)₂, 5-tetrazolyl, 4-pyridinyl, N-ethyl-4-piperidinyl, or C(O)N-morpholinyl. R²¹ is —COOH, N-morpholinyl, C(O)NH₂, N-pyrrolidin-2-onyl, N-imidazolyl, or N-pyrrolidinyl. R²² is —COOH, C(O)N(CH₂CH₃)₂, C(O)NH(CH₂CH₃), C(O)NH₂, C(O)NHS(O)₂CH₃, C(O)NHOH, C(O)OCH₂CH₃, NH₂, C(O)CH₃, CN, NHS(O)₂CF₃, C(O)N-pyrrolidinyl, N-pyrrolidinyl, 5-tetrazolyl, 5-(1,2,4)oxadiazolyl, N-morpholinyl, or N-imidazolyl.

In other embodiments, compounds of Structural Formula (X-A) (or a pharmaceutically acceptable salt thereof) are provided:

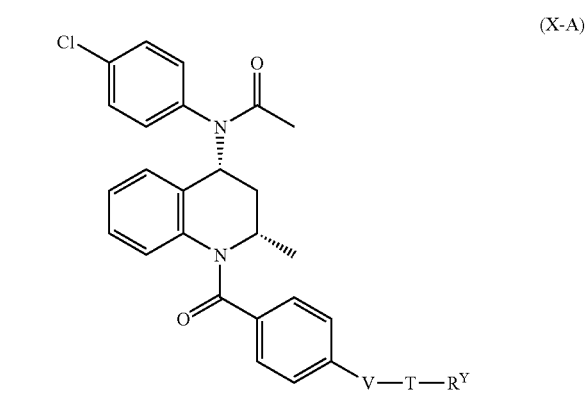

(X-A)

or a pharmaceutically acceptable salt thereof, wherein:
V is a covalent bond or —O—;
T is an straight chained C₁₋₁₀ alkylene substituted with alkyl, gem dialkyl, haloalkyl, spiro cycloalkyl, or an optionally N-substituted nitrogen containing spiro non-aromatic heterocyclic group;
$R^Y$ is $R^Y$ is —C(O)OR⁵, —C(O)R⁵, —OC(O)R⁵, —C(O)N(R⁵)₂, —NR⁵C(O)R⁵, —NR⁵C(O)OR⁵, —S(O)₂R⁵, —S(O)₂COR⁵, —S(O)₂N(R⁵)₂, —NR⁵S(O)₂, —NR⁵S(O)₂R⁵, S(O)₂OR⁵, —S(O)OR⁵, —SR⁵, —C(O)NR⁵S(O)₂R⁵, —CN, —NR⁵C(O)N(R⁵)₂, —OC(O)N(R⁵)₂, —N(R⁵)₂, —OR⁵, an optionally substituted non-aromatic heterocyclic group or an optionally substituted heteroaryl group; and
each R⁵ is independently —H, alkyl, haloalkyl, hydroxyalkyl, carboxyalkyl, —C(O)OCH₂C₆H₅, S(O)₂CH₃, —C(O)OH, —C(O)OMe, —C(O)OEt, C(O)NH₂, benzyl, pyrrolidinyl, morpholinyl, or —N(R⁵)₂ is an optionally substituted nitrogen-containing non-aromatic heterocyclic group.

In yet other embodiments, compounds of Structural Formula (X-A) (or a pharmaceutically acceptable salt thereof) are provided:

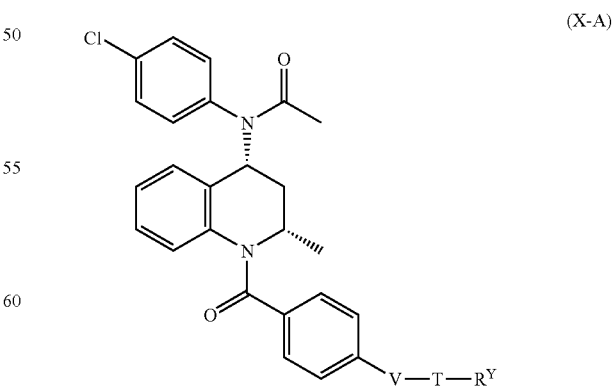

(X-A)

wherein:
V is —O—;

T is an straight chained $C_{1-10}$ alkylene optionally substituted at any one or more substitutable carbon atoms with halide, alkyl, gem dialkyl, gem dihalo, haloalkyl, alkoxy, haloalkoxy, spiro cycloalkyl, optionally N-substituted nitrogen containing spiro non-aromatic heterocyclic group, amine, alkylamine, dialkylamine, or hydroxyl;

$R^Y$ is $R^Y$ is —C(O)OR$^5$, —C(O)R$^5$, —OC(O)R$^5$, —C(O)N(R$^5$)$_2$, —NR$^5$C(O)R$^5$, —NR$^5$C(O)OR$^5$, —S(O)$_2$R$^5$, —S(O)$_2$COR$^5$, —S(O)$_2$N(R$^5$)$_2$, —NR$^5$S(O)$_2$, —NR$^5$S(O)$_2$R$^5$, S(O)$_2$OR$^5$, —S(O)OR$^5$, —SR$^5$, —C(O)NR$^5$S(O)$_2$R$^5$, —CN, —NR$^5$C(O)N(R$^5$)$_2$, —OC(O)N(R$^5$)$_2$, —N(R$^5$)$_2$, —OR$^5$, an optionally substituted non-aromatic heterocyclic group or an optionally substituted heteroaryl group; and each $R^5$ is independently —H, alkyl, haloalkyl, hydroxyalkyl, carboxyalkyl, —C(O)OCH$_2$C$_6$H$_5$, S(O)$_2$CH$_3$, —C(O)OH, —C(O)OMe, —C(O)OEt, C(O)NH$_2$, benzyl, pyrrolidinyl, morpholinyl, or —N(R$^5$)$_2$ is an optionally substituted nitrogen-containing non-aromatic heterocyclic group.

Compounds of general formula I-A (and subsets thereof as described directly above in section 2) include those described generally above, and are further illustrated by the classes, subclasses, and species disclosed above and herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001.

The term "alkylene" as used herein means a straight chained hydrocarbon which is completely saturated. An alkylene group is typically $C_{1-10}$, more typically $C_{1-6}$, more preferably from $C_{1-5}$ and more preferably from $C_{1-3}$. A "substituted alkylene" is an alkylene group in which one or more methylene hydrogen atoms are replaced with a substituent. Suitable substituents are as described below for a substituted alkyl group. Preferred substituents for the alkylene group represented by T are fluoro, methyl, gem dimethyl, gem difluoro fluoromethyl, spiro cyclopropyl, spiro cyclobutyl, optionally N-substituted spiro azetidinyl, optionally N-substituted spiro aziridinyl, optionally N-substituted spiro pyrrolidinyl, optionally N-substituted spiro piperidinyl, amine, methylamine, dimethylamine, or hydroxyl. A "substitutable alkylene carbon atom" is an alkylene carbon atom that is bonded to one or more hydrogen atoms. The hydrogen atoms can therefore optionally be replaced with the substituent.

The terms "alkyl", "hydroxyalkyl", "carboxyalkyl", "haloalkyl", "alkylamine", "dialkylamine", used alone or as part of a larger moiety include both straight and branched saturated chains containing one to ten carbon atoms, preferably one to six, more preferably one to five, and even more preferably one to three.

The term "allyl" as used herein has the formula —CH$_2$CH=CH$_2$, and may be optionally substituted at any substitutable carbon atom. A "substitutable allyl carbon atom" is an allyl carbon atom that is bonded to one or more hydrogen atoms. The hydrogen atom can therefore optionally be replaced with the substituent. Suitable substituents are as described for alkyl group.

The terms "gem dialkyl", and "gem dihalo" includes compounds where two alkyl substituents or two halo substituents, respectively, are attached to the same carbon atom, e.g., —C(CH$_3$)$_2$— or C(F)$_2$—.

A "spiro cycloalkyl" or "spiro non-aromatic heterocyclic" group is a cycloalkyl or non-aromatic heterocyclic group which shares one ring carbon atom with a carbon atom in an alkylene group or alkyl group.

The terms "non-aromatic carbocyclic" or "cycloaliphatic" shall include cyclic $C_{3-10}$ hydrocarbons which are completely saturated or which contain one or more units of unsaturation, but which are not aromatic. Cycloaliphatic groups are typically $C_{3-10}$, more typically $C_{3-7}$.

"Alkoxy" means (alkyl)-O—; "haloalkoxy", means (halide)-O—; "alkoxyalkylene" means (alkyl)-O-(alkylene) such as methoxymethylene (CH$_3$OCH$_2$); "hydroxyalkyl" means hydroxy substituted alkyl group, acylated means "—C(O)-(alkyl)".

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The term "aromatic group", includes carbocyclic aromatic ring groups and heteroaryl ring groups. The term "aromatic group" may be used interchangeably with the terms "aryl", "aryl ring" or "aromatic ring".

Carbocyclic aromatic ring groups have only carbon ring atoms and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (aliphatic or heterocyclic), such as in an indanyl, phthalimidyl, naphthimidyl, phenantriidinyl, or tetrahydronaphthyl, where the radical or point of attachment is on the aromatic ring.

The term "heteroaryl" or "heteroaromatic", refers to heteroaromatic ring groups having five to fourteen members, including monocyclic heteroaromatic rings and polycyclic aromatic rings in which a monocyclic aromatic ring is fused to one or more other carbocyclic or heteroaromatic aromatic rings. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, 2-oxadiazolyl, 5-oxadiazolyl, 2-oxazolyl, 4-oxazolyl, 5-oxazolyl, N-pyrrolyl, 2-pyrrolyl, 3-pyrrolyl, pyrazolyl, 2-pyridinyl, 3-pyridinyl, 4-pyridinyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisazolyl.

Also included within the scope of the term "heteroaryl", as it is used herein, is a group in which a heteroaryl ring is fused to one or more cycloaliphatic or non-aromatic heterocyclic groups where the radical or point of attachment is on the heteroaromatic ring. Examples include tetrahydro-quinolinyl, tetrahydroisoquinolinyl, and pyrido[3,4-d]pyrimidinyl. The term "heteroaryl" may be interchangeably with the term "heteroaryl ring" or the term "heteroaromatic".

The term "non-aromatic heterocyclic group", or "non-aromatic heterocyclic ring" refers to non-aromatic ring systems typically having three to fourteen members, preferably three to six, in which one or more ring carbons, preferably one to four, are each replaced by a heteroatom such as N, O, or S. Examples of non-aromatic heterocyclic rings include 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, N-morpholinyl, 2-thiomorpholinyl, 3-thiomorpholinyl, 4-thiomorpholinyl, N-pyrrolidinyl, 2-pyrrolidinyl, 3-pyrorolidinyl, N-piperazinyl, 2-piperazinyl, N-piperidinyl, 2-piperidinyl, 3-piperidinyl, 4-piperidinyl, piperidinonyl, 4-thiazolidinyl, diazolonyl, N-substituted diazolonyl, oxazolidinyl, oxazolidinyl, tetrahydrothienyl, imidazolidinyl, imidazolidinonyl, pyrrolidinonyl, isothiazolidinyl S,S, dioxide, piperidinyl, 1-pthalimidinyl, 3-1H-benzimidazol-2-one, benzoxanyl, benzopyrrolidinyl, benzopiperidinyl, benzoxolanyl, benzothiolanyl, and benzothianyl.

A "substituted aromatic group" is an aromatic group with a substituent at one or more substitutable ring carbon atoms or ring nitrogen atoms. Each substituent is independently selected. Examples of suitable substituents on an unsaturated carbon atom or substitutable carbon atom of an aromatic group are as described above for $R^Z$, $R^{11}$, and $R^{14}$.

A "substitutable ring carbon atom" in an aromatic ring (including the aromatic groups represented by Ring A, phenyl ring A, $R^1$ and $R^3$) is a ring carbon atom that is bonded to a hydrogen atom. The hydrogen atom can therefore optionally be replaced with the substituent. The term "substitutable ring carbon atom" in an aromatic ring therefore excludes ring carbon atoms that are fused with other rings or that are depicted as already being bonded to a substituent.

An alkyl group or a non-aromatic carbocycle or heterocycle may contain one or more substituents on any substitutable carbon atom. A "substitutable alkyl carbon atom" is an alkyl carbon atom that is bonded to one or more hydrogen atoms. The hydrogen atoms can therefore optionally be replaced with the substituent. Examples of suitable substituents on the saturated carbon of an alkyl group or a non-aromatic heterocycle include those listed above for the unsaturated carbon of an aromatic group and, at the internal carbon atoms of an alkyl group or on ring carbon atoms of a non-aromatic heterocyclic group, the following: $=$O, $=$S, $=$NNHR*, $=$NN(R*)$_2$, $=$NNHC(O)R*, $=$NNHCO$_2$(alkyl), $=$NNHSO$_2$(alkyl), or $=$NR*. Each R* is independently selected from hydrogen, an unsubstituted alkyl group or a substituted alkyl group. Examples of substituents on the alkyl group represented by R* include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the substitutable nitrogen of a heteroaryl or non-aromatic heterocyclic group include —$R^{12}$, —N($R^{12}$)$_2$, —C(O)$R^{12}$, —CO$_2R^{12}$, —C(O)C(O)$R^{12}$, —C(O)CH$_2$C(O)$R^{12}$, —SO$_2R^{12}$, —SO$_2$N($R^{12}$)$_2$, —C($=$S)N($R^{12}$)$_2$, —C($=$NH)—N($R^{12}$)$_2$, and —NR$^{12}$SO$_2R^{12}$; wherein $R^{12}$ is hydrogen, an alkyl group, a substituted alkyl group, phenyl (Ph), substituted Ph, —O(Ph), substituted —O(Ph), CH$_2$(Ph), or an unsubstituted heteroaryl or non-aromatic heterocyclic ring. Examples of substituents on the alkyl group or the phenyl ring represented by $R^{12}$ include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl. A "substitutable ring nitrogen atom" in a heteroaryl or nitrogen-containing non-aromatic heterocyclic group is a ring nitrogen atom that is bonded to a hydrogen atom. The hydrogen atom can therefore optionally be replaced with the substituent. The term "substitutable ring nitrogen atom" therefore excludes ring nitrogen atoms that are depicted as already being bonded to a substituent, and ring nitrogen atoms that are ring atoms in two fused rings (as in, e.g., indolizine) and ring nitrogen atoms that have three covalent bonds to other ring atoms (as e.g., pyridine).

In certain instances compounds of the present invention may associated in isolated form with solvent or water, as in a "solvate" or "hydrate". References to the disclosed compounds or structural formulas depicting the disclosed compounds are meant to include such solvates and hydrates.

3. Uses, Formulation and Administration

As discussed above, the present invention provides compounds that are useful as inhibitors of CRTH2, and thus the present compounds are useful for treating (therapeutically or prophylactically) disorders with an inflammatory component and allergic conditions. They can also be used to inhibit inflammatory disorders and allergic conditions mediated by Th2 cells, eosinophils and basophils.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, a method for the treatment of an inflammatory disease or a disease with an inflammatory component is provided comprising administering an effective amount of a compound, or a pharmaceutical composition thereof to a subject in need thereof. Compounds and compositions of the invention are inhibitors of CRTH2, and thus, without wishing to be bound by any particular theory, the compounds and compositions are particularly useful for treating or lessening the severity of a disease, condition, or disorder where activation of one or more of CRTH2, PGD2 (including DP activity), Th2 cells, eosinophils, and/or basophils is implicated in the disease, condition, or disorder. When activation of one or more of CRTH2, PGD2 (including DP activity), Th2 cells, eosinophils, and/or basophils is implicated in a particular disease, condition, or disorder, the disease, condition, or disorder may also be referred to as a "CRTH2-mediated disease" or disease symptom. Accordingly, in another aspect, the present invention provides a method for treating or lessening the severity of a disease, condition, or disorder where activation of one or more of CRTH2, PGD2 (including DP activity), Th2 cells, eosinophils, and/or basophils is implicated in the disease state.

In certain embodiments of the present invention an "effective amount" of the compound or pharmaceutically acceptable composition is that amount effective for treating an inflammatory disease or disease with an inflammatory component. In other embodiments, an "effective amount" of a compound is an amount which inhibits binding of PGD2 to its receptor CRTH2 and thereby inhibits one or more processes mediated by the binding in a subject, for example, the release of proinflammatory mediators. An "effective amount" of a compound can achieve a desired therapeutic and/or prophylactic effect, such as an amount which results in the prevention of or a decrease in the symptoms associated with an inflammatory disease or a disease mediated by one or more of CRTH2, PGD2 (including DP activity), Th2 cells, eosinophils, and basophils.

In one embodiment, the inflammatory disease is an allergic condition. Examples of allergic conditions for which the disclosed compounds, pharmaceutical compositions and methods are believed to be particularly effective include atopic dermatitis, allergic rhinitis, rheumatoid arthritis, chronic obstructive pulmonary disorder, or allergic asthma. Other allergic conditions include systemic anaphylaxis or hypersensitivity responses, drug allergies (e.g., to penicillin, cephalosporins), insect sting allergies and dermatoses such as dermatitis, eczema, atopic dermatitis, allergic contact dermatitis and urticaria.

Examples of diseases with an inflammatory component for which the disclosed compounds, pharmaceutical composition and methods are believed to be particularly effective include osteoarthritis, inflammatory bowel disease [e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis] and disorders of the skin [e.g., psoriasis, erythema, pruritis, and acne].

Many autoimmune diseases also have an inflammatory component. Examples include multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease). The inflammatory component of these disorders is believed to be mediated, at least in part, by CRTH2.

Diseases characterized by repurfusion have an inflammatory component that is believed to be mediated, at least in part by, by CRTH2. Examples include stroke, cardiac ischemia, and the like. The disclosed compounds and compositions also can be used to treat these disorders.

Other diseases and conditions with an inflammatory component believed to be mediated by CRTH2 include mastitis (mammary gland), vaginitis, cholecystitis, cholangitis or pericholangitis (bile duct and surrounding tissue of the liver), chronic bronchitis, chronic sinusitis, chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases and sarcoidosis. Yet other diseases or conditions with inflammatory components which are amendable to treatment according to methods disclosed herein include vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

In a preferred embodiment, the invention provides a method of treating asthma comprising administering an effective amount of a compound of general formula I (and subsets thereof as described herein) to a subject in need thereof.

The compounds and compositions, according to the method of the present invention, may be administered using any amount and any route of administration effective for treating an inflammatory disease or allergic condition. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents which are normally administered to treat or prevent a particular disease, or condition, are known as "appropriate for the disease, or condition, being treated".

For example, compounds of the invention can also be administered in combination with one or more additional therapeutic agents, such as, theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1a, IFNδ-1b)) and the like.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Another aspect of the invention relates to inhibiting CRTH2 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of CRTH2 activity in a biological sample is useful for a variety of purposes that are known to one of skill in the art. Examples of such purposes include, but are not limited to, blood transfusion, organ-transplantation, biological specimen storage, and biological assays.

4. General Synthetic Methods

Another embodiment of the present invention is a method of preparing an amino acid compound represented by Structural Formula (XI-A):

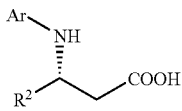

(XI-A)

The method comprises the step of reacting Ar—NH$_2$ with a lactone represented by Structural Formula (XXII-A):

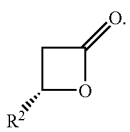

(XII-A)

Ar is an optionally substituted monocyclic aromatic group and R$^2$ is C$_1$-C$_3$ alkyl. Preferably, Ar is an optionally substituted phenyl group and R$^2$ is methyl or ethyl. Suitable substituents for Ar are as described above for Ring A or Phenyl Ring A, provided, however, that functional groups which can interfere with the reaction are protected. Functional groups which require protection will be readily apparent to the skilled artisan and include amines, alcohols, carboxylic acids, and the like. Examples of preferred substituents include halo, cyano, R°, —OR$^{30}$, —CO$_2$R$^{31}$, —C(O)R°, C(O)N(R$^X$)$_2$, —OC(O)R°, (CH$_2$)$_n$CO$_2$R$^{31}$, O(CH$_2$)$_n$CO$_2$R$^{31}$, NHSO$_2$R°, NHC(O)NR$^X{}_2$, (CH$_2$)$_n$OR$^{30}$, O(CH$_2$)$_n$OR$^{30}$, (CH$_2$)$_n$C(O)N(R$^X$)$_2$, O(CH$_2$)$_n$C(O)N(R$^X$)$_2$; n is an integer from 1-4; R° is independently hydrogen, C$_{1-3}$ haloalkyl or a C$_{1-3}$ alkyl group; one R$^X$ is —H or C$_1$-C$_3$ alkyl and the other is an amine protecting group; R$^{30}$ is an alcohol protecting group; and R$^{31}$ is a carboxylic acid protecting group. Suitable protecting groups are well know in the art and are disclosed in, for example, in Greene and Wuts, "Protective Groups in Organic Synthesis", John Wiley & Sons (1991). The entire teachings of Greene and Wits are incorporated herein by reference. More commonly, Ar is a phenyl group.

Also encompassed within the present invention is the corresponding reaction with the enantiomer of the amino acid compound represented by Structural Formula (XII-A), thereby forming the enantiomer of the compound represented by Structural Formula (XI-A).

The reaction of the aryl amine and cyclic lactone above can be carried out in solvents in which both reagents are soluble. Examples include protic solvents (e.g., water and methanol) and polar aprotic solvents (dimethylformamide, dimethyl sulfoxide, hexamethylphosphoramide and the like). An excess of one reagent relative to the other can be used (e.g., up to a ten fold excess), however equimolar amounts are more typical. The reaction is typically carried out at the boiling point of the solvent being used, but can also commonly carried out at temperatures ranging from ambient temperature to temperatures as high as 200° C. Temperatures from 70° C. to 90° C. are most commonly used.

Another embodiment is a method of preparing an intermediate compound represented by Structural Formula (XIII-A) from the amino acid compound represented by Structural Formula (XI-A):

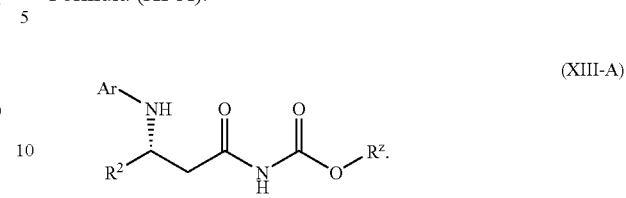

(XIII-A)

The method comprises the step of amidating the carboxylic acid group of the amino acid compound with NH$_2$C(O)OR$^Z$. The group —C(O)OR$^Z$ is an amine protecting group that taken together with —NH$_2$ forms a carbamate. Thus, R$^Z$ is a substituted or unsubstituted alkyl, allyl or aryl group. Substituents that can be present on the alkyl, allyl or aryl group represented by R$^Z$ are those which do not interfere in the reactions being carried and are readily recognizable to the skilled artisan. Examples include alkyl, halogen and alkoxy. Thus, suitable values for R$^Z$ are well known to the skilled artisan and are described, for example, in Green and Wuts, "Protective Groups in Organic Synthesis", John Wiley & Sons (1991). Specific examples include, but are not limited to, benzyl, methyl, ethyl, allyl, 2,2,2,-trichloromethyl, 2,2,2-trichloro-tert-butyl, tert-butyl or fluorenylmethyl.

The term "amidating a carboxylic acid with NH$_2$C(O)OR$^Z$" refers to converting a carboxylic acid (—COOH) to the amide —C(O)NHC(O)OR$^Z$ in one or more reaction steps. Many methods for converting a carboxylic acid to an amide are known in the art. Typically, the carboxylic acid is first converted into a group that is more readily displaced by an amine or amide than —OH. Thus, —OH is converted into a better leaving group. A "leaving group" is a group which can readily be displaced by a nucleophile. In the present invention, the amino acid compound can be converted directly to the intermediate compound by activating the carboxylic acid of the amino acid compound and then reacting with NH$_2$C(O)OR$^Z$. Alternatively, the carboxylic can be first be converted to carboxamide (—C(O)NH$_2$) by activating the carboxylic acid group of the amino acid compound and then reacting with NH$_3$ or a functional equivalent thereof (e.g., NH$_4$Cl) and then protecting the resulting carboxamide. When NH$_2$C(O)OR$^Z$ is used as a nucleophile, the amidation is preferably carried out in the presence of at least one equivalent of a non-nucleophilic base such as an alkoxide (lithium ter-butoxide, potassium tert-butoxide, ilithium isopropoxide and potassium isopropoxide) or amide base (e.g., lithium or potassium isopropylamide or hexamethylpiperidide).

In one example, —OH of the carboxylic acid is converted into a better leaving group by replacing it with a halogen, typically with chloride. The carboxylic acid is thereby converted into an acid halide, e.g., an acid chloride. Reagents suitable for preparing acid chlorides from carboxylic acids are well known in the art and include thionyl chloride, oxalyl chloride, phosphorus trichloride and phosphorus pentachloride. Typically, each carboxylic acid group is reacted with about one equivalent or a slight excess of thionyl chloride, oxalyl chloride, phosphorus trichloride and phosphorus pentachloride in an inert solvent such as an ethereal solvent (e.g., diethyl ether, tetrahydrofuran or 1,4-dioxane), a halogenated solvent (e.g., methylene chloride or 1,2-dichloroethane) or aromatic solvent (e.g., benzene or toluene). When oxalyl chloride is used, a tertiary amine is often added to accelerate the reaction in quantities ranging from a catalytic amount to about one equivalent relative to oxalyl chloride.

Alternatively, the carboxylic acid is first converted into an "activated ester". An ester —COOR is said to be "activated" when —OR is readily displaced by an amine or amide than —OH. —OR is more easily displaced as R becomes more electron withdrawing. Some activated esters are sufficiently stable that they can be isolated, e.g., esters wherein R is phenyl or substituted phenyl. For example, diphenylmalonate can be prepared from malonyl chloride and phenol, both commercially available from Aldrich Chemical Co., Milwaukee, Wis., by procedures described above Other activated esters are more reactive and are generally prepared and used in situ.

Formation of an activated ester in situ requires a "coupling agent", also referred to as a "carboxylic acid activating agent", which is a reagent that replaces the hydroxyl group of a carboxyl acid with a group which is susceptible to nucleophilic displacement. Examples of coupling agents include 1,1'-carbonyldiimidazole (CDI), isobutyl chloroformate, dimethylaminopropylethyl-carbodiimide (EDC), dicyclohexyl carbodiimide (DCC). When amidating by in situ generation of an activated ester, an excess of either the carboxylic acid or amine can be used (typically a 50% excess, more typically about a 10-15% excess). However, it is more common when carrying out the present invention to use equimolar amounts of both reagents. Generally, from about 1.0 equivalent to about 10 equivalents of coupling agent are used relative to each carboxylic acid group, preferably from about 1.0 equivalent to about 1.5 equivalents. When DCC is used, a weak acid such as 1-hydroxybenzotriazole (HOBt) is often added to accelerate the reaction. Typically, about between one to about 1.5 equivalents of HOBt relative to DCC is used, preferably between about one to about 1.2 equivalents. The reaction is generally carried out in inert, aprotic solvents, for example, halogenated solvents such as methylene chloride, dichloroethane and chloroform, ethereal solvents such as tetrahydrofuran, 1,4-dioxane and diethyl ether and dimethylformamide. Suitable reaction temperature generally range from between about 0° to about 100°, but the reaction is preferably carried out at ambient temperature.

Yet another embodiment of the present invention is a method of preparing a product compound represented by Structural Formula (XIV-A):

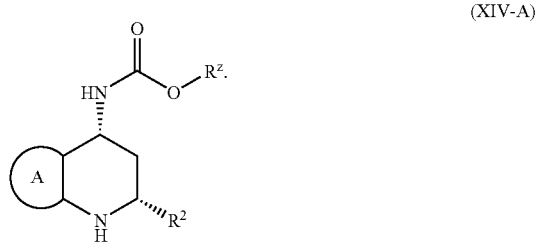

(XIV-A)

The method comprises the step of reducing the amide carbonyl of the intermediate compound to form a second intermediate and then cyclizing the second intermediate to form the product compound. The variables in Structural Formula (XIV-A) are as described above for Structural Formulas (XI-A)-(XIII-A). The "amide carbonyl" is understood to be the carbonyl between the methylene carbon and nitrogen atom and not the carbonyl that is bonded to both a nitrogen and oxygen atom.

To carry out the reduction step, a reducing agent is used which can reduces the amide carbonyl but not the carbamate group. Sodium borohydride together with a Lewis Acid such as magnesium chloride or calcium chloride is one common example. The reduction step is typically carried out in an alcoholic solvent such as methanol or ethanol. An excess of sodium borohydride and Lewis Acid of up to 50% can be used, but typically from 0.5 to 1.0 equivalents of sodium borohydride and 0.5 to 2.0 equivalents of Lewis Acid are used.

The cyclization step is carried out in dilute aqueous or alcoholic acid, using, for example, 0.1 N to 10 N HCl, $H_2SO_4$, $H_3PO_4$ or a sulfonic acid such as methane sulfonic acid, toluene sulfonic acid or phenyl sulfonic acid. More typically, between 0.8 N and 1.2 N acid is used. Commonly, an organic acid such acetic acid, benzoic acid, citric acid, and the like is also be present, for example between 0.5 equivalents to 10 equivalents. Typically, a co-solvent immiscible in water or alcohol is used. Common co-solvents include halogentated solvents such as dichloromethane or chloroform and ethereal solvents such as tetrahydrofuran and diethyl ether.

Another embodiment of the present invention is a method of preparing the product compound represented by Structural Formula (XIV-A) from the cyclic lactone represented by Structural Formula (XII-A). The method comprises combining the three reaction steps described above. Alternatively, the enantiomer of the compound represented by Structural Formula (XIV-A) is prepared using the same three reaction steps, provided, however, that the enantiomer of the starting lactone represented by Structural Formula (XII-A) is used.

Yet another embodiment of the present invention is a compound represented by any one of Structural Formulas (XI-A)-(XIV-A).

The invention is illustrated by the following examples which are not intended to be limiting in any way.

EXEMPLIFICATION

General. All reactions involving air-sensitive reagents were performed under a nitrogen atmosphere. Reagents were used as received from commercial suppliers unless otherwise noted. $^1$H NMR data were recorded using the Bruker UltraShield 300 MHz/54 mm instrument equipped with Bruker B-ACS60 Auto Sampler or the Varian 300 MHz instrument. Intermediates and final compounds were purified by flash chromatography using one of the following instruments: 1. Biotage 4-channel Quad UV Flash Collector equipped with a Quad 1 Pump Module and the Quad 12/25 Cartridge module. 2. Biotage 12-channel Quad UV Flash Collector equipped with a Quad 3 Pump Module and a Quad 3 Cartridge module. 3. ISCO combi-flash chromatography instrument. LC/MS spectra were obtained using a MicroMass Platform LC (Phenomenex C18 column, 5 micron, 50×4.6 mm) equipped with a Gilson 215 Liquid Handler. Standard LC/MS conditions is as follows:

| Formic acid-Standard conditions: | |
|---|---|
| % C (Water) | 95.0 |
| % D (Acetonitrile) | 5.0 |
| % Formic Acid | 0.1 |
| Flow (ml/min) | 3.500 |
| Stop Time (mins) | 4.4 |
| Min Pressure (bar) | 0 |
| Max Pressure (bar) | 400 |
| Oven Temperature Left (° C.) | 25.0 |
| Oven Temperature Right (° C.) | 25.0 |

-continued

HP1100 LC Pump Gradient Timetable
The gradient Timetable contains 5 entries which are:

| Time | A % | B % | C % | D % | Flow | Pressure |
|------|-----|-----|-----|-----|-------|----------|
| 0.00 | 0.0 | 0.0 | 95.0 | 5.0 | 3.500 | 400 |
| 3.50 | 0.0 | 0.0 | 0.0 | 100.0 | 3.500 | 400 |
| 4.30 | 0.0 | 0.0 | 0.0 | 100.0 | 3.500 | 400 |
| 4.40 | 0.0 | 0.0 | 95.0 | 5.0 | 4.000 | 400 |
| 5.00 | 0.0 | 0.0 | 95.0 | 5.0 | 4.000 | 400 |

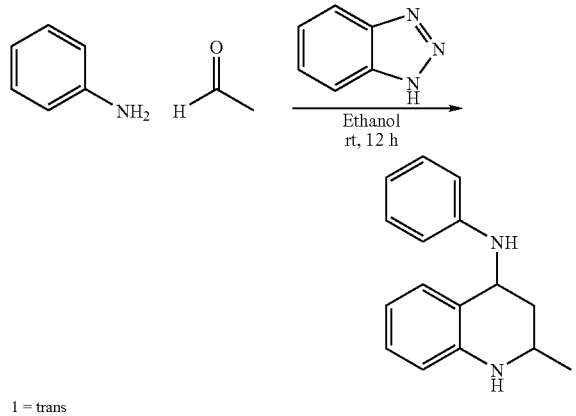

Scheme 1

1 = trans
2 = cis

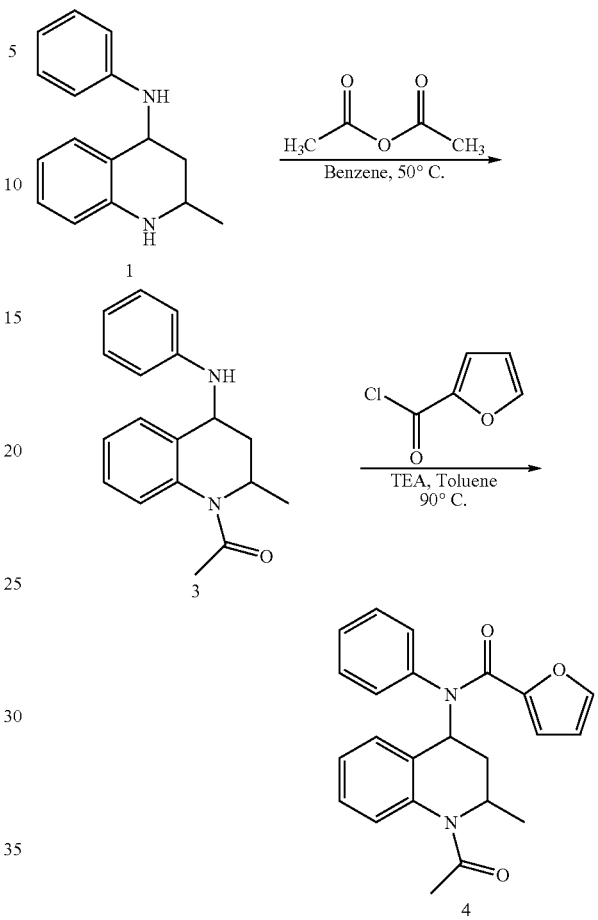

Scheme 2

(±)-Cis- and (±)-trans-(2-ethyl-1,2,3,4-tetrahydro-quinolin-4-yl)-phenyl-amine (1) & (2)

A 250 mL flask under nitrogen atmosphere was charged with aniline (1.0 g, 10.7 mmol, 1.0 equiv), acetaldehyde (0.599 mL, 10.7 mmol), benzotriazole (0.255 g, 2.1 mmol, 0.2 equiv) and dry toluene (100 mL) (Caution: an exotherm was observed). The precipitated benzotriazole/aldehyde adduct was observed immediately. The solution was allowed to stir at room temperature for 12 h. The precipitate that forms after stirring over night was filtered and washed with minimal diethyl ether, to afford the cis-isomer exclusively. The trans-isomer could be obtained by concentration of the filtrate. The residue was purified by Biotage flash system (95% hexane/5% diethyl ether) to yield the cis and trans isomers as a mixture. The resulting oily residue was then triturated with hexane to separate the cis isomer as a white solid and the filtrate was concentrated to give the trans isomer.

(±)-Cis-isomer—$^1$H-NMR (CDCl$_3$)δ: 1.24 (d, 3H), 1.52 (q, 1H), 2.38 (dddd, 1H), 3.63 (m, 1H), 3.75 (bs, 2H, —NH), 4.83 (dd, 1H), 6.51 (d, 1H), 6.68 (m, 4H), 7.05 (m, 1H), 7.19-7.26 (m, 2H), 7.39 (d, 1H).

(±)-Trans-isomer—$^1$H-NMR (CDCl$_3$)δ: 1.22 (d, 3H), 1.56 (m, 1H), 2.20 (dt, 1H), 3.4 (m, 1H), 3.89 (bs, 2H, —NH), 4.55 (dt, 1H), 6.56 (dd, 1H), 6.66-6.75 (m, 4H), 7.08 (m, 1H), 7.19-7.26 (m, 3H).

Cis-(±)-1-(2-methyl-4-phenylamino-3,4-dihydro-2H-quinolin-1-yl)-ethanone (3)

A 30 mL flask under nitrogen atmosphere was charged with (±)-cis-(2-methyl-1,2,3,4-tetrahydro-quinolin-4-yl)-phenyl-amine (0.520 g, 2.2 mmol, 1.0 equiv), and acetic anhydride (0.209 mL, 2.2 mmol, 1.0 equiv) and dry toluene (31 mL). The solution was heated to 50° C. for 15 h. The reaction mixture was evaporated in vacuo. The residue was purified by Biotage flash system (70% hexane/30% ethyl acetate) to yield the 2-acetyl cis isomers 67% yield.

$^1$H-NMR (CDCl$_3$)δ: 1.17 (d, 3H), 1.25 (q, 1H), 2.19 (s, 3H), 2.22 (bs, 1H), 2.65 (m, 1H), 4.21 (dd, 1H), 4.96 (m, 1H), 6.65 (d, 2H), 6.75 (t, 1H), 7.12-7.33 (m, 6H).

Cis-(±)-furan-2-carboxylic acid (1-acetyl-2-methyl-1,2,3,4-tetrahydro-quinolin-4-yl)-phenyl-amide (4)

A round bottom flask under nitrogen atmosphere was charged with cis-(2-methyl-4-phenylamino-3,4-dihydro-2H-quinolin-1-yl)-ethanone (0.163 g, 0.58 mmol, 1.0 equiv) and 2-furoyl chloride (0.285 mL, 2.9 mmol, 5.0 equ), pyridine (1.0 equiv.) and dry toluene (3 mL). The solution was heated to 90° C. for 15 h. The reaction mixture was evaporated in vacuo. The residue was purified by Biotage flash system (50% hexane/50% ethyl acetate) to yield the cis isomer 40% yield.

$^1$H-NMR (CDCl$_3$)δ: 1.08 (d, 3H), 1.63 (m, 1H), 2.14 (s, 3H), 2.2 (bs, 1H), 4.77 (m, 1H), 5.75 (bs, 1H), 6.23 (dd, 1H), 7.12-7.45 (m, 10H).

Scheme 3

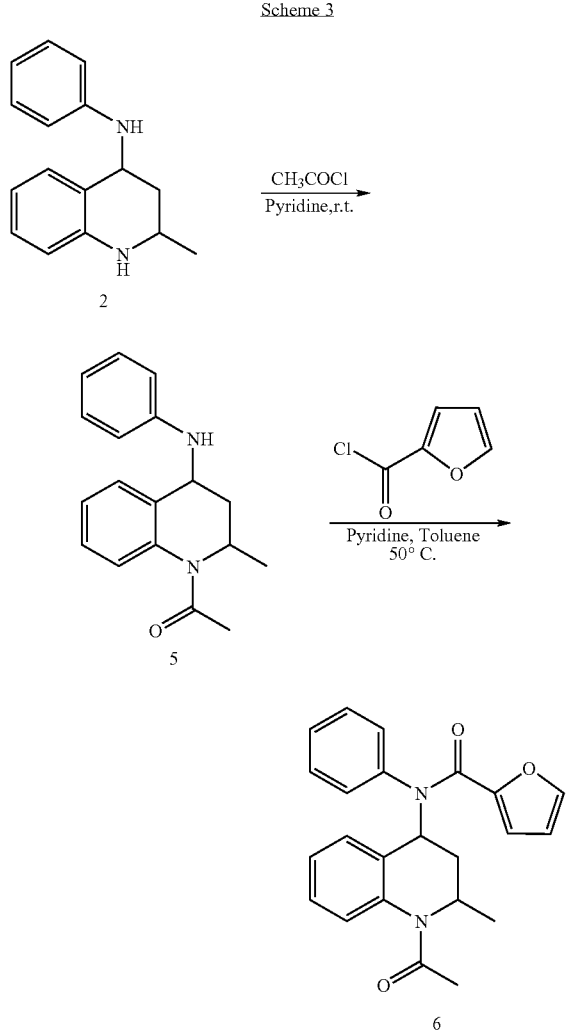

(±)-Trans-1-(2-Methyl-4-phenylamino-3,4-dihydro-2H-quinolin-1-yl)-ethanone (5)

A 30 mL flask under nitrogen atmosphere was charged with (±)-trans-(2-methyl-1,2,3,4-tetrahydro-quinolin-4-yl)-phenyl-amine (0.260 g, 1.1 mmol, 1.0 equiv) and acetyl chloride (0.075 mL, hexane/30% ethyl acetate to 60% hexane/40% ethyl acetate to 50% hexane/50% ethyl acetate) to yield the 2-acetyl trans isomers 35% yield.

$^1$H-NMR (CDCl$_3$)δ: 1.19 (d, 3H), 1.76 (m, 1H), 2.17 (s, 3H), 2.52 (dd, 1H), 4.60 (t, 1H), 4.93 (m, 1H), 6.67 (d, 2H), 6.71 (t, 1H), 7.13-7.36 (m, 6H), 7.41 (d, 1H).

(±)-Trans-furan-2-carboxylic acid (1-acetyl-2-methyl-1,2,3,4-tetrahydro-quinolin-4-yl)-phenyl-amide (6)

A round bottom flask under nitrogen atmosphere was charged with (±)-trans-1-(2-methyl-4-phenylamino-3,4-dihydro-2H-quinolin-1-yl)-ethanone (0.110 g, 0.39 mmol, 1.0 equiv) and 2-furoyl chloride (0.193 mL, 1.9 mmol, 5.0 equiv), pyridine (1.0 equ.) and dry toluene (5 mL). The solution was heated to 50° C. for 5 h. The reaction mixture was evaporated in vacuo. The residue was purified by Biotage flash system (30% hexane/70% ethyl acetate to 50% hexane/50% ethyl acetate) to yield the trans isomer 34% yield.

$^1$H-NMR (CDCl$_3$)δ: 1.11 (d, 3H), 1.76 (s, 3H), 2.07 (dd, 1H), 2.37 (m, 1H), 5.00 (m, 1H), 5.48 (d, 1H), 6.14 (dd, 1H), 6.29 (t, 1H), 6.90 (m, 1H), 6.99 (m, 1H), 7.22-7.32 (m, 6H), 7.34 (d, 1H), 7.54 (dd, 1H).

(±)-Cis-N-(1-Acetyl-2-methyl-1,2,3,4-tetrahydro-quinolin-4-yl)-4-fluoro-N-phenyl-benzamide (7)

A 30 mL flask under nitrogen atmosphere was charged with (±)-cis-(2-methyl-1,2,3,4-tetrahydro-quinolin-4-yl)-phenyl-amine (0.520 g, 2.2 mmol, 1.0 equiv) and acetic anhydride (0.209 mL, 2.2 mmol, 1.0 eq.) and dry toluene (31 mL). The solution was heated to 50° C. for 15 h. The reaction mixture was evaporated in vacuo. The residue was purified by Biotage flash system (70% hexane/30% ethyl acetate) to yield the 2-acetyl cis isomers 67% yield.

$^1$H-NMR (CDCl$_3$)δ: 1.17 (d, 3H), 1.25 (q, 1H), 2.19 (s, 3H), 2.22 (bs, 1H), 2.65 (m, 1H), 4.21 (dd, 1H), 4.96 (m, 1H), 6.65 (d, 2H), 6.75 (t, 1H), 7.12-7.33 (m, 6H).

A round bottom flask under nitrogen atmosphere was charged with (±)-cis-1-(2-methyl-4-phenylamino-3,4-dihydro-2H-quinolin-1-yl)-ethanone (1.0 equiv) and 2-fluorobenzoyl chloride (5.0 equ), pyridine (1.0 equ.) and dry toluene (3 mL). The solution was heated to 90° C. for 15 h. The reaction mixture was evaporated in vacuo. The residue was purified by Biotage flash system (50% hexane/50% ethyl acetate) to yield the cis isomer 40% yield.

$^1$H-NMR (CDCl$_3$)δ: 1.1 (3H, d), 1.2 (1H, m), 2.1 (3H, s), 2.1 (1H, m), 4.8 (1H, m), 5.4 (1H, m), 6.8 (2H, m), 6.9-7.4 (9H, m), 7.5 (1H, m).

MS m/z: 403 (M+1).

(±)-Trans-N-(1-Acetyl-2-methyl-1,2,3,4-tetrahydro-quinolin-4-yl)-4-fluoro-N-phenyl-benzamide (8)

A 30 mL flask under nitrogen atmosphere was charged with (±)-trans-(2-methyl-1,2,3,4-tetrahydro-quinolin-4-yl)-phenyl-amine (0.260 g, 1.1 mmol, 1.0 equiv) and acetyl chloride (0.075 mL, hexane/30% ethyl acetate to 60% hexane/40% ethyl acetate to 50% hexane/50% ethyl acetate) to yield the 2-acetyl trans isomers 35% yield.

$^1$H-NMR (CDCl$_3$)δ: 1.19 (d, 3H), 1.76 (m, 1H), 2.17 (s, 3H), 2.52 (dd, 1H), 4.60 (t, 1H), 4.93 (m, 1H), 6.67 (d, 2H), 6.71 (t, 1H), 7.13-7.36 (m, 6H), 7.41 (d, 1H).

A round bottom flask under nitrogen atmosphere was charged with (±)-trans-1-(2-methyl-4-phenylamino-3,4-dihydro-2H-quinolin-1-yl)-ethanone (1.0 equiv) and 4-fluorobenzoyl chloride (5.0 equ) pyridine (1.0 equ.) and dry toluene (5 mL). The solution was heated to 50° C. for 5 h. The reaction mixture was evaporated in vacuo. The residue was purified by Biotage flash system (30% hexane/70% ethyl acetate to 50% hexane/50% ethyl acetate) to yield the trans isomer 34% yield.

$^1$H-NMR (CDCl$_3$)δ: 1.2 (3H, d), 1.9 (3H, s), 2.0 (1H, m), 2.3 (1H, m), 5.0 (1H, m), 6.2 (1H, m), 6.6-6.8 (4H, m), 7.1 (3H, m), 7.3 (4H, m), 7.6 (1H, m).

MS m/z: 403 (M+1).

General Procedure A

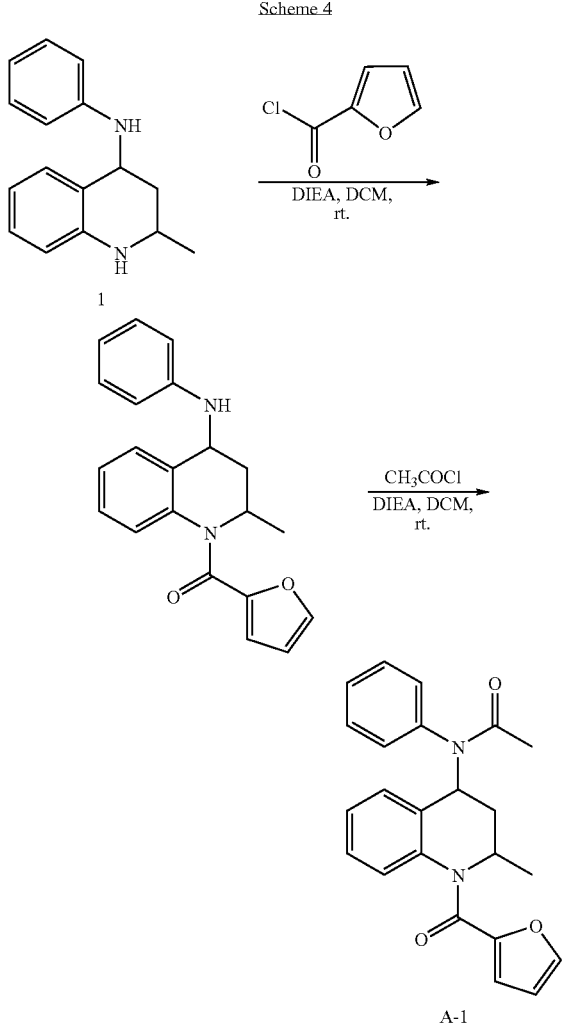

(±)-Cis-N-[1-(furan-2-carbonyl)-2-methyl-1,2,3,4-tetrahydro-quinolin-4-yl]-N-phenyl-acetamide (A-1)

To a solution of (±)-cis-(2-Methyl-1,2,3,4-tetrahydroquinolin-4-yl)-phenyl-amine (430 mg, 1.83 mmol) in dichloromethane (18 mL) at room temperature was added diisopropylethylamine (318 uL, 1.83 mmol) followed by 2-furoyl chloride. It was allowed to let stir at room temperature for 12 h. The mixture was poured into water and extracted with dichloromethane. The extracts were washed with 1 M(aq) NaOH and brine, dried over magnesium sulfate, filtered and concentrated. The crude residue was purified by silica gel chromatography (80% hexanes/20% ethyl acetate) to afford the amide (500 mg, 83 %).

To a solution of (±)-cis-furan-2-yl-(2-methyl-4-phenylamino-3,4-dihydro-2H-quinolin-1-yl)-methanone (360 mg, 1.0 mmol) in methylene chloride (5 mL) was added diisopropylethylamine (1.9 mL, 10 mmol) followed by acetyl chloride (388 uL, 5 mmol). The mixture was stirred at room temperature over night. The mixture was poured into water and extracted with dichloromethane. The extracts were washed with 1 M (aq) NaOH and brine, dried over magnesium sulfate, filtered and concentrated. The crude residue was purified by silica gel chromatography (50% hexanes/50% ethyl acetate) to afford the amide (230 mg, 57%).

$^1$H-NMR (CDCl$_3$)δ: 1.12 (d, 3H), 1.25 (t, 1H), 2.01 (s, 3H), 2.32 (m, 1H), 4.12 (sextet, 1H), 5.49 (bs, 1H), 6.22 (m, 2H), 6.84 (d, 1H), 7.10 (t, 1H), 7.28-7.31 (m, 4H), 7.38 (m, 4H).
MS m/z: 375 (M+1).

(±)-Cis-2-methoxy-N-[1-(3-methoxy-benzoyl)-2-methyl-1,2,3,4-tetrahydro-quinolin-4-yl]-N-phenyl-acetamide (A-2)

(±)-Cis-2-methoxy-N-[1-(3-methoxy-benzoyl)-2-methyl-1,2,3,4-tetrahydro-quinolin-4-yl]-N-phenyl-acetamide was made following general procedure A, substituting 3-methoxybenzoyl chloride for 2-furoyl chloride and methoxyacetyl chloride for acetyl chloride.

$^1$H-NMR (CDCl$_3$)δ: 1.14 (d, 3H), 1.25 (t, 1H), 2.33 (m, 1H), 3.39 (s, 3H), 3.60 (s, 3H), 3.85 (d, 1H), 3.98 (d, 1H), 4.79 (sextet, 1H), 5.62 (bs, 1H), 6.53 (d, 1H), 6.72 (s, 1H), 6.81 (d, 1H), 6.92 (t, 1H), 7.08 (t, 1H), 7.16 (t, 1H), 7.29 (m, 2H), 7.35-7.42 (m, 3H).
MS m/z: 445 (M+1).

(±)-Cis-4-chloro-N-[1-(3-methoxy-benzoyl)-2-methyl-1,2,3,4-tetrahydro-quinolin-4-yl]-N-phenyl-benzamide (A-3)

(±)-Cis-4-Chloro-N-[1-(3-methoxy-benzoyl)-2-methyl-1,2,3,4-tetrahydro-quinolin-4-yl]-N-phenyl-benzamide was made following general procedure A, substituting 3-methoxybenzoyl chloride for 2-furoyl chloride and 4-chlorobenzoyl chloride for acetyl chloride.

$^1$H-NMR (CDCl$_3$)δ: 1.24 (d, 3H), 1.26 (m, 1H), 2.29 (m, 1H), 3.60 (s, 3H), 4.84 (sextet, 1H), 5.92 (bs, 1H), 6.58 (d, 1H), 6.78 (d, 2H), 6.82 (s, 1H), 6.95 (t, 1H), 7.08 (t, 2H), 7.16-7.25 (m, 7H), 7.34 (d, 2H), 7.53 (d, 1H).
MS m/z: 511.0 (M+1).

(±)-Cis-N-[1-(3-Methoxy-benzoyl)-2-methyl-1,2,3,4-tetrahydro-quinolin-4-yl]-N-phenyl-isobutyramide (A-4)

(±)-Cis-N-[1-(3-methoxy-benzoyl)-2-methyl-1,2,3,4-tetrahydro-quinolin-4-yl]-N-phenyl-isobutyramide was made following general procedure A, substituting 3-methoxybenzoyl chloride for 2-furoyl chloride and isobutyryl chloride for acetyl chloride.

$^1$H-NMR (CDCl$_3$)δ: 1.14 (d, 9H), 1.23 (t, 1H), 2.28 (m, 1H), 2.65 (sextet, 1H), 3.65 (s, 3H), 4.77 (sextet, 1H), 5.63 (bs, 1H), 6.51 (d, 1H), 6.67 (d, 1H), 6.78 (d, 1H), 6.86 (m, 2H), 7.01 (t, 1H), 7.14 (t, 1H), 7.24-7.37 (m, 6H).
MS m/z: 443.0 (M+1).

(±)-Cis-N-[2-Methyl-1-(thiophene-2-carbonyl)-1,2,3,4-tetrahydro-quinolin-4-yl]-N-phenyl-acetamide (A-5)

(±)-Cis-N-[2-methyl-1-(thiophene-2-carbonyl)-1,2,3,4-tetrahydro-quinolin-4-yl]-N-phenyl-acetamide was made following general procedure A, substituting 2-thiophene carbonyl chloride for 2-furoyl chloride.

(±)-Cis-N-[2-methyl-1-(thiophene-2-carbonyl)-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-N-[2-methyl-1-(thiophene-2-carbonyl)-1,2,3,4-tetrahydro-quinolin-4-yl]-N-phenyl-acetamide (A-11 & A-10, respectively).

$^1$H-NMR (CDCl$_3$)δ: 1.15 (d, 3H), 1.25 (m, 1H), 2.02 (s, 3H), 2.31 (m, 1H), 4.73 (sextet, 1H), 5.53 (bs, 1H), 6.68 (dd, 1H), 6.77 (t, 1H), 6.88 (d, 1H), 7.06 (t, 1H), 7.25-7.32 (m, 4H), 7.39 (m, 4H).

MS m/z: 391.0 (M+1).

(±)-Cis-N-[1-(4-tert-butyl-benzoyl)-2-methyl-1,2,3,4-tetrahydro-quinolin-4-yl]-N-phenyl-acetamide (A-6)

(±)-Cis-N-[1-(4-tert-butyl-benzoyl)-2-methyl-1,2,3,4-tetrahydro-quinolin-4-yl]-N-phenyl-acetamide was made following general procedure A, substituting 4-tert-butylbenzoyl chloride for 2-furoyl chloride.

(±)-Cis-N-[1-(4-tert-butyl-benzoyl)-2-methyl-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[1-(4-tert-butyl-benzoyl)-2-methyl-1,2,3,4-tetrahydro-quinolin-4-yl]-N-phenyl-acetamide (A-8 & A-9, respectively).

$^1$H-NMR (CDCl$_3$)δ: 1.14 (d, 3H), 1.16 (m, 1H), 1.23 (s, 9H), 2.04 (s, 3H), 2.33 (m, 1H), 4.78 (sextet, 1H), 5.62 (bs, 1H), 6.53 (d, 1H), 6.91 (t, 1H), 7.15-7.40 (m, 11H).

MS m/z: 441 (M+1).

(±)-Cis-N-[1-(4-fluoro-benzoyl)-2-methyl-1,2,3,4-tetrahydro-quinolin-4-yl]-N-phenyl-acetamide (A-7)

(±)-Cis-N-[1-(4-fluoro-benzoyl)-2-methyl-1,2,3,4-tetrahydro-quinolin-4-yl]-N-phenyl-acetamide was made following general procedure A, substituting 4-fluorobenzoyl chloride for 2-furoyl chloride.

(±)-Cis-N-[1-(4-fluoro-benzoyl)-2-methyl-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[1-(4-fluoro-benzoyl)-2-methyl-1,2,3,4-tetrahydro-quinolin-4-yl]-N-phenyl-acetamide (A-52 & A-44, respectively).

$^1$H-NMR (CDCl$_3$)δ: 1.13 (d, 3H), 1.25 (m, 1H), 2.03 (s, 3H), 2.32 (m, 1H), 4.78 (sextet, 1H), 5.62 (bs, 1H), 6.47 (d, 1H), 6.83-6.95 (m, 3H), 7.16-7.40 (m, 9H).

MS m/z: 403 (M+1).

(±)-Cis-N-[2-methyl-1-(5-methyl-thiophene-2-carbonyl)-1,2,3,4-tetrahydro-quinolin-4-yl]-N-phenyl-acetamide (A-12)

(±)-Cis-N-[2-methyl-1-(5-methyl-thiophene-2-carbonyl)-1,2,3,4-tetrahydro-quinolin-4-yl]-N-phenyl-acetamide was made following general procedure A, substituting 5-methyl-2-thiophenecarbonyl chloride for 2-furoyl chloride.

(±)-Cis-N-[2-methyl-1-(5-methyl-thiophene-2-carbonyl)-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[2-methyl-1-(5-methyl-thiophene-2-carbonyl)-1,2,3,4-tetrahydro-quinolin-4-yl]-N-phenyl-acetamide (A-59 & A-60, respectively).

$^1$H-NMR (CDCl$_3$)δ: 1.07 (m, 1H), 1.12 (d, 3H), 2.01 (s, 3H), 2.31 (m, 1H), 2.39 (s, 3H), 4.69 (sextet, 1H), 5.50 (bs, 1H), 6.44 (s, 1H), 6.51 (d, 1H), 6.94 (d, 1H), 7.09 (t, 1H), 7.21-7.30 (m, 3H), 7.39-7.41 (m, 4H).

MS m/z: 405 (M+1)

(±)-Cis-N-[2-methyl-1-(4-methyl-2-pyrazin-2-yl-thiazole-5-carbonyl)-1,2,3,4-tetrahydro-quinolin-4-yl]-N-phenyl-acetamide (A-13)

(±)-Cis-N-[2-ethyl-1-(4-methyl-2-pyrazin-2-yl-thiazole-5-carbonyl)-1,2,3,4-tetrahydro-quinolin-4-yl]-N-phenyl-acetamide was made following general procedure A, substituting 4-methyl-2-(2-pyrazinyl)-1,3-thiazole-5-carbonyl chloride for 2-furoyl chloride.

$^1$H-NMR (CDCl$_3$)δ: 1.18 (d, 3H), 1.77 (bs, 1H), 2.03 (s, 3H), 2.10 (s, 3H), 2.32 (m, 1H), 4.79 (sextet, 1H), 5.50 (bs, 1H), 6.74 (d, 1H), 7.03 (t, 1H), 7.26-7.41 (m, 7H), 8.55 (d, 1H), 9.32 (s, 1H).

MS m/z: 484 (M+1).

(±)-Cis-N-[2-methyl-1-(3-methyl-thiophene-2-carbonyl)-1,2,3,4-tetrahydro-quinolin-4-yl]-N-phenyl-acetamide (A-14)

(±)-Cis-N-[2-methyl-1-(3-methyl-thiophene-2-carbonyl)-1,2,3,4-tetrahydro-quinolin-4-yl]-N-phenyl-acetamide was made following general procedure A, substituting 3-methyl-2-thiophenecarbonyl chloride for 2-furoyl chloride.

$^1$H-NMR (CDCl$_3$)δ: 1.13 (d, 3H), 1.16 (m, 1H), 1.80 (s, 3H), 2.00 (s, 3H), 2.29 (m, 1H), 4.73 (sextet, 1H), 5.49 (bs, 1H), 6.56 (d, 1H), 6.66 (d, 1H), 6.97 (t, 1H), 7.16 (d, 2H), 7.25 (d, 2H), 7.32 (d, 1H), 7.38 (bs, 3H).

MS m/z: 405 (M+1).

(±)-Cis-N-[2-methyl-1-(5-phenyl-thiophene-2-carbonyl)-1,2,3,4-tetrahydro-quinolin-4-yl]-N-phenyl-acetamide (A-15)

(±)-Cis-N-[2-methyl-1-(5-phenyl-thiophene-2-carbonyl)-1,2,3,4-tetrahydro-quinolin-4-yl]-N-phenyl-acetamide was made following general procedure A, substituting 5-phenyl-2-thiophenecarbonyl chloride for 2-furoyl chloride.

$^1$H-NMR (CDCl$_3$)δ: 1.15 (d, 3H), 1.17 (m, 1H), 2.03 (s, 3H), 2.31 (m, 1H), 4.73 (sextet, 1H), 5.55 (bs, 1H), 6.59 (s, 1H), 6.95 (d, 2H), 6.99 (s, 1H), 7.10 (t, 1H), 7.26-7.44 (m, 9H), 7.53 (d, 2H).

MS m/z: 467 (M+1).

(±)-Cis-N-[2-methyl-1-(4-methyl-2-phenyl-thiazole-5-carbonyl)-1,2,3,4-tetrahydro-quinolin-4-yl]-N-phenyl-acetamide (A-16)

(±)-Cis-N-[2-methyl-1-(4-methyl-2-phenyl-thiazole-5-carbonyl)-1,2,3,4-tetrahydro-quinolin-4-yl]-N-phenyl-acetamide was made following general procedure A, substituting 4-methyl-2-phenyl-1,3-thiazole-5-carbonyl chloride for 2-furoyl chloride.

$^1$H-NMR (CDCl$_3$)δ: 1.16 (d, 3H), 1.18 (m, 1H), 2.03 (s, 3H), 2.14 (s, 3H), 2.32 (m, 1H), 4.74 (sextet, 1H), 5.53 (bs, 1H), 6.77 (d, 2H), 7.04 (t, 1H), 7.24-7.28 (m, 3H), 7.38-7.40 (m, 7H), 7.83 (d, 2H).

MS m/z: 482 (M+1).

(±)-Cis-N-[2-methyl-1-(4-methyl-[1,2,3]thiadiazole-5-carbonyl)-1,2,3,4-tetrahydro-quinolin-4-yl]-N-phenyl-acetamide (A-17)

(±)-Cis-N-[2-methyl-1-(4-methyl-[1,2,3]thiadiazole-5-carbonyl)-1,2,3,4-tetrahydro-quinolin-4-yl]-N-phenyl-acetamide was made following general procedure A, substituting 4-methyl-[1,2,3]thiadiazole-5-carbonyl chloride for 2-furoyl chloride.

¹H-NMR (CDCl₃)δ: 1.17 (d, 3H), 1.21 (m, 1H), 2.01 (s, 3H), 2.36 (s, 3H), 2.24 (m, 1H), 4.81 (sextet, 1H), 5.48 (bs, 1H), 6.52 (d, 1H), 6.98 (t, 1H), 7.22-7.26 (m, 3H), 7.37-7.42 (m, 4H).

MS m/z: 407 (M+1).

(±)-Cis-N-[1-(5-isopropyl-thiophene-2-carbonyl)-2-methyl-1,2,3,4-tetrahydro-quinolin-4-yl]-N-phenyl-acetamide (A-19)

(±)-Cis-N-[1-(5-isopropyl-thiophene-2-carbonyl)-2-methyl-1,2,3,4-tetrahydro-quinolin-4-yl]-N-phenyl-acetamide was made following general procedure A, substituting 5-isopropylthiophene carbonyl chloride for 2-furoyl chloride.

¹H-NMR (CDCl₃)δ: 1.11 (d, 3H), 1.15 (m, 1H), 1.19-1.25 (m, 6H), 2.01 (s, 3H), 2.30 (m, 1H), 2.70 (m, 1H), 4.69 (sextet, 1H), 5.51 (bs, 1H), 6.45 (s, 1H), 6.55 (s, 1H), 6.87-6.95 (m, 1H), 7.04-7.08 (m, 1H), 7.27 (s, 3H), 7.38 (s, 4H).

MS m/z: 433 (M+1).

(±)-Cis-N-[2-methyl-1-(3,4,5-trifluoro-benzoyl)-1,2,3,4-tetrahydro-quinolin-4-yl]-N-phenyl-acetamide (A-20)

(±)-Cis-N-[2-methyl-1-(3,4,5-trifluoro-benzoyl)-1,2,3,4-tetrahydro-quinolin-4-yl]-N-phenyl-acetamide was made following general procedure A, substituting 3,4,5-trifluorobenzoyl chloride for 2-furoyl chloride.

¹H-NMR (CDCl₃)δ: 1.12 (d, 3H), 1.21 (m, 1H), 2.03 (s, 3H), 2.31 (m, 1H), 4.71 (sextet, 1H), 5.55 (bs, 1H), 6.50 (d, 1H), 6.82 (t, 1H), 6.99 (t, 1H), 7.06 (t, 1H), 7.24-7.27 (m, 3H), 7.39 (m, 3H), 7.46 (d, 1H).

MS m/z: 439 (M+1).

(±)-Cis-N-[1-(4-fluoro-3-methyl-benzoyl)-2-methyl-1,2,3,4-tetrahydro-quinolin-4-yl]-N-phenyl-acetamide (A-21)

(±)-Cis-N-[1-(4-fluoro-3-methyl-benzoyl)-2-methyl-1,2,3,4-tetrahydro-quinolin-4-yl]-N-phenyl-acetamide was made following general procedure A, substituting 4-fluoro-3-methyl benzoyl chloride for 2-furoyl chloride.

¹H-NMR (CDCl₃)δ: 1.12 (d, 3H), 1.22 (m, 1H), 2.04 (s, 3H), 2.15 (s, 3H), 2.29 (m, 1H), 4.75 (sextet, 1H), 5.60 (bs, 1H), 6.50 (d, 1H), 6.73 (t, 1H), 6.86 (s, 1H), 6.93 (t, 1H), 7.15-7.39 (m, 8H).

MS m/z: 417 (M+1).

(±)-Cis-N-[1-(4-fluoro-3-trifluoromethyl-benzoyl)-2-methyl-1,2,3,4-tetrahydro-quinolin-4-yl]-N-phenyl-acetamide (A-22)

(±)-Cis-N-[1-(4-fluoro-3-trifluoromethyl-benzoyl)-2-methyl-1,2,3,4-tetrahydro-quinolin-4-yl]-N-phenyl-acetamide was made following general procedure A, substituting 4-fluoro-3-(trifluoromethyl)-benzoyl chloride for 2-furoyl chloride.

¹H-NMR (CDCl₃)δ: 1.15 (d, 3H), 1.24 (m, 1H), 2.04 (s, 3H), 2.33 (m, 1H), 4.75 (sextet, 1H), 5.58 (bs, 1H), 6.46 (d, 1H), 6.87-6.96 (m, 3H), 7.10-7.41 (m, 6H), 7.49 (d, 1H), 7.74 (d, 1H).

MS m/z: 471 (M+1).

(±)-Cis-N-[1-(3-chloro-4-fluoro-benzoyl)-2-methyl-1,2,3,4-tetrahydro-quinolin-4-yl]-N-phenyl-acetamide (A-23)

(±)-Cis-N-[1-(3-chloro-4-fluoro-benzoyl)-2-methyl-1,2,3,4-tetrahydro-quinolin-4-yl]-N-phenyl-acetamide was made following general procedure A, substituting 3-chloro-4-fluorobenzoyl chloride for 2-furoyl chloride.

¹H-NMR (CDCl₃)δ: 1.13 (d, 3H), 1.24 (m, 1H), 2.04 (s, 3H), 2.31 (m, 1H), 4.76 (sextet, 1H), 5.59 (bs, 1H), 6.50 (d, 1H), 6.85 (d, 2H), 6.96 (t, 1H), 7.21 (t, 1H), 7.27 (m, 2H), 7.39 (m, 4H), 7.50 (d, 1H).

MS m/z: 437 (M+1).

(±)-Cis-N-[2-methyl-1-(2,4,6-trifluoro-benzoyl)-1,2,3,4-tetrahydro-quinolin-4-yl]-N-phenyl-acetamide (A-24)

(±)-Cis-N-[2-methyl-1-(2,4,6-trifluoro-benzoyl)-1,2,3,4-tetrahydro-quinolin-4-yl]-N-phenyl-acetamide was made following general procedure A, substituting 2,4,6-trifluorobenzoyl chloride for 2-furoyl chloride.

¹H-NMR (CDCl₃)δ: 1.13 (d, 3H), 1.21 (m, 1H), 2.05 (s, 3H), 2.29 (m, 1H), 4.86 (sextet, 1H), 5.45 (bs, 1H), 6.35 (t, 1H), 6.70 (d, 2H), 6.95 (t, 1H), 7.2-7.5 (m, 7H).

MS m/z: 439 (M+1).

(±)-Cis-N-[1-(4-chloro-benzoyl)-2-methyl-1,2,3,4-tetrahydro-quinolin-4-yl]-N-phenyl-propionamide (A-25)

(±)-Cis-N-[1-(4-chloro-benzoyl)-2-methyl-1,2,3,4-tetrahydro-quinolin-4-yl]-N-phenyl-propionamide was made following general procedure A, substituting 4-chlorobenzoyl chloride for 2-furoyl chloride and propionyl chloride for acetyl chloride.

¹H-NMR (CDCl₃)δ: 1.09 (t, 3H), 1.12 (d, 3H), 1.22 (m, 1H), 2.23 (m, 3H), 4.73 (sextet, 1H), 5.58 (bs, 1H), 6.46 (d, 1H), 6.78 (d, 1H), 6.88 (t, 1H), 6.98 (t, 1H), 7.15 (t, 1H), 7.18-7.44 (m, 8H).

MS m/z: 433 (M+1).

(±)-Cis-N-[2-methyl-1-(4-trifluoromethoxy-benzoyl)-1,2,3,4-tetrahydro-quinolin-4-yl]-N-phenyl-acetamide (A-26)

(±)-Cis-N-[2-methyl-1-(4-trifluoromethoxy-benzoyl)-1,2,3,4-tetrahydro-quinolin-4-yl]-N-phenyl-acetamide was made following general procedure A, substituting 4-(trifluoromethoxy)benzoyl chloride for 2-furoyl chloride.

¹H-NMR (CDCl₃)δ: 1.16 (d, 3H), 1.24 (m, 1H), 2.28 (m, 3H), 4.78 (sextet, 1H), 5.61 (bs, 1H), 6.46 (d, 1H), 6.91 (t, 1H), 6.92 (t, 1H), 7.02 (d, 2H), 7.18 (t, 1H), 7.23-7.27 (m, 4H), 7.33 (d, 1H), 7.39 (s, 3H).

MS m/z: 469 (M+1).

(±)-Cis-N-[2-methyl-1-(3-trifluoromethoxy-benzoyl)-1,2,3,4-tetrahydro-quinolin-4-yl]-N-phenyl-acetamide (A-27)

(±)-Cis-N-[2-methyl-1-(3-trifluoromethoxy-benzoyl)-1,2,3,4-tetrahydro-quinolin-4-yl]-N-phenyl-acetamide was made following general procedure A, substituting 3-(trifluoromethoxy)benzoyl chloride for 2-furoyl chloride.

¹H-NMR (CDCl₃)δ: 1.14 (t, 3H), 1.15 (d, 3H), 1.25 (m, 1H), 2.25 (m, 3H), 4.78 (sextet, 1H), 5.59 (bs, 1H), 6.46 (d, 1H), 6.91 (t, 1H), 6.95 (d, 1H), 7.12-7.27 (m, 6H), 7.34 (d, 1H), 7.39 (s, 3H).

MS m/z: 469 (M+1).

(±)-Cis-N-[2-methyl-1-(3-phenyl-isoxazole-5-carbonyl)-1,2,3,4-tetrahydro-quinolin-4-yl]-N-phenyl-propionamide (A-28)

(±)-Cis-N-[2-methyl-1-(3-phenyl-isoxazole-5-carbonyl)-1,2,3,4-tetrahydro-quinolin-4-yl]-N-phenyl-propionamide was made following general procedure A, substituting 3-phenyl-5-isoxazole carbonyl chloride for 2-furoyl chloride and propionyl chloride for acetyl chloride.

¹H-NMR (CDCl₃)δ: 1.14 (t, 3H), 1.19 (d, 3H), 1.61 (m, 1H), 2.24 (m, 3H), 4.78 (sextet, 1H), 5.49 (bs, 1H), 6.34 (bs, 1H), 6.85 (d, 1H), 7.10 (t, 1H), 7.26 (s, 3H), 7.32 (t, 1H), 7.40 (m, 6H), 7.67 (s, 2H).

MS m/z: 466 (M+1).

(±)-Cis-N-{2-methyl-1-[4-(5-methyl-tetrazol-1-yl)-benzoyl]-1,2,3,4-tetrahydro-quinolin-4-yl}-N-phenyl-propionamide (A-29)

(±)-Cis-N-{2-methyl-1-[4-(5-methyl-tetrazol-1-yl)-benzoyl]-1,2,3,4-tetrahydro-quinolin-4-yl}-N-phenyl-propionamide was made following general procedure A, substituting 4-(5-methyl-1H-tetrazole-1-yl)-benzoyl chloride for 2-furoyl chloride and propionyl chloride for acetyl chloride.

¹H-NMR (CDCl₃)δ: 1.16 (t, 3H), 1.17 (d, 3H), 1.24 (m, 1H), 2.26 (m, 3H), 2.55 (s, 3H), 4.82 (sextet, 1H), 5.64 (bs, 1H), 6.50 (d, 1H), 6.94 (t, 1H), 7.21-7.41 (m, 11H).

MS m/z: 481 (M+1).

(±)-Cis-N-{1-[3-(4-chloro-phenyl)-isoxazole-5-carbonyl]-2-methyl-1,2,3,4-tetrahydro-quinolin-4-yl}-N-phenyl-propionamide (A-30)

(±)-Cis-N-{1-[3-(4-chloro-phenyl)-isoxazole-5-carbonyl]-2-methyl-1,2,3,4-tetrahydro-quinolin-4-yl}-N-phenyl-propionamide was made following general procedure A substituting 3-(4-chlorophenyl)-5-isoxazole carbonyl chloride for 2-furoyl chloride and propionyl chloride for acetyl chloride.

¹H-NMR (CDCl₃)δ: 1.21 (m, 6H), 1.24 (m, 1H), 2.23 (m, 3H), 4.76 (sextet, 1H), 5.48 (bs, 1H), 6.28 (s, 1H), 6.84 (d, 1H), 7.07 (m, 2H), 7.26-7.67 (m, 7H), 7.78 (d, 1H), 8.03 (t, 2H).

MS m/z: 500 (M+1).

(±)-Cis-N-[1-(4-fluoro-benzoyl)-2-methyl-1,2,3,4-tetrahydro-quinolin-4-yl]-2-hydroxy-N-phenyl-acetamide (A-31)

(±)-N-[1-(4-fluoro-benzoyl)-2-methyl-1,2,3,4-tetrahydro-quinolin-4-yl]-2-hydroxy-N-phenyl-acetamide was made following general procedure A substituting 4-fluorobenzoyl chloride for 2-furoyl chloride and acetoxyacetyl chloride for acetyl chloride.

¹H-NMR (CDCl₃)δ: 1.13 (d, 3H), 1.22 (m, 1H), 2.39 (m, 1H), 3.42 (s, 1H), 3.85 (d, 1H), 4.04 (d, 1H), 4.77 (sextet, 1H), 5.54 (bs, 1H), 6.49 (d, 1H), 6.85 (t, 2H), 6.94 (t, 1H), 7.18-7.27 (m, 5H), 7.33 (d, 1H), 7.43 (s, 3H).

MS m/z: 419 (M+1).

(±)-Cis-N-[1-(1H-indole-2-carbonyl)-2-methyl-1,2,3,4-tetrahydro-quinolin-4-yl]-N-phenyl-propionamide (A-32)

(±)-Cis-N-[1-(1H-indole-2-carbonyl)-2-methyl-1,2,3,4-tetrahydro-quinolin-4-yl]-N-phenyl-propionamide was made following general procedure A substituting indole-2-carbonyl chloride for 2-furoyl chloride and propionyl chloride for acetyl chloride.

¹H-NMR (CDCl₃)δ: 1.25 (t, 3H), 1.26 (d, 3H), 1.27 (m, 1H), 2.36 (m, 3H), 4.86 (sextet, 1H), 5.62 (bs, 1H), 5.95 (s, 1H), 7.11 (t, 1H), 7.18 (t, 2H), 7.29 (t, 1H), 7.37 (m, 4H), 7.44-7.55 (m, 5H).

MS m/z: 438 (M+1).

(±)-Cis-N-[2-methyl-1-(4-pyrazol-1-yl-benzoyl)-1,2,3,4-tetrahydro-quinolin-4-yl]-N-phenyl-propionamide (A-33)

(±)-Cis-N-[2-methyl-1-(4-pyrazol-1-yl-benzoyl)-1,2,3,4-tetrahydro-quinolin-4-yl]-N-phenyl-propionamide was made following general procedure A substituting 4-(1H-pyrazol-1-yl)-benzoyl chloride for 2-furoyl chloride and propionyl chloride for acetyl chloride.

¹H-NMR (CDCl₃)δ: 1.03 (t, 3H), 1.11 (d, 3H), 1.20 (m, 1H), 2.19 (m, 3H), 4.73 (sextet, 1H), 5.62 (bs, 1H), 6.39 (s, 1H), 6.48 (d, 1H), 6.86 (t, 1H), 7.10-7.34 (m, 9H), 7.48 (d, 2H), 7.65 (s, 1H), 7.81 (s, 1H).

MS m/z: 465 (M+1).

(±)-Cis-N-[1-(benzofuran-2-carbonyl)-2-methyl-1,2,3,4-tetrahydro-quinolin-4-yl]-N-phenyl-propionamide (A-34)

(±)-Cis-N-[1-(benzofuran-2-carbonyl)-2-methyl-1,2,3,4-tetrahydro-quinolin-4-yl]-N-phenyl-propionamide was made following general procedure A substituting 2-benzofuran carbonyl chloride for 2-furoyl chloride and propionyl chloride for acetyl chloride.

¹H-NMR (CDCl₃)δ: 1.04 (t, 3H), 1.07 (d, 3H), 1.18 (m, 1H), 2.19 (m, 3H), 4.69 (sextet, 1H), 5.54 (bs, 1H), 6.41 (d, 1H), 6.70-7.39 (m, 12H), 7.43 (d, 1H).

MS m/z: 439 (M+1).

(±)-Cis-N-[1-(3-chloro-benzoyl)-2-methyl-1,2,3,4-tetrahydro-quinolin-4-yl]-N-phenyl-propionamide (A-35)

(±)-Cis-N-[1-(3-chloro-benzoyl)-2-methyl-1,2,3,4-tetrahydro-quinolin-4-yl]-N-phenyl-propionamide was following general procedure A made substituting 3-chlorobenzoyl chloride for 2-furoyl chloride and propionyl chloride for acetyl chloride.

¹H-NMR (CDCl₃)δ: 1.09 (t, 3H), 1.12 (d, 3H), 1.22 (m, 1H), 2.23 (m, 3H), 4.73 (sextet, 1H), 5.58 (bs, 1H), 6.46 (d, 1H), 6.78 (d, 1H), 6.88 (t, 1H), 6.98 (t, 1H), 7.15 (t, 1H), 7.18-7.44 (m, 8H).

MS m/z: 433 (M+1).

(±)-Cis-{4-[2-methyl-4-(phenyl-propionyl-amino)-3,4-dihydro-2H-quinoline-1-carbonyl]-phenoxy}-acetic acid ethyl ester (A-36)

(±)-Cis-{4-[2-methyl-4-(phenyl-propionyl-amino)-3,4-dihydro-2H-quinoline-1-carbonyl]-phenoxy}-acetic acid ethyl ester was made from (±)-N-[1-(4-Hydroxy-benzoyl)-2-methyl-1,2,3,4-tetrahydro-quinolin-4-yl]-N-phenyl-propionamide. (±)-N-[1-(4-Methoxy-benzoyl)-2-methyl-1,2,3,4-tetrahydro-quinolin-4-yl]-N-phenyl propionamide (0.147 g) was dissolved in DMF (5 mL) at room temperature. Sodium hydride (60% in oil, 0.021 g) was added and the mixture allowed to stir 30 min. Ethyl 4-bromoacetate (0.065 g) was added and the reaction was allowed to stir over night. Ethanol was added and the reaction was concentrated in vacuo. The crude residue was purified by silica gel chromatography (80/20 hexanes/ethyl acetate-50/50 hexanes ethyl acetate gradient) to afford the product (130 mg, 73%).

$^1$H-NMR (CDCl$_3$)δ: 1.08-1.16 (m, 9H), 1.21 (t, 1H), 2.24 (m, 3H), 4.09 (q, 2H), 4.53 (s, 2H), 4.74 (sextet, 1H), 5.59 (bs, 1H), 6.48 (d, 1H), 6.67 (d, 2H), 6.89 (t, 1H), 7.11-7.37 (m, 9H).

MS m/z: 500 (M+1).

(±)-Cis-N-[1-(4-hydroxy-benzoyl)-2-methyl-1,2,3,4-tetrahydro-quinolin-4-yl]-N-phenyl-propionamide (A-37)

(±)-Cis-N-[1-(4-hydroxy-benzoyl)-2-methyl-1,2,3,4-tetrahydro-quinolin-4-yl]-N-phenyl-propionamide was made from (±)-cis-N-[1-(4-methoxy-benzoyl)-2-methyl-1,2,3,4-tetrahydro-quinolin-4-yl]-N-phenyl-propionamide substituting 3-chlorobenzoyl chloride. (±)-Cis-N-[1-(4-methoxy-benzoyl)-2-methyl-1,2,3,4-tetrahydro-quinolin-4-yl]-N-phenyl-propionamide was (0.548 g, 0.001 mol) was dissolved in dichloromethane and a solution of BBr$_3$ (1.0 M in dichloromethane, 10 mL) was added; the reaction was allowed to stir at room temperature for 4 h or until no starting material remained. The reaction was carefully washed with sat NaHCO$_3$ and brine. The organics were dried over MgSO$_4$, filtered and concentrated under reduced pressure. The phenol was concentrated and the residue was purified by Biotage flash chromatography using 100% EtOAc to give a white solid, 68% yield.

$^1$H-NMR (CDCl$_3$)δ: 1.09 (d, 3H), 1.11 (t, 3H), 1.19 (m, 1H), 2.26 (m, 3H), 4.74 (sextet, 1H), 5.54 (bs, 1H), 6.46 (d, 1H), 6.53 (d, 1H), 6.96 (t, 1H), 7.14-7.40 (m, 9H).

MS m/z: 415 (M+1)

(±)-Cis-N-[1-(4-methoxy-benzoyl)-2-methyl-1,2,3,4-tetrahydro-quinolin-4-yl]-N-phenyl-propionamide (A-38)

(±)-Cis-N-[1-(4-methoxy-benzoyl)-2-methyl-1,2,3,4-tetrahydro-quinolin-4-yl]-N-phenyl-propionamide was made following general procedure A substituting 4-methoxybenzoyl chloride for 2-furoyl chloride and propionyl chloride for acetyl chloride.

$^1$H-NMR (CDCl$_3$)δ: 1.12 (d, 3H), 1.15 (t, 3H), 1.17 (m, 1H), 2.23 (m, 3H), 3.74 (s, 3H), 4.74 (sextet, 1H), 5.61 (bs, 1H), 6.52 (d, 1H), 6.67 (d, 2H), 6.92 (d, 1H), 7.17 (d, 2H), 7.25-7.34 (m, 4H), 7.39 (bs, 3H).

MS m/z: 429 (M+1).

(±)-Cis-{4-[2-Methyl-4-(phenyl-propionyl-amino)-3,4-dihydro-2H-quinoline-1-carbonyl]-phenoxy}-acetic acid (A-39)

(±)-Cis-{4-[2-methyl-4-(phenyl-propionyl-amino)-3,4-dihydro-2H-quinoline-1-carbonyl]-phenoxy}-acetic acid was made from (±)-cis-{4-[2-methyl-4-(phenyl-propionyl-amino)-3,4-dihydro-2H-quinoline-1-carbonyl]-phenoxy}-acetic acid ethyl ester. (±)-Cis-{4-[2-methyl-4-(phenyl-propionyl-amino)-3,4-dihydro-2H-quinoline-1-carbonyl]-phenoxy}-acetic acid ethyl ester was dissolved in ethanol (5 mL) and 0.5 mL of 1N NaOH was added at room temperature. The reaction was allowed to stir for 4 h. The ethanol was removed in vacuo and the aqueous solution was acidified with 1N HCl to give a white precipitate which was filtered to give the desired product in 88% yield.

$^1$H-NMR (CDCl$_3$)δ: 1.12 (d, 3H), 1.16 (t, 3H), 1.15 (m, 1H), 2.28 (m, 3H), 4.52 (s, 2H), 4.74 (sextet, 1H), 5.63 (bs, 1H), 6.50 (d, 1H), 6.68 (d, 2H), 6.91 (t, 1H), 7.16 (t, 1H), 7.18 (d, 2H), 7.26-7.32 (m, 4H), 7.40 (bs, 2H).

MS m/z: 473.0 (M+1).

(±)-Cis-N-{2-methyl-1-[4-(2-morpholin-4-yl-ethoxy)-benzoyl]-1,2,3,4-tetrahydro-quinolin-4-yl}-N-phenyl-propionamide (A-40)

(±)-Cis-N-{2-methyl-1-[4-(2-morpholin-4-yl-ethoxy)-benzoyl]-1,2,3,4-tetrahydro-quinolin-4-yl}-N-phenyl-propionamide was made from (±)-cis-N-[1-(4-hydroxy-benzoyl)-2-methyl-1,2,3,4-tetrahydro-quinolin-4-yl]-N-phenyl-propionamide. (±)-Cis-N-[1-(4-methoxy-benzoyl)-2-methyl-1,2,3,4-tetrahydro-quinolin-4-yl]-N-phenyl-propionamide was dissolved in DMF (5 mL) at room temperature. Sodium hydride (60% in oil, 0.061 g) was added and the mixture allowed to stir 30 min. 4-(2-chloroethyl) morpholine hydrochloride (0.143 g) was added and the reaction was allowed to stir over night. Ethanol was added and the reaction was concentrated in vacuo. The residue was partition between ethyl acetate and water, then extracted 3× with ethyl acetate, dried over MgSO$_4$, filtered and concentrated. The crude residue was purified by silica gel chromatography (2/98 methanol/dichloromethane-5/95 methanol/dichloromethane gradient) to afford the product (200 mg).

$^1$H-NMR (CDCl$_3$)δ: 1.09 (d, 3H), 1.12 (m, 4H), 1.22 (s, 4H), 2.23 (m, 3H), 2.50 (s, 4H), 2.70 (m, 2H), 4.01 (t, 2H), 4.70 (sextet, 1H), 5.59 (bs, 1H), 6.49 (d, 1H), 6.64 (d, 2H), 6.89 (t, 1H), 7.13 (d, 2H), 7.23-7.36 (m, 7H).

MS m/z: 528.1 (M+1).

(±)-Cis-N-[1-(4-carbamoylmethoxy-benzoyl)-2-methyl-1,2,3,4-tetrahydro-quinolin-4-yl]-N-phenyl-propionamide (A-41)

(±)-Cis-N-[1-(4-carbamoylmethoxy-benzoyl)-2-methyl-1,2,3,4-tetrahydro-quinolin-4-yl]-N-phenyl-propionamide was made from (±)-cis-N-[1-(4-hydroxy-benzoyl)-2-methyl-1,2,3,4-tetrahydro-quinolin-4-yl]-N-phenyl-propionamide. (±)-Cis-N-[1-(4-hydroxy-benzoyl)-2-methyl-1,2,3,4-tetrahydro-quinolin-4-yl]-N-phenyl-propionamide (0.120 g) was dissolved in DMF (5 mL) at room temperature. Sodium hydride (60% in oil, 0.70 g) was added and the mixture allowed to stir 30 min. 2-Bromoacetamide (0.320 g) was added and the reaction was allowed to stir over night. Ethanol was added and the reaction was concentrated in vacuo. The residue was partitioned between ethyl acetate and water, then extracted 3× with ethyl acetate, dried over MgSO$_4$, filtered and concentrated down. The crude residue was purified by silica gel chromatography (2/98 methanol/dichloromethane-10/90 methanol/dichloromethane gradient) to afford the product (20 mg, 15%).

$^1$H-NMR (CDCl$_3$)δ: 1.12 (d, 3H), 1.14 (t, 3H), 1.24 (t, 1H), 2.25 (m, 3H), 4.42 (s, 2H), 4.73 (sextet, 1H), 5.61 (bs, 1H), 5.79 (s, 1H), 6.49 (d, 2H), 6.70 (d, 2H), 6.92 (t, 1H), 7.14-7.39 (m, 8H).

MS m/z: 472.0 (M+1).

(±)-Cis-N-{1-[4-(2-hydroxy-2-methyl-propoxy)-benzoyl]-2-methyl-1,2,3,4-tetrahydro-quinolin-4-yl}-N-phenyl-propionamide (A-42)

(±)-Cis-N-{1-[4-(2-hydroxy-2-methyl-propoxy)-benzoyl]-2-methyl-1,2,3,4-tetrahydro-quinolin-4-yl}-N-phenyl-propionamide was made from (±)-Cis-{4-[2-methyl-4-(phenyl-propionyl-amino)-3,4-dihydro-2H-quinoline-1-carbonyl]-phenoxy}-acetic acid ethyl ester. (±)-Cis-{4-[2-methyl-4-(phenyl-propionyl-amino)-3,4-dihydro-2H-quinoline-1-carbonyl]-phenoxy}-acetic acid ethyl ester (0.170 g) was dissolved in THF and cooled to 0° C. Methylmagnesium bromide (3.0M sol in diethyl ether, 0.5 mL) was added and the reaction was allowed to stir at 0° C. for 30 min. The reaction was quenched with a saturated solution of ammonium chloride and diluted with ethyl acetate. The organics were seperated and washed with brine, dried over $MgSO_4$, filtered and concentrated down. The crude residue was purified by silica gel chromatography (50/50 hexanes/ethyl acetate-75/25 hexanes ethyl acetate gradient) to afford the product (132 mg, 80%).

$^1$H-NMR (CDCl$_3$)δ: 1.10 (d, 3H), 1.14 (t, 3H), 1.23 (t, 1H), 1.29 (s, 6H), 2.24 (m, 3H), 3.70 (s, 2H), 4.74 (sextet, 1H), 5.61 (bs, 1H), 6.50 (d, 1H), 6.66 (d, 2H), 6.91 (t, 1H), 7.13 (t, 1H), 7.14 (d, 2H), 7.25 (d, 1H), 7.32 (d, 1H), 7.37 (bs, 4H).

MS m/z: 487.1 (M+1).

(±)-Cis-N-[1-(4-dimethylcarbamoylmethoxy-benzoyl)-2-methyl-1,2,3,4-tetrahydro-quinolin-4-yl]-N-phenyl-propionamide (A-43)

(±)-Cis-N-[1-(4-dimethylcarbamoylmethoxy-benzoyl)-2-methyl-1,2,3,4-tetrahydro-quinolin-4-yl]-N-phenyl-propionamide was made from (±)-cis-{4-[2-methyl-4-(phenyl-propionyl-amino)-3,4-dihydro-2H-quinoline-1-carbonyl]-phenoxy}-acetic acid. (±)-Cis-{4-[2-Methyl-4-(phenyl-propionyl-amino)-3,4-dihydro-2H-quinoline-1-carbonyl]-phenoxy}-acetic acid (0.146 g) was dissolved in THF (2 mL) at room temperature. HOBt (0.063 g), EDCI (0.071 g), and dimethylamine (2.0M solution in THF, 0.162 mL) was added along with 2 drops of DMF and stirred at room temperature for 11 h. The reaction was diluted with ethyl acetate, washed with 1N NaOH, 1N HCl and brine. The organics were dried over $MgSO_4$, filtered and concentrated down. The crude residue was purified by silica gel chromatography (100% ethyl acetate) to afford the product (84 mg, 54%).

$^1$H-NMR (CDCl$_3$)δ: 1.10 (d, 3H), 1.13 (t, 3H), 1.22 (t, 1H), 2.23 (m, 3H), 2.94 (s, 3H), 3.00 (s, 3H), 4.60 (s, 2H), 4.71 (sextet, 1H), 5.58 (bs, 1H), 6.49 (d, 1H), 6.70 (d, 2H), 6.89 (t, 1H), 7.13 (d, 1H), 7.24 (d, 2H), 7.30 (d, 1H), 7.37 (bs, 7H).

MS m/z: 500.1 (M+1).

(±)-Cis-N-[1-(3-dimethylamino-benzoyl)-2-methyl-1,2,3,4-tetrahydro-quinolin-4-yl]-N-phenyl-propionamide (A-45)

(±)-Cis-N-[1-(3-dimethylamino-benzoyl)-2-methyl-1,2,3,4-tetrahydro-quinolin-4-yl]-N-phenyl-propionamide was made following general procedure A, substituting 3-dimethylaminobenzoyl chloride for 2-furoyl chloride and propionyl chloride for acetyl chloride.

$^1$H-NMR (300 MHz, CDCl$_3$)δ: 1.11-1.24 (m, 7H), 2.12-2.40 (m, 3H), 2.83 (s, 6H), 4.80 (ddd, 1H), 5.59 (br s, 1H), 6.49 (d, 1H), 6.55-6.69 (m, 3H), 6.92 (dd, 1H), 7.00 (ddd, 1H), 7.15 (ddd, 1H), 7.23 -7.34 (m, 3H), 7.35-7.44 (m, 3H).

MS m/z: 442 (M+1).

(±)-Cis-N-[1-(4-dimethylamino-benzoyl)-2-methyl-1,2,3,4-tetrahydro-quinolin-4-yl]-N-phenyl-propionamide (A-46)

(±)-Cis-N-[1-(4-dimethylamino-benzoyl)-2-methyl-1,2,3,4-tetrahydro-quinolin-4-yl]-N-phenyl-propionamide was made following general procedure A substituting 4-dimethylaminobenzoyl chloride for 2-furoyl chloride and propionyl chloride for acetyl chloride.

$^1$H-NMR (300 MHz, CDCl$_3$)δ: 1.09-1.28 (m, 7H), 2.12-2.39 (m, 3H), 2.93 (s, 6H), 4.73 (ddd, 1H), 5.61 (br s, 1H), 6.47 (d, 2H), 6.62 (d, 1H), 6.96 (dd, 1H), 7.12-7.20 (m, 3H), 7.26-7.36 (m, 3H), 7.38-7.46 (m, 3H).

MS m/z: 442 (M+1).

(±)-Cis-N-[2-methyl-1-(pyridine-3-carbonyl)-1,2,3,4-tetrahydro-quinolin-4-yl]-N-phenyl-propionamide (A-47)

(±)-Cis-[2-ethyl-1-(pyridine-3-carbonyl)-1,2,3,4-tetrahydro-quinolin-4-yl]-N-phenyl-propionamide was made following general procedure A substituting 3-pyridinyl chloride for 2-furoyl chloride and propionyl chloride for acetyl chloride.

$^1$H-NMR (300 MHz, CDCl$_3$)δ: 1.08-1.32 (m, 7H), 2.16-2.44 (m, 3H), 4.84 (ddd, 1H), 5.62 (br s, 1H), 6.53 (d, 1H), 6.97 (dd, 1H), 7.11 (dd, 1H), 7.20-7.51 (m, 8H), 8.55 (dd, 1H), 8.68 (br s, 1H).

MS m/z: 400 (M+1).

(±)-Cis-N-[1-(4-fluoro-benzoyl)-2-methyl-1,2,3,4-tetrahydro-quinolin-4-yl]-4-methoxy-N-phenyl-butyramide (A-48)

(±)-Cis-N-[1-(4-fluoro-benzoyl)-2-methyl-1,2,3,4-tetrahydro-quinolin-4-yl]-4-methoxy-N-phenyl-butyramide was made following general procedure A substituting 4-fluorobenzoyl chloride for 2-furoyl chloride and 4-methoxy-butyryl chloride for acetyl chloride.

$^1$H-NMR (300 MHz, CDCl$_3$)δ: 1.08-1.20 (m, 4H), 1.86-2.02 (m, 2H), 2.21-2.41 (m, 3H), 3.26 (m, 3H), 3.28-3.44 (m, 2H), 4.76 (ddd, 1H), 5.64 (br s, 1H), 6.43 (d, 1H), 6.83-6.96 (m, 3H), 7.17 -7.34 (m, 5H), 7.36-7.51 (m, 4H).

MS m/z: 461 (M+1).

(±)-Cis-2-(acetyl-methyl-amino)-N-[1-(4-fluoro-benzoyl)-2-methyl-1,2,3,4-tetrahydro-quinolin-4-yl]-N-phenyl-acetamide (A-49)

(±)-Cis-2-(acetyl-methyl-amino)-N-[1-(4-fluoro-benzoyl)-2-methyl-1,2,3,4-tetrahydro-quinolin-4-yl]-N-phenyl-acetamide was made following general procedure A substituting 4-fluorobenzoyl chloride for 2-furoyl chloride and (acetyl-methyl-amino)-acetyl chloride for acetyl chloride.

$^1$H-NMR (300 MHz, CDCl$_3$)δ: 1.10-1.18 (m, 4H), 2.13 (s, 3H), 2.27-2.43 (m, 1H), 3.14 (m, 3H), 3.77 (d, 1H), 4.03 (d, 1H), 4.76 (ddd, 1H), 5.55 (br s, 1H), 6.45 (d, 1H), 6.81-6.95 (m, 3H), 7.15 -7.26 (m, 3H), 7.31-7.49 (m, 5H), 7.54 (d, 1H).

MS m/z=474 (M+1).

(±)-Cis-cyclohexanecarboxylic acid [1-(3-methoxy-benzoyl)-2-methyl-1,2,3,4-tetrahydro-quinolin-4-yl]-phenylamide (A-54)

(±)-Cis-cyclohexanecarboxylic acid [1-(3-methoxy-benzoyl)-2-methyl-1,2,3,4-tetrahydro-quinolin-4-yl]-phenylamide was made following procedure A substituting 3-methoxybenzoyl chloride for 2-furoyl chloride and cyclohexane carbonyl chloride for acetyl chloride.
¹H-NMR (CDCl₃)δ: 0.8 (8H, m), 1.5-1.8 (5H, m), 2.0-2.4 (3H, m), 3.7 (3H, d), 4.8 (1H, m), 5.6 (1H, d), 6.2-6.6 (2H, m), 6.6-7.5 (11H, m).
MS m/z: 483 (M+1).

(±)-Cis-isoxazole-5-carboxylic acid [1-(3-methoxybenzoyl)-2-methyl-1,2,3,4-tetrahydro-quinolin-4-yl]-phenyl-amid (A-55)

(±)-Cis-isoxazole-5-carboxylic acid [1-(3-methoxy-benzoyl)-2-methyl-1,2,3,4-tetrahydro-quinolin-4-yl]-phenyl-amide was made following general procedure A substituting 3-methoxybenzoyl chloride for 2-furoyl chloride and isoxazole-5-carbonyl chloride for acetyl chloride.
¹H-NMR (CDCl₃)δ: 1.2 (3H, d), 1.2 (1H, m), 2.4 (1H, m), 3.6 (3H, s), 4.9 (1H, m), 5.8 (1H, m), 6.4 (1H, d), 6.7-7.7 (12H, m), 8.2 (1H, s), 8.4 (1H, m).
MS m/z: 468 (M+1).

(±)-Cis-N-[1-(furan-3-carbonyl)-2-methyl-1,2,3,4-tetrahydro-quinolin-4-yl]-N-phenyl-acetamide (A-56)

(±)-Cis-N-[1-(furan-3-carbonyl)-2-methyl-1,2,3,4-tetrahydro-quinolin-4-yl]-N-phenyl-acetamide was made following general procedure A substituting 3-furoyl chloride for 2-furoyl chloride.
¹H-NMR (CDCl₃)δ: 1.1 (3H, d), 1.2 (1H, m), 2.0 (3H, s), 2.2 (1H, m), 4.7 (1H, m), 5.5 (1H, m), 5.9 (1H, s), 6.9 (1H, d), 7.1 (2H, m) 7.2-7.4 (7H, m).
MS m/z: 375 (M+1).

(±)-Cis-N-[1-(3-fluoro-benzoyl)-2-methyl-1,2,3,4-tetrahydro-quinolin-4-yl]-N-phenyl-acetamide (A-61)

(±)-Cis-N-[1-(3-fluoro-benzoyl)-2-methyl-1,2,3,4-tetrahydro-quinolin-4-yl]-N-phenyl-acetamide was made following general procedure A substituting 3-fluorobenzoyl chloride for 2-furoyl chloride.
¹H-NMR (CDCl₃)δ: 1.1 (3H, d), 1.1 (1H, m), 2.0 (3H, s), 2.3 (1H, m), 4.7 (1H, m), 5.6 (1H, m), 6.4 (1H, d), 6.8 (1H, d), 6.9-7.4 (11H, m).
MS m/z: 403 (M+1).

(±)-Cis-N-[1-(3,4-difluoro-benzoyl)-2-methyl-1,2,3,4-tetrahydro-quinolin-4-yl]-N-phenyl-acetamide (A-62)

(±)-Cis-N-[1-(3,4-difluoro-benzoyl)-2-methyl-1,2,3,4-tetrahydro-quinolin-4-yl]-N-phenyl-acetamide was made following general procedure A substituting 3,4-difluorobenzoyl chloride for 2-furoyl chloride.
¹H-NMR (CDCl₃)δ: 1.1 (3H, d), 1.1 (1H, m), 2.0 (3H, s), 2.3 (1H, m), 4.7 (1H, m), 5.6 (1H, m), 6.5 (1H, d), 6.8-7.0 (4H, d), 7.3-7.5 (7H, m).
MS m/z: 421 (M+1).

(±)-Cis-N-[1-(benzo[b]thiophene-3-carbonyl)-2-methyl-1,2,3,4-tetrahydro-quinolin-4-yl]-N-phenyl-acetamide (A-63)

(±)-Cis-N-[1-(benzo[b]thiophene-3-carbonyl)-2-methyl-1,2,3,4-tetrahydro-quinolin-4-yl]-N-phenyl-acetamide was made following general procedure A substituting benzo[b]thiophene-3-carbonyl chloride for 2-furoyl chloride.
¹H-NMR (CDCl₃)δ: 1.2 (3H, d), 1.3 (1H, m), 2.0 (3H, s), 2.3 (1H, m), 4.9 (1H, m), 5.7 (1H, m), 6.5 (1H, d), 6.8 (1H, m), 7.1-7.5 (10H, m), 7.8 (1H, d), 8.0 (1H, d).
MS m/z: 442 (M+2).

(±)-Cis-N-[1-(3,5-dimethyl-thiophene-2-carbonyl)-2-methyl-1,2,3,4-tetrahydro-quinolin-4-yl]-N-phenyl-acetamide (A-64)

(±)-Cis-N-[1-(3,5-dimethyl-thiophene-2-carbonyl)-2-methyl-1,2,3,4-tetrahydro-quinolin-4-yl]-N-phenyl-acetamide was made following general procedure A substituting 3,5-dimethyl-thiophene-2-carbonyl chloride for 2-furoyl chloride.
¹H-NMR (CDCl₃)δ: 1.1 (3H, d), 1.1 (1H, m), 1.7 (3H, s), 2.0 (3H, d), 2.0 (1H, m), 2.3 (3H, s), 4.7 (1H, m), 5.5 (1H, m), 6.2 (1H, s), 6.7 (1H, d), 7.0 (1H, t), 7.1-7.4 (7H, m).
MS m/z: 419 (M+1).

(±)-Cis-N-[1-(3-fluoro-benzoyl)-2-methyl-1,2,3,4-tetrahydro-quinolin-4-yl]-N-phenyl-isobutyramide (A-65)

(±)-Cis-N-[1-(3-fluoro-benzoyl)-2-methyl-1,2,3,4-tetrahydro-quinolin-4-yl]-N-phenyl-isobutyramide was made following general procedure A substituting 3-fluorobenzoyl chloride for 2-furoyl chloride and isopropyl chloride for acetyl chloride.
¹H-NMR (CDCl₃)δ: 1.0-1.2 (10H, m), 2.3 (1H, m), 2.7 (1H, m), 4.8 (1H, m), 5.6 (1H, m), 6.5 (1H, m), 6.8-7.6 (12H, m).
MS m/z: 431 (M+1).

(±)-Cis-N-[1-(4-fluoro-benzoyl)-2-methyl-1,2,3,4-tetrahydro-quinolin-4-yl]-N-phenyl-isobutyramide (A-66)

(±)-Cis-N-[1-(4-fluoro-benzoyl)-2-methyl-1,2,3,4-tetrahydro-quinolin-4-yl]-N-phenyl-isobutyramide was made following general procedure A substituting 4-fluorobenzoyl chloride for 2-furoyl chloride and isopropyl chloride for acetyl chloride.
¹H-NMR (CDCl₃)δ: 1.0-1.2 (10H, m), 2.3 (1H, m), 2.6 (1H, m), 4.8 (1H, m), 5.6 (1H, m), 6.5 (1H, d), 6.8-7.0 (3H, m), 7.1-7.4 (9H, m).
MS m/z: 431 (M+1).

(±)-Cis-N-[1-(2,4-dimethyl-thiazole-5-carbonyl)-2-methyl-1,2,3,4-tetrahydro-quinolin-4-yl]-N-phenyl-acetamide (A-67)

(±)-Cis-N-[1-(2,4-dimethyl-thiazole-5-carbonyl)-2-methyl-1,2,3,4-tetrahydro-quinolin-4-yl]-N-phenyl-acetamide was made following general procedure A substituting 2,4-dimethyl-thiazole-5-carbonyl chloride for 2-furoyl chloride.
¹H-NMR (CDCl₃)δ: 1.2 (3H, d), 1.2 (1H, m), 2.0 (3H, s), 2.2 (3H, s), 2.3 (1H, m), 2.6 (3H, s), 4.7 (1H, m), 5.4 (1H, m), 6.8 (1H, d), 7.1 (2H, m), 7.2-7.5 (6H, m).
MS m/z: 420 (M+1).

(±)-Cis-N-[1-(furan-2-carbonyl)-2-methyl-1,2,3,4-tetrahydro-quinolin-4-yl]-N-phenyl-propionamide (A-68)

(±)-Cis-N-[1-(furan-2-carbonyl)-2-methyl-1,2,3,4-tetrahydro-quinolin-4-yl]-N-phenyl-propionamide was made following general procedure A substituting propionyl chloride for acetyl chloride.

$^1$H-NMR (CDCl$_3$)δ: 1.0-1.2 (7H, m), 2.2-2.4 (3H, m), 4.7 (1H, m), 5.4 (1H, m), 6.2 (2H, m), 6.8 (1H, d), 7.0-7.4 (9H, m).

MS m/z: 389 (M+1).

(±)-Cis-N-[1-(4-fluoro-benzoyl)-2-methyl-1,2,3,4-tetrahydro-quinolin-4-yl]-N-phenyl-butyramide (A-69)

(±)-Cis-N-[1-(4-fluoro-benzoyl)-2-methyl-1,2,3,4-tetrahydro-quinolin-4-yl]-N-phenyl-butyramide was made following general procedure A substituting 4-fluorobenzoyl chloride for 2-furoyl chloride and butyryl chloride for acetyl chloride.

$^1$H-NMR (CDCl$_3$)δ: 0.8 (3H, t), 1.2 (3H, d), 1.2 (1H, m), 1.5 (2H, m), 2.0 (3H, m), 4.7 (1H, m), 5.4 (1H, m), 6.5 (1H, d), 6.6-6.8 (4H, m), 6.9-7.3 (8H, m).

MS m/z: 432 (M+2).

(±)-Cis-N-[1-(4-fluoro-benzoyl)-2-methyl-1,2,3,4-tetrahydro-quinolin-4-yl]-2-phenoxy-N-phenyl-acetamide (A-72)

(±)-Cis-N-[1-(4-fluoro-benzoyl)-2-methyl-1,2,3,4-tetrahydro-quinolin-4-yl]-2-phenoxy-N-phenyl-acetamide was made following general procedure A substituting 4-fluorobenzoyl chloride for 2-furoyl chloride and 1-chloro-3-phenoxy-propan-2-one for acetyl chloride.

$^1$H-NMR (CDCl$_3$)δ: 1.1 (3H, d), 1.1 (1H, m), 2.3 (1H, m), 4.5 (2H, s), 4.7 (1H, m), 5.7 (1H, m), 6.4 (1H, d), 6.7-6.9 (7H, m), 7.1-7.4 (9H, m), 10.0 (1H, m).

MS m/z: 496 (M+2).

(±)-Cis-N-[1-(4-fluoro-benzoyl)-2-methyl-1,2,3,4-tetrahydro-quinolin-4-yl]-3,N-diphenyl-propionamide (A-73)

(±)-Cis-N-[1-(4-Fluoro-benzoyl)-2-methyl-1,2,3,4-tetrahydro-quinolin-4-yl]-3,N-diphenyl-propionamide was made following general procedure A substituting 4-fluorobenzoyl chloride for 2-furoyl chloride and 3-phenylpropionyl chloride for acetyl chloride.

$^1$H-NMR (CDCl$_3$)δ: 1.2 (3H, d), 1.2 (1H, m), 2.2 (1H, m), 2.7 (2H, t), 3.1 (2H, t), 4.7 (1H, m), 5.7 (1H, m), 6.6 (1H, d), 6.8-7.6 (17H, m).

MS m/z: 494 (M+2).

(±)-Cis-N-[1-(benzo[b]thiophene-2-carbonyl)-2-methyl-1,2,3,4-tetrahydro-quinolin-4-yl]-N-phenyl-propionamide (A-75)

(±)-Cis-N-[1-(benzo[b]thiophene-2-carbonyl)-2-methyl-1,2,3,4-tetrahydro-quinolin-4-yl]-N-phenyl-propionamide was made following general procedure A substituting benzo[b]thiophene-2-carbonyl chloride for 2-furoyl chloride and propionyl chloride for acetyl chloride.

$^1$H-NMR (CDCl$_3$)δ: 1.1-1.2 (7H, m), 2.1-2.3 (3H, m), 4.8 (1H, m), 5.6 (1H, m), 6.9 (1H, d), 7.0 (2H, m), 7.2-7.5 (9H, m), 7.6 (1H, d), 7.8 (1H, d).

MS m/z: 456 (M+2).

(±)-Cis-N-[1-(4-cyano-benzoyl)-2-methyl-1,2,3,4-tetrahydro-quinolin-4-yl]-N-phenyl-propionamide (A-76)

(±)-Cis-N-[1-(4-cyano-benzoyl)-2-methyl-1,2,3,4-tetrahydro-quinolin-4-yl]-N-phenyl-propionamide was made following general procedure A substituting 4-cyanobenzoyl chloride for 2-furoyl chloride and propionyl chloride for acetyl chloride.

$^1$H-NMR (CDCl$_3$)δ: 1.1-1.3 (7H, m), 2.2-2.4 (3H, m), 4.8 (1H, m), 5.6 (1H, m), 6.4 (1H, d), 6.9 (1H, t), 7.2-7.6 (11H, m).

MS m/z: 424 (M+1).

(±)-Cis-N-[1-(3-fluoromethoxy-benzoyl)-2-methyl-1,2,3,4-tetrahydro-quinolin-4-yl]-N-phenyl-propionamide (A-77)

(±)-Cis-N-[1-(3-fluoro-4-methoxy-benzoyl)-2-methyl-1,2,3,4-tetrahydro-quinolin-4-yl]-N-phenyl-propionamide was made following general procedure A substituting 3-fluoro-4-methoxybenzoyl chloride for 2-furoyl chloride and propionyl chloride for acetyl chloride.

$^1$H-NMR (CDCl$_3$)δ: 1.1-1.2 (7H, m), 2.1-2.3 (3H, m), 3.8 (3H, s), 4.8 (1H, m), 5.6 (1H, m), 6.5 (1H, d), 6.7 (1H, t), 6.8 (1H, d), 6.9 (1H, t), 7.2-7.5 (8H, m).

MS m/z: 447 (M+1).

(±)-Cis-N-[1-(4-methoxy-3-methyl-benzoyl)-2-methyl-1,2,3,4-tetrahydro-quinolin-4-yl]-N-phenyl-propionamide (A-78)

(±)-Cis-N-[1-(4-methoxy-3-methyl-benzoyl)-2-methyl-1,2,3,4-tetrahydro-quinolin-4-yl]-N-phenyl-propionamide was made following general procedure A substituting 3-methyl-4-methoxybenzoyl chloride for 2-furoyl chloride and propionyl chloride for acetyl chloride.

$^1$H-NMR (CDCl$_3$)δ: 0.9-1.1 (7H, m), 1.8-2.2 (6H, m), 3.8 (3H, s), 4.8 (1H, m), 5.6 (1H, m), 6.5 (2H, m), 6.7-7.8 (10H, m).

MS m/z: 443 (M+1).

(±)-Cis-N-[1-(4-ethoxy-benzoyl)-2-methyl-1,2,3,4-tetrahydro-quinolin-4-yl]-N-phenyl-propionamide (A-79)

(±)-Cis-N-[1-(4-ethoxy-benzoyl)-2-methyl-1,2,3,4-tetrahydro-quinolin-4-yl]-N-phenyl-propionamide was made following general procedure A substituting 4-ethoxybenzoyl chloride for 2-furoyl chloride and propionyl chloride for acetyl chloride.

$^1$H-NMR (CDCl$_3$)δ: 1.1-1.3 (7H, m), 1.4 (3H, t), 2.2-2.4 (3H, m), 4.0 (2H, q), 4.8 (1H, m), 5.6 (1H, m), 6.5 (1H, d), 6.9 (2H, d), 6.9 (1H, t), 7.2-7.6 (9H, m).

MS m/z: 443 (M+1).

(±)-Cis-N-[2-methyl-1-(4-trifluoromethyl-benzoyl)-1,2,3,4-tetrahydro-quinolin-4-yl]-N-phenyl-propionamide (A-80)

(±)-Cis-N-[2-methyl-1-(4-trifluoromethyl-benzoyl)-1,2,3,4-tetrahydro-quinolin-4-yl]-N-phenyl-propionamide was made following general procedure A substituting 4-trifluoromethylbenzoyl chloride for 2-furoyl chloride and propionyl chloride for acetyl chloride.

¹H-NMR (CDCl₃) δ: 1.1-1.3 (7H, m), 2.2-2.4 (3H, m), 4.8 (1H, m), 5.6 (1H, m), 6.4 (1H, d), 6.9 (1H, t), 7.2-7.6 (11H, m).
MS m/z: 319 (M–147).

(±)-Cis-N-[1-(4-benzyl-morpholne-2-carbonyl)-2-methyl-1,2,3,4-tetrahydro-quinolin-4-yl]-N-phenyl-propionamide (A-81)

(±)-Cis-N-[1-(4-benzyl-morpholine-2-carbonyl)-2-methyl-1,2,3,4-tetrahydro-quinolin-4-yl]-N-phenyl-propionamide was made following general procedure A substituting 4-benzyl-morpholine-2-carbonyl chloride for 2-furoyl chloride and propionyl chloride for acetyl chloride.
¹H-NMR (CDCl₃) δ: 1.1-1.2 (7H, m), 2.1-2.3 (4H, m), 2.6 (3H, m), 3.5 (2H, m), 3.9 (1H, m), 4.2 (1H, m), 4.7 (1H, m), 5.2 (1H, m), 7.1-7.5 (14H, m).
MS m/z: 498 (M+1).

(±)-Cis-N-[1-(4-ethyl-morpholne-2-carbonyl)-2-methyl-1,2,3,4-tetrahydro-quinolin-4-yl]-N-phenyl-propionamide (A-82)

(±)-Cis-N-[1-(4-Ethyl-morpholine-2-carbonyl)-2-methyl-1,2,3,4-tetrahydro-quinolin-4-yl]-N-phenyl-propionamide was made following general procedure A substituting 4-ethyl-morpholine-2-carbonyl chloride for 2-furoyl chloride and propionyl chloride for acetyl chloride.
¹H-NMR (CDCl₃) δ: 1.1-1.2 (10H, m), 2.1-2.4 (6H, m), 2.6 (2H, m), 3.6 (1H, t), 3.9 (1H, m), 4.2 (1H, m), 4.7 (1H, m), 5.2 (1H, m), 7.2-7.5 (14H, m).
MS m/z: 436 (M+1).

(±)-Cis-N-[2-methyl-1-(4-phenoxy-benzoyl)-1,2,3,4-tetrahydro-quinolin-4-yl]-N-phenyl-propionamide (A-83)

(±)-Cis-N-[2-methyl-1-(4-phenoxy-benzoyl)-1,2,3,4-tetrahydro-quinolin-4-yl]-N-phenyl-propionamide was made following general procedure A substituting 4-phenoxy benzoyl chloride for 2-furoyl chloride and propionyl chloride for acetyl chloride.
¹H-NMR (CDCl₃) δ: 1.0-1.2 (7H, m), 2.2-2.4 (3H, m), 4.7 (1H, m), 5.6 (1H, m), 6.5 (1H, d), 6.5 (1H, d), 6.8 (2H, d), 7.0-7.4 (15H, m).
MS m/z: 491 (M+1).

(±)-Cis-N-[1-(4-fluoro-3-methoxy-benzoyl)-2-methyl-1,2,3,4-tetrahydro-quinolin-4-yl]-N-phenyl-propionamide (A-84)

(±)-Cis-N-[1-(4-fluoro-3-methoxy-benzoyl)-2-methyl-1,2,3,4-tetrahydro-quinolin-4-yl]-N-phenyl-propionamide was made following general procedure A substituting 4-fluoro-3-methoxy benzoyl chloride for 2-furoyl chloride and propionyl chloride for acetyl chloride. ¹H-NMR (CDCl₃) δ: 1.0-1.2 (7H, m), 2.2-2.4 (3H, m), 3.6 (3H, s), 4.7 (1H, m), 5.6 (1H, m), 6.4 (1H, d), 6.7-6.9 (4H, m), 7.1-7.4 (7H, m). MS m/z: 447 (M+1).

(±)-Cis-N-[1-(4-methoxy-3-trifluoromethyl-benzoyl)-2-methyl-1,2,3,4-tetrahydro-quinolin-4-yl]-N-phenyl-propionamide (A-85)

(±)-Cis-N-[1-(4-methoxy-3-trifluoromethyl-benzoyl)-2-methyl-1,2,3,4-tetrahydro-quinolin-4-yl]-N-phenyl-propionamide was made following general procedure A substituting 4-methoxy-3-trifluoromethyl benzoyl chloride for 2-furoyl chloride and propionyl chloride for acetyl chloride.
¹H-NMR (CDCl₃) δ: 1.0-1.2 (7H, m), 2.2-2.4 (3H, m), 3.8 (3H, s), 4.7 (1H, m), 5.6 (1H, m), 6.5 (1H, d), 6.7 (1H, d), 7.0 (2H, m), 7.2-7.4 (7H, m), 7.8 (1H, s).
MS m/z: 497 (M+1).

(±)-Cis-N-[1-(2,3-dihydro-benzofuran-5-carbonyl)-2-methyl-1,2,3,4-tetrahydro-quinolin-4-yl]-N-phenyl-propionamide (A-86)

(±)-Cis-N-[1-(2,3-dihydro-benzofuran-5-carbonyl)-2-methyl-1,2,3,4-tetrahydro-quinolin-4-yl]-N-phenyl-propionamide was made following general procedure A substituting 2,3-dihydro-benzofuran-5-carbonyl chloride for 2-furoyl chloride and propionyl chloride for acetyl chloride.
¹H-NMR (CDCl₃) δ: 1.1-1.2 (7H, m), 2.1-2.3 (3H, m), 4.5 (2H, t), 4.8 (1H, m), 5.6 (1H, m), 6.5 (2H, m), 6.9 (2H, m), 7.1-7.4 (7H, m).
MS m/z: 441 (M+1).

(±)-Cis-N-{2-methyl-1-[4-(3-methyl-ureido)-benzoyl]-1,2,3,4-tetrahydro-quinolin-4-yl}-N-phenyl-acetamide (A-87)

(±)-Cis-N-{2-methyl-1-[4-(3-methyl-ureido)-benzoyl]-1,2,3,4-tetrahydro-quinolin-4-yl}-N-phenyl-acetamide was made from (±)-cis-N-[1-(4-amino-benzoyl)-2-methyl-1,2,3,4-tetrahydro-quinolin-4-yl]-N-phenyl-acetamide. (±)-Cis-N-[1-(4-amino-benzoyl)-2-methyl-1,2,3,4-tetrahydro-quinolin-4-yl]-N-phenyl-propionamide was made following general procedure A, substituting 4-nitrobenzoyl chloride for 2-furoyl chloride and propionyl chloride for acetyl chloride. The resulting nitro analog was reduced with Pd/C (10%) in ethanol in a Parr shaker at 35 psi. (±)-Cis-N-[1-(4-amino-benzoyl)-2-methyl-1,2,3,4-tetrahydro-quinolin-4-yl]-N-phenyl-acetamide (150 mg, 0.376 mmol) was dissolved in 10 ml toluene and 64 mg methylisocyanate (1.13 mmol) was added. The resulting reaction mixture was stirred at room temperature for 2 hours, then was heated to 50° C. overnight. The mixture was concentrated under vacuum. The residue was purified by silica gel chromatography, eluting with methanol-dichloromethane (1:19) to give the title compound (87 mg, 51%).
¹H-NMR (CDCl₃) δ: 1.1 (3H, d), 1.1 (1H, m), 2.0 (3H, s), 2.3 (1H, m), 2.7 (3H, s), 4.7 (1H, m), 5.1 (2H, m), 5.6 (1H, m), 6.5 (1H, d), 6.9-7.0 (6H, m), 7.2 (1H, t), 7.2-7.4 (5H, m).
MS m/z: 457 (M+1).

(±)-Cis-N-[1-(4-diethylamino-benzoyl)-2-methyl-1,2,3,4-tetrahydro-quinolin-4-yl]-N-phenyl-acetamide (A-88)

(±)-Cis-N-[1-(4-diethylamino-benzoyl)-2-methyl-1,2,3,4-tetrahydro-quinolin-4-yl]-N-phenyl-acetamide was made from (±)-cis-N-[1-(4-amino-benzoyl)-2-methyl-1,2,3,4-tetrahydro-quinolin-4-yl]-N-phenyl-acetamide. (±)-Cis-N-[1-(4-amino-benzoyl)-2-methyl-1,2,3,4-tetrahydro-quinolin-4-yl]-N-phenyl-acetamide was dissolved in methylene chloride and ethyl iodide (1.5 equiv.) was added followed by K₂CO₃. The reaction was allowed to stir at room temperature for 12 h. The reaction mixture was filtered and concentrated under vacuum. The residue was purified by silica gel chromatography, eluting with methanol-dichloromethane (1:19) to give the title compound.

¹H-NMR (CDCl₃) δ: 1.0-1.2 (10H, m), 2.0 (3H, s), 2.4 (1H, m), 3.3 (4H, q), 4.7 (1H, m), 5.6 (1H, m), 6.4 (2H, d), 6.6 (1H, d), 6.9 (1H, t), 7.0-7.4 (9H, m).

MS m/z: 456 (M+1).

(±)-Cis-{4-[4-(acetyl-phenyl-amino)-2-methyl-3,4-dihydro-2H-quinoline-1-carbonyl]-phenylamino}-acetic acid (A-89)

(±)-Cis-{4-[4-(acetyl-phenyl-amino)-2-methyl-3,4-dihydro-2H-quinoline-1-carbonyl]-phenylamino}-acetic acid was made from (±)-cis-N-[1-(4-amino-benzoyl)-2-methyl-1,2,3,4-tetrahydro-quinolin-4-yl]-N-phenyl-acetamide. (±)-Cis-N-[1-(4-amino-benzoyl)-2-methyl-1,2,3,4-tetrahydro-quinolin-4-yl]-N-phenyl-acetamide was dissolved in dimethylformamide and bromoacetic acid ethyl ester was added followed by K₂CO₃. The reaction was allowed to heat to 90° C. for 12 h. The reaction mixture was filtered and concentrated under vacuum. The residue was purified by silica gel chromatography, eluting with methanol-dichloromethane (2:18) to give the ester. The ester was hydrolyzed using NaOH (aqueous) in methanol and water to give the title compound.

¹H-NMR (CDCl₃) δ: 1.1 (3H, d), 1.1 (1H, m), 2.0 (3H, s), 2.3 (1H, m), 3.6 (1H, s), 4.7 (3H, b), 5.6 (1H, m), 6.3 (1H, m), 6.6 (1H, d), 6.8-7.4 (11H, m).

MS m/z: 458 (M+1).

(±)-Cis-{N-[1-(4-methanesulfonylamino-benzoyl)-2-methyl-1,2,3,4-tetrahydro-quinolin-4-yl]-N-phenyl-propionamide (A-90)

(±)-Cis-{N-[1-(4-methanesulfonylamino-benzoyl)-2-methyl-1,2,3,4-tetrahydro-quinolin-4-yl]-N-phenyl-propionamide was made from (±)-cis-N-[1-(4-amino-benzoyl)-2-methyl-1,2,3,4-tetrahydro-quinolin-4-yl]-N-phenyl-acetamide. (±)-cis-N-[1-(4-amino-benzoyl)-2-methyl-1,2,3,4-tetrahydro-quinolin-4-yl]-N-phenyl-acetamide (50 mg, 0.12 mmol) was dissolved in 5 ml DMF and methanesulfonic anhydride (21 mg, 0.12 mmol) was added. The resulting reaction mixture was heated to 45° C. and stirred for 1 hour. The mixture was concentrated under vacuum. The residue was purified by silica gel chromatography, eluting with methanol-dichloromethane (1:9) to give the title compound (15 mg, 25%).

¹H-NMR (CDCl₃) δ: 1.1-1.2 (7H, m), 2.1-2.3 (3H, m), 3.0 (3H, s), 4.7 (1H, m), 5.6 (1H, m), 6.5 (1H, d), 6.7 (2H, d), 6.9 (1H, t), 7.1 (2H, m), 7.2-7.4 (7H, m).

MS m/z: 491 (M).

(±)-Cis-N-[6-Fluoro-1-(4-fluoro-benzoyl)-2-methyl-1,2,3,4-tetrahydro-quinolin-4-yl]-N-(4-fluoro-phenyl)-propionamide (A-91)

(±)-Cis-N-[6-fluoro-1-(4-fluoro-benzoyl)-2-methyl-1,2,3,4-tetrahydro-quinolin-4-yl]-N-(4-fluoro-phenyl)-propionamide was made following general procedure A, substituting 4-fluorobenzoyl chloride for 2-furoyl chloride, (±)-cis-(6-fluoro-2-methyl-1,2,3,4-tetrahydro-quinolin-4-yl)-(4-fluoro-phenyl)-amine for (±)-cis-(2-methyl-1,2,3,4-tetrahydro-quinolin-4-yl)-phenyl-amine and propionyl chloride for acetyl chloride. (±)-Cis-(6-fluoro-2-methyl-1,2,3,4-tetrahydro-quinolin-4-yl)-(4-fluoro-phenyl)-amine was synthesized following the reactions detailed in scheme 1, substituting 4-fluoroaniline for aniline.

¹H-NMR (CDCl₃) δ: 1.1-1.2 (6H, m), 2.2-2.4 (4H, m), 4.8 (1H, dd), 5.4-5.6 (1H, br), 6.4 (1H, dd), 6.6 (1H, td), 6.8-7.0 (2H, m), 7.0-7.4 (6H, m).

MS m/z: 453 (M+1).

(±)-Cis-N-[6-bromo-1-(4-fluoro-benzoyl)-2-methyl-1,2,3,4-tetrahydro-quinolin-4-yl]-N-(4-bromo-phenyl)-propionamide (A-92)

(±)-Cis-N-[6-bromo-1-(4-fluoro-benzoyl)-2-methyl-1,2,3,4-tetrahydro-quinolin-4-yl]-N-(4-bromo-phenyl)-propionamide was made following general procedure A, substituting 4-fluorobenzoyl chloride for 2-furoyl chloride, (±)-cis-(6-bromo-2-methyl-1,2,3,4-tetrahydro-quinolin-4-yl)-(4-bromo-phenyl)-amine for (±)-cis-(2-methyl-1,2,3,4-tetrahydro-quinolin-4-yl)-phenyl-amine and propionyl chloride for acetyl chloride. (±)-cis-(6-bromo-2-methyl-1,2,3,4-tetrahydro-quinolin-4-yl)-(4-bromo-phenyl)-amine was synthesized following the reactions detailed in scheme 1, substituting 4-bromoaniline for aniline.

¹H-NMR (CDCl₃) δ: 1.1-1.2 (6H, m), 1.6 (1H, m), 2.2-2.4 (3H, m), 4.8 (1H, m), 5.4-5.6 (1H, br), 6.4 (1H, d), 6.8 (2H, m), 7.0-7.4 (6H, m), 7.8-7.9 (2H, m).

MS m/z: 573 (M+1).

(±)-Cis-N-[1-(3-ethoxy-benzoyl)-2-methyl-1,2,3,4-tetrahydro-quinolin-4-yl]-N-phenyl-acetamide (A-93)

(±)-Cis-N-[1-(3-ethoxy-benzoyl)-2-methyl-1,2,3,4-tetrahydro-quinolin-4-yl]-N-phenyl-acetamide was made following general procedure A, substituting 3-ethoxybenzoyl chloride for 2-furoyl chloride.

¹H-NMR (CDCl₃) δ: 1.2 (3H, m), 1.4 (4H, m), 2.1 (3H, s), 2.4 (1H, m), 4.0 (2H, m), 4.9 (1H, m), 5.6 (1H, br), 6.6 (1H, d), 6.9 (2H, m), 7.0 (1H, m), 7.2 (1H, m), 7.3 (1H, m), 7.4-7.5 (7H, m).

MS m/z: 429 (M+1).

(±)-Cis-N-[1-(4-isopropoxy-benzoyl)-2-methyl-1,2,3,4-tetrahydro-quinolin-4-yl]-N-phenyl-propionamide (A-94)

(±)-Cis-N-[1-(4-isopropoxy-benzoyl)-2-methyl-1,2,3,4-tetrahydro-quinolin-4-yl]-N-phenyl-propionamide was made following general procedure A, substituting 4-isopropoxybenzoyl chloride for 2-furoyl chloride and propionyl chloride for acetyl chloride.

¹H-NMR (CDCl₃) δ: 0.9-1.2 (12H, m), 1.4 (1H, m), 2.0 (3H, m), 4.3 (1H, m), 4.5 (1H, m), 5.4 (1H, br), 6.3 (1H, d), 6.4 (2H, d), 6.7 (1H, m), 6.9-7.2 (9H, m).

MS m/z: 457 (M+1).

(±)-Cis-N-[1-(1-isopropyl-1H-benzotriazole-5-carbonyl)-2-methyl-2,4-tetrahydro-quinolin-4-yl]-N-phenyl-propionamide (A-95)

(±)-Cis-N-[1-(1-Isopropyl-1H-benzotriazole-5-carbonyl)-2-methyl-1,2,3,4-tetrahydro-quinolin-4-yl]-N-phenyl-propionamide was made following general procedure A, substituting 1-isopropyl-1H-benzotriazole-5-carbonyl chloride for 2-furoyl chloride and propionyl chloride for acetyl chloride.

¹H-NMR (CDCl₃) δ: 1.3 (7H, m), 1.8 (6H, m), 2.4 (3H, m), 5.0 (1H, m), 5.1 (1H, m), 5.7 (1H, br), 6.6 (1H, d), 7.0 (1H, m), 7.2-7.5 (9H, m), 8.3 (1H, s).

MS m/z: 482 (M+1).

(±)-Cis-N-[1-(3-Ethoxy-benzoyl)-2-methyl-1,2,3,4-tetrahydro-quinolin-4-yl]-N-phenyl-propionamide (A-96)

(±)-Cis-N-[1-(3-ethoxy-benzoyl)-2-methyl-1,2,3,4-tetrahydro-quinolin-4-yl]-N-phenyl-propionamide was made following general procedure A, substituting 3-ethoxybenzoyl chloride for 2-furoyl chloride and propionyl chloride for acetyl chloride. $^1$H-NMR (CDCl$_3$) δ: 1.2 (6H, m), 1.5 (4H, m), 2.4 (3H, m), 4.0 (2H, m), 4.9 (1H, m), 5.7 (1H, br), 6.6 (1H, d), 6.8 (1H, m), 6.9 (1H, m), 7.1 (2H, m), 7.2 (1H, m), 7.3-7.6 (7H, m).

MS m/z: 443 (M+1).

(±)-Cis-4-{4-[2-methyl-4-(phenyl-propionyl-amino)-3,4-dihydro-2H-quinoline-1-carbonyl]-phenyl}-piperidine-1-carboxylic acid ethyl ester (A-97)

(±)-Cis-4-{4-[2-methyl-4-(phenyl-propionyl-amino)-3,4-dihydro-2H-quinoline-1-carbonyl]-phenyl}-piperidine-1-carboxylic acid ethyl ester was made following general procedure A, substituting 4-(4-chlorocarbonyl-phenyl)-piperidine-1-carboxylic acid ethyl ester for 2-furoyl chloride and propionyl chloride for acetyl chloride.

$^1$H-NMR (CDCl$_3$) δ: 1.1-1.3 (10H, m), 1.5 (2H, m), 1.7 (2H, m), 2.3 (3H, m), 2.6 (1H, m), 2.8 (2H, t), 4.1 (2H, m), 4.2 (2H, m), 4.8 (1H, m), 5.6 (1H, br), 6.5 (1H, d), 6.9 (1H, m), 7.2 (2H, m), 7.3-7.4 (9H, m).

MS m/z: 554 (M+1).

(±)-Cis-N-[2-methyl-1-(4-piperidin-4-yl-benzoyl)-1,2,3,4-tetrahydro-quinolin-4-yl]-N-phenyl-propionamide (A-98)

(±)-Cis-N-[2-methyl-1-(4-piperidin-4-yl-benzoyl)-1,2,3,4-tetrahydro-quinolin-4-yl]-N-phenyl-propionamide was prepared from (±)-cis-4-{4-[2-methyl-4-(phenyl-propionyl-amino)-3,4-dihydro-2H-quinoline-1-carbonyl]-phenyl}-piperidine-1-carboxylic acid ethyl ester. (±)-Cis-4-{4-[2-methyl-4-(phenyl-propionyl-amino)-3,4-dihydro-2H-quinoline-1-carbonyl]-phenyl}-piperidine-1-carboxylic acid ethyl ester (96 mg, 0.17 mmol) was dissolved in acetonitrile (2 mL). Iodotrimethylsilane (74 uL, 0.51 mmol) was added and the reaction was allowed to stir at room temperature over night. Excess reagent was quenched by the addition of methanol (1 mL) and the mixture was concentrated under reduced pressure. The crude residue was partitioned between ethyl acetate and saturated aqueous sodium bicarbonate. The extracts were washed with 1 M sodium hydroxide, saturated aqueous sodium thiosulfate and brine, dried over sodium sulfate, filtered, concentrated and purified by silica gel chromatography (3:1 methylene chloride/methanol) (77 mg, 94%).

$^1$H-NMR (CDCl$_3$) δ: 1.1 (6H, m), 1.3 (1H, t), 1.6 (2H, m), 1.7 (2H, d), 2.3 (3H, m), 2.6 (1H, m), 2.7 (2H, t), 3.2 (2H, d), 4.8 (1H, m), 5.6 (1H, br), 6.5 (1H, d), 6.9 (1H, m), 7.0 (2H, d), 7.2 (3H, m), 7.3-7.4 (6H, m).

MS m/z: 482 (M+1).

(±)-Cis-N-[1-(4-Bromo-benzoyl)-2-methyl-1,2,3,4-tetrahydro-quinolin-4-yl]-N-phenyl-propionamide (A-99)

(±)-Cis-N-[1-(4-bromo-benzoyl)-2-methyl-1,2,3,4-tetrahydro-quinolin-4-yl]-N-phenyl-propionamide was made following general procedure A, substituting 4-bromobenzoyl chloride for 2-furoyl chloride and propionyl chloride for acetyl chloride.

$^1$H-NMR (CDCl$_3$) δ: 1.2 (6H, m), 1.25 (1H, m), 2.3 (3H, m), 4.8 (1H, m), 5.6 (1H, br), 6.4 (1H, d), 6.9 (1H, m), 7.1 (2H, d), 7.2 (1H, m), 7.3-7.4 (8H, m).

MS m/z: 477 (M+1).

(±)-Cis-N-{1-[4-(1-acetyl-piperidin-4-yl)-benzoyl]-2-methyl-1,2,3,4-tetrahydro-quinolin-4-yl}-N-phenyl-propionamide (A-100)

To a solution of (±)-cis-(2-methyl-1,2,3,4-tetrahydro-quinolin-4-yl)-phenyl-amine (636 mg, 2.70 mmol) in dichloromethane (10 mL) at room temperature was added diisopropylethylamine (1.04 g, 1.44 mL, 2.98 mmol) followed by freshly prepared 4-(4-chlorocarbonyl-phenyl)-piperidine-1-carboxylic acid tert-butyl ester (2.98 mmol). The mixture was stirred at room temperature over night, poured into water and extracted with dichloromethane. The extracts were washed with 1 M(aq) NaOH and brine, dried over magnesium sulfate, filtered dried and concentrated. The crude residue was purified by silica gel chromatography (100% hexanes to 70/30 hexanes ethyl acetate gradient) to afford the pure amide (827 mg, 58%).

The (±)-cis-4-[4-(2-methyl-4-phenylamino-3,4-dihydro-2H-quinoline-1-carbonyl)-phenyl]-piperidine-1-carboxylic acid tert-butyl ester (827 mg, 1.57 mmol) thus formed was dissolved in methylene chloride (50 mL). Trifluoroacetic acid (3 mL) was added and the mixture was stirred at rt 70 min. Solvent and excess acid were removed under reduced pressure. The crude residue was dissolved in ethyl acetate and neutralized with 1 M sodium hydroxide (to pH=10.5). The aqueous phase was extracted twice with additional ethyl acetate. The extracts were combined and washed with brine, dried over sodium sulfate, filtered and concentrated to afford the crude diamine (676 mg, 100%) as an oil.

To a solution of the piperidine amine obtained above (676 mg, 1.59 mmol) in methylene chloride (25 mL) was added diisopropylethylamine (616 mg, 849 uL, 4.77 mmol), followed by acetyl chloride (162 mg, 156 uL, 2.06 mmol). The mixture was stirred at room temperature over night. The reaction mixture was poured into saturated aqueous sodium bicarbonate and extracted with additional methylene chloride. The extracts were combined, washed with brine, dried over sodium sulfate, filtered, dried and concentrated to afford the piperidine acetamide (844 mg, >100%).

The crude piperidine acetamide obtained above (844 mg) was dissolved in methylene chloride (25 mL) to which was then added diisopropylethylamine (205 mg, 283 uL, 1.59 mmol) followed by propionyl chloride (4.42 g, 4.2 mL, 47.7 mmol). The resulting reaction mixture was stirred at room temperature 96 h and concentrated. The resulting residue was partitioned between ethyl acetate and saturated aqueous sodium bicarbonate. The extracts were washed with brine and dried over sodium sulfate, filtered, dried and concentrated. The crude residue was purified by silica gel chromatography (50/50 ethyl acetate/hexanes to 100% ethyl acetate gradient) to afford the product (437 mg, 52%).

(±)-Cis-N-{1-[4-(1-acetyl-piperidin-4-yl)-benzoyl]-2-methyl-1,2,3,4-tetrahydro-quinolin-4-yl}-N-phenyl-propionamide was separated by chiral HPLC using a chiral cel OD column and eluting with 90% hexane/10% ethanol isocratic system to give (2R,4S)- and (2S,4R)-cis-N-{1-[4-(1-acetyl-piperidin-4-yl)-benzoyl]-2-methyl-1,2,3,4-tetrahydro-quinolin-4-yl}-N-phenyl-propionamide (A-51 & A-50, respectively).

¹H-NMR (CDCl₃) δ: 1.2 (7H, m), 1.6 (2H, m), 1.8 (2H, d), 2.1 (3H, s), 2.3 (3H, m), 2.6 (2H, m), 3.1 (1H, t), 3.9 (1H, m), 4.8 (2H, m), 5.6 (1H, br), 6.5 (1H, d), 6.9 (1H, m), 7.0 (2H, d), 7.1 (2H, d), 7.2-7.4 (7H, m).

MS m/z: 524 (M+1)

(±)-Cis-N-{1-[4-(-ethyl-piperidin-4-yl)-benzoyl]-2-methyl-1,2,3,4-tetrahydro-quinolin-4-yl}-N-phenyl-propionamide (A-101)

(±)-Cis-N-{1-[4-(1-ethyl-piperidin-4-yl)-benzoyl]-2-methyl-1,2,3,4-tetrahydro-quinolin-4-yl}-N-phenyl-propionamide was made from (±)-cis-N-[2-methyl-1-(4-piperidin-4-yl-benzoyl)-1,2,3,4-tetrahydro-quinolin-4-yl]-N-phenyl-propionamide. (±)-Cis-N-[2-methyl-1-(4-piperidin-4-yl-benzoyl)-1,2,3,4-tetrahydro-quinolin-4-yl]-N-phenyl propionamide was dissolved in dichloromethane (3 mL). Acetaldehyde (18 uL, 0.33 mmol) was added in a single portion. The mixture was stirred at room temperature 30 minutes and then a solution sodium triacetoxyborohydride (35 mg, 0.165 mmol) in dichloromethane (1 mL) was slowly added, followed by I drop acetic acid. The mixture was allowed to stir at room temperature over night and was quenched by aqueous sodium bicarbonate. The biphasic mixture was extracted three times with methylene chloride (20 mL); the combined extracts were washed with brine, dried over magnesium sulfate, filtered, concentrated and purified by HPLC to afford the product (35 mg, 62%).

¹H-NMR (CDCl₃) δ: 1.0-1.2 (9H, m), 1.3 (1H, m), 1.8 (4H, br), 2.0 (2H, m), 2.3 (3H, m), 2.5 (2H, m), 3.1 (3H, m), 4.8 (1H, m), 5.6 (1H, br), 6.5 (1H, d), 6.9 (1H, m), 7.0 (2H, d), 7.1-7.4 (9H, m).

MS m/z: 511 (M+2).

(±)-Cis-N-[2-Methyl-1-(4-nitro-benzoyl)-1,2,3,4-tetrahydro-quinolin-4-yl]-N-phenyl-propionamide (A-102)

(±)-Cis-N-[2-methyl-1-(4-nitro-benzoyl)-1,2,3,4-tetrahydro-quinolin-4-yl]-N-phenyl-propionamide was made following general procedure A, substituting 4-nitrobenzoyl chloride for 2-furoyl chloride and propionyl chloride for acetyl chloride.

¹H-NMR (CDCl₃) δ: 1.2 (7H, m), 2.3 (3H, m), 4.8 (1H, m), 5.6 (1H, br), 6.4 (1H, d), 6.9 (1H, m), 7.2-7.4 (9H, m), 8.0 (2H, d).

MS m/z: 444 (M+1).

(±)-Cis-N-[1-(4-amino-benzoyl)-2-methyl-1,2,3,4-tetrahydro-quinolin-4-yl]-N-phenyl-propionamide (A-103)

(±)-Cis-N-[1-(4-amino-benzoyl)-2-methyl-1,2,3,4-tetrahydro-quinolin-4-yl]-N-phenyl-propionamide was prepared from (±)-cis-N-[2-methylmethyl-1-(4-nitro-benzoyl)-1,2,3,4-tetrahydro-quinolin-4-yl]-N-phenyl-propionamide. (±)-Cis-N-[2-methyl-1-(4-nitro-benzoyl)-1,2,3,4-tetrahydro-quinolin-4-yl]-N-phenyl-propionamide (200 mg, 0.45 mmol) was dissolved in ethanol (20 mL). Palladium on carbon (10%) was carefully added and the resulting suspension was shaken under hydrogen gas (40 psi) over night. The suspension was filtered through Celite® to remove solids, and the filter cake washed three times with ethanol. Concentration of the solution afforded pure product (160 mg, 86%).

¹H-NMR (CDCl₃) δ: 1.2 (7H, m), 2.3 (3H, m), 3.9 (2H, br), 4.7 (1H, m), 5.6 (1H, br), 6.4 (2H, d), 6.6 (1H, d), 6.9 (1H, m), 7.0 (2H, d), 7.1 (1H, m), 7.2-7.4 (6H, m).

MS m/z: 414 (M+1).

(±)-Cis-N-[2-methyl-1-(4-pyrrol-1-yl-benzoyl)-1,2,3,4-tetrahydro-quinolin-4-yl]-N-phenyl-propionamide (A-104)

(±)-Cis-N-[2-methyl-1-(4-pyrrol-1-yl-benzoyl)-1,2,3,4-tetrahydro-quinolin-4-yl]-N-phenyl-propionamide was made following general procedure A, substituting 4-pyrrol-1-yl-benzoyl chloride for 2-furoyl chloride and propionyl chloride for acetyl chloride.

¹H-NMR (CDCl₃) δ: 1.2 (6H, m), 1.3 (1H, m), 2.3 (3H, m), 4.8 (1H, m), 5.6 (1H, br), 6.3 (2H, s), 6.6 (1H, d), 6.9 (1H, m), 7.1 (2H, s), 7.2-7.4 (11H, m).

MS m/z: 464 (M+1).

(±)-Cis-N-[1-(4-acetylamino-benzoyl)-2-methyl-1,2,3,4-tetrahydro-quinolin-4-yl]-N-phenyl-propionamide (A-105)

(±)-Cis-N-[1-(4-acetylamino-benzoyl)-2-methyl-1,2,3,4-tetrahydro-quinolin-4-yl]-N-phenyl-propionamide was prepared from (±)-cis-N-[1-(4-amino-benzoyl)-2-methyl-1,2,3,4-tetrahydro-quinolin-4-yl]-N-phenyl-propionamide. To a solution of (±)-cis-N-[1-(4-amino-benzoyl)-2-methyl-1,2,3,4-tetrahydro-quinolin-4-yl]-N-phenyl-propionamide (100 mg, 0.24 mmol) in 2.5 ml tetrahydrofuran was added acetyl chloride (44 μL, 0.63 mmol) followed by triethylamine (88 μL, 0.63 mmol). The reaction was stirred at room temperature overnight. The mixture was concentrated under reduced pressure. The residue was purified by silica gel chromatography, eluting with hexane-ethyl acetate (3:1) to give the title compound (51 mg, 46%).

¹H-NMR (CDCl₃) δ: 1.1 (7H, m), 2.2 (3H, s), 2.3 (3H, m), 4.8 (1H, m), 5.6 (1H, br), 6.5 (1H, d), 6.9 (1H, m), 7.1 (2H, d), 7.2 (1H, d), 7.3-7.4 (8H, m), 8.4 (1H, br).

MS m/z: 456 (M+1)

(±)-Cis-{4-[2-methyl-4-(phenyl-propionyl-amino)-3,4-dihydro-2H-quinoline-1-carbonyl]-phenyl}-carbamic acid ethyl ester (A-106)

(±)-Cis-{4-[2-methyl-4-(phenyl-propionyl-amino)-3,4-dihydro-2H-quinoline-1-carbonyl]-phenyl}-carbamic acid ethyl ester was made from (±)-cis-N-[1-(4-aminoamino-benzoyl)-2-methyl-1,2,3,4-tetrahydro-quinolin-4-yl]-N-phenyl-propionamide, following the method described above in the synthesis of (±)-cis-N-[1-(4-acetylamino-benzoyl)-2-methyl-1,2,3,4-tetrahydro-quinolin-4-yl]-N-phenyl-propionamide, substituting ethyl chloroformate for acetyl chloride.

¹H-NMR (CDCl₃) δ: 1.1 (6H, m), 1.3 (4H, m), 2.3 (3H, m), 4.2 (2H, m), 4.8 (1H, m), 5.6 (1H, br), 6.5 (1H, d), 6.7 (1H, br), 6.9 (1H, m), 7.1-7.4 (10H, m).

MS m/z: 486 (M+1).

(±)-Cis-N-{2-methyl-1-[4-(4-methyl-piperazin-1-yl)-benzoyl]-1,2,3,4-tetrahydro-quinolin-4-yl}-N-phenyl-propionamide (A-107)

(±)-Cis-N-{2-methyl-1-[4-(4-methyl-piperazin-1-yl)-benzoyl]-1,2,3,4-tetrahydro-quinolin-4-yl}-N-phenyl-propionamide was made from (±)-cis-N-[1-(4-bromo-benzoyl)-2-methyl-1,2,3,4-tetrahydro-quinolin-4-yl]-N-phenyl-propionamide. (±)-Cis-N-[1-(4-bromo-benzoyl)-2-methyl- 1,2,3,4-tetrahydro-quinolin-4-yl]-N-phenyl-propionamide (100 mg, 0.22 mmol) was combined with cesium carbonate (355 mg, 1.09 mmol), racemic BINAP (25 mg, 0.04 mmol), Pd$_2$dba$_3$ (36 mmol, 0.04 mmol) and 1-methyl piperazine and dissolved in toluene (10 mL). The reaction mixture was heated at 100° C. under argon overnight. The reaction was cooled to room temperature, filtered and the solids washed with ether. The filtrate was washed with water and brine, dried over magnesium sulfate, filtered and concentrated. The crude product was purified by HPLC.

$^1$H-NMR (CDCl$_3$) δ: 1.2 (6H, m), 1.3 (1H, m), 2.2 (3H, m), 2.3 (3H, s), 2.5 (4H, m), 3.2 (4H, m), 4.7 (1H, m), 5.6 (1H, bs), 6.6 (1H, d), 6.7 (2H, d), 7.0 (1H, m), 7.2-7.4 (9H, m).

MS m/z: 498 (M+2)

(±)-Cis-N-[2-methyl-1-(4-pyrimidin-2-yl-benzoyl)-1, 2,3,4-tetrahydro-quinolin-4-yl]-N-phenyl-propionamide (A-108)

(±)-Cis-N-[2-methyl-1-(4-pyrimidin-2-yl-benzoyl)-1,2,3, 4-tetrahydro-quinolin-4-yl]-N-phenyl-propionamide was made following general procedure A, substituting 4-pyrimidin-2-yl-benzoyl chloride for 2-furoyl chloride and propionyl chloride for acetyl chloride.

$^1$H-NMR (CDCl$_3$) δ: 1.2 (7H, m), 2.3 (3H, m), 4.8 (1H, m), 5.6 (1H, br), 6.5 (1H, d), 6.9 (1H, m), 7.2-7.4 (10H, m), 8.3 (2H, d), 8.8 (2H, d).

MS m/z: 478 (M+2).

(±)-Cis-N-[2-methyl-1-(4-methyl-3,4-dihydro-2H-benzo[1,4]oxazine-7-carbonyl)-1,2,3,4-tetrahydro-quinolin-4-yl]-N-phenyl-propionamide (A-109)

(±)-Cis-N-[2-methyl-1-(4-methyl-3,4-dihydro-2H-benzo[1,4]oxazine-7-carbonyl)-1,2,3,4-tetrahydro-quinolin-4-yl]-N-phenyl-propionamide was made following general procedure A, substituting 4-methyl-3,4-dihydro-2H-benzo[1,4]oxazine-7-carbonyl chloride for 2-furoyl chloride and propionyl chloride for acetyl chloride.

$^1$H-NMR (CDCl$_3$) δ: 1.1 (6H, m), 1.3 (1H, t), 2.3 (3H, m), 2.8 (3H, s), 3.3 (2H, t), 4.2 (2H, t), 4.7 (1H, m), 5.6 (1H, br), 6.3 (1H, d), 6.5 (1H, d), 6.6 (1H, d), 6.9 (1H, s), 7.0 (1H, m), 7.1 (1H, m), 7.3-7.4 (7H, m).

MS m/z: 471 (M+2).

(±)-Cis-N-[2-Methyl-1-(4-morpholin-4-yl-benzoyl)-1,2,3,4-tetrahydro-quinolin-4-yl]-N-phenyl-propionamide (A-110)

(±)-Cis-N-[2-methyl-1-(4-morpholin-4-yl-benzoyl)-1,2,3,4-tetrahydro-quinolin-4-yl]-N-phenyl-propionamide was made from (±)-cis-N-[1-(4-bromo-benzoyl)-2-methyl-1,2,3,4-tetrahydro-quinolin-4-yl]-N-phenyl-propionamide, following the procedure used to make (±)-cis-N-{2-methyl-1-[4-(4-methyl-piperazin-1-yl)-benzoyl]-1,2,3,4-tetrahydro-quinolin-4-yl}-N-phenyl-propionamide substituting morpholine for 1-methyl piperazine.

(±)-Cis-N-[2-methyl-1-(4-morpholin-4-yl-benzoyl)-1,2,3,4-tetrahydro-quinolin-4-yl]-N-phenyl-propionamide was separated by chiral HPLC using a chiral cel OD column and eluting with 90% hexane/10% ethanol isocratic system to give (2R,4S)- and (2S,4R)-cis-N-[2-methyl-1-(4-morpholin-4-yl-benzoyl)-1,2,3,4-tetrahydro-quinolin-4-yl]-N-phenyl-propionamide (A-120 & A-119, respectively).

$^1$H-NMR (CDCl$_3$) δ: 1.1 (7H, m), 2.3 (3H, m), 3.1 (4H, t), 3.8 (4H, t), 4.7 (1H, m), 5.6 (1H, br), 6.6 (1H, d), 6.7 (2H, d), 6.9 (1H, m), 7.2-7.4 (9H, m).

MS m/z: 485 (M+2).

(±)-Cis-N-{1-[4-(2,5-dimethyl-pyrrol-1-yl)-benzoyl]-2-methyl-1,2,3,4-tetrahydro-quinolin-4-yl}-N-phenyl-propionamide (A-111)

(±)-Cis-N-{1-[4-(2,5-dimethyl-pyrrol-1-yl)-benzoyl]-2-methyl-1,2,3,4-tetrahydro-quinolin-4-yl}-N-phenyl-propionamide was prepared from (±)-cis-N-[1-(4-amino-benzoyl)-2-methyl-1,2,3,4-tetrahydro-quinolin-4-yl]-N-phenyl-propionamide. A solution of (±)-cis-N-[1-(4-amino-benzoyl)-2-methyl-1,2,3,4-tetrahydro-quinolin-4-yl]-N-phenyl-propionamide (150 mg, 0.36 mmol), and propionic acid (0.5 ml) in dry benzene (20 ml) was heated at reflux under argon in a flask equipped with a Dean-Stark trap while stirring with the exclusion of light. The resulting solution was cooled to room temperature, and concentrated under vacuum. Recovered oil was purified by silica gel chromatography, eluting with hexane-ethyl acetate (3:1) to give the title compound (140 mg, 80%).

$^1$H-NMR (CDCl$_3$) δ: 1.2 (7H, m), 2.0 (6H, s), 2.3 (3H, m), 4.8 (1H, m), 5.6 (1H, br), 5.9 (2H, s), 6.5 (1H, d), 6.9 (1H, m), 7.0 (1H, d), 7.2 (2H, m), 7.3-7.4 (8H, m).

MS m/z: 493 (M+2).

(±)-Cis-N-{1-[4-(2-ethyl-butylamino)-benzoyl]-2-methyl-1,2,3,4-tetrahydro-quinolin-4-yl}-N-phenyl-propionamide (A-112)

(±)-Cis-N-{1-[4-(2-ethyl-butylamino)-benzoyl]-2-methyl-1,2,3,4-tetrahydro-quinolin-4-yl}-N-phenyl-propionamide was prepared from (±)-cis-N-[1-(4-amino-benzoyl)-2-methyl-1,2,3,4-tetrahydro-quinolin-4-yl]-N-phenyl-propionamide. To a solution of (±)-cis-N-[1-(4-Amino-benzoyl)-2-methyl-1,2,3,4-tetrahydro-quinolin-4-yl]-N-phenyl-propionamide (75 mg, 0.145 mmol) in dichloromethane (3 mL) was added 2-ethylbutyraldehyde (26 uL, 0.2 mmol) in one portion. The mixture was stirred at room temperature for a 0.5 h before a solution of sodium triacetoxyborohydride (74 mg, 0.348 mmol) 1 ml DCM was added slowly. A single drop of acetic acid was added and the reaction was allowed to stir at room temperature over night. Excess reagent was quenched by the addition of saturated aqueous sodium bicarbonate. The resulting mixture was extracted three times with 20 mL dichloromethane. The combined extracts were washed with brine, dried over magnesium sulfate, filtered and concentrated. Crude product was purified by HPLC to afford the title compound (60 mg, 83%).

$^1$H-NMR (CDCl$_3$) δ: 0.9 (6H, m), 1.2 (7H, m), 1.4 (5H, m), 2.3 (3H, m), 3.0 (2H, d), 4.7 (1H, m), 5.6 (1H, br), 6.3 (2H, d), 6.6 (1H, d), 7.0 (1H, m), 7.1 (2H, d), 7.2 (1H, m), 7.3-7.4 (6H, m).

MS m/z: 499 (M+2).

(±)-Cis-N-[2-Methyl-1-(4-propylamino-benzoyl)-1,2,3,4-tetrahydro-quinolin-4-yl]-N-phenyl-propionamide (A-113)

(±)-Cis-N-[2-methyl-1-(4-propylamino-benzoyl)-1,2,3,4-tetrahydro-quinolin-4-yl]-N-phenyl-propionamide was prepared from (±)-cis-N-[1-(4-amino-benzoyl)-2-methyl-1,2,3,4-tetrahydro-quinolin-4-yl]-N-phenyl-propionamide utilizing the reductive amination conditions described for the synthesis of (±)-cis-N-{1-[4-(2-ethyl-butylamino)-benzoyl]-

2-methyl-1,2,3,4-tetrahydro-quinolin-4-yl}-N-phenyl-propionamide. Propionaldehyde was substituted for 2-ethylbutyraldehyde. The reaction was poorly selective and afforded approximately equivalent amounts of mono- and di-alkylated products (i.e., (±)-cis-N-[1-(4-dipropylamino-benzoyl)-2-methyl-1,2,3,4-tetrahydro-quinolin-4-yl]-N-phenyl propionamidel see below).

$^1$H-NMR (CDCl$_3$) δ: 1.0 (3H, m), 1.1 (7H, m), 1.6 (2H, m), 2.3 (3H, m), 3.0 (2H, d), 4.0 (1H, br), 4.7 (1H, m), 5.6 (1H, br), 6.3 (2H, d), 6.6 (1H, d), 6.9 (1H, m), 7.06 (2H, d), 7.14 (1H, m), 7.3-7.4 (6H, m).

MS m/z: 457 (M+2).

(±)-Cis-N-[1-(4-dipropylamino-benzoyl)-2-methyl-1,2,3,4-tetrahydro-quinolin-4-yl]-N-phenyl-propionamide (A-114)

(±)-Cis-N-[1-(4-Dipropylamino-benzoyl)-2-methyl-1,2,3,4-tetrahydro-quinolin-4-yl]-N-phenyl-propionamide was prepared as a by-product in the synthesis of (±)-cis-N-[2-methyl-1-(4-propylamino-benzoyl)-1,2,3,4-tetrahydro-quinolin-4-yl]-N-phenyl-propionamide described above.

$^1$H-NMR (CDCl$_3$) δ: 1.0 (6H, t), 1.1 (6H, m), 1.4 (1H, m), 1.5 (4H, m), 2.3 (3H, m), 3.2 (4H, t), 4.7 (1H, m), 5.6 (1H, br), 6.4 (2H, d), 6.7 (1H, d), 7.0 (1H, m), 7.1-7.2 (3H, m), 7.3-7.4 (6H, m).

MS m/z: 499 (M+2).

(±)-Cis-N-[2-methyl-1-(4-pyrrolidin-1-yl-benzoyl)-1,2,3,4-tetrahydro-quinolin-4-yl]-N-phenyl-propionamide (A-115)

(±)-Cis-N-[2-methyl-1-(4-pyrrolidin-1-yl-benzoyl)-1,2,3,4-tetrahydro-quinolin-4-yl]-N-phenyl-propionamide was made from (±)-cis-N-[1-(4-bromo-benzoyl)-2-methyl-1,2,3,4-tetrahydro-quinolin-4-yl]-N-phenyl-propionamide following the procedure used to make (±)-cis-N-{2-methyl-1-[4-(4-methyl-piperazin-1-yl)-benzoyl]-1,2,3,4-tetrahydro-quinolin-4-yl}-N-phenyl-propionamide substituting pyrollidine for 1-methylpiperazine.

$^1$H-NMR (CDCl$_3$) δ: 1.1 (7H, m), 2.0 (4H, m), 2.3 (3H, m), 3.2 (4H, m), 4.7 (1H, m), 5.6 (1H, br), 6.3 (2H, d), 6.6 (1H, d), 6.9 (1H, m), 7.1-7.4 (9H, m).

MS m/z: 468 (M+1).

(±)-Cis-N-[2-methyl-1-(4-ureido-benzoyl)-1,2,3,4-tetrahydro-quinolin-4-yl]-N-phenyl-propionamide (A-116)

(±)-Cis-N-[2-methyl-1-(4-ureido-benzoyl)-1,2,3,4-tetrahydro-quinolin-4-yl]-N-phenyl-propionamide was made from (±)-cis-N-[1-(4-amino-benzoyl)-2-methyl-1,2,3,4-tetrahydro-quinolin-4-yl]-N-phenyl-propionamide. A mixture of (±)-cis-N-[1-(4-Amino-benzoyl)-2-methyl-1,2,3,4-tetrahydro-quinolin-4-yl]-N-phenyl-propionamide (100 mg, 0.24 mmol) and trimethylsilyl isocyanate (120 µL, 30.72 mmol) in dry DMF (0.5 mL) was stirred at room temperature for 3 days and then concentrated under reduced pressure at 30° C. to dryness. The residual syrup was stirred with ethyl acetate to which was added an additional 10 mL of ethyl acetate with 10 mL water. The pH was adjusted to 3.0 with 3 N HCl, and the separated aqueous layer was extracted with ethyl acetate. The combined ethyl acetate extracts were washed with water and brine, dried over magnesium sulfate and concentrated in vacuo, yielding the product (10 mg, 9% yield).

$^1$H-NMR (CDCl$_3$) δ: 1.2 (7H, m), 2.3 (3H, m), 4.7 (1H, m), 5.1 (2H, br), 5.6 (1H, br), 6.5 (1H, d), 6.9 (5H, m), 7.2 (7H, m), 7.9 (1H, br).

MS m/z: 457 (M+1).

(±)-Cis-2-{4-[4-(acetyl-phenyl-amino)-2-methyl-3,4-dihydro-2H-quinoline-1-carbonyl]-phenylamino}-propionic acid methyl ester (A-117)

(±)-Cis-2-{4-[4-(acetyl-phenyl-amino)-2-methyl-3,4-dihydro-2H-quinoline-1-carbonyl]-phenylamino}-propionic acid methyl ester was prepared from (±)-cis-N-[1-(4-amino-benzoyl)-2-methyl-1,2,3,4-tetrahydro-quinolin-4-yl]-N-phenyl-propionamide. A mixture of (±)-cis-N-[1-(4-amino-benzoyl)-2-methyl-1,2,3,4-tetrahydro-quinolin-4-yl]-N-phenyl-propionamide (210 mg, 0.53 mmol), potassium carbonate (123 mg, 0.89 mmol), and methyl 2-bromopropionate (70 uL, 0.63 mmol) in dry dimethylformamide (2 mL) was heated at 100° C. for 6 h, then cooled to room temperature and stirred with 20 ml water until all of the salts dissolved. The aqueous layer was separated and was extracted with ethyl acetate. The combined extracts were washed with water and brine, dried over magnesium sulfate, filtered and concentrated under reduced pressure. The resulting oil was purified by silica gel chromatography, eluting with (97:3 methylene chloride/methanol) to afford the title compound (220 mg, 87%).

$^1$H-NMR (CDCl$_3$) δ: 1.2 (4H, m), 1.4 (3H, d), 2.0 (3H, s), 2.3 (1H, br), 3.7 (3H, s), 4.1 (1H, m), 4.7 (1H, m), 5.6 (1H, br), 6.3 (2H, d), 6.6 (1H, d), 6.9 (1H, m), 7.0 (2H, d), 7.3-7.4 (7H, m).

MS m/z: 487 (M+2).

(±)-Cis-2-{4-[4-(acetyl-phenyl-amino)-2-methyl-3,4-dihydro-2H-quinoline-1-carbonyl]-phenylamino}-propionamide (A-118)

(±)-Cis-2-{4-[4-(acetyl-phenyl-amino)-2-methyl-3,4-dihydro-2H-quinoline-1-carbonyl]-phenylamino}-propionamide was prepared from (±)-cis-2-{4-[4-(acetyl-phenyl-amino)-2-methyl-3,4-dihydro-2H-quinoline-1-carbonyl]-phenylamino}-propionic acid methyl ester.

To concentrated ammonium hydroxide (2 mL, 2.0 M) were added crude (±)-cis-2-{4-[4-(acetyl-phenyl-amino)-2-methyl-3,4-dihydro-2H-quinoline-1-carbonyl]-phenylamino}-propionic acid methyl ester (180 mg, 0.37 mmol) and trace amount ammonium chloride; the mixture was heated at 100° C. for 6 h in a pressure reactor with good mixing. After cooling to 0° C., the resulting precipitate was filtered and washed with ice-water and extracted with ether. The combined extracts were washed with water and brine, dried over magnesium sulfate and concentrated under reduced pressure. The crude product was purified by HPLC to give the title compound (10 mg, 6%).

$^1$H-NMR (CDCl$_3$) δ: 1.2 (4H, m), 1.5 (3H, d), 2.1 (3H, s), 2.3 (1H, br), 3.8 (1H, s), 4.4 (2H, br), 4.7 (1H, m), 5.6 (2H, m), 6.3 (2H, m), 6.6 (2H, d), 7.0 (1H, m), 7.1 (2H, d), 7.2 (1H, m), 7.3-7.4 (5H, m).

MS m/z: 471 (M+1)

(±)-Cis-N-[1-(3-methoxy-benzoyl)-2-methyl-1,2,3,4-tetrahydro-quinolin-4-yl]-N-phenyl-acetamide (A-123)

(±)-Cis-N-[1-(3-methoxy-benzoyl)-2-methyl-1,2,3,4-tetrahydro-quinolin-4-yl]-N-phenyl-acetamide was made following general procedure A, substituting 3-methoxybenzoyl chloride for 2-furoyl chloride.

(±)-Cis-N-[1-(3-methoxy-benzoyl)-2-methyl-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[1-(3-methoxy-benzoyl)-2-methyl-1,2,3,4-tetrahydro-quinolin-4-yl]-N-phenyl-acetamide (A-126 & A-127, respectively).

$^1$H-NMR (CDCl$_3$) δ: 1.15 (3H, d; overlapping 1H, t), 2.05 (3H, s), 2.33 (1H, m), 3.60 (3H, s), 4.80 (1H, m), 5.65 (1H, m), 6.55 (1H, d), 6.75-6.85 (3H, complex), 6.95 (1H, t), 7.15 (1H, t), 7.25 (1H, t), 7.25-7.55 (6H, m).

MS m/z: 415 (M+1).

(±)-Trans-N-[1-(3-methoxy-benzoyl)-2-methyl-1,2,3,4-tetrahydro-quinolin-4-yl]-N-phenyl-acetamide (A-124)

(±)-Trans-N-[1-(3-methoxy-benzoyl)-2-methyl-1,2,3,4-tetrahydro-quinolin-4-yl]-N-phenyl-acetamide was made following general procedure A, substituting 3-methoxybenzoyl chloride for 2-furoyl chloride, and trans-(2-ethyl-1,2,3,4-tetrahydro-quinolin-4-yl)-phenyl-amine for cis-(2-ethyl-1,2,3,4-tetrahydro-quinolin-4-yl)-phenyl-amine.

(±)-Cis-N-[1-(3-methoxy-benzoyl)-2-methyl-1,2,3,4-tetrahydro-quinolin-4-yl]-N-phenyl-propionamide (A-128)

(±)-Cis-N-[1-(3-methoxy-benzoyl)-2-methyl-1,2,3,4-tetrahydro-quinolin-4-yl]-N-phenyl-propionamide was made following general procedure A, substituting 3-methoxybenzoyl chloride for 2-furoyl chloride, and propionyl chloride for acetyl chloride.

$^1$H-NMR (CDCl$_3$) δ: 1.15 (3H, d; overlapping 3H, t, 1H, t), 2.20 (2H, q), 2.33 (1H, m), 3.65 (3H, s), 4.80 (1H, m), 5.60 (1H, m), 6.55 (1H, d), 6.75-6.85 (3H, complex), 6.95 (1H, t), 7.15 (1H, t), 7.20 (1H, t), 7.25-7.55 (6H, m).

MS m/z: 429 (M+1).

(±)-Cis-N-[6-chloro-1-(3-methoxy-benzoyl)-2-methyl-1,2,3,4-tetrahydro-quinolin-4-yl]-N-(4-chloro-phenyl)-acetamide (A-129)

(±)-Cis-N-[6-chloro-1-(3-methoxy-benzoyl)-2-methyl-1,2,3,4-tetrahydro-quinolin-4-yl]-N-(4-chloro-phenyl)-acetamide was made following general procedure A, substituting 3-methoxybenzoyl chloride for 2-furoyl chloride, and (±)-cis-(6-chloro-2-methyl-1,2,3,4-tetrahydro-quinolin-4-yl)-(4-chloro-phenyl)-amine for (±)-cis-(2-methyl-1,2,3,4-tetrahydro-quinolin-4-yl)-phenyl-amine. (±)-Cis-(6-chloro-2-methyl-1,2,3,4-tetrahydro-quinolin-4-yl)-(4-chloro-phenyl)-amine was synthesized following the reactions detailed in scheme 1, substituting 4-chloroaniline for aniline.

$^1$H-NMR (CDCl$_3$) δ: 1.15 (3H, d; overlapping 1H, t), 2.02 (3H, s), 2.35 (1H, m), 3.65 (3H, s), 4.80 (1H, m), 5.60 (1H, m), 6.42 (1H, d), 6.65-6.95 (overlapping 1H, d; 1H, dd; 1H dd), 7.15 (1H, t), 7.20-7.30 (6H, m), 7.40 (1H, d).

MS m/z: 484 (M+1).

(±)-Cis-N-[2-methyl-1-(1-methyl-1H-pyrrole-2-carbonyl)-1,2,3,4-tetrahydro-quinolin-4-yl]-N-phenyl-acetamide (A-130)

(±)-Cis-N-[2-methyl-1-(1-methyl-1H-pyrrole-2-carbonyl)-1,2,3,4-tetrahydro-quinolin-4-yl]-N-phenyl-acetamide was made following general procedure A, substituting 1-methyl-1H-pyrrole-2-carbonyl chloride for 2-furoyl chloride.

$^1$H-NMR (CDCl$_3$) δ: 1.12 (3H, d; overlapping 1H, t), 2.00 (3H, s), 2.35 (1H, m), 3.80 (3H, s), 4.70 (1H, m), 5.50 (1H, m), 5.80 (1H, d), 6.55 (1H, d), 6.80 (1H, d), 7.00 (1H, t), 7.20-7.50 (6H, m).

MS m/z: 388 (M+1).

(±)-Cis-N-[2-methyl-1-(2-methyl-pyridine-4-carbonyl)-1,2,3,4-tetrahydro-quinolin-4-yl]-N-phenyl-propionamide (A-131)

(±)-Cis-N-[2-methyl-1-(2-methyl-pyridine-4-carbonyl)-1,2,3,4-tetrahydro-quinolin-4-yl]-N-phenyl-propionamide was made following general procedure A, substituting 2-methyl-isonicotinoyl chloride for 2-furoyl chloride and propionyl chloride for acetyl chloride.

$^1$H-NMR (CDCl$_3$) δ: 1.11-1.16 (3H, d; overlapping 3H, t, and 1H, t), 2.20-2.35 (overlapping 2H, q; and 1H, m), 2.47 (3H, s), 4.80 (1H, m), 5.60 (1H, m), 6.48 (1H, d), 6.65 (1H, d), 6.85 (1H, t), 7.10-7.40 (8H, m), 8.30 (1H, d).

MS m/z: 414 (M+1).

(±)-Cis-N-[1-(4-fluoro-benzoyl)-2-methyl-1,2,3,4-tetrahydro-quinolin-4-yl]-3-methyl-N-phenyl-butyramide (A-132)

(±)-Cis-N-[1-(4-fluoro-benzoyl)-2-methyl-1,2,3,4-tetrahydro-quinolin-4-yl]-3-methyl-N-phenyl-butyramide was made following general procedure A, substituting 4-fluorobenzoyl chloride for 2-furoyl chloride and 3-methyl-butyryl chloride for acetyl chloride.

$^1$H-NMR (CDCl$_3$) δ: 0.90 (2×3H, d), 1.15 (3H, d; overlapping 1H, t), 2.15 (1H, m), 2.20-2.35 (overlapping 2H, m; 1H, m), 4.80 (1H, m), 5.65 (1H, m), 6.50 (1H, d), 6.90 (4H, complex), 7.20-7.60 (8H, m).

MS m/z: 445 (M+1).

(±)-Cis-N-[2-methyl-1-(6-methyl-pyridine-3-carbonyl)-1,2,3,4-tetrahydro-quinolin-4-yl]-N-phenyl-propionamide (A-133)

(±)-Cis-N-[2-methyl-1-(6-methyl-pyridine-3-carbonyl)-1,2,3,4-tetrahydro-quinolin-4-yl]-N-phenyl-propionamide was made following general procedure A, substituting 6-methyl-nicotinoyl chloride for 2-furoyl chloride and propionyl chloride for acetyl chloride.

$^1$H-NMR (CDCl$_3$) δ: 1.11-1.16 (3H, d; overlapping 3H, t, and 1H, t), 2.20-2.40 (overlapping 2H, q; and 1H, m), 2.49 (3H, s), 4.80 (1H, m), 5.60 (1H, m), 6.48 (1H, d), 6.80-7.00 (1H, d; 1H, t), 7.10-7.50 (9H, m), 8.60 (1H, d).

MS m/z: 414 (M+1).

(±)-Cis-N-[1-(4-fluoro-benzoyl)-2-methyl-1,2,3,4-tetrahydro-quinolin-4-yl]-2-morpholin-4-yl-N-phenyl-acetamide (A-134)

(±)-Cis-N-[1-(4-fluoro-benzoyl)-2-methyl-1,2,3,4-tetrahydro-quinolin-4-yl]-2-morpholin-4-yl-N-phenyl-acetamide was made following general procedure A, substituting 4-fluorobenzoyl chloride for 2-furoyl chloride and morpholinoacetyl chloride for acetyl chloride.

(±)-Cis-N-[1-(2,3-dihydro-benzo[1,4]dioxine-6-carbonyl)-2-methyl-1,2,3,4-tetrahydro-quinolin-4-yl]-N-phenyl-propionamide (A-135)

(±)-Cis-N-[1-(2,3-dihydro-benzo[1,4]dioxine-6-carbonyl)-2-methyl-1,2,3,4-tetrahydro-quinolin-4-yl]-N-phenylpropionamide was made following general procedure A, substituting (±)-cis-2,3-dihydro-benzo[1,4]dioxine-6-carbonyl chloride for 2-furoyl chloride and propionyl chloride for acetyl chloride.

$^1$H-NMR (CDCl$_3$) δ: 1.10 (3H, d; overlapping 3H, t; 1H, t), 2.10 (2H, q, 1H, m), 4.10 (2×2H, m), 4.70 (1H, m), 5.65 (1H, m), 6.50-6.60 (2×1H, d), 7.20-7.40 (7H, m).

MS m/z: 457 (M+1).

(±)-Cis-N-[2-methyl-1-(5-trifluoromethyl-thiophene-2-carbonyl)-1,2,3,4-tetrahydro-quinolin-4-yl]-N-phenyl-propionamide (A-136)

(±)-Cis-N-[2-methyl-1-(5-trifluoromethyl-thiophene-2-carbonyl)-1,2,3,4-tetrahydro-quinolin-4-yl]-N-phenyl-propionamide was made following general procedure A, substituting 5-trifluoromethyl-thiophene-2-carbonyl chloride for 2-furoyl chloride and propionyl chloride for acetyl chloride.

$^1$H-NMR (CDCl$_3$) δ: 1.10-1.15 (3H, d; overlapping 3H, t; 1H, t), 2.15-2.35 (2H, q, 1H, m), 4.70 (1H, m), 5.55 (1H, m), 6.45 (1H, d), 6.85 (1H, d), 7.00-7.20 (overlapping 1H, d; 1H, t), 7.20-7.60 (7H, m).

MS m/z: 473 (M+1).

(±)-Cis-N-[2-methyl-1-(6-trifluoromethyl-pyridine-3-carbonyl)-1,2,3,4-tetrahydro-quinolin-4-yl]-N-phenyl-propionamide (A-137)

(±)-Cis-N-[2-methyl-1-(6-trifluoromethyl-pyridine-3-carbonyl)-1,2,3,4-tetrahydro-quinolin-4-yl]-N-phenyl-propionamide was made following general procedure A, substituting 6-trifluoromethyl-nicotinoyl chloride for 2-furoyl chloride and propionyl chloride for acetyl chloride.

$^1$H-NMR (CDCl$_3$) δ: 1.10 (3H, d; overlapping 3H, t; 1H, t), 2.00-2.40 (2H, q, 1H, m), 4.80 (1H, m), 5.65 (1H, m), 6.40 (1H, d), 7.00 (1H, d), 7.20-7.50 (9H, m), 8.70 (1H).

MS m/z: 468 (M+1).

(±)-Cis-N-[2-methyl-1-(3-methyl-isoxazole-5-carbonyl)-1,2,3,4-tetrahydro-quinolin-4-yl]-N-phenyl-propionamide (A-138)

(±)-Cis-N-[2-methyl-1-(3-methyl-isoxazole-5-carbonyl)-1,2,3,4-tetrahydro-quinolin-4-yl]-N-phenyl-propionamide was made following general procedure A, substituting 3-methyl-isoxazole-5-carbonyl chloride for 2-furoyl chloride and propionyl chloride for acetyl chloride.

$^1$H-NMR (CDCl$_3$) δ: 1.10 (overlapping 3H, d; 3H, t; 1H, t), 2.10-2.40 (overlapping 3H, s; 2H, q; 1H, m), 4.80 (1H, m), 5.50 (1H, m), 6.80 (1H, d), 7.10 (1H, t), 7.20-7.50 (9H, m).

MS m/z: 404 (M+1).

(±)-Cis-N-[2-methyl-1-(4-oxazol-5-yl-benzoyl)-1,2,3,4-tetrahydro-quinolin-4-yl]-N-phenyl-propionamide (A-139)

(±)-Cis-N-[2-Methyl-1-(4-oxazol-5-yl-benzoyl)-1,2,3,4-tetrahydro-quinolin-4-yl]-N-phenyl-propionamide was made following general procedure A, substituting 4-oxazol-5-yl-benzoyl chloride for 2-furoyl chloride and propionyl chloride for acetyl chloride.

$^1$H-NMR (CDCl$_3$) δ: 1.00-1.20 (overlapping 3H, t; 3H, d; 1H, t), 2.20-2.40 (2H, q; 1H, m), 4.80 (1H, m), 5.65 (1H, m), 6.55 (1H, d), 6.90 (1H, t), 7.20-7.60 (12H, m), 7.90 (1H, s).

MS m/z: 466 (M+1).

(±)-Cis-N-[1-(benzo[c]isoxazole-3-carbonyl)-2-methyl-1,2,3,4-tetrahydro-quinolin-4-yl]-N-phenyl-propionamide (A-140)

(±)-Cis-N-[1-(benzo[c]isoxazole-3-carbonyl)-2-methyl-1,2,3,4-tetrahydro-quinolin-4-yl]-N-phenyl-propionamide was made following general procedure A, substituting benzo[c]isoxazole-3-carbonyl chloride for 2-furoyl chloride and propionyl chloride for acetyl chloride.

$^1$H-NMR (CDCl$_3$) δ: 1.14 (3H, t); 1.23 (3H, d), 2.20 (2H, q), 2.40 (1H, m), 4.80 (1H, m), 5.60 (1H, m), 6.60 (1H, d), 7.00 (3H, complex), 7.00-7.40 (8H, m), 7.55 (1H, d).

MS m/z: 440 (M+1).

(±)-Cis-N-[1-(4-fluoro-benzoyl)-2-methyl-1,2,3,4-tetrahydro-quinolin-4-yl]-N-phenyl-succinamic acid methyl ester (A-141)

(±)-Cis-N-[1-(4-fluoro-benzoyl)-2-methyl-1,2,3,4-tetrahydro-quinolin-4-yl]-N-phenyl-succinamic acid methyl ester was made following general procedure A, substituting 4-fluorobenzoyl chloride for 2-furoyl chloride and 3-chlorocarbonyl-propionic acid methyl ester for acetyl chloride.

(±)-Cis-N-{1-[5-(4-chloro-phenyl)-furan-2-carbonyl]-2-methyl-1,2,3,4-tetrahydro-quinolin-4-yl}-N-phenyl-propionamide (A-142)

(±)-Cis-N-{1-[5-(4-chloro-phenyl)-furan-2-carbonyl]-2-methyl-1,2,3,4-tetrahydro-quinolin-4-yl}-N-phenyl-propionamide was made following general procedure A, substituting 5-(4-chloro-phenyl)-furan-2-carbonyl chloride for 2-furoyl chloride and propionyl chloride for acetyl chloride.

$^1$H-NMR (CDCl$_3$) δ: 1.08-1.36 (7H, m), 2.15-2.35 (3H, m), 4.72 (1H, q), 5.40-5.60 (1H, br), 6.53 (2H, d), 6.89 (1H, d), 7.04-7.09 (1H, m), 7.17-7.40 (10H, m).

MS m/z: 499 (M+1).

(±)-Cis-N-{1-[5-(2-chloro-4-trifluoromethyl-phenyl)-furan-2-carbonyl]-2-methyl-1,2,3,4-tetrahydro-quinolin-4-yl}-N-phenyl-propionamide (A-143)

(±)-Cis-N-{1-[5-(2-chloro-4-trifluoromethyl-phenyl)-furan-2-carbonyl]-2-methyl-1,2,3,4-tetrahydro-quinolin-4-yl}-N-phenyl-propionamide was made following general procedure A, substituting 5-(2-chloro-4-trifluoromethyl-phenyl)-furan-2-carbonyl chloride for 2-furoyl chloride and propionyl chloride for acetyl chloride.

$^1$H-NMR (CDCl$_3$) δ: 1.08-1.36 (7H, m), 2.15-2.35 (3H, m), 4.72 (1H, q), 5.40-5.60 (1H, br), 6.78-6.87 (2H, m), 7.05-7.49 (11H, m).

MS m/z: 567 (M+1).

(±)-Cis-N-{2-methyl-1-[5-(4-nitro-phenyl)-furan-2-carbonyl]-1,2,3,4-tetrahydro-quinolin-4-yl}-N-phenyl-propionamide (A-144)

(±)-Cis-N-{2-methyl-1-[5-(4-nitro-phenyl)-furan-2-carbonyl]-1,2,3,4-tetrahydro-quinolin-4-yl}-N-phenyl-propionamide propionamide was made following general procedure A, substituting 5-(4-nitro-phenyl)-furan-2-carbonyl chloride for 2-furoyl chloride and propionyl chloride for acetyl chloride.

$^1$H-NMR (CDCl$_3$) δ: 1.13-1.22 (7H, m), 2.20-2.36 (3H, m), 4.70 (1H, q), 5.40-5.60 (1H, br), 6.70 (2H, d), 6.87 (1H, d), 7.03 (1H, t), 7.25-7.47 (8H, m), 8.15 (2H, d).

MS m/z: 510 (M+1).

(±)-Cis-N-[2-methyl-1-(5-methyl-isoxazole-3-carbonyl)-1,2,3,4-tetrahydro-quinolin-4-yl]-N-phenyl-propionamide (A-145)

(±)-Cis-N-[2-methyl-1-(5-methyl-isoxazole-3-carbonyl)-1,2,3,4-tetrahydro-quinolin-4-yl]-N-phenyl-propionamide was made following general procedure A, substituting 5-methyl-isoxazole-3-carbonyl chloride for 2-furoyl chloride and propionyl chloride for acetyl chloride.

$^1$H-NMR (CDCl$_3$) δ: 1.10-1.27 (7H, m), 2.13-2.35 (6H, m), 4.78 (1H, q), 5.40-5.60 (1H, br), 6.84-6.86 (1H, d), 7.05 (1H, t), 7.22-7.38 (7H, m).

MS m/z: 404 (M+1).

(±)-Cis-N-[2-methyl-1-(2-methyl-thiophene-3-carbonyl)-1,2,3,4-tetrahydro-quinolin-4-yl]-N-phenyl-propionamide (A-146)

(±)-Cis-N-[2-methyl-1-(2-methyl-thiophene-3-carbonyl)-1,2,3,4-tetrahydro-quinolin-4-yl]-N-phenyl-propionamide was made following general procedure A, substituting 2-methyl-thiophene-3-carbonyl chloride for 2-furoyl chloride and propionyl chloride for acetyl chloride.

$^1$H-NMR (CDCl$_3$) δ: 1.01-1.27 (7H, m), 2.13-2.39 (6H, m), 4.62-4.78 (1H, m), 5.40-5.60 (1H, br), 6.31-6.45 (2H, m), 6.60-6.83 (2H, m), 7.02-7.38 (6H, m).

MS m/z: 420 (M+1).

(±)-Cis-but-3-enoic acid [1-(4-fluoro-benzoyl)-2-methyl-1,2,3,4-tetrahydro-quinolin-4-yl]-phenyl-amide (A-147)

(±)-Cis-but-3-enoic acid [1-(4-fluoro-benzoyl)-2-methyl-1,2,3,4-tetrahydro-quinolin-4-yl]-phenyl-amide was made following general procedure A, substituting 4-fluorobenzoyl chloride for 2-furoyl chloride and but-3-enoyl chloride for acetyl chloride.

$^1$H-NMR (CDCl$_3$) δ: 0.98-1.17 (4H, m), 2.13-2.29 (1H, m), 2.98-3.15 (2H, m), 4.60-4.78 (1H, m), 4.98-5.20 (2H, m), 5.40-5.60 (1H, m), 5.70-5.91 (1H, m), 6.40 (1H, d), 6.75-7.46 (11H, m).

MS m/z: 429 (M+1).

(±)-Cis-N-{1-[3-(4-fluoro-phenyl)-[1,2,4]oxadiazole-5-carbonyl]-2-methyl-1,2,3,4-tetrahydro-quinolin-4-yl}-N-phenyl-propionamide (A-148)

(±)-Cis-N-{1-[3-(4-fluoro-phenyl)-[1,2,4]oxadiazole-5-carbonyl]-2-methyl-1,2,3,4-tetrahydro-quinolin-4-yl}-N-phenyl-propionamide was made following general procedure A, substituting 3-(4-fluoro-phenyl)-[1,2,4]oxadiazole-5-carbonyl chloride for 2-furoyl chloride and propionyl chloride for acetyl chloride.

$^1$H-NMR (CDCl$_3$) δ: 1.14 (3H, t), 1.23-1.25 (4H, m), 2.17-2.39 (3H, m), 4.78-4.80 (1H, m), 5.40-5.60 (1H, br), 7.03-7.09 (3H, m), 7.10-7.22 (4H, m), 7.24-7.40 (4H, m), 7.97-8.02 (2H, m).

MS m/z: 485 (M+1).

(±)-Cis-N-(1-benzoyl-2-methyl-1,2,3,4-tetrahydro-quinolin-4-yl)-N-phenyl-acetamide (A-150)

(±)-Cis-N-(1-benzoyl-2-methyl-1,2,3,4-tetrahydro-quinolin-4-yl)-N-phenyl-acetamide was made following general procedure A, substituting benzoyl chloride for 2-furoyl chloride.

$^1$H-NMR (CDCl$_3$) δ: 1.14 (3H, d), 1.58-1.69 (1H, m), 2.03 (3H, s), 2.22-2.37 (1H, m), 4.72-4.86 (1H, m), 5.62 (1H, br s), 6.49 (1H, d), 6.88 (1H, t), 7.13-7.46 (12H, m).

MS m/z: 385 (M+1).

(±)-Cis-N-[1-(4-chloro-benzoyl)-2-methyl-1,2,3,4-tetrahydro-quinolin-4-yl]-N-phenyl-acetamide (A-151)

(±)-Cis-N-[1-(4-chloro-benzoyl)-2-methyl-1,2,3,4-tetrahydro-quinolin-4-yl]-N-phenyl-acetamide was made following general procedure A, substituting 4-chlorobenzoyl chloride for 2-furoyl chloride.

$^1$H-NMR (CDCl$_3$) δ: 1.14 (3H, d), 1.61 (1H, br s), 2.03 (3H, s), 2.24-2.36 (1H, m), 4.71-4.83 (1H, m), 5.51-5.69 (1H, m), 6.48 (1H, d), 6.93 (1H, t), 7.12-7.28 (7H, m), 7.35-7.40 (4H, m).

MS m/z: 419 (M)

(±)-Cis-N-[1-(4-methoxy-benzoyl)-2-methyl-1,2,3,4-tetrahydro-quinoin-4-yl]-N-phenyl-acetamide (A-152)

(±)-Cis-N-[1-(4-methoxy-benzoyl)-2-methyl-1,2,3,4-tetrahydro-quinolin-4-yl]-N-phenyl-acetamide was made following general procedure A, substituting 4-methoxybenzoyl chloride for 2-furoyl chloride.

$^1$H-NMR (CDCl$_3$) δ: 1.12 (3H, d), 1.65 (1H, br s), 2.03 (3H, s), 2.24-2.37 (1H, m), 3.74 (3H, s), 4.66-4.84 (1H, m), 5.53-5.70 (1H, m), 6.50-6.54 (1H, d), 6.68 (2H, d), 6.89-6.96 (1H, m), 7.05-7.55 (9H, m).

MS m/z: 415 (M+1).

(±)-Cis-N-[2-methyl-1-(2-methyl-benzoyl)-1,2,3,4-tetrahydro-quinolin-4-yl]-N-phenyl-acetamide (A-153)

(±)-Cis-N-[2-methyl-1-(2-methyl-benzoyl)-1,2,3,4-tetrahydro-quinolin-4-yl]-N-phenyl-acetamide was made following general procedure A, substituting 2-toluoyl chloride for 2-furoyl chloride.

$^1$H-NMR (CDCl$_3$) δ: 1.11 (3H, d), 1.60-1.64 (1H, m), 1.97 (3H, s), 2.03-2.3 (4H, m), 4.77-4.89 (1H, m), 5.41-5.58 (1H, m), 6.38-6.44 (1H, m), 6.79 (1H, t), 6.91-7.14 (4H, m), 7.16-7.28 (4H, m), 7.28-7.41 (3H, m).

MS m/z: 399 (M+1).

(±)-Cis-N-[1-(3,5-dimethyl-isoxazole-4-carbonyl)-2-methyl-1,2,3,4-tetrahydro-quinolin-4-yl]-N-phenyl-acetamide (A-154)

(±)-Cis-N-[1-(3,5-dimethyl-isoxazole-4-carbonyl)-2-methyl-1,2,3,4-tetrahydro-quinolin-4-yl]-N-phenyl-acetamide was made following general procedure A, substituting 3,5-dimethyl-isoxazole-4-carbonyl chloride for 2-furoyl chloride.

$^1$H-NMR (CDCl$_3$) δ: 1.13 (3H, d), 1.57-181 (3H, m), 1.96-2.03 (5H, m), 2.15-2.63 (3H, m), 4.66-4.81 (1H, m), 5.41-5.50 (1H, m), 6.12 (1H, d), 7.03-7.15 (1H, m), 7.24-7.48 (7H, m).

MS m/z: 404 (M+1).

(±)-Cis-N-[1-(isoxazole-5-carbonyl)-2-methyl-1,2,3,4-tetrahydro-quinolin-4-yl]-N-phenyl-acetamide (A-155)

(±)-Cis-N-[1-(isoxazole-5-carbonyl)-2-methyl-1,2,3,4-tetrahydro-quinolin-4-yl]-N-phenyl-acetamide was made following general procedure A, substituting isoxazole-5-carbonyl chloride for 2-furoyl chloride.

(±)-Cis-N-[1-(isoxazole-5-carbonyl)-2-methyl-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[1-(isoxazole-5-carbonyl)-2-methyl-1,2,3,4-tetrahydro-quinolin-4-yl]-N-phenyl-acetamide (A-70 & A-71, respectively).

$^1$H-NMR (CDCl$_3$) δ: 1.12 (3H, d), 1.64 (1H, s), 1.96 (3H, s), 2.21-2.31 (1H, m), 4.63-4.75 (1H, m), 5.34-5.44 (1H, s), 5.98 (1H, s), 6.70 (1H, d), 7.04 (1H, t), 7.21-7.35 (7H, m), 8.04-8.08 (1H, m).

MS m/z: 376 (M+1).

(±)-Cis-N-(1-cyclohexanecarbonyl-2-methyl-1,2,3,4-tetrahydro-quinolin-4-yl)-N-phenyl-acetamide (A-157)

(±)-Cis-N-(1-cyclohexanecarbonyl-2-methyl-1,2,3,4-tetrahydro-quinolin-4-yl)-N-phenyl-acetamide was made following general procedure A, substituting cyclohexanecarbonyl chloride for 2-furoyl chloride.

$^1$H-NMR (CDCl$_3$) δ: 0.97 (3H, d), 1.13-1.27 (3H, m), 1.31-1.47 (2H, m), 1.58-1.89 (7H, m), 1.99 (3H, s), 2.14-2.24 (1H, m), 2.62-2.71 (1H, m), 4.70-4.78 (1H, m), 5.24-5.29 (1H, m), 7.07-7.10 (1H, m), 7.21-7.24 (2H, m), 7.28-7.33 (2H, m), 7.34-7.42 (4H, m).

MS m/z: 391 (M+1).

(±)-Cis-N-[2-methyl-1-(pyridine-4-carbonyl)-1,2,3,4-tetrahydro-quinolin-4-yl]-N-phenyl-acetamide (A-158)

(±)-Cis-N-[2-methyl-1-(pyridine-4-carbonyl)-1,2,3,4-tetrahydro-quinolin-4-yl]-N-phenyl-acetamide was made following general procedure A, substituting isonicotinoyl chloride for 2-furoyl chloride.

$^1$H-NMR (CDCl$_3$) δ: 1.16 (3H, d), 2.04 (3H, s), 2.25-2.35 (1H, m), 4.75-4.83 (1H, m), 5.56-5.67 (1H, m), 6.45-6.48 (1H, m), 6.92 (1H, t), 7.08 (2H, d), 7.19-7.27 (3H, m), 7.34-7.42 (4H, m), 8.49 (2H, d).

MS m/z: 386 (M+1).

(±)-Cis-N-[1-(2,5-dimethyl-2H-pyrazole-3-carbonyl)-2-methyl-1,2,3,4-tetrahydro-quinolin-4-yl]-N-phenyl-acetamide (A-159)

(±)-Cis-N-[1-(2,5-dimethyl-2H-pyrazole-3-carbonyl)-2-methyl-1,2,3,4-tetrahydro-quinolin-4-yl]-N-phenyl-acetamide was made following general procedure A, substituting 2,5-dimethyl-2H-pyrazole-3-carbonyl chloride for 2-furoyl chloride.

$^1$H-NMR (CDCl$_3$) δ: 1.14 (3H, d), 2.02 (3H, m), 2.07 (3H, m), 2.23-2.32 (2H, m), 4.68-4.76 (1H, m), 5.50 (1H, s), 6.66 (1H, d), 7.04 (1H, t), 7.21-7.28 (4H, m), 7.34-7.48 (4H, m).

MS m/z: 404 (M+1).

(±)-Cis-N-[2-methyl-1-(pyridine-2-carbonyl)-1,2,3,4-tetrahydro-quinolin-4-yl]-N-phenyl-acetamide (A-160)

(±)-Cis-N-[2-methyl-1-(pyridine-2-carbonyl)-1,2,3,4-tetrahydro-quinolin-4-yl]-N-phenyl-acetamide was made following general procedure A, substituting pyridine-2-carbonyl chloride for 2-furoyl chloride.

$^1$H-NMR (CDCl$_3$) δ: 1.17 (3H, d), 1.93-2.03 (1H, m), 2.02 (3H, s), 2.32 (1H, br s), 4.78-4.86 (1H, m), 5.60-5.61 (1H, m), 6.51 (1H, d), 6.86 (1H, t), 6.99 (1H, d), 7.14-7.50 (9H, m), 8.53 (1H, d).

MS m/z: 385 (M+1).

(±)-Cis-N-[1-(isoxazole-5-carbonyl)-2-methyl-1,2,3,4-tetrahydro-quinolin-4-yl]-N-phenyl-propionamide (A-161)

(±)-Cis-N-[1-(isoxazole-5-carbonyl)-2-methyl-1,2,3,4-tetrahydro-quinolin-4-yl]-N-phenyl-propionamide following general procedure A, substituting isoxazole-5-carbonyl chloride for 2-furoyl chloride.

$^1$H-NMR (CDCl$_3$) δ: 0.95-1.20 (5H, m), 2.10-2.30 (4H, m), 4.69-4.74 (1H, m), 5.30-5.43 (1H, m), 5.96 (1H, s), 6.75 (1H, d), 7.75 (1H, t), 7.25-7.38 (8H, m), 8.06 (1H, s).

MS m/z: 390 (M+1).

Scheme 5

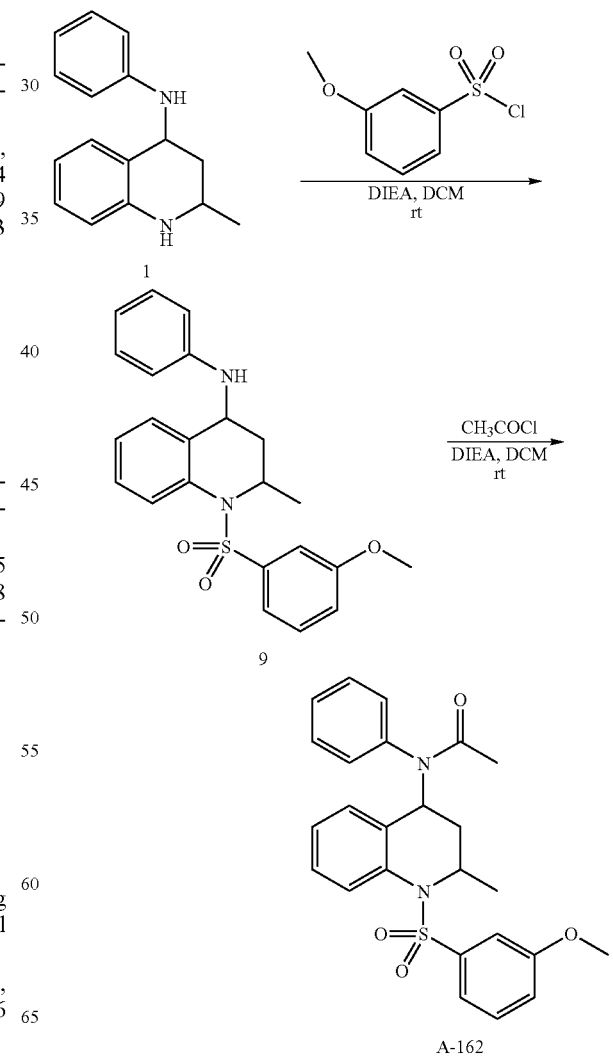

(±)-Cis-N-[1-(3-Methoxy-benzenesulfonyl)-2-methyl-1,2,3,4-tetrahydro-quinolin-4-yl]-N-phenyl-acetamide (A-162)

(±)-Cis-N-[1-(3-methoxy-benzenesulfonyl)-2-methyl-1,2,3,4-tetrahydro-quinolin-4-yl]-N-phenyl-acetamide was synthesized using general procedure A, substituting 3-methoxy-benzenesulfonyl chloride for 2-furoyl chloride.

$^1$H-NMR (CDCl$_3$) δ: 1.4 (3H, d), 1.4 (1H, m), 1.9 (3H, s), 2.0 (1H, m), 3.6 (3H, s), 4.1 (1H, m), 6.4 (1H, m), 6.9-7.4 (12H, m), 7.7 (1H, d).

MS m/z: 451 (M+1).

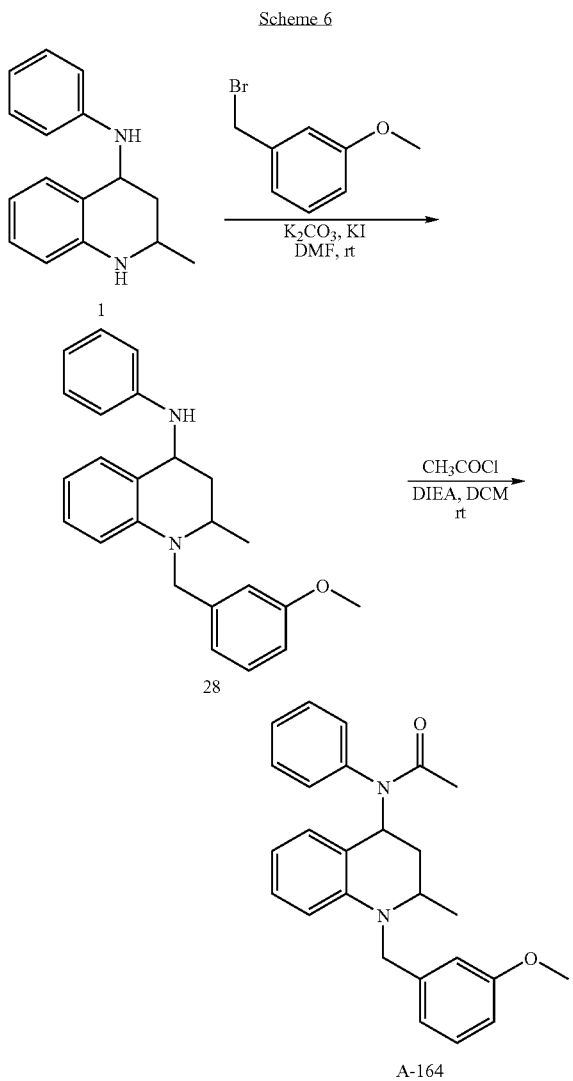

(±)-Cis-N-[1-(3-Methoxy-benzyl)-2-methyl-1,2,3,4-tetrahydro-quinolin-4-yl]-N-phenyl-acetamide (A-164)

(±)-Cis-N-[1-(3-methoxy-benzyl)-2-methyl-1,2,3,4-tetrahydro-quinolin-4-yl]-N-phenyl-acetamide was synthesized by dissolving (±)-cis-(2-methyl-1,2,3,4-tetrahydroquinol-4-yl)aniline in dimethylformamide and adding potassium carbonate (1.0-10.0 equiv.), and the 1-bromomethyl-3-methoxy-benzene (1.1-3.0 equiv), catalytic potassium iodide and was stirred at room temperature for 18 hours. The reaction mixture was filtered for removal of inorganic salts and concentrated. The crude mixture was purified by flash chromatography on silica gel using gradient elution hexane-ethyl acetate (5-20%). The corresponding aniline was then acylated as previously described in general procedure A to give (±)-cis-N-[1-(3-methoxy-benzyl)-2-methyl-1,2,3,4-tetrahydro-quinolin-4-yl]-N-phenyl-acetamide.

$^1$H-NMR (CDCl$_3$) δ: 1.15 (3H, d; overlapping 1H, t), 1.90 (1H, m; 2H, m), 2.00 (3H, s), 3.33 (1H, m), 3.60 (3H, s), 4.30 (1H, m), 6.30 (1H, complex), 6.90 (1H, t), 6.90-7.40 (10H, m).

MS m/z: 443 (M+1).

(±)-Cis-N-(1-Benzyl-2-methyl-1,2,3,4-tetrahydro-quinolin-4-yl)-N-phenyl-acetamide (A-165)

(±)-Cis-N-(1-benzyl-2-methyl-1,2,3,4-tetrahydro-quinolin-4-yl)-N-phenyl-acetamide was made following the procedure describing the synthesis of A-164, substituting benzyl bromide for 1-bromomethyl-3-methoxy-benzene.

$^1$H-NMR (CDCl3) δ: 1.15 (3H, d; overlapping 1H, t), 1.90 (1H, m; 2H, m), 2.00 (3H, s), 3.33 (1H, m), 4.30 (1H, m), 6.30 (1H, m), 6.70 (1H, t), 6.90-7.40 (11H, m).

MS m/z: 413 (M+1).

(±)-Cis-N-(1-Ethyl-2-methyl-1,2,3,4-tetrahydro-quinolin-4-yl)-N-phenyl-acetamide (A-166)

(±)-Cis-N-(1-Ethyl-2-methyl-1,2,3,4-tetrahydro-quinolin-4-yl)-N-phenyl-acetamide was made following the procedure describing the synthesis of A-164, substituting ethyl bromide for 1-bromomethyl-3-methoxy-benzene.

$^1$H-NMR (CDCl$_3$) δ: 1.01 (3H, t), 1.15 (3H, d; overlapping 1H, t), 1.40 (1H, m), 1.90-2.00 (overlapping 3H, s; 1H, m), 3.20 (1H, m), 3.40 (1H, q), 3.60 (1H, m), 4.60 (1H, s), 6.20 (1H, br, m), 6.60-6.80 (2H, m), 7.00-7.50 (7H, m).

MS m/z: 309 (M+1).

(±)-Cis-[4-(acetyl-phenyl-amino)-2-methyl-3,4-dihydro-2H-quinolin-1-yl]-aceticacid methyl ester (A-167)

(±)-Cis-[4-(acetyl-phenyl-amino)-2-methyl-3,4-dihydro-2H-quinolin-1-yl]-aceticacid methyl ester was made following the procedure describing the synthesis of A-164, substituting bromo-acetic acid methyl ester for 1-bromomethyl-3-methoxy-benzene.

$^1$H-NMR (CDCl3) δ: :1.20 (3H, d; overlapping 1H, t), 1.80 (1H, m, 2.00 (3H, s), 3.40 (1H, m), 3.70 (3H, s), 3.90 (2H, s), 4.50 (1H, m), 6.10 (1H, t), 6.20 (1H, d), 6.75 (1H, m), 6.90-7.10 (3H, complex), 7.20-7.50 (3H, m).

MS m/z: 353 (M+1).

(±)-Cis-[4-(acetyl-phenyl-amino)-2-methyl-3,4-dihydro-2H-quinolin-1-yl]-aceticacid (A-168)

(±)-Cis-[4-(acetyl-phenyl-amino)-2-methyl-3,4-dihydro-2H-quinolin-1-yl]-acetic acid was made from (±)-cis-[4-(acetyl-phenyl-amino)-2-methyl-3,4-dihydro-2H-quinolin-1-yl]-aceticacid methyl ester. To a solution of (±)-cis-[4-(acetyl-phenyl-amino)-2-methyl-3,4-dihydro-2H-quinolin-1-yl]-acetic acid methyl ester was added 1.0 N aqueous sodium hydroxide and heated to 80° C. for 1 hr. The reaction mixture was concentrated and aqueous mixture was acidified to pH 6.0 using hydrochloric acid (1N) followed by extraction with ethyl acetate twice. Organics were dried over sodium sulfate, filtered and concentrated to yield the desired product.

¹H-NMR (CDCl3) δ: 1.20 (3H, d; overlapping 1H, t), 1.80 (1H, m, 2.00 (3H, s), 3.40 (1H, m), 3.90 (2H, s), 4.50 (1H, m), 6.10 (1H, t), 6.20 (1H, d), 6.75 (1H, m), 6.90-7.10 (3H, m), 7.20-7.50 (3H, m).

MS m/z: 339 (M+1).

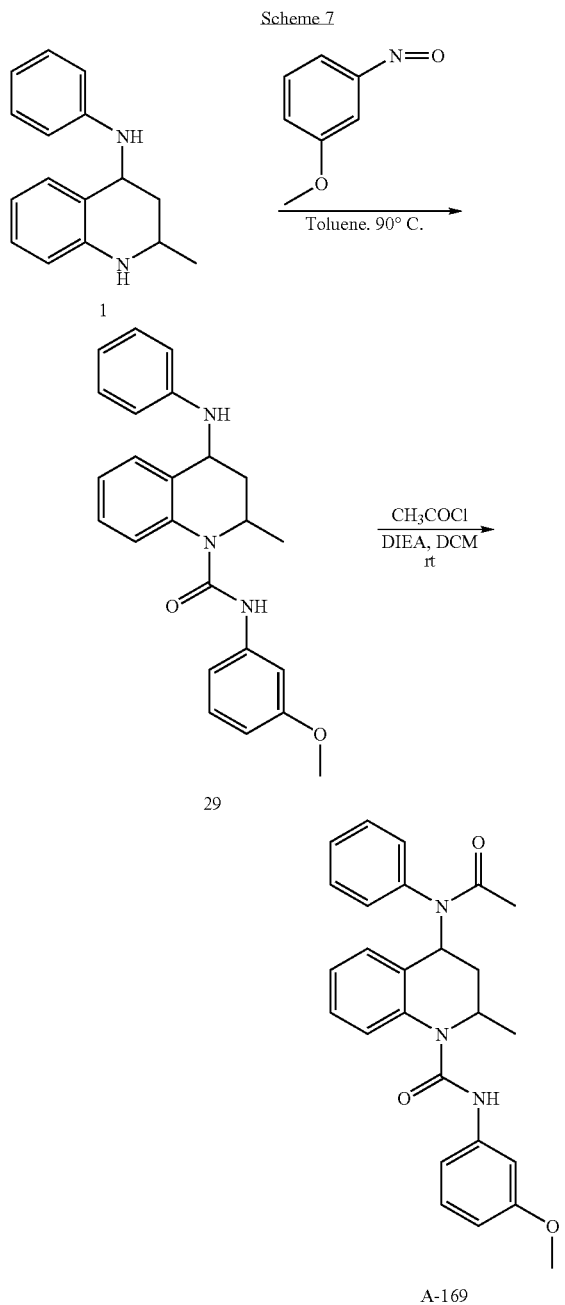

A-169

(±)-Cis-(acetyl-phenyl-amino)-2-methyl-3,4-dihydro-2H-quinoline-1-carboxylicacid (3-methoxy-phenyl)-amide (A-169)

(±)-Cis-(acetyl-phenyl-amino)-2-methyl-3,4-dihydro-2H-quinoline-1-carboxylicacid (3-methoxy-phenyl)-amide was synthesized using general procedure A, substituting 3-methoxyphenylisocyanate for 2-furoyl chloride using the following procedure. To a solution of (±)-cis-(3-methoxy-phenyl)-(2-methyl-4-anilino-3,4-dihydro-2H-quinolin-1-yl)-methanone (0.1 g, 0.42 mmol) in toluene was added 3-methoxyphenylisocyanate (0.056 mL, 0.4255 mmol) and the reaction mixture was heated to 90° C. for 18 hours. Reaction was cooled to room temperature and concentrated. The crude mixture was purified by flash chromatography on silica gel using gradient elution hexane-ethyl acetate (80%/20%) to give 38% of the desired product.

¹H-NMR (CDCl₃) δ: 1.1 (3H, d), 1.2 (1H, m), 2.0 (3H, s), 2.3 (1H, m), 3.8 (3H, s), 4.5 (1H, m), 5.4 (1H, m), 6.6 (1H, d), 6.8 (2H, m) 7.1-7.5 (11H, m).

MS m/z: 430 (M+1).

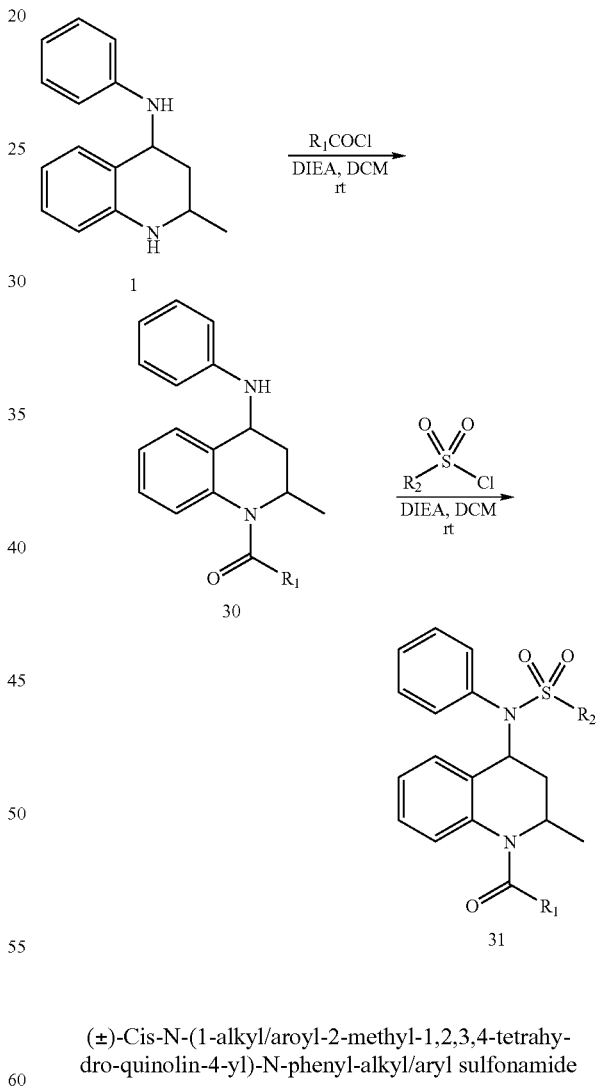

(±)-Cis-N-(1-alkyl/aroyl-2-methyl-1,2,3,4-tetrahydro-quinolin-4-yl)-N-phenyl-alkyl/aryl sulfonamide (±)-Cis-1-(2-Methyl-4-phenylamino-3,4-dihydro-2H-quinolin-1-yl)-alkanone or (±)-cis-(2-Methyl-4-phenylamino-3,4-dihydro-2H-quinolin-1-yl)-aryl-methanone can be prepared from compound 1 using general procedure A, substituting the corresponding sulfonyl chloride for acetyl chloride.

Scheme 9

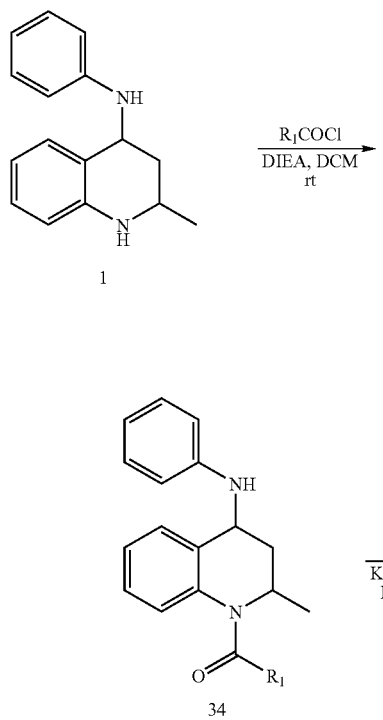

Scheme 10

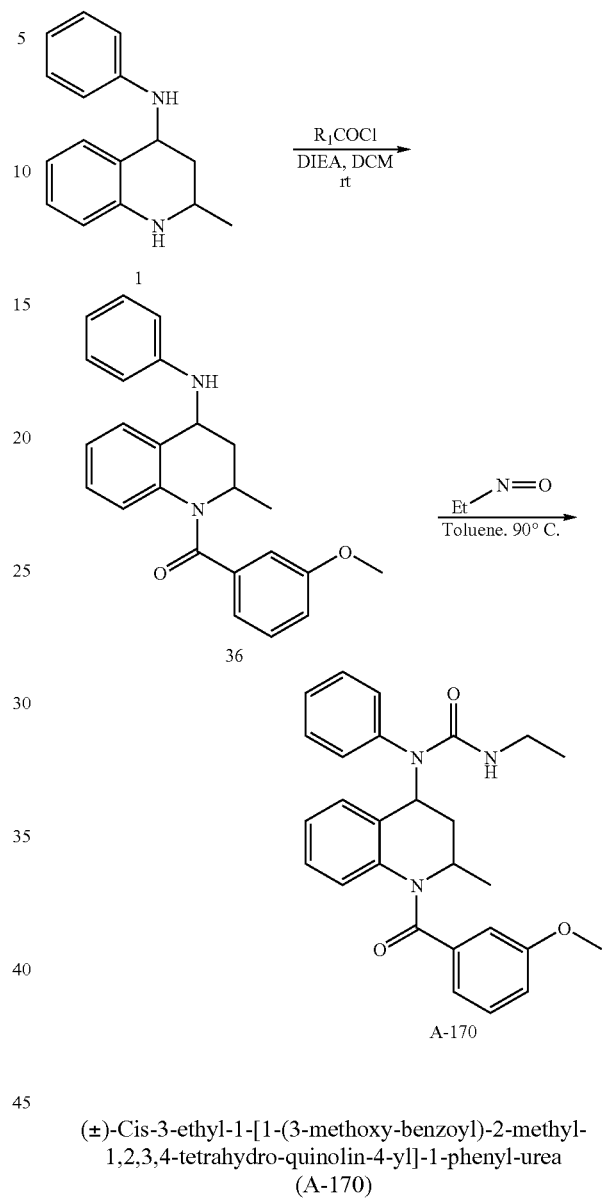

(±)-Cis-3-ethyl-1-[1-(3-methoxy-benzoyl)-2-methyl-1,2,3,4-tetrahydro-quinolin-4-yl]-1-phenyl-urea
(A-170)

(±)-Cis-1-[4-(alkyl-phenyl-amino)-2-methyl-3,4-dihydro-2H-quinolin-1-yl]-alkanone or (±)-Cis-1-[4-(alkyl-phenyl-amino)-2-methyl-3,4-dihydro-2H-quinolin-1-yl]-aryl methadone (±)-Cis-1-[4-(alkyl-phenyl-amino)-2-methyl-3,4-dihydro-2H-quinolin-1-yl]-alkanone or (±)-cis-1-[4-(alkyl-phenyl-amino)-2-methyl-3,4-dihydro-2H-quinolin-1-yl]-aryl methanone may be prepared from compound 1 using general procedure A, substituting the corresponding alkyl chloride for acetyl chloride and using the alkylation procedure in the synthesis of A-164. Representative examples of compound 35 are shown in the table below.

(±)-Cis-3-ethyl-1-[1-(3-methoxy-benzoyl)-2-methyl-1,2,3,4-tetrahydro-quinolin-4-yl]-1-phenyl-urea was synthesized using general procedure A, substituting ethyl isocyanate for acetyl chloride using the following procedure. To a solution of (±)-cis-(3-methoxy-phenyl)-(2-methyl-4-anilino-3,4-dihydro-2H-quinolin-1-yl)-methanone in DMF was added ethyl isocyanate and reaction mixture was heated to 90° C. for 18 hours. The reaction was cooled to room temperature and concentrated. Crude mixture was purified by flash chromatography on silica gel using gradient elution hexane-ethyl acetate (5-20%).

$^1$H-NMR (CDCl3) δ: 1.05-1.20 (3H, t; overlapping 3H, d; and 1H, t), 2.35 (1H, m), 3.30 (2H, q), 3.67 (3H, s), 4.36 (1H, t), 4.80 (1H, m), 5.65 (1H, m), 6.50 (1H, d), 6.65 (1H, d), 6.80 (1H, d), 6.85 (2H, complex), 7.00 (1H, t), 7.18 (1H, t), 7.35-7.50 (6H, m).

MS m/z: 444 (M+1).

Compounds A-163, A-171-A-232 can be prepared by the schemes set forth in Schemes 1-10 and by the general procedures A and others described herein. Those skilled in the art will be able to recognize, or be able to ascertain, using no more than routine experimentation, many equivalents to the specific embodiments of the invention described herein.

TABLE 1

Compounds Derived from General Procedure A

| No. | Structure |
|---|---|
| A-1 | 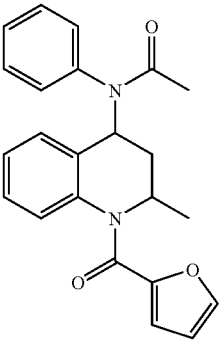 |
| A-2 | 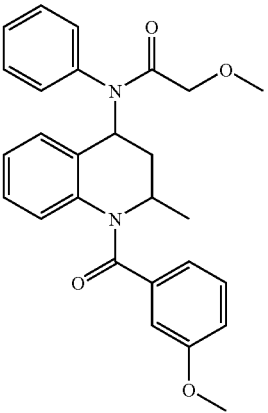 |
| A-3 | 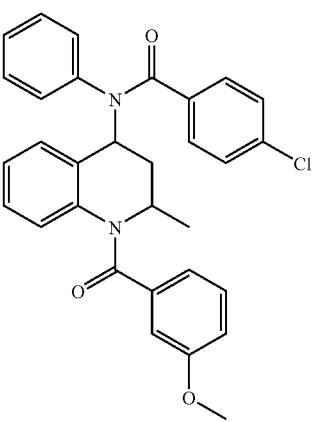 |

TABLE 1-continued

Compounds Derived from General Procedure A

| No. | Structure |
|---|---|
| A-4 | 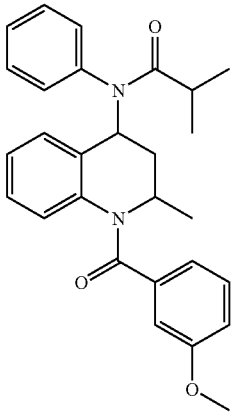 |
| A-5 | 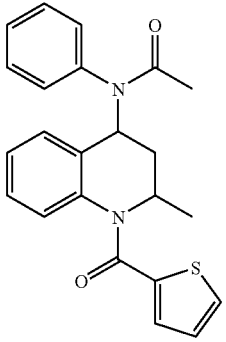 |
| A-6 | 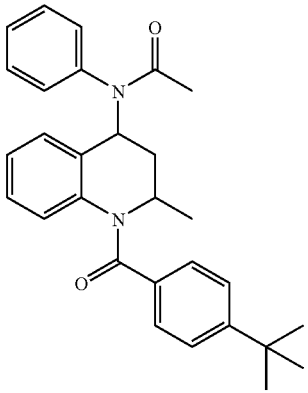 |
| A-7 | 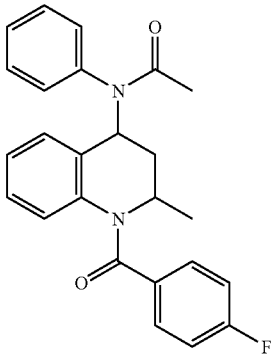 |

TABLE 1-continued

Compounds Derived from General Procedure A

| No. | Structure |
|---|---|
| A-8 | 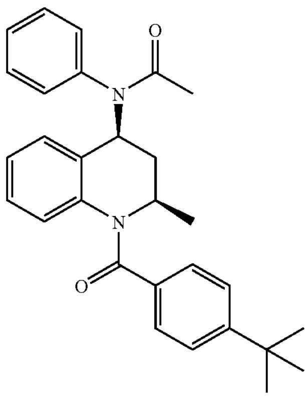 |
| A-9 | 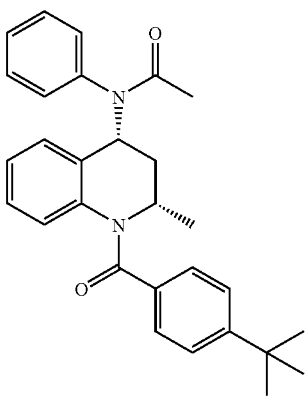 |
| A-10 | 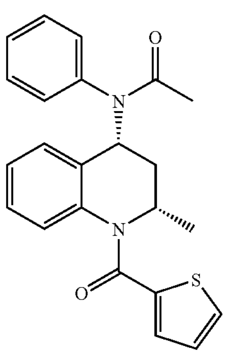 |
| A-11 | 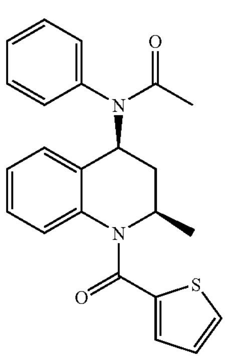 |
| A-12 | |
| A-13 | |
| A-14 | |
| A-15 | |

TABLE 1-continued

Compounds Derived from General Procedure A

| No. | Structure |
|---|---|
| A-16 | 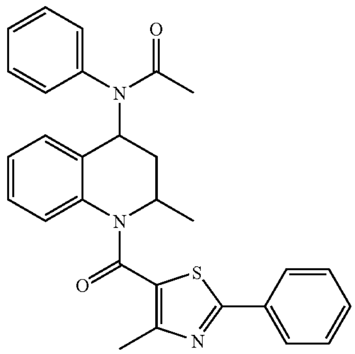 |
| A-17 | 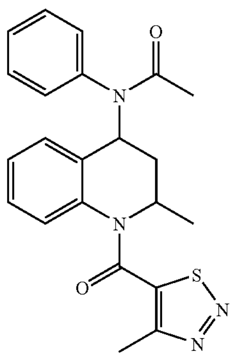 |
| A-18 | 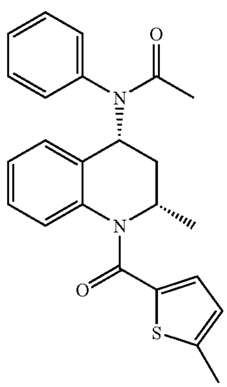 |
| A-19 | 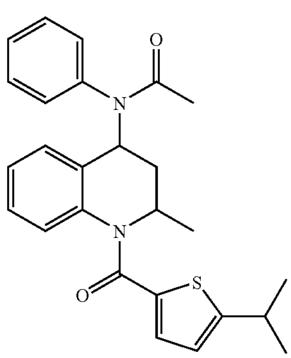 |
| A-20 | 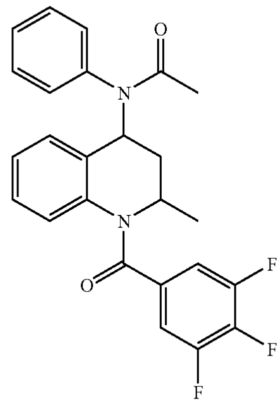 |
| A-21 | 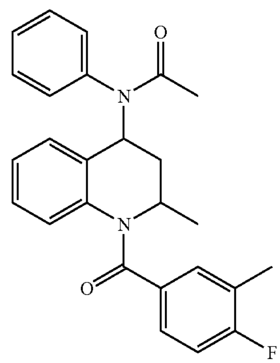 |
| A-22 | 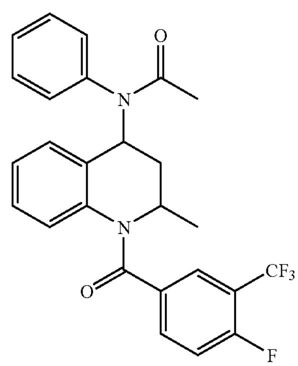 |
| A-23 | 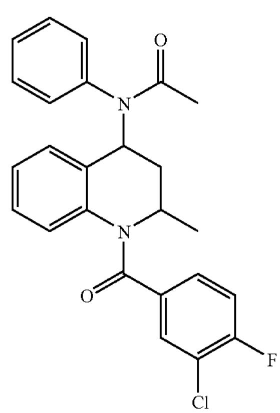 |

TABLE 1-continued

Compounds Derived from General Procedure A

| No. | Structure |
|---|---|
| A-24 | 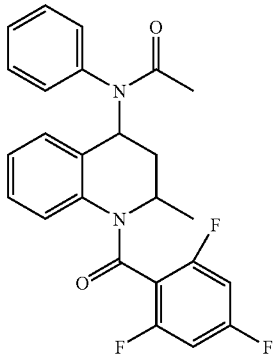 |
| A-25 | 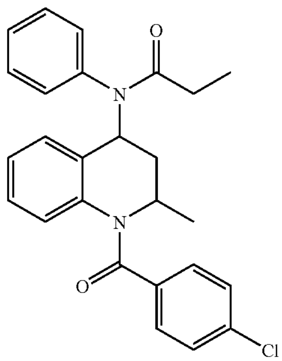 |
| A-26 | 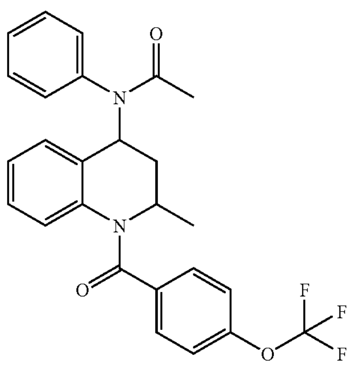 |
| A-27 | 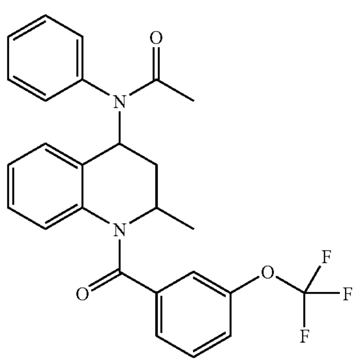 |
| A-28 | |
| A-29 | |
| A-30 | |

TABLE 1-continued

Compounds Derived from General Procedure A

| No. | Structure |
|---|---|
| A-31 | 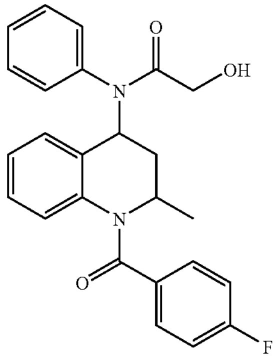 |
| A-32 | 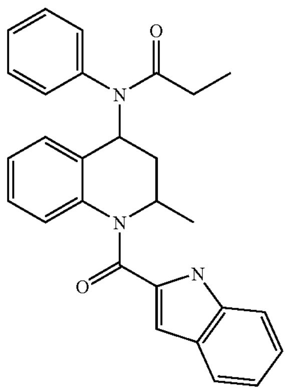 |
| A-33 | 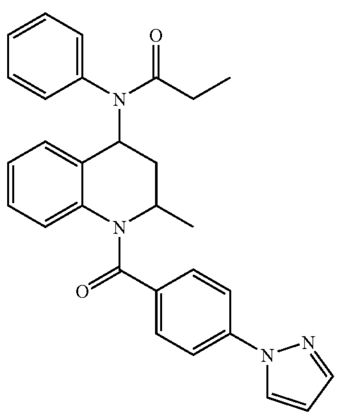 |
| A-34 | 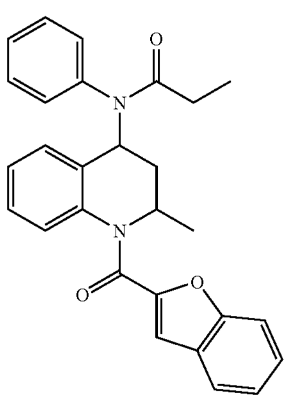 |
| A-35 | |
| A-36 | |
| A-37 | |
| A-38 | |

TABLE 1-continued

Compounds Derived from General Procedure A

| No. | Structure |
|---|---|
| A-39 | 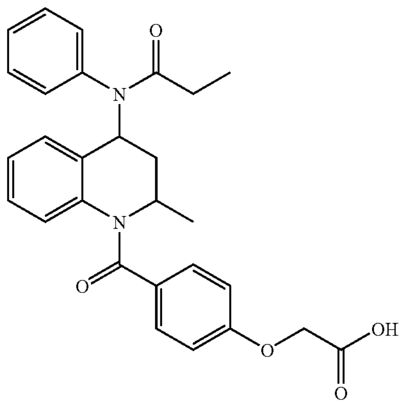 |
| A-40 | 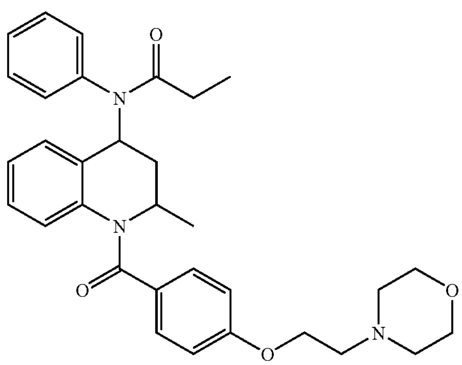 |
| A-41 | 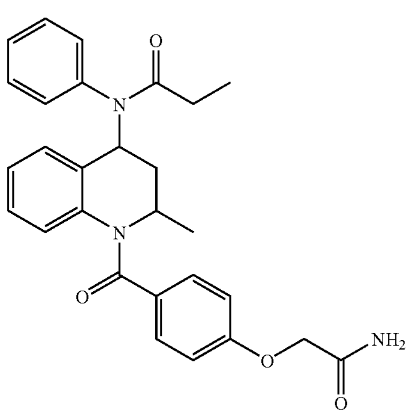 |
| A-42 | 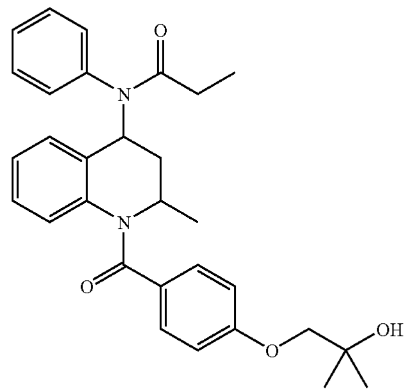 |
| A-43 | 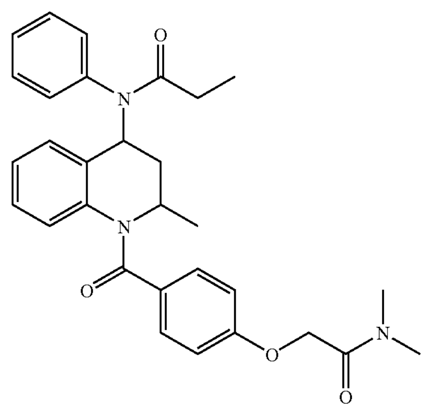 |
| A-44 | 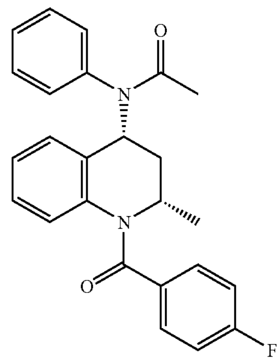 |

TABLE 1-continued

Compounds Derived from General Procedure A

| No. | Structure |
|-----|-----------|
| A-45 | 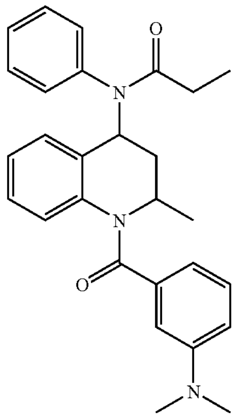 |
| A-46 | 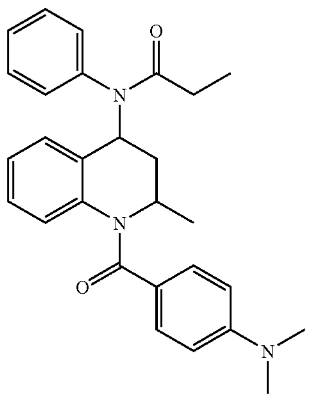 |
| A-47 | 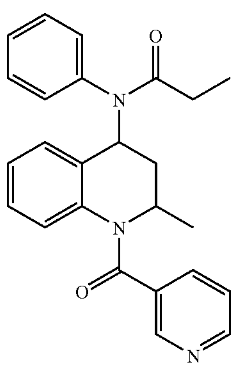 |
| A-48 | 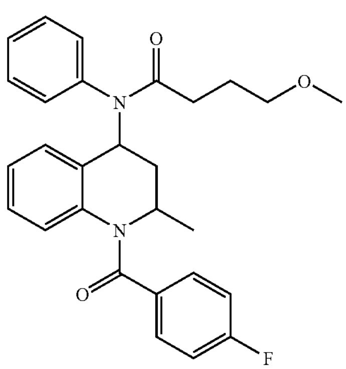 |
| A-49 | |
| A-50 | |
| A-51 | |

TABLE 1-continued

Compounds Derived from General Procedure A

| No. | Structure |
|---|---|
| A-52 | 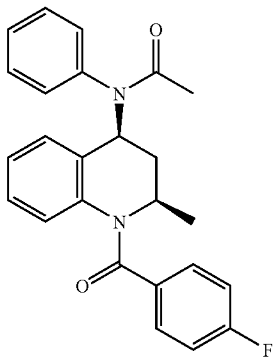 |
| A-53 | 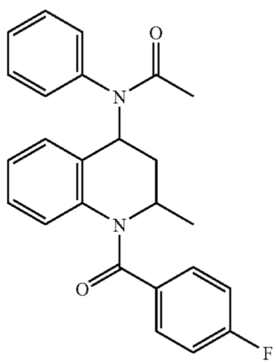 |
| A-54 | 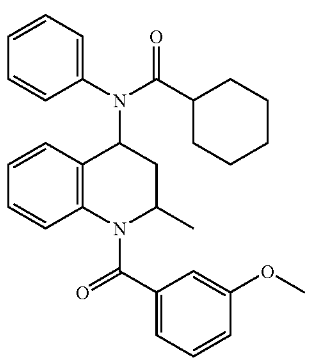 |
| A-55 | 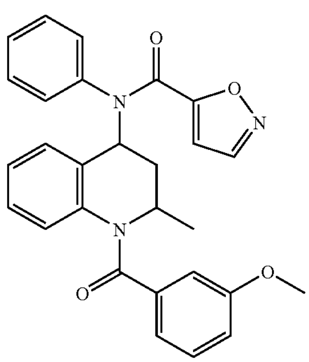 |
| A-56 | |
| A-57 | |
| A-58 | |
| A-59 | |

TABLE 1-continued

Compounds Derived from General Procedure A

| No. | Structure |
|---|---|
| A-60 | (structure) |
| A-61 | (structure) |
| A-62 | (structure) |
| A-63 | (structure) |
| A-64 | (structure) |
| A-65 | (structure) |
| A-66 | (structure) |
| A-67 | (structure) |

TABLE 1-continued

Compounds Derived from General Procedure A

| No. | Structure |
|---|---|
| A-68 | 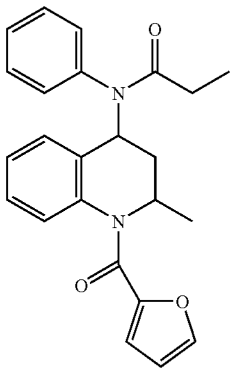 |
| A-69 | 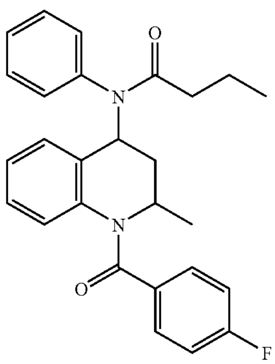 |
| A-70 | 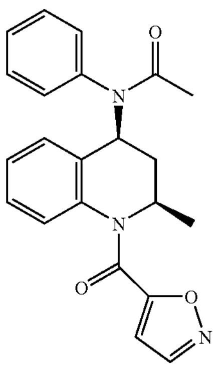 |
| A-71 | 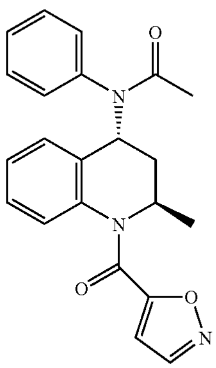 |
| A-72 | |
| A-73 | |
| A-74 | |
| A-75 | |

TABLE 1-continued
Compounds Derived from General Procedure A
| No. | Structure |
|---|---|
| A-76 | 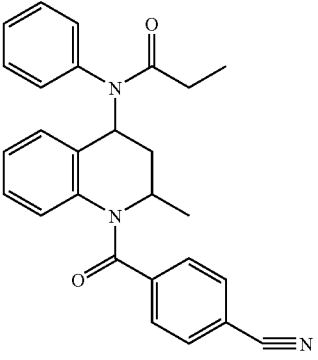 |
| A-77 | 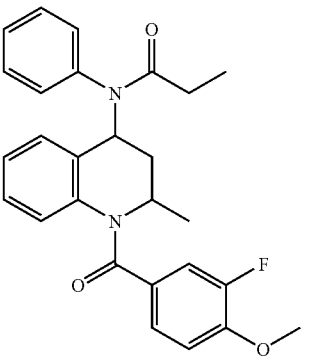 |
| A-78 | 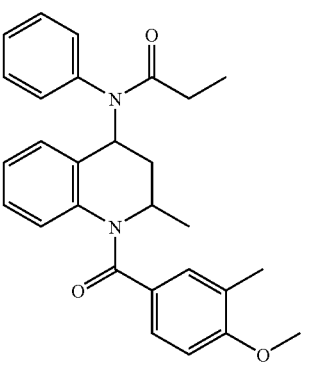 |
| A-79 | 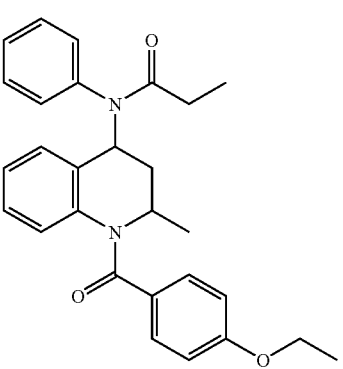 |
| A-80 | 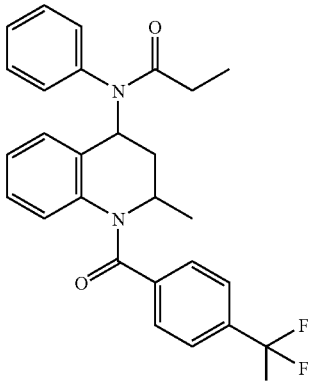 |
| A-81 | 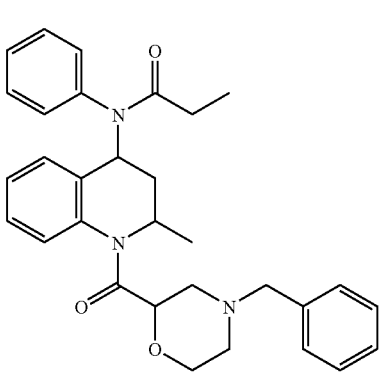 |
| A-82 | 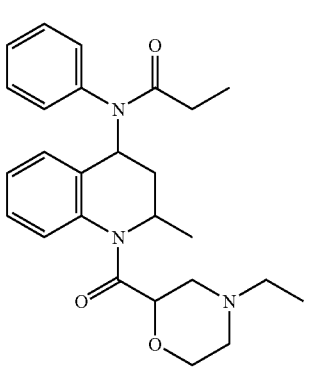 |
| A-83 | 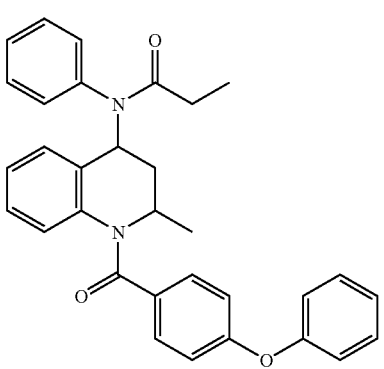 |

TABLE 1-continued

Compounds Derived from General Procedure A

| No. | Structure |
|---|---|
| A-84 | 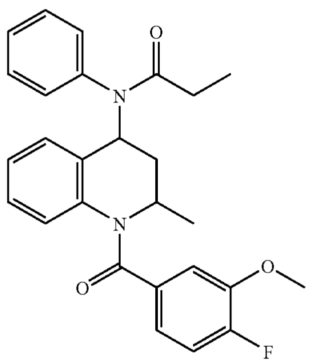 |
| A-85 | 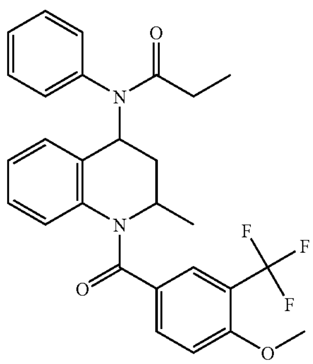 |
| A-86 | 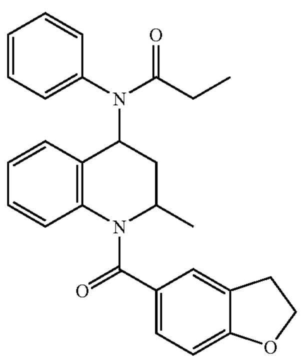 |
| A-87 | 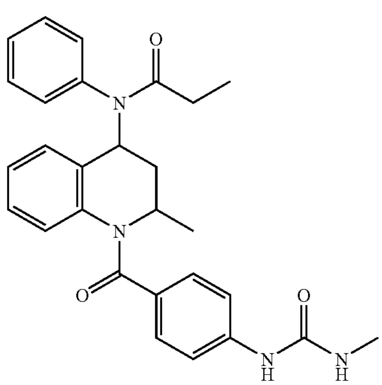 |
| A-88 | |
| A-89 | |
| A-90 | |

TABLE 1-continued

Compounds Derived from General Procedure A

| No. | Structure |
|---|---|
| A-91 | 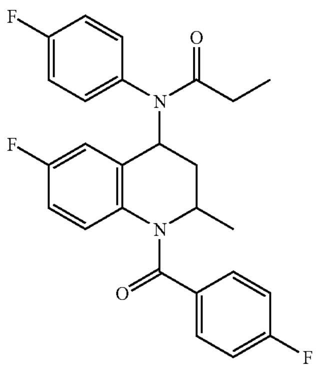 |
| A-92 | 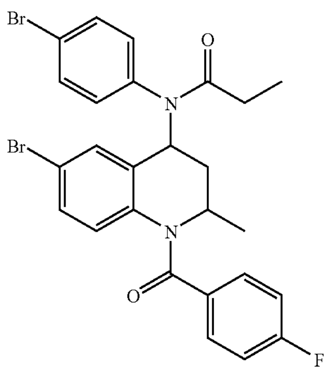 |
| A-93 | 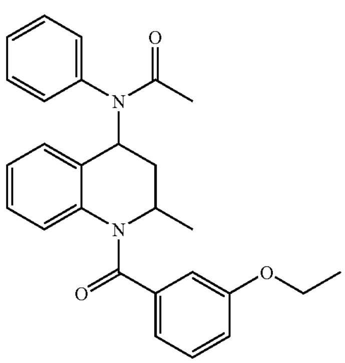 |
| A-94 | 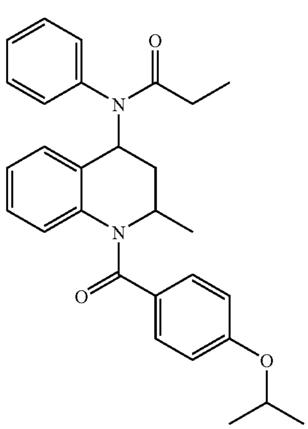 |
| A-95 | |
| A-96 | |
| A-97 | |

TABLE 1-continued

Compounds Derived from General Procedure A

| No. | Structure |
|---|---|
| A-98 | 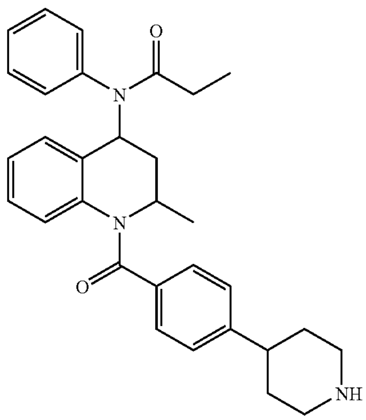 |
| A-99 | 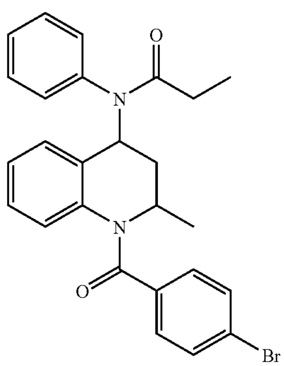 |
| A-100 | 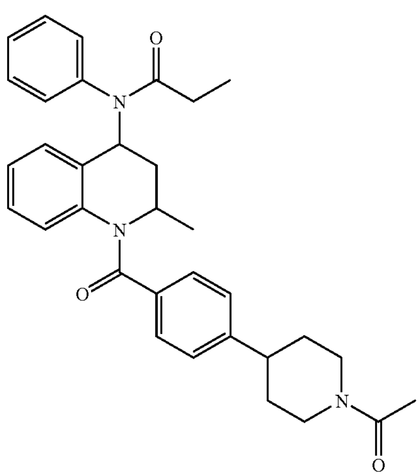 |
| A-101 | |
| A-102 | |
| A-103 | |

TABLE 1-continued

Compounds Derived from General Procedure A

| No. | Structure |
|---|---|
| A-104 | 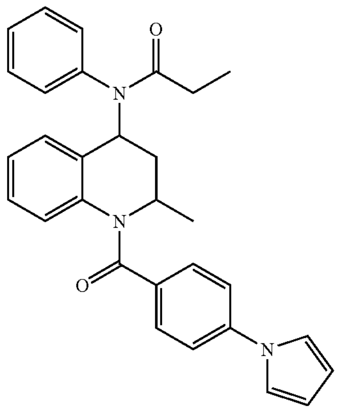 |
| A-105 | 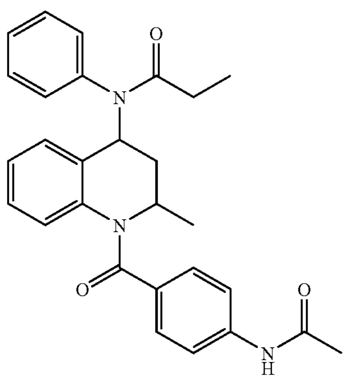 |
| A-106 | 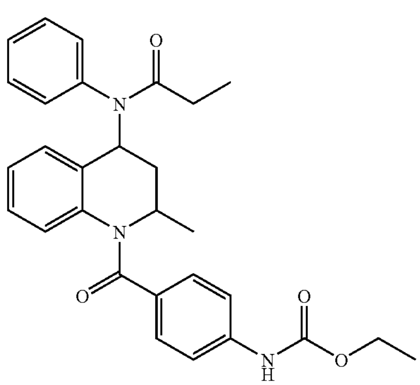 |
| A-107 | |
| A-108 | |
| A-109 | |

TABLE 1-continued

Compounds Derived from General Procedure A

| No. | Structure |
|---|---|
| A-110 | 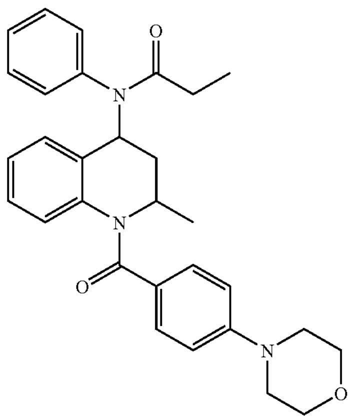 |
| A-111 | 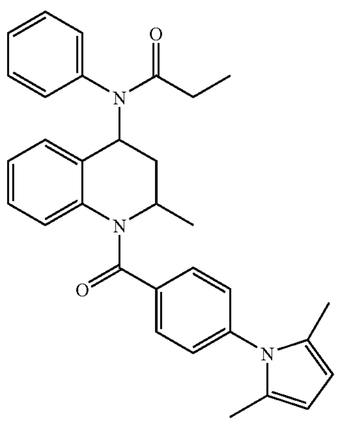 |
| A-112 | 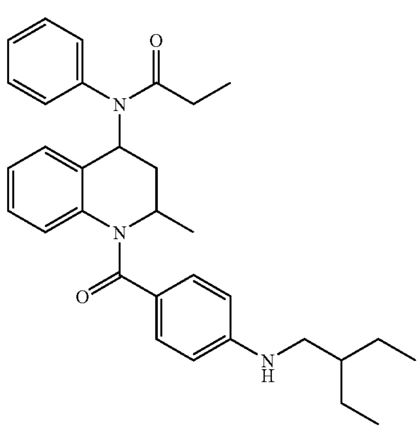 |
| A-113 | |
| A-114 | |
| A-115 | |

TABLE 1-continued

Compounds Derived from General Procedure A

| No. | Structure |
|---|---|
| A-116 | *(structure)* |
| A-117 | *(structure)* |
| A-118 | *(structure)* |
| A-119 | *(structure)* |
| A-120 | *(structure)* |
| A-121 | *(structure)* |

TABLE 1-continued
Compounds Derived from General Procedure A
| No. | Structure |
|---|---|
| A-122 | 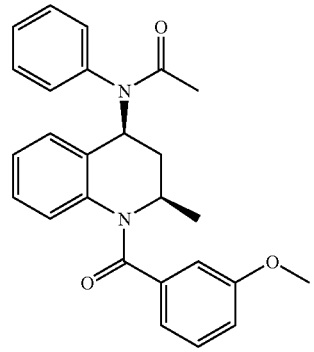 |
| A-123 | 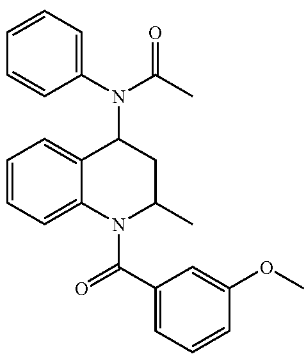 |
| A-124 | 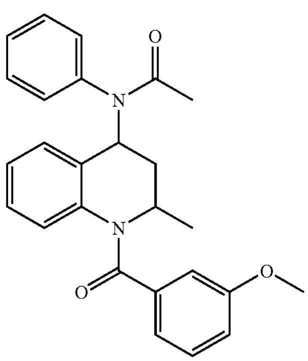 |
| A-125 | 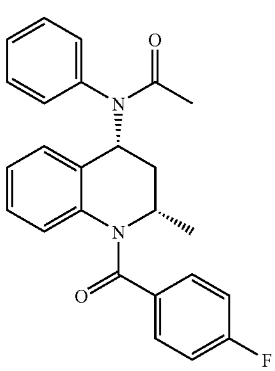 |
| A-126 | 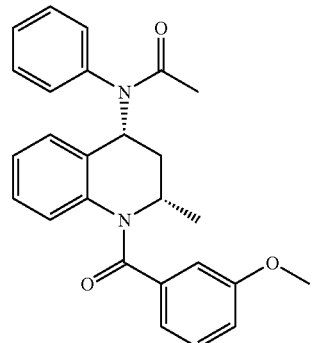 |
| A-127 | |
| A-128 | |
| A-129 | |

TABLE 1-continued

Compounds Derived from General Procedure A

| No. | Structure |
|-----|-----------|
| A-130 | 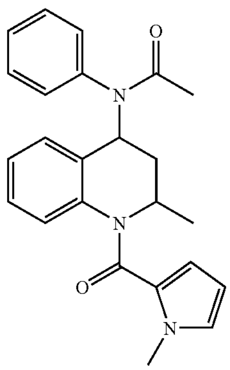 |
| A-131 | 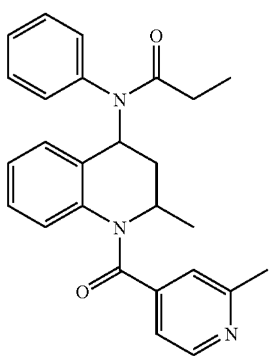 |
| A-132 | 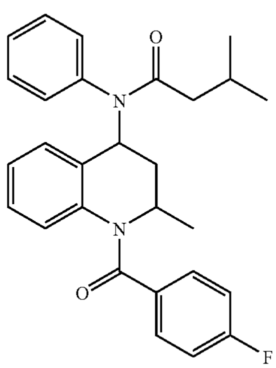 |
| A-133 | 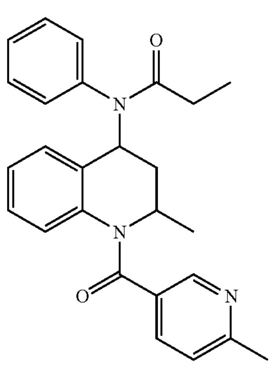 |
| A-134 | |
| A-135 | |
| A-136 | |
| A-137 | |

TABLE 1-continued

Compounds Derived from General Procedure A

| No. | Structure |
| --- | --- |
| A-138 | 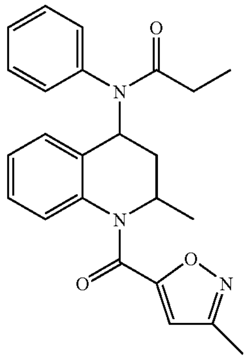 |
| A-139 | 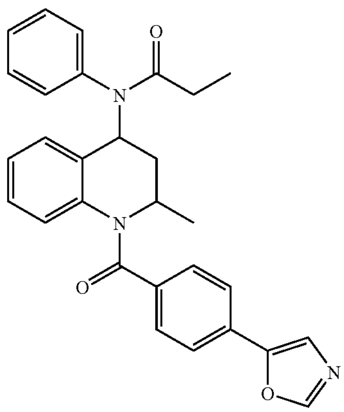 |
| A-140 | 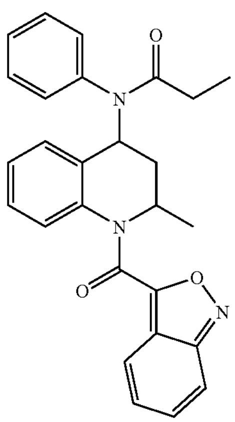 |
| A-141 | 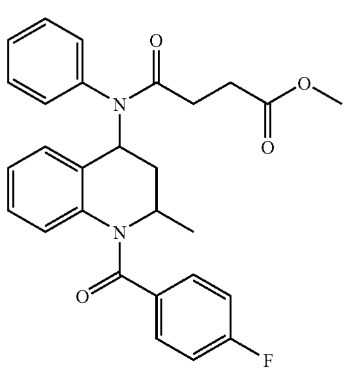 |
| A-142 | |
| A-143 | |
| A-144 | |

TABLE 1-continued

Compounds Derived from General Procedure A

| No. | Structure |
|---|---|
| A-145 | 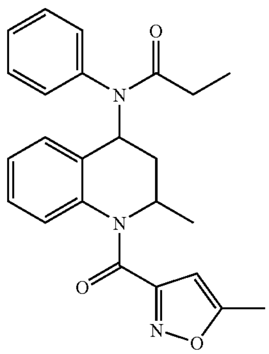 |
| A-146 | 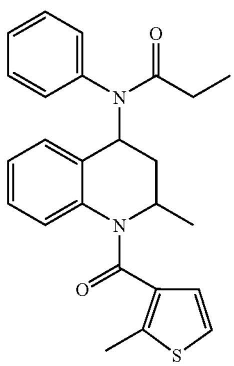 |
| A-147 | 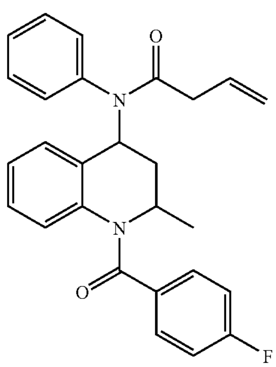 |
| A-148 | 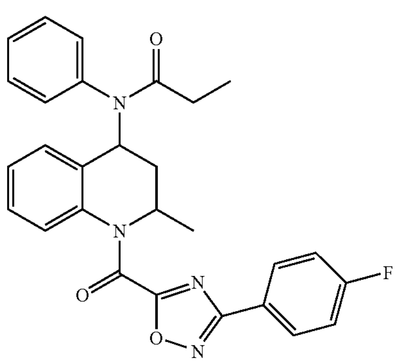 |
| A-149 | |
| A-150 | |
| A-151 | |
| A-152 | |

TABLE 1-continued

Compounds Derived from General Procedure A

| No. | Structure |
|---|---|
| A-153 | 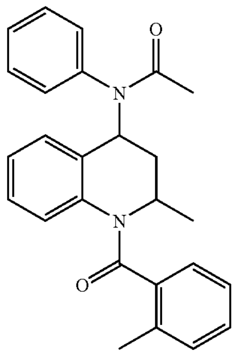 |
| A-154 | 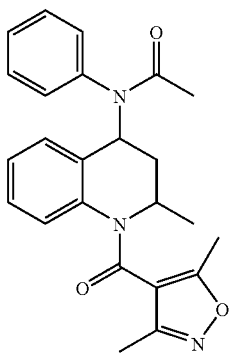 |
| A-155 | 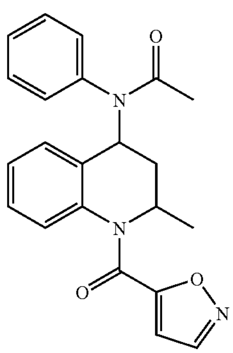 |
| A-156 | 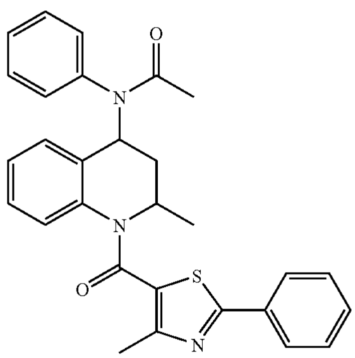 |
| A-157 | |
| A-158 | |
| A-159 | |
| A-160 | |

TABLE 1-continued

Compounds Derived from General Procedure A

| No. | Structure |
|---|---|
| A-161 | 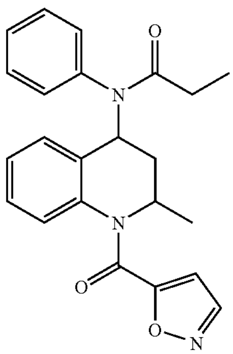 |
| A-162 | 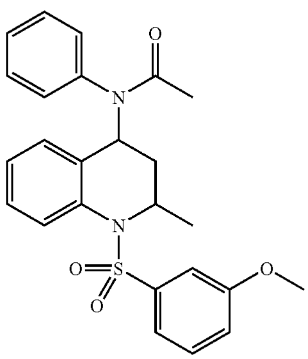 |
| A-163 | 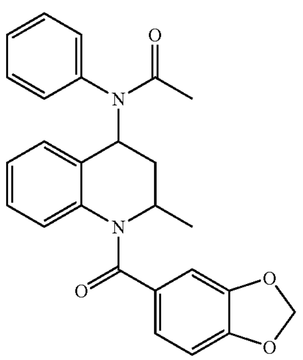 |
| A-164 | 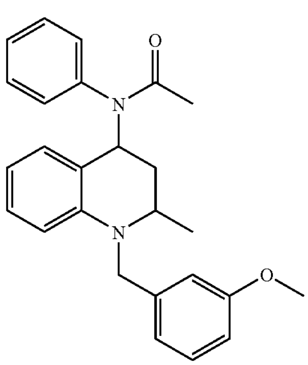 |
| A-165 | |
| A-166 | |
| A-167 | |
| A-168 | |

TABLE 1-continued
Compounds Derived from General Procedure A
| No. | Structure |
|---|---|
| A-169 | 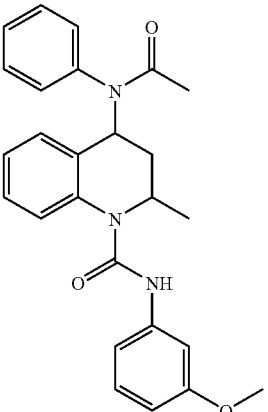 |
| A-170 | 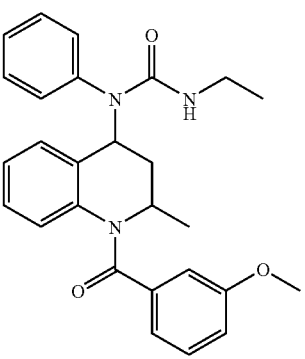 |
| A-171 | 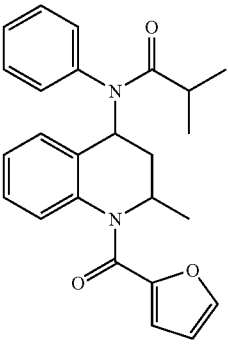 |
| A-172 | 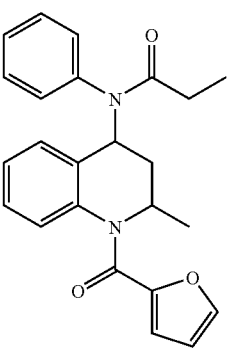 |
| A-173 | 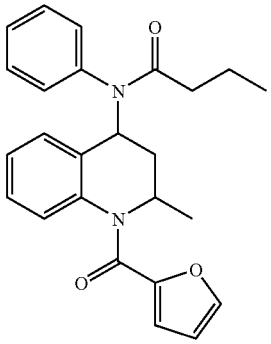 |
| A-174 | 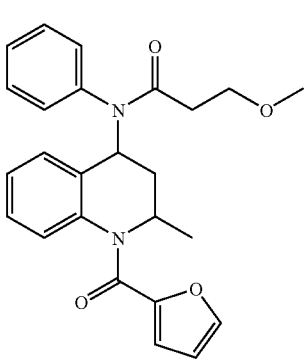 |
| A-175 | 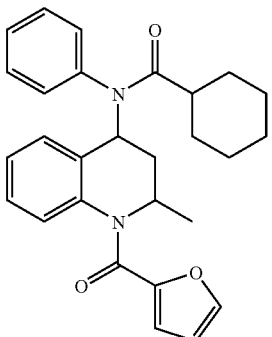 |
| A-176 | 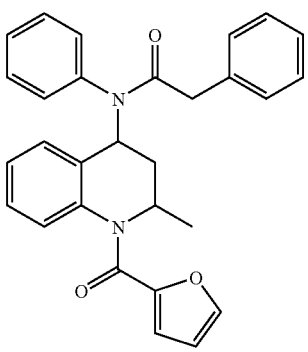 |

TABLE 1-continued

Compounds Derived from General Procedure A

| No. | Structure |
|-----|-----------|
| A-177 | 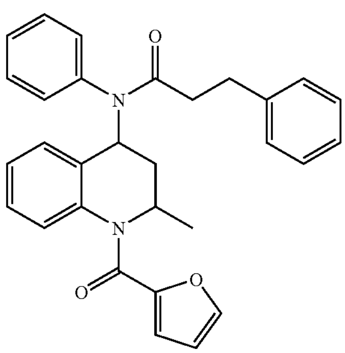 |
| A-178 | 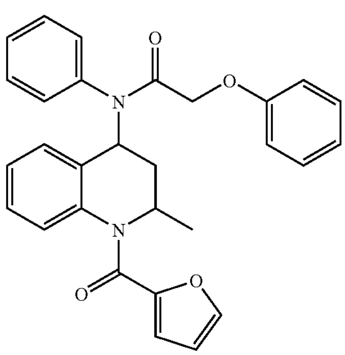 |
| A-179 | 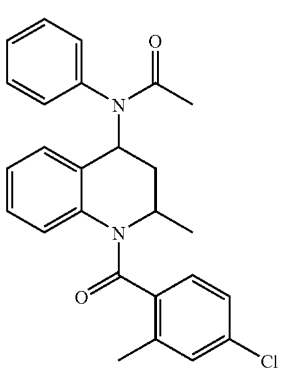 |
| A-180 | 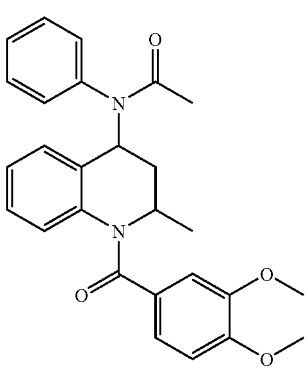 |
| A-181 | |
| A-182 | |
| A-183 | |
| A-184 | |

TABLE 1-continued

Compounds Derived from General Procedure A

| No. | Structure |
|---|---|
| A-185 | 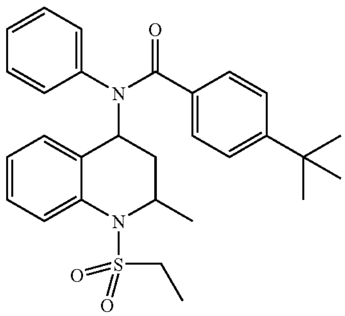 |
| A-186 | 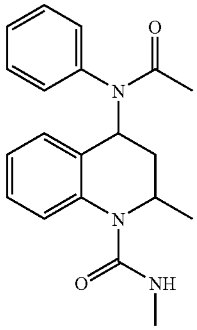 |
| A-187 | 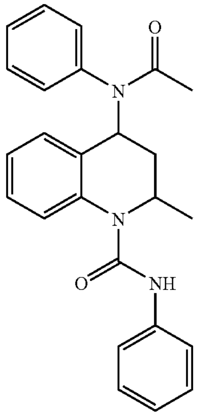 |
| A-188 | 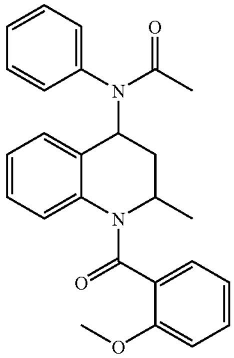 |
| A-189 | |
| A-190 | |
| A-191 | |
| A-192 | |

TABLE 1-continued

Compounds Derived from General Procedure A

| No. | Structure |
|---|---|
| A-193 | 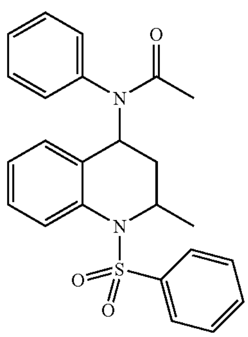 |
| A-194 | 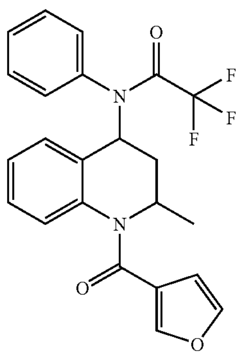 |
| A-195 | 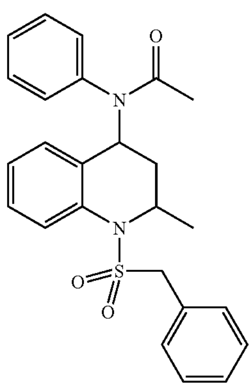 |
| A-196 | 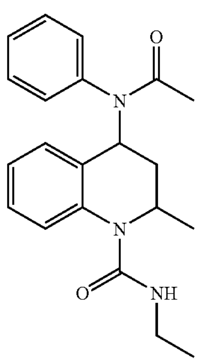 |
| A-197 | |
| A-198 | |
| A-199 | |

TABLE 1-continued

Compounds Derived from General Procedure A

| No. | Structure |
|---|---|
| A-200 | 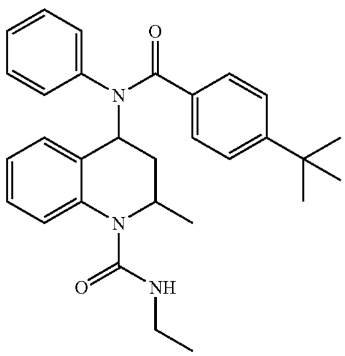 |
| A-201 | 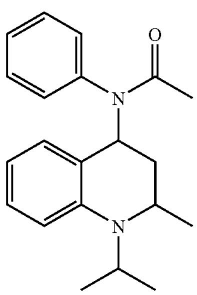 |
| A-202 | 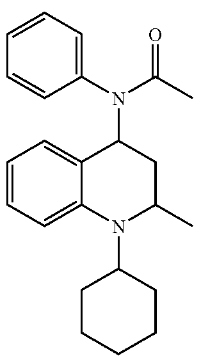 |
| A-203 | 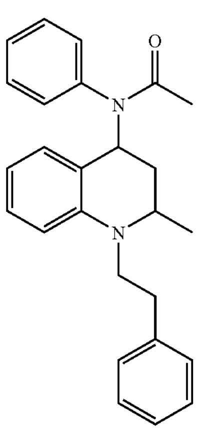 |
| A-204 | |
| A-205 | |
| A-206 | |
| A-207 | |

TABLE 1-continued
Compounds Derived from General Procedure A
| No. | Structure |
|---|---|
| A-208 | 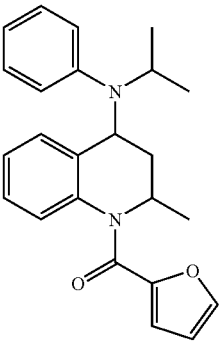 |
| A-209 | 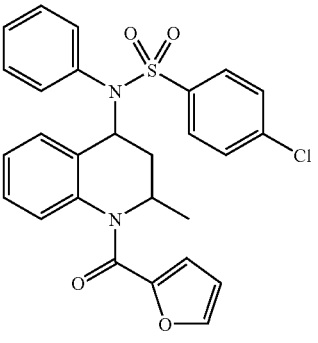 |
| A-210 | 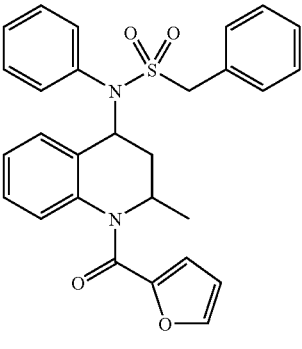 |
| A-211 | 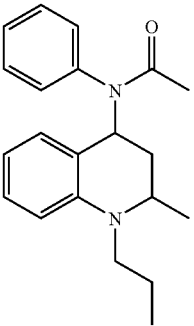 |
| A-212 | 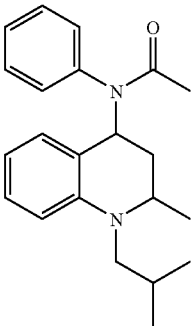 |
| A-213 | 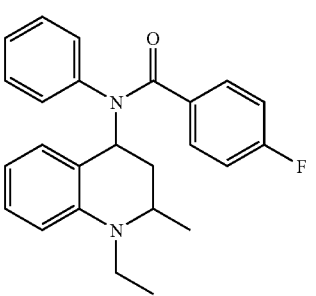 |
| A-214 | 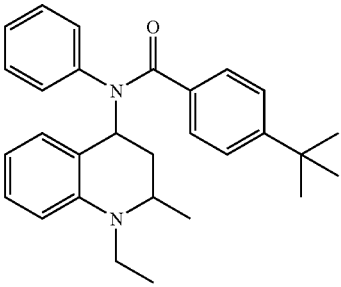 |
| A-215 | 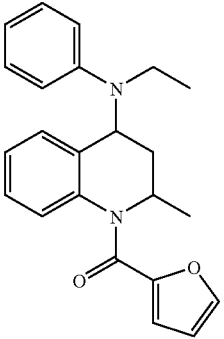 |

TABLE 1-continued
Compounds Derived from General Procedure A
| No. | Structure |
|---|---|
| A-216 | 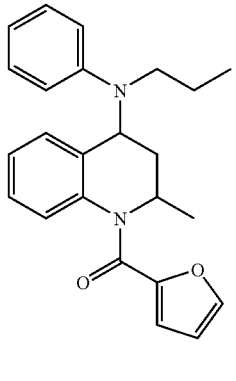 |
| A-217 | 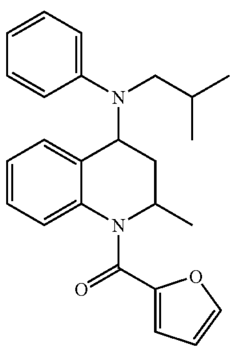 |
| A-218 | 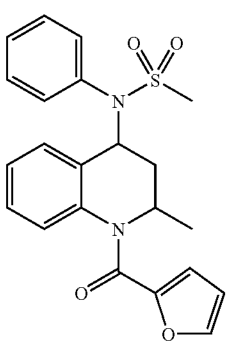 |
| A-219 | 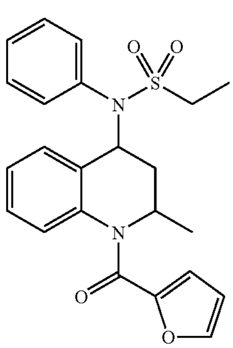 |
| A-220 | 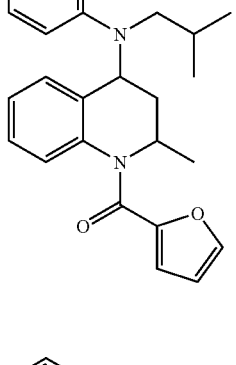 |
| A-221 | 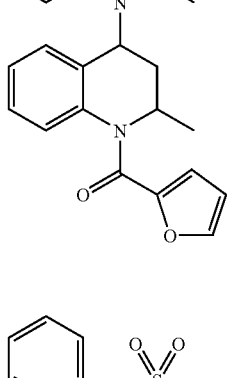 |
| A-222 | 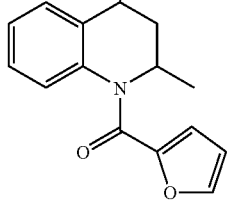 |

TABLE 1-continued

Compounds Derived from General Procedure A

| No. | Structure |
|---|---|
| A-223 | 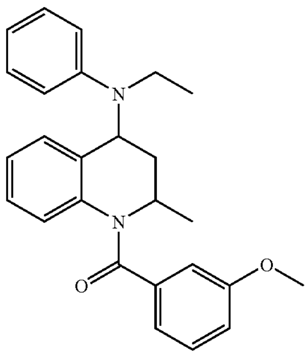 |
| A-224 | 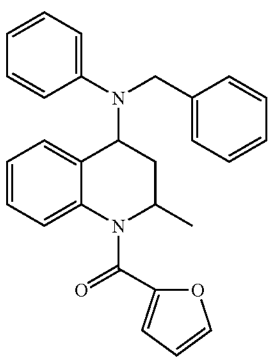 |
| A-225 | 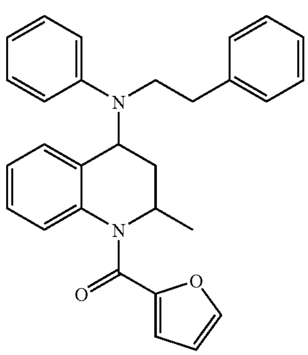 |
| A-226 | 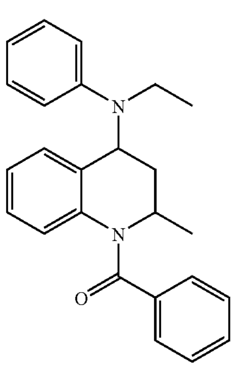 |
| A-227 | |
| A-228 | |
| A-229 | |
| A-230 | |

TABLE 1-continued

Compounds Derived from General Procedure A

| No. | Structure |
|---|---|
| A-231 | 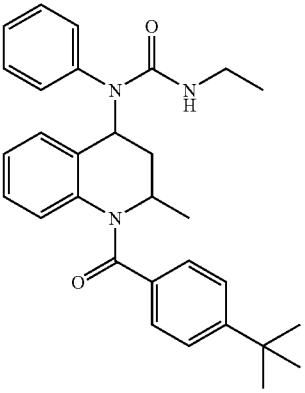 |
| A-232 | 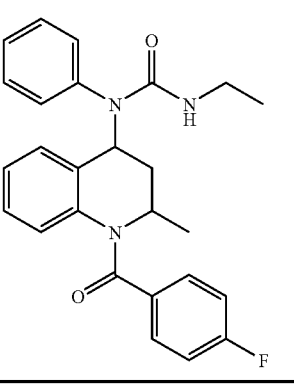 |

Scheme 11

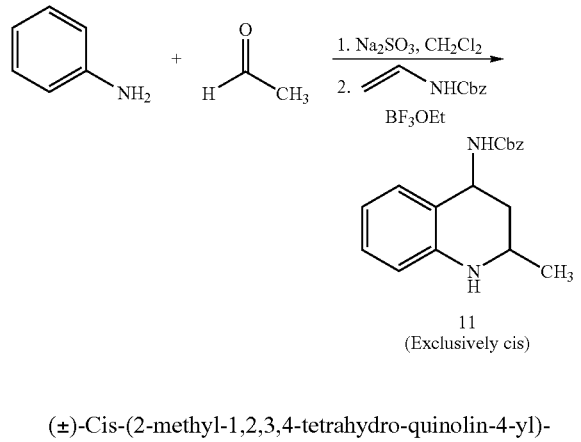

(±)-Cis-(2-methyl-1,2,3,4-tetrahydro-quinolin-4-yl)-carbamic acid benzyl ester (11)

Aniline (3.64 mL, 39.97 mmol, 1.0 equ) was dissolved in methylene chloride (100 mL) and Na$_2$SO$_4$ (2 g) was added and cooled to −25° C. Acetaldehyde (2.23 mL, 39.97 mmol, 1.0 equ.) was added to the solution and stirred for 1 h at −25° C. Sodium sulfate was filtered off and N-vinyl-carbamic acid benzyl ester (7.07 g, 39.97 mmol, 1.0 equiv) was added to the filtrate at −25° C., followed by boron triflouride diethyl etherate (0.50 mL, 3.9 mmol, 0.1 equ). The reaction was allowed to stir at −25° C. for 1 h and then warmed to room temperature and stirred for 10 h. The reaction was evaporated in vacuo and the residue was purified by Biotage flash system (20% ethyl acetate/80% hexane) to yield 4.0 g, 33% of (±)-cis-(2-methyl-1,2,3,4-tetrahydro-quinolin-4-yl)-carbamic acid benzyl ester as a white solid.

H$^1$ NMR (300 MHz, CDCl$_3$) δ: 7.38 (m, 5H), 7.17 (d, 1H), 7.02 (t, 1H, C7-H), 6.68 (t, 1H), 6.47 (d, 1H), 5.17 (bs, 2H), 5.07 (m, 1H), 4.92 (d, 1H), 3.57 (m, 1H), 2.30 (m, 1H), 1.47 (q, 1H), 1.21 (d, 3H).

General Procedure B

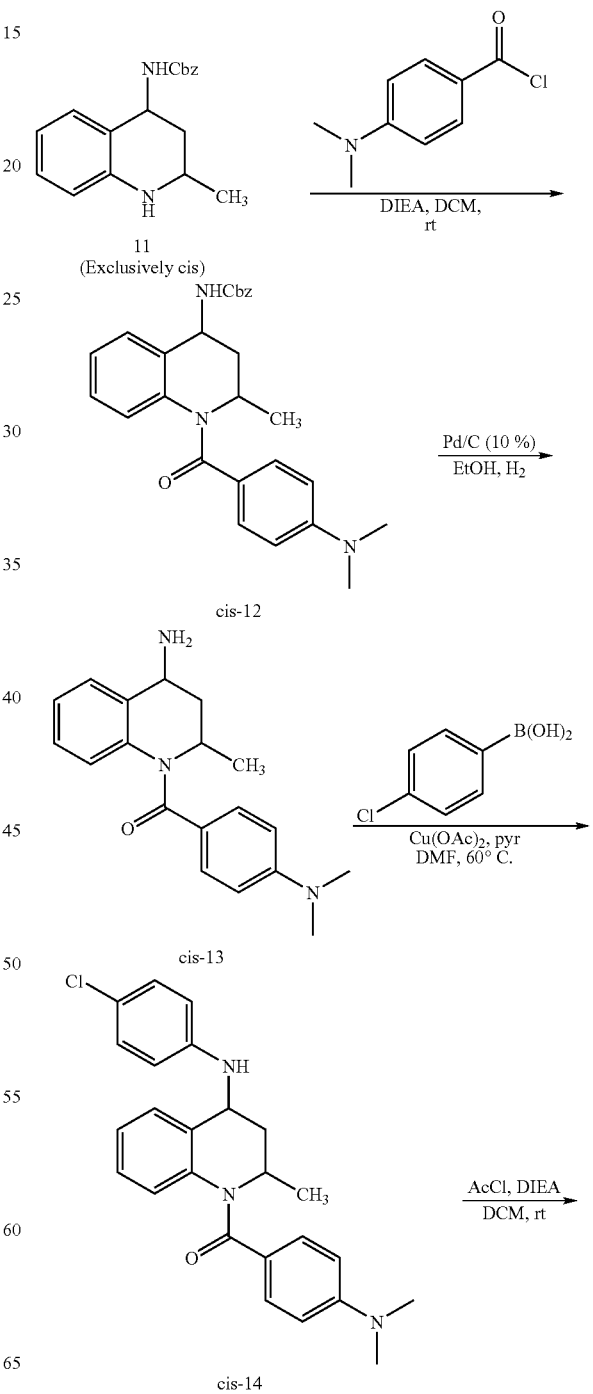

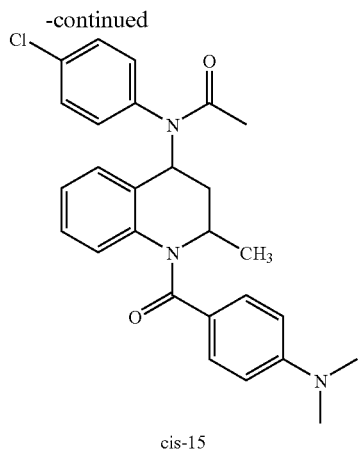

cis-15

(±)-Cis-[1-(4-dimethylamino-benzoyl)-2-methyl-1,2,
3,4-tetrahydro-quinolin-4-yl]-carbamic acid benzyl
ester (12)

To a solution of (±)-cis-(2-methyl-1,2,3,4-tetrahydro-quinolin-4-yl)-carbamic acid benzyl ester (500 mg, 1.68 mmol) in methylene chloride (20 mL) at room temperature was added diisopropylethylamine (542 mg, 749 uL, 4.2 mmol) followed by 4-dimethylaminobenzoyl chloride and stirred at room temperature until no starting material was present. The mixture was poured into water and extracted with ethyl acetate. The extracts were washed with 1 M (aq) NaOH and brine, dried over sodium sulfate, filtered dried and concentrated. The crude residue was purified by silica gel chromatography (100% hexanes to 70% hexanes/30% ethyl acetate gradient) to afford the amide (665 mg, 89%).

$^1$H-NMR (300 MHz, CDCl$_3$) δ: 1.24 (d, 3H), 1.36 (m, 1H), 2.75 (ddd, 1H), 2.91 (s, 6H), 4.79-4.92 (m, 3H), 5.22 (s, 2H), 6.43 (d, 2H), 6.65 (d, 1H), 6.90 (dd, 1H), 7.07-7.18 (m, 5H), 7.2-7.48 (m, 4H).

MS m/z: 444 (M+1).

(±)-Cis-1-(4-dimethylamino-benzoyl)-2-methyl-1,2,
3,4-tetrahydro-4-aminoquinoline (13)

(±)-Cis-[1-(4-dimethylamino-benzoyl)-2-methyl-1,2,3,4-tetrahydro-quinolin-4-yl]-carbamic acid benzyl ester (665 mg, 1.49 mmol) was dissolved in ethanol (30 mL). The resulting solution was evacuated and backfilled with argon. A catalytic amount of palladium on carbon (10%) was added. The vessel was once again evacuated and this time was backfilled with hydrogen from a balloon. The reaction was then allowed to react at room temperature over night under a hydrogen atmosphere. Reaction was complete after 18 h. The mixture was carefully filtered and concentrated to 10% volume. The resulting concentrated solution was filtered through an Acrodisc® and concentrated to afford the crude amine (423 mg, 92%).

$^1$H-NMR (300 MHz, CDCl$_3$) δ: 1.19-1.40 (m, 4H), 2.76 (ddd, 1H), 2.95 (s, 6H), 4.08 (dd, 1H), 4.81 (m, 1H), 6.42 (d, 2H), 6.64 (d, 1H), 6.99 (dd, 1H), 7.08-7.23 (m, 5H), 7.52 (d, 1H).

MS m/z: 310 (M+1).

(±)-Cis-1-(4-dimethylamino-benzoyl)-2-methyl-1,2,
3,4-tetrahydro-4-(N-4-chlorophenyl)aminoquinoline
(14)

To a solution of (±)-cis-1-(4-dimethylamino-benzoyl)-2-methyl-1,2,3,4-tetrahydro-4-aminoquinoline (423 mg, 1.36 mmol) in DMF (15 mL, dry) was added 4-chlorophenylboronic acid (425 mg, 2.72 mmol), pyridine (322 mg, 330 uL, 4.08 mmol) and copper(II)acetate (494 mg, 2.72 mmol). The heterogeneous green mixture was stirred open to air for 1 h and then warmed to 60° C. and stirred over night (14 h). The mixture was then cooled to rt, poured into rapidly stirred ethyl acetate (150 mL); solids were removed by filtration. The extracts were washed several times with water and then once with brine. The extracts were then dried over anhydrous sodium sulfate, filtered, and concentrated under reduced pressure. The crude residue was purified by silica gel chromatography (100% hexanes to 50/50 hexanes/ethyl acetate gradient) to afford the aniline product (120 mg, 22%) as a yellow oil.

$^1$H-NMR (300 MHz, CDCl$_3$) δ: 1.22 (d, 3H), 1.36 (ddd, 1H), 2.82 (ddd, 1H), 2.95 (s, 6H), 4.90 (br s, 1H), 4.41 (br d, 1H), 4.87 (ddd, 1H), 6.65 (d, 2H), 6.62-6.76 (m, 3H), 6.97-7.11 (m, 2H), 7.17-7.29 (m, 5H).

MS m/z: 420 (M+1)

(±)-Cis-N-(4-chloro-phenyl)-N-[1-(4-dimethylamino-benzoyl)-2-methyl-1,2,3,4-tetrahydro-quinolin-4-yl]-acetamide (15)

To a solution of (±)-cis-1-(4-dimethylamino-benzoyl)-2-methyl-1,2,3,4-tetrahydro-4-(N-4-chlorophenyl)aminoquinoline (120 mg, 0.29 mmol) in methylene chloride (2 mL) was added diisopropylethylamine (37 mg, 0.051 mL, 0.29 mmol) followed by acetyl chloride (2 mL). The mixture was stirred at rt 4 h. The mixture was concentrated under reduced pressure, dissolved in ethyl acetate, washed with sat. aqueous sodium bicarbonate, brine and dried over sodium sulfate. The drying agent was removed by filtration under reduced pressure, concentrated and purified by silica gel chromatography (100% hexanes-25/75 hexanes/ethyl acetate gradient) to afford pure (±)-cis-N-(4-chloro-phenyl)-N-[1-(4-dimethylamino-benzoyl)-2-methyl-1,2,3,4-tetrahydro-quinolin-4-yl]-acetamide (45 mg, 34%).

$^1$H-NMR (300 MHz, CDCl$_3$) δ: 1.14-1.33 (m, 4H), 2.13 (s, 3H), 2.24-2.39 (m, 1H), 2.94 (s, 6H), 4.75 (ddd, 1H), 5.61 (br s, 1H), 6.44 (d, 2H), 6.63 (d, 1H), 6.96 (dd, 1H), 7.07-7.36 (m, 6H), 7.40 (d, 2H).

MS m/z: 420 (M+1)

(±)-Cis-N-[1-(3-methoxy-benzoyl)-2-methyl-1,2,3,4-tetrahydro-quinolin-4-yl]-N-o-tolyl-acetamide (B-1)

(±)-Cis-N-[1-(3-methoxy-benzoyl)-2-methyl-1,2,3,4-tetrahydro-quinolin-4-yl]-N-o-tolyl-acetamide was made following general procedure B, substituting 3-methoxybenzoyl chloride for 4-dimethylaminobenzoyl chloride and 2-tolylboronic acid for 4-chlorophenylboronic acid.

$^1$H-NMR (CDCl$_3$) δ: 1.14 (d, 3H), 1.26 (s, 1H), 1.58 (s, 3H), 1.97 (s, 3H), 2.08 (m, 1H), 3.63 (s, 3H), 4.80 (sextet, 1H), 5.55 (bs, 1H), 6.53 (d, 1H), 6.76 (s, 1H), 6.83 (t, 2H), 6.93 (t, 1H), 7.10 (t, 1H), 7.15-7.37 (m, 6H).

MS m/z: 429 (M+1)

N-(4-chloro-phenyl)-N-[1-(3-methoxy-benzoyl)-2-methyl-1,2,3,4-tetrahydro-quinolin-4-yl]-acetamide (B-2)

(±)-Cis-N-(4-chloro-phenyl)-N-[1-(3-methoxy-benzoyl)-2-methyl-1,2,3,4-tetrahydro-quinolin-4-yl]-acetamide was made following general procedure B, substituting 3-methoxybenzoyl chloride for 4-dimethylaminobenzoyl chloride.

(±)-Cis-N-(4-chloro-phenyl)-N-[1-(3-methoxy-benzoyl)-2-methyl-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-chloro-phenyl)-N-[1-(3-methoxy-benzoyl)-2-methyl-1,2,3,4-tetrahydro-quinolin-4-yl]-acetamide (B-9 & B-8, respectively)

$^1$H-NMR (CDCl$_3$) δ: 1.17 (d, 3H), 1.25 (t, 1H), 2.03 (s, 3H), 2.29 (m, 1H), 3.62 (s, 3H), 4.80 (sextet, 1H), 5.60 (bs, 1H), 6.54 (d, 1H), 6.74 (s, 1H), 6.80 (t, 1H), 6.93 (t, 1H), 7.08 (t, 1H), 7.14-7.30 (m, 5H), 7.38 (d, 2H).

MS m/z: 449 (M+1)

(±)-Cis-N-(4-chloro-phenyl)-N-[2-methyl-1-(thiophene-2-carbonyl)-1,2,3,4-tetrahydro-quinolin-4-yl]-acetamide (B-3)

(±)-Cis-N-(4-chloro-phenyl)-N-[2-methyl-1-(thiophene-2-carbonyl)-1,2,3,4-tetrahydro-quinolin-4-yl]-acetamide was made following general procedure B, substituting 2-thiophenecarbonyl chloride for 4-dimethylaminobenzoyl chloride.

(±)-Cis-N-(4-chloro-phenyl)-N-[2-methyl-1-(thiophene-2-carbonyl)-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-chloro-phenyl)-N-[2-methyl-1-(thiophene-2-carbonyl)-1,2,3,4-tetrahydro-quinolin-4-yl]-acetamide (B-7 & B-6, respectively).

$^1$H-NMR (300 MHz, CDCl$_3$) δ: 1.11-1.24 (m, 4H), 2.03 (s, 3H), 2.22-2.35 (m, 1H), 4.73 (ddd, 1H), 5.52 (br s, 1H), 6.69 (dd, 1H), 6.67 (dd, 1H), 6.89 (d, 1H), 7.08 (dd, 1H), 7.21 (d, 2H), 7.27-7.43 (m, 5H).

MS m/z: 425 (M+1).

(±)-Cis-N-(4-chloro-phenyl)-N-[2-methyl-1-(5-methyl-thiophene-2-carbonyl)-1,2,3,4-tetrahydro-quinolin-4-yl]-isobutyramide (B-4)

(±)-Cis-N-(4-chloro-phenyl)-N-[2-methyl-1-(5-methyl-thiophene-2-carbonyl)-1,2,3,4-tetrahydro-quinolin-4-yl]-isobutyramide was made following general procedure B, substituting 5-methyl-2-thiophenecarbonyl chloride for 4-dimethylaminobenzoyl chloride and isobutyryl chloride for acetyl chloride.

(±)-Cis-N-(4-chloro-phenyl)-N-[2-methyl-1-(5-methyl-thiophene-2-carbonyl)-1,2,3,4-tetrahydro-quinolin-4-yl]-isobutyramide was separated by chiral HPLC using a chiral cel OD column and eluting with 90% hexane/10% ethanol isocratic system to give (2R,4S)- and (2S,4R)-cis-N-(4-Chloro-phenyl)-N-[2-methyl-1-(5-methyl-thiophene-2-carbonyl)-1,2,3,4-tetrahydro-quinolin-4-yl]-isobutyramide (B-11 & B-10 respectively).

$^1$H-NMR (CDCl$_3$) δ: 1.13 (d, 6H), 1.16 (d, 3H), 1.25 (m, 1H), 2.23 (m, 3H), 2.39 (s, 1H), 2.60 (septet, 1H), 4.66 (sextet, 1H), 5.50 (bs, 1H), 6.42 (s, 1H), 6.51 (s, 1H), 6.93 (d, 1H), 7.08 (t, 1H), 7.21 (d, 2H), 7.27 (d, 2H), 7.37 (bs, 2H).

MS m/z: 468 (M+1)

(±)-Cis-N-[1-(4-fluoro-benzoyl)-2-methyl-1,2,3,4-tetrahydro-quinolin-4-yl]-N-(4-fluoro-phenyl)-propionamide (B-5)

(±)-Cis-N-[1-(4-fluoro-benzoyl)-2-methyl-1,2,3,4-tetrahydro-quinolin-4-yl]-N-(4-fluoro-phenyl)-propionamide was made following general procedure B, substituting 4-fluorobenzoyl chloride for 4-dimethylaminobenzoyl chloride, 4-fluorophenylboronic acid for 4-chlorophenylboronic acid, and propionyl chloride for acetyl chloride.

$^1$H-NMR (CDCl$_3$) δ: 1.14 (t, 3H), 1.15 (d, 3H), 1.24 (m, 1H), 2.26 (m, 3H), 4.75 (sextet, 1H), 5.61 (bs, 1H), 6.46 (d, 1H), 6.87 (m, 3H), 7.10-7.26 (m, 8H).

MS m/z: 435 (M+1)

(±)-Cis-N-(4-chloro-3-methyl-phenyl)-N-[1-(4-fluoro-benzoyl)-2-methyl-1,2,3,4-tetrahydro-quinolin-4-yl]-propionamide (B-12)

(±)-Cis-N-(4-chloro-3-methyl-phenyl)-N-[1-(4-fluoro-benzoyl)-2-methyl-1,2,3,4-tetrahydro-quinolin-4-yl]-propionamide was made following general procedure B, substituting 4-fluorobenzoyl chloride for 4-dimethylaminobenzoyl chloride, propionyl chloride for acetyl chloride and 4-chloro-3-tolylboronic acid for 4-chlorophenylboronic acid.

$^1$H-NMR (CDCl$_3$) δ: 1.08 (t, 3H), 1.09 (d, 3H), 1.18 (m, 1H), 2.18 (m, 3H), 2.31 (s, 3H), 4.69 (sextet, 1H), 5.49 (bs, 1H), 6.42 (d, 1H), 6.79 (t, 2H), 6.86 (t, 1H), 6.96 (dd, 1H), 7.05-7.22 (m, 6H).

MS m/z: 465 (M+1).

(±)-Cis-N-[1-(4-Fluoro-benzoyl)-2-methyl-1,2,3,4-tetrahydro-quinolin-4-yl]-N-(4-trifluoromethyl-phenyl)-propionamide (B-13)

(±)-Cis-N-[1-(4-fluoro-benzoyl)-2-methyl-1,2,3,4-tetrahydro-quinolin-4-yl]-N-(4-trifluoro-methyl-phenyl)-propionamide was made following general procedure B, substituting 4-fluorobenzoyl chloride for 4-dimethylaminobenzoyl chloride, propionyl chloride for acetyl chloride and 4-trifluoromethylphenylboronic acid for 4-chlorophenylboronic acid.

$^1$H-NMR (CDCl$_3$) δ: 1.15 (t, 3H), 1.17 (d, 3H), 1.20 (m, 1H), 2.29 (m, 3H), 4.79 (sextet, 1H), 5.62 (bs, 1H), 6.49 (d, 1H), 6.87 (m, 3H), 7.19-7.28 (m, 6H), 7.41 (d, 1H), 7.69 (d, 1H).

MS m/z: 485 (M+1).

(±)-Cis-N-(4-chloro-phenyl)-N-[1-(4-methoxy-benzoyl)-2-methyl-1,2,3,4-tetrahydro-quinolin-4-yl]-propionamide (B-14)

(±)-Cis-N-(4-chloro-phenyl)-N-[1-(4-methoxy-benzoyl)-2-methyl-1,2,3,4-tetrahydro-quinolin-4-yl]-propionamide was made following general procedure B, substituting 4-methoxybenzoyl chloride for 4-dimethylaminobenzoyl chloride and propionyl chloride for acetyl chloride.

(±)-Cis-N-(4-chloro-phenyl)-N-[1-(4-methoxy-benzoyl)-2-methyl-1,2,3,4-tetrahydro-quinolin-4-yl]-propionamide was separated by chiral HPLC using a chiral cel OD column and eluting with 90% hexane/10% ethanol isocratic system to give (2R,4S)- and (2S,4R)-cis-N-(4-chloro-phenyl)-N-[1-(4-methoxy-benzoyl)-2-methyl-1,2,3,4-tetrahydro-quinolin-4-yl]-propionamide (B-18 & B-17, respectively).

$^1$H-NMR (CDCl$_3$) δ: 1.14 (t, 3H), 1.15 (d, 3H), 1.25 (t, 1H), 2.29 (m, 3H), 3.74 (s, 3H), 4.74 (sextet, 1H), 5.61 (bs, 1H), 6.53 (d, 1H), 6.68 (d, 2H), 6.93 (t, 1H), 7.14-7.28 (m, 6H), 7.38 (d, 2H).

MS m/z: 463 (M+1).

(±)-Cis-N-(4-chloro-phenyl)-N-[1-(4-methoxy-benzoyl)-2-methyl-1,2,3,4-tetrahydro-quinolin-4-yl]-acetamide (B-15)

(±)-Cis-N-(4-chloro-phenyl)-N-[1-(4-methoxy-benzoyl)-2-methyl-1,2,3,4-tetrahydro-quinolin-4-yl]-acetamide was made following general procedure B, substituting 4-methoxybenzoyl chloride for 4-dimethylaminobenzoyl chloride.

(±)-Cis-N-(4-chloro-phenyl)-N-[1-(4-methoxy-benzoyl)-2-methyl-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-Chloro-phenyl)-N-[1-(4-methoxy-benzoyl)-2-methyl-1,2,3,4-tetrahydro-quinolin-4-yl]-acetamide (B-34 & B-35, respectively).

$^1$H-NMR (CDCl$_3$) δ: 1.14 (d, 3H), 1.25 (t, 1H), 2.04 (s, 3H), 2.29 (m, 1H), 3.74 (s, 3H), 4.74 (sextet, 1H), 5.61 (bs, 1H), 6.53 (d, 1H), 6.68 (d, 2H), 6.93 (t, 1H), 7.14-7.28 (m, 6H), 7.38 (d, 2H).

MS m/z: 449 (M+1).

(±)-Cis-N-(4-chloro-phenyl)-N-[1-(4-hydroxy-benzoyl)-2-methyl-1,2,3,4-tetrahydro-quinolin-4-yl]-propionamide (B-16)

(±)-Cis-N-(4-chloro-phenyl)-N-[1-(4-hydroxy-benzoyl)-2-methyl-1,2,3,4-tetrahydro-quinolin-4-yl]-propionamide was made from (±)-cis-N-(4-chloro-phenyl)-N-[1-(4-methoxy-benzoyl)-2-methyl-1,2,3,4-tetrahydro-quinolin-4-yl]-propionamide. (±)-Cis-N-[1-(4-methoxy-benzoyl)-2-methyl-1,2,3,4-tetrahydro-quinolin-4-yl]-N-phenyl-propionamide (0.548 g, 0.001 mol) was dissolved in dichloromethane and a solution of BBr$_3$ (1.0 M in dichloromethane, 10 mL) was added; the reaction was allowed to stir at room temperature for 4 h or until no starting material remained. The reaction was washed with sat NaHCO$_3$ carefully and brine. The organics were dried over MgSO$_4$, filtered and concentrated down. The phenol was concentrated down and the residue was purified by Biotage flash chromatography using 100% EtOAc to give a white solid, 74% yield.

$^1$H-NMR (CDCl$_3$) δ: 1.09 (d, 3H), 1.11 (t, 3H), 1.19 (m, 1H), 2.26 (m, 3H), 4.74 (sextet, 1H), 5.54 (bs, 1H), 6.46 (d, 1H), 6.53 (d, 1H), 6.96 (t, 1H), 7.14-7.40 (m, 9H).

MS m/z: 415 (M+1).

(±)-Cis-N-[1-(4-fluoro-benzoyl)-2-methyl-1,2,3,4-tetrahydro-quinolin-4-yl]-N-p-tolyl-propionamide (B-21)

(±)-Cis-N-[1-(4-fluoro-benzoyl)-2-methyl-1,2,3,4-tetrahydro-quinolin-4-yl]-N-p-tolyl propionamide was made following general procedure B, substituting 4-fluorobenzoyl chloride for 4-dimethylaminobenzoyl chloride, propionyl chloride for acetyl chloride and 4-tolylboronic acid for 4-chlorophenylboronic acid.

$^1$H-NMR (300 MHz, CDCl$_3$) δ: 1.05-1.21 (m, 7H), 2.11-2.54 (m, 6H), 4.73 (ddd, 1H), 5.56 (br s, 1H), 6.37 d, 1H), 6.8-7.0 (m, 3H), 7.1-7.4 (m, 8H).

MS m/z: 431 (M+1).

(±)-Cis-N-(4-chloro-phenyl)-N-[1-(4-fluoro-benzoyl)-2-methyl-1,2,3,4-tetrahydro-quinolin-4-yl]-acetamide (B-22)

(±)-Cis-N-(4-chloro-phenyl)-N-[1-(4-fluoro-benzoyl)-2-methyl-1,2,3,4-tetrahydro-quinolin-4-yl]-acetamide was made following general procedure B, substituting 4-fluorobenzoyl chloride for 4-dimethylaminobenzoyl chloride.

(±)-Cis-N-(4-chloro-phenyl)-N-[1-(4-fluoro-benzoyl)-2-methyl-1,2,3,4-tetrahydro-quinolin-4-yl]-acetamide was separated by chiral HPLC using a chiral cel OD column and eluting with 95% hexane/5% ethanol isocratic system to give (2R,4S)- and (2S,4R)-cis-N-(4-chloro-phenyl)-N-[1-(4-fluoro-benzoyl)-2-methyl-1,2,3,4-tetrahydro-quinolin-4-yl]-acetamide (B-26 & B-27, respectively).

$^1$H-NMR (CDCl$_3$) δ: 1.1 (d, 3H), 1.1 (m, 1H), 2.0 (d, 3H), 2.3 (m, 1H), 4.7 (m, 1H), 5.6 (m, 1H), 6.5 (d, 1H), 6.7-7.0 (m, 3H), 7.1-7.4 (m, 8H).

MS m/z: 436 (M+1).

(±)-Cis-N-(4-chloro-phenyl)-N-[2-methyl-1-(5-methyl-thiophene-2-carbonyl)-1,2,3,4-tetrahydro-quinolin-4-yl]-acetamide (B-24)

(±)-Cis-N-(4-chloro-phenyl)-N-[2-methyl-1-(5-methyl-thiophene-2-carbonyl)-1,2,3,4-tetrahydro-quinolin-4-yl]-acetamide was made following general procedure B, substituting 5-methyl-2-thiophenecarbonyl chloride for 4-dimethylaminobenzoyl chloride.

(±)-Cis-N-(4-chloro-phenyl)-N-[2-methyl-1-(5-methyl-thiophene-2-carbonyl)-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-Chloro-phenyl)-N-[2-methyl-1-(5-methyl-thiophene-2-carbonyl)-1,2,3,4-tetrahydro-quinolin-4-yl]-acetamide (B-28 & B-25, respectively).

$^1$H-NMR (CDCl$_3$) δ: 1.1 (3H, d), 1.1 (1H, m), 2.0 (3H, d), 2.3 (1H, m), 2.4 (3H, s), 4.7 (1H, m), 5.6 (1H, m), 6.4 (1H, m), 6.6 (1H, m), 7.0 (1H, m), 7.1 (1H, m), 7.2-7.4 (6H, m).

MS m/z: 439 (M+1).

(±)-Cis-N-(4-chloro-phenyl)-N-[2-methyl-1-(5-methyl-thiophene-2-carbonyl)-1,2,3,4-tetrahydro-quinolin-4-yl]-propionamide (B-29)

(±)-Cis-N-(4-chloro-phenyl)-N-[2-methyl-1-(5-methyl-thiophene-2-carbonyl)-1,2,3,4-tetrahydro-quinolin-4-yl]-propionamide was made following general procedure B, substituting 5-methyl-2-thiophenecarbonyl chloride for 4-dimethylaminobenzoyl chloride and propionyl chloride for acetyl chloride.

$^1$H-NMR (CDCl$_3$) δ: 1.1-1.2 (7H, m), 2.1-2.3 (3H, m), 2.3 (3H, s), 4.8 (1H, m), 5.6 (1H, m), 6.2-6.4 (2H, m), 6.8-7.4 (8H, m).

MS m/z: 452 (M+2).

(±)-Cis-4-(4-{4-[(4-chloro-phenyl)-propionyl-amino]-2-methyl-3,4-dihydro-2H-quinoline-1-carbonyl}-phenoxy)-butyric acid ethyl ester (B-30)

(±)-Cis-4-(4-{4-[(4-chloro-phenyl)-propionyl-amino]-2-methyl-3,4-dihydro-2H-quinoline-1-carbonyl}-phenoxy)-butyric acid ethyl ester was prepared from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-chloro-phenyl)-N-[1-(4-hydroxy-benzoyl)-2-methyl-1,2,3,4-tetrahydroquinolin-4-yl]-propionamide (140 mg, 0.31 mmol) was dissolved in DMF (5 mL) at room temperature. Sodium hydride (60% in oil, 32 mg, 0.81 mmol) was added and the mixture allowed to stir 30 min. Ethyl 4-bromobutyrate (207 mg, 1.06 mmol) was added and the reaction was allowed to stir over night. Ethanol was added and the reaction was concentrated in vacuo. The crude residue was purified by silica gel chromatography (80/20 hexanes/ethyl acetate-50/50 hexanes ethyl acetate gradient) to afford the product (171 mg, 0.304 mmol, 98%).

$^1$H-NMR (CDCl$_3$) δ: 1.1-1.2 (7H, m), 1.3 (3H, t), 2.1 (2H, m), 2.3 (3H, m), 2.5 (2H, t), 3.9 (2H, t), 4.2 (2H, q), 4.8 (1H, m), 5.6 (1H, m), 6.5 (1H, d), 6.7 (2H, d), 6.9 (1H, t), 7.1-7.3 (6H, m), 7.4 (2H, m).

MS m/z: 563 (M+1).

(±)-Cis-4-(4-{4-[(4-chloro-phenyl)-propionyl-amino]-2-methyl-3,4-dihydro-2H-quinoline-1-carbonyl}-phenoxy)-butyric acid (B-31)

(±)-Cis-4-(4-{4-[(4-chloro-phenyl)-propionyl-amino]-2-methyl-3,4-dihydro-2H-quinoline1-carbonyl}-phenoxy)-butyric acid was prepared from (±)-cis-4-(4-{4-[(4-chloro-phenyl)-propionyl-amino]-2-methyl-3,4-dihydro-2H-quinoline-1-carbonyl}-phenoxy)-butyric acid ethyl ester. Potassium carbonate (300 mg) was dissolved in water (5 mL) and (±)-cis-4-(4-{4-[(4-chloro-phenyl)-propionyl-amino]-2-methyl-3,4-dihydro-2H-quinoline-1-carbonyl}-phenoxy)-butyric acid ethyl ester (171 mg, 0.303 mmol) was dissolved in methanol (5 mL) was added. The reaction was allowed to stir over night at room temperature. The methanol was removed in vacuo and hydrochloric acid (1 N) was added until acidic. Dichloromethane was added, extracted 2×; the combined organics were dried over magnesium sulfate, filtered and concentrated to afford the carboxylic acid (50 mg, 31%).

$^1$H-NMR (CDCl$_3$) δ: 1.1-1.2 (7H, m), 2.0 (2H, m), 2.3 (2H, m), 2.4 (3H, m), 3.3 (1H, s), 4.0 (2H, t), 4.8 (1H, m), 5.6 (1H, m), 6.5 (1H, d), 6.7 (2H, d), 6.9 (1H, t), 7.1-7.3 (3H, m), 7.4-7.6 (5H, m).

MS m/z: 535 (M+1).

(±)-Cis-N-(4-chloro-phenyl)-N-{2-methyl-1-[4-(1H-tetrazol-5-ylmethoxy)-benzoyl]-1,2,3,4-tetrahydro-quinolin-4-yl}-propionamide (B-32)

(±)-Cis-N-(4-chloro-phenyl)-N-{2-methyl-1-[4-(1H-tetrazol-5-ylmethoxy)-benzoyl]-1,2,3,4-tetrahydro-quinolin-4-yl}-propionamide was prepared from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-chloro-phenyl)-N-[1-(4-hydroxy-benzoyl)-2-methyl-1,2,3,4-tetrahydro-quinolin-4-yl]-propionamide (700 mg, 1.42 mmol) was dissolved in DMF (10 mL) at room temperature. Sodium hydride (60% in oil, 227 mg, 5.68 mmol) was added and the mixture allowed to stir 30 min. Bromoacetonitrile (850 mg, 7.11 mmol) was added and the reaction was allowed to stir over night. Ethanol was added and the reaction was concentrated in vacuo. The crude residue was purified by silica gel chromatography (30/70 ethyl acetate/dichloromethane) to afford the product (320 mg, 42%).

The nitrile (140 mg, 0.25 mmol) was dissolved in toluene, sodium azide (160 mg, 2.5 mmol) and triethylammonium hydrochloride (345 mg, 2.5 mmol) were added and the mixture was heated to 80° C. over night. Reaction was cooled to room temperature and water was added, followed by hydrochloric acid (1 N) until acidic. The aqueous solution was extracted three times with dichloromethane. The combined extracts were dried over magnesium sulfate, filtered, dried and concentrated. The crude product was triturated with ethyl ether/hexanes to yield a white solid (82 mg, 63%).

$^1$H-NMR (CDCl$_3$) δ: 1.0-1.2 (7H, m), 2.2-2.4 (3H, m), 4.8 (1H, m), 5.2 (2H, dd), 5.6 (1H, m), 6.7 (2H, m), 6.9 (1H, t), 7.1 (2H, d), 7.2-7.6 (7H, m).

MS m/z: 531 (M+1).

(±)-Cis-N-(4-chloro-phenyl)-N-[1-(4-isobutoxy-benzoyl)-2-methyl-1,2,3,4-tetrahydro-quinolin-4-yl]-acetamide (B-33)

(±)-Cis-N-(4-chloro-phenyl)-N-[1-(4-isobutoxy-benzoyl)-2-methyl-1,2,3,4-tetrahydro-quinolin-4-yl]-acetamide was made following general procedure B, substituting 4-isobutyloxybenzoyl chloride for 4-dimethylaminobenzoyl chloride.

$^1$H-NMR (CDCl$_3$) δ: 0.9-1.0 (8H, m), 1.2 (3H, d), 2.0 (3H, s), 2.3 (1H, m), 3.6 (2H, d), 4.7 (1H, m), 5.6 (1H, m), 6.5 (1H, d), 6.6 (2H, d), 6.9 (1H, m), 7.1-7.4 (8H, m).

MS m/z: 491 (M+1).

(±)-Cis-N-(4-chloro-phenyl)-N-{1-[4-(3-hydroxy-2,2-dimethyl-propoxy)-benzoyl]-2-methyl-1,2,3,4-tetrahydro-quinolin-4-yl}-acetamide (B-37)

(±)-Cis-N-(4-chloro-phenyl)-N-{1-[4-(3-hydroxy-2,2-dimethyl-propoxy)-benzoyl]-2-methyl-1,2,3,4-tetrahydro-quinolin-4-yl}-acetamide was prepared from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-chloro-phenyl)-N-[1-(4-hydroxy-benzoyl)-2-methyl-1,2,3,4-tetrahydro-quinolin-4-yl]-propionamide (210 mg, 0.484 mmol) was dissolved in DMF (10 mL) at room temperature. Potassium carbonate (1 g, 7.1 mmol) was added, followed by 3-bromo-2,2-dimethyl-propan-1-ol (813 mg, 4.84 mmol), the reaction was heated to 95° C. and stirred over night. The reaction mixture was cooled to room temperature, filtered and concentrated in vacuo. The crude product was purified by silica gel chromatography (95/5 dichloromethane/ethyl acetate-70/30 dichloromethane/ethyl acetate) to afford the pure ester (110 mg, 44%)

$^1$H-NMR (CDCl$_3$) δ: 1.0 (6H, s), 1.1 (3H, d), 1.1 (1H, m), 1.7 (1H, br), 2.0 (3H, s), 2.3 (1H, m), 3.5 (2H, s), 3.7 (2H, s), 4.8 (1H, m), 5.6 (1H, m), 6.5 (1H, d), 6.7 (2H, d), 6.9 (1H, t), 7.1-7.3 (7H, m), 7.4 (1H, d).

MS m/z: 521 (M+1).

(±)-Cis-3-(4-{4-[acetyl-(4-chloro-phenyl)-amino]-2-methyl-3,4-dihydro-2H-quinoline-1-carbonyl}-phenoxy)-2,2-dimethyl-propionic acid methyl ester (B-38)

(±)-Cis-3-(4-{4-[acetyl-(4-chloro-phenyl)-amino]-2-methyl-3,4-dihydro-2H-quinoline-1-carbonyl}-phenoxy)-2,2-dimethyl-propionic acid methyl ester was prepared from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-chloro-phenyl)-N-[1-(4-hydroxy-benzoyl)-2-methyl-1,2,3,4-tetrahydro-quinolin-4-yl]-propionamide (400 mg, 0.92 mmol) was dissolved in DMF (25 mL) at room temperature. Potassium carbonate (1 g, 7.1 mmol) was added, followed by 3-bromo-2,2-dimethyl-propionic acid methyl ester (400 mg, 0.92 mmol), the reaction was heated to 95° C. and stirred over night. The reaction mixture was cooled to room temperature, filtered and concentrated in vacuo. The crude product was purified by silica gel chromatography (95/5 dichloromethane/ethyl acetate-70/30 dichloromethane/ethyl acetate) to afford the pure ester (40 mg, 8%).

$^1$H-NMR (CDCl$_3$) δ: 1.1 (3H, d), 1.1 (1H, m), 1.3 (6H, s), 2.0 (3H, s), 2.3 (1H, m), 3.7 (3H, s), 3.9 (2H, dd), 4.8 (1H, m), 5.6 (1H, m), 6.5 (1H, d), 6.7 (2H, d), 6.9 (1H, t), 7.1-7.3 (7H, m), 7.4 (1H, d).

MS m/z: 549 (M+1).

(±)-Cis-(4-{acetyl-[1-(4-methoxy-benzoyl)-2-methyl-1,2,3,4-tetrahydro-quinolin-4-yl]-amino}-phenyl)-acetic acid (B-39)

(±)-Cis-(4-{acetyl-[1-(4-methoxy-benzoyl)-2-methyl-1,2,3,4-tetrahydro-quinolin-4-yl]-amino}-phenyl)-acetic acid was made from (±)-cis-N-(4-cyanomethyl-phenyl)-N-[1-(4-methoxy-benzoyl)-2-methyl-1,2,3,4-tetrahydro-quinolin-4-yl]-acetamide. (±)-Cis-N-(4-cyanomethyl-phenyl)-N-[1-(4-methoxy-benzoyl)-2-methyl-1,2,3,4-tetrahydro-quinolin-4-yl]-acetamide was made following general procedure B, substituting 4-methoxybenzoylchloride for 4-dimethylaminobenzoyl chloride and 4-(phenylboronic acid)-acetonitrile for 4-chlorophenylboronic acid. (±)-Cis-N-(4-cyanomethyl-phenyl)-N-[1-(4-methoxy-benzoyl)-2-methyl-1,2,3,4-tetrahydro-quinolin-4-yl]-acetamide was dissolved in ethanol (4 mL), potassium hydroxide (120 mg in 0.3 mL water) was added and the reaction was heated at 80° C. over night. The ethanol was removed in vacuo and hydrochloric acid (1 N) was added until acidic. Dichloromethane was added, extracted 2×; the combined organics were dried over magnesium sulfate, filtered and concentrated to afford the carboxylic acid (30 mg) after HPLC purification.

$^1$H-NMR (CDCl$_3$) δ: 1.1 (3H, d), 1.1 (1H, m), 2.0 (3H, s), 2.3 (1H, m), 3.6 (2H, s), 3.8 (3H, s), 4.8 (1H, m), 5.7 (1H, m), 6.5 (1H, m), 6.6 (2H, m), 6.9 (1H, m), 7.1-7.3 (8H, m).

MS m/z: 495 (M+23).

(±)-Cis-3-{acetyl-[1-(4-methoxy-benzoyl)-2-methyl-1,2,3,4-tetrahydro-quinolin-4-yl]-amino}-benzoic acid (B-40)

(±)-Cis-3-{acetyl-[1-(4-methoxy-benzoyl)-2-methyl-1,2,3,4-tetrahydro-quinolin-4-yl]-amino}-benzoic acid was made following the procedure for (±)-cis-(4-{acetyl-[1-(4-methoxy-benzoyl)-2-methyl-1,2,3,4-tetrahydro-quinolin-4-yl]-amino}-phenyl)-acetic acid, substituting 3-cyanophenylboronic acid for 4-(phenylboronic acid)-acetonitrile.

Basic nitrile hydrolysis using 1N NaOH in methanol and water afforded both the carboxylic acid and the primary amide, (±)-cis-3-{Acetyl-[1-(4-methoxy-benzoyl)-2-methyl-1,2,3,4-tetrahydro-quinolin-4-yl]amino}-benzamide.

$^1$H-NMR (CDCl$_3$) δ: 1.1 (3H, d), 1.1 (1H, m), 2.0 (3H, s), 2.3 (1H, m), 3.8 (3H, s), 4.8 (1H, m), 5.6 (1H, m), 6.5 (1H, d), 6.6 (2H, d), 6.9 (2H, m), 7.1-7.5 (5H, m), 7.9-8.2 (2H, m).

MS m/z: 481 (M+23).

(±)-Cis-3-{Acetyl-[1-(4-methoxy-benzoyl)-2-methyl-1,2,3,4-tetrahydro-quinolin-4-yl]-amino}-benzamide (B-41)

$^1$H-NMR (CDCl$_3$) δ: 1.1 (3H, d), 1.1 (1H, m), 2.0 (3H, s), 2.3 (1H, m), 3.8 (3H, s), 4.8 (1H, m), 5.7 (1H, m), 6.5 (1H, m), 6.6 (2H, m), 6.9 (1H, m), 7.1-7.3 (4H, m), 7.4-7.6 (2H, m), 7.7-7.8 (2H, m).

MS m/z: 480 (M+23).

(±)-Cis-N-(4-Chloro-phenyl)-N-[1-(isoxazole-5-carbonyl)-2-methyl-1,2,3,4-tetrahydro-quinolin-4-yl]-propionamide (B-44)

(±)-Cis-N-(4-Chloro-phenyl)-N-[1-(isoxazole-5-carbonyl)-2-methyl-1,2,3,4-tetrahydro-quinolin-4-yl]-propionamide was made following general procedure B, substituting 5-isoxazolecarbonyl chloride for 4-dimethylaminobenzoyl chloride and propionyl chloride for acetyl chloride.

$^1$H-NMR (CDCl$_3$) δ: 1.14 (3H, d; overlapping 3H, t, and 1H, t), 2.30 (overlapping 2H, q; and 1H, m), 4.75 (1H, m), 5.45 (1H, m), 6.00 (1H, d), 6.80 (1H, d), 7.10-7.40 (7H, m), 8.05 (1H, s).

MS m/z: 424 (M+1).

(±)-Cis-N-(4-chloro-phenyl)-N-[1-(4-cyclopentyloxy-benzoyl)-2-methyl-1,2,3,4-tetrahydro-quinolin-4-yl]-acetamide (B-45)

(±)-Cis-N-(4-chloro-phenyl)-N-[1-(4-cyclopentyloxy-benzoyl)-2-methyl-1,2,3,4-tetrahydro-quinolin-4-yl]-acetamide was prepared from (±)-cis-N-(4-chloro-phenyl)-N-[1-(4-hydroxy-benzoyl)-2-methyl-1,2,3,4-tetrahydro-quinolin-4-yl]-propionamide. To a solution of (±)-cis-N-(4-Chloro-phenyl)-N-[1-(4-hydroxy-benzoyl)-2-methyl-1,2,3,4-tetrahydro-quinolin-4-yl]-acetamide in dimethylformamide was added cyclopentyl bromide, potassium carbonate (3.0 equiv), potassium iodide (catalytic) and heated to 65° C. overnight. Reaction mixture was filtered for removal of inorganic salts and concentrated. Crude mixture was purified by flash chromatography on silica gel using gradient elution ethyl acetate-methanol (2-20% methanol)

$^1$H-NMR (CDCl$_3$) δ: 1.15 (3H, d; overlapping 1H, t), 1.57 (2H, m), 1.79 (3×2H, m), 2.04 (3H, s), 2.30 (1H, m), 4.60-4.80 (1H, q, 1H, m), 5.60 (1H, m), 6.50 (1H, d), 6.62 (1H, d), 6.90 (1H, t), 7.10-7.30 (9H, m), 7.40 (1H, d).

MS m/z: 504 (M+1).

(±)-Cis-N-{1-[4-(4-Acetyl-piperazin-1-yl)-benzoyl]-2-methyl-1,2,3,4-tetrahydro-quinolin-4-yl}-N-(4-chloro-phenyl)-acetamide (B-46)

(±)-Cis-N-{1-[4-(4-Acetyl-piperazin-1-yl)-benzoyl]-2-methyl-1,2,3,4-tetrahydro-quinolin-4-yl}-N-(4-chloro-phenyl)-acetamide was made from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-Chloro-phenyl)-N-[1-(4-hydroxy-benzoyl)-2-methyl-1,2,3,4-tetrahydro-quinolin-4-yl]-propionamide (1.07 g, 2.39 mmol) was dissolved in pyridine (5 mL) and trifluoro-methanesulfonic anhydride (703 uL, 2.5 mmol) was added. The reaction was stirred at room temperature 3 h. The reaction was partitioned between ether and water, and the aqueous was extracted three times with ether. The combined extracts were dried over sodium sulfate, filtered and concentrated. The crude triflate was purified by silica gel chromatography (70/30 hexanes/ethyl acetate-40/60 hexanes/ethyl acetate gradient) to afford (1.0 g 74%) of pure material.

To the triflate, Pd$_2$(dba)$_3$, BINAP, cesium carbonate, 18-crown-6 ether in toluene was added N-acetyl piperazine and reaction mixture was heated to reflux for 18 hours. Reaction mixture was cooled to room temperature and filtered through Celite® and concentrated. Crude mixture was purified by flash chromatography on silica gel using gradient elution ethyl acetate-methanol (2-20%).

$^1$H-NMR (CDCl$_3$) δ: 1.13 (3H, d; overlapping 1H, t), 2.02 (3H, s), 2.10 (3H, s), 2.35 (1H, m), 3.20 (2×2H, m), 3.60 (2H, t), 3.70 (2H, t), 4.80 (1H, m), 5.65 (1H, m), 6.55 (1H, d), 6.70 (1H, d), 6.95 (1H, t), 7.10-7.40 (9H, m).

MS m/z: 546 (M+1).

(±)-Cis-N-(3-chloro-phenyl)-N-[1-(4-fluoro-benzoyl)-2-methyl-1,2,3,4-tetrahydro-quinolin-4-yl]-acetamide (B-50)

(±)-Cis-N-(3-chloro-phenyl)-N-[1-(4-fluoro-benzoyl)-2-methyl-1,2,3,4-tetrahydro-quinolin-4-yl]-acetamide was made following general procedure B, substituting 4-fluorobenzoylchloride for 4-dimethylaminobenzoyl chloride and 3-chlorophenylboronic acid for 4-chlorophenylboronic acid.

$^1$H-NMR (CDCl$_3$) δ: 1.16-1.26 (4H, m), 2.05 (3H, s), 2.25-2.39 (1H, m), 4.69-4.88 (1H, m), 5.47-5.68 (1H, broad), 6.49 (1H, d), 6.84-6.97 (4H, m), 7.18-7.42 (7H, m).

MS m/z 437 (M$^+$), 439 (M+2).

(±)-Cis-N-[1-(4-fluoro-benzoyl)-2-methyl-1,2,3,4-tetrahydro-quinolin-4-yl]-N-(4-phenoxy-phenyl)-acetamide (B-51)

(±)-Cis-N-[1-(4-fluoro-benzoyl)-2-methyl-1,2,3,4-tetrahydro-quinolin-4-yl]-N-(4-phenoxy-phenyl)-acetamide was made following general procedure B, substituting 4-fluorobenzoylchloride for 4-dimethylaminobenzoyl chloride and 4-phenoxyphenylboronic acid for 4-chlorophenylboronic acid.

$^1$H-NMR (CDCl$_3$) δ: 1.16-1.18 (4H, m), 2.06 (3H, s), 2.34-2.38 (1H, m), 4.74-4.82 (1H, m), 5.29 (1H, br), 6.47 (1H, d), 6.83-7.40 (16H, m).

MS m/z: 496 (M+1).

(±)-Cis-N-[1-(3-methoxy-benzoyl)-2-methyl-1,2,3,4-tetrahydro-quinolin-4-yl]-N-pyridin-2-yl-acetamide (B-52)

(±)-Cis-N-[1-(3-methoxy-benzoyl)-2-methyl-1,2,3,4-tetrahydro-quinolin-4-yl]-N-pyridin-2-yl-acetamide was made following general procedure B, substituting 3-methoxy benzoyl chloride for 4-dimethylaminobenzoyl chloride and synthesis of the N-pyridinyl instead of the 4-chlorophenyl was accomplished using the following procedure.

Pd$_2$(dba)$_3$ (0.05 equ.), and rac-BINAP (0.1 equ.) were added to a flask with degassed toluene and stirred for 1 h. To the above solution was added 2-bromopyridine (1.1 equ.) and NaO$^t$Bu (1.1 equ.) and stirred for 30 min. (±)-Cis-(4-amino-2-methyl-3,4-dihydro-2H-quinolin-1-yl)-(3-methoxy-phenyl)-methanone was dissolved in degassed toluene and added to the solution and heated to 100° C. for 17 h. The reaction was diluted with ether and filtered through celite and concentrated down. The compound was purified by Biotage with 20% EtOAc/80% Hexane to 30% EtOAc/70% Hexane to 50% EtOAc/50% Hexane to give 43% of the product. (±)-Cis-(3-methoxy-phenyl)-[2-methyl-4-(pyridin-2-ylamino)-3,4-dihydro-2H-quinolin-1-yl]-methanone was acetylated with acetyl chloride as previously described to give (±)-cis-N-[1-(3-methoxy-benzoyl)-2-methyl-1,2,3,4-tetrahydro-quinolin-4-yl]-N-pyridin-2-yl-acetamide.

$^1$H-NMR (CDCl$_3$) δ: 1.16 (d, 3H), 1.24 (t, 1H), 2.02 (s, 3H), 2.43 (m, 1H), 3.61 (s, 3H), 4.81 (sextet, 1H), 5.65 (bs, 1H), 6.52 (d, 1H), 6.75 (s, 1H), 6.79 (d, 2H), 6.90 (t, 1H), 7.07 (t, 1H), 7.14 (t, 1H), 7.25-7.33 (m, 2H), 7.49 (d, 1H), 7.77 (t, 1H), 8.56 (s, 1H).

MS m/z: 416.0 (M+1).

(±)-Cis-N-cyclohexyl-N-[1-(3-methoxy-benzoyl)-2-methyl-1,2,3,4-tetrahydro-quinolin-4-yl]-acetamide (B-53)

(±)-Cis-N-cyclohexyl-N-[1-(3-methoxy-benzoyl)-2-methyl-1,2,3,4-tetrahydro-quinolin-4-yl]-acetamide was made following general procedure B, substituting 3-methoxy benzoyl chloride for 4-dimethylaminobenzoyl chloride and synthesis of the N-cyclohexyl instead of the 4-chlorophenyl was accomplished using the following procedure.

(±)-Cis-(4-amino-2-methyl-3,4-dihydro-2H-quinolin-1-yl)-(3-methoxy-phenyl)-methanone (1.0 equ.), and cyclohexanone (1.0 equ.) were dissolved in ethanol and a catalytic amount of acetic acid was added. The reaction was stirred for ~30 minutes and NaBH$_4$ (1.0 equ.) was added and stirred for an additional 2 h at room temperature. Additional NaBH$_4$ was added (1.0 equ.) and stirred for an additional 12 h. The reaction was concentrated down and partitioned between CH$_2$Cl$_2$ and 1N NaOH. The organics were separated and dried over Na$_2$SO$_4$, filtered and concentrated down. The compound was purified by Biotage with 30% EtOAc/70% hexane to 50% EtOAc/50% hexane give 96% of the product. Cis-(±)-N-(4-cyclohexylamino-2-methyl-3,4-dihydro-2H-quinolin-1-yl)-(3-methoxy-phenyl)-methanone was acetylated with acetyl chloride as previously described to give cis-(±)-N-cyclohexyl-N-[1-(3-methoxy-benzoyl)-2-methyl-1,2,3,4-tetrahydro-quinolin-4-yl]-acetamide.

$^1$H-NMR (CDCl$_3$) δ: 1.1-1.45 (m, 6H), 1.5-1.75 (m, 3H), 1.85-2.1 (m, 3H), 2.3 (s, 3H), 2.4 (m, 1H), 2.7 (m, 1H), 3.5 (q, 1H), 3.63 (s, 3H), 3.7 (m, 1H), 4.3 (dd, 1H), 4.90 (sextet, 1H), 6.6 (t, 1H), 6.7 (d, 1H)<6.8 (s, 1H), 6.85 (m, 2H), 7.0 (m, 3H).

MS m/z: 421 (M+1).

(±)-Cis-N-(5-chloro-pyridin-2-yl)-N-[1-(3-methoxy-benzoyl)-2-methyl-1,2,3,4-tetrahydro-quinolin-4-yl]-acetamide (B-54)

(±)-Cis-N-(5-chloro-pyridin-2-yl)-N-[1-(3-methoxy-benzoyl)-2-methyl-1,2,3,4-tetrahydro-quinolin-4-yl]-acetamide was made following general procedure B, substituting 3-methoxy benzoyl chloride for 4-dimethylaminobenzoyl chloride and addition of the N-(4-chloropyridinyl) instead of the 4-chlorophenyl was accomplished using the following procedure To a flask was added Pd$_2$(dba)$_3$ (molar 0.05 equ.), and rac-BINAP (0.1 equ.) in degassed toluene and stirred for 1 h. To the above solution was added 2,5-dichloropyridinepyridine (1.1 equ.) and NaO$^t$Bu (1.1 equ.) and stirred for 30 min. The corresponding amine, (±)-cis-(4-amino-2-methyl-3,4-dihydro-2H-quinolin-1-yl)-(3-methoxy-phenyl)-methanone was dissolved in degassed toluene and added to the solution and heated to 60° C. for 40 h. The reaction was diluted with ether and filtered through celite and concentrated down. The compound was purified by Biotage with 20% EtOAc/80% Hexane to give 45% of the product. (±)-Cis-[4-(5-chloro-pyridin-2-ylamino)-2-methyl-3,4-dihydro-2H-quinolin-1-yl]-(3-methoxy-phenyl)-methanone was acetylated with propionyl chloride as previously described to give (±)-cis-N-(5-chloro-pyridin-2-yl)-N-[1-(3-methoxy-benzoyl)-2-methyl-1,2,3,4-tetrahydro-quinolin-4-yl]-acetamide.

$^1$H-NMR (CDCl$_3$) δ: 1.14 (t, 3H), 1.15 (d, 3H), 1.22 (m, 1H), 2.31 (m, 3H), 4.79 (sextet, 1H), 5.64 (bs, 1H), 6.44 (d, 1H), 6.81-6.92 (m, 3H), 7.10-7.22 (m, 4H), 7.43 (d, 1H), 7.72 (dd, 1H), 8.50 (d, 1H).

MS m/z: 452 (M+1).

(±)-Cis-N-(4-chloro-phenyl)-N-[1-(4-methoxy-benzoyl)-2,5-dimethyl-1,2,3,4-tetrahydro-quinolin-4-yl]-acetamide (B-55)

(±)-Cis-N-(4-chloro-phenyl)-N-[1-(4-methoxy-benzoyl)-2,5-dimethyl-1,2,3,4-tetrahydro-quinolin-4-yl]-acetamide was made following general procedure B, substituting 3-toluidine for aniline and 4-methoxybenzoyl chloride for 4-dimethylaminobenzoyl chloride. The reaction was non-selective and also (±)-cis-N-(4-chloro-phenyl)-N-[1-(4-methoxy-benzoyl)-2,7-dimethyl-1,2,3,4-tetrahydro-quinolin-4-yl]-acetamide was obtained in a 1:1 mixture with the product.

$^1$H-NMR (CDCl$_3$) δ: 1.07 (d, 3H), 1.25 (t, 1H), 1.91 (s, 3H), 2.15 (m, 1H), 2.43 (s, 3H), 3.76 (s, 3H), 4.26 (sextet, 1H), 6.28 (d, 1H), 6.33 (t, 1H), 6.58 (t, 1H), 6.62 (d, 2H), 6.77 (t, 1H), 6.88 (d, 3H), 7.28 (m, 2H), 7.44 (d, 1H).

MS m/z: 463.0 (M+1)

(±)-Cis-N-(4-chloro-phenyl)-N-[1-(4-methoxy-benzoyl)-2,7-dimethyl-1,2,3,4-tetrahydro-quinolin-4-yl]-acetamide (B-56)

(±)-Cis-N-(4-chloro-phenyl)-N-[1-(4-methoxy-benzoyl)-2,7-dimethyl-1,2,3,4-tetrahydro-quinolin-4-yl]-acetamide was made following general procedure B, substituting 3-toluidine for aniline and 4-methoxybenzoyl chloride for 4-dimethylaminobenzoyl chloride. The reaction was non-selective, and also (±)-cis-N-(4-chloro-phenyl)-N-[1-(4-methoxy-benzoyl)-2,5-dimethyl-1,2,3,4-tetrahydro-quinolin-4-yl]-acetamide was obtained in a 1:1 mixture with the titled compound.

(±)-Cis-N-(4-chloro-phenyl)-N-[1-(4-methoxy-benzoyl)-2,7-dimethyl-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-chloro-phenyl)-N-[1-(4-methoxy-benzoyl)-2,7-dimethyl-1,2,3,4-tetrahydro-quinolin-4-yl]-acetamide (B-58 & B-57, respectively).

$^1$H-NMR (CDCl$_3$) δ: 1.13 (d, 3H), 1.26 (t, 1H), 2.03 (s, 3H), 2.05 (s, 3H), 2.27 (m, 1H), 3.76 (s, 3H), 4.75 (sextet, 1H), 5.59 (bs, 1H), 6.35 (s, 1H), 6.68 (d, 2H), 6.95 (d, 1H), 7.18 (m, 1H), 7.20 (d, 2H), 7.37 (d, 2H).

MS m/z: 463.5 (M+1)

(±)-Cis-N-(4-chloro-phenyl)-N-[1-(4-fluoro-benzoyl)-6-methoxy-2-methyl-1,2,3,4-tetrahydro-quinolin-4-yl]-propionamide (B-59)

(±)-Cis-N-(4-chloro-phenyl)-N-[1-(4-fluoro-benzoyl)-6-methoxy-2-methyl-1,2,3,4-tetrahydro-quinolin-4-yl]-propionamide was made following general procedure B, substituting 4-anisidine for aniline, 4-fluorobenzoyl chloride for 4-dimethylaminobenzoyl chloride and propionyl chloride for acetyl chloride.

$^1$H-NMR (300 MHz, CDCl$_3$) δ: 1.08-1.22 (m, 7H), 2.09-2.38 (m, 3H), 3.79 (s, 3H), 4.77 (ddd, 1H), 5.58 (br s, 1H), 6.41-6.50 (m, 2H), 6.82-6.94 (m, 3H), 7.16-7.32 (m, 4H), 7.35-7.44 (m, 2H).

MS m/z=481 (M+1).

(±)-Cis-N-(4-chloro-phenyl)-N-[1-(4-fluoro-benzoyl)-6-hydroxy-2-methyl-1,2,3,4-tetrahydro-quinolin-4-yl]-propionamide (B-60)

(±)-Cis-N-(4-chloro-phenyl)-N-[1-(4-fluoro-benzoyl)-6-hydroxy-2-methyl-1,2,3,4-tetrahydro-quinolin-4-yl]-propionamide was made from (±)-cis-N-(4-chloro-phenyl)-N-[1-(4-fluoro-benzoyl)-6-methoxy-2-methyl-1,2,3,4-tetrahydro-quinolin-4-yl]-propionamide using the procedure described previously for the preparation of (±)-cis-N-(4-chloro-phenyl)-N-[1-(4-hydroxy-benzoyl)-2-methyl-1,2,3,4-tetrahydro-quinolin-4-yl]-propionamide.

$^1$H-NMR (300 MHz, CDCl$_3$) δ: 1.04-1.18 (m, 7H), 2.07-2.41 (m, 5H), 4.76 (ddd, 1H), 5.50 (br s, 1H), 6.27 (d, 1H), 6.36 (d, 1H), 6.65 (s, 1H), 6.70-6.91 (m, 3H), 7.03-7.44 (m, 4H).

MS m/z: 467 (M+1).

(±)-Cis-N-(4-chloro-phenyl)-N-[1-(4-fluoro-benzoyl)-2,7-dimethyl-1,2,3,4-tetrahydro-quinolin-4-yl]-propionamide (B-61)

(±)-Cis-N-(4-chloro-phenyl)-N-[1-(4-fluoro-benzoyl)-2,7-dimethyl-1,2,3,4-tetrahydro-quinolin-4-yl]-propionamide was made following general procedure B, substituting 3-toluidine for aniline, 4-fluorobenzoyl chloride for 4-dimethylaminobenzoyl chloride, and propionyl chloride for acetyl chloride.

$^1$H-NMR (300 MHz, CDCl$_3$) δ: 1.10 (m, 7H), 2.04 (s, 3H), 2.14-2.32 (m, 3H), 4.74 (ddd, 1H), 5.57 (br s, 1H), 6.26 (s, 1H), 6.81-6.98 (m, 4H), 7.11-7.33 (m, 4H), 7.31-7.43 (m, 2H).

MS m/z: 465 (M+1).

(±)-Cis-[4-[(4-Chloro-phenyl)-propionyl-amino]-1-(4-fluoro-benzoyl)-2-methyl-1,2,3,4-tetrahydro-quinolin-6-yloxy]-acetic acid methyl ester (B-62)

(±)-Cis-[4-[(4-Chloro-phenyl)-propionyl-amino]-1-(4-fluoro-benzoyl)-2-methyl-1,2,3,4-tetrahydro-quinolin-6-yloxy]-acetic acid methyl ester was made from (±)-cis-N-(4-chloro-phenyl)-N-[1-(4-fluoro-benzoyl)-6-hydroxy-2-methyl-1,2,3,4-tetrahydro-quinolin-4-yl]-propionamide following the phenol alkylation procedure used to make (±)-cis-4-(4-{4-[(4-chloro-phenyl)-propionyl-amino]-2-methyl-3,4-dihydro-2H-quinoline-1-carbonyl}-phenoxy)-butyric acid ethyl ester. Methyl bromoacetate was substituted for ethyl-4-bromobutyrate.

$^1$H-NMR (300 MHz, CDCl$_3$) δ: 1.07-1.22 (m, 7H), 2.10-2.38 (m, 3H), 3.80 (s, 2H), 4.58 (s, 3H), 4.75 (m, 1H), 5.54 (br s, 1H), 6.39 (m, 2H), 6.81-6.94 (m, 3H), 7.18-7.35 (m, 5H, 7.36-7.44 (m, 2H).

MS m/z: 539 (M+1).

(±)-Cis-N-(4-Chloro-phenyl)-N-[6-(2-diethylamino-ethoxy)-1-(4-fluoro-benzoyl)-2-methyl-1,2,3,4-tetrahydro-quinolin-4-yl]-propionamide (B-63)

(±)-Cis-N-(4-Chloro-phenyl)-N-[6-(2-diethylamino-ethoxy)-1-(4-fluoro-benzoyl)-2-methyl-1,2,3,4-tetrahydro-quinolin-4-yl]-propionamide was made from (±)-cis-N-(4-chloro-phenyl)-N-[1-(4-fluoro-benzoyl)-6-hydroxy-2-methyl-1,2,3,4-tetrahydro-quinolin-4-yl]-propionamide following the phenol alkylation procedure used to make (±)-cis-4-(4-{4-[(4-chloro-phenyl)-propionyl-amino]-2-methyl-3,4-dihydro-2H-quinoline-1-carbonyl}-phenoxy)-butyric acid ethyl ester. (2-Bromo-ethyl)-diethyl-amine was substituted for ethyl-4-bromobutyrate.

$^1$H-NMR (300 MHz, CDCl$_3$) δ: 0.95-1.11 (m, 13H), 2.09-2.38 (m, 3H), 2.51-2.77 (m, 4H), 2.79 -2.92 (m, 2H), 3.86-4.08 (m, 2H), 4.76 (ddd, 1H), 5.58 (br s, 1H), 6.34-6.51 (m, 2H), 6.78-6.94 (m, 3H), 7.14-7.31 (m, 4H), 7.37-7.42 (m, 2H).

MS m/z: 566 (M+1).

(±)-Cis-2-[4-[(4-chloro-phenyl)-propionyl-amino]-1-(4-fluoro-benzoyl)-2-methyl-1,2,3,4-tetrahydro-quinolin-6-yloxy]-2-methyl-propionic acid ethyl ester (B-64)

(±)-Cis-2-[4-[(4-chloro-phenyl)-propionyl-amino]-1-(4-fluoro-benzoyl)-2-methyl-1,2,3,4-tetrahydro-quinolin-6-yloxy]-2-methyl-propionic acid ethyl ester was made from (±)-cis-N-(4-chloro-phenyl)-N-[1-(4-fluoro-benzoyl)-6-hydroxy-2-methyl-1,2,3,4-tetrahydro-quinolin-4-yl]-propionamide following the phenol alkylation procedure used to make (±)-cis-4-(4-{4-[(4-chloro-phenyl)-propionyl-amino]-2-methyl-3,4-dihydro-2H-quinoline-1-carbonyl}-phenoxy)-butyric acid ethyl ester. 2-Bromo-2-methyl-propionic acid ethyl ester was substituted for ethyl-4-bromobutyrate.

$^1$H-NMR (300 MHz, CDCl$_3$) δ: 1.13-1.28 (m, 10H), 1.56 (s, 3H), 1.58 (s, 3H), 2.16-2.29 (m, 3H), 4.73 (ddd, H), 5.56 (br s, 1H), 6.31-6.39 (m, 2H), 6.76-6.88 (m, 3H), 7.16-7.22 (m, 4H), 7.38 -7.41 (m, 2H).
MS m/z: 581 (M+1).

(±)-Cis-[4-[(4-chloro-phenyl)-propionyl-amino]-1-(4-fluoro-benzoyl)-2-methyl-1,2,3,4tetrahydro-quinolin-6-yloxy]-acetic acid (B-65)

(±)-Cis-[4-[(4-chloro-phenyl)-propionyl-amino]-1-(4-fluoro-benzoyl)-2-methyl-1,2,3,4-tetrahydro-quinolin-6-yloxy]-acetic acid was prepared from (±)-cis-[4-[(4-chloro-phenyl)-propionyl-amino]-1-(4-fluoro-benzoyl)-2-methyl-1,2,3,4-tetrahydro-quinolin-6-yloxy]-acetic acid methyl ester. To a solution of (±)-cis-[4-[(4-chloro-phenyl)-propionyl-amino]-1-(4-fluoro-benzoyl)-2-methyl-1,2,3,4-tetrahydro-quinolin-6-yloxy]-acetic acid methyl ester (83 mg, 0.155 mmol) in methanol (3 mL) was added sodium hydroxide (1 M in water, 310 uL, 0.310 mmol). The reaction was stirred at room temperature 3 h and concentrated under reduced pressure to remove methanol. The pH of the remaining aqueous solution was adjusted to 6 with 1 M hydrochloric acid. The suspension was extracted twice with ethyl acetate. The combined extracts were washed with brine, dried over sodium sulfate, filtered and concentrated to afford the carboxylic acid (76 mg, 94%).

$^1$H-NMR (300 MHz, CDCl$_3$) δ: 1.09-1.26 (m, 7H), 2.08-2.18 (m, 3H), 4.58 (AB q, 2H), 4.79 (ddd, 1H), 5.57 (br s, 1H), 6.40 (m, 2H), 6.86 (m, 3H), 7.09-7.30 (m, 4H), 7.35-7.46 (m, 2H), 8.18 (br s, 1H).
MS m/z: 523 (M−1).

(±)-Cis-2-[4-[(4-chloro-phenyl)-propionyl-amino]-1-(4-fluoro-benzoyl)-2-methyl-1,2,3,4-tetrahydro-quinolin-6-yloxy]-2-methyl-propionic acid (B-66)

(±)-Cis-2-[4-[(4-chloro-phenyl)-propionyl-amino]-1-(4-fluoro-benzoyl)-2-methyl-1,2,3,4-tetrahydro-quinolin-6-yloxy]-2-methyl-propionic acid was prepared from (±)-cis-2-[4-[(4-chloro-phenyl)-propionyl-amino]-1-(4-fluorobenzoyl)-2-methyl-1,2,3,4-tetrahydro-quinolin-6-yloxy]-2-methyl-propionic acid ethyl ester. The saponification conditions detailed in the procedure for the synthesis of (±)-cis-[4-[(4-chloro-phenyl)-propionyl-amino]-1-(4-fluoro-benzoyl)-2-methyl-1,2,3,4-tetrahydro-quinolin-6-yloxy]-acetic acid were used.

$^1$H-NMR (300 MHz, CDCl$_3$) δ: 1.04-1.21 (m, 7H), 1.54-1.66 (m, 6H), 2.12-2.37 (m, 3H), 4.77 (ddd, 1H), 5.53 (br s, 1H), 6.37 (d, 1H), 6.48 (d, 1H), 6.66-6.92 (m, 1H), 7.12-7.26 (m, 4H), 7.43 (m, 2H), 9.00 (br s, 1H).
MS m/z: 553 (M+1).

(±)-Cis-N-[6-carbamoylmethoxy-1-(4-fluoro-benzoyl)-2-methyl-1,2,3,4-tetrahydro-quinolin-4-yl]-N-(4-chloro-phenyl)-propionamide (B-67)

(±)-Cis-N-[6-carbamoylmethoxy-1-(4-fluoro-benzoyl)-2-methyl-1,2,3,4-tetrahydro-quinolin-4-yl]-N-(4-chloro-phenyl)-propionamide was prepared from (±)-cis-4-[(4-chloro-phenyl)-propionyl-amino]-1-(4-fluoro-benzoyl)-2-methyl-1,2,3,4-tetrahydro-quinolin-6-yloxy]-acetic acid ester. To solid (±)-cis-[4-[(4-chloro-phenyl)-propionyl-amino]-1-(4-fluoro-benzoyl)-2-methyl-1,2,3,4-tetrahydro-quinolin-6-yloxy]-acetic acid methyl ester (76 mg, 0.14 mmol) was added a solution of ammonia in methanol (2 M, 10 mL). The resulting solution was stirred over night at room temperature and concentrated. The resulting crude amide was purified by silica gel chromatography (100% hexanes-100% ethyl acetate gradient) to afford pure product (59 mg, 76%).

$^1$H-NMR (300 MHz, CDCl$_3$) δ: 1.10-1.23 (m, 7H), 2.16-2.39 (m, 3H), 4.44 (s, 2H), 4/77 (ddd, 1H), 5.56 (br s, 1H), 6.25 (br s, 1H), 6.40-6.62 (m, 3H), 7.16-7.26 (m, 4H), 7.35-7.48 (m, 2H).
MS m/z: 524 (M+1).

(±)-Cis-N-[6-Bromo-1-(4-fluoro-benzoyl)-2-methyl-1,2,3,4-tetrahydro-quinolin-4-yl]-N-(4-chloro-phenyl)-propionamide (B-69)

(±)-Cis-N-[6-bromo-1-(4-fluoro-benzoyl)-2-methyl-1,2,3,4-tetrahydro-quinolin-4-yl]-N-(4-chloro-phenyl)-propionamide was made following general procedure B, substituting 4-bromoaniline for aniline and 4-fluorobenzoyl chloride for 4-dimethylaminobenzoyl chloride and propionyl chloride for acetyl chloride.

$^1$H-NMR (CDCl$_3$) δ: 1.1-1.2 (7H, m), 2.1-2.3 (3H, m), 4.8 (1H, m), 5.6 (1H, m), 6.4 (1H, d), 6.9 (3H, t), 7.1 (H, m), 7.2 (4H, m), 7.4 (3H, m).
MS m/z: 531 (M+2).

(±)-Cis-N-(4-chloro-phenyl)-N-[1-(4-fluoro-benzoyl)-2-methyl-6-morpholin-4-yl-1,2,3,4-tetrahydro-quinolin-4-yl]-propionamide (B-70)

(±)-Cis-N-(4-chloro-phenyl)-N-[1-(4-fluoro-benzoyl)-2-methyl-6-morpholin-4-yl-1,2,3,4-tetrahydro-quinolin-4-yl]-propionamide was made from (±)-cis-N-[6-bromo-1-(4-fluoro-benzoyl)-2-methyl-1,2,3,4-tetrahydro-quinolin-4-yl]-N-(4-chloro-phenyl)-propionamide. (±)-Cis-N-[6-bromo-1-(4-fluoro-benzoyl)-2-methyl-1,2,3,4-tetrahydro-quinolin-4-yl]-N-(4-chloro-phenyl)-propionamide was dissolved in toluene, followed by Pd$_2$(dba)$_3$, BINAP, sodium tert-butoxide, and morpholine. The reaction mixture was heated to 90° C. for 24 hours. The reaction mixture was cooled to room temperature and filtered through Celite® and concentrated. Crude mixture was purified by flash chromatography on silica gel using a gradient elution of hexane-ethylacetate (10-50%).

$^1$H-NMR (CDCl$_3$) δ: 1.1-1.2 (7H, m), 2.1-2.3 (3H, m), 3.1 (4H, t), 3.8 (4H, t), 4.8 (1H, m), 5.6 (1H, m), 6.3 (1H, d), 6.4 (1H, m), 6.7 (1H, s), 6.9 (3H, m), 7.1-7.4 (5H, m).
MS m/z: 536 (M+1).

(±)-Cis-1-(4-chloro-phenyl)-N-[6-diethylamino-1-(4-fluoro-benzoyl)-2-methyl-1,2,3,4-tetrahydro-quinolin-4-yl]-propionamide (B-71)

(±)-Cis-N-(4-chloro-phenyl)-N-[6-diethylamino-1-(4-fluoro-benzoyl)-2-methyl-1,2,3,4-tetrahydro-quinolin-4-yl]-propionamide was made in the same way as (±)-cis-N-(4- chloro-phenyl)-N-[1-(4-fluoro-benzoyl)-2-methyl-6-morpholin-4-yl-1,2,3,4-tetrahydro-quinolin-4-yl]-propionamide except diethylamine was substituted for morpholine. The reaction was non-selective and yielded (±)-cis-N-[6-diethylamino-1-(4-fluoro-benzoyl)-2-methyl-1,2,3,4-tetrahydro-quinolin-4-yl]-N-(4-diethylamino-phenyl)-propionamide in addition to the titled compound.

¹H-NMR (CDCl₃) δ: 1.1-1.3 (13H, m), 1.6 (1H, m), 2.1-2.3 (3H, m), 3.3 (4H, m), 4.7 (1H, m), 5.6 (1H, m), 6.2 (1H, m), 6.3 (1H, m), 6.5 (1H, s), 6.9 (2H, m), 7.3 (4H, m), 7.4 (2H, m).

MS m/z: 523 (M+2).

(±)-Cis-N-[6-diethylamino-1-(4-fluoro-benzoyl)-2-methyl-1,2,3,4-tetrahydro-quinolin-4-yl]-N-(4-diethylamino-phenyl)-propionamide (B-72)

(±)-Cis-N-[6-diethylamino-1-(4-fluoro-benzoyl)-2-methyl-1,2,3,4-tetrahydro-quinolin-4-yl]-N(4-diethylamino-phenyl)-propionamide was made in the same way as (±)-cis-N-(4-chloro-phenyl)-N-[1 -(4-fluoro-benzoyl)-2-methyl-6-morpholin-4-yl-1,2,3,4-tetrahydro-quinolin-4-yl]-propionamide except diethylamine was substituted for morpholine. The reaction was non-selective and yielded (±)-cis-N-(4-chloro-phenyl)-N-[6-diethylamino-1-(4-fluoro-benzoyl)-2-methyl-1,2,3,4-tetrahydro-quinolin-4-yl]-propionamide in addition to the titled compound.

¹H-NMR (CDCl₃) δ: 1.1-1.3 (19H, m), 2.3 (3H, m), 3.3 (8H, m), 4.7 (1H, m), 5.6 (1H, m), 6.1 (1H, m), 6.2 (1H, m), 6.6 (3H, m), 6.9 (1H, m), 7.1 (3H, m), 7.3 (2H, m).

MS m/z: 560 (M+2).

(±)-Cis-3-[4-[(4-chloro-phenyl)-propionyl-amino]-1-(4-fluoro-benzoyl)-2-methyl-1,2,3,4-tetrahydro-quinolin-6-yl]-acrylic acid (B-73)

(±)-Cis-3-[4-[(4-chloro-phenyl)-propionyl-amino]-1-(4-fluoro-benzoyl)-2-methyl-1,2,3,4-tetrahydro-quinolin-6-yl]-acrylic acid was made from (±)-cis-N-[6-bromo-1-(4-fluoro-benzoyl)-2-methyl-1,2,3,4-tetrahydro-quinolin-4-yl]-N-(4-chloro-phenyl)-propionamide. To a solution of (±)-cis-N-[6-bromo-1-(4-fluoro-benzoyl)-2-methyl-1,2,3,4-tetrahydro-quinolin-4-yl]-N-(4-chloro-phenyl)-propionamide (250 mg, 0.47 mmol), TEA (0.2 ml, 1.4 mmol), palladium acetate (11 mg, 0.047 mmol), 1,3-Bis(diphenylphosphino)propane (39 mg, 0.094 mmol), in 10 ml DMF was added 0.13 ml methyl acrylate (1.41 mmol). The resulting reaction mixture was heated to 80° C. overnight. The mixture was filtered through celite and the filtrate was concentrated under vacuum. The residue was purified by silica gel chromatography, eluting with ethyl acetate-hexane (2:3) to give (±)-cis-3-[4-[(4-chloro-phenyl)-propionyl-amino]-1-(4-fluoro-benzoyl)-2-methyl-1,2,3,4-tetrahydro-quinolin-6-yl]-acrylic acid methyl ester (110 mg, 44%).

To a solution of (±)-cis-3-[4-[(4-chloro-phenyl)-propionyl-amino]-1-(4-fluoro-benzoyl)-2-methyl-1,2,3,4-tetrahydro-quinolin-6-yl]-acrylic acid methyl ester (110 mg, 0.21 mmol) in 4 ml methanol was added 50 mg K₂CO₃, (0.36 mmol, in 2 ml water). The resulting reaction mixture was stirred at room temperature overnight. The methanol was removed under vacuum. 1M HCl was added until the mixture was acidic. Dichloromethane (25 ml) was added. Organic layer was dried with magnesium sulfate. Dichloromethane was removed under vacuum. The residue was purified by HPLC to give 10 mg title compound.

¹H-NMR (CDCl₃) δ: 1.0-1.2 (7H, m), 2.4 (2H, m), 2.5 (1H, m), 3.3 (1H, br), 4.8 (1H, m), 5.6 (1H, m), 6.4 (1H, d), 6.6 (1H, d), 7.0 (2H, t), 7.2-7.6 (9H, m).

MS m/z: 522 (M+2).

(±)-Cis-N-(4-chloro-phenyl)-N-[1-(3-methoxy-benzoyl)-2,8-dimethyl-1,2,3,4-tetrahydro-quinolin-4-yl]-acetamide (B-74)

(±)-Cis-N-(4-chloro-phenyl)-N-[1-(3-methoxy-benzoyl)-2,8-dimethyl-1,2,3,4-tetrahydro-quinolin-4-yl]-acetamide was made following general procedure B, substituting 2-toluidine for aniline and 3-methoxybenzoyl chloride for 4-dimethylaminobenzoyl chloride.

¹H-NMR (CDCl₃) δ: 1.11 (3H, d; overlapping 1H, t), 1.76 (3H, s), 2.00 (3H, s), 2.35 (1H, m), 3.55 (3H, s), 5.00 (1H, m), 5.60 (1H, m), 6.65 (1H, s), 6.80 (1H, t), 6.85 (1H, t), 6.95 (1H, t), 7.15 (1H, t), 7.25 (1H, t), 7.25-7.55 (6H, m)

MS m/z: 429 (M+1).

(±)-Cis-N-(4-Chloro-phenyl)-N-[1-(3-methoxy-benzoyl)-2,6-dimethyl-1,2,3,4-tetrahydro-quinolin-4-yl]-acetamide (B-75)

(±)-Cis-N-(4-chloro-phenyl)-N-[1-(3-methoxy-benzoyl)-2,6-dimethyl-1,2,3,4-tetrahydro-quinolin-4-yl]-acetamide was made following general procedure B, substituting 4-toluidine for aniline and 3-methoxybenzoyl chloride for 4-dimethylaminobenzoyl chloride.

¹H-NMR (CDCl₃) δ: 1.12 (3H, d; overlapping 1H, t), 2.02 (3H, s), 2.33-2.35 (3H, s; overlapping 1H, m), 3.63 (3H, s), 4.80 (1H, m), 5.60 (1H, m), 6.44 (1H, d), 6.70-6.85 (3H, complex), 7.05 (1H, t), 7.15 (1H, s), 7.25-7.55 (6H, complex).

MS m/z: 429 (M+1).

(±)-Cis-N-(4-chloro-phenyl)-N-[1-(3-methoxy-benzoyl)-2-methyl-6-trifluoromethyl-1,2,3,4-tetrahydro-quinolin-4-yl]-acetamide (B-76)

(±)-Cis-N-(4-chloro-phenyl)-N-[1-(3-methoxy-benzoyl)-2-methyl-6-trifluoromethyl-1,2,3,4-tetrahydro-quinolin-4-yl]-acetamide was made following general procedure B, substituting 4-trifluoromethylaniline for aniline and 3-methoxybenzoyl chloride for 4-dimethylaminobenzoyl chloride.

¹H-NMR (CDCl₃) δ: 1.15 (3H, d; overlapping 1H, t), 2.03 (3H, s), 2.38 (1H, m), 3.63 (3H, s), 4.80 (1H, m), 5.60 (1H, m), 6.60 (1H, d), 6.70 (1H, d), 6.80 (1H, dd), 7.15 (1H, t), 7.25-7.40 (6H, m), 7.60 (1H, s).

MS m/z: 483 (M+1).

(±)-Cis-N-(4-chloro-phenyl)-N-[6-methoxy-1-(3-methoxy-benzoyl)-2-methyl-1,2,3,4-tetrahydro-quinolin-4-yl]-acetamide (B-77)

(±)-Cis-N-(4-chloro-phenyl)-N-[6-methoxy-1-(3-methoxy-benzoyl)-2-methyl-1,2,3,4-tetrahydro-quinolin-4-yl]-acetamide was made following general procedure B, substituting 4-methoxyaniline for aniline and 3-methoxybenzoyl chloride for 4-dimethylaminobenzoyl chloride.

¹H-NMR (CDCl₃) δ: 1.12 (3H, d; overlapping 1H, t), 2.02 (3H, s), 2.35 (1H, m), 3.63 (3H, s), 3.76 (3H, s), 4.80 (1H, m), 5.60 (1H, m), 6.44 (1H, s), 6.70-6.95 (4H, complex), 7.15 (1H, t), 7.25-7.55 (6H, m).

MS m/z: 445 (M+1).

(±)-Cis-N-(4-chloro-phenyl)-N-[2-methyl-1-(thiophene-2-carbonyl)-6-trifluoromethyl-1,2,3,4-tetrahydro-quinolin-4-yl]-acetamide (B-78)

(±)-Cis-N-(4-chloro-phenyl)-N-[2-methyl-1-(thiophene-2-carbonyl)-6-trifluoromethyl-1,2,3,4-tetrahydro-quinolin-4-yl]-acetamide was made following general procedure B, substituting 4-trifluoromethylaniline for aniline and 2-thiophene carbonyl chloride for 4-dimethylaminobenzoyl chloride.

$^1$H-NMR (CDCl$_3$) δ: 1.14 (3H, d; overlapping 1H, t), 2.02 (3H, s), 2.35 (1H, m), 4.80 (1H, m), 5.65 (1H, m), 6.65 (1H, d), 6.80 (1H, d), 7.00 (1H, d), 7.20 (overlapping 2×1H, d), 7.24-7.42 (3H, m), 7.60 (1H, s).
MS m/z: 539 (M+1).

(±)-Cis-N-(4-chloro-phenyl)-N-[2-methyl-1-(5-methyl-thiophene-2-carbonyl)-6-trifluoromethyl-1,2,3,4-tetrahydro-quinolin-4-yl]-acetamide (B-79)

(±)-Cis-N-(4-chloro-phenyl)-N-[2-methyl-1-(5-methyl-thiophene-2-carbonyl)-6-trifluoromethyl-1,2,3,4-tetrahydro-quinolin-4-yl]-acetamide was made following general procedure B, substituting 4-trifluoromethylaniline for aniline and 5-methyl-2-thiophene carbonyl chloride for 4-dimethylaminobenzoyl chloride.

$^1$H-NMR (CDCl$_3$) δ: 1.14 (3H, d; overlapping 1H, t), 2.02 (3H, s), 2.35 (1H, m), 2.40 (3H, s), 4.80 (1H, m), 5.65 (1H, m), 6.45 (1H, d), 6.55 (1H, d), 7.00 (1H, d), 7.20 (overlapping 2×1H, d), 7.24-7.42 (3H, m), 7.55 (1H, s).
MS m/z: 554 (M+1).

(±)-Cis-N-(4-chloro-phenyl)-N-[1-(4-fluoro-benzoyl)-2-methyl-7-trifluoromethyl-1,2,3,4-tetrahydro-quinolin-4-yl]-propionamide (B-80)

(±)-Cis-N-(4-chloro-phenyl)-N-[1-(4-fluoro-benzoyl)-2-methyl-7-trifluoromethyl-1,2,3,4-tetrahydro-quinolin-4-yl]-propionamide was made following general procedure B, substituting 3-trifluoromethylaniline for aniline, 4-fluorobenzoyl chloride for 4-dimethylaminobenzoyl chloride and propionyl chloride for acetyl chloride. A mixture of the 5 and 7 position isomer was obtained.

$^1$H-NMR (CDCl$_3$) δ: 1.15 (3H, d; overlapping 1H, t), 2.20-2.40 (2H, q; 1H, m), 4.80 (1H,'m),'5.65 (1H, m), 6.70 (1H, s), 6.95 (2×1H, t), 7.10-7.60 (8H, m)
MS m/z: 519 (M+1).

(±)-Cis-N-[7-bromo-1-(4-dimethylamino-benzoyl)-2-methyl-1,2,3,4-tetrahydro-quinolin-4-yl]-N-(4-chloro-phenyl)-acetamide (B-81)

(±)-Cis-N-[7-bromo-1-(4-dimethylamino-benzoyl)-2-methyl-1,2,3,4-tetrahydro-quinolin-4-yl]-N-(4-chloro-phenyl)-acetamide was made following general procedure B, substituting 3-bromoaniline for aniline. A mixture of the 5 and 7 position isomer was obtained.

(±)-Cis-N-(4-chloro-phenyl)-N-[1-(4-dimethylamino-benzoyl)-7-isopropyl-2-methyl-1,2,3,4-tetrahydro-quinolin-4-yl]-acetamide (B-82)

(±)-Cis-N-(4-chloro-phenyl)-N-[1-(4-dimethylamino-benzoyl)-7-isopropyl-2-methyl-1,2,3,4-tetrahydro-quinolin-4-yl]-acetamide was made following general procedure B, substituting 3-isopropylaniline for aniline. A mixture of the 5 and 7 position isomer was obtained.

$^1$H-NMR (CDCl3) δ: 0.89 (2×3H, t), 1.15 (3H, d; overlapping 1H, t), 2.01 (3H, s), 2.33 (1H, m), 2.60 (1H, m), 2.87 (2×3H, s), 4.80 (1H, m), 5.65 (1H, m), 6.40 (overlapping 1H, s, 2H, d), 6.90 (1H, d), 7.10 (1H, d), 7.15-7.35 (5H, m) 7.40 (1H, d).
MS m/z: 505 (M+1).

(±)-Cis-N-(4-chloro-phenyl)-N-[1-(4-dimethylamino-benzoyl)-2-methyl-7-morpholin-4-yl-1,2,3,4-tetrahydro-quinolin-4-yl]-acetamide (B-83)

(±)-Cis-N-(4-chloro-phenyl)-N-[1-(4-dimethylamino-benzoyl)-2-methyl-7-morpholin-4-yl-1,2,3,4-tetrahydro-quinolin-4-yl]-acetamide was made from (±)-cis-N-[7-bromo-1-(4-dimethylamino-benzoyl)-2-methyl-1,2,3,4-tetrahydro-quinolin-4-yl]-N-(4-chloro-phenyl)-acetamide. (±)-Cis-N-[7-bromo-1-(4-dimethylamino-benzoyl)-2-methyl-1,2,3,4-tetrahydro-quinolin-4-yl]-N-(4-chloro-phenyl)-acetamide was dissolved in toluene, followed by Pd$_2$(dba)$_3$, BINAP, sodium tert-butoxide, and morpholine. The reaction mixture was heated to 90° C. for 24 hours. The reaction mixture was cooled to room temperature and filtered through Celite® and concentrated. Crude mixture was purified by flash chromatography on silica gel using gradient elution hexane-ethylacetate (10-50%).

$^1$H-NMR (CDCl3) δ: 1.11 (3H, d; overlapping 1H, t), 1.99 (3H, s), 2.33 (1H, m), 2.60-2.80 (2×2H, m), 2.89 (2×3H, s), 3.70 (2×2H, m), 4.70 (1H, m), 5.60 (1H, m), 6.10 (1H, s), 6.44 (2×1H, d), 7.00-7.40 (8H, m).
MS m/z: 548 (M+1).

(±)-Cis-N-[7-diethylamino-1-(4-dimethylamino-benzoyl)-2-methyl-1,2,3,4-tetrahydro-quinolin-4-yl]-N-(4-diethylamino-phenyl)-acetamide (B-84)

(±)-Cis-N-[7-diethylamino-1-(4-dimethylamino-benzoyl)-2-methyl-1,2,3,4-tetrahydro-quinolin-4-yl]-N-(4-diethylamino-phenyl)-acetamide was made in the same way as (±)-cis-N-(4-chloro-phenyl)-N-[1-(4-dimethylamino-benzoyl)-2-methyl-7-morpholin-4-yl-1,2,3,4-tetrahydro-quinolin-4-yl]-acetamide except diethylamine was substituted for morpholine. The reaction was non-selective and yielded (±)-cis-N-(4-chloro-phenyl)-N-[7-diethylamino-1-(4-dimethylamino-benzoyl)-2-methyl-1,2,3,4-tetrahydro-quinolin-4-yl]-acetamide in addition to the titled compound.

$^1$H-NMR (CDCl3) δ: 0.78 (2×3H, t), 1.15 (overlapping 3H, d; 1H, t), 1.98 (3H, s), 2.33 (1H, m), 2.87 (2×3H, s), 2.90-3.10 (2×2H, q), 4.70 (1H, m), 5.60 (1H, m), 5.90 (1H, s), 6.46 (3×1H, d), 7.00-7.40 (7H, m).
MS m/z: 557 (M+1).

(±)-Cis-N-(4-chloro-phenyl)-N-[7-diethylamino-1-(4-dimethylamino-benzoyl)-2-methyl-1,2,3,4-tetrahydro-quinolin-4-yl]-acetamide (B-85)

(±)-Cis-N-(4-chloro-phenyl)-N-[7-diethylamino-1-(4-dimethylamino-benzoyl)-2-methyl-1,2,3,4-tetrahydro-quinolin-4-yl]-acetamide was made in the same way as (±)-cis-N-(4-chloro-phenyl)-N-[1-(4-dimethylamino-benzoyl)-2-methyl-7-morpholin-4-yl-1,2,3,4-tetrahydro-quinolin-4-yl]-acetamide except diethylamine was substituted for morpholine. The reaction was non-selective and yielded (±)-cis-N-[7-diethylamino-1-(4-dimethylamino-benzoyl)-2-methyl-1,2,3,4-tetrahydro-quinolin-4-yl]-N-(4-diethylamino-phenyl)-acetamide in addition to the titled compound.

$^1$H-NMR (CDCl3) δ: 0.78 (2×3H, t), 1.15 (overlapping 2×3H, t; 3H, d; 1H, t), 2.00 (3H, s), 2.33 (1H, m), 2.76 (2×3H, s), 2.80-3.00 (2×2H, q), 3.24 (2×2H, q), 4.60 (1H, m), 5.60 (1H, m), 5.90 (1H, s), 6.46 (2×1H, d), 6.60 (1H, m), 6.90 (2×1H, d), 7.00-7.20 (6H, m).
MS m/z: 609 (M+1).

(±)-Cis-N-(4-chloro-phenyl)-N-[1-(4-fluoro-benzoyl)-5-methoxy-2-methyl-1,2,3,4-tetrahydro-quinolin-4-yl]-propionamide (B-86)

(±)-Cis-N-(4-chloro-phenyl)-N-[1-(4-fluoro-benzoyl)-5-methoxy-2-methyl-1,2,3,4-tetrahydro-quinolin-4-yl]-propionamide was prepared following general procedure B, substituting 3-anisidine for aniline, 4-fluorobenzoyl chloride for 4-dimethylaminobenzoyl chloride and propionyl chloride for acetyl chloride.
$^1$H-NMR (CDCl$_3$) δ: 1.09-1.14 (6H, m), 1.50-1.66 (1H, m), 1.97-2.34 (3H, m), 3.83 (3H, s), 4.65 (1H, q),-5.70-5.80 (1H, br), 6.08 (1H, d), 6.68 (1H, d). 6.81-6.89 (3H, m), 7.14-7.18 (4H, m), 7.33-7.36 (2H, m).
MS m/z: 481 (M+1).

(±)-Cis-2,2-dimethyl-propionic acid 4-[acetyl-(4-chloro-phenyl)-amino]-1-(4-dimethylamino-benzoyl)-2-methyl-1,2,3,4-tetrahydro-quinolin-7-yl ester (B-87)

(±)-Cis-2,2-dimethyl-propionic acid 4-[acetyl-(4-chloro-phenyl)-amino]-1-(4-dimethylamino-benzoyl)-2-methyl-1,2,3,4-tetrahydro-quinolin-7-yl ester was prepared following general procedure B, substituting 2,2-dimethyl-propionic acid 3-amino-phenyl ester for aniline.
$^1$H-NMR (CDCl$_3$) δ: 1.11-1.25 (13H, m), 2.02 (3H, s), 2.20-2.40 (1H, m), 2.92 (6H, s), 4.60-4.72 (1H, m), 5.45-5.55 (1H, br), 6.26 (1H, s), 6.46 (2H, d), 6.85 (1H, d), 7.09-7.39 (7H, m).
MS m/z: 562 (M+1).

(±)-Cis-N-(4-chloro-phenyl)-N-[1-(4-dimethylamino-benzoyl)-7-hydroxy-2-methyl-1,2,3,4-tetrahydro-quinolin-4-yl]-acetamide (B-88)

(±)-Cis-N-(4-chloro-phenyl)-N-[1-(4-dimethylamino-benzoyl)-7-hydroxy-2-methyl-1,2,3,4-tetrahydro-quinolin-4-yl]-acetamide was made from (±)-cis-2,2-dimethyl-propionic acid 4-[acetyl-(4-chloro-phenyl)-amino]-1-(4-dimethylamino-benzoyl)-2-methyl-1,2,3,4-tetrahydro-quinolin-7-yl ester. (±)-Cis-2,2-dimethyl-propionic acid 4-[acetyl-(4-chloro-phenyl)-amino]-1-(4-dimethylamino-benzoyl)-2-methyl-1,2,3,4-tetrahydro-quinolin-7-yl ester (100 mg, 0.178 mmol) was dissolved in tetrahydrofuran and sodium hydroxide (1 M, 356 uL, 0.356 mmol) was added. The mixture was stirred at room temperature 4 hours, then heated at reflux 2 h. The mixture was cooled to rt, acidified, concentrated and purified by silica gel chromatography (20 mg, 23%).
$^1$H-NMR (MeOD) δ: 1.06-1.08 (4H, m), 2.00 (3H, s), 2.35-2.45 (1H, m), 2.93 (6H, s), 4.65-4.68 (1H, m), 5.42-5.50 (1H, br), 6.07 (1H, s), 6.53 (2H, d), 6.63 (1H, d), 7.10-7.20 (3H, m), 7.35-7.48 (4H, m).
MS m/z: 478 (M+1).

(±)-Cis-[4-[acetyl-(4-chloro-phenyl)-amino]-1-(4-dimethylamino-benzoyl)-2-methyl-1,2,3,4-tetrahydro-quinolin-7-yloxy]-acetic acid ethyl ester (B-89)

(±)-Cis-[4-[acetyl-(4-chloro-phenyl)-amino]-1-(4-dimethylamino-benzoyl)-2-methyl-1,2,3,4-tetrahydro-quinolin-7-yloxy]-acetic acid ethyl ester was prepared from (±)-cis-N-(4-chloro-phenyl)-N-[1-(4-dimethylamino-benzoyl)-7-hydroxy-2-methyl-1,2,3,4-tetrahydro-quinolin-4-yl]-acetamide, following the alkylation conditions described for the synthesis of (±)-cis-4-(4-{4-[(4-chloro-phenyl)-propionyl-amino]-2-methyl-3,4-dihydro-2H-quinoline-1-carbonyl}-phenoxy)-butyric acid ethyl ester, substituting ethyl bromoacetate for ethyl 4-bromobutyrate.
$^1$H-NMR (MeOD) δ: 1.10-1.38 (7H, m), 2.00 (3H, s), 2.39-2.45 (1H, m), 2.94 (6H, s), 4.04-4.20 (2H, m), 4.29 (2H, s), 4.60-4.75 (1H, m), 5.40-5.50 (1H, br), 6.16 (1H, s), 6.54 (2H, d), 6.79 (1H, d), 7.08 (2H, d), 7.20-7.48 (5H, m).
MS m/z: 564 (M+1).

(±)-Cis-2-[4-[acetyl-(4-chloro-phenyl)-amino]-1-(4-dimethylamino-benzoyl)-2-methyl-1,2,3,4-tetrahydro-quinolin-7-yloxy]-acetamide (B-90)

(±)-Cis-2-[4-[acetyl-(4-chloro-phenyl)-amino]-1-(4-dimethylamino-benzoyl)-2-methyl-1,2,3,4-tetrahydro-quinolin-7-yloxy]-acetamide was prepared from (±)-cis-[4-[acetyl-(4-chloro-phenyl)-amino]-1-(4-dimethylamino-benzoyl)-2-methyl-1,2,3,4-tetrahydro-quinolin-7-yloxy]-acetic acid ethyl ester, via the same amidation procedure used in the synthesis of (±)-cis-N-[6-carbamoylmethoxy-1-(4-fluoro-benzoyl)-2-methyl-1,2,3,4-tetrahydro-quinolin-4-yl]-N-(4-chloro-phenyl)-propionamide.
$^1$H-NMR (MeOD) δ: 1.09-1.15 (4H, m), 2.00 (3H, s), 2.39-2.45 (1H, m), 2.94 (6H, s), 4.04-4.20 (2H, m), 4.60-4.75 (1H, m), 5.40-5.50 (1H, br), 6.14 (1H, s), 6.53 (2H, d), 6.81 (1H, d), 7.09 (2H, d), 7.20-7.48 (5H, m).
MS m/z: 535 (M+1).

(±)-Cis-[4-[acetyl-(4-chloro-phenyl)-amino]-1-(4-dimethylamino-benzoyl)-2-methyl-1,2,3,4-tetrahydro-quinolin-7-yloxy]-acetic acid (B-91)

(±)-Cis-[4-[acetyl-(4-chloro-phenyl)-amino]-1-(4-dimethylamino-benzoyl)-2-methyl-1,2,3,4-tetrahydro-quinolin-7-yloxy]-acetic acid was prepared from (±)-cis-[4-[acetyl-(4-chloro-phenyl)-amino]-1-(4-dimethylamino-benzoyl)-2-methyl-1,2,3,4-tetrahydro-quinolin-7-yloxy]-acetic acid ethyl ester following the saponification procedure described above for the synthesis of (±)-cis-[4-[(4-chloro-phenyl)-propionyl-amino]-1-(4-fluoro-benzoyl)-2-methyl-1,2,3,4-tetrahydro-quinolin-6-yloxy]-acetic acid.
$^1$H-NMR (MeOD) δ: 1.08-1.10 (4H, m), 1.98 (3H, s), 2.39-2.45 (1H, m), 2.93 (6H, s), 4.20 (2H, s), 4.61-4.70 (1H, m), 5.40-5.50 (1H, br), 6.17 (1H, s), 6.53 (2H, d), 6.79 (1H, d), 7.08 (2H, d), 7.28-7.48 (5H, m).
MS m/z: 536 (M+1).

(±)-Cis-N-(4-chloro-phenyl)-N-[1-(4-dimethylamino-benzoyl)-7-(2-hydroxy-2-methyl-propoxy)-2-methyl-1,2,3,4-tetrahydro-quinolin-4-yl]-acetamide (B-92)

(±)-Cis-N-(4-chloro-phenyl)-N-[1-(4-dimethylamino-benzoyl)-7-(2-hydroxy-2-methyl-propoxy)-2-methyl-1,2,3,4-tetrahydro-quinolin-4-yl]-acetamide was prepared from (±)-cis-[4-[acetyl-(4-chloro-phenyl)-amino]-1-(4-dimethylamino-benzoyl)-2-methyl-1,2,3,4-tetrahydro-quinolin-7-yloxy]-acetic acid ethyl ester was using the same alkylation procedure described for the synthesis of (±)-cis-N-{1-[4-(2-hydroxy-2-methyl-propoxy)-benzoyl]-2-methyl-1,2,3,4-tetrahydro-quinolin-4-yl}-N-phenyl-propionamide.

¹H-NMR (CDCl₃) δ: 1.01-1.20 (4H, m), 1.30 (6H, s), 2.01 (3H, s), 2.20-2.40 (1H, m), 2.92 (6H, s), 3.70 (2H, s), 4.65-4.72 (1H, m), 5.45-5.55 (1H, br), 6.13 (1H, s), 6.45 (2H, d), 6.65 (1H, d), 7.12-7.46 (7H, m).

MS m/z: 551 (M+1).

(±)-Cis-N-(4-chloro-phenyl)-N-[1-(4-dimethylamino-benzoyl)-7-ethoxy-2-methyl-1,2,3,4-tetrahydro-quinolin-4-yl]-acetamide (B-93)

(±)-Cis-N-(4-chloro-phenyl)-N-[1-(4-dimethylamino-benzoyl)-7-ethoxy-2-methyl-1,2,3,4-tetrahydro-quinolin-4-yl]-acetamide was made from (±)-cis-N-(4-chloro-phenyl)-N-[1-(4-dimethylamino-benzoyl)-7-hydroxy-2-methyl-1,2,3,4-tetrahydro-quinolin-4-yl]-acetamide using the same alkylation procedure described for the synthesis of (±)-cis-4-(4-{4-[(4-chloro-phenyl)-propionyl-amino]-2-methyl-3,4-dihydro-2H-quinoline-1-carbonyl}-phenoxy)-butyric acid ethyl ester, substituting ethyl iodide for ethyl-4-bromobutyrate.

¹H-NMR (CDCl₃) δ: 1.01-1.20 (7H, m), 2.01 (3H, s), 2.20-2.40 (1H, m), 2.92 (6H, s), 3.60 (2H, q), 4.65-4.72 (1H, m), 5.45-5.55 (1H, br), 6.15 (1H, s), 6.44 (2H, d), 6.69 (1H, d), 7.11-7.46 (7H, m).

MS m/z: 506 (M+1).

(±)-Cis-4-[4-[acetyl-(4-chloro-phenyl)-amino]-1-(4-dimethylamino-benzoyl)-2-methyl-1,2,3,4-tetrahydro-quinolin-7-yloxy]-butyric acid ethyl ester (B-94)

(±)-Cis-4-[4-[acetyl-(4-chloro-phenyl)-amino]-1-(4-dimethylamino-benzoyl)-2-methyl-1,2,3,4-tetrahydro-quinolin-7-yloxy]-butyric acid ethyl ester was made from (±)-cis-N-(4-chloro-phenyl)-N-[1-(4-dimethylamino-benzoyl)-7-hydroxy-2-methyl-1,2,3,4-tetrahydro-quinolin-4-yl]-acetamide using the same alkylation procedure described for the synthesis of (±)-cis-4-(4-{4-[(4-chloro-phenyl)-propionyl-amino]-2-methyl-3,4-dihydro-2H-quinoline-1-carbonyl}-phenoxy)-butyric acid ethyl ester.

¹H-NMR (CDCl₃) δ: 1.09-1.11 (4H, m), 1.23 (3H, t), 1.81-1.85 (2H, m), 2.01 (3H, s), 2.30-2.33 (3H, m), 2.92 (6H, s), 3.50-3.54 (1H, m), 3.72-3.76 (1H, m), 4.09 (2H, q), 4.66-4.73 (1H, m), 5.57-5.63 (1H, m), 6.14 (1H, s), 6.46 (2H, d), 6.68 (1H, d), 7.11-7.39 (7H, m).

MS m/z: 593 (M+1).

(±)-Cis-4-[4-[acetyl-(4-chloro-phenyl)-amino]-1-(4-dimethylamino-benzoyl)-2-methyl-1,2,3,4-tetrahydro-quinolin-7-yloxy]-butyric acid (B-95)

(±)-Cis-4-[4-[acetyl-(4-chloro-phenyl)-amino]-1-(4-dimethylamino-benzoyl)-2-methyl-1,2,3,4-tetrahydro-quinolin-7-yloxy]-butyric acid was made from (±)-cis-4-[4-[acetyl-(4-chloro-phenyl)-amino]-1-(4-dimethylamino-benzoyl)-2-methyl-1,2,3,4-tetrahydro-quinolin-7-yloxy]-butyric acid ethyl ester following the saponification conditions described for the synthesis of (±)-cis-[4-[(4-chloro-phenyl)-propionyl-amino]-1-(4-fluoro-benzoyl)-2-methyl-1,2,3,4-tetrahydro-quinolin-6-yloxy]-acetic acid.

¹H-NMR (CDCl₃) δ: 1.08-1.11 (4H, m), 1.80-1.86 (2H, m), 1.99 (3H, s), 2.28-2.35 (3H, m), 2.89 (6H, s) 3.37-3.46 (1H, m), 3.66-3.73 (1H, m), 4.64-4.72 (1H, m), 5.54-5.63 (1H, m), 6.07 (1H, s), 6.52 (2H, d), 6.67 (1H, d), 7.08-7.36 (7H, m).

MS m/z: 564 (M+1).

(±)-Cis-N-(4-chloro-phenyl)-N-[1-(4-dimethylamino-benzoyl)-2,7-dimethyl-1,2,3,4-tetrahydro-quinolin-4-yl]-acetamide (B-96)

(±)-Cis-N-(4-chloro-phenyl)-N-[1-(4-dimethylamino-benzoyl)-2,7-dimethyl-1,2,3,4-tetrahydro-quinolin-4-yl]-acetamide was made following general procedure B, substituting 3-toluidine for aniline. Both the 5 and 7-position isomers were obtained in this procedure.

¹H-NMR (CDCl₃) δ: 1.11 (3H, d), 1.45-1.59 (4H, m), 2.02-2.07 (3H, m), 2.24-2.28 (1H, m), 2.92 (6H, s) 4.67-4.74 (1H, m), 5.52-5.59 (1H, m), 6.43-6.45 (3H, m), 6.95 (1H, d), 7.13-7.22 (6H, m), 7.35-7.43 (1H, m).

MS m/z: 307 (M).

(±)-Cis-N-(4-chloro-phenyl)-N-[1-(4-fluoro-benzoyl)-2-phenethyl-1,2,3,4-tetrahydro-quinolin-4-yl]-propionamide (B-97)

(±)-Cis-N-(4-chloro-phenyl)-N-[1-(4-fluoro-benzoyl)-2-phenethyl-1,2,3,4-tetrahydro-quinolin-4-yl]-propionamide was made following general procedure B, substituting 4-fluorobenzoyl chloride for 4-dimethylaminobenzoyl chloride, 3-phenyl-propionaldehyde for acetaldehyde and propionyl chloride for acetyl chloride.

¹H-NMR (CDCl₃) δ: 1.16 (dt, 3H), 1.25 (m, 1H), 1.54 (m, 1H), 1.97 (m, 1H), 2.30 (m, 3H), 2.56 (t, 2H), 4.85 (sextet, 1H), 5.66 (bs, 1H), 6.44 (d, 1H), 6.86 (t, 2H), 6.93 (m, 2H), 7.03 (d, 2H), 7.12-7.29 (m, 8H), 7.37 (d, 2H).

MS m/z: 542 (M+1).

(±)-Cis-N-(4-chloro-phenyl)-N-[2-(2-cyano-ethyl)-1-(4-fluoro-benzoyl)-1,2,3,4-tetrahydro-quinolin-4-yl]-propionamide (B-98)

(±)-Cis-N-(4-chloro-phenyl)-N-[2-(2-cyano-ethyl)-1-(4-fluoro-benzoyl)-1,2,3,4-tetrahydro-quinolin-4-yl]-propionamide was made following general procedure B, substituting 4-fluorobenzoyl chloride for 4-dimethylaminobenzoyl chloride, 4-oxobutyrylnitrile for acetaldehyde and propionyl chloride for acetyl chloride.

¹H-NMR (300 MHz, CDCl₃) δ: 1.19-1.23 (m, 4H), 1.65-1.79 (m, 2H), 2.07-2.57 (m, 5H), 4.90 (ddd, 1H), 5.61 (br s, 1H), 6.61 (d, 1H), 6.86 (m, 2H), 6.95 (dd, 1H), 7.14-7.43 (m, 8H).

MS m/z=490 (M+1).

(±)-Cis-N-[2-ethyl-1-(3-methoxy-benzoyl)-1,2,3,4-tetrahydro-quinolin-4-yl]-N-phenyl-acetamide (B-99)

(±)-Cis-N-[2-ethyl-1-(3-methoxy-benzoyl)-1,2,3,4-tetrahydro-quinolin-4-yl]-N-phenyl-acetamide was made following general procedure B, substituting 3-methoxybenzoyl chloride for 4-dimethylaminobenzoyl chloride, propionyl aldehyde for acetaldehyde and phenylboronic acid for 4-chlorophenylboronic acid.

¹H-NMR (CDCl₃) δ: 0.8 (3H, t), 1.3 (2H, m), 1.6 (1H, m), 2.0 (3H, s), 2.3 (1H, m), 3.7 (3H, s), 4.7 (1H, m), 5.7 (1H, m), 6.5 (1H, d), 6.7 (1H, s), 6.8 (2H, m), 6.9-7.4 (9H, m)

MS m/z: 429 (M+1).

(±)-Cis-N-[1-(3-methoxy-benzoyl)-2-phenyl-1,2,3,4-tetrahydro-quinolin-4-yl]-N-phenyl-acetamide (B-100)

(±)-Cis-N-[1-(3-methoxy-benzoyl)-2-phenyl-1,2,3,4-tetrahydro-quinolin-4-yl]-N-phenyl-acetamide was made following general procedure B, substituting 3-methoxybenzoyl chloride for 4-dimethylaminobenzoyl chloride, benzaldehyde for acetaldehyde and phenylboronic acid for 4-chlorophenylboronic acid.

$^1$H-NMR (CDCl$_3$) δ: 1.5 (1H, m), 2.0 (3H, s), 2.5 (1H, m), 3.6 (3H, s), 5.7 (1H, t) 5.8 (1H, m), 6.6 (1H, d), 6.9 (2H, m), 6.9-7.4 (15H, m).

MS m/z: 494 (M−18).

(±)-Cis-4-(acetyl-phenyl-amino)-1-(4-fluoro-benzoyl)-1,2,3,4-tetrahydro-quinoline-2-carboxylic acid ethyl ester (B-101)

(±)-Cis-4-(acetyl-phenyl-amino)-1-(4-fluoro-benzoyl)-1,2,3,4-tetrahydro-quinoline-2-carboxylic acid ethyl ester was made following general procedure B, substituting 4-fluorobenzoyl chloride for 4-dimethylaminobenzoyl chloride, ethyl glyoxylate for acetaldehyde and phenylboronic acid for 4-chlorophenylboronic acid.

$^1$H-NMR (CDCl$_3$) δ: 1.2 (3H, t), 1.2 (1H, m), 2.0 (3H, s), 2.5 (1H, m), 4.1 (2H, q), 5.0 (1H, t), 5.7 (1H, m), 6.6 (1H, d), 6.8-7.0 (4H, d), 7.1-7.4 (8H, m).

MS m/z: 461 (M+1).

(±)-Cis-4-(acetyl-phenyl-amino)-1-(4-fluoro-benzoyl)-1,2,3,4-tetrahydro-quinoline-2-carboxylic acid (B-102)

(±)-Cis-4-(acetyl-phenyl-amino)-1-(4-fluoro-benzoyl)-1,2,3,4-tetrahydro-quinoline-2-carboxylic acid was made from (±)-cis-4-(acetyl-phenyl-amino)-1-(3-methoxy-benzoyl)-1,2,3,4-tetrahydro-quinoline-2-carboxylic acid ethyl ester by basic hydrolysis with 1N sodium hydroxide, ethanol and water.

$^1$H-NMR (CDCl$_3$) δ: 1.2 (1H, m), 2.0 (3H, s), 2.6 (1H, m), 5.0 (1H, t), 5.6 (1H, m), 6.6 (1H, d), 6.9-7.0 (3H, m), 7.2 (2H, m), 7.3-7.5 (7H, m).

MS m/z: 433 (M+1).

(±)-Cis-N-(4-chloro-phenyl)-N-[1-(4-fluoro-benzoyl)-2-propyl-1,2,3,4-tetrahydro-quinolin-4-yl]-propionamide (B-103)

(±)-Cis-N-(4-chloro-phenyl)-N-[1-(4-fluoro-benzoyl)-2-propyl-1,2,3,4-tetrahydro-quinolin-4-yl]-propionamide was made following general procedure B, substituting 4-fluorobenzoyl chloride for 4-dimethylaminobenzoyl chloride, butyryl aldehyde for acetaldehyde and propionyl chloride for acetyl chloride.

$^1$H-NMR (CDCl$_3$) δ: 0.8 (3H, t), 1.1-1.2 (7H, m), 1.4 (1H, m), 2.1-2.3 (3H, m), 4.8 (1H, m), 5.6 (1H, m), 6.7 (1H, d), 6.9-7.1 (4H, m), 7.2-7.5 (7H, m).

MS m/z: 479 (M+1).

(±)-Cis-propionic acid 4-[(4-chloro-phenyl)-propionyl-amino]-1-(4-fluoro-benzoyl)-1,2,3,4-tetrahydro-quinolin-2-ylmethyl ester (B-104)

(±)-Cis-propionic acid 4-[(4-chloro-phenyl)-propionyl-amino]-1-(4-fluoro-benzoyl)-1,2,3,4-tetrahydro-quinolin-2-ylmethyl ester was prepared following general procedure B, substituting propionic acid 2-oxo-ethyl ester for acetaldehyde, 4-fluorobenzoyl chloride for 4-dimethylaminobenzoyl chloride and propionyl chloride for acetyl chloride.

$^1$H-NMR (CDCl$_3$) δ: 0.8 (3H, t), 1.1 (3H, t), 1.1 (1H, m), 2.1 (2H, m), 2.2 (3H, s), 3.8 (1H, m), 4.2 (1H, m), 5.0 (1H, m), 5.4 (1H, m), 6.4 (1H, d), 6.8 (3H, m), 7.1-7.4 (8H, m).

MS m/z: 523 (M+1).

(±)-Cis-N-(4-chloro-phenyl)-N-[1-(4-fluoro-benzoyl)-2-hydroxymethyl-1,2,3,4-tetrahydro-quinolin-4-yl]-propionamide (B-105)

(±)-Cis-N-(4-chloro-phenyl)-N-[1-(4-fluoro-benzoyl)-2-hydroxymethyl-1,2,3,4-tetrahydro-quinolin-4-yl]-propionamide was prepared from (±)-cis-propionic acid 4-[(4-chloro-phenyl)-propionyl-amino]-1-(4-fluoro-benzoyl)-1,2,3,4-tetrahydro-quinolin-2-ylmethyl ester using the saponification conditions utilized in the synthesis of (±)-cis-[4-[(4-chloro-phenyl)-propionyl-amino]-1-(4-fluoro-benzoyl)-2-methyl-1,2,3,4-tetrahydro-quinolin-6-yloxy]-acetic acid.

$^1$H-NMR (CDCl$_3$) δ: 1.1 (3H, t), 1.3 (1H, m), 1.8 (1H, m), 2.1 (2H, m), 3.4 (1H, t), 3.6 (2H, m), 4.2 (1H, m), 6.2 (1H, m), 6.4 (1H, d), 6.7 (2H, t), 6.8-7.0 (5H, m), 7.1-7.3 (4H, m).

MS m/z: 367 (M−99).

(±)-Cis-N-(4-chloro-phenyl)-N-[2-diethylaminomethyl-1-(4-fluoro-benzoyl)-1,2,3,4-tetrahydro-quinolin-4-yl]-propionamide (B-106)

(±)-Cis-N-(4-chloro-phenyl)-N-[2-diethylaminomethyl-1-(4-fluoro-benzoyl)-1,2,3,4-tetrahydro-quinolin-4-yl]-propionamide was made following general procedure B, substituting diethylamino-acetaldehyde for acetaldehyde, 4-fluorobenzoyl chloride for 4-dimethylaminobenzoyl chloride, and propionyl chloride for acetyl chloride.

$^1$H-NMR (CDCl$_3$) δ: 0.8 (6H, m), 1.1 (3H, t), 1.1 (1H, m), 1.8 (2H, m), 2.2-2.5 (6H, m), 2.6 (1H, m), 4.8 (1H, m), 5.7 (1H, m), 6.4 (1H, d), 6.9 (3H, m), 7.1-7.4 (8H, m).

MS m/z: 523 (M+2).

(±)-Cis-N-(4-chloro-phenyl)-N-[1-(4-fluoro-benzoyl)-2-methoxymethyl-1,2,3,4-tetrahydro-quinolin-4-yl]-propionamide (B-107)

(±)-Cis-N-(4-chloro-phenyl)-N-[1-(4-fluoro-benzoyl)-2-methoxymethyl-1,2,3,4-tetrahydro-quinolin-4-yl]-propionamide was prepared following general procedure B, substituting methoxyacetaldehyde for acetaldehyde, 4-fluorobenzoyl chloride for 4-dimethylamino-benzoyl chloride, and propionyl chloride for acetyl chloride.

$^1$H-NMR (CDCl$_3$) δ: 1.1 (3H, t), 1.3 (1H, m), 1.8 (1H, m), 2.1 (1H, m), 3.4 (4H, m), 3.6 (2H, m), 4.2 (1H, m), 6.3 (1H, m), 6.5 (1H, d), 6.7 (1H, m), 6.8-7.0 (4H, m), 7.1-7.4 (6H, m).

MS m/z: 381 (M−99).

(±)-Cis-N-(4-chloro-phenyl)-N-[1-(4-fluoro-benzoyl)-2-phenyl-1,2,3,4-tetrahydro-quinolin-4-yl]-propionamide (B-108)

(±)-Cis-N-(4-chloro-phenyl)-N-[1-(4-fluoro-benzoyl)-2-phenyl-1,2,3,4-tetrahydro-quinolin-4-yl]-propionamide was made following general procedure B, substituting benzaldehyde for acetaldehyde, 4-fluorobenzoyl chloride for 4-dimethylaminobenzoyl chloride, and propionyl chloride for acetyl chloride.

$^1$H-NMR (CDCl$_3$) δ: 1.1-1.2 (3H, m), 1.2-1.4 (1H, m), 2.2-2.4 (2H, m), 2.4-2.6 (1H, m), 5.6 (1H, t), 5.8 (1H, m), 6.6 (1H, d), 6.8 (2H, m), 7.0 (1H, m), 7.2-7.4 (13H, m).

MS m/z: 513 (M+1).

(±)-Cis-N-(4-chloro-phenyl)-N-[1-(4-fluoro-benzoyl)-6-methoxy-2-trifluoromethyl-1,2,3,4-tetrahydro-quinolin-4-yl]-propionamide (B-109)

(±)-Cis-N-(4-chloro-phenyl)-N-[1-(4-fluoro-benzoyl)-6-methoxy-2-trifluoromethyl-1,2,3,4-tetrahydro-quinolin-4-yl]-propionamide was prepared following general procedure B, substituting N-(4-chloro-phenyl)-N-vinyl-propionamide for N-vinyl carbamic acid benzyl ester and trifluoroacetaldehyde for acetaldehyde in the synthesis of 11 and 4-fluorobenzoyl chloride for 4-dimethylaminobenzoyl chloride and propionyl chloride for acetyl chloride.

$^1$H-NMR (CDCl$_3$) δ: 1.1-1.2 (3H, m), 1.6 (1H, br), 2.2-2.4 (3H, m), 3.8 (3H, s), 5.5 (1H, m), 5.6 (1H, m), 6.5 (1H, s), 6.8 (1H, s), 6.9 (2H, t), 7.1-7.3 (4H, m), 7.4 (2H, d).
MS m/z: 535 (M+1).

(±)-Cis-N-(4-chloro-phenyl)-N-[6-methoxy-1-(3-methoxy-benzoyl)-2-trifluoromethyl-1,2,3,4-tetrahydro-quinolin-4-yl]-propionamide (B-110)

(±)-Cis-N-(4-chloro-phenyl)-N-[6-methoxy-1-(3-methoxy-benzoyl)-2-trifluoromethyl-1,2,3,4-tetrahydro-quinolin-4-yl]-propionamide was made following the procedure for the synthesis of (±)-N-(4-chloro-phenyl)-N-[1-(4-fluoro-benzoyl)-6-methoxy-2-trifluoromethyl-1,2,3,4-tetrahydro-quinolin-4-yl]-propionamide, substituting 3-methoxybenzoyl chloride for 4-fluorobenzoyl chloride.

$^1$H-NMR (CDCl$_3$) δ: 1.1-1.2 (3H, m), 1.6 (1H, br), 2.2-2.4 (3H, m), 3.7 (3H, s), 3.8 (3H, s), 5.5 (1H, m), 5.6 (1H, m), 6.5 (2H, m), 6.6 (1H, m), 6.8 (3H, m), 7.1 (1H, t), 7.2 (2H, d), 7.4 (2H, d).
MS m/z: 547 (M+1).

(±)-Cis-N-(4-chloro-phenyl)-N-[1-(furan-2-carbonyl)-6-methoxy-2-trifluoromethyl-1,2,3,4-tetrahydro-quinolin-4-yl]-propionamide (B-111)

(±)-Cis-N-(4-chloro-phenyl)-N-[1-(furan-2-carbonyl)-6-methoxy-2-trifluoromethyl-1,2,3,4-tetrahydro-quinolin-4-yl]-propionamide propionamide was made following the procedure for the synthesis of (±)-cis-N-(4-chloro-phenyl)-N-[1-(4-fluoro-benzoyl)-6-methoxy-2-trifluoromethyl-1,2,3,4-tetrahydro-quinolin-4-yl]-propionamide, substituting 2-furoyl chloride chloride for 4-fluorobenzoyl chloride.

$^1$H-NMR (CDCl$_3$) δ: 1.1-1.2 (3H, m), 1.6 (1H, br), 2.2-2.4 (3H, m), 3.8 (3H, s), 5.4 (2H, m), 6.0 (1H, m), 6.3 (1H, m), 6.8 (1H, m), 6.9 (1H, s), 7.0 (1H, m), 7.2 (2H, m), 7.4 (3H, m).
MS m/z: 507 (M+1).

(±)-Cis-N-[2-benzyl-1-(4-fluoro-benzoyl)-1,2,3,4-tetrahydro-quinolin-4-yl]-N-(4-chloro-phenyl)-propionamide (B-112)

(±)-Cis-N-[2-benzyl-1-(4-fluoro-benzoyl)-1,2,3,4-tetrahydro-quinolin-4-yl]-N-(4-chloro-phenyl)-propionamide was made following general procedure B, substituting phenylacetaldehyde for acetaldehyde, 4-fluorobenzoyl chloride for 4-dimethylamionbenzoyl chloride, and propionyl chloride for acetyl chloride.

$^1$H-NMR (CDCl$_3$) δ: 1.14 (3H, t), 2.05-2.52 (5H, m), 3.18-3.24 (1H, m), 4.89-4.93 (1H, m) 5.45 -5.55 (1H, br), 6.46 (1H, d), 6.83-7.37 (16H, m).
MS m/z: 528 (M+1).

(±)-Cis-N-(4-chloro-phenyl)-N-[2-methyl-1-(3-methyl-isoxazole-5-carbonyl)-1,2,3,4-tetrahydro-quinolin-4-yl]-acetamide (B-113)

(±)-Cis-N-(4-chloro-phenyl)-N-[2-methyl-1-(3-methyl-isoxazole-5-carbonyl)-1,2,3,4-tetrahydro-quinolin-4-yl]-acetamide was made following general procedure B, substituting 3-methylisoxazole-5-carbonyl chloride for 4-dimethylamionbenzoyl chloride.

(±)-Cis-N-(4-chloro-phenyl)-N-[2-methyl-1-(3-methyl-isoxazole-5-carbonyl)-1,2,3,4-tetrahydro-quinolin-4-yl]-acetamide was separated by chiral HPLC using a chiral celOD column and eluting with 90% hexane/10% ethanol isocratic system to give (2R,4S)- and (2S,4R)-cis-N-(4-chloro-phenyl)-N-[2-methyl-1-(3-methyl-isoxazole-5-carbonyl)-1,2,3,4-tetrahydro-quinolin-4-yl]-acetamide (B-42 & B-36, respectively)

$^1$H-NMR (CDCl$_3$) δ: 1.1 (3H, d), 1.1 (1H, m), 2.0 (3H, s), 2.2 (3H, s), 2.3 (1H, m), 4.7 (1H, m), 5.4 (1H, m), 5.8 (1H, s), 6.8 (1H, d), 7.1-7.4 (7H, m).
MS m/z: 424 (M+1).

Compounds B-114-B-147 can be prepared by the schemes set forth in Scheme 13 and 14 and by the general procedures B and others described herein. Those skilled in the art will be able to recognize, or be able to ascertain, using no more than routine experimentation, many equivalents to the specific embodiments of the invention described herein.

TABLE 2

Compounds Derived from General Procedure B

| No. | Structure |
|---|---|
| B-1 | 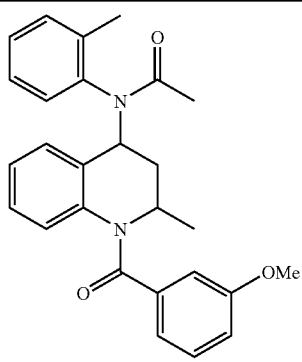 |

TABLE 2-continued

Compounds Derived from General Procedure B

| No. | Structure |
|---|---|
| B-2 | 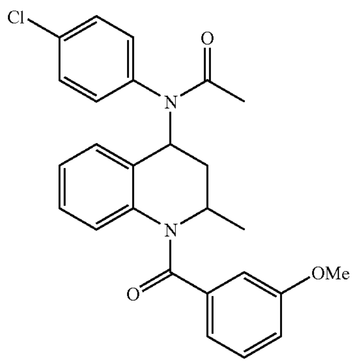 |
| B-3 | 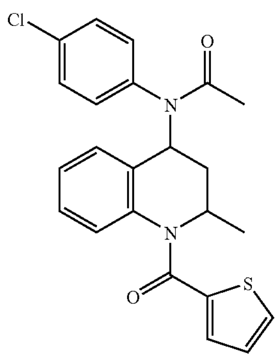 |
| B-4 | 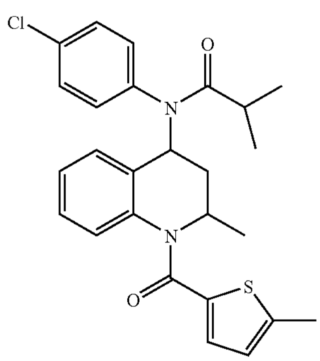 |
| B-5 | 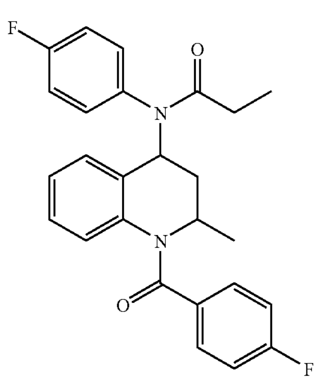 |

TABLE 2-continued

Compounds Derived from General Procedure B

| No. | Structure |
|---|---|
| B-6 | 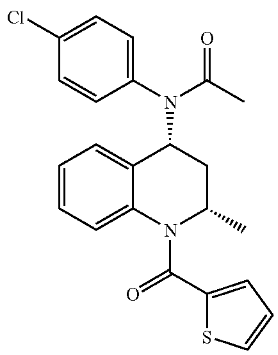 |
| B-7 | 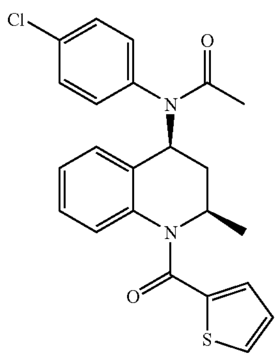 |
| B-8 | 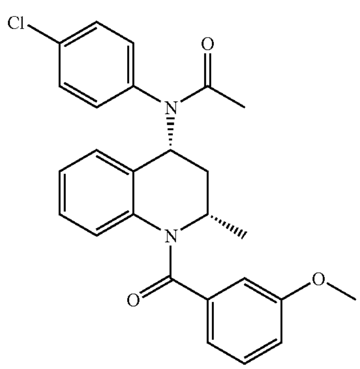 |
| B-9 | 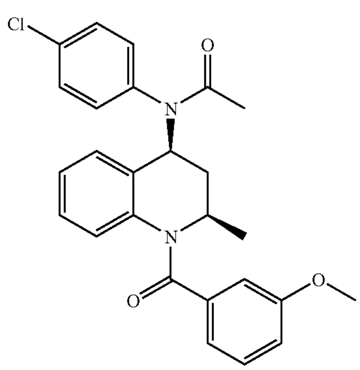 |

TABLE 2-continued
Compounds Derived from General Procedure B
| No. | Structure |
|---|---|
| B-10 | 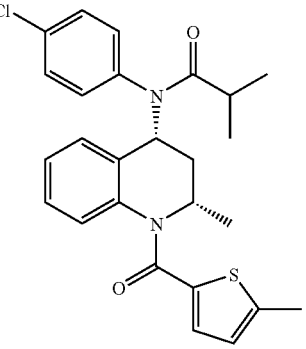 |
| B-11 | 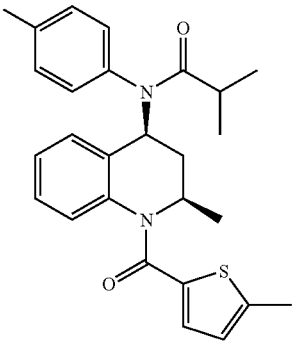 |
| B-12 | 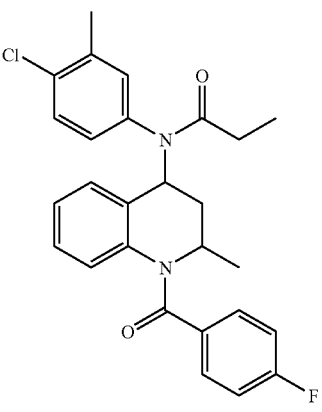 |
| B-13 | 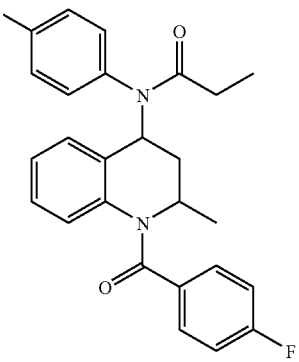 |

TABLE 2-continued
Compounds Derived from General Procedure B
| No. | Structure |
|---|---|
| B-14 | 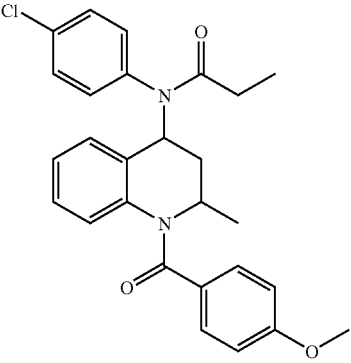 |
| B-15 | 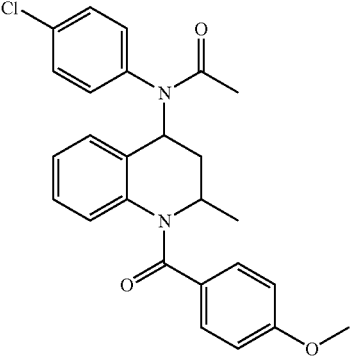 |
| B-16 | 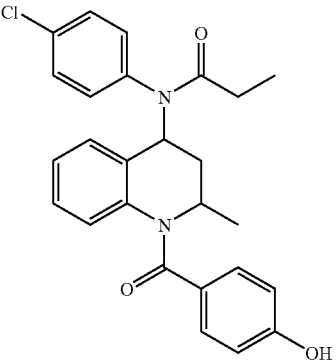 |
| B-17 | 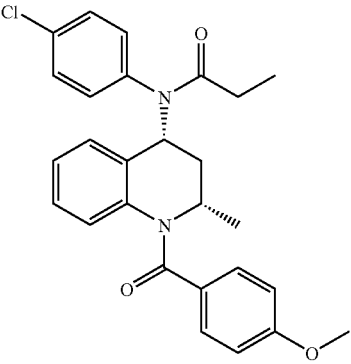 |

TABLE 2-continued
Compounds Derived from General Procedure B
| No. | Structure |
|---|---|
| B-18 | 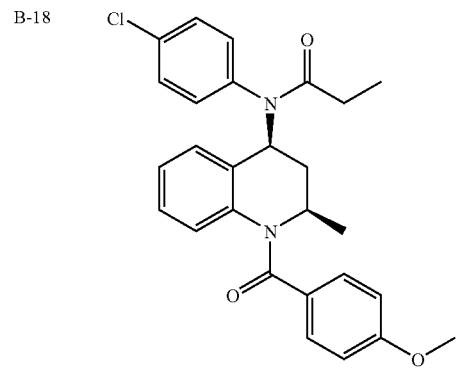 |
| B-19 | 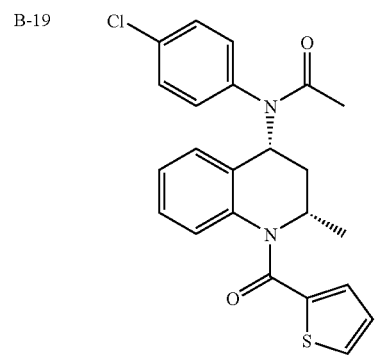 |
| B-20 | 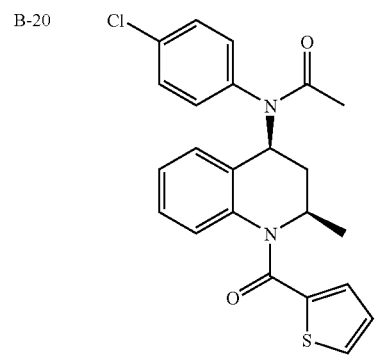 |
| B-21 | 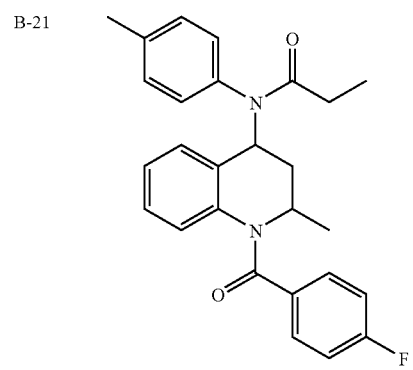 |

TABLE 2-continued

Compounds Derived from General Procedure B

| No. | Structure |
|---|---|
| B-22 | 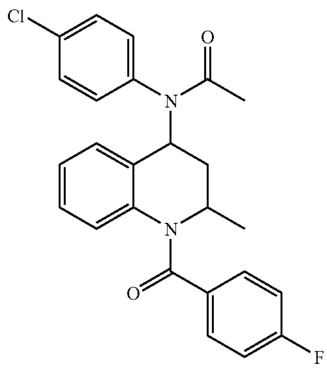 |
| B-23 | 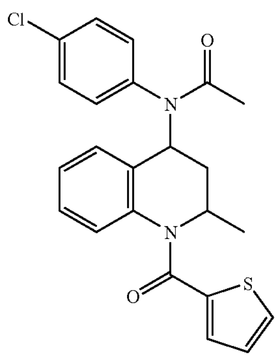 |
| B-24 | 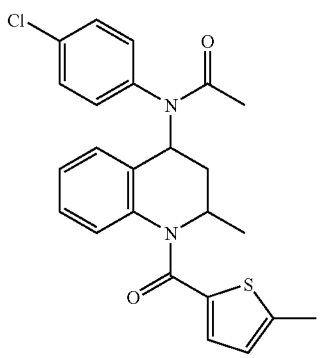 |
| B-25 | 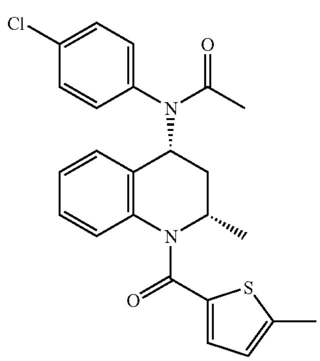 |

TABLE 2-continued

Compounds Derived from General Procedure B

| No. | Structure |
|---|---|
| B-26 | 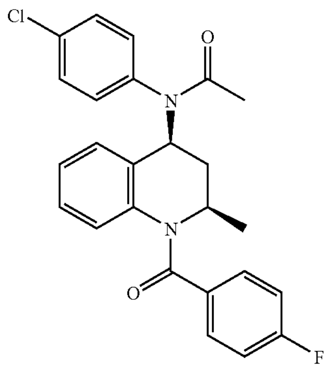 |
| B-27 | 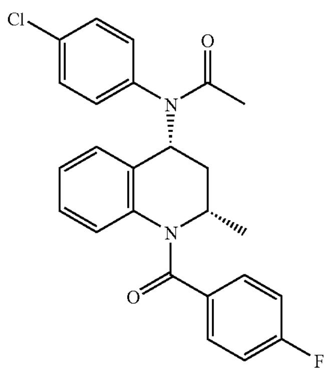 |
| B-28 | 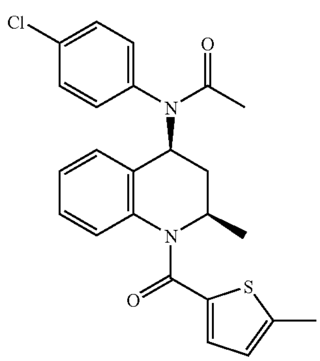 |
| B-29 | 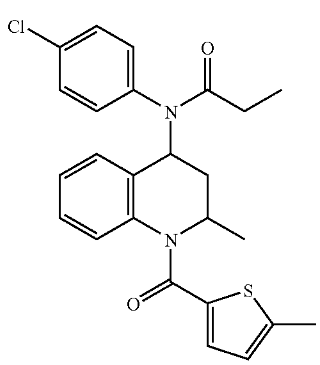 |

TABLE 2-continued

Compounds Derived from General Procedure B

| No. | Structure |
|---|---|
| B-30 | (4-chlorophenyl)-N-propionyl structure with 2-methyl-1,2,3,4-tetrahydroquinoline linked to 4-(3-ethoxycarbonylpropoxy)benzoyl group |
| B-31 | (4-chlorophenyl)-N-propionyl structure with 2-methyl-1,2,3,4-tetrahydroquinoline linked to 4-(3-carboxypropoxy)benzoyl group |
| B-32 | (4-chlorophenyl)-N-propionyl structure with 2-methyl-1,2,3,4-tetrahydroquinoline linked to 4-((1H-tetrazol-5-yl)methoxy)benzoyl group |

TABLE 2-continued
Compounds Derived from General Procedure B
| No. | Structure |
|---|---|
| B-33 | 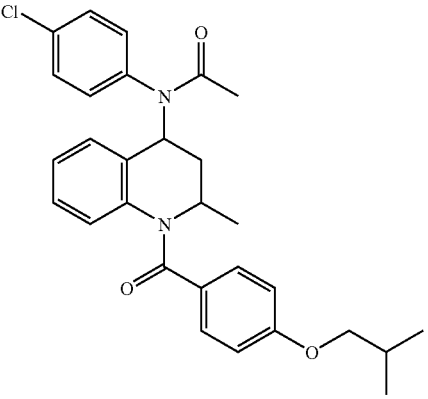 |
| B-34 | 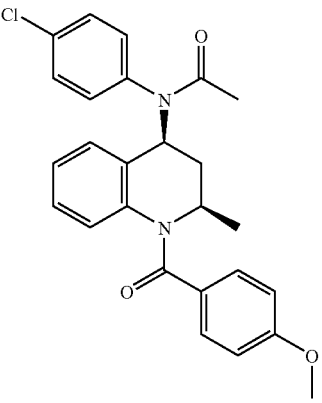 |
| B-35 | 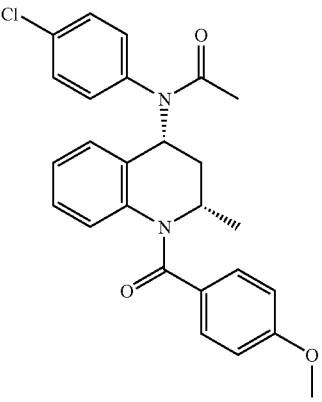 |

TABLE 2-continued
Compounds Derived from General Procedure B
| No. | Structure |
|---|---|
| B-36 | 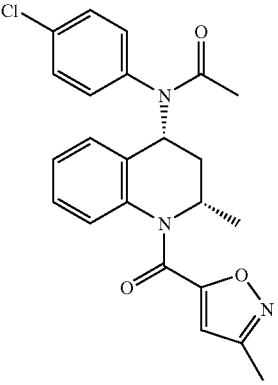 |
| B-37 | 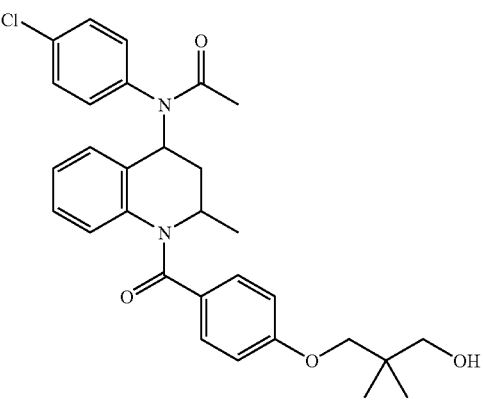 |
| B-38 | 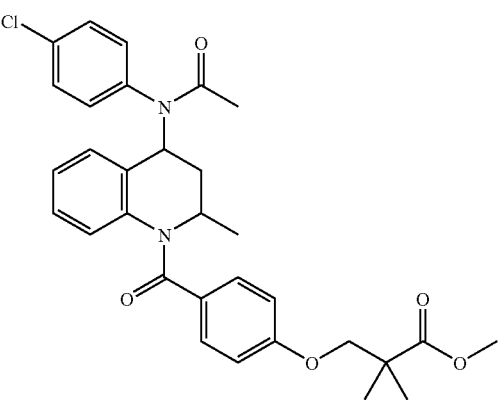 |

TABLE 2-continued
Compounds Derived from General Procedure B
| No. | Structure |
|---|---|
| B-39 | 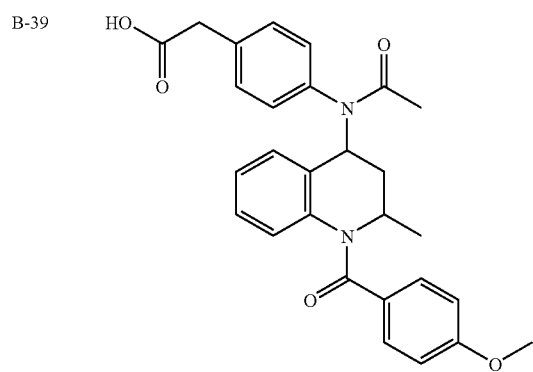 |
| B-40 | 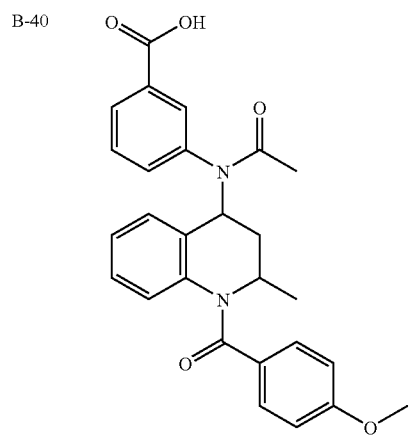 |
| B-41 | 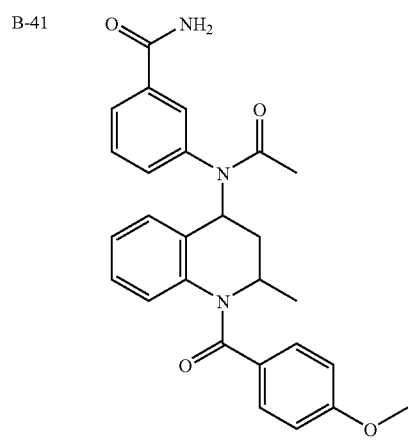 |

TABLE 2-continued

Compounds Derived from General Procedure B

| No. | Structure |
|---|---|
| B-42 | 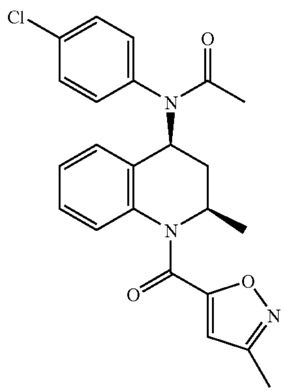 |
| B-43 | 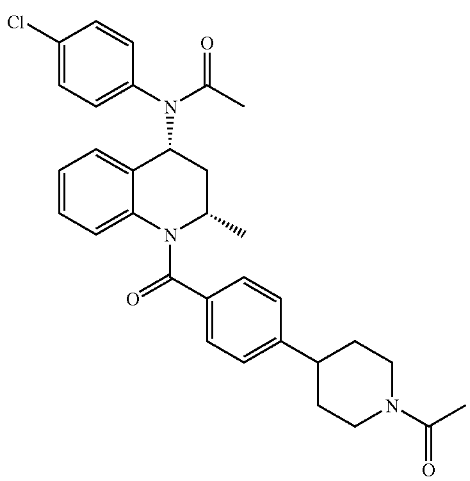 |
| B-44 | 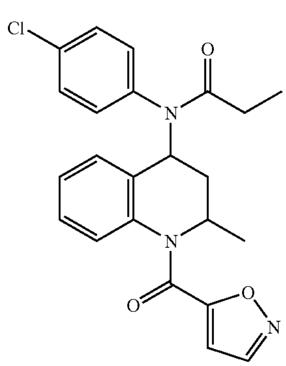 |

TABLE 2-continued
Compounds Derived from General Procedure B
| No. | Structure |
|---|---|
| B-45 | 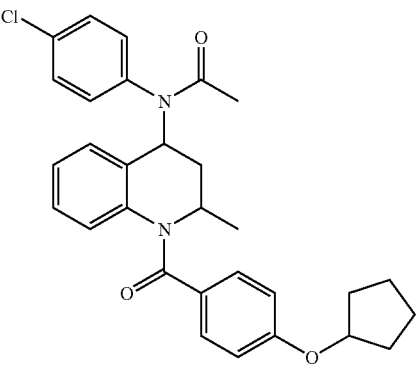 |
| B-46 | 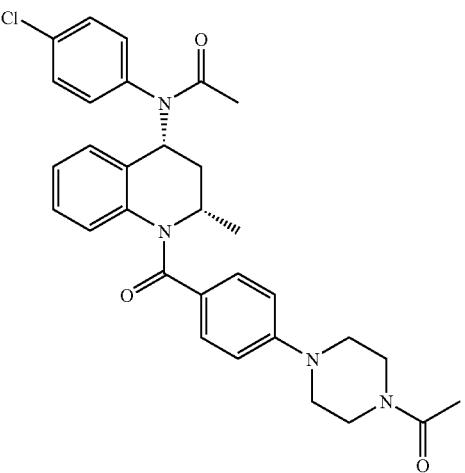 |
| B-47 | 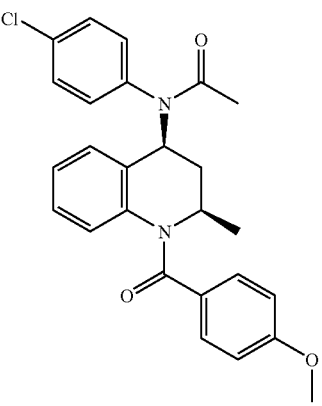 |

TABLE 2-continued
Compounds Derived from General Procedure B
| No. | Structure |
|---|---|
| B-48 | 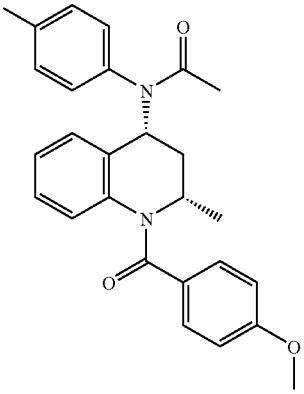 |
| B-49 | 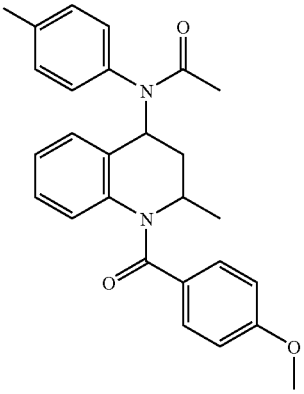 |
| B-50 | 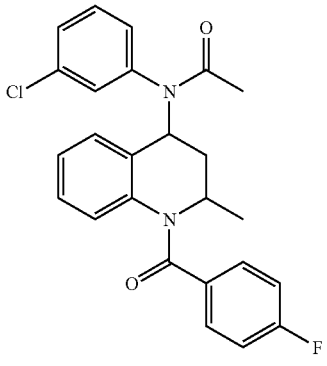 |
| B-51 | 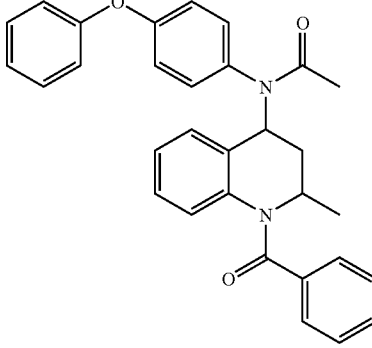 |

TABLE 2-continued
Compounds Derived from General Procedure B
| No. | Structure |
| --- | --- |
| B-52 | 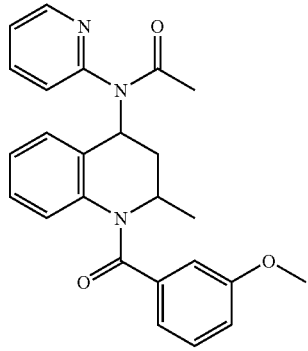 |
| B-53 | 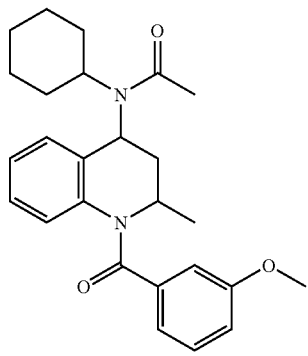 |
| B-54 | 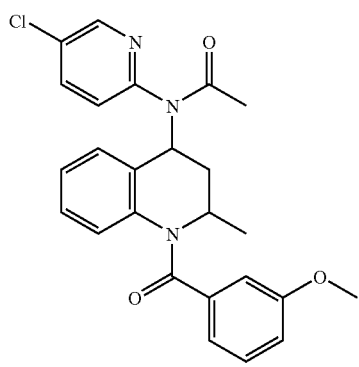 |
| B-55 | 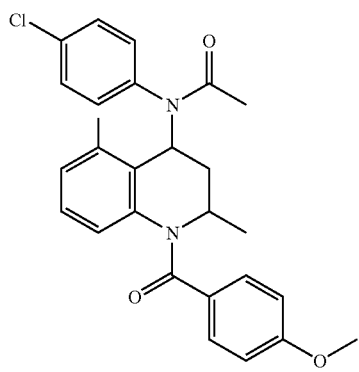 |

TABLE 2-continued
Compounds Derived from General Procedure B
| No. | Structure |
|---|---|
| B-56 | 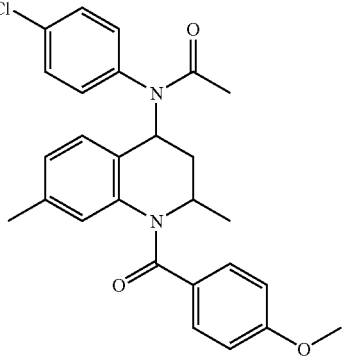 |
| B-57 | 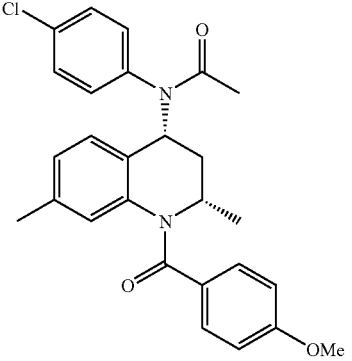 |
| B-58 | 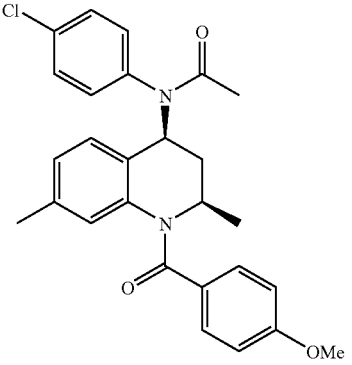 |
| B-59 | 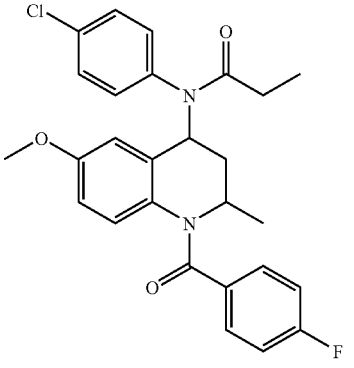 |

TABLE 2-continued
Compounds Derived from General Procedure B
| No. | Structure |
|---|---|
| B-60 | 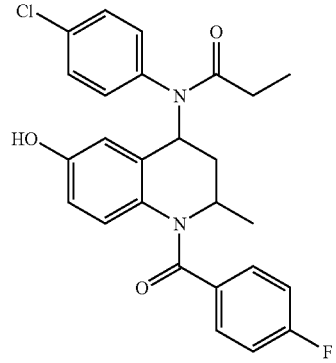 |
| B-61 | 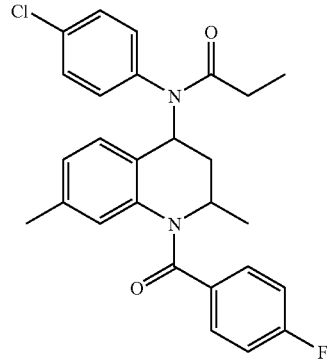 |
| B-62 | 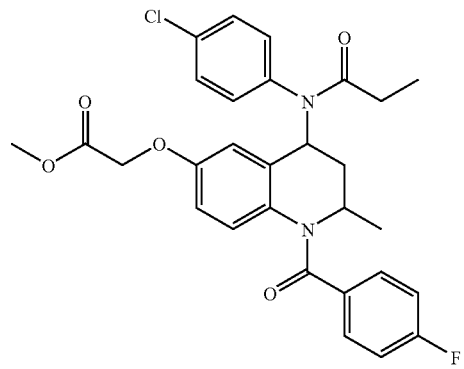 |
| B-63 | 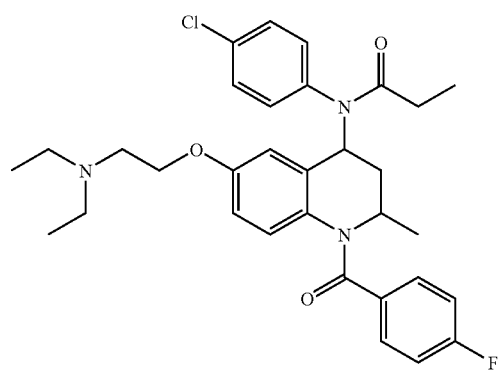 |

TABLE 2-continued
Compounds Derived from General Procedure B
| No. | Structure |
|---|---|
| B-64 | 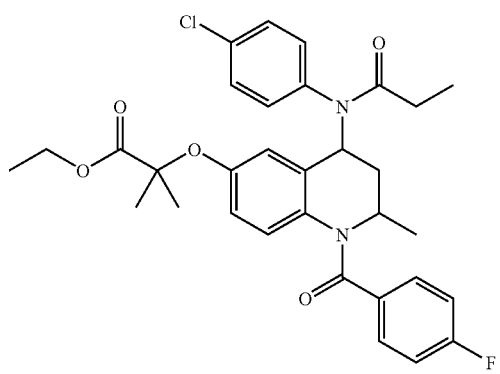 |
| B-65 | 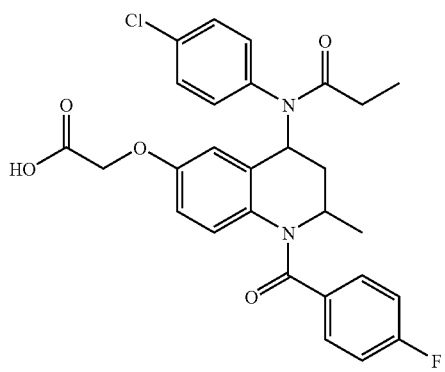 |
| B-66 | 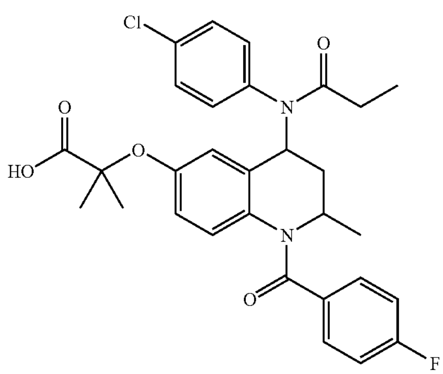 |
| B-67 | 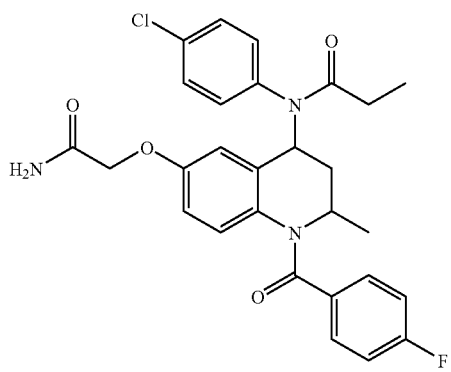 |

TABLE 2-continued

Compounds Derived from General Procedure B

| No. | Structure |
| --- | --- |
| B-68 | 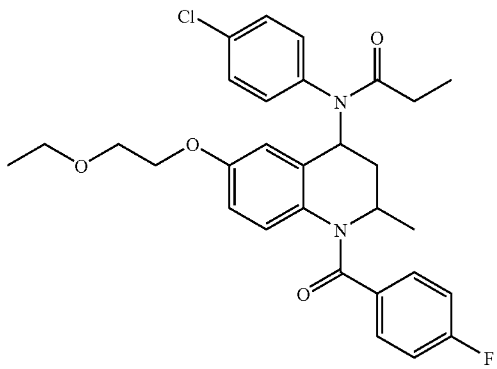 |
| B-69 | 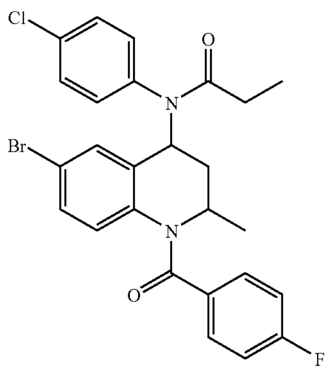 |
| B-70 | 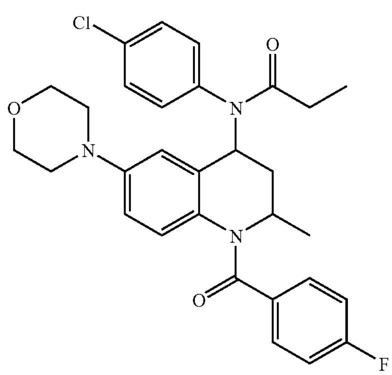 |
| B-71 | 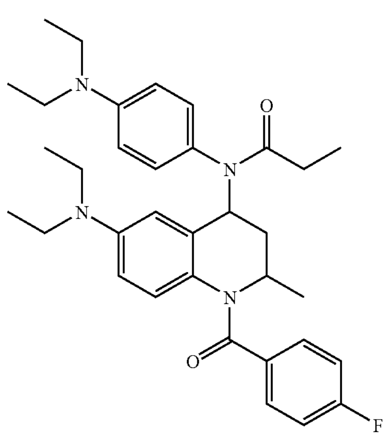 |

TABLE 2-continued
Compounds Derived from General Procedure B
| No. | Structure |
|---|---|
| B-72 | 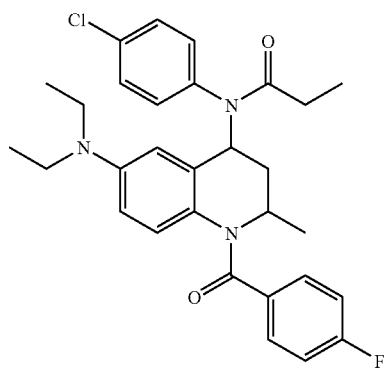 |
| B-73 | 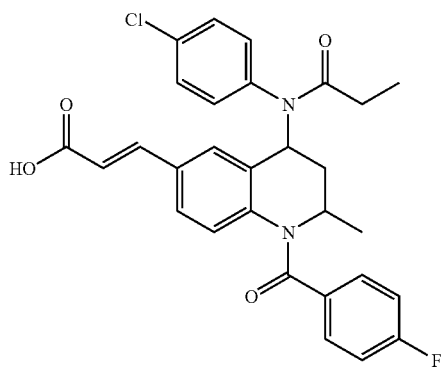 |
| B-74 | 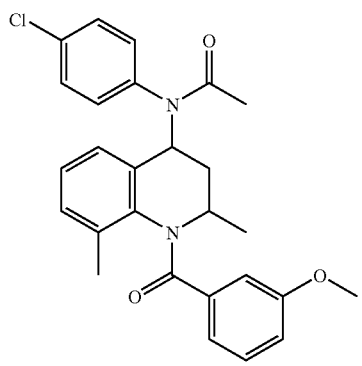 |
| B-75 | 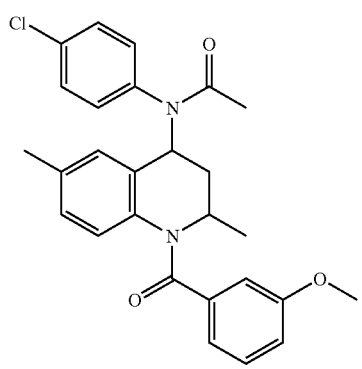 |

TABLE 2-continued
Compounds Derived from General Procedure B
| No. | Structure |
|---|---|
| B-76 | 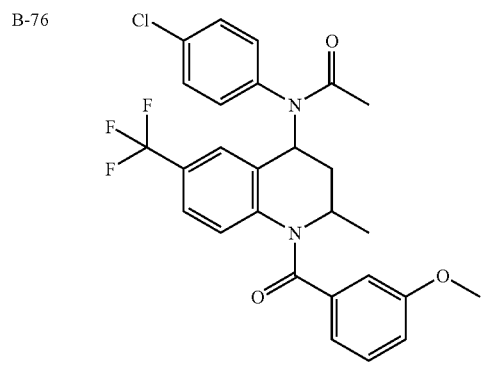 |
| B-77 | 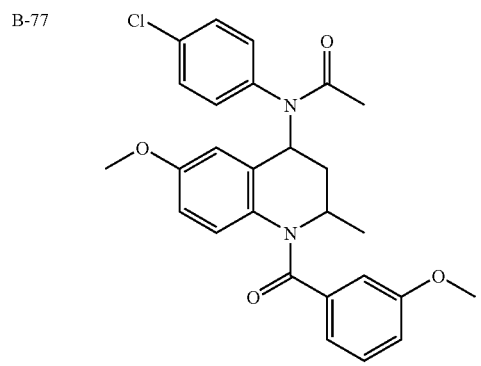 |
| B-78 | 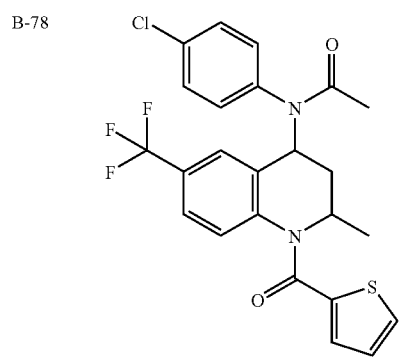 |
| B-79 | 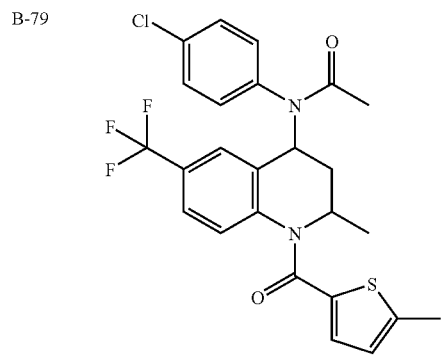 |

TABLE 2-continued
Compounds Derived from General Procedure B
| No. | Structure |
|---|---|
| B-80 | 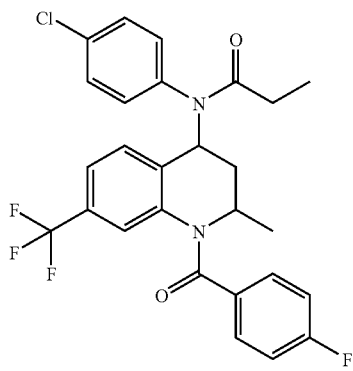 |
| B-81 | 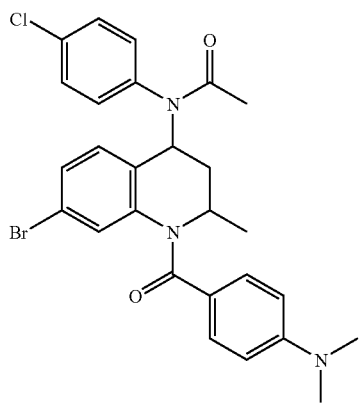 |
| B-82 | 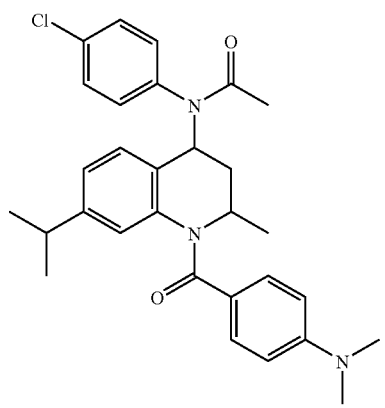 |

TABLE 2-continued
Compounds Derived from General Procedure B
| No. | Structure |
|---|---|
| B-83 | 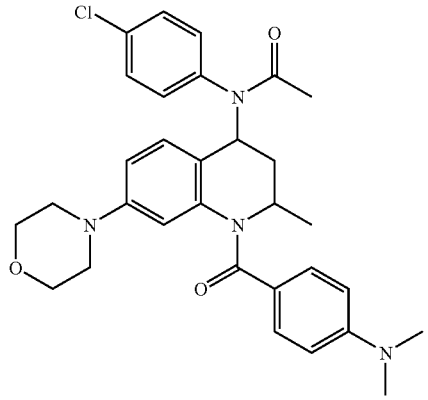 |
| B-84 | 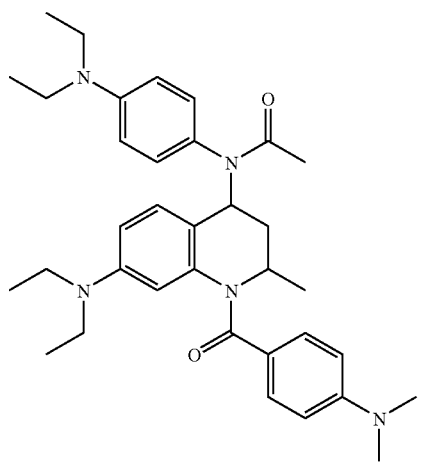 |
| B-85 | 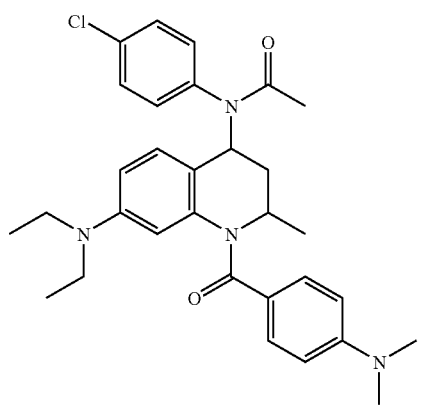 |

TABLE 2-continued
Compounds Derived from General Procedure B
| No. | Structure |
|---|---|
| B-86 | 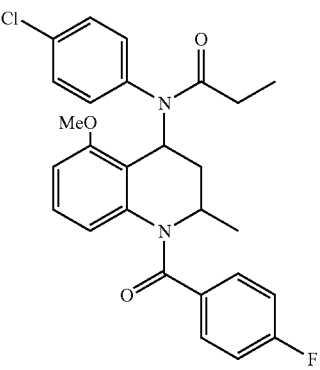 |
| B-87 | 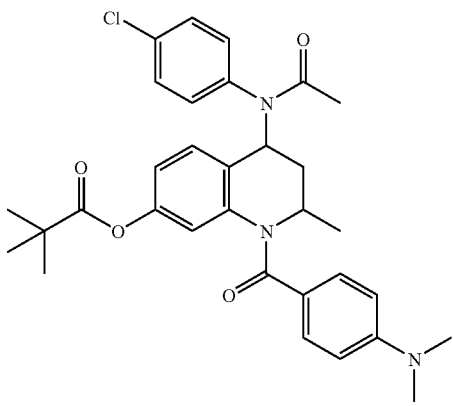 |
| B-88 | 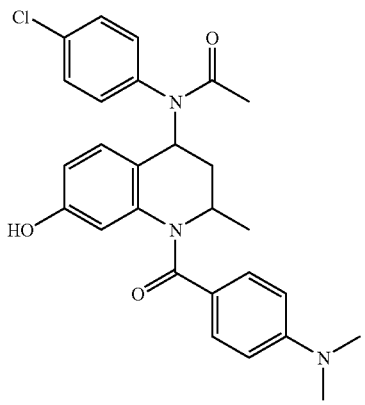 |

TABLE 2-continued
Compounds Derived from General Procedure B
| No. | Structure |
|---|---|
| B-89 | 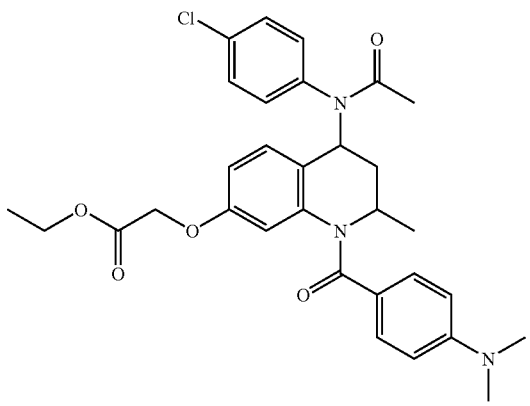 |
| B-90 | 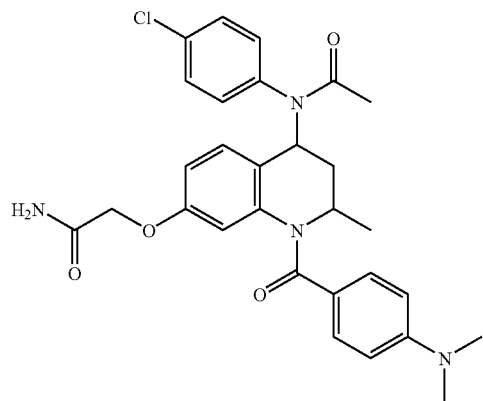 |
| B-91 | 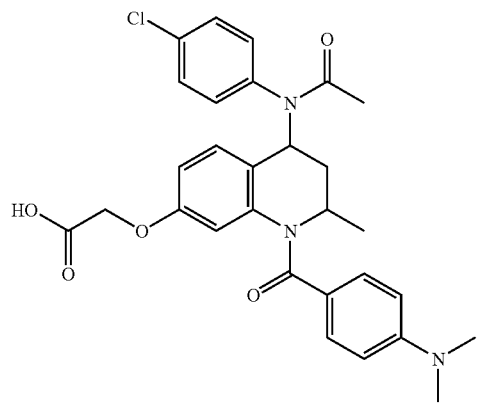 |

TABLE 2-continued
Compounds Derived from General Procedure B
| No. | Structure |
|---|---|
| B-92 | 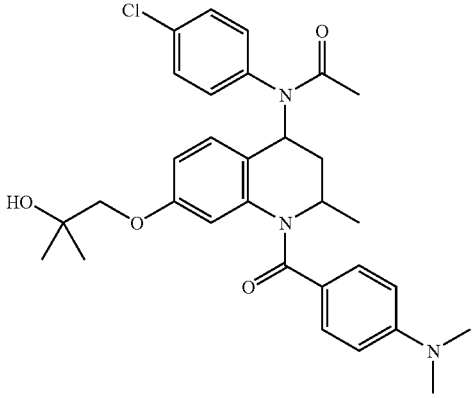 |
| B-93 | 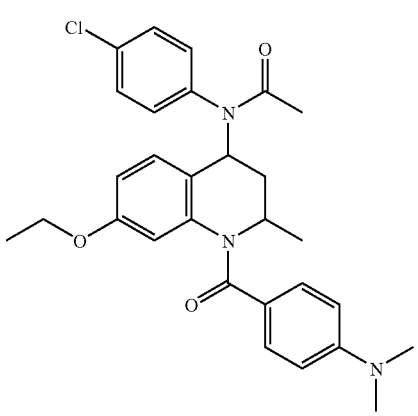 |
| B-94 | 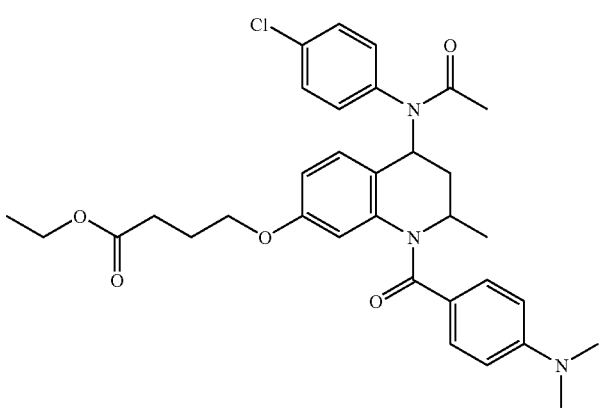 |

TABLE 2-continued

Compounds Derived from General Procedure B

| No. | Structure |
| --- | --- |
| B-95 | 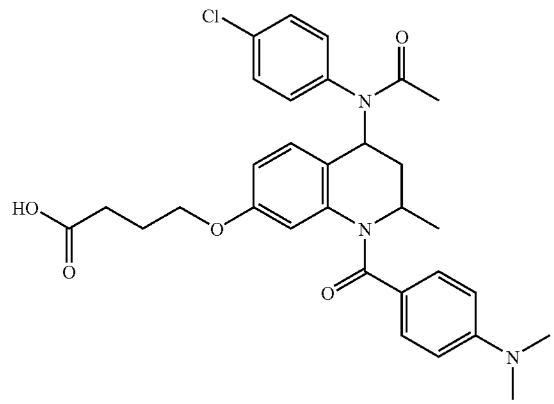 |
| B-96 | 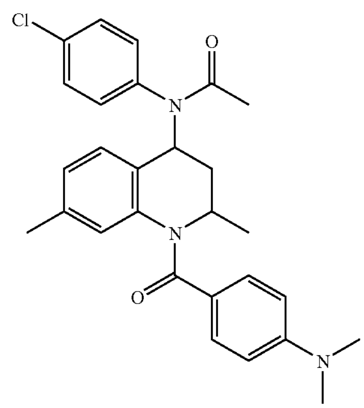 |
| B-97 | 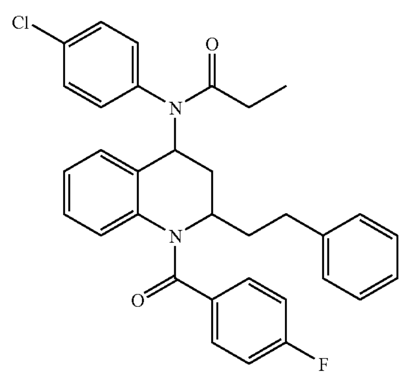 |
| B-98 | 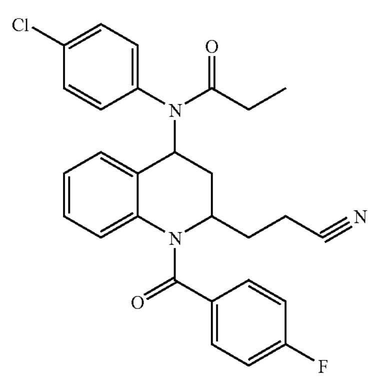 |

TABLE 2-continued
Compounds Derived from General Procedure B
| No. | Structure |
|---|---|
| B-99 | 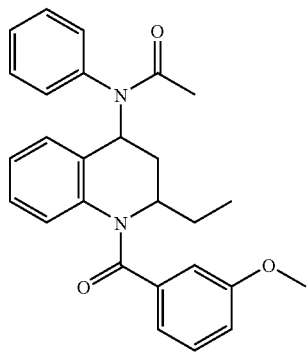 |
| B-100 | 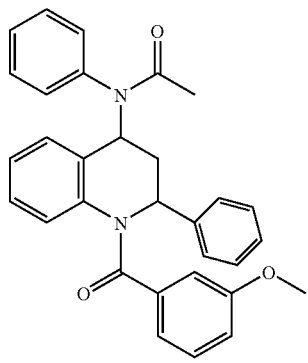 |
| B-101 | 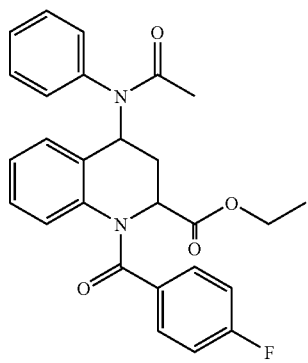 |
| B-102 | 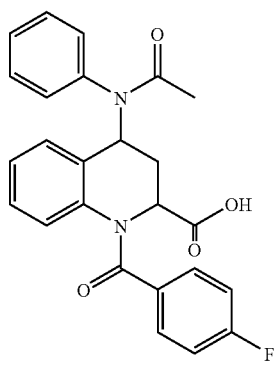 |

TABLE 2-continued
Compounds Derived from General Procedure B
| No. | Structure |
|---|---|
| B-103 | 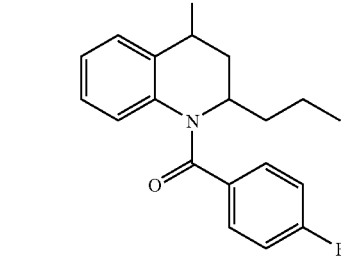 |
| B-104 | 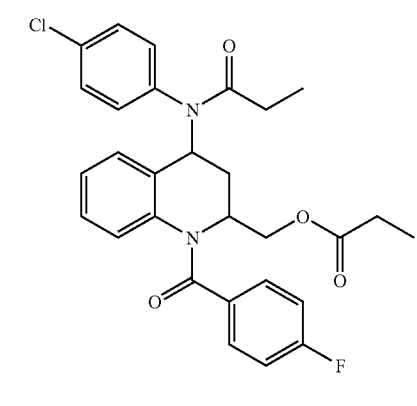 |
| B-105 | 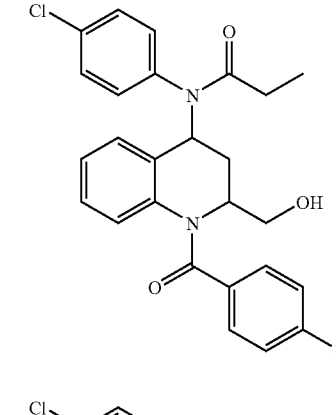 |
| B-106 | 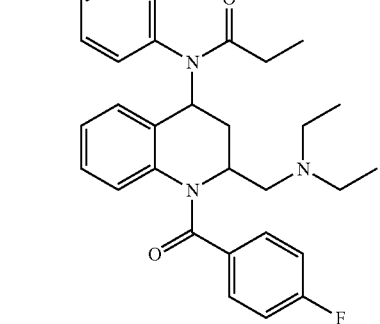 |

TABLE 2-continued
Compounds Derived from General Procedure B
| No. | Structure |
|---|---|
| B-107 | 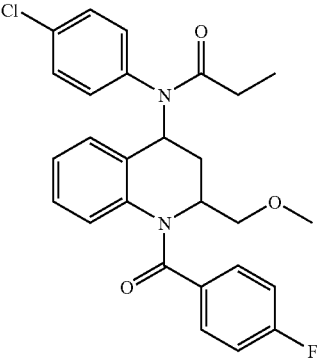 |
| B-108 | 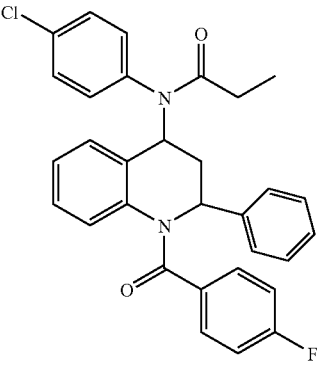 |
| B-109 | 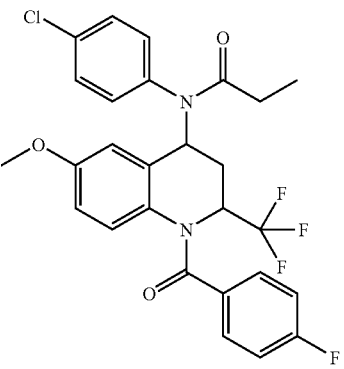 |
| B-110 | 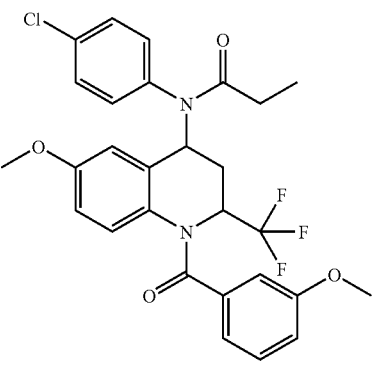 |

TABLE 2-continued
Compounds Derived from General Procedure B
No. Structure
B-111 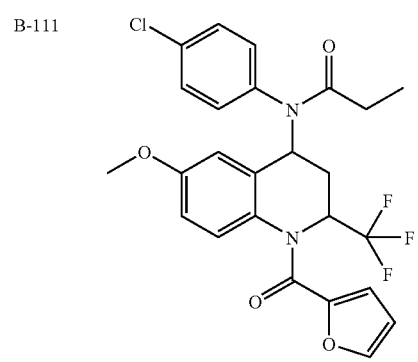
B-112 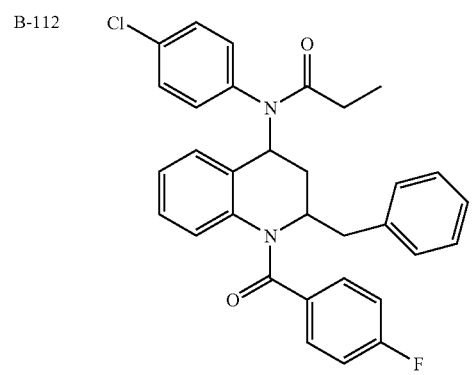
B-113 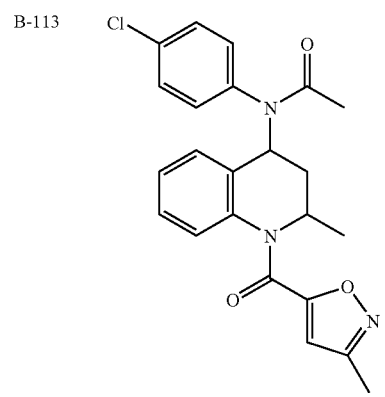
B-114 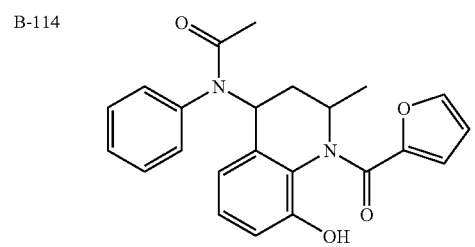

TABLE 2-continued
Compounds Derived from General Procedure B
| No. | Structure |
|---|---|
| B-115 | 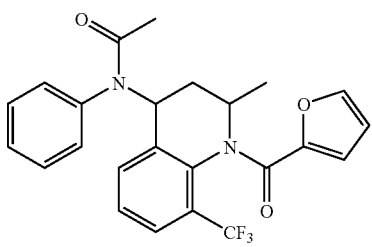 |
| B-116 | 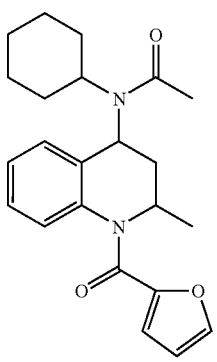 |
| B-117 | 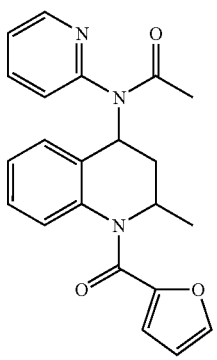 |
| B-118 | 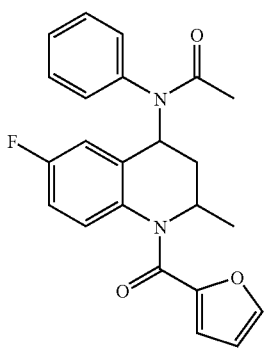 |

TABLE 2-continued
Compounds Derived from General Procedure B
| No. | Structure |
|---|---|
| B-119 | 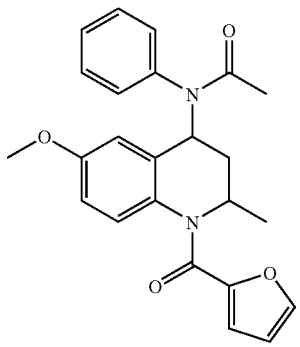 |
| B-120 | 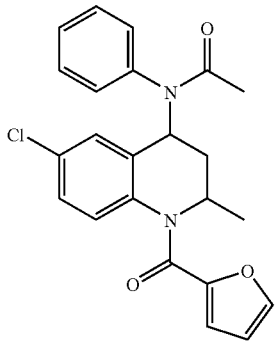 |
| B-121 | 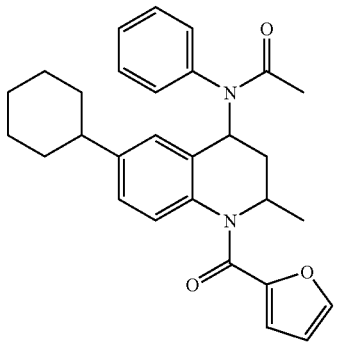 |
| B-122 | 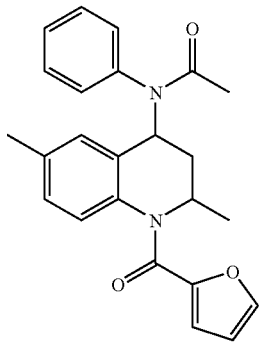 |

TABLE 2-continued
Compounds Derived from General Procedure B
| No. | Structure |
| --- | --- |
| B-123 | 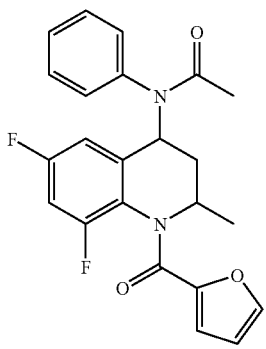 |
| B-124 | 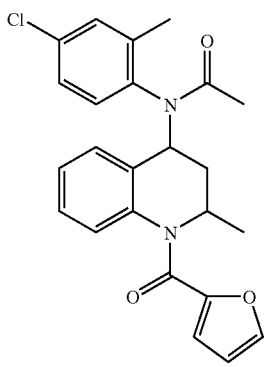 |
| B-125 | 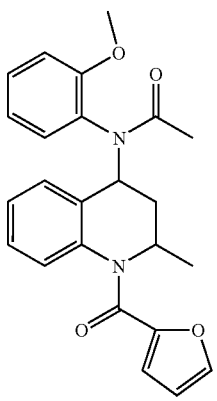 |
| B-126 | 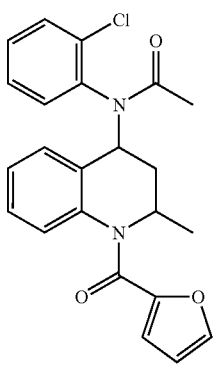 |

TABLE 2-continued
Compounds Derived from General Procedure B
| No. | Structure |
|---|---|
| B-127 | 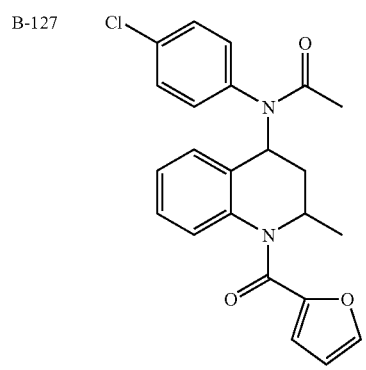 |
| B-128 | 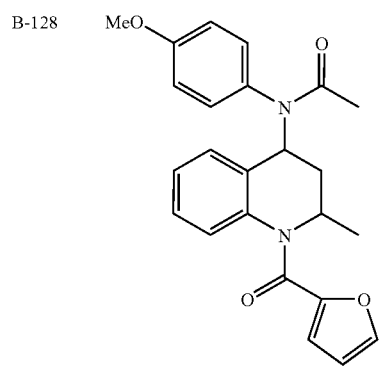 |
| B-129 | 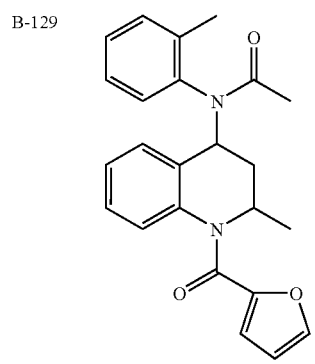 |
| B-130 | 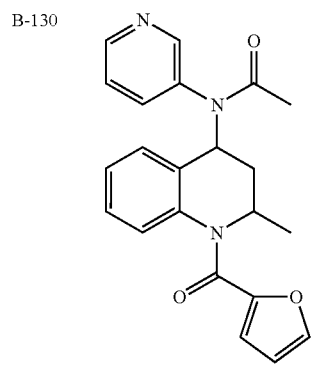 |

TABLE 2-continued
Compounds Derived from General Procedure B
| No. | Structure |
|---|---|
| B-131 | 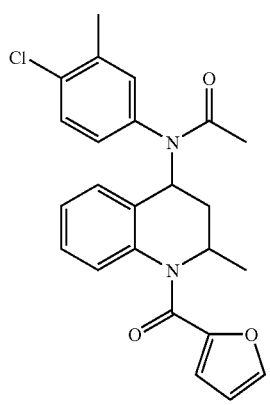 |
| B-132 | 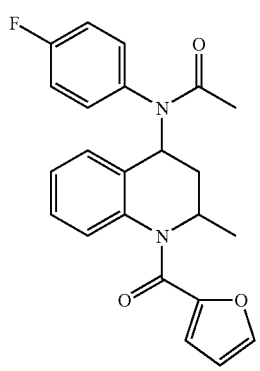 |
| B-133 | 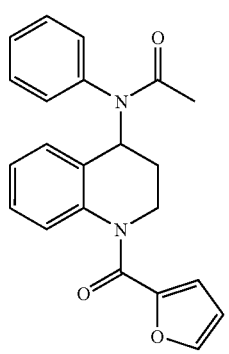 |
| B-134 | 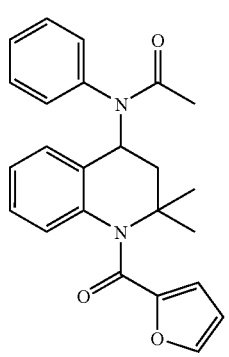 |

TABLE 2-continued
Compounds Derived from General Procedure B
| No. | Structure |
|---|---|
| B-135 | 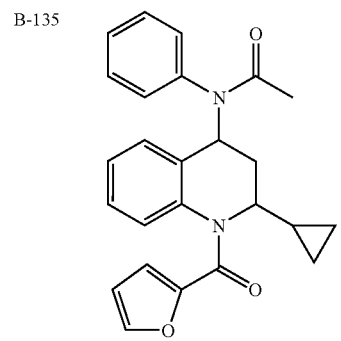 |
| B-136 | 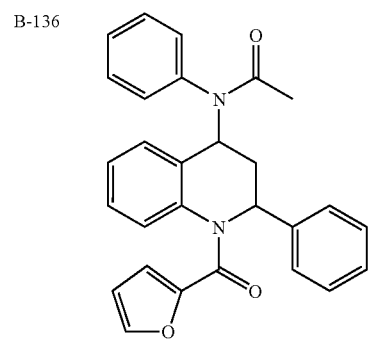 |
| B-137 | 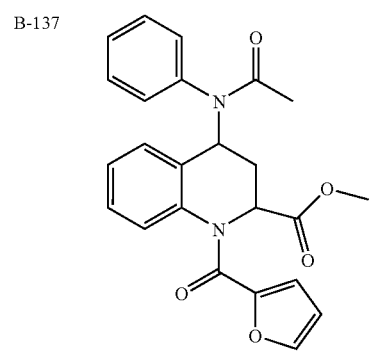 |
| B-138 | 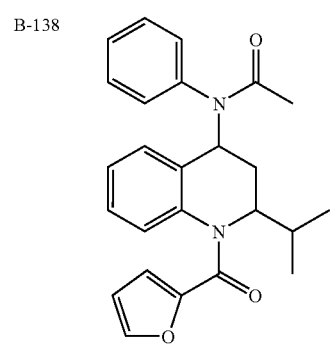 |

TABLE 2-continued
Compounds Derived from General Procedure B
| No. | Structure |
|---|---|
| B-139 | 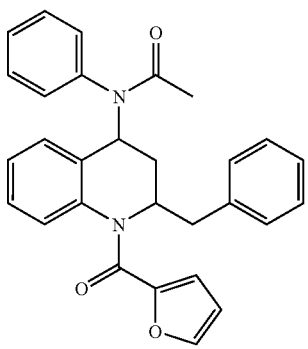 |
| B-140 | 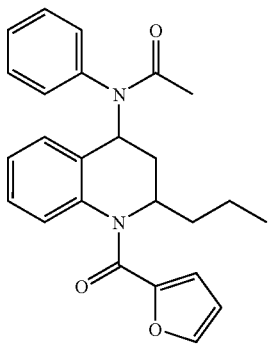 |
| B-141 | 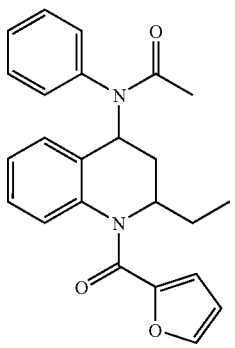 |
| B-142 | 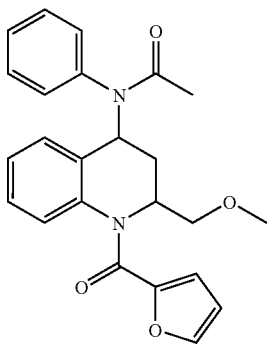 |

TABLE 2-continued
Compounds Derived from General Procedure B
| No. | Structure |
|---|---|
| B-143 | 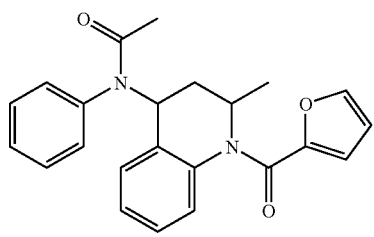 |
| B-144 | 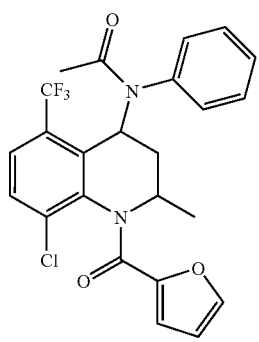 |
| B-145 | 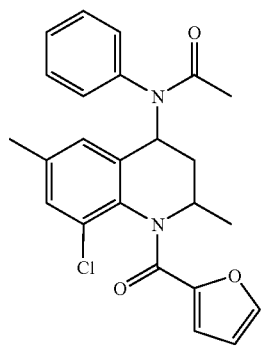 |
| B-146 | 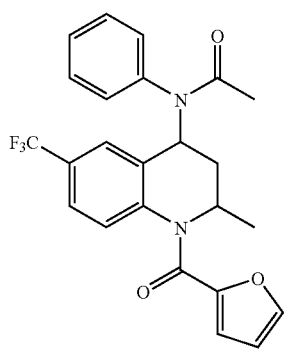 |

TABLE 2-continued

Compounds Derived from General Procedure B

| No. | Structure |
|-----|-----------|
| B-147 | 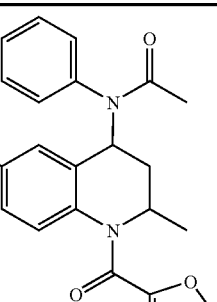 |

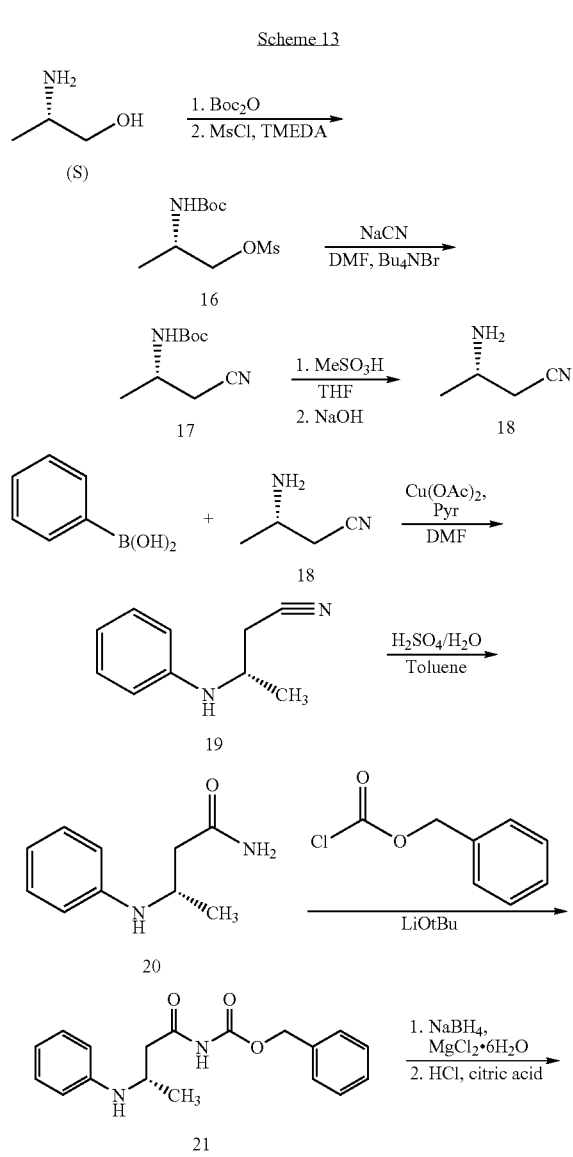

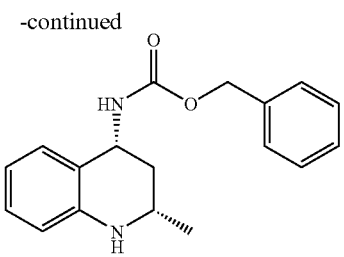

(Exclusively cis)

Methanesulfonic acid 2-(S)-tert-butoxycarbonylamino-propyl ester (16)

To a room temperature solution of S-2-amino-propan-1-ol (28.23 g, 0.375 mol) in ethyl acetate (300 mL) was added BOC anhydride (86.13 g, 0.395 mol) dissolved in 30 mL of ethyl acetate via an addition funnel (exothermic). The solution turns cloudy then clear. The reaction mixture was stirred for approximately 30 minutes. Tetramethylethylenediamine (TMEDA) (59.6 mL, 0.395 mol) was added and the reaction mixture was cooled to approximately 0° C. Methanesulfonyl chloride (30.6 mL, 0.395 mol) was added to the reaction mixture over a 30-minute period. After stirring for 2.5 hour at 0° C., during which time a white precipitate formed. The reaction mixture was filtered and the filtrate was concentrated to ½ volume and poured into hexanes (800 mL) and rapidly stirred. The mixture was cooled in an ice-bath for 2 h and then filtered to give 82 g (86%) of methanesulfonic acid 2-(S)-tert-butoxycarbonylamino-propyl ester.

$^1$H NMR (300 MHz, CDCl$_3$) δ 1.23 (d, 3H), 1.44 (s, 9H), 3.03 (s, 2H), 3.96 (m, 1H), 4.15 (dd, 1H), 4.23 (dd, 1H), 4.58 (bs, 1H).

(S)-(2-Cyano-1-methyl-ethyl)-carbamic acid tert-butyl ester (17)

Sodium cyanide (48.92 g, 0.421 mol) was added to dimethylformamide (DMF) (420 mL) and the mixture was stirred at 35° C. for 30 minutes. Tetrabutylammonium bromide (5.22 g, 0.016 mol) was added and the reaction mixture was stirred for an additional 2 h at 35° C. Methanesulfonic acid 2-(S)-tert-butoxycarbonylamino-propyl ester (82.03 g, 0.324 mol) was added and the reaction mixture was stirred at 35° C. overnight. Add an additional 5.22 g of tetrabutylammonium bromide (0.016 mol) was added and stirred overnight at 35° C. The mixture was then partitioned between 1200 mL water and 1600 mL of ethyl acetate. The resulting organic and aqueous phases were separated and extracted sequentially 2 times with 800 mL of ethyl acetate. The combined extracts were washed 3 times with 500 mL of water and a saturated solution of sodium chloride in water. The organic layer was dried over magnesium sulfate, filtered and concentrated to afford a solid in 84% of (S)-(2-cyano-1-methyl-ethyl)-carbamic acid tert-butyl ester.

(S)-3-Amino-butyronitrile (18)

To a solution of (S)-(2-cyano-1-methyl-ethyl)-carbamic acid tert-butyl ester (50.29 g, 0.273 mol) dissolved in THF (550 mL) was added methanesulfonic acid (44 mL, 0.682 mol) and stirred for 20 minutes. The reaction mixture was heated to 65° C. for approximately 3 h (make sure the reaction is vented during this time). The mixture was allowed to cool to ambient temperature. The resulting solids were isolated by filtration to afford the title compound. The solids were suspended in dichloromethane, and 300 mL of sat. $Na_2CO_3$ and the pH was adjusted to 13 with 6M NaOH (~20 mL). Extract 2×500 mL dichloromethane. Combine the organics and wash with a saturated solution of sodium chloride in water. The organic layer was dried over sodium sulfate, filtered and concentrated to give (S)-3-amino-butyronitrile in 64% yield.

$^1$H NMR (300 MHz, $CDCl_3$) δ 1.23 (d, 3H), 1.46 (bs, 2H), 2.34 (dd, 1H), 2.43 (dd, 1H), 3.34 (sextet, 1H).

(S)-3-Phenylamino-butyronitrile (19)

(S)-3-Amino-butyronitrile (2.51 g, 0.030 mol) was dissolved in 40 mL of DMF, phenyl boronic acid (4.73 g, 0.0389 mol), $Cu(OAc)_2$ (7.06 g, 0.0389 mol) and pyridine (6.29 mL, 0.077 mol) were added and the reaction was heated to 65° C. open to the air until no starting material was apparent by LCMS (It is very important that this reaction not be run under argon or nitrogen, it needs the air to catalyze the reaction. Also, the reaction should be stirred very vigourously to allow the air to mix with the reaction.) Once the starting material was gone (~18 h), the reaction was allowed to cool to room temperature and poured into ethyl acetate and filter. Wash the precipitate well with ethyl acetate. The filtrate is washed 2 times with $H_2O$ and dried over $Na_2SO_4$, filtered and concentrated. Isco chromatography (100% hexane to 30% ethyl acetate/70% hexane gradient) afforded the N-phenyl nitrile in 2.13 g (41%) as a white solid.

$^1$H NMR (300 MHz, $CDCl_3$) δ 1.44.(d, 3H), 2.61 (d, 2H), 3.64 (bs, 1H), 3.90 (bs, 1H), 6.60 (d, 2H), 6.77 (t, 1H), 7.18-7.26 (m, 2H).

(S)-3-Phenylamino-butyramide (20)

To a solution of (S)-3-phenylamino-butyronitrile (6.06 g, 0.0378 mol) in toluene (150 mL) was added a cooled solution of conc. sulfuric acid in $H_2O$ (20.12 mL $H_2SO_4$/3 mL)—(The ratio of toluene to acid/$H_2O$ is very important and should be followed strictly). Stir the biphasic mixture at room temperature for 0.5 h and warm to 35° C. and stir for 22 h. The reaction was cooled to room temperature and quenched with 13 g of $Na_2CO_3$ in water (add slowly some foaming). Separate the organic and extract 2×EtOAc. Combine all the organics and wash the organics with brine, dry over $MgSO_4$, filter and concentrate to give the desired product in 2.11 g (90%)

$^1$H NMR (300 MHz, $CDCl_3$) δ: 1.29 (d, 3H), 2.40 (dd, 1H), 2.48 (dd, 1H), 3.73 (bs, 1H), 3.92 (sextet, 1H), 5.52 (bs, 1H), 6.00 (bs, 1H), 6.66 (d, 2H), 6.74 (t, 1H), 7.19 (m, 2H).

(S)-(3-Phenylamino-butyryl)-carbamic acid benzyl ester (21)

A clean, dry and nitrogen gas purged flask was charged with (S)-3-phenylamino-butyramide (3.25 g, 0.018 mmol) in THF (65 mL) and the mixture was cooled to −10° C. Benzyl chloroformate (3.12 mL, 0.022 mmol) was then added followed by the slow addition of 1.0 M lithium tert-butoxide in THF solution (18 mL). The lithium tert-butoxide solution was added at such a rate that the internal temperature remained below 0° C. Fifteen minutes after the completion of base addition, the reaction (starting material gone by TLC) was quenched by adding EtOAc (65 mL) and 1.0 M hydrochloric acid (10 mL). The aqueous phase was then basified with 1N NaOH. The aqueous phase was extracted 3×EtOAc. The organics were collected together and with saturated aqueous sodium chloride solution (130 mL). The phases were separated, the organic layer was dried ($MgSO_4$), filtered, and concentrated. Flash chromatography using a Biotage system (10% EtOAc/90% hexane to 20% EtOAc/80% Hexane) afforded the title compound in 82% yield.

$^1$H NMR (300 MHz, $CDCl_3$) δ: 1.30 (d, 3H), 2.87 (dd, 1H), 3.04 (dd, 1H), 3.80 (bs, 1H), 4.02 (m, 1H), 5.17 (s, 2H), 6.62 (d, 2H), 6.73 (t, 1H), 7.17 (t, 2H), 7.37 (s, 5H), 8.13 (bs, 1H).

(2S,4R)-(2-Methyl-1,2,3,4-tetrahydro-quinolin-4-yl)-carbamic acid benzyl ester (22)

A clean, dry flask was charged with (S)-(3-phenylamino-butyryl)-carbamic acid benzyl ester (0.821 g, 2.63 mmol) followed by reagent grade ethanol (20 mL) and cooled to −10° C. Sodium borohydride (0.070 g, 1.84 mmol) was added to the solution in one portion. Nitrogen gas purging is maintained for 5 minutes. A solution of 3.3 M aqueous magnesium chloride solution (0.561 g $MgCl_2$ $6H_2O$ in 1.5 mL water) was added at such a rate that the internal temperature did not exceed −5° C. Once addition was completed, the reaction solution was warmed to 0° C. for 30 min. The reaction was quenched with methylene chloride (10 mL), and 1 M hydrochloric acid/citric acid solution (10.52 mL 1 N HCl, and 1.38 g citric acid). This bilayer was stirred at room temperature for six hours. The reaction mixture was diluted with ethyl acetate (200 mL) and neutralized with sat. aqueous $NaHCO_3$ solution (pH=10). The organics were collected together and washed with sat. NaCl solution and dried over $Na_2SO_4$, filtered and concentrated. Flash chromatography using an Isco system (100% hexane to 50% EtOAc/50% hexane gradient) afforded the title compound (0.733 g). (91%).

$^1$H-NMR (300 MHz, $CDCl_3$) δ: 7.38 (m, 5H), 7.17 (d, 1H), 7.02 (t, 1H), 6.68 (t, 1H, C6-H), 6.47 (d, 1H), 5.17 (bs, 2H), 5.07 (m, 1H), 4.92 (d, 1H), 3.78 (bs, 1H), 3.57 (m, 1H), 2.30 (m, 1H), 1.47 (q, 1H), 1.21 (d, 3H).

General Procedure C

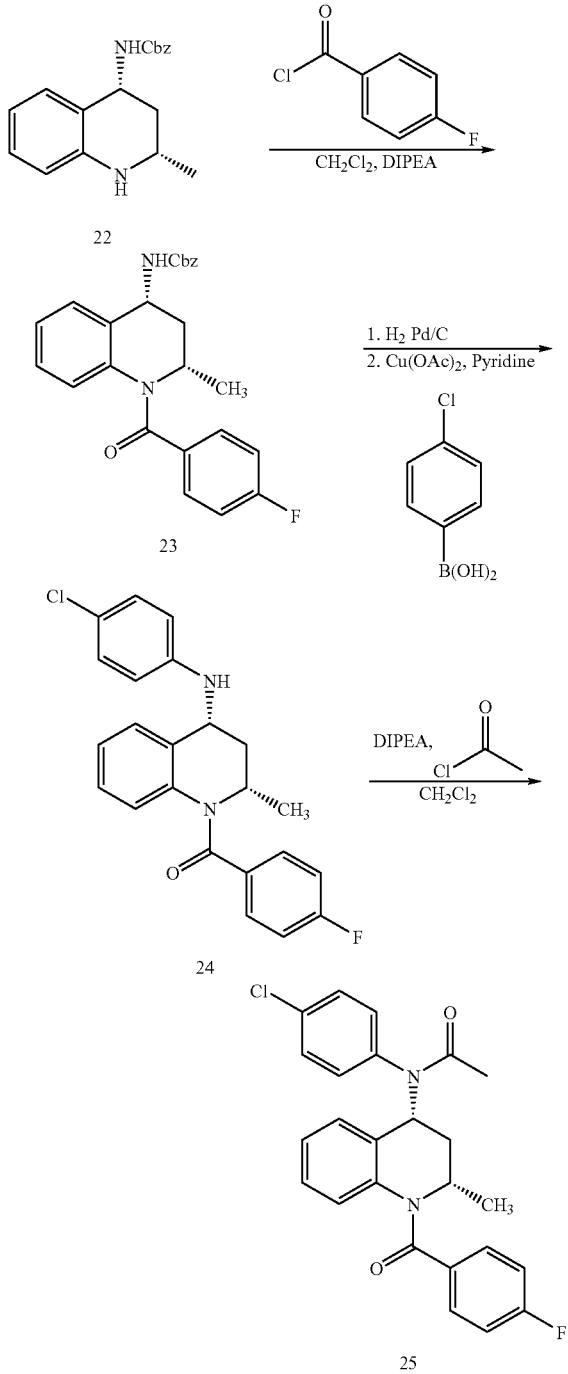

Scheme 15

(2S,4R)-N-(4-Chloro-phenyl)-N-[1-(4-fluoro-benzoyl)-2-methyl-1,2,3,4-tetrahydro-quinolin-4-yl]-acetamide (25)

To a solution of (2S,4R)-(2-methyl-1,2,3,4-tetrahydro-quinolin-4-yl)-carbamic acid benzyl ester (1.0 g, 3.38 mmol) in methylene chloride (50 mL) at room temperature was added diisopropylethylamine (650 uL, 3.72 mmol) followed by 4-fluorobenzoyl chloride. The reaction was stirred over night at room temperature. The mixture was poured into water and extracted with ethyl acetate. The extracts were washed with 1 M (aq) NaOH and brine, dried over magnesium sulfate, filtered dried and concentrated. The crude residue was purified by silica gel chromatography (75% hexanes/25% ethyl acetate) to afford the pure amide (720 mg, 51%).

(2S,4R)-[1-(4-fluorobenzoyl)-2-methyl-1,2,3,4-tetrahydro-quinolin-4-yl]-carbamic acid benzyl ester (720 mg, 1.73 mmol) was dissolved in ethanol (30 mL). The vessel in which resided the resulting solution was evacuated and backfilled with argon. A catalytic amount of Palladium on Carbon (10%) was added. The vessel was once again evacuated and this time was backfilled with hydrogen and shaken in a Parr bottle at 40 psi hydrogen. Reaction was complete after 4 h. The mixture was carefully filtered and concentrated to 10% volume. The resulting concentrated solution was filtered through an Celite® and concentrated to afford the crude amine.

To a solution of (2S,4R)-(4-amino-2-methyl-3,4-dihydro-2H-quinolin-1-yl)-(4-fluoro-phenyl)-methanone (1.0 g, 3.5 mmol) in DMF (20 mL, dry) was added 4-chlorophenylboronic acid (1.1 g, 7.0 mmol), pyridine (850 uL, 10.5 mmol) and copper(II)acetate (1.27 g, 7.0 mmol). The heterogeneous green mixture was stirred open to air for 1 h and then warmed to 60° C. and stirred over night (14 h). The mixture was then cooled to rt, poured into rapidly stirred ethyl acetate (150 mL); solids were removed by filtration through Celite®. The extracts were washed several times with water and then once with brine. The extracts were then dried over anhydrous magnesium sulfate, filtered, and concentrated under reduced pressure. The crude residue was purified by silica gel chromatography (95% methylene chloride/5% ethyl acetate) to afford the aniline product (250 mg, 18%) as a yellow oil.

To a solution of (2S,4R)-[4-(4-chloro-phenylamino)-2-methyl-3,4-dihydro-2H-quinolin-1-yl]-(4-fluoro-phenyl)-methanone (250 mg, 0.636 mmol) in methylene chloride (5 mL) was added diisopropylethylamine (120 uL, 0.70 mmol) followed by acetyl chloride (90 uL, 1.27 mmol). The mixture was stirred at rt 4 h. The mixture was concentrated under reduced pressure, dissolved in ethyl acetate, washed with sat. aqueous sodium bicarbonate, brine and dried over magnesium sulfate, filtered, and concentrated under reduced pressure. The residue was purified by silica gel chromatography (25/75 hexanes/ethyl acetate gradient) to afford pure N-(4-chloro-phenyl)-N-[1-(4-fluoro-benzoyl)-2-methyl-1,2,3,4-tetrahydro-quinolin-4-yl]-acetamide (200 mg, 71%).

$^1$H-NMR (CDCl$_3$) δ: 1.1 (3H, d), 1.1 (1H, m), 2.0 (3H, d), 2.3 (1H, m), 4.7 (1H, m), 5.6 (1H, m), 6.5 (1H, d), 6.7-7.0 (3H, m), 7.1-7.4 (8H, m).

MS m/z: 436 (M+1).

(2S,4R)-N-(4-Chloro-phenyl)-N-[2-methyl-1-(4-morpholin-4-yl-benzoyl)-1,2,3,4-tetrahydro-quinolin-4-yl]-acetamide (C-1)

(2S,4R)-N-(4-Chloro-phenyl)-N-[2-methyl-1-(4-morpholin-4-yl-benzoyl)-1,2,3,4-tetrahydro-quinolin-4-yl]-acetamide was made following general procedure C, substituting 4-bromobenzoyl chloride for 4-fluorobenzoyl chloride. Further elaboration to the morpholine was done following the same procedure as described for (±)-N-(4-chloro-phenyl)-N-[1-(4-fluoro-benzoyl)-2-methyl-6-morpholin-4-yl-1,2,3,4-tetrahydro-quinolin-4-yl]-propionamide.

$^1$H-NMR (CDCl$_3$) δ: 1.13 (d, 3H), 1.22 (t, 1H), 2.03 (s, 3H), 2.29 (s, 1H), 3.31 (t, 4H), 3.80 (t, 4H), 4.75 (sextet, 1H), 5.61 (bs, 1H), 6.58 (d, 1H), 6.64 (d, 2H), 6.94 (t, 1H), 7.15 (d, 2H), 7.18 (t, 1H), 7.21 (d, 2H), 7.28-7.39 (m, 3H).
MS m/z: 505.4 (M+1).

(2S,4R)-4-(4-{4-[Acetyl-(4-chloro-phenyl)-amino]-2-methyl-3,4-dihydro-2H-quinoline-1-carbonyl}-phenoxy)-butyric acid (C-2)

(2S,4R)-4-(4-{4-[Acetyl-(4-chloro-phenyl)-amino]-2-methyl-3,4-dihydro-2H-quinoline-1-carbonyl}-phenoxy)-butyric acid was prepared was made following general procedure C, substituting 4-methoxybenzoyl chloride for 4-fluorobenzoyl chloride. Further elaboration to the acid was done following the same procedure as described for (±)-4-(4-{4-[(4-chloro-phenyl)-propionyl-amino]-2-methyl-3,4-dihydro-2H-quinoline-1-carbonyl}-phenoxy)-butyric acid.

$^1$H-NMR (CDCl$_3$) δ: 1.1 (3H, d), 1.1 (1H, m), 2.0 (3H, s), 2.1 (2H, m), 2.3 (1H, m), 2.5 (2H, m), 3.9 (2H, m), 4.7 (1H, m), 5.6 (1H, m), 6.5 (1H, d), 6.7 (2H, d), 6.9 (1H, t), 7.1-7.3 (7H, m), 7.4 (1H, d).
MS m/z: 522 (M+2).

(2S,4R)-N-(4-Chloro-phenyl)-N-[1-(4-dimethylamino-benzoyl)-2-methyl-1,2,3,4-tetrahydro-quinolin-4-yl]-acetamide (C-3)

(2S,4R)-N-(4-Chloro-phenyl)-N-[1-(4-dimethylaminobenzoyl)-2-methyl-1,2,3,4-tetrahydro-quinolin-4-yl]-acetamide was prepared following general procedure C, substituting 4-dimethylaminobenzoyl chloride for 4-fluorobenzoyl chloride.

$^1$H-NMR (300 MHz, CDCl$_3$) δ: 1.14-1.33 (m, 4H), 2.13 (s, 3H), 2.24-2.39 (m, 1H), 2.94 (s, 6H), 4.75 (ddd, 1H), 5.61 (br s, 1H), 6.44 (d, 2H), 6.63 (d, 1H), 6.96 (dd, 1H), 7.07-7.36 (m, 6H), 7.40 (d, 2H).
MS m/z: 420 (M+1).

(2S,4R)-N-(4-Chloro-phenyl)-N-[1-(4-isopropoxy-benzoyl)-2-methyl-1,2,3,4-tetrahydro-quinolin-4-yl]-acetamide (C-4)

(2S,4R)-N-(4-Chloro-phenyl)-N-[1-(4-isopropoxy-benzoyl)-2-methyl-1,2,3,4-tetrahydro-quinolin-4-yl]-acetamide was prepared following general procedure C, substituting 4-isopropoxybenzoyl chloride for 4-fluorobenzoyl chloride.

$^1$H-NMR (300 MHz, CDCl$_3$) δ: 1.14 (d, 3H), 1.23-1.31 (m, 7H), 2.03 (s, 3H), 2.23-2.35 (m, 1H), 4.48 (sept., 1H), 4.74 (ddd, 1H), 5.61 (br s, 1H), 6.55 (d, 1H), 6.64 (d, 2H), 6.92 (dd, 1H), 7.09-7.24 (m, 5H), 7.29 (d, 1H), 7.34-7.41 (m, 2H).
MS m/z: 477 (M+1).

(2S,4R)-N-(4-Chloro-phenyl)-N-[2-methyl-1-(6-morpholin-4-yl-pyridine-3-carbonyl)-1,2,3,4-tetrahydro-quinolin-4-yl]-acetamide (C-5)

(2S,4R)-N-(4-Chloro-phenyl)-N-[2-methyl-1-(6-morpholin-4-yl-pyridine-3-carbonyl)-1,2,3,4-tetrahydro-quinolin-4-yl]-acetamide was prepared following general procedure C, substituting 2-chloronicotinoyl chloride for 4-fluorobenzoyl chloride. Prior to removal of the benzyl carbamate, the chloronicotinamide was converted to the 2-morpholinonicotinamide as follows. A solution of the (2S,4R)-[1-(6-chloro-nicotinoyl)-2-methyl-1,2,3,4-tetrahydro-quinolin-4-yl]-carbamic acid benzyl ester (525 mg, 1.20 mol) was dissolved in morpholine (5 mL). The resulting solution was heated at 70° C. over night. Upon completion of reaction (12 h), the solution was concentrated under reduced pressure; the crude residue was dissolved in ethyl acetate and washed with water and brine to remove remaining morpholine. The extracts were dried over sodium sulfate, filtered and concentrated to afford the crude morpholinonicotinate (639 mg, >100%). The resulting product was carried on to fully elaborated (2S,4R)-N-(4-chloro-phenyl)-N-[2-methyl-1-(6-morpholin-4-yl-pyridine-3-carbonyl)-1,2,3,4-tetrahydro-quinolin-4-yl]-acetamide as described in general procedure C.

$^1$H-NMR (300 MHz, CDCl$_3$) δ: 1.11-1.22 (m, 4H), 2.03 (s, 3H), 2.24-2.38 (m, 1H), 3.48'-3.56 (m, 4H), 3.74-3.80 (m, 4H), 4.73 (ddd, 1H), 5.56 (br s, 1H), 6.30 (d, 1H), 6.66 (d, 1H), 7.02 (dd, 1H), 7.12 (dd, 1H), 7.16-7.25 (m, 3H), 7.32 (d, 1H), 7.40 (d, 2H), 8.24 (br s, 1H).
MS m/z: 505 (M+1).

(2S,4R)-N-(4-Chloro-phenyl)-N-[1-(3-ethyl-isoxazole-5-carbonyl)-2-methyl-1,2,3,4-tetrahydro-quinolin-4-yl]-acetamide (C-6)

(2S,4R)-N-(4-Chloro-phenyl)-N-[1-(3-ethyl-isoxazole-5-carbonyl)-2-methyl-1,2,3,4-tetrahydro-quinolin-4-yl]-acetamide was prepared following general procedure C, substituting 3-ethylisoxazole carbonyl chloride for 4-fluorobenzoyl chloride.

$^1$H-NMR (300 MHz, CDCl$_3$) δ: 1.06-1.23 (m, 7H), 2.02 (s, 3H), 2.21-2.37 (m, 1H), 2.52-2.66 (m, 2H), 4.72 (ddd, 1H), 5.34-5.56 (br s, 1H), 5.88 (s, 1H), 6.80 (d, 1H), 7.11 (dd, 1H), 7.20 (d, 2H), 7.28-7.43 (m, 4H).
MS m/z: 438 (M+1).

(2S,4R)-N-[1-(3-Benzyl-isoxazole-5-carbonyl)-2-methyl-1,2,3,4-tetrahydro-quinolin-4-yl]-N-(4-chloro-phenyl)-acetamide (C-7)

(2S,4R)-N-[1-(3-Benzyl-isoxazole-5-carbonyl)-2-methyl-1,2,3,4-tetrahydro-quinolin-4-yl]-N-(4-chloro-phenyl)-acetamide was prepared following general procedure C, substituting 3-benzylisoxazole carbonyl chloride for 4-fluorobenzoyl chloride.

$^1$H-NMR (300 MHz, CDCl$_3$) δ: 1.06-1.43 (m, 4H), 2.01 (s, 3H), 2.16-2.35 (m, 1H), 3.81-4.01 (m, 2H), 4.70 (ddd, 1H), 5.40 (br s, 1H), 5.83 (s, 1H), 6.75 (d, 1H), 7.02 (dd, 1H), 7.10 (m, d, 2H), 7.14 -7.22 (m, 2H), 7.22-7.34 (m, 5H), 7.38 (d, 2H).
MS m/z: 500 (M+1).

(2S,4R)-N-(4-Chloro-phenyl)-N-[1-(3-methoxymethyl-isoxazole-5-carbonyl)-2-methyl-1,2,3,4-tetrahydro-quinolin-4-yl]-acetamide (C-8)

2S,4R)-N-(4-Chloro-phenyl)-N-[1-(3-methoxymethyl-isoxazole-5-carbonyl)-2-methyl-1,2,3,4-tetrahydro-quinolin-4-yl]-acetamide was prepared following general procedure C, substituting 3-methoxymethyl ether isoxazole carbonyl chloride for 4-fluorobenzoyl chloride.

$^1$H-NMR (300 MHz, CDCl$_3$) δ: 1.11-1.24 (m, 4H), 2.02 (s, 3H), 2.22-2.39 (m, 1H), 3.28 (s, 3H), 4.42 (s, 2H), 4.73 (ddd, 1H), 5.46 (br s, 1H), 6.09 (s, 1H), 6.79 (d, 1H), 7.10 (d, 1H), 7.10 (d, 2H), 7.27-7.42 (m, 4H).
MS m/z: 454 (M+1).

(2S,4R)-4-(4-{4-[Acetyl-(4-chloro-phenyl)-amino]-2-methyl-3,4-dihydro-2H-quinoline-1-carbonyl}-phenoxy)-piperidine-1-carboxylic acid ethyl ester (C-9)

(2S,4R)-4-(4-{4-[Acetyl-(4-chloro-phenyl)-amino]-2-methyl-3,4-dihydro-2H-quinoline-1-carbonyl}-phenoxy)-piperidine-1-carboxylic acid ethyl ester was prepared following general procedure C, substituting 4-(4-chlorocarbonyl-phenoxy)-piperidine-1-carboxylic acid ethyl ester for 4-fluorobenzoyl chloride.

$^1$H-NMR (CDCl$_3$) δ: 1.1 (3H, d), 1.1 (1H, m), 1.2 (3H, t), 1.7 (2H, m), 1.9 (2H, m), 2.0 (3H, s), 2.3 (1H, m), 3.3 (2H, m), 3.7 (2H, m), 4.1 (2H, q), 4.4 (1H, m), 4.8 (1H, m), 5.6 (1H, m), 6.5 (1H, d), 6.7 (2H, d), 6.9 (1H, t), 7.1-7.3 (7H, m), 7.4 (1H, d).

MS m/z: 590 (M).

(2S,4R)-2-(4-{4-[Acetyl-(4-chloro-phenyl)-amino]-2-methyl-3,4-dihydro-2H-quinoline-1-carbonyl}-phenoxy)-acetamide (C-10)

(2S,4R)-2-(4-{4-[Acetyl-(4-chloro-phenyl)-amino]-2-methyl-3,4-dihydro-2H-quinoline-1-carbonyl}-phenoxy)-acetamide was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. Further elaboration to the amide was done following the same procedure as described for (±)-N-[1-(4-carbamoylmethoxy-benzoyl)-2-methyl-1,2,3,4-tetrahydro-quinolin-4-yl]-N-phenyl-propionamide $^1$H-NMR (CDCl$_3$) δ: 1.1 (3H, m), 1.8 (1H, s), 2.0 (3H, s), 2.3 (1H, m), 4.4 (2H, s), 4.7 (1H, m), 5.6 (1H, br), 5.9 (2H, brs) 6.5 (2H, d), 6.7 (2H, d), 6.9 (1H, t), 7.2-7.4 (7H, m).

MS m/z: 492 (M+1).

(2S,4R)-N-(4-Chloro-phenyl)-N-{2-methyl-1-[4-(2-morpholin-4-yl-ethoxy)-benzoyl]-1,2,3,4-tetrahydro-quinolin-4-yl}-acetamide (C-11)

(2S,4R)-N-(4-Chloro-phenyl)-N-{2-methyl-1-[4-(2-morpholin-4-yl-ethoxy)-benzoyl]-1,2,3,4-tetrahydro-quinolin-4-yl}-acetamide was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. Further elaboration to the morpholine was done following the same procedure as described for (±)-N-{2-methyl-1-[4-(2-morpholin-4-yl-ethoxy)-benzoyl]-1,2,3,4-tetrahydro-quinolin-4-yl}-N-phenyl-propionamide.

$^1$H-NMR (CDCl$_3$) δ: 1.1 (3H, d), 1.1 (1H, m), 2.0 (3H, s), 2.3 (1H, m), 2.6 (4H, m), 2.8 (2H, m), 3.7 (4H, m), 4.1 (2H, m), 4.7 (1H, m), 5.6 (1H, m), 6.5 (1H, d), 6.7 (2H, d), 6.9 (1H, t), 7.1-7.3 (7H, m), 7.4 (1H, d).

MS m/z: 549 (M+2).

(2S,4R)-(4-{4-[Acetyl-(4-chloro-phenyl)-amino]-2-methyl-3,4-dihydro-2H-quinoline-1-carbonyl}-phenoxy)-acetic acid (C-13)

(2S,4R)-(4-{4-[Acetyl-(4-chloro-phenyl)-amino]-2-methyl-3,4-dihydro-2H-quinoline-1-carbonyl}-phenoxy)-acetic acid was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. Further elaboration to the acid was done following the same procedure as described for {(±)-4-[2-methyl-4-(phenyl-propionyl-amino)-3,4-dihydro-2H-quinoline-1-carbonyl]-phenoxy}-acetic.

$^1$H-NMR (CDCl$_3$) δ: 1.1 (3H, d), 1.1 (1H, m), 2.0 (3H, s), 2.3 (1H, m), 4.3 (2H, s), 4.6 (1H, m), 5.6 (1H, m), 6.4-6.9 (5H, m), 7.0-7.4 (7H, m).

MS m/z: 494 (M+2).

(2S,4R)-N-(4-Chloro-phenyl)-N-{2-methyl-1-[4-(1H-tetrazol-5-ylmethoxy)-benzoyl]-1,2,3,4-tetrahydro-quinolin-4-yl}-acetamide (C-14)

(2S,4R)-N-(4-Chloro-phenyl)-N-{2-methyl-1-[4-(1H-tetrazol-5-ylmethoxy)-benzoyl]-1,2,3,4-tetrahydro-quinolin-4-yl}-acetamide was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. Further elaboration to the tetrazole was done following the same procedure as described for (±)-N-(4-chloro-phenyl)-N-{2-methyl-1-[4-(1H-tetrazol-5-ylmethoxy)-benzoyl]-1,2,3,4-tetrahydro-quinolin-4-yl}-propionamide.

$^1$H-NMR (CDCl$_3$) δ: 1.1 (3H, d), 1.1 (1H, m), 2.0 (3H, s), 2.3 (1H, m), 4.8 (1H, m), 5.2 (2H, dd), 5.6 (1H, m), 6.4 (1H, m), 6.5 (1H, d), 7.0 (2H, m), 7.1-7.4 (8H, m).

MS m/z: 517 (M+1).

(2S,4R)-N-{1-[4-(1-Acetyl-piperidin-4-yloxy)-benzoyl]-2-methyl-1,2,3,4-tetrahydro-quinolin-4-yl}-N-(4-chloro-phenyl)-acetamide (C-15)

(2S,4R)-N-{1-[4-(1-Acetyl-piperidin-4-yloxy)-benzoyl]-2-methyl-1,2,3,4-tetrahydro-quinolin-4-yl}-N-(4-chloro-phenyl)-acetamide was prepared from (2S,4R)-4-(4-{4-[acetyl-(4-chloro-phenyl)-amino]-2-methyl-3,4-dihydro-2H-quinoline-1-carbonyl}-phenoxy)-piperidine-1-carboxylic acid ethyl ester, followed by removal of the ethoxy carbamate using basic hydrolysis and then acetylation.

$^1$H-NMR (CDCl$_3$) δ: 1.1 (3H, d), 1.1 (1H, m), 1.6-2.1 (4H, m), 2.0 (6H, s), 2.3 (1H, m), 3.4 (1H, m), 3.5-3.8 (3H, m), 4.4 (1H, m), 4.7 (1H, m), 5.6 (1H, m), 6.5 (1H, d), 6.7 (2H, d), 6.9 (1H, t), 7.1-7.3 (7H, m), 7.4 (1H, d).

MS m/z: 560 (M+1).

(2S,4R)-N-(4-Chloro-phenyl)-N-{2-methyl-1-[4-(pyridin-4-ylmethoxy)-benzoyl]-1,2,3,4-tetrahydro-quinolin-4-yl}-acetamide (C-16)

(2S,4R)-N-(4-Chloro-phenyl)-N-{2-methyl-1-[4-(pyridin-4-ylmethoxy)-benzoyl]-1,2,3,4-tetrahydro-quinolin-4-yl}-acetamide (2S,4R)-N-(4-Chloro-phenyl)-N-{2-methyl- 1-[4-(1H-tetrazol-5-ylmethoxy)-benzoyl]-1,2,3,4-tetrahydro-quinolin-4-yl}-acetamide was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. (2S,4R)-N-(4-Chloro-phenyl)-N-[1-(4-methoxy-benzoyl)-2-methyl-1,2,3,4-tetrahydro-quinolin-4-yl]-acetamide was dissolved in dichloromethane and a solution of $BBr_3$ (1.0 M in dichloromethane, 10 mL) was added; the reaction was allowed to stir at room temperature for until no starting material remained. The reaction was washed with sat $NaHCO_3$ carefully and brine. The organics were dried over $MgSO_4$, filtered and concentrated down. The residue was purified by Biotage flash chromatography using 100% EtOAc to give a white solid.

The phenol was dissolved in DMF (5 mL) at room temperature. Sodium hydride (60% in oil) was added and the mixture allowed to stir 30 min. 4-Bromomethyl-pyridine was added and the reaction was allowed to stir over night. Ethanol was added and the reaction was concentrated in vacuo. The residue was partitioned between ethyl acetate and water, then extracted three times with ethyl acetate, dried over $MgSO_4$, filtered and concentrated down. The crude residue was purified by silica gel chromatography (2/98 methanol/dichloromethane-5/95 methanol/dichloromethane gradient) to afford the product.

$^1$H-NMR (CDCl$_3$) δ: 1.1 (3H, d), 1.1 (1H, m), 2.0 (3H, s), 2.3 (1H, m), 4.7 (1H, m), 5.0 (2H, s), 5.6 (1H, m), 6.5 (1H, d), 6.7 (2H, d), 6.9 (1H, t), 7.0-7.4 (10H, m), 8.6 (2H, d).

MS m/z: 526 (M+1).

(2S,4R)-4-(3-{4-[Acetyl-(4-chloro-phenyl)-amino]-2-methyl-3,4 hydro-2H-quinoline-1-carbonyl}-phenoxy)-butyric acid (C-17)

(2S,4R)-4-(3-{4-[Acetyl-(4-chloro-phenyl)-amino]-2-methyl-3,4-dihydro-2H-quinoline-1-carbonyl}-phenoxy)-butyric acid was prepared following general procedure C, substituting 3-methoxybenzoyl chloride for 4-fluorobenzoyl chloride. Further elaboration to the acid was done following the same procedure as described for (±)-4-(4-{4-[(4-chloro-phenyl)-propionyl-amino]-2-methyl-3,4-dihydro-2H-quinoline-1-carbonyl}-phenoxy)-butyric acid.

$^1$H-NMR (CDCl$_3$) δ: 1.1 (3H, d), 1.1 (1H, m), 1.8-2.0 (2H, m), 2.0 (3H, s), 2.3 (1H, m), 2.4 (2H, m), 3.8 (2H, m), 4.8 (1H, m), 5.7 (1H, m), 6.4 (1H, m), 6.5 (1H, d), 6.8 (1H, m), 7.0 (1H, t), 7.1-7.4 (7H, m), 7.5 (1H, m).

MS m/z: 521 (M+1).

(2S,4R)-N-(4-Chloro-phenyl)-N-[1-(4-hydroxy-benzoyl)-2-methyl-1,2,3,4-tetrahydro-quinolin-4-yl]-acetamide (C-18)

(2S,4R)-N-(4-Chloro-phenyl)-N-[1-(4-hydroxy-benzoyl)-2-methyl-1,2,3,4-tetrahydro-quinolin-4-yl]-acetamide was prepared was made following general procedure C, substituting 3-methoxybenzoyl chloride for 4-fluorobenzoyl chloride. Further elaboration to the phenol was done following the same procedure as described for (±)-N-[1-(4-hydroxy-benzoyl)-2-methyl-1,2,3,4-tetrahydro-quinolin-4-yl]-N-phenyl-propionamide.

$^1$H-NMR (CDCl$_3$) δ: 1.1 (3H, d), 1.1 (1H, m), 2.0 (3H, s), 2.3 (1H, m), 4.7 (1H, m), 5.6 (1H, m), 6.4 (2H, d), 6.5 (1H, d), 6.9 (3H, m), 7.1-7.3 (4H, m), 7.4 (2H, m), 8.0 (1H, br).

MS m/z: 435 (M+1).

(2S,4R)-4-(4-{4-[Acetyl-(4-chloro-phenyl)-amino]-2-methyl-3,4-dihydro-2H-quinoline-1-carbonyl}-phenyl)-piperidine-1-carboxylic acid ethyl ester (C-19)

(2S,4R)-4-(4-{4-[Acetyl-(4-chloro-phenyl)-amino]-2-methyl-3,4-dihydro-2H-quinoline-1-carbonyl}-phenyl)-piperidine-1-carboxylic acid ethyl ester was prepared following general procedure C, substituting 4-(4-chlorocarbonyl-phenyl)-piperidine-1-carboxylic acid ethyl ester for 4-fluorobenzoyl chloride.

$^1$H-NMR (CDCl$_3$) δ: 1.1 (4H, m), 1.3 (3H, m), 1.5 (2H, m), 1.7 (2H, m), 2.0 (3H, s), 2.3 (1H, m), 2.6 (1H, m), 2.8 (2H, t), 4.1 (2H, m), 4.2 (2H, m), 4.8 (1H, m), 5.6 (1H, br), 6.5 (1H, d), 6.9 (1H, m), 7.0 (2H, d), 7.1 (2H, d), 7.3 (5H, m), 7.4 (2H, m).

MS m/z: 474 (M+1).

(2S,4R)-N-(4-Chloro-phenyl)-N-[1-(3-ethoxy-benzoyl)-2-methyl-1,2,3,4-tetrahydro-quinolin-4-yl]-acetamide (C-20)

(2S,4R)-N-(4-Chloro-phenyl)-N-[1-(3-ethoxy-benzoyl)-2-methyl-1,2,3,4-tetrahydro-quinolin-4-yl]-acetamide was prepared following general procedure C, substituting 3-ethoxybenzoyl chloride for 4-fluorobenzoyl chloride.

$^1$H-NMR (CDCl$_3$) δ: 1.2 (3H, m), 1.3 (4H, m), 2.0 (3H, s), 2.2 (1H, m), 3.9 (2H, m), 4.8 (1H, m), 5.6 (1H, br), 6.5 (1H, d), 6.7 (1H, d), 6.8 (2H, m), 6.9 (1H, m), 7.0 (1H, m), 7.1-7.3 (4H, m), 7.4 (2H, d).

MS m/z: 463 (M+1).

(2S,4R)-(4-{4-[Acetyl-(4-chloro-phenyl)-amino]-2-methyl-3,4-dihydro-2H-quinoline-1-carbonyl}-phenyl)-carbamic acid ethyl ester (C-22)

(2S,4R)-(4-{4-[Acetyl-(4-chloro-phenyl)-amino]-2-methyl-3,4-dihydro-2H-quinoline-1-carbonyl}-phenyl)-carbamic acid ethyl ester was prepared following general procedure C, substituting (4-chlorocarbonyl-phenyl)-carbamic acid ethyl ester for 4-fluorobenzoyl chloride.

$^1$H-NMR (CDCl$_3$) δ: 1.1 (3H, m), 1.3 (4H, m), 2.0 (3H, s), 2.3 (1H, m), 4.2 (2H, m), 4.8 (1H, m), 5.6 (1H, br), 6.5 (1H, d), 6.9 (1H, m), 7.1-7.3 (8H, m), 7.4 (2H, d).

MS m/z: 506 (M+1).

(2S,4R)-N-(4-Chloro-phenyl)-N-[2-methyl-1-(4-oxazol-5-yl-benzoyl)-1,2,3,4-tetrahydro-quinolin-4-yl]-acetamide (C-24)

(2S,4R)-N-(4-Chloro-phenyl)-N-[2-methyl-1-(4-oxazol-5-yl-benzoyl)-1,2,3,4-tetrahydro-quinolin-4-yl]-acetamide was prepared following general procedure C, substituting 4-oxazol-5-yl-benzoyl chloride for 4-fluorobenzoyl chloride.

$^1$H-NMR (CDCl$_3$) δ: 1.2 (3H, m), 1.3 (1H, m), 2.1 (3H, s), 2.3 (1H, m), 4.8 (1H, m), 5.6 (1H, br), 6.5 (1H, d), 6.9 (1H, m), 7.1-7.3 (8H, m), 7.4 (1H, d), 7.5 (2H, d), 7.9 (1H, s).

MS m/z: 486 (M+1).

(2S,4R)-N-(3,4-Dichloro-phenyl)-N-[1-(4-methoxy-benzoyl)-2-methyl-1,2,3,4-tetrahydro-quinolin-4-yl]-acetamide (C-25)

(2S,4R)-N-(3,4-Dichloro-phenyl)-N-[1-(4-methoxy-benzoyl)-2-methyl-1,2,3,4-tetrahydro-quinolin-4-yl]-acetamide was made following general procedure C, substituting 3,4-dichlorophenylboronic acid for 4-chlorophenylboronic acid and 4-methoxybenzoyl chloride for 4-fluorobenzoyl chloride.

$^1$H-NMR (CDCl$_3$) δ: 1.2 (3H, m), 1.3 (1H, m), 2.0 (3H, s), 2.3 (1H, m), 3.7 (3H, s), 4.8 (1H, m), 5.6 (1H, br), 6.6 (1H, d), 6.7 (2H, d), 7.0 (1H, m), 7.2 (3H, m), 7.3 (2H, d), 7.4 (1H, s), 7.5 (1H, d).

MS m/z: 483 (M+1).

(2S,4R)-N-(2,3-Dihydro-benzo[1,4]dioxin-6-yl)-N-[1-(4-methoxy-benzoyl)-2-methyl-1,2,3,4-tetrahydro-quinolin-4-yl]-acetamide (C-26)

(2S,4R)-N-(2,3-Dihydro-benzo[1,4]dioxin-6-yl)-N-[1-(4-methoxy-benzoyl)-2-methyl-1,2,3,4-tetrahydro-quinolin-4-yl]-acetamide was made following general procedure C, substituting 2,3-dihydro-benzo[1,4]dioxine-6-carboxylic acid for 4-chlorophenylboronic acid and 4-methoxyphenylbenzoyl chloride for 4-fluorobenzoyl chloride.

$^1$H-NMR (CDCl$_3$) δ: 1.2 (3H, m), 1.3 (1H, m), 2.0 (3H, s), 2.4 (1H, m), 3.7 (3H, s), 4.3 (4H, s), 4.8 (1H, m), 5.6 (1H, br), 6.5 (1H, d), 6.68 (2H, d), 6.7-6.9 (3H, m), 7.10-7.3 (5H, m).

MS m/z: 474 (M+2).

(2S,4R)-N-[1-(4Methoxy-benzoyl)-2-methyl-1,2,3,4-tetrahydro-quinolin-4-yl]-N-p-tolyl-acetamide (C-27)

(2S,4R)-N-[1-(4-Methoxy-benzoyl)-2-methyl-1,2,3,4-tetrahydro-quinolin-4-yl]-N-p-tolyl-acetamide was prepared following general procedure C, substituting 4-methoxybenzoyl chloride for 4-fluorobenzoyl chloride and 4-toluene boronic acid for 4-chlorophenylboronic acid $^1$H-NMR (CDCl3) δ: 1.15 (3H, d; overlapping 1H, t), 2.01 (3H, s), 2.33-2.36 (overlapping 1H, m, 1H, s), 3.73 (3H, s), 4.70 (1H, m), 5.65 (1H, m), 6.50 (1H, d), 6.68 (2×1H, d), 6.95 (1H, t), 7.00-7.40 (8H, m).

MS m/z: 429 (M+1).

(2S,4R)-N-(4-Chloro-phenyl)-N-[2-methyl-1-(4-pyrrolidin-1-yl-benzoyl)-1,2,3,4-tetrahydro-quinolin-4-yl]-acetamide (C-28)

(2S,4R)-N-(4-Chloro-phenyl)-N-[2-methyl-1-(4-pyrrolidin-1-yl-benzoyl)-1,2,3,4-tetrahydro-quinolin-4-yl]-acetamide was prepared following general procedure C, substituting 4-pyrrolidin-1-yl-benzoyl chloride for 4-fluorobenzoyl chloride.

$^1$H-NMR (CDCl$_3$) δ: 1.11-1.15 (4H, m), 1.94-1.98 (4H, m), 2.03 (3H, s), 2.24-2.34 (1H, m), 3.21-3.25 (4H, m), 4.68-4.75 (1H, m), 5.61-5.65 (1H, br), 6.30 (2H, d), 6.63 (1H, d), 6.92-7.52 (9H, m).

MS m/z: 488 (M+1).

(2S,4R)-N-(4-Chloro-phenyl)-N-[1-(1-isopropyl-1H-benzotriazole-5-carbonyl)-2-methyl-1,2,3,4-tetrahydro-quinolin-4-yl]-acetamide (C-29)

(2S,4R)-N-(4-Chloro-phenyl)-N-[1-(1-isopropyl-1H-benzotriazole-5-carbonyl)-2-methyl-1,2,3,4-tetrahydro-quinolin-4-yl]-acetamide was made following general procedure C, substituting 1-isopropyl-1H-benzotriazole-5-carbonyl chloride for 4-fluorobenzoyl chloride.

$^1$H-NMR (CDCl$_3$) δ: 1.19-1.27 (4H, m), 1.68 (6H, m), 2.04 (3H, s), 2.30-2.40 (1H, m), 4.83 (1H, q), 4.98 (1H, q) 5.45-5.55 (1H, br), 6.48 (1H, d), 6.83 (1H, t), 7.10-7.41 (8H, m), 8.13 (1H, br).

MS m/z: 503 (M+1).

(2S,4R)-N-(4-Chloro-phenyl)-N-{1-[4-(1-hydroxy-1-methyl-ethyl)-benzoyl]-2-methyl-1,2,3,4-tetrahydro-quinolin-4-yl}-acetamide (C-30)

(2S,4R)-N-(4-Chloro-phenyl)-N-{1-[4-(1-hydroxy-1-methyl-ethyl)-benzoyl]-2-methyl-1,2,3,4-tetrahydro-quinolin-4-yl}-acetamide was prepared from (2S,4R)-N-[1-(4-acetyl-benzoyl)-2-methyl-1,2,3,4-tetrahydro-quinolin-4-yl]-N-(4-chloro-phenyl)-acetamide. (2S,4R)-N-[1-(4-Acetyl-benzoyl)-2-methyl-1,2,3,4-tetrahydro-quinolin-4-yl]-N-(4-chloro-phenyl)-acetamide (112 mg, 124 mmol) was dissolved in THF (5 mL) and cooled to 0° C. Methyl magnesium bromide (1.4 M in ether, 2 mL, 2.4 mmol) was added and the mixture stirred at 0° C. for 2 h. The reaction was warmed to rt and stirred an additional 2 h. The reaction was poured into saturated aqueous ammonium chloride. The phases were separated and the aqueous was extracted with ethyl acetate. The extracts were washed with brine, dried over magnesium sulfate, filtered, dried and concentrated. The crude alcohol was purified by silica gel chromatography to afford pure product (20 mg, 24%).

$^1$H-NMR (CDCl$_3$) δ: 1.12-1.21 (4H, m), 1.48 (6H, d), 2.02 (3H, s), 2.25-2.34 (1H, m), 4.70-4.80 (1H, m), 5.45-5.54 (1H, br), 6.50 (1H, d), 6.88 (1H, t), 7.11-7.38 (10H, m).

MS m/z: 478 (M+1).

(2S,4R)-N-(4-Chloro-phenyl)-N-[1-(3-ethoxy-isoxazole-5-carbonyl)-2-methyl-1,2,3,4-tetrahydro-quinolin-4-yl]-acetamide (C-31)

(2S,4R)-N-(4-Chloro-phenyl)-N-[1-(3-ethoxy-isoxazole-5-carbonyl)-2-methyl-1,2,3,4-tetrahydro-quinolin-4-yl]-acetamide was prepared following general procedure C, substituting 3-ethoxy-isoxazole-5-carbonyl chloride for 4-fluorobenzoyl chloride.

$^1$H-NMR (CDCl$_3$) δ: 1.16 (3H, d), 1.33 (3H, t), 1.69 (1H, br s), 2.00 (3H, s), 2.21-2.38 (1H, m), 4.21 (2H, q), 4.66-4.73 (1H, m), 5.65 (1H, s), 6.86 (1H, d), 7.13-7.39 (8H, m).

MS m/z: 454 (M).

(2S,4R)-3-(4-{4-[Acetyl-(4-chloro-phenyl)-amino]-2-methyl-3,4-dihydro-2H-quinoline-1-carbonyl}-phenyl)-propionic acid (C-32)

(2S,4R)-3-(4-{4-[Acetyl-(4-chloro-phenyl)-amino]-2-methyl-3,4-dihydro-2H-quinoline-1-carbonyl}-phenyl)-propionic acid was prepared from (2S,4R)-3-(4-{4-[acetyl-(4-chloro-phenyl)-amino]-2-methyl-3,4-dihydro-2H-quinoline-1-carbonyl}-phenyl)-acrylic acid. A solution of (2S,4R)-3-(4-{4-[acetyl-(4-chloro-phenyl)-amino]-2-methyl-3,4-dihydro-2H-quinoline-1-carbonyl}-phenyl)-acrylic acid (50 mg, 0.102 mmol) in EtOH (2 ml) and CH$_2$Cl$_2$ (10 drops for solubility) was subjected to Pd-C (10%, ca. 50 mg) and 1 atm H$_2$ gas. After 1 hour, the mixture was filtered, concentrated and subjected to silica gel chromatography (2% MeOH in EtOAc to 10% MeOH in EtOAc), to afford the title compound (50 mg, 99%).

$^1$H-NMR (CDCl$_3$ 300 MHz) δ 1.09 (3H, d), 1.17-1.18 (1H, m), 2.00 (3H, s), 2.20-2.35 (1H, m), 2.46-2.60 (2H, m), 2.80-2.90 (2H, m), 4.65-4.80 (1H, m), 5.40-5.71 (1H, m), 6.48 (1H, d), 6.89 (1H, t), 7.0 (2H, d), 7.12 (2H, d), 7.20-7.48 (5H, m), 7.72 (1H, d).

MS m/z: 322 (M-C$_8$H$_7$NO).

(2S,4R)-3-(4-{4-[Acetyl-(4-chloro-phenyl)-amino]-2-methyl-3,4-dihydro-2H-quinoline-1-carbonyl}-phenyl)-acrylic acid (C-33)

(2S,4R)-3-(4-{4-[Acetyl-(4-chloro-phenyl)-amino]-2-methyl-3,4-dihydro-2H-quinoline-1-carbonyl}-phenyl)-acrylic acid was prepared following general procedure C, substituting 3-(4-chlorocarbonyl-phenyl)-acrylic acid methyl ester for 4-fluorobenzoyl chloride. The ester was hydrolyzed as follows. To a solution of (2S,4R)-3-(4-{4-[acetyl-(4-chloro-phenyl)-amino]-2-methyl-3,4-dihydro-2H-quinoline-1-carbonyl}-phenyl)-acrylic acid methyl ester (112 mg, 0.239 mmol) in THF/MeOH (2 ml, 2 ml) was added LiOH (4 ml: 1.0 M in $H_2O$). Upon consumption of the starting unit (1 hour), the mixture was neutralized with aq. HCl (1.0 M), partioned with EtOAc (10 ml) and separated. The organic layer was separated and concentrated whereby the resulting oil was subjected to silica gel chromatography (2% MeOH in EtOAc to 10% MeOH in EtOAc) to afford the title compound (110 mg, 99%).

$^1$H-NMR (MeOD, 300 MHz) δ 0.85-0.95 (1H, m), 1.12 (3H, d), 2.04 (3H, s), 2.40-2.53 (1H, m), 4.70-4.80 (1H, m), 5.50-5371 (1H, m), 6.46 (1H, d), 6.57 (1H, d), 6.96 (1H, t), 7.20-7.55 (8H, m), 7.60 (2H, d), 7.81 (1H, d).

MS m/z: 320 (M-$C_8H_7NO$).

(2S,4R)-N-[1-(4-Methoxy-benzoyl)-2-methyl-1,2,3,4-tetrahydro-quinolin-4-yl]-N-(4-methoxy-phenyl)-acetamide (C-34)

(2S,4R)-N-[1-(4-Methoxy-benzoyl)-2-methyl-1,2,3,4-tetrahydro-quinolin-4-yl]-N-(4-methoxy-phenyl)-acetamide was prepared following general procedure C, substituting 4-methoxybenzoyl chloride for 4-fluorobenzoyl chloride and 4-methoxyphenylboronic acid for 4-chlorophenylboronic acid.

$^1$H-NMR ($CDCl_3$ 300 MHz) δ 1.12 (3H, d), 1.20-1.23 (1H, m), 2.09 (3H, s), 2.30-2.42 (1H, m), 3.71 (3H, s), 3.81 (3H, s) 4.70-4.81 (1H, m), 5.50-5.80 (1H, m), 6.52 (1H, d), 6.67 (2H, d), 6.80-6.94 (4H, m), 7.10-7.40 (5H, m).

MS m/z: 280 (M-$C_9H_{10}NO_2$).

(2S,4R)-N-(4-Isopropyl-phenyl)-N-[1-(4-methoxy-benzoyl)-2-methyl-1,2,3,4-tetrahydro-quinolin-4-yl]-acetamide (C-35)

(2S,4R)-N-(4-Isopropyl-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride and 4-isopropylphenylboronic acid for 4-chlorophenylboronic acid.

$^1$H-NMR ($CDCl_3$ 300 MHz) δ 1.21 (6H, d), 1.20-1.23 (1H, m), 1.23 (3H, d), 2.09 (3H, s), 2.30-2.42 (1H, m), 2.80-2.95 (1H, m), 3.74 (3H, s), 4.65-4.83 (1H, m), 5.50-5.80 (1H, m), 6.53 (1H, d), 6.67 (2H, d), 6.72 (2H, d), 6.92 (1H, t), 7.02-7.12 (3H, m), 7.21 (2H, d), 7.38 (1H, d).

MS m/z: 280 (M-$C_{11}H_{14}NO$).

(2S,4R)-N-(4-Bromo-phenyl)-N-[1-(4-methoxy-benzoyl)-2-methyl-1,2,3,4-tetrahydro-quinolin-4-yl]-acetamide (C-36)

(2S,4R)-N-(4-Bromo-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride and 4-bromophenylboronic acid for 4-chlorophenylboronic acid.

$^1$H-NMR ($CDCl_3$ 300 MHz) δ 1.12 (3H, d), 1.20-1.24 (1H, m), 2.05 (3H, s), 2.20-2.38 (1H, m), 3.72 (3H, s), 4.66-4.81 (1H, m), 5.50-5.75 (1H, m), 6.52 (1H, d), 6.67 (2H, d), 6.92 (1H, t), 7.10-7.18 (5H, m), 7.26 (1H, t), 7.48-7.58 (2H, m).

MS m/z: 493 (M+1).

(2S,4R)-4-{Acetyl-[1-(4-methoxy-benzoyl)-2-methyl-1,2,3,4-tetrahydro-quinolin-4-yl]-amino}-benzoic acid (C-37)

(2S,4R)-4-{Acetyl-[1-(4-methoxy-benzoyl)-2-methyl-1,2,3,4-tetrahydro-quinolin-4-yl]-amino}-benzoic acid was made from (2S,4R)-4-{acetyl-[1-(4-methoxy-benzoyl)-2-methyl-1,2,3,4-tetrahydro-quinolin-4-yl]-amino}-benzoic acid methyl ester. (2S,4R)-4-{acetyl-[1-(4-methoxy-benzoyl)-2-methyl-1,2,3,4-tetrahydro-quinolin-4-yl]-amino}-benzoic acid methyl ester prepared following general procedure C, substituting 4-methoxybenzoyl chloride for 4-fluorobenzoyl chloride and 4-phenylboronic acid methyl ester for 4-chlorophenylboronic acid. (2S,4R)-4-{acetyl-[1-(4-methoxy-benzoyl)-2-methyl-1,2,3,4-tetrahydro-quinolin-4-yl]-amino}-benzoic acid methyl ester was converted to the acid using the following procedure. To a solution of 4-{acetyl-[1-(4-methoxy-benzoyl)-2-methyl-1,2,3,4-tetrahydro-quinolin-4-yl]-amino}-benzoic acid methyl ester (10 mg, 0.038 mmol) in 4 ml methanol was added 100 mg $K_2CO_3$ (0.72 mmol, in 0.5 ml water). The resulting reaction mixture was stirred at room temperature overnight. The methanol was removed under vacuum. 1M HCl was added until the mixture is acidic. Dichloromethane (20 ml) and 5 ml water was added. Organic layer was dried with magnesium sulfate. Dichloromethane was removed under vacuum to give the title compound (15 mg, 86%)

$^1$H-NMR ($CDCl_3$) δ: 1.1 (3H, d), 1.1 (1H, m), 2.0 (3H, s), 2.3 (1H, m), 3.8 (3H, s), 4.8 (1H, m), 5.6 (1H, m), 6.5 (1H, d), 6.6 (2H, d), 6.9 (1H, t), 7.1-7.4 (6H, m), 8.1 (2H, d).

MS m/z: 460 (M+2).

(2S,4R)-N-(3-Aminomethyl-phenyl)-N-[1-(4-methoxy-benzoyl)-2-methyl-1,2,3,4-tetrahydro-quinolin-4-yl]-acetamide (C-38)

(2S,4R)-N-(3-Aminomethyl-phenyl)-N-[1-(4-methoxy-benzoyl)-2-methyl-1,2,3,4-tetrahydro-quinolin-4-yl]-acetamide was prepared from (2S,4R)-N-(3-cyano-phenyl)-N-[1-(4-methoxy-benzoyl)-2-methyl-1,2,3,4-tetrahydro-quinolin-4-yl]-acetamide. (2S,4R)-N-(3-cyano-phenyl)-N-[1-(4-methoxy-benzoyl)-2-methyl-1,2,3,4-tetrahydro-quinolin-4-yl]-acetamide was prepared following standard procedure C, substituting 3-cyanophenylboronic acid for 4-fluorobenzoyl chloride. To a mixture of (2S,4R)-N-(3-cyano-phenyl)-N-[1-(4-methoxy-benzoyl)-2-methyl-1,2,3,4-tetrahydro-quinolin-4-yl]-acetamide (48 mg, 0.11 mmol) in 2 ml ethanol was added cobalt chloride (14 mg, 0.11 mmol). Sodium borohydride (12 mg, 0.33 mmol) was added at 0° C., and the temperature was held at 0° for 30 min. The mixture was then warmed to rt, and stirred overnight. The reaction was quenched by adding saturated aqueous ammonium chloride. The separated aqueous layer was extracted with ethyl acetate. The combined extracts were washed with water and brine, dried over magnesium sulfate, filtered and concentrated under reduced pressure. The crude oil was purified by HPLC to give the title compound (10 mg, 10%).

$^1$H-NMR ($CDCl_3$) δ: 1.1-1.2 (4H, m), 2.0 (3H, s), 2.3 (1H, m), 3.4 (2H, br), 3.8 (3H, s), 4.3 (1H, d), 4.8 (2H, d), 5.6 (1H, br), 6.4 (1H, m), 6.6 (2H, m), 6.9 (1H, m), 7.1-7.4 (8H, m).

MS m/z: 444 (M+1)

(2S,4R)-N-(4-Butyl-phenyl)-N-[1-(4-methoxy-benzoyl)-2-methyl-1,2,3,4-tetrahydro-quinolin-4-yl]-acetamide (C-39)

(2S,4R)-N-(4-Butyl-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride and 4-butylphenylboronic acid for 4-chlorophenylboronic acid.

$^1$H-NMR (CDCl$_3$) δ: 0.9 (3H, m), 1.2 (3H, d), 1.4 (3H, m), 1.6 (2H, m), 2.0 (3H, s), 2.4 (1H, m), 2.6 (2H, m), 3.8 (3H, s), 4.8 (1H, m), 5.6 (1H, br), 6.5 (1H, d), 6.7 (2H, d), 7.0 (1H, m), 7.1-7.2 (7H, m), 7.4 (1H, d).
MS m/z: 471 (M+1).

Compounds C-40-C-147 can be prepared by the schemes set forth in Schemes 15-16 and by the general procedures C and others described herein. Those skilled in the art will be able to recognize, or be able to ascertain, using no more than routine experimentation, many equivalents to the specific embodiments of the invention described herein.

TABLE 3

Compounds Derived from General Procedure C

| No. | Structure |
|---|---|
| C-1 | 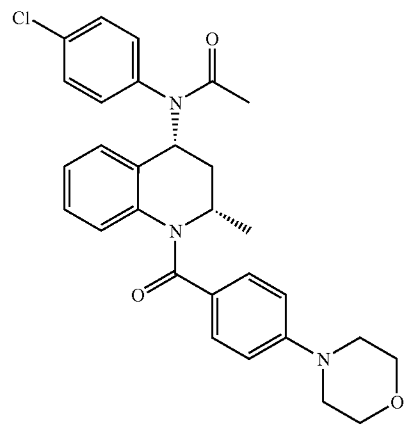 |
| C-2 | 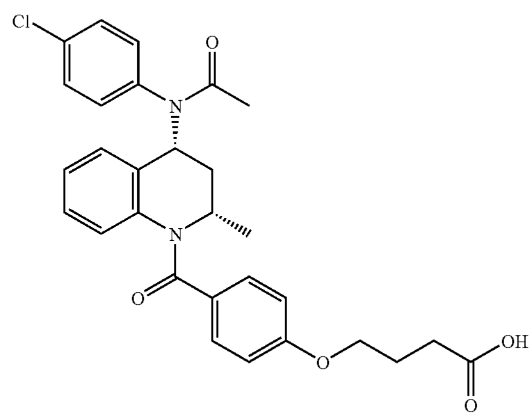 |
| C-3 | 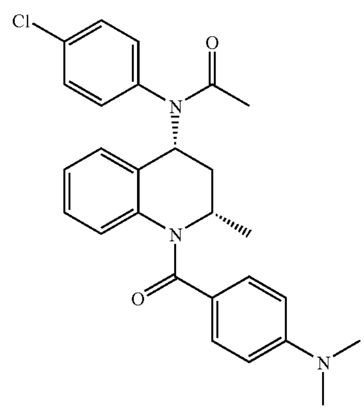 |

TABLE 3-continued
Compounds Derived from General Procedure C
| No. | Structure |
| --- | --- |
| C-4 | 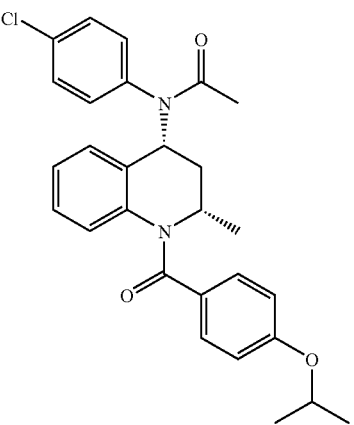 |
| C-5 | 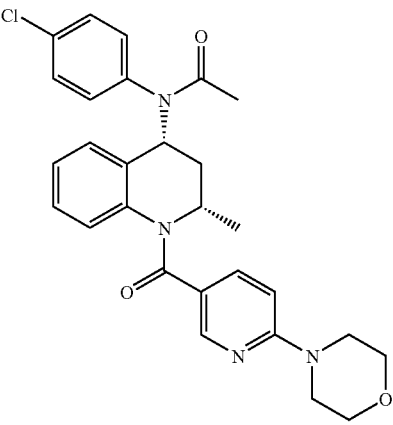 |
| C-6 | 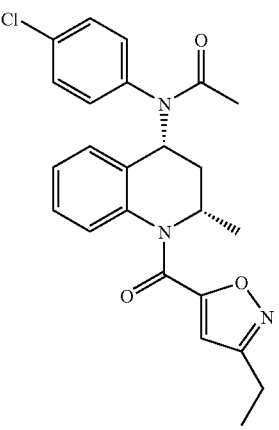 |

TABLE 3-continued

Compounds Derived from General Procedure C

| No. | Structure |
|---|---|
| C-7 | 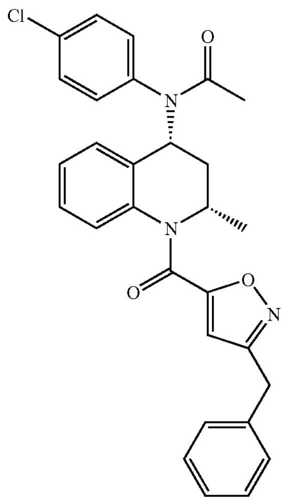 |
| C-8 | 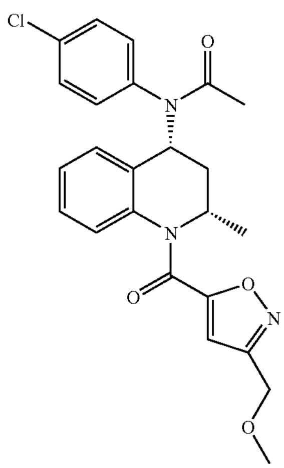 |
| C-9 | 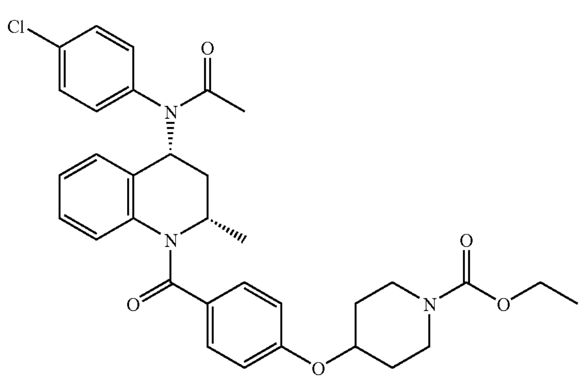 |

TABLE 3-continued

Compounds Derived from General Procedure C

| No. | Structure |
|---|---|
| C-10 | 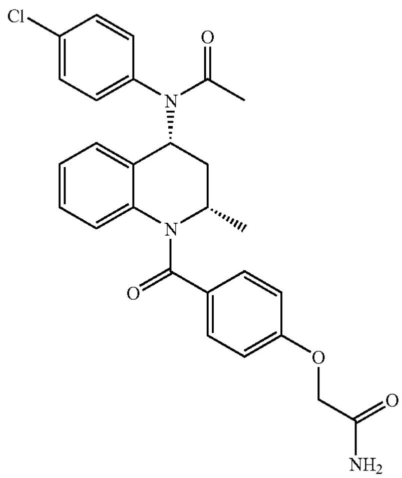 |
| C-11 | 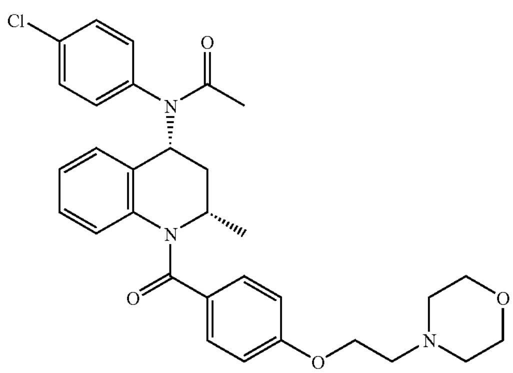 |
| C-12 | 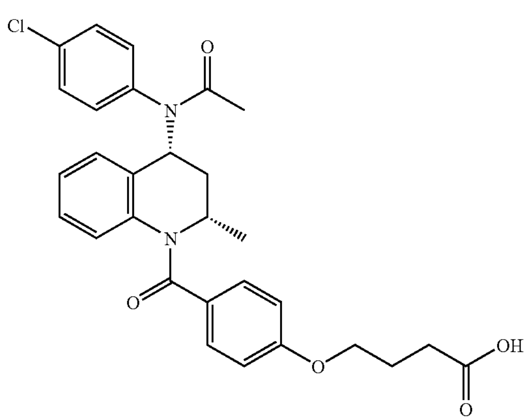 |

TABLE 3-continued
Compounds Derived from General Procedure C
| No. | Structure |
|---|---|
| C-13 | 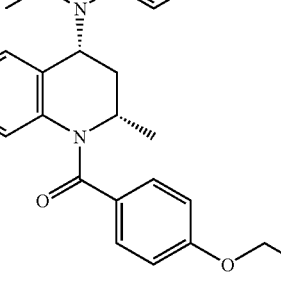 |
| C-14 | 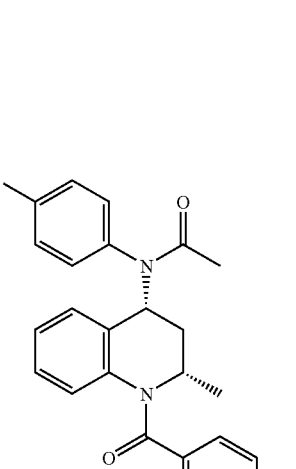 |
| C-15 | 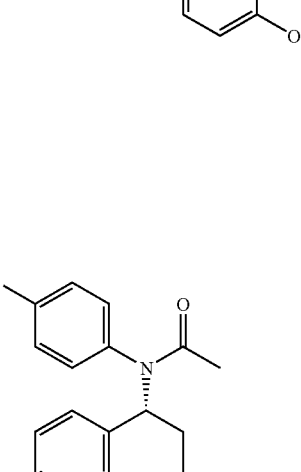 |

TABLE 3-continued

Compounds Derived from General Procedure C

| No. | Structure |
|-----|-----------|
| C-16 | 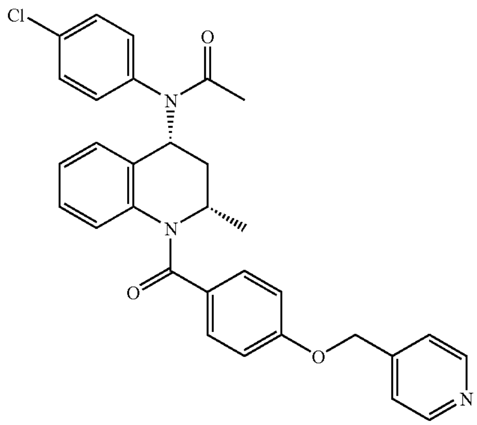 |
| C-17 | 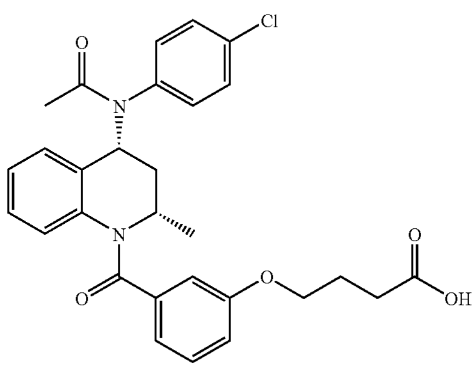 |
| C-18 | 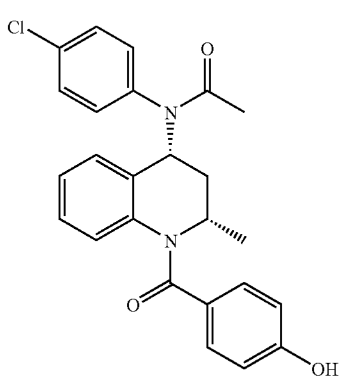 |

TABLE 3-continued
Compounds Derived from General Procedure C
| No. | Structure |
|---|---|
| C-19 | 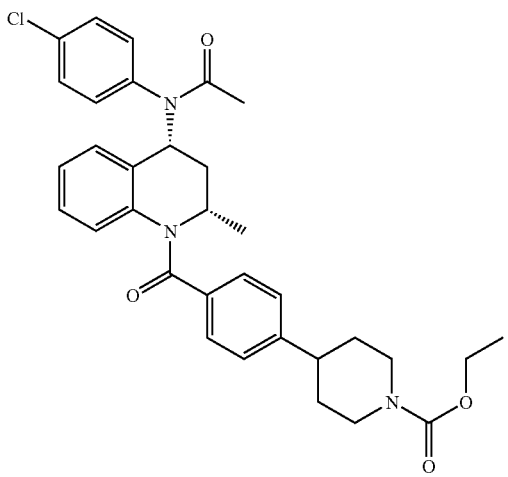 |
| C-20 | 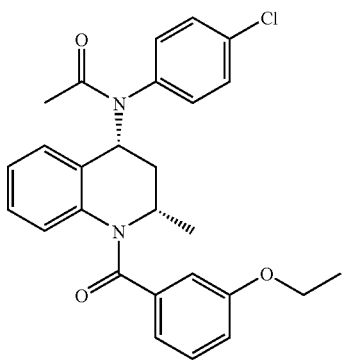 |
| C-21 | 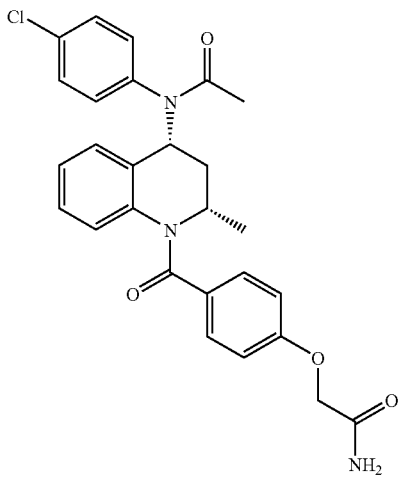 |

TABLE 3-continued
Compounds Derived from General Procedure C
| No. | Structure |
|---|---|
| C-22 | 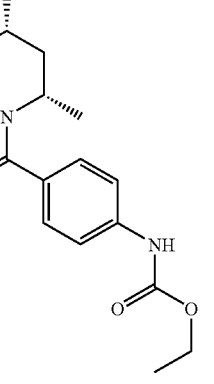 |
| C-23 | 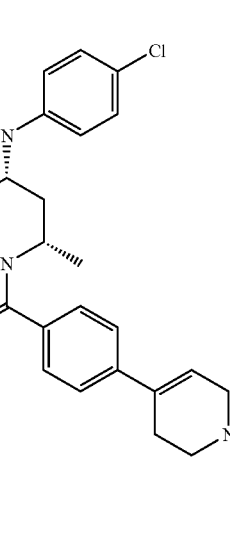 |
| C-24 | 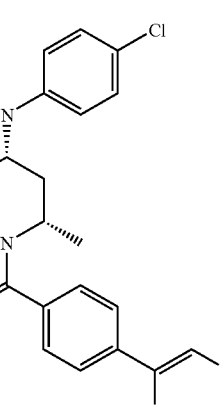 |

TABLE 3-continued
Compounds Derived from General Procedure C
| No. | Structure |
|---|---|
| C-25 | 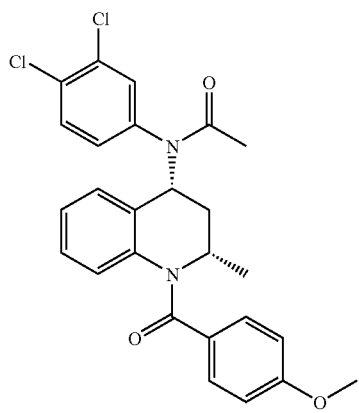 |
| C-26 | 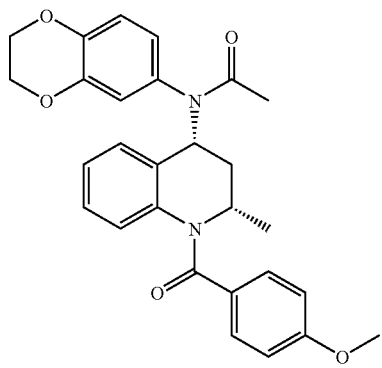 |
| C-27 | 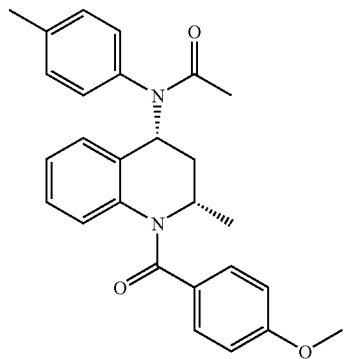 |

TABLE 3-continued
Compounds Derived from General Procedure C
| No. | Structure |
|---|---|
| C-28 | 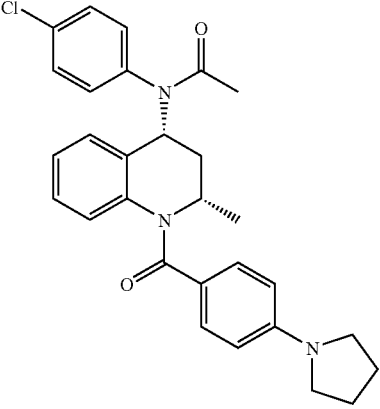 |
| C-29 | 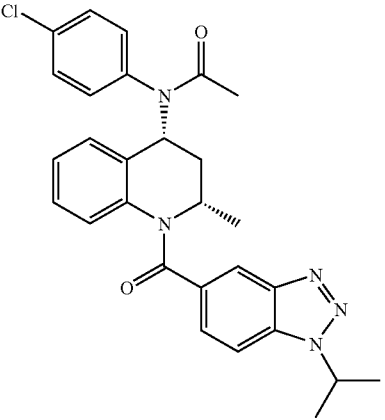 |
| C-30 | 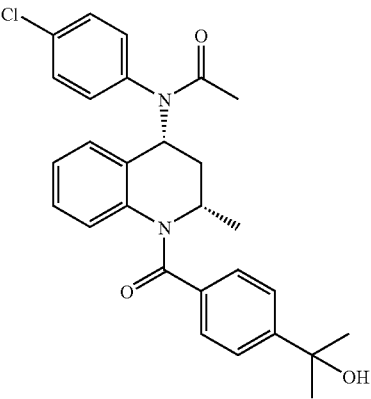 |

TABLE 3-continued
Compounds Derived from General Procedure C
| No. | Structure |
|---|---|
| C-31 | 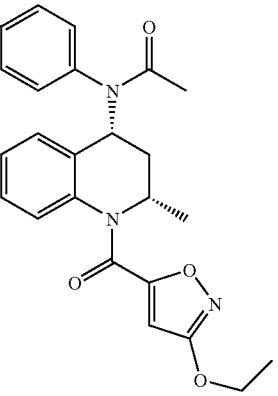 |
| C-32 | 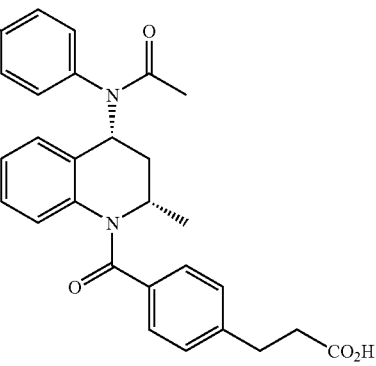 |
| C-33 | 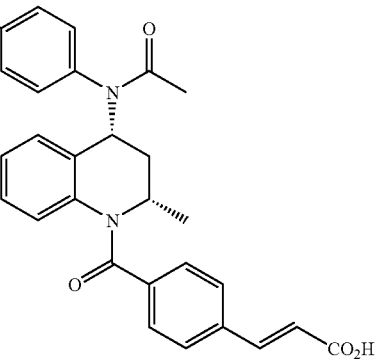 |
| C-34 | 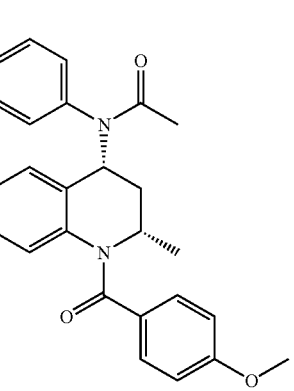 |

TABLE 3-continued
Compounds Derived from General Procedure C
| No. | Structure |
|---|---|
| C-35 | 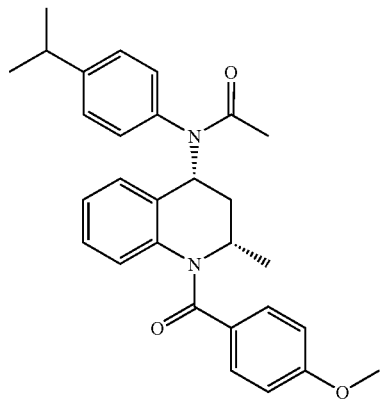 |
| C-36 | 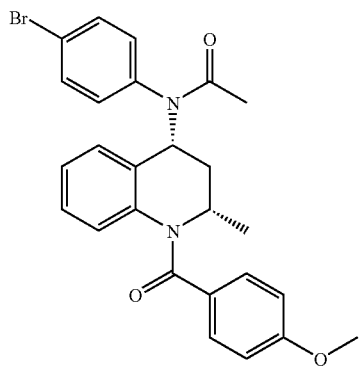 |
| C-37 | 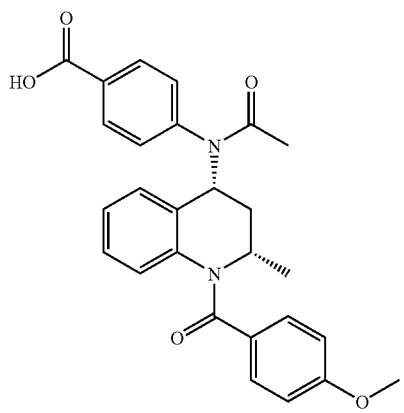 |

TABLE 3-continued

Compounds Derived from General Procedure C

| No. | Structure |
|---|---|
| C-38 | 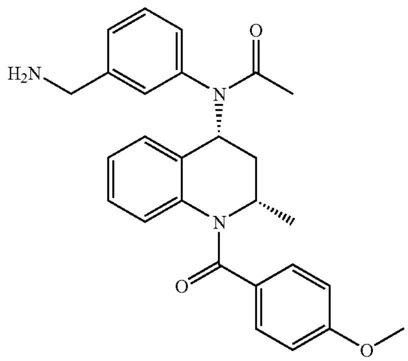 |
| C-39 | 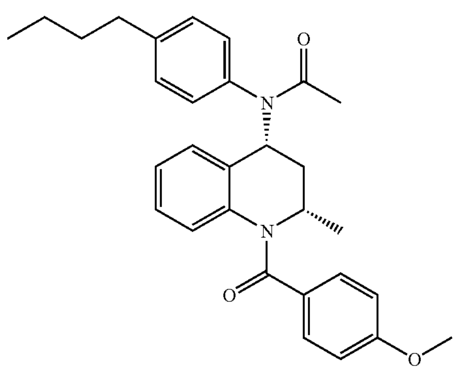 |
| C-40 | 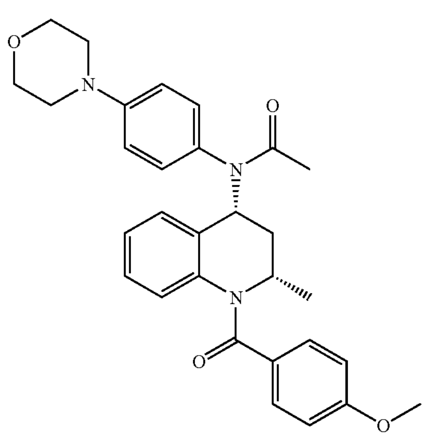 |

TABLE 3-continued
Compounds Derived from General Procedure C
| No. | Structure |
|---|---|
| C-41 | 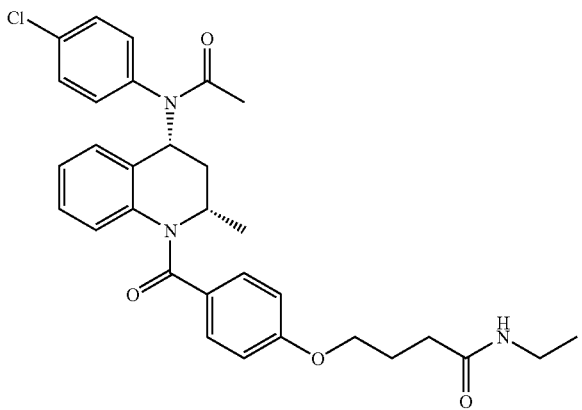 |
| C-42 | 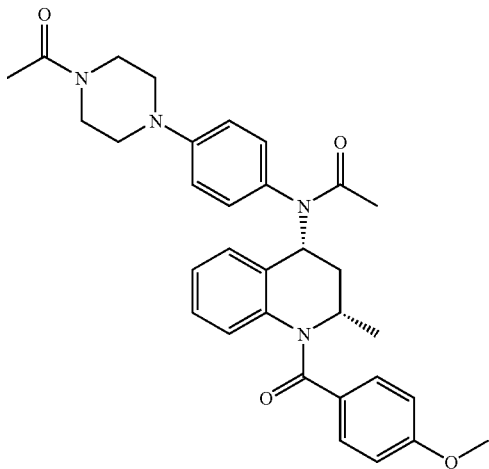 |
| C-43 | 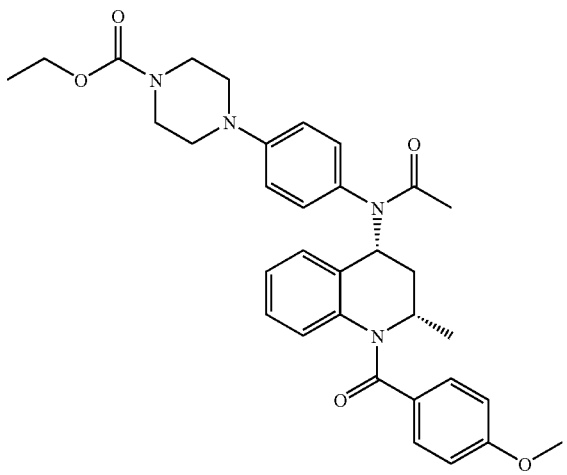 |

TABLE 3-continued
Compounds Derived from General Procedure C
| No. | Structure |
|---|---|
| C-44 | 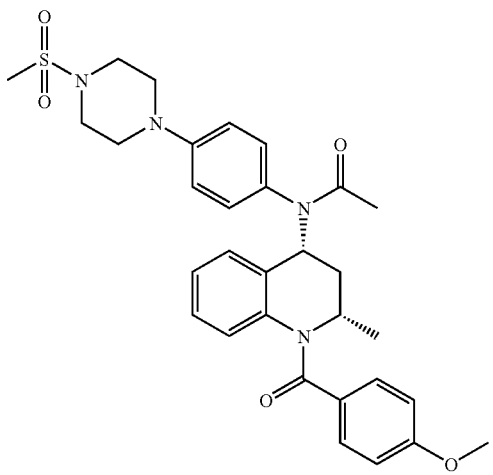 |
| C-45 | 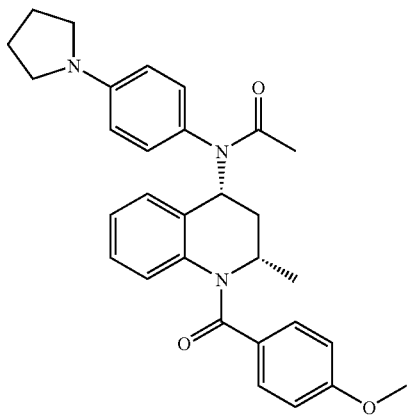 |
| C-46 | 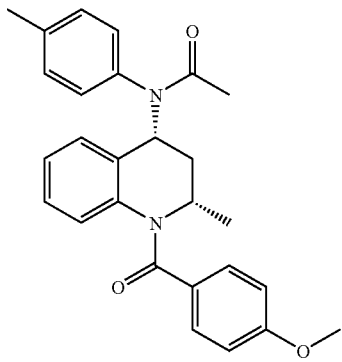 |

TABLE 3-continued

Compounds Derived from General Procedure C

| No. | Structure |
| --- | --- |
| C-47 | 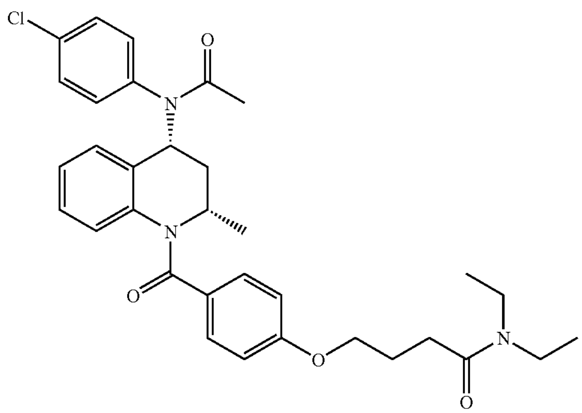 |
| C-48 | 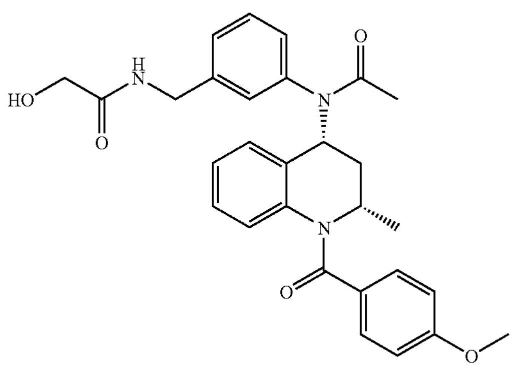 |
| C-49 | 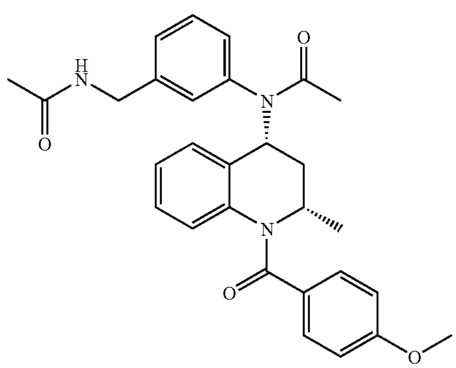 |
| C-50 | 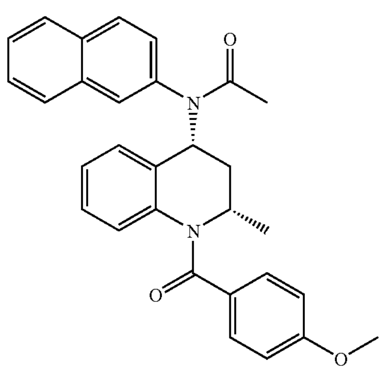 |

TABLE 3-continued
Compounds Derived from General Procedure C
| No. | Structure |
|-----|-----------|
| C-51 | 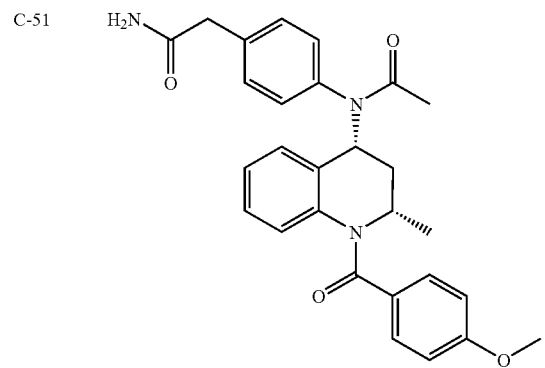 |
| C-52 | 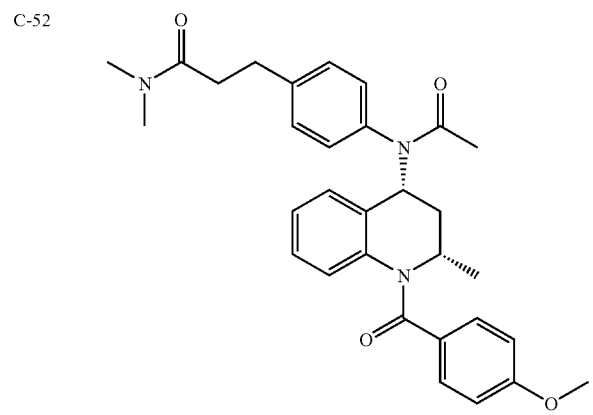 |
| C-53 | 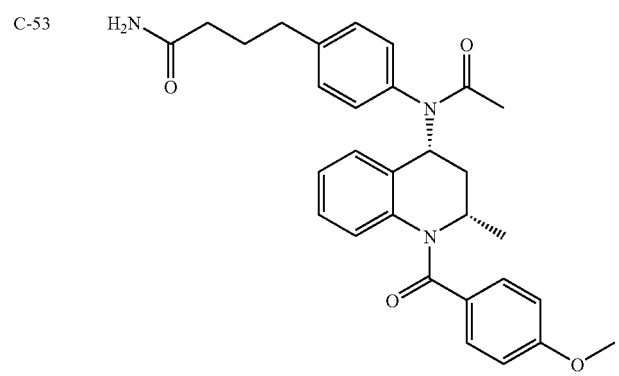 |

TABLE 3-continued
Compounds Derived from General Procedure C
| No. | Structure |
|---|---|
| C-54 | 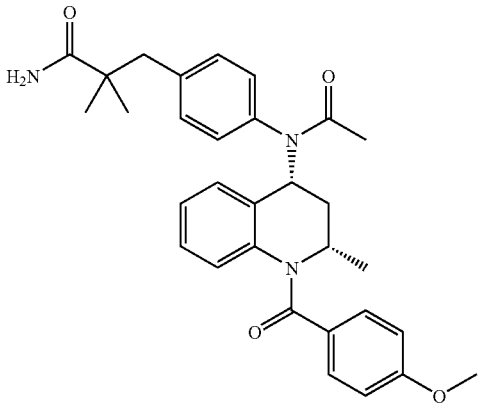 |
| C-55 | 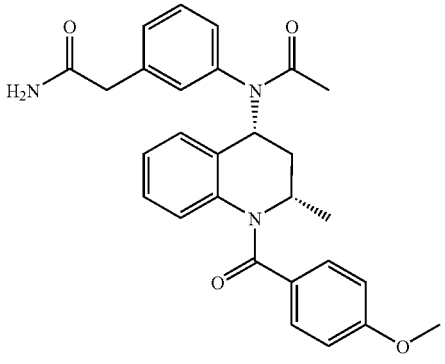 |
| C-56 | 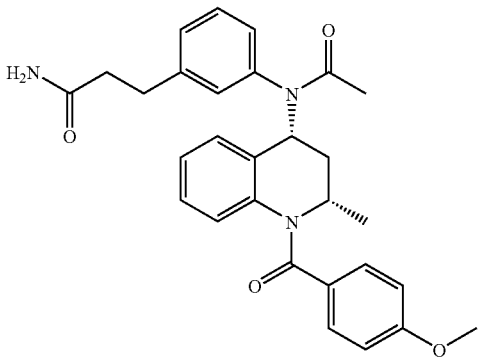 |
| C-57 | 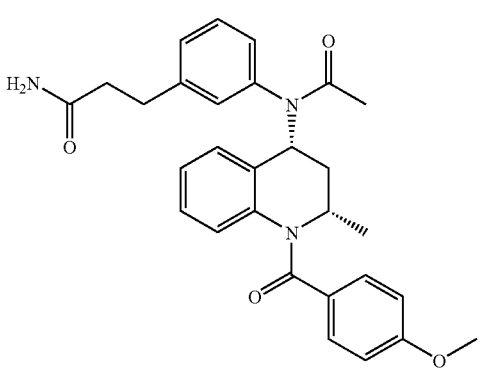 |

TABLE 3-continued

Compounds Derived from General Procedure C

| No. | Structure |
|---|---|
| C-58 | 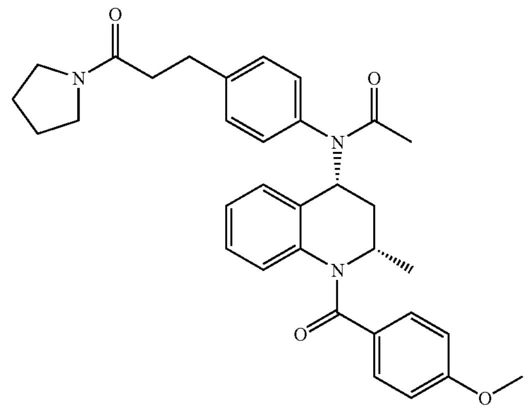 |
| C-59 | 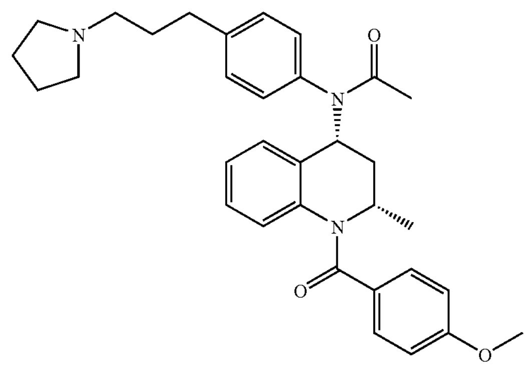 |
| C-60 | 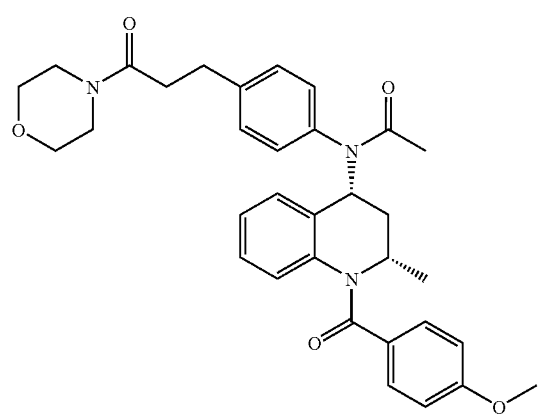 |
| C-61 | 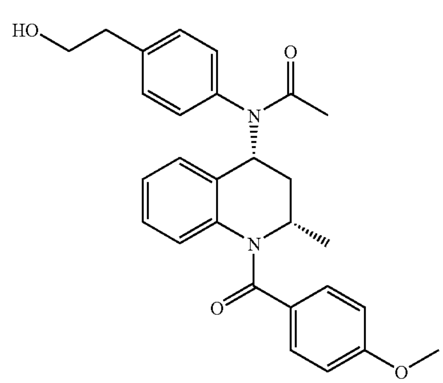 |

TABLE 3-continued
Compounds Derived from General Procedure C
| No. | Structure |
|---|---|
| C-62 | 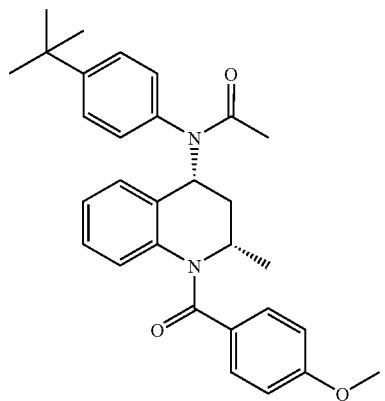 |
| C-63 | 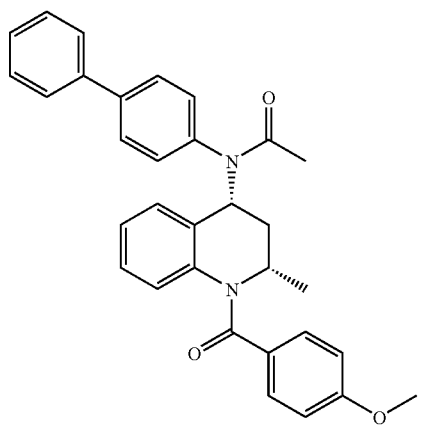 |
| C-64 | 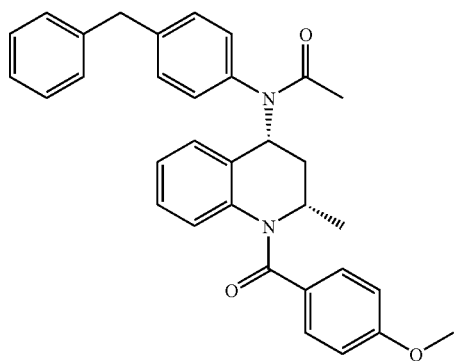 |

TABLE 3-continued

Compounds Derived from General Procedure C

| No. | Structure |
|---|---|
| C-65 | 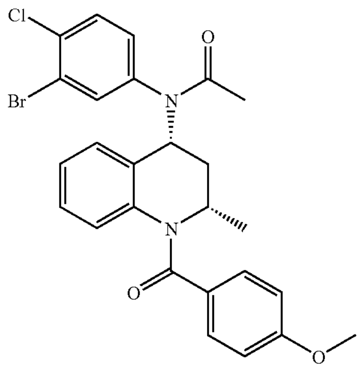 |
| C-66 | 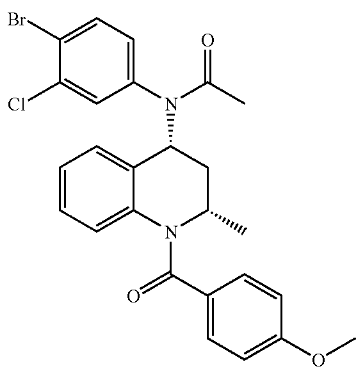 |
| C-67 | 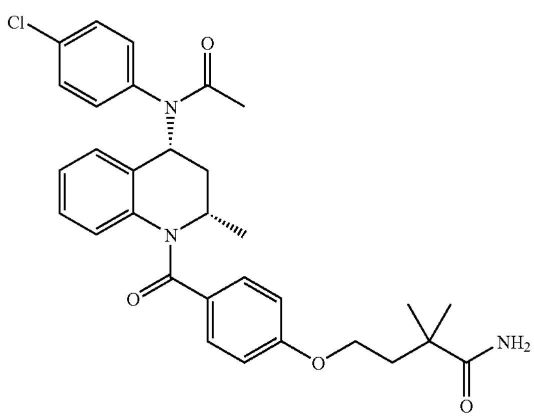 |
| C-68 | 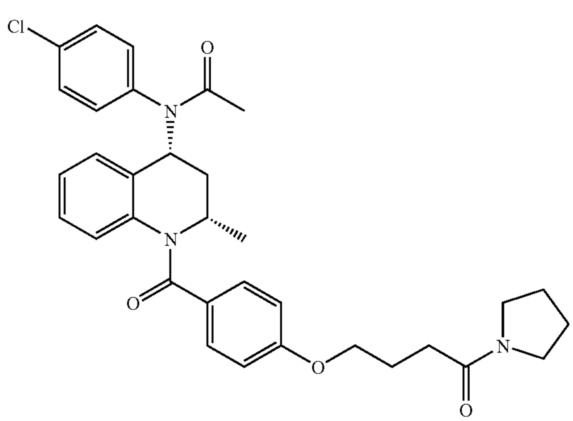 |

TABLE 3-continued
Compounds Derived from General Procedure C
| No. | Structure |
| --- | --- |
| C-69 | 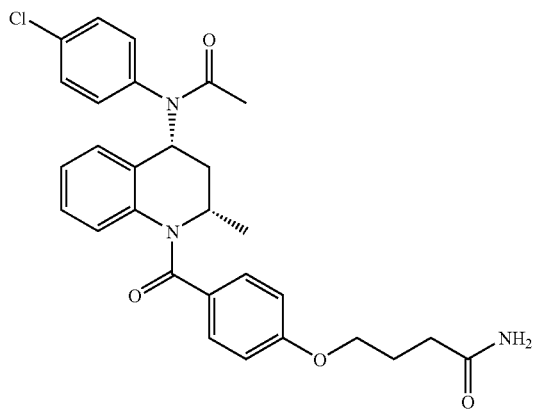 |
| C-70 | 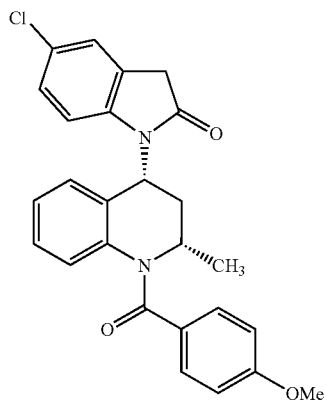 |
| C-71 | 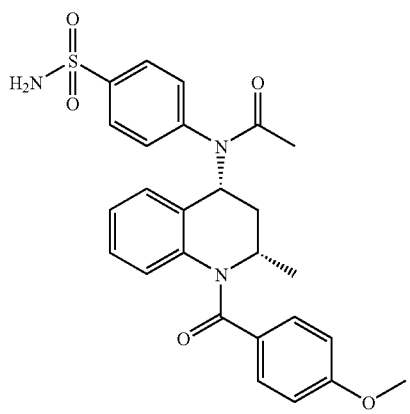 |

TABLE 3-continued
Compounds Derived from General Procedure C
| No. | Structure |
|-----|-----------|
| C-72 | 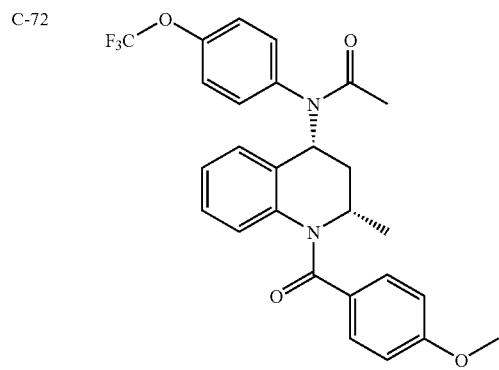 |
| C-73 | 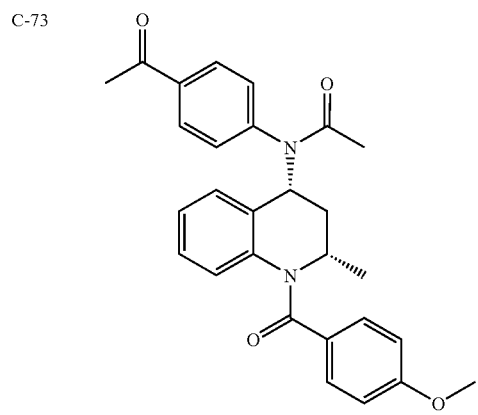 |
| C-74 | 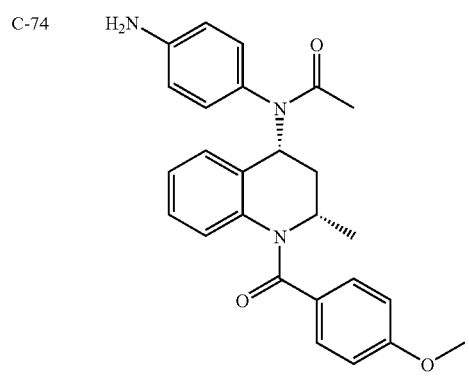 |

TABLE 3-continued
Compounds Derived from General Procedure C
| No. | Structure |
|---|---|
| C-75 | 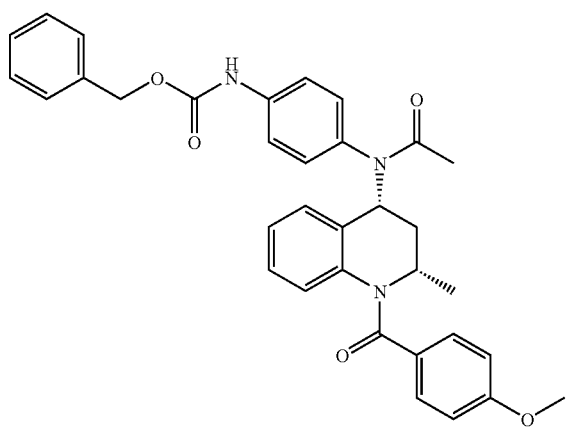 |
| C-76 | 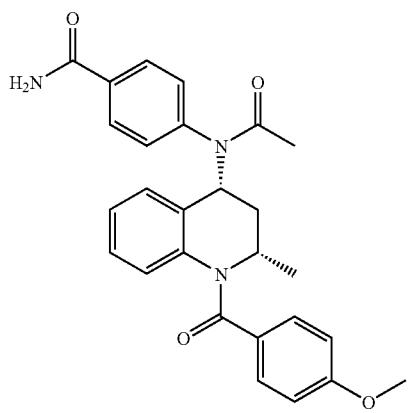 |
| C-77 | 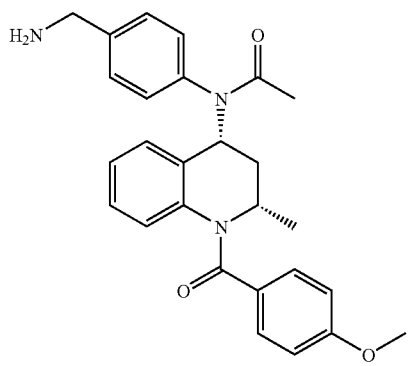 |

TABLE 3-continued
Compounds Derived from General Procedure C
| No. | Structure |
|---|---|
| C-78 | 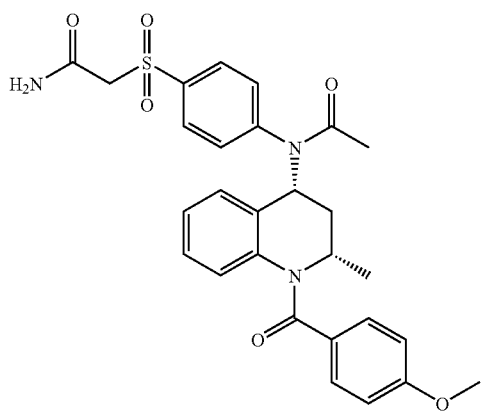 |
| C-79 | 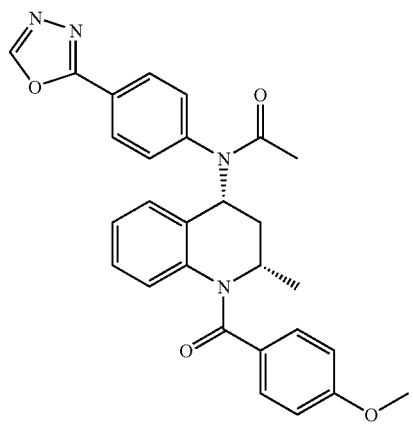 |
| C-80 | 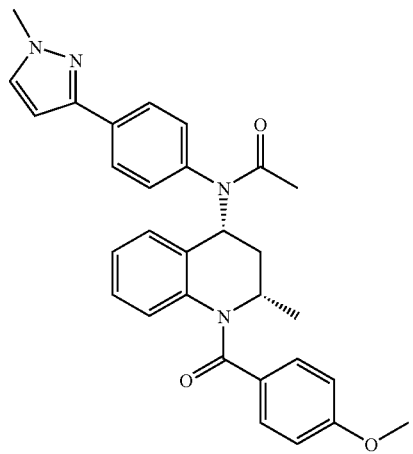 |

TABLE 3-continued

Compounds Derived from General Procedure C

| No. | Structure |
|---|---|
| C-81 | 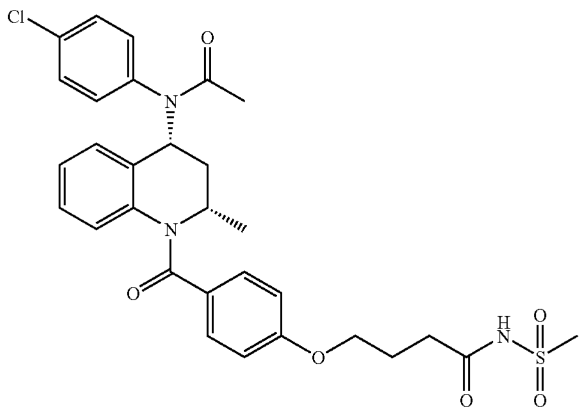 |
| C-82 | 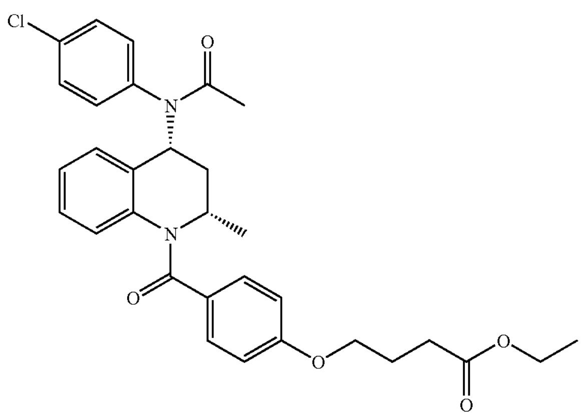 |
| C-83 | 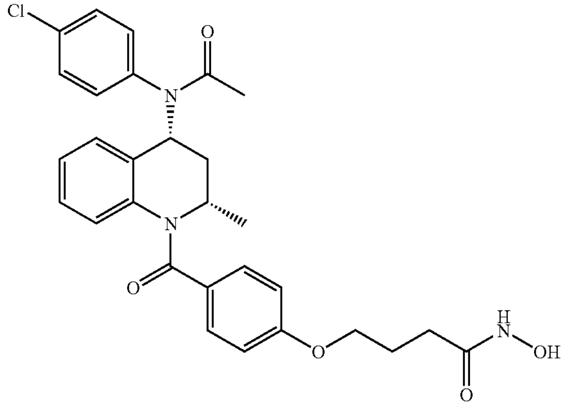 |

TABLE 3-continued

Compounds Derived from General Procedure C

| No. | Structure |
|---|---|
| C-84 | 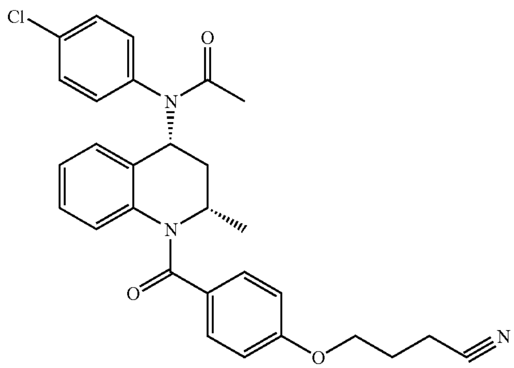 |
| C-85 | 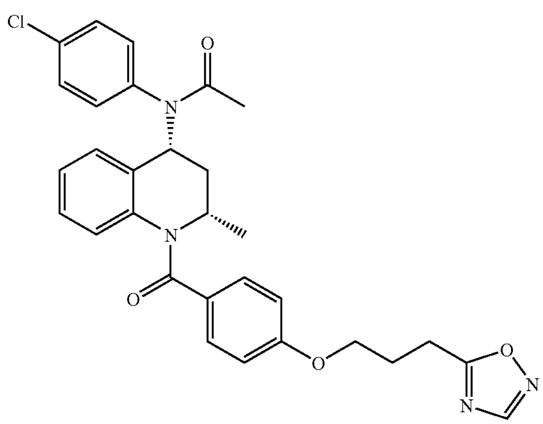 |
| C-86 | 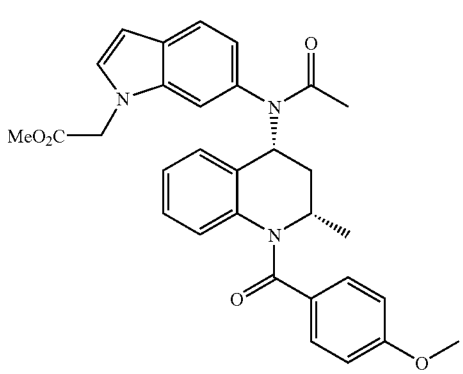 |

TABLE 3-continued
Compounds Derived from General Procedure C
| No. | Structure |
|---|---|
| C-87 | 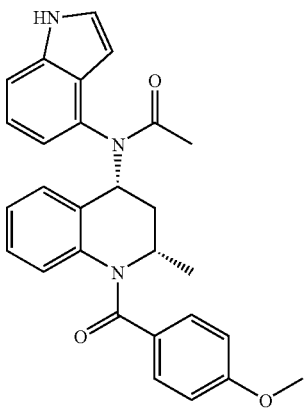 |
| C-88 | 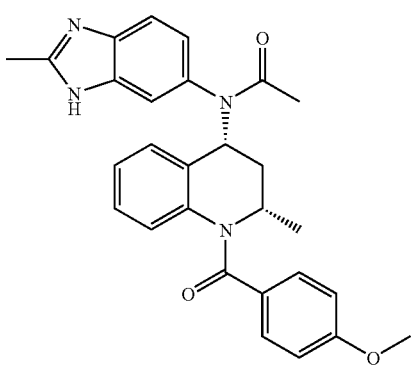 |
| C-89 | 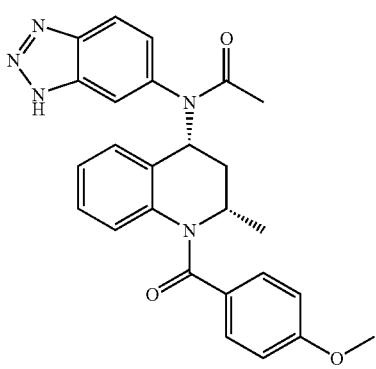 |
| C-90 | 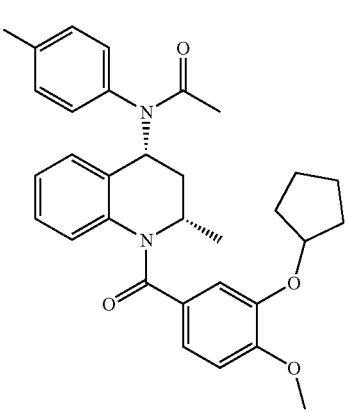 |

TABLE 3-continued

Compounds Derived from General Procedure C

| No. | Structure |
|---|---|
| C-91 | 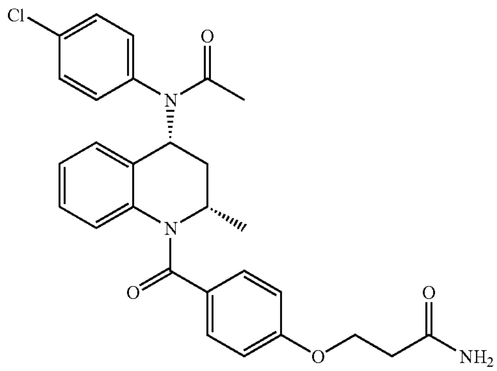 |
| C-92 | 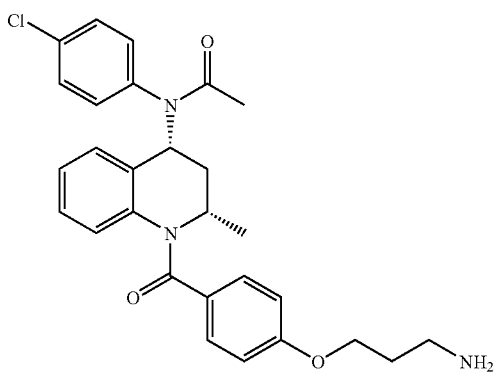 |
| C-93 | 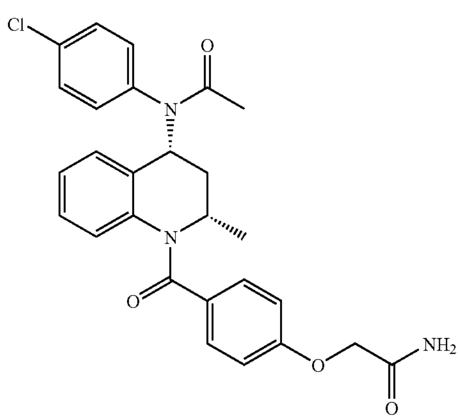 |

TABLE 3-continued
Compounds Derived from General Procedure C
| No. | Structure |
|---|---|
| C-94 | 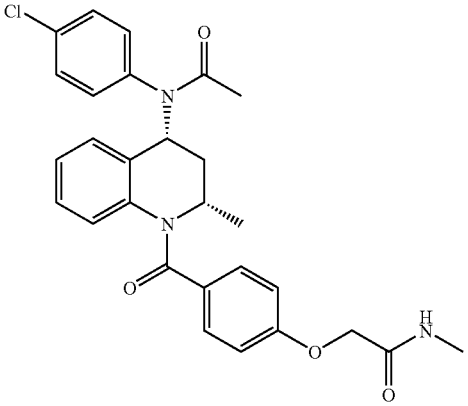 |
| C-95 | 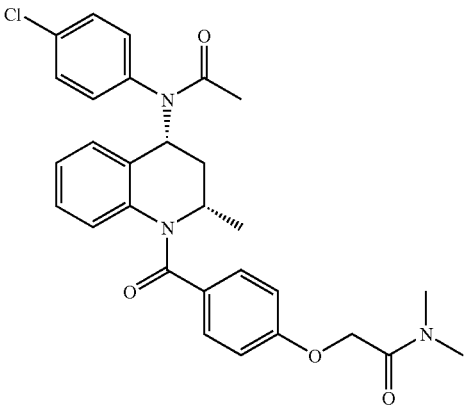 |
| C-96 | 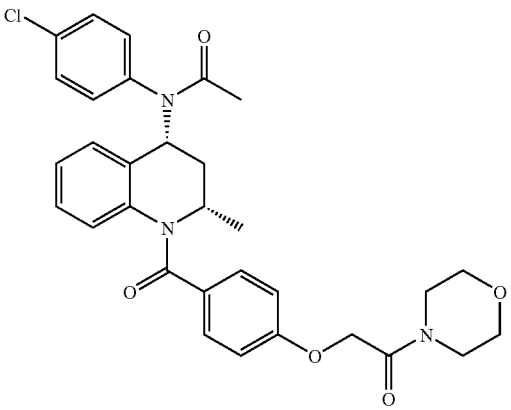 |

TABLE 3-continued
Compounds Derived from General Procedure C
| No. | Structure |
| --- | --- |
| C-97 | 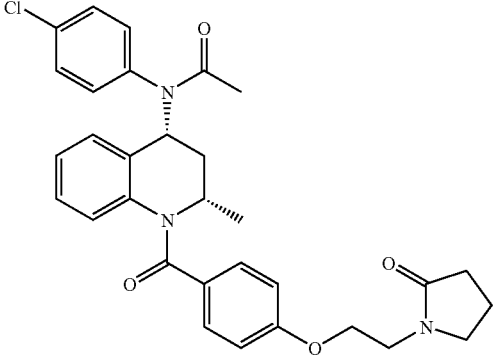 |
| C-98 | 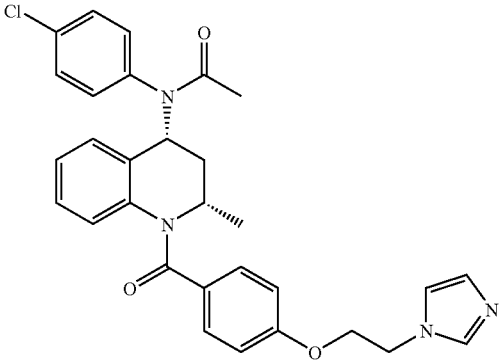 |
| C-99 | 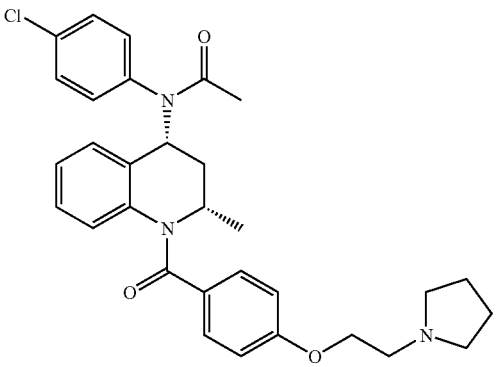 |
| C-100 | 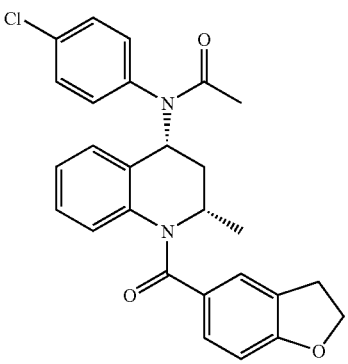 |

TABLE 3-continued
Compounds Derived from General Procedure C
| No. | Structure |
| --- | --- |
| C-101 | 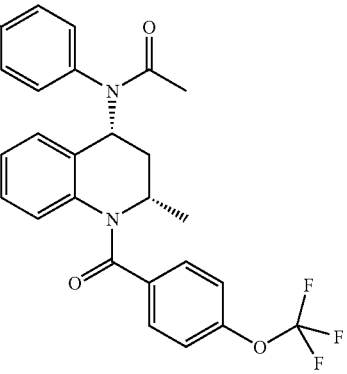 |
| C-102 | 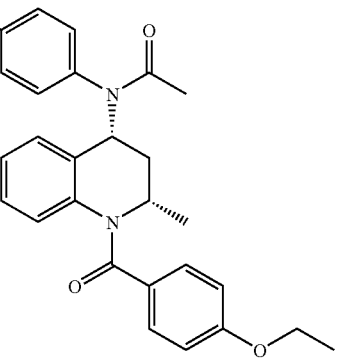 |
| C-103 | 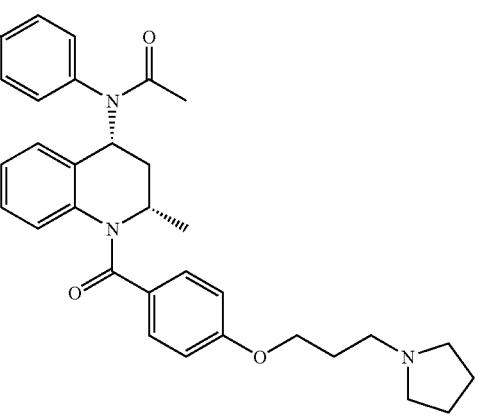 |

TABLE 3-continued
Compounds Derived from General Procedure C
| No. | Structure |
|-----|-----------|
| C-104 | 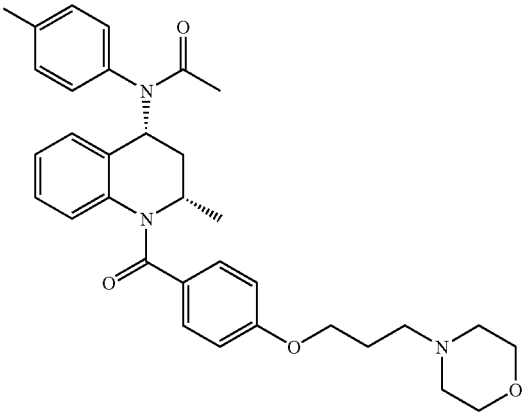 |
| C-105 | 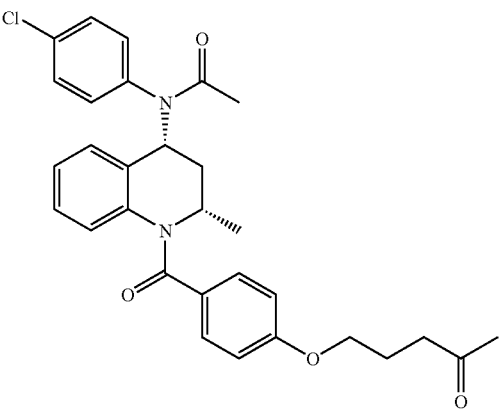 |
| C-106 | 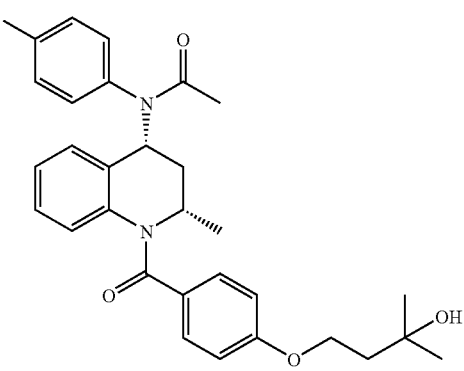 |

TABLE 3-continued
Compounds Derived from General Procedure C
| No. | Structure |
|---|---|
| C-107 | 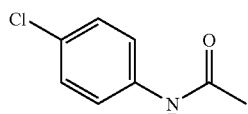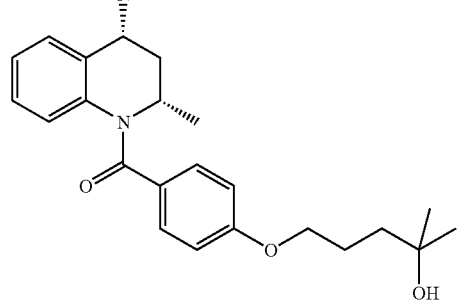 |
| C-108 | 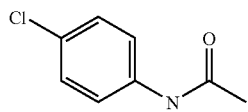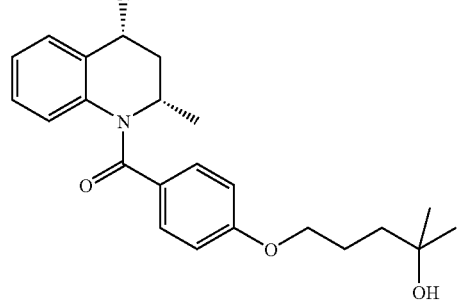 |
| C-109 | 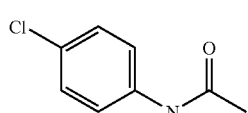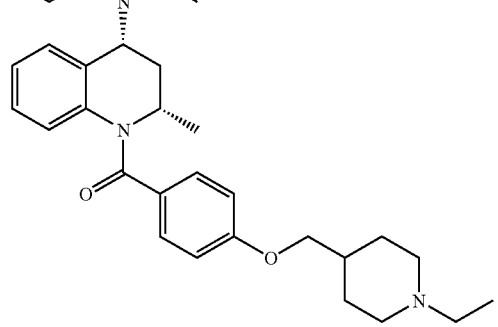 |

TABLE 3-continued
Compounds Derived from General Procedure C
| No. | Structure |
|---|---|
| C-110 | 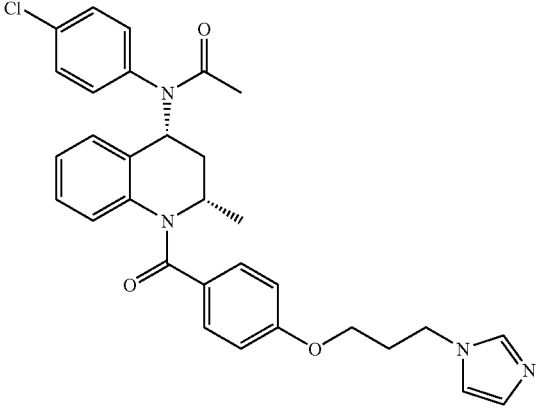 |
| C-111 | 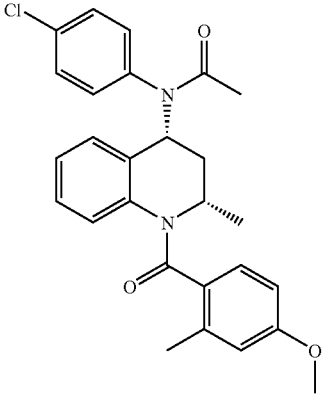 |
| C-112 | 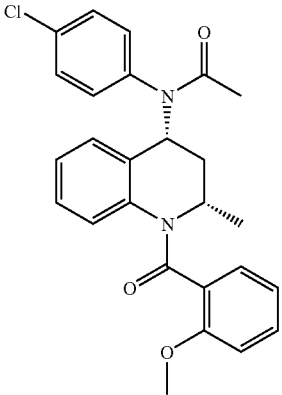 |

TABLE 3-continued
Compounds Derived from General Procedure C
| No. | Structure |
|---|---|
| C-113 | 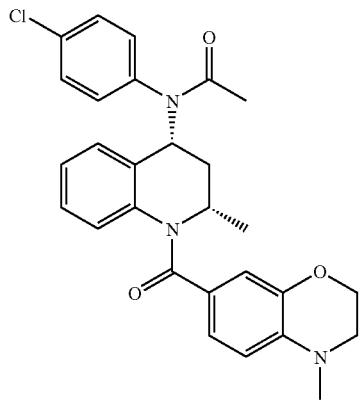 |
| C-114 | 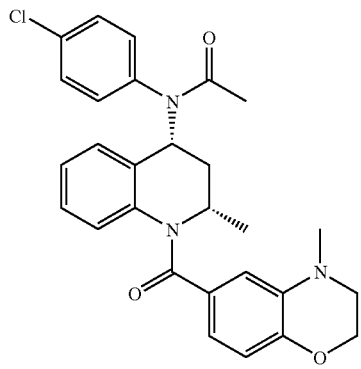 |
| C-115 | 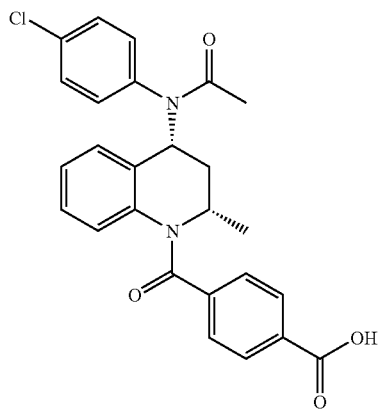 |

TABLE 3-continued

Compounds Derived from General Procedure C

| No. | Structure |
|---|---|
| C-116 | 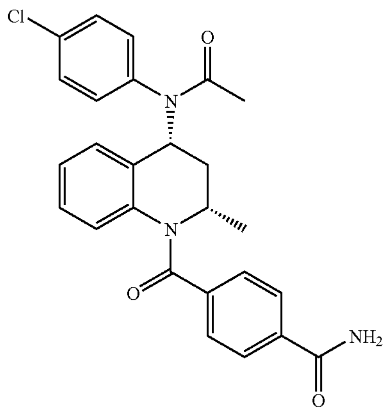 |
| C-117 | 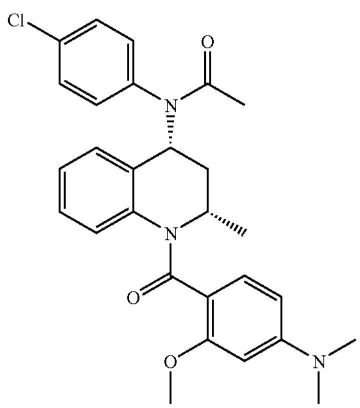 |
| C-118 | 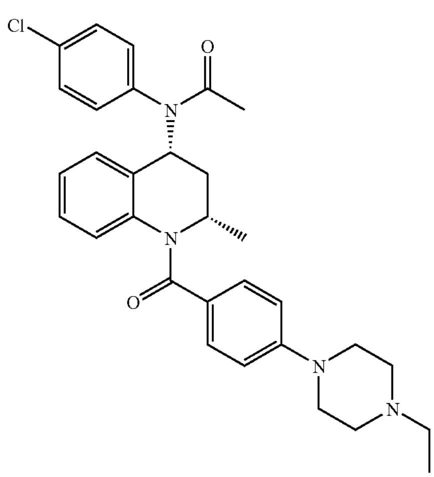 |

TABLE 3-continued
Compounds Derived from General Procedure C
| No. | Structure |
|---|---|
| C-119 | 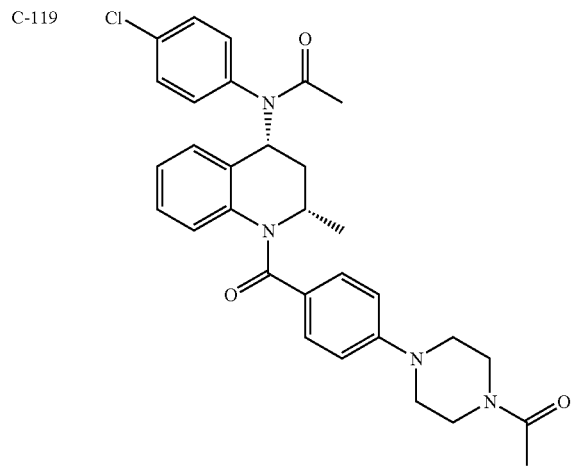 |
| C-120 | 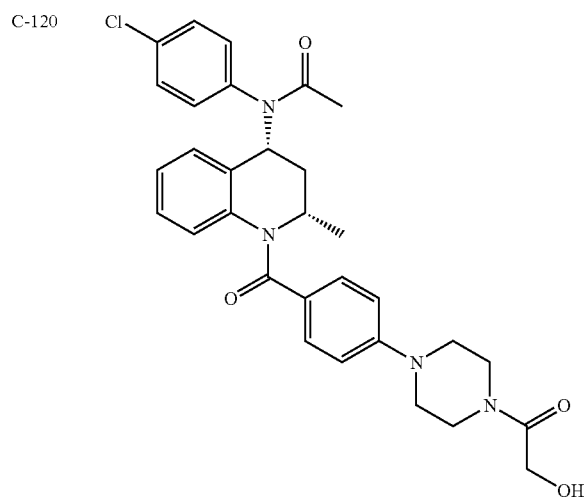 |
| C-121 | 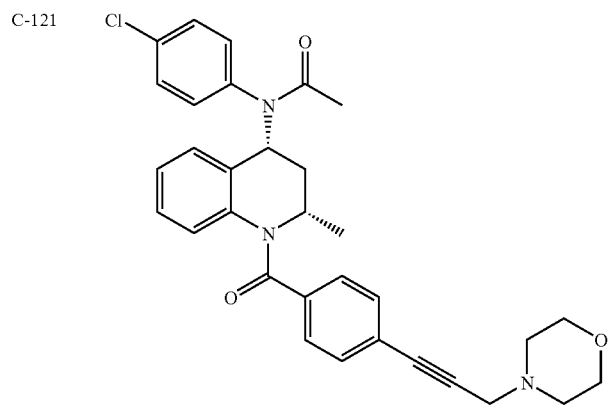 |

TABLE 3-continued

Compounds Derived from General Procedure C

| No. | Structure |
|---|---|
| C-122 | 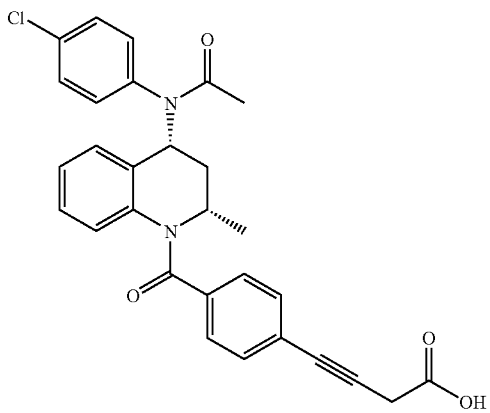 |
| C-123 | 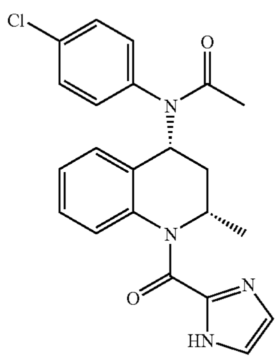 |
| C-124 | 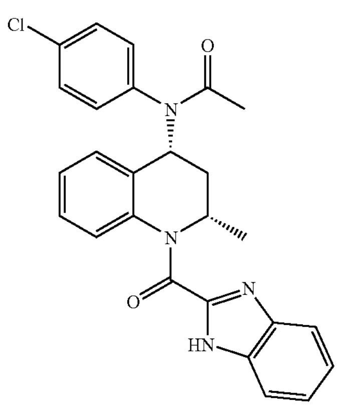 |
| C-125 | 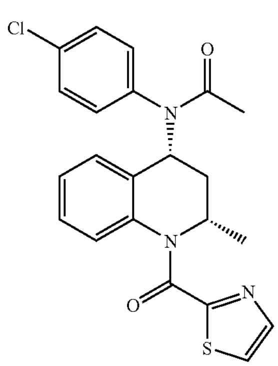 |

TABLE 3-continued
Compounds Derived from General Procedure C
| No. | Structure |
|---|---|
| C-126 | 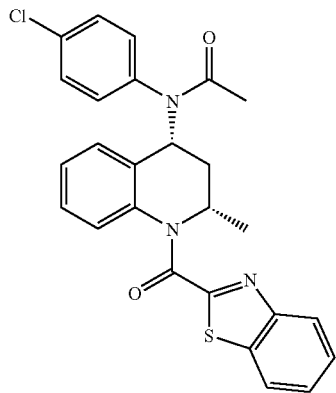 |
| C-127 | 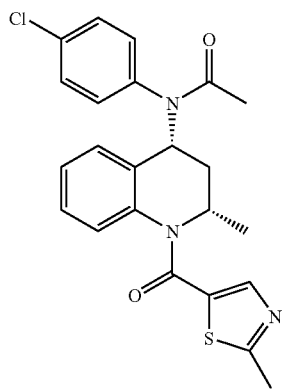 |
| C-128 | 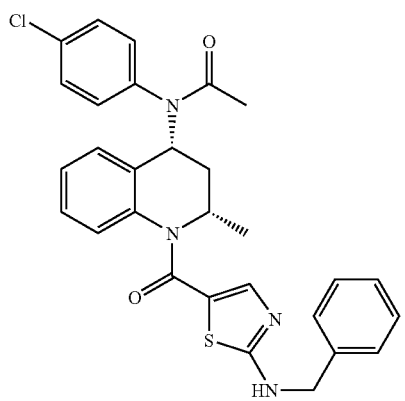 |

TABLE 3-continued
Compounds Derived from General Procedure C
| No. | Structure |
|---|---|
| C-129 | 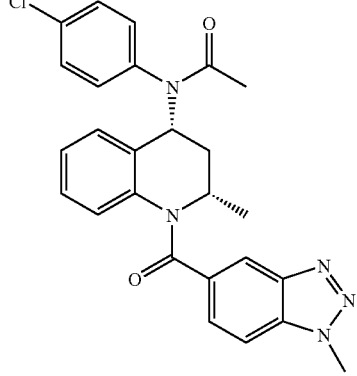 |
| C-130 | 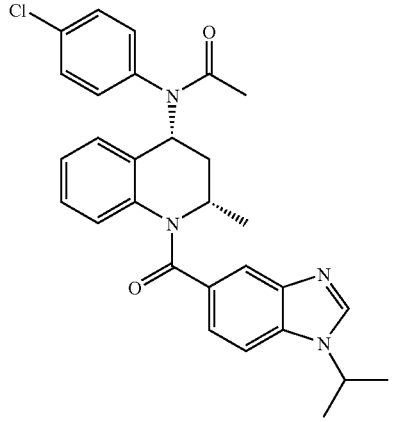 |
| C-131 | 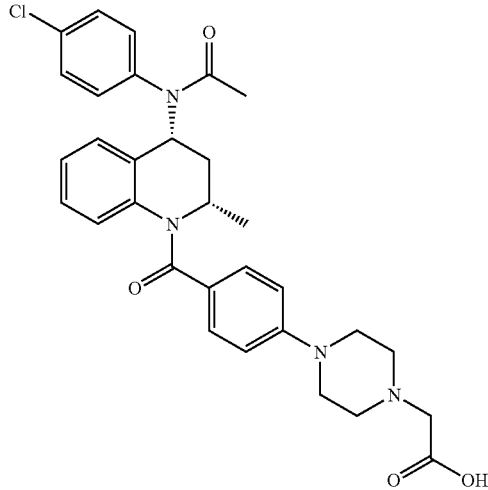 |

TABLE 3-continued

Compounds Derived from General Procedure C

| No. | Structure |
|---|---|
| C-132 | 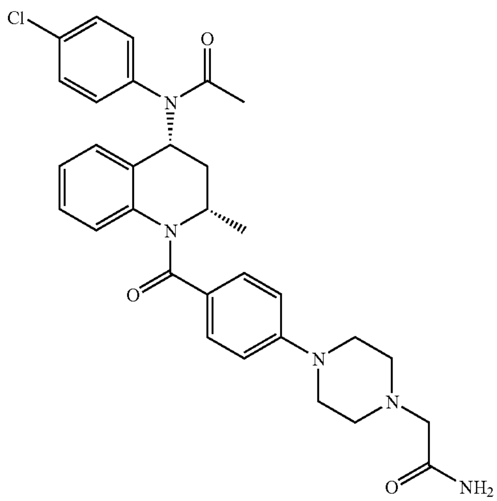 |
| C-133 | 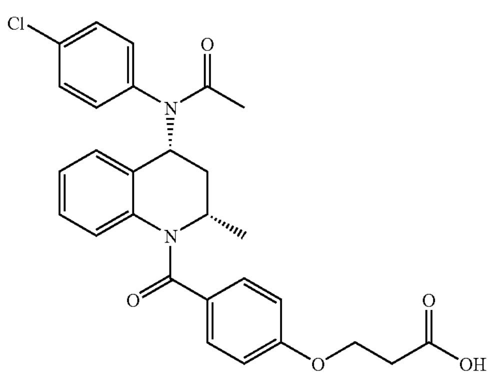 |
| C-134 | 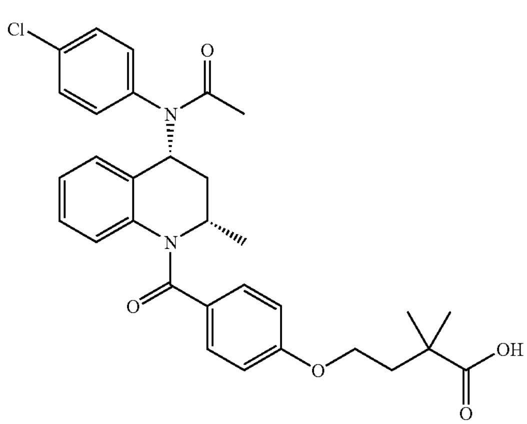 |

TABLE 3-continued
Compounds Derived from General Procedure C
| No. | Structure |
| --- | --- |
| C-135 | 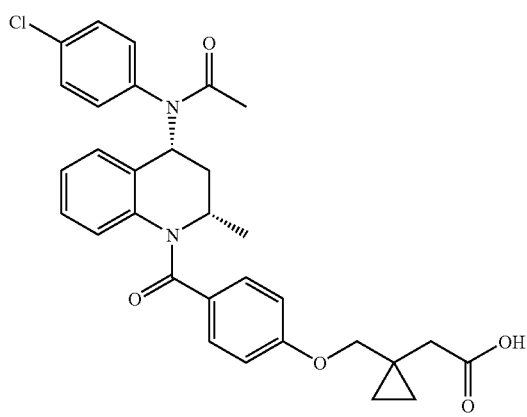 |
| C-136 | 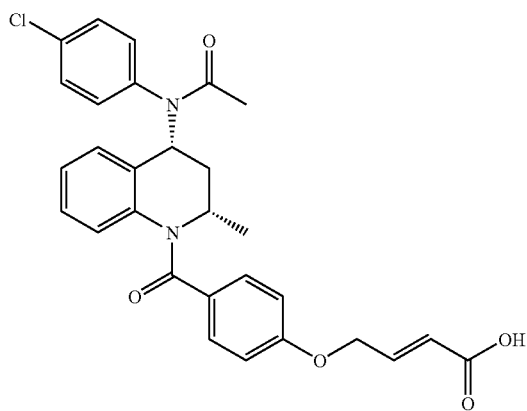 |
| C-137 | 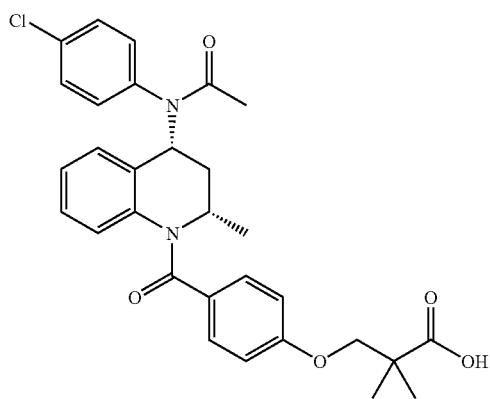 |

TABLE 3-continued

Compounds Derived from General Procedure C

| No. | Structure |
|-----|-----------|
| C-138 | 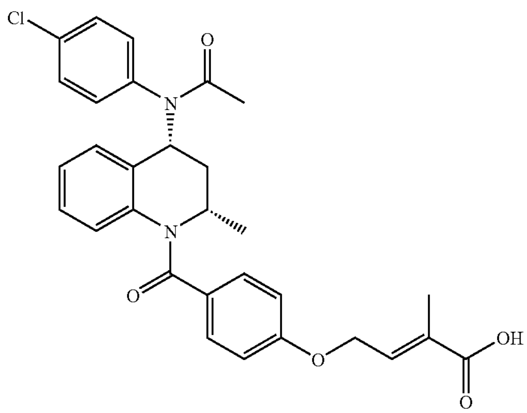 |
| C-139 | 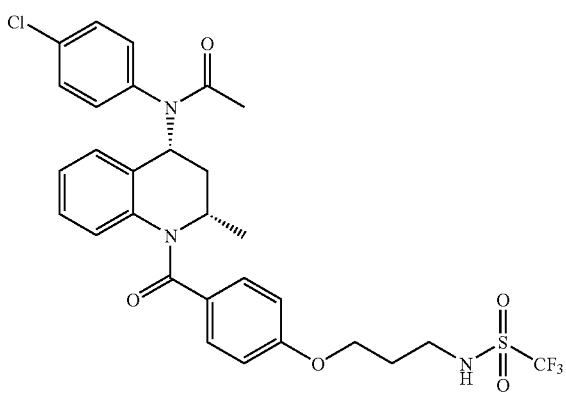 |
| C-140 | 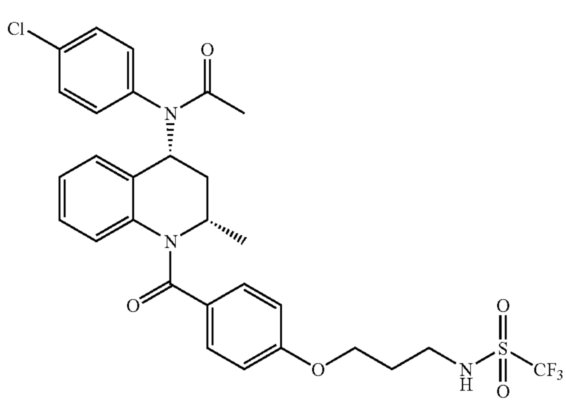 |

TABLE 3-continued
Compounds Derived from General Procedure C
| No. | Structure |
|---|---|
| C-141 | 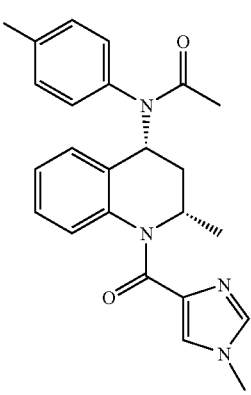 |
| C-142 | 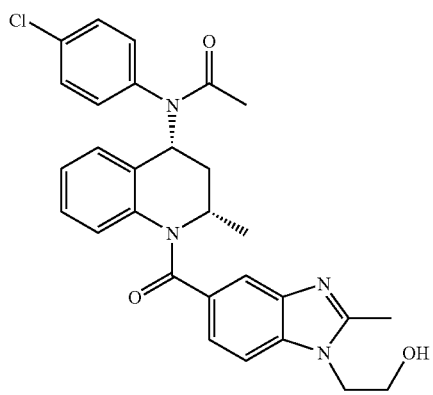 |
| C-143 | 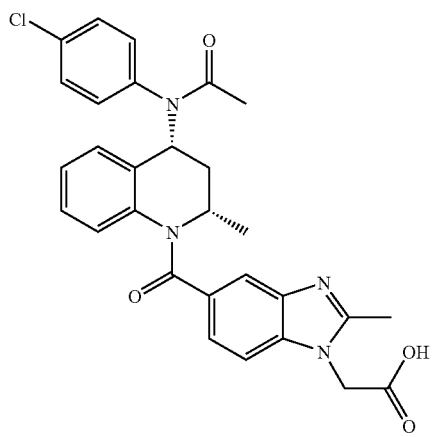 |

TABLE 3-continued
Compounds Derived from General Procedure C
| No. | Structure |
|---|---|
| C-144 | 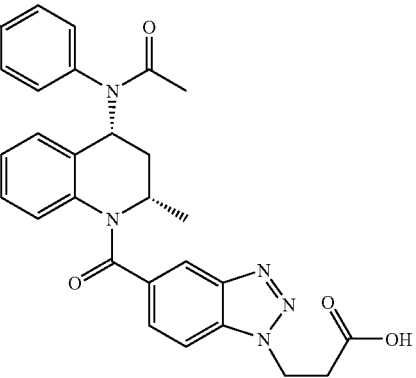 |
| C-145 | 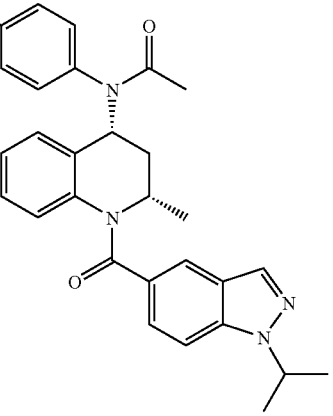 |
| C-146 | 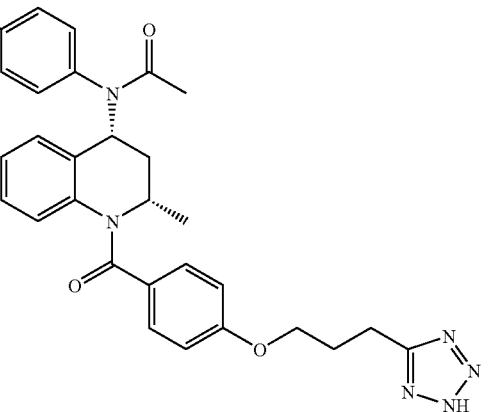 |

General Procedure D

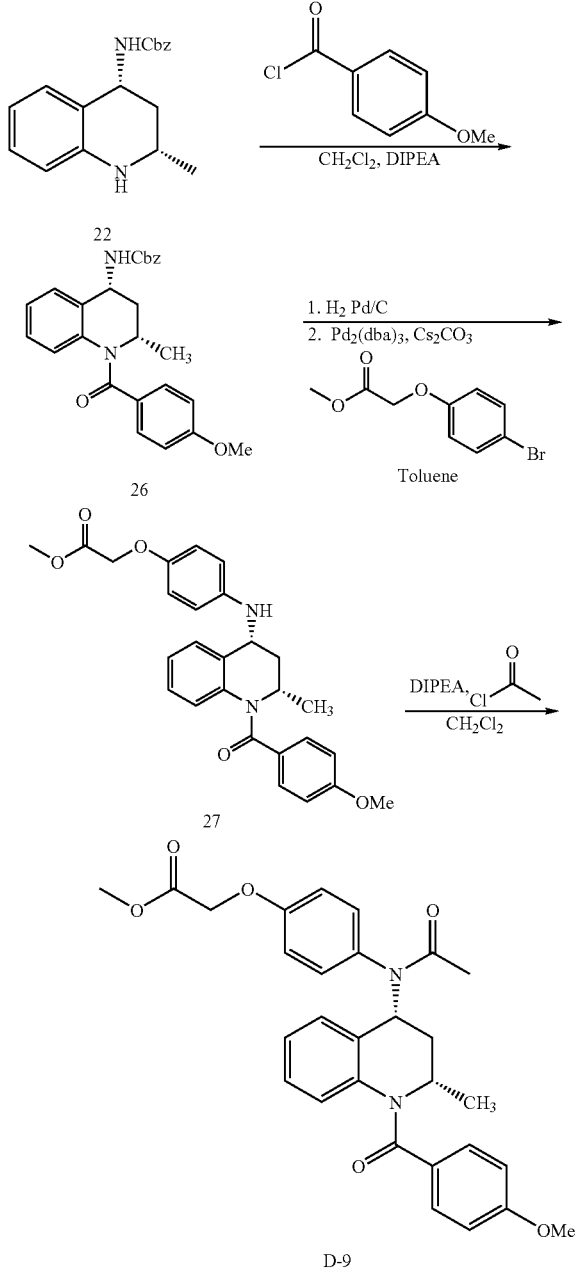

Scheme 15

D-9

(2S,4R)-((4-{Acetyl-[1-(4-methoxy-benzoyl)-2-methyl-1,2,3,4-tetrahydro-quinolin-4-yl]-amino)-phenoxy)-acetic acid methyl ester (D-9)

(2S,4R)-((4-{Acetyl-[1-(4-methoxy-benzoyl)-2-methyl-1,2,3,4-tetrahydro-quinolin-4-yl]amino}-phenoxy)-acetic acid methyl ester was prepared from (2S,4R)-(2-methyl-1,2,3,4-tetrahydro-quinolin-4-yl)-carbamic acid benzyl ester as shown below. (2S,4R)-(2-Methyl-1,2,3,4-tetrahydro-quinolin-4-yl)-carbamic acid benzyl ester (7.6 g, 25.65 mmol) was dissolved in dichloromethane (50 mL) and the resulting solution was cooled to 0° C. Triethylamine (14.3 mL) followed by freshly distilled anisoyl chloride (8.75 mL, 51.3 mmol) dissolved in dichloromethane (15 mL) were added dropwise to this solution. The resulting reaction mixture was allowed to warm to room temperature and stir over night. The mixture was partitioned between dichloromethane and 1 M sodium hydroxide. The extracts were washed with brine, dried over magnesium sulfate, filtered and concentrated. The crude amide was purified by silica gel chromatography (2:1 hexane:ethyl acetate) to afford pure product (10 g, 91%).

The (2S,4R)-[1-(4-methoxy-benzoyl)-2-methyl-1,2,3,4-tetrahydro-quinolin-4-yl]-carbamic acid benzyl ester thus formed (10 g) was dissolved in ethanol (400 mL). Palladium (10% on Carbon) was added. The black suspension was stirred under an atmosphere of hydrogen for 3 h. The mixture was filtered and concentrated. The crude amine was purified by filtration through a short silica plug (elution with ethyl acetate to 90/10 ethyl acetate/methanol gradient) to afford pure amine (5.17 g, 72%).

(2S,4R)-(4-Amino-2-methyl-3,4-dihydro-2H-quinolin-1-yl)-(4-methoxyphenyl)-methanone (100 mg, 0.34 mmol), methyl-2-(4-bromophenoxy)-acetate (91 mg, 0.37 mmol), Pd$_2$(dba)$_3$ (17 mg, 0.02 mmol), 2-dicyclohexylphosphino-2'-(N,N-dimethylamino)biphenyl (8 mg, 0.00002 mol) and cesium carbonate (0.163 g, 0.0005 mol) were taken in a round bottom flask which was then flushed with nitrogen gas through a rubber septum. Toluene (2 mL) was injected into the flask through the rubber septum and the reaction mixture was stirred at 100° C. for 24 h. After cooling to room temperature the reaction mixture was filtered through Celite® and evaporated to give the crude product (0.236 g). This crude product was purified by silica gel chromatography eluting with 100% hexanes to 50/50 hexanes/ethyl acetate gradient give the title compound (37 mg, 24%).

Freshly distilled acetyl chloride (0.5 mL) was added to a solution of the aniline thus prepared (0.037 g, 0.00008 mol) followed by diisopropylethylamine (0.0114 g, 0.015 mL, 0.088 mmol) in dichloromethane (0.5 mL); the mixture was stirred at room temperature for 2 days. The reaction mixture was neutralized with 1 M sodium bicarbonate. The organic layer was separated, washed thrice with water, brine, dried over magnesium sulfate and evaporated. The resulting crude product was purified by silica gel chromatography eluting with (0% to 70% ethyl acetate in hexanes to afford the titled compound (15 mg, 38%).

$^1$H-NMR (CDCl$_3$) δ: 1.12-1.14 (4H, m), 2.02 (3H, s), 2.18-2.43 (1H, m), 3.75 (3H, s) 3.82 (3H, s), 4.65 (2H, s), 4.67-4.82 (1H, m), 5.45-5.73 (1H, broad), 6.52 (1H), 6.68 (2H, d), 6.89-6.95 (3H, m), 7.13-7.21 (5H, m), 7.32 (1H, d). MS m/z: 504 (M+1).

(2S,4R)-(4-{Acetyl-[1-(4-methoxybenzoyl)-2-methyl-1,2,3,4-tetrahydro-quinolin-4-yl]-amino}-phenoxy)-acetic acid (D-10)

(2S,4R)-(4-{Acetyl-[1-(4-methoxybenzoyl)-2-methyl-1,2,3,4-tetrahydro-quinolin-4-yl]-amino}-phenoxy)-acetic acid was prepared from (2S,4R)-(4-{acetyl-[1-(4-methoxy-benzoyl)-2-methyl-1,2,3,4-tetrahydro-quinolin-4-yl]-amino}-phenoxy)-acetic acid methyl ester (15 mg, 0.03 mmol). The methyl ester was dissolved in methanol (1 mL), sodium hydroxide (1 mL, 0.1 M in water) was added and the resulting solution was stirred at room temperature for 18 h. The reaction mixture was acidified with hydrochloric acid (1 M) and concentrated under reduced pressure. The residue was extracted with ethyl acetate and the extract was washed thrice with water, brine, dried over sodium sulphate, filtered and concentrated to yield the title compound (13 mg, 89%).

¹H-NMR (CDCl₃) δ: 1.07 (4H, m), 1.99 (3H, s), 2.12-2.38 (1H, broad), 3.7 (3H, s), 4.61 (2H, s), 4.66 -4.78 (1H, m), 5.47-5.75 (1H, broad), 6.49 (1H, d), 6.64 (2H, d), 6.86-6.9 (3H, m), 7.09-7.16 (5H, m), 7.27 (1H, d).

MS m/z 489 (M⁺), 490 (M+1)

(2S,4R)-2-(4-{Acetyl-[1-(4-methoxy-benzoyl)-2-methyl-1,2,3,4-tetrahydro-quinolin-4-yl]-amino}-phenyl)-2-methyl-propionic acid (D-1)

(2S,4R)-2-(4-{Acetyl-[1-(4-methoxy-benzoyl)-2-methyl-1,2,3,4-tetrahydro-quinolin-4-yl]-amino}-phenyl)-2-methyl-propionic acid was prepared via saponification of 2-(4-{acetyl-[1-(4-methoxy-benzoyl)-2-methyl-1,2,3,4-tetrahydro-quinolin-4-yl]amino}-phenyl)-2-methyl-propionic acid methyl ester, as described in the synthesis of (2S,4R)-(4-{acetyl-[1-(4-methoxybenzoyl)-2-methyl-1,2,3,4-tetrahydro-quinolin-4-yl]-amino}-phenoxy)-acetic acid. The methyl ester was prepared following general procedure D, substituting 2-(4-bromo-phenyl)-2-methyl-propionic acid for methyl-2-(4-bromophenoxy)-acetate.

¹H-NMR (300 MHz, CD₃OD) δ: 1.07-1.18 (m, 4H), 1.58 (s, 6H), 2.02 (s, 3H), 2.42-2.56 (m, 1H), 3.76 (s, 3H), 4.74 (ddd, 1H), 5.55 (br s, 1H), 6.56 (d, 1H), 6.75 (d, 2H), 6.97 (dd, 1H), 7.13-7.27 (m, 3H), 7.36 (d, 2H), 7.42-7.55 (m, 3H).

(2S,4R)-4-(4-{Acetyl-[1-(4-methoxy-benzoyl)-2-methyl-1,2,3,4-tetrahydro-quinolin-4-yl]-amino}-2-chloro-phenyl)-4-oxo-butyric acid (D-2)

(2S,4R)-4-(4-{Acetyl-[1-(4-methoxy-benzoyl)-2-methyl-1,2,3,4-tetrahydro-quinolin-4-yl]-amino)-2-chloro-phenyl)-4-oxo-butyric acid was prepared from the corresponding methyl ester following the procedure above for the synthesis of (2S,4R)-(4-{acetyl-[1-(4-methoxybenzoyl)-2-methyl-1,2,3,4-tetrahydroquinolin-4-yl]amino}-phenoxy)-acetic acid. The corresponding methyl ester was prepared following general procedure D, substituting 4-(4-bromo-2-chloro-phenyl)-4-oxo-butyric acid methyl ester for methyl-2-(4-bromophenoxy)-acetate.

¹H-NMR (300 MHz, CD₃OD) δ: 1.10-1.19 (m, 4H), 2.08 (br s, 3H), 2.41-2.56 (m, 1H), 2.69-2.74 (m, 2H), 3.20-3.26 (m, 2H), 3.75 (s, 3H), 4.74 (ddd, 1H), 5.45-5.62 (br s, 1H), 6.57 (d, 1H), 6.74 (d, 2H), 6.98 (dd, 1H), 7.16 (d, 2H), 7.20-7.27 (m, 1H), 7.42-7.49 (m, 2H), 7.60 (br s, 1H), 7.73 (d, 1H).

MS m/z: 549 (M+1).

(2S,4R)-N-(4-Dimethylsulfamoyl-phenyl)-N-[1-(4-methoxy-benzoyl)-2-methyl-1,2,3,4tetrahydro-quinolin-4-yl]-acetamide (D-3)

(2S,4R)-N-(4-Dimethylsulfamoyl-phenyl)-N-[1-(4-methoxy-benzoyl)-2-methyl-1,2,3,4-tetrahydro-quinolin-4-yl]-acetamide was prepared following general procedure D, substituting 4-bromo-N,N-dimethyl-benzenesulfonamide for methyl-2-(4-bromophenoxy)-acetate.

¹H-NMR (CDCl₃) δ: 1.1 (3H, d), 1.1 (1H, m), 2.0 (3H, s), 2.3 (1H, m), 2.8 (6H, s), 3.8 (3H, s), 4.8 (1H, m), 5.6 (1H, m), 6.6 (1H, d), 6.7 (2H, d), 6.9 (1H, t), 7.2 (3H, m), 7.3 (1H, m), 7.5 (2H, d), 7.8 (2H, d).

MS m/z: 522 (M+1).

(2S,4R)-N-[1-(4-Methoxy-benzoyl)-2-methyl-1,2,3,4-tetrahydro-quinolin-4-yl]-N-[4-(pyrrolidine-1-sulfonyl)-phenyl]-acetamide (D-4)

(2S,4R)-N-[1-(4-Methoxy-benzoyl)-2-methyl-1,2,3,4-tetrahydro-quinolin-4-yl]-N-[4-(pyrrolidine-1-sulfonyl)-phenyl]-acetamide was prepared following general procedure D, substituting 1-(4-bromo-benzenesulfonyl)-pyrrolidine for methyl-2-(4-bromophenoxy)-acetate.

¹H-NMR (CDCl₃) δ: 1.1 (3H, d), 1.1 (1H, m), 1.7 (4H, m), 2.0 (3H, s), 2.3 (1H, m), 3.3 (4H, m), 3.7 (3H, s), 4.7 (1H, m), 5.6 (1H, m), 6.5 (1H, d), 6.6 (2H, d), 6.9 (1H, t), 7.3 (4H, m), 7.4 (2H, d), 7.9 H, d).

MS m/z: 548 (M+1).

(2S,4R)-N-(4-Methanesulfonyl-phenyl)-N-[1-(4-methoxy-benzoyl)-2-methyl-12,3,4-tetrahydro-quinolin-4-yl]-acetamide (D-5)

(2S,4R)-N-(4-Methanesulfonyl-phenyl)-N-[1-(4-methoxy-benzoyl)-2-methyl-1,2,3,4-tetrahydro-quinolin-4-yl]-acetamide was made following general procedure D, substituting 1-bromo-4-methanesulfonyl-benzene for methyl-2-(4-bromophenoxy)-acetate.

¹H-NMR (CDCl₃) δ: 1.1-1.2 (3H, m), 2.0-2.2 (4H, m), 2.3 (1H, m), 3.1 (3H, s), 3.7 (3H, s), 4.8 (1H), 5.6-5.8 (1H, br), 6.5 (1H, d), 6.6 (2H, d), 6.9 (1H, t), 7.1-7.3 (4H, m), 7.4 (2H, d), 8.0 (2H, d).

MS m/z: 493 (M+1).

(2S,4R)-3-(4-{Acetyl-[1-(4-methoxy-benzoyl)-2-methyl-1,2,3,4-tetrahydro-quinolin-4-yl]-amino}-phenyl)-propionic acid (D-6)

(2S,4R)-3-(4-{Acetyl-[1-(4-methoxy-benzoyl)-2-methyl-1,2,3,4-tetrahydro-quinolin-4-yl]-amino}-phenyl)-propionic acid was prepared from (2S,4R)-N-(4-bromo-phenyl)-N-[1-(4-methoxy-benzoyl)-2-methyl-1,2,3,4-tetrahydro-quinolin-4-yl]-acetamide. (2S,4R)-N-(4-Bromo-phenyl)-N-[1-(4-methoxy-benzoyl)-2-methyl-1,2,3,4-tetrahydro-quinolin-4-yl]-acetamide was converted to the acrylic acid using the same procedure described in the synthesis of (±)-3-[4-[(4-chloro-phenyl)-propionyl-amino]-1-(4-fluoro-benzoyl)-2-methyl-1,2,3,4-tetrahydro-quinolin-6-yl]-acrylic acid. The reduction and saponification were carried out as in the procedure describing the preparation of (2S,4R)-3-(4-{4-[acetyl-(4-chloro-phenyl)-amino]-2-methyl-3,4-dihydro-2H-quinoline-1-carbonyl}-phenyl)-propionic acid.

¹H-NMR (CDCl₃ 300 MHz) δ: 1.12 (3H, d), 1.20-1.24 (1H, m), 2.00 (3H, s), 2.22-2.38 (1H, m), 2.52 (2H, t), 3.00 (2H, t), 3.72 (3H, s), 4.64-4.79 (1H, m), 5.44-5.70 (1H, m), 6.50 (1H, d), 6.65 (2H, d), 6.90 (1H, t), 7.10-7.28 (7H, m), 7.32 (1H, d).

(2S,4R)-3-(4-{Acetyl-[1-(4-methoxy-benzoyl)-2-methyl-1,2,3,4-tetrahydro-quinolin-4-yl]-amino}-phenyl)-propionamide (D-7)

(2S,4R)-3-(4-{Acetyl-[1-(4-methoxy-benzoyl)-2-methyl-1,2,3,4-tetrahydro-quinolin-4-yl]-amino}-phenyl)-propionamide was prepared from (2S,4R)-3-(4-{Acetyl-[1-(4-methoxy-benzoyl)-2-methyl-1,2,3,4-tetrahydro-quinolin-4-yl]-amino}-phenyl)-propionic acid. To a solution of 3-(4-{acetyl-[1-(4-methoxy-benzoyl)-2-methyl-1,2,3,4-tetrahydro-quinolin-4-yl]-amino}-phenyl)-propionic acid (21 mg, 0.042 mmol) in dimethylformamide (200 μl) was added HATU (24 mg, 0.063 mmol), HOBt (8.5 mg, 0.063 mmol), NH₄Cl (4.5 mg, 0.084 mmol) and DIPEA (29 μl, 0.168 mmol). Upon consumption of the starting unit (2.5 hours), the mixture was diluted with EtOAc (10 ml) and washed with sat. NaHCO₃ (4X 10 ml). The EtOAc layer was collected, dried over Na₂SO₄, filtered, and concentrated to afford the title compound (17.2 mg, 82%).

¹H-NMR (CDCl₃ 300 MHz) δ 1.09 (3H, d), 1.20-1.24 (1H, m), 2.02 (3H, s), 2.22-2.38 (1H, m), 2.52 (2H, t), 3.00 (2H, t), 3.73 (3H, s), 4.64-4.79 (1H, m), 5.30-5.70 (3H, m), 6.50 (1H, d), 6.68 (2H, d), 6.91 (1H, t), 7.10-7.28 (7H, m), 7.32 (1H, d).

(2S,4R)-N-[1-(4-Methoxy-benzoyl)-2-methyl-1,2,3,4-tetrahydro-quinolin-4-yl]-N-(4-nitro-phenyl)-acetamide (D-8)

(2S,4R)-N-[1-(4-Methoxy-benzoyl)-2-methyl-1,2,3,4-tetrahydro-quinolin-4-yl]-N-(4-nitro-phenyl)-acetamide was made following general procedure D, substituting 4-bromonitrobenzene for methyl-2-(4-bromophenoxy)-acetate.

¹H-NMR (CDCl₃ 300 MHz) δ 1.12 (3H, d), 1.20-1.24 (1H, m), 2.07 (3H, s), 2.20-2.35 (1H, m), 3.73 (3H, s), 4.66-4.81 (1H, m), 5.50-5.78 (1H, m), 6.55 (1H, d), 6.68 (2H, d), 6.96 (1H, t), 7.10-7.32 (4H, m), 7.46 (2H, d), 8.28 (2H, d).

MS m/z: 460 (M+1).

TABLE 4

Compounds Derived from General Procedure D

| No. | Structure |
| --- | --- |
| D-1 | |
| D-2 | |
| D-3 | 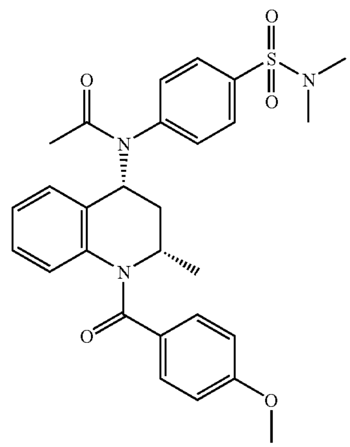 |
| D-4 | 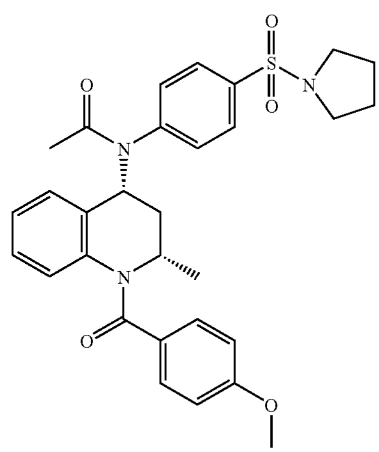 |
| D-5 | 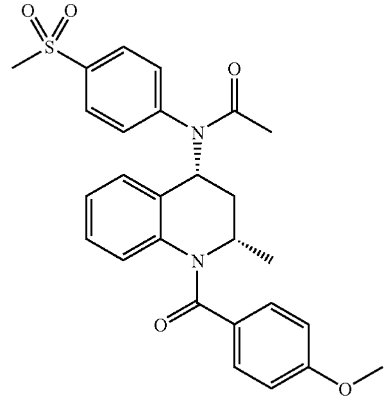 |

TABLE 4-continued
Compounds Derived from General Procedure D
| No. | Structure |
|---|---|
| D-6 | 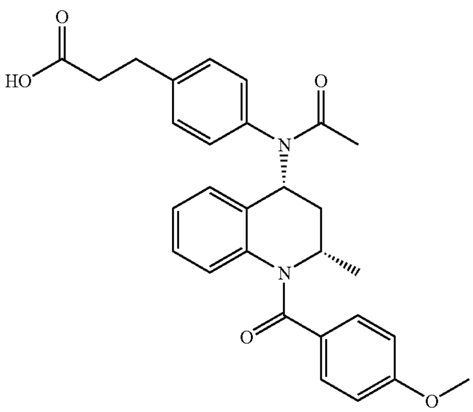 |
| D-7 | 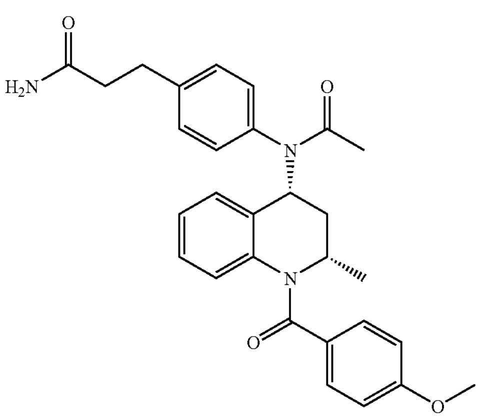 |
| D-8 | 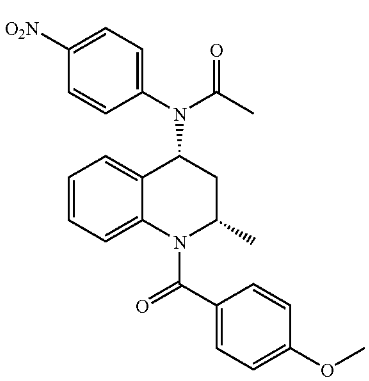 |
| D-9 | 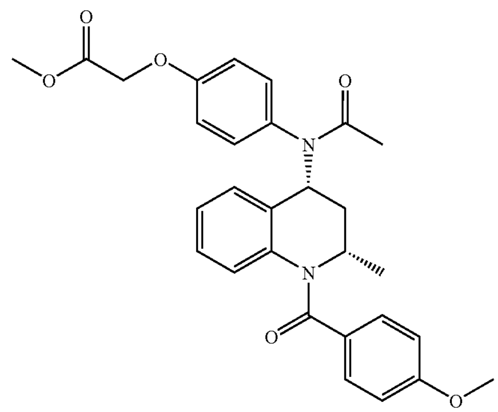 |
| D-10 | 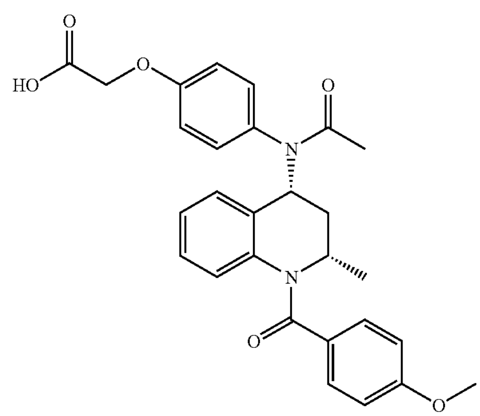 |
General procedure E
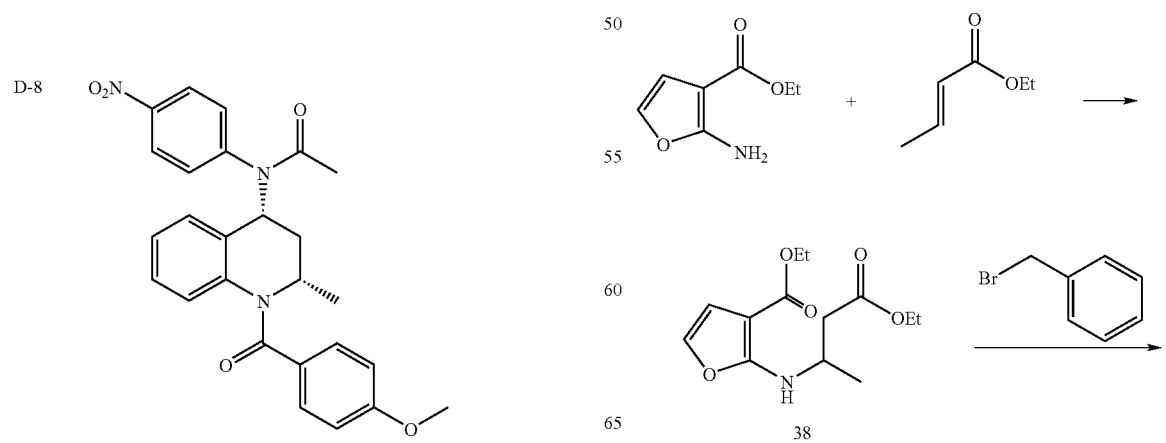
Scheme 16

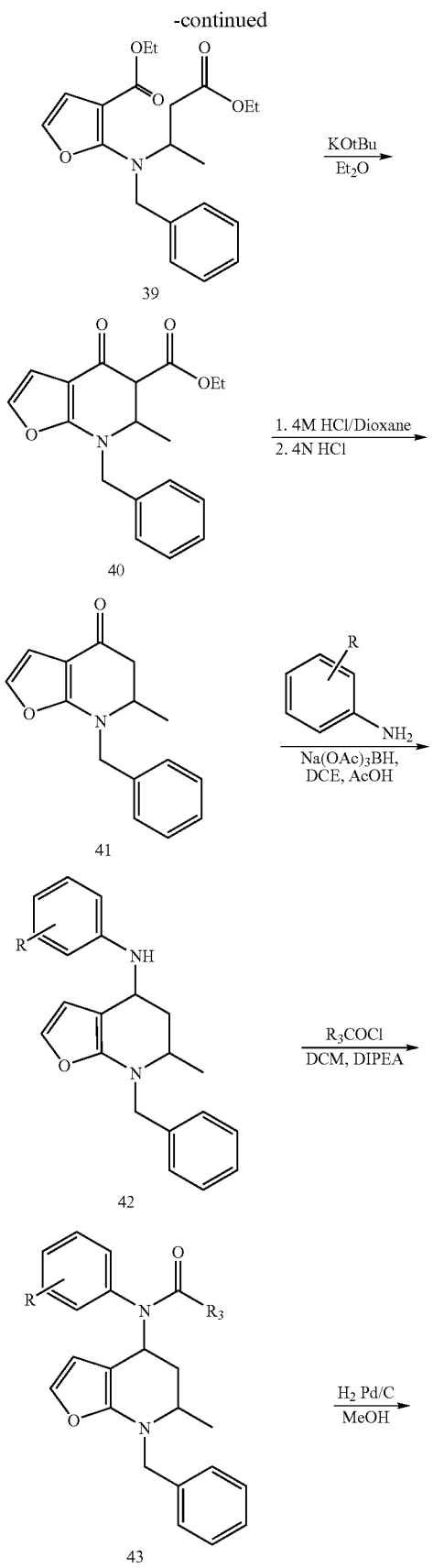

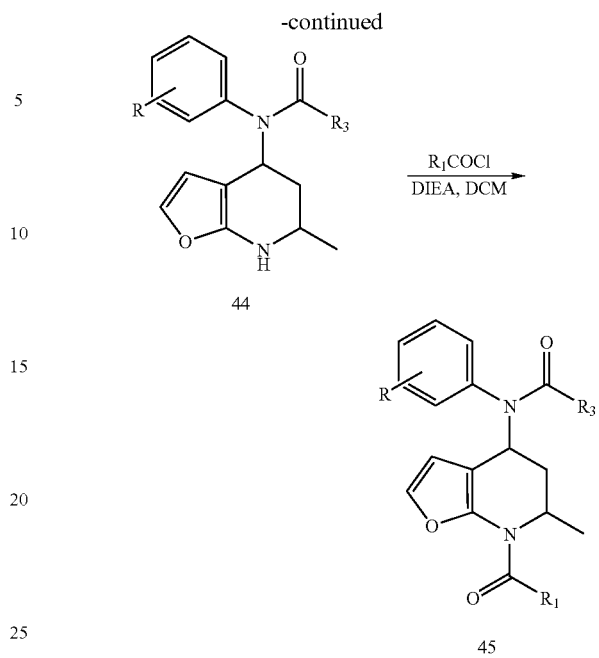

(±)-N-(7-acetyl-6-methyl-4,5,6,7-tetrahydrohetero[2,3-b]pyridin-4-yl)-N-substituted phenylacetamides (45)

2-(2-Ethoxycarbonyl-1-methyl-ethylamino)-furan-3-carboxylic acid ethyl ester (38)

2-Amino-furan-3-carboxylic acid ethyl ester and but-2-enoic acid ethyl ester is dissolved in ethanol and heat to reflux in the presence of $Al_2O_3$, until no starting material remains and filter and concentrate down. The residue is purified by flash chromatography to afford the corresponding diketone.

2-[Benzyl-(2-ethoxycarbonyl-1-methyl-ethyl)-amino]-furan-3-carboxylic acid ethyl ester (39)

The synthesis is accomplished using the alkylation described for the synthesis of A-164, substituting benzyl bromide for the 3-methoxybenzyl bromide.

7-Benzyl-6-methyl-4-oxo-4,5,6,7-tetrahydro-furo[2,3-b]pyridine-5-carboxylic acid ethyl ester (40)

To a solution of the diester in ethyl ether at room temperature is added potassium tert-butoxide and the mixture is allowed to stir for 1 hour. The mixture is filtered to remove any hydrolyzed material. The solvent was removed in vacuo to afford the potassium salt of the bicyclic ester.

7-Benzyl-6-methyl-6,7-dihydro-5H-furo[2,3-b]pyridin-4-one (41)

The α-keto-ester is dissolved in 4M HCl in dioxane and stirred for 2 hours at room temperature. Then 4 N HCl is added and the mixture was heated in a 100° C. oil bath for 12 hours. The mixture is then cooled to room temperature and neutralize with 1N NaOH. The aqueous layer is extracted with ethyl acetate, dried over magnesium sulfate and filter.

Evaporate the solvent in vacuo and purify the residue by flash chromatography to afford the corresponding ketone.

(±)-(7-Benzyl-6-methyl-4,5,6,7-tetrahydro-furo[2,3-b]pyridin-4-yl)-substituted phenyl-amine (42)

Synthesis of the substituted phenyl amine is accomplished using the procedure described for F-1, substituting aniline for the corresponding aniline.

(±)-N-(7-Benzyl-6-methyl-4,5,6,7-tetrahydro-furo[2,3-b]pyridin-4-yl)-N-substituted phenyl-substituted amide (45)

Synthesis of the corresponding phenyl amide is accomplished using the hydrogenation and acylation procedures described in general procedure B with the corresponding acid chlorides. Representative examples of compound 45 are shown in the table below.

Compounds E-1-E-30 can be prepared by the schemes set forth in Schemes 18 and by the general procedures E and others described herein. Those skilled in the art will be able to recognize, or be able to ascertain, using no more than routine experimentation, many equivalents to the specific embodiments of the invention described herein.

TABLE 5

Examples using General Procedure E

| No. | Structure |
|-----|-----------|
| E-1 | |
| E-2 | |
| E-3 | 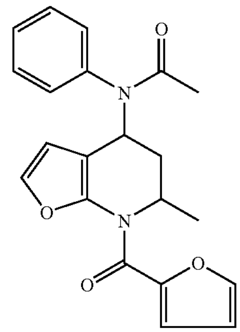 |
| E-4 | 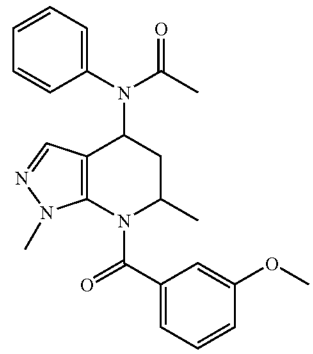 |
| E-5 | 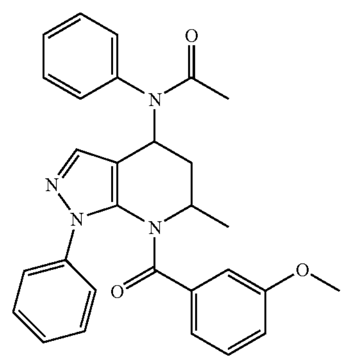 |
| E-6 | 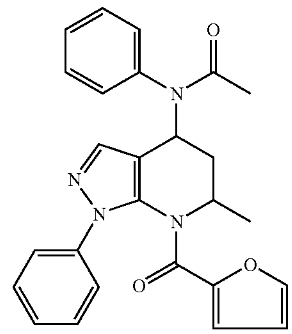 |

TABLE 5-continued

Examples using General Procedure E

| No. | Structure |
|---|---|
| E-7 | 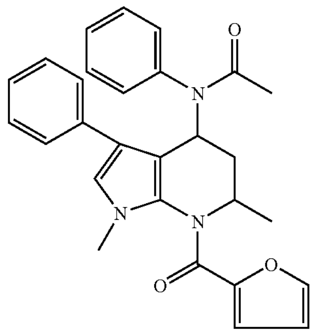 |
| E-8 | 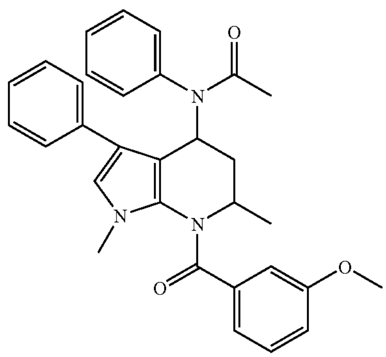 |
| E-9 | 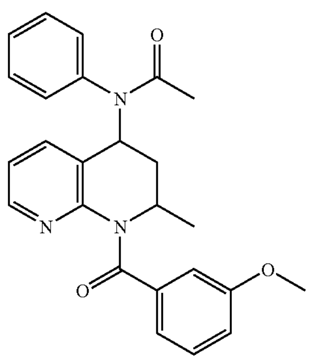 |
| E-10 | 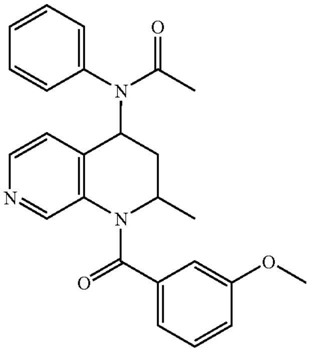 |
| E-11 | |
| E-12 | |
| E-13 | |
| E-14 | |

TABLE 5-continued

Examples using General Procedure E

| No. | Structure |
|---|---|
| E-15 | 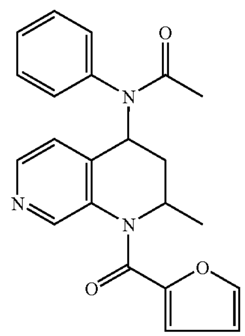 |
| E-16 | 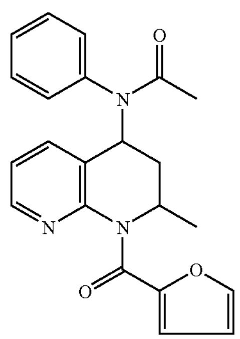 |
| E-17 | 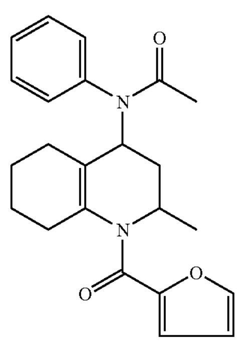 |
| E-18 | 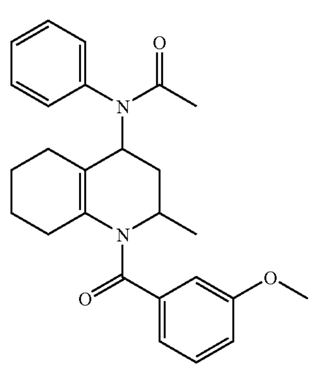 |
| E-19 | |
| E-20 | |
| E-21 | |
| E-22 | |

TABLE 5-continued
Examples using General Procedure E
| No. | Structure |
|---|---|
| E-23 | 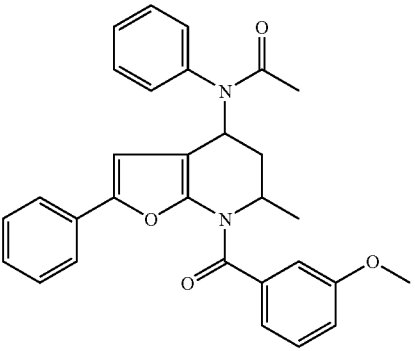 |
| E-24 | 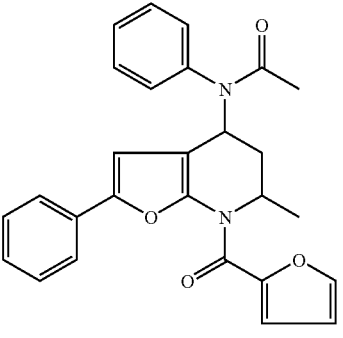 |
| E-25 | 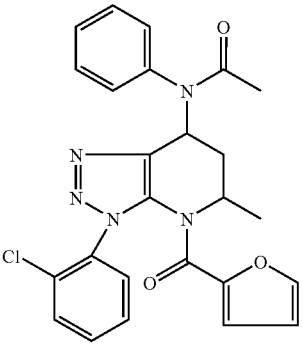 |
| E-26 | 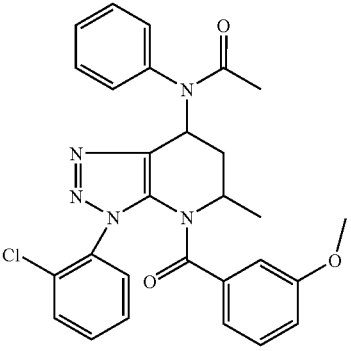 |
| E-27 | 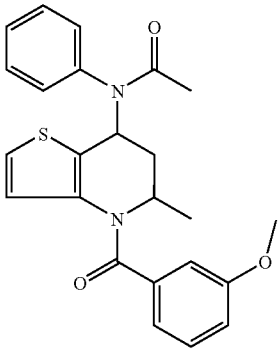 |
| E-28 | 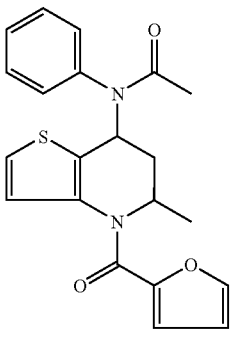 |
| E-29 | 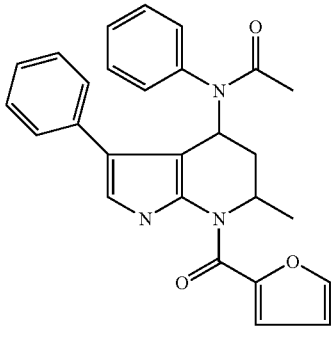 |
| E-30 | 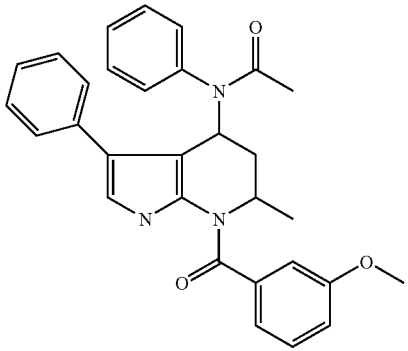 |

General Procedures F

N-[1-(3-Methoxy-benzoyl)-2,2-dimethyl-1,2,3,4-tetrahydro-quinolin-4-yl]-N-phenyl-acetamide (F-1)

N-[1-(3-Methoxy-benzoyl)-2,2-dimethyl-1,2,3,4-tetrahydro-quinolin-4-yl]-N-phenyl-acetamide from 4-(hydroxy-2,2-dimethyl-3,4-dihydro-2H-quinolin-1-yl)-(3-methoxy-phenyl)-methanone which was synthesized according to reference Hamann, L. G.; Higuchi, R. I.; Zhi, L.; Edwards, J. P.; Wang, X.; Marrschke, K. B.; Kong, J. W.; Farmer, L. J.; Jones, T. D. *J. Med. Chem* 1998, 41, 623. This was further elaborated to N-[1-(3-methoxy-benzoyl)-2,2-dimethyl-1,2,3,4-tetrahydro-quinolin-4-yl]-N-phenyl-acetamide using an in-situ formation of the iodide and displacement with the aniline according to the following procedure To a chilled solution of (4-hydroxy-2,2-dimethyl-3,4-dihydro-2H-quinolin-1-yl)-(3-methoxy-phenyl)-methanone (500 mg, 1.6 mmol) in 10 ml dichloromethane was added slowly 0.8 ml iodotrimethylsilane (5.6 mmol) at 0° C. The resulting reaction mixture was stirred at 0° C. for 6 hours. Then the mixture was concentrated under vacuum. The residue was dissolved in 12 ml THF. $BaCO_3$ (630 mg, 3.2 mmol) and aniline (0.17 ml, 1.92 mmol) was added. The mixture was stirred at RT overnight. The mixture was filtered and the filtrate was concentrated under vacuum. The residue was purified by silica gel chromatography, eluting with ethyl acetate-hexane (1:4) to give (2,2-dimethyl-4-phenylamino-3,4-dihydro-2H-quinolin-1-yl)-(3-methoxy-phenyl)-methanone (150 mg, 24%).

To a solution of (2,2-dimethyl-4-phenylamino-3,4-dihydro-2H-quinolin-1-yl)-(3-methoxy-phenyl)-methanone in methylene chloride (5 mL) was added diisopropylethylamine followed by acetyl chloride. The mixture was stirred at room temperature over night. The mixture was poured into water and extracted with dichloromethane. The extracts were washed with 1 M (aq) NaOH and brine, dried over magnesium sulfate, filtered, dried and concentrated. The crude residue was purified by silica gel chromatography (50% hexanes/50% ethyl acetate) to afford N-[1-(3-methoxy-benzoyl)-2,2-dimethyl-1,2,3,4-tetrahydro-quinolin-4-yl]-N-phenyl-acetamide.

$^1$H-NMR (CDCl$_3$) δ: 1.5 (1H, m), 1.6 (3H, s), 1.7 (3H, s), 1.9 (1H, m), 2.0 (3H, 3), 3.7 (3H, m), 5.8 (1H, m), 6.5 (1H, d), 6.6-7.1 (8H, m), 7.2 (1H, m), 7.3-7.5 (3H, d).

MS m/z: 429 (M+1).

(2S,4R)-4-Chloro-N-ethyl-N-[1-(4-methoxy-benzoyl)-2-methyl-1,2,3,4-tetrahydro-quinolin-4-yl]-benzamide (F-2)

(2S,4R)-4-Chloro-N-ethyl-N-[1-(4-methoxy-benzoyl)-2-methyl-1,2,3,4-tetrahydro-quinolin-4-yl]-benzamide was synthesized as described in general procedure C, except following benzyl carbamate removal the amine was modified in the following manner. To a solution of (2S,4R)-(4-amino-2-methyl-3,4-dihydro-2H-quinolin-1-yl)-(4-methoxy-phenyl)-methanone (200 mg, 0.68 mmol) in 20 ml dichloromethane was added acetaldehyde (0.042 mL, 0.75 mmol). The reaction mixture was stirred 30 min at room temperature. Then sodium triacetoxyborohydride (0.156 g, 0.75 mmol) was added and the resulting reaction mixture was stirred at room temperature for 6 hours. N,N-diisopropylethylamine (0.3 mL, 2.3 mmol) and 4-chlorobenzoyl chloride (0.4 mL, 3.1 mmol) was added and stirred at room temperature overnight. Dichloromethane (40 ml) was added. The mixture was washed with 30 ml sodium hydroxide (1N). The organic layer was dried with magnesium sulfate, filtered and concentrated in vacuo. The residue was purified by silica gel chromatography, eluting with ethyl acetate-dichloromethane (1:4) to give 80 mg (24%) title compound $^1$H-NMR (CDCl$_3$) δ: 1.2-1.4 (7H, m), 1.7 (1H, m), 2.7 (1H, m), 3.1 (1H, m), 3.8 (3H, s), 4.2 (1H, m), 4.8 (1H, m), 6.5 (1H, d), 6.6 (2H, d), 6.8 (2H, m), 6.9 (1H, m), 7.1-7.5 (6H, m)

MS m/z: 463 (M+1).

N-[3-(3-Methoxy-benzoyl)-1,2,3,4-tetrahydro-quinolin-4-yl]-N-phenyl-acetamide (F-3)

N-[1-(3-Methoxy-benzoyl)-1,2,3,4-tetrahydro-quinolin-4-yl]-N-phenyl-acetamide was made from 1-(4-methoxy-benzoyl)-2,3-dihydro-1H-quinolin-4-one which was synthesized according to reference Bellassou-Fargeau, M. C.; Graffe, B.; Sacquet, M. C.; Maitte, P. *J. of Heter. Chem.* 1985, 22(3), 713. This was further elaborated to (4-hydroxy-3,4-dihydro-2H-quinolin-1-yl)-(3-methoxy-phenyl)-methanone by reduction of the ketone to the alcohol and in-situ formation of the iodide and displacement with the aniline according to the following procedure the following procedure. To a solution of 1-(3-methoxy-benzoyl)-2,3-dihydro-1H-quinolin-4-one (310 mg, 1.1 mmol) in 5 ml methanol was added 410 mg sodium borohydride (4.4 mmol). The resulting reaction mixture was stirred at room temperature for 3 hours. The mixture was concentrated under vacuum and the residue was purified by silica gel chromatography, eluting with ethyl acetate-hexane (1:2) to give (4-hydroxy-3,4-dihydro-2H-quinolin-1-yl)-(3-methoxy-phenyl)-methanone (215 mg, 69%). This was further elaborated to (3-methoxy-phenyl)-(4-phenylamino-3,4-dihydro-2H-quinolin-1-yl)-methanone using the following procedure. To a chilled solution of (4-hydroxy-3,4-dihydro-2H-quinolin-1-yl)-(4-methoxy-phenyl)-methanone in dichloromethane was added slowly iodotrimethylsilane at 0° C. The resulting reaction mixture was stirred at 0° C. for 6 hours. Then the mixture was concentrated under vacuum. The residue was dissolved in THF. BaCO$_3$ and aniline was added. The mixture was stirred at room temperature overnight. The mixture was filtered and the filtrate was concentrated under vacuum. The residue was purified by silica gel chromatography, eluting with ethyl acetate-hexane (1:4) to give (4-phenylamino-3,4-dihydro-2H-quinolin-1-yl)-(3-methoxy-phenyl)-methanone To a solution of (4-phenylamino-3,4-dihydro-2H-quinolin-1-yl)-(4-methoxy-phenyl)-methanone in methylene chloride was added diisopropylethylamine followed by acetyl chloride. The mixture was stirred at room temperature over night. The mixture was poured into water and extracted with dichloromethane. The extracts were washed with 1 M (aq) NaOH and brine, dried over magnesium sulfate, filtered dried and concentrated. The crude residue was purified by silica gel chromatography (50% hexanes/50% ethyl acetate) to afford (±)-N-[1-(3-methoxy-benzoyl)-1,2,3,4-tetrahydro-quinolin-4-yl]-N-phenyl-acetamide.

$^1$H-NMR (CDCl$_3$) δ: 1.2 (1H, m), 1.9 (3H, s), 2.1 (1H, m), 2.3 (1H, m), 3.5 (1H, m), 3.7 (3H, m), 4.1 (1H, m), 6.4 (2H, m), 6.6 (1H, m), 6.8-7.3 (6H, m), 7.4 (3H, m), 7.5 (1H, d).

MS m/z: 401 (M+1).

TABLE 6

Structurally Diverse Series

| No. | Structure |
|---|---|
| F-1 | 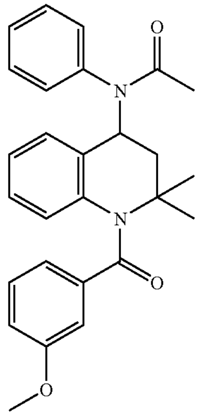 |
| F-2 | 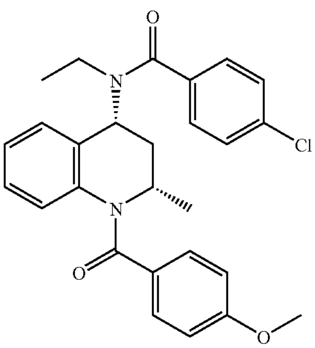 |
| F-3 | 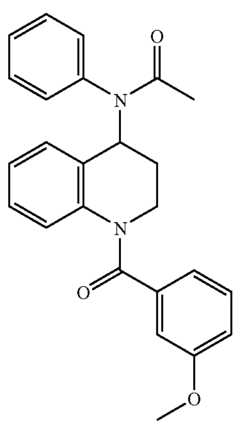 |

The Disclosed Compounds Inhibit Binding of PGD$_2$ to CRTH2

This radioligand membrane binding assay evaluates the ability of compounds to inhibit [$^3$H] Prostaglandin D$_2$ (PGD$_2$) binding to the cloned human CRTH2 receptor stably expressed in HEK-293 cells (expressing human CRTh2 receptor and α subunit or the heteronimeric G protein 16 were prepared by Biosignal Company) using Scintillation Proximity Assay.

A binding buffer containing 50 mM Tris-HCl (pH 7.5), 5 mM MgCl$_2$ and 1 mM EDTA was prepared immediately prior to performing the assay. A bead/membrane solution at twice the final assay concentration comprising membranes (membranes bought from Biosignal) from the HEK-293 cells cloned to express CRTH2 receptor bound to and [3H] PGD$_2$ at twotimes the final assay concentration were prepared and stored on ice before adding to wells. Cold PGD$_2$ at twenty times the final assay concentration was prepared and stored on ice before adding to wells defining non-specific binding (NSB) corning plates #3653 were used for this assay.

10 mM stock concentrations of compounds in 100% DMSO were prepared and stored at room temperature. A 10 point concentration response curve was then constructed for each compound, starting at 10 µM (final assay concentration). The compounds were prepared at 40 times final assay concentrations with nine consequent-3-fold dilutions.

0.1 µl of each concentration of compound were added to the appropriate well of the 384 plate and 2 µl of cold PGD$_2$ was added into the wells defining NSB. 20 µl of [$^3$H] PGD$_2$ and then 20 µl of 2× of bead/membrane solution were then added to each well.

The plates were allowed to incubate at room temperature for approximately 2 hours and then counted on Packard Topcount using SPA tritium protocol for 1 minute/well.

The percent inhibition of PGD$_2$ binding (PGD$_2$ used at the K$_D$ value or lower) to the HEK-293 cell membranes was determined, the assay was always run as duplicate for n=1 for a total of n=2.

Compounds A-3, A-11, A-16, A-17, A-20, A-24, A-35, A49, A-51, A-54, A-55, A-67, A-70, A-72, A-73, A-81, A-82, A-120, A-130, A-131, A-132, A-143, A-144, A-147, A-153, A-156, A-157, A-159, B-7, B-9, B-11, B-13, B-18, B-20, B-26, B-28, B-34, B-39, B40, B47, B-51, B-58, B-59, B-63 to B-66, B-68, B-70, B-73, B-74, B-84, B-86, B-97, B-101 to B-112, C-33, C-37, C-38, D-1, D-2, D-6, D-10, F-3 have K$_i$<10 uM.

Compounds A-8, A-53, A-58, A-124, A-126, A-154, B-53, B-100, F-l have K$_i$<60 uM.

All remaining compounds have K$_i$<1 uM

| Ammonium acetate-standard conditions: | |
|---|---|
| % A (Water) | 95.0 |
| % B (Acetonitrile) | 5.0 |
| % Ammonium acetate | 0.1 |
| Flow (ml/min) | 2.500 |
| Stop Time (mins) | 3.8 |
| Min Pressure (bar) | 0 |
| Max Pressure (bar) | 400 |
| Oven Temperature Left (° C.) | 10.0 |
| Oven Temperature Right (° C.) | 10.0 |

HP1100 LC Pump Gradient Timetable
The gradient Timetable contains 4 entries which are:

| Time | A % | B % | C % | D % | Flow | Pressure |
|---|---|---|---|---|---|---|
| 0.00 | 95.0 | 5.0 | 0.0 | 0.0 | 2.500 | 400 |
| 2.00 | 0.0 | 100.0 | 0.0 | 0.0 | 2.500 | 400 |
| 3.00 | 0.0 | 100.0 | 0.0 | 0.0 | 2.500 | 400 |
| 3.05 | 95.0 | 5.0 | 0.0 | 0.0 | 2.000 | 400 |

LC-MS data were acquired using the "Ammonium acetate-standard" method unless otherwise noted.

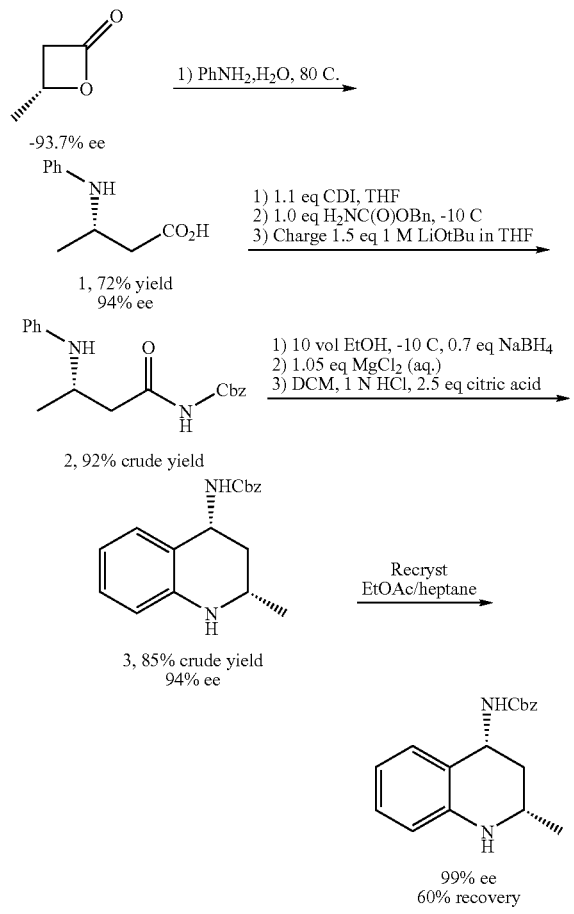

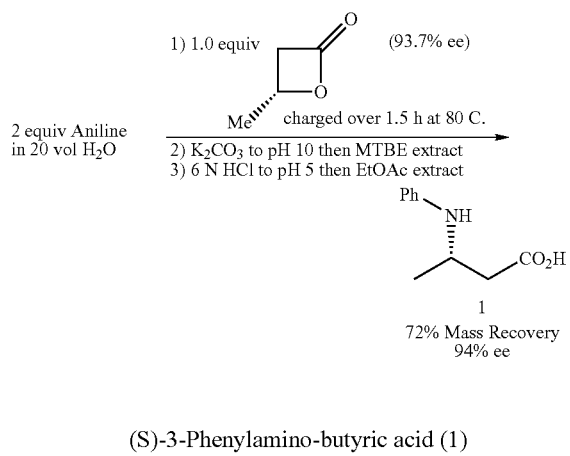

(S)-3-Phenylamino-butyric acid (1)

A jacketed 30-L 3-neck bottom-valve cylindrical reactor equipped with overhead stirrer, reflux condenser, addition funnel, and N₂ inlet was flushed with N₂. Water (8.7 L) was charged followed by aniline (423 L, 4.9 mol). Stirring was initiated and the internal temperature set for 80° C. After the internal temperature reached 77° C., (R)-β-butyrolactone was charged over 1.5 h via addition funnel. The internal temperature was maintained between 80-81.7° C. during the course of addition. Once addition was completed, reaction was cooled to 20° C. over 1 h. K₂CO₃ (250 g, 1.8 mol, 0.75 equiv) was charged as a solid, and the aqueous pH was determined to be 10. The aqueous phase was extracted with MTBE (3×2 L), and the extracts were discarded. After adjusting the pH of the aqueous phase to 5 with 6 N HCl (225 mL), it was extracted with EtOAc (3×2 L). After each extraction, the pH was checked and was readjusted to 5 with 6 N HCl as necessary. The combined EtOAc extracts were washed with saturated brine (2 L), dried with MgSO₄, and concentrated via rotary evaporation to produce a pink oil. Recovery: 300 g (72%). Enantiomeric excess was determined by chiral HPLC to be 94%.

¹H-NMR (CDCl₃) δ: 7.24 (t, 2H); 6.81 (t, 1H); 6.73 (d, 2H); 3.93 (m, 1H); 2,68 (dd, 1H); 2.51 (dd, 1H); 1.30 (d, 3H).

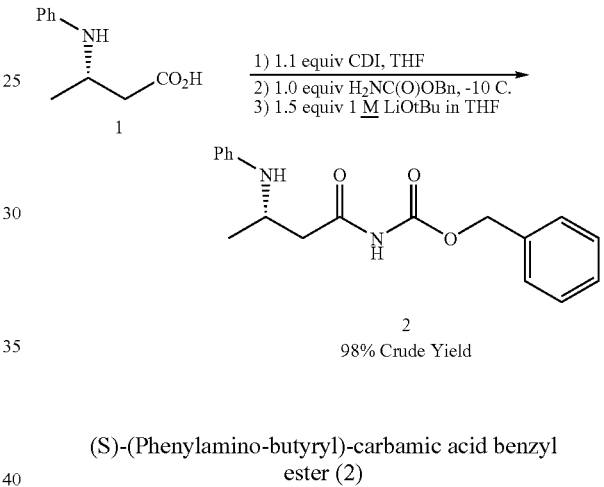

(S)-(Phenylamino-butyryl)-carbamic acid benzyl ester (2)

A 5-L, jacketed, glass reactor equipped with overhead stirrer, addition funnel and thermocouple was flushed with N₂. A solution of (S)-3-phenylaminobutyric acid (1, 100 g, 558 mmol) in 800 mL THF (8 volumes relative to amino acid) was charged to the reactor. The internal temperature of the reaction mixture was set to 20° C. 1,1'-Carbonyldiimidazole (99.5 g, 614 mmol) was charged to the stirred solution to produce a clear solution along with a mild exotherm (5° C.) and much gas evolution. After 1 h, benzyl carbamate (84.3 g, 558 mmol) was charged, and the internal temperature was set for −15° C. At −15° C., a 1 M solution of LiOt-Bu in THF (837 mL, 837 mmol) was charged to the reaction via addition funnel in 30 min so as to maintain the internal temperature between −10 and −15° C. The solution becomes opaque pale brown and more viscous. The internal temperature is maintained at about −10° C. for another 15 min and then allowed to warm to ambient temperature. After 16 h, the reaction was quenched by the addition of 1000 mL EtOAc (10 volumes) followed by the 280 mL 1N HCl and 1000 mL H₂O (10 volumes). The resulting aqueous phase was pH 9. The phases were separated, and the aqueous phase was extracted with another 600 mL EtOAc (6 volumes). The organic phases were combined and washed with 1000 mL 10% brine (10 volumes). The resulting organic solution of crude product is distilled down to a minimal volume of 500 to 700 mL at 170 to 200 torr and a pot temperature of 35 to 40° C. This crude product was partitioned between 2.0 L 1N HCl (20 volumes) and 1.0 L MTBE. An amber oily phase formed which was the HCl salt of the product and was kept with the aqueous acid phase. The MTBE phase was extracted with another 1000 mL 1N HCl (10 volumes), and the combined HCl phases were backwashed with another 500 mL MTBE. The pH of the aqueous solution was adjusted to 9-10 by the addition of 495 mL saturated aqueous $K_2CO_3$. The aqueous basic solution was extracted twice with 800 mL EtOAc (8 volumes), and the organic phases were combined, washed with 500 mL brine, dried over $Na_2SO_4$ and evaporated to produce 161 g (92%) of crude amber oil.

$^1$H-NMR (CDCl$_3$) δ: 7.35 (m, 5H); 7.15 (t, 2H); 6.72 (t, 1H); 6.61 (d, 2H); 5.15 (s, 2H); 4.03 (m, 1H); 3.02 (dd, 1H); 2.84 (dd, 1H); 1.28 (d, 3H).

begins around 58 to 68° C. At ambient temperature, another 1300 mL heptane (10 volumes) was slowly added. After stirring at ambient another 2 hr, the solids are filtered and washed with 4 volumes of 9/1 heptane/EtOAc. The solids were dried in a vacuum oven to provide 90 g (60% recovery). The product had an enantiomeric excess of 99.2% as determined by chiral HPLC.

$^1$H-NMR (CDCl$_3$) δ: 7.38 (m, 5H); 7.22 (d, 1H); 7.07 (t, 1H); 6.78 (t, 1H); 6.69 (d, 1H); 5.17 (s, 2H); 5.07 (m, 1H); 4.94 (d, 1H); 3.58 (m, 1H); 2.33 (m, 1H); 1.60 (q, 1H); 1.30 (d, 3H).

Scheme 20

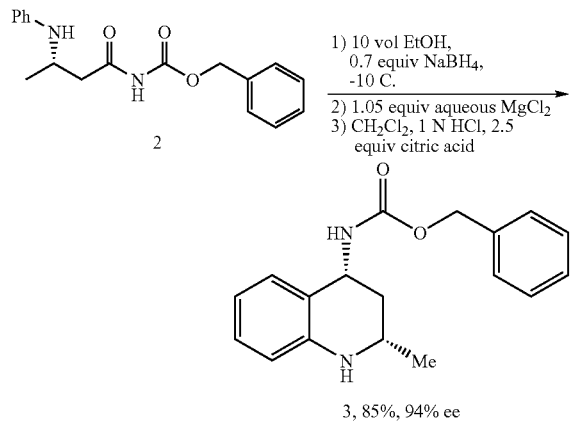

3, 85%, 94% ee

(2S,4R)-(2-Methyl-1,2,3,4-tetrahydro-quinolin-4-yl)-carbamic acid benzyl ester (3)

A 5-L, jacketed, glass reactor equipped with overhead stirrer, addition funnel and thermocouple was flushed with $N_2$. A solution of (S)-(Phenylamino-butyryl)-carbamic acid benzyl ester (2) (160 g, 512 mmol) in EtOH (960 mL, 6 volumes) was charged to the reactor, and the internal temperature was set to −15° C. The NaBH$_4$ (13.6 g, 359 mmol) was charged to the stirred solution in 3 portions. An aqueous solution of MgCl$_2$.6H$_2$O (109 g, 538 mmol in 110 mL water) was charged to the reactor via addition funnel over 1 h to maintain the internal temperature between −10 to −5° C. After the addition was complete, the internal temperature was adjusted to 0° C. and the mixture was allowed to stir another 30 min. The reactor was charged with 960 mL CH$_2$Cl$_2$ (6 volumes), citric acid (246 g, 1280 mmol), and 960 mL 1N HCl (6 volumes). The internal temperature was set for 20° C. and the mixture was allowed to stir for 16 h. The reaction mixture was diluted with 960 mL EtOAc and the aqueous pH was adjusted to 9 by the addition of 470 mL saturated aqueous K$_2$CO$_3$. The phases were separated and the organic phase washed twice with 640 mL water and then 640 mL brine. The organic phase was dried over Na$_2$SO$_4$ and evaporated to provide 130 g of a solid (86% yield). The crude product was recrystallized from 20 volumes of a 9/1, heptane/EtOAc mixture. The solid was slurried with 260 mL EtOAc (2 volumes) and 780 mL heptane (6 volumes) and heated to 75° C. to provide a clear solution. At 75° C., another 260 mL heptane (2 volumes) was slowly added followed by gradual cooling. Crystallization usually Scheme 21

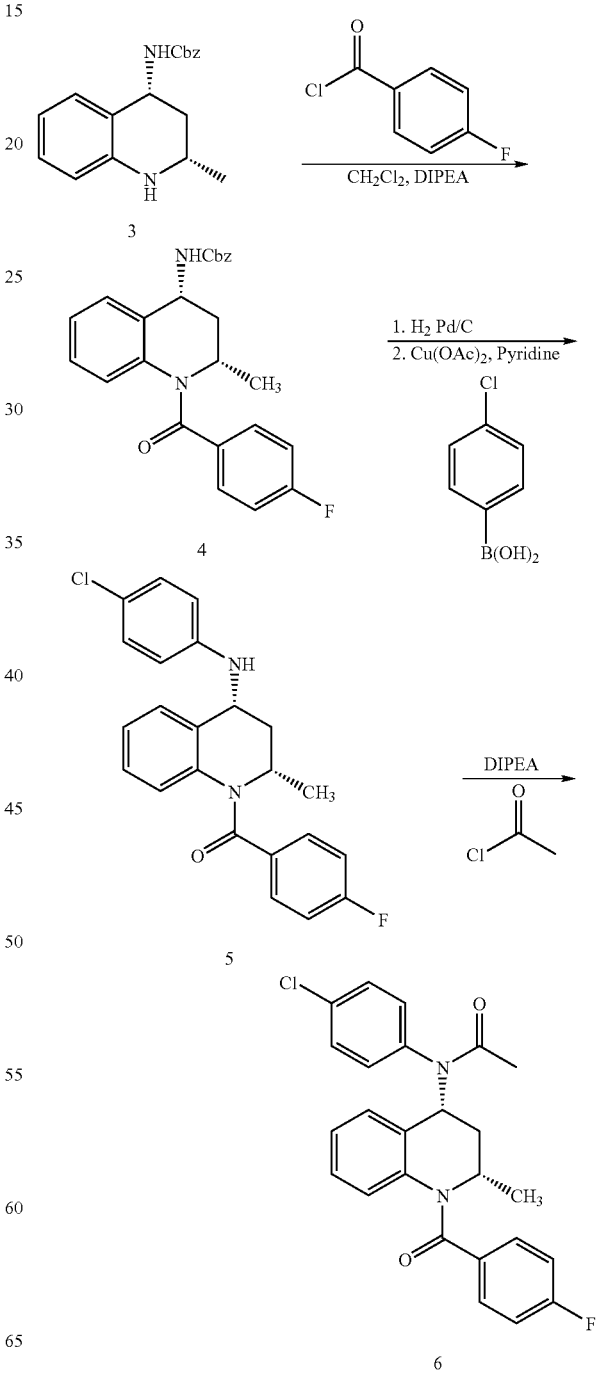

General Procedure G:

(2S,4R)-N-(4-Chloro-phenyl)-N-[1-(4-fluoro-benzoyl)-2-methyl-1,2,3,4-tetrahydro-quinolin-4-yl]-acetamide (6)

To a solution of (2S,4R)-(2-methyl-1,2,3,4-tetrahydroquinolin-4-yl)-carbamic acid benzyl ester (1.0 g, 3.38 mmol) in methylene chloride (50 mL) at room temperature was added diisopropylethylamine (650 uL, 3.72 mmol) followed by 4-fluorobenzoyl chloride. The reaction was stirred over night at room temperature. The mixture was poured into water and extracted with ethyl acetate. The extracts were washed with 1 M (aq) NaOH and brine, dried over magnesium sulfate, filtered dried and concentrated. The crude residue was purified by silica gel chromatography (75% hexanes/25% ethyl acetate) to afford the pure amide (720 mg, 51%).

(2S,4R)-[1-(4-fluorobenzoyl)-2-methyl-1,2,3,4-tetrahydro-quinolin-4-yl]-carbamic acid benzyl ester (720 mg, 1.73 mmol) was dissolved in ethanol (30 mL). The vessel in which resided the resulting solution was evacuated and backfilled with argon. A catalytic amount of Palladium on Carbon (10%) was added. The vessel was once again evacuated and this time was backfilled with hydrogen and shaken in a Parr bottle at 40 psi hydrogen. Reaction was complete after 4 h. The mixture was carefully filtered and concentrated to 10% volume. The resulting concentrated solution was filtered through an Celite® and concentrated to afford the crude amine.

To a solution of (2S,4R)-(4-amino-2-methyl-3,4-dihydro-2H-quinolin-1-yl)-(4-fluoro-phenyl)-methanone (1.0 g, 3.5 mmol) in DMF (20 mL, dry) was added 4-chlorophenylboronic acid (1.1 g, 7.0 mmol), pyridine (850 uL, 10.5 mmol) and copper(II)acetate (1.27 g, 7.0 mmol). The heterogeneous green mixture was stirred open to air for 1 h and then warmed to 60° C. and stirred over night (14 h). The mixture was then cooled to rt, poured into rapidly stirred ethyl acetate (150 mL); solids were removed by filtration through Celite®. The extracts were washed several times with water and then once with brine. The extracts were then dried over anhydrous magnesium sulfate, filtered, and concentrated under reduced pressure. The crude residue was purified by silica gel chromatography (95% methylene chloride/5% ethyl acetate) to afford the aniline product (250 mg, 18%) as a yellow oil.

To a solution of (2S,4R)-[4-(4-chloro-phenylamino)-2-methyl-3,4-dihydro-2H-quinolin-1-yl]-(4-fluoro-phenyl)-methanone (250 mg, 0.636 mmol) in acetyl chloride (5 mL) was added diisopropylethylamine (120 uL, 0.70 mmol). The mixture was stirred at rt 4 h. The mixture was concentrated under reduced pressure, dissolved in ethyl acetate, washed with sat. aqueous sodium bicarbonate, brine and dried over magnesium sulfate, filtered, and concentrated under reduced pressure. The residue was purified by silica gel chromatography (25/75 hexanes/ethyl acetate gradient) to afford pure N-(4-chloro-phenyl)-N-[1-(4-fluoro-benzoyl)-2-methyl-1,2,3,4-tetrahydro-quinolin-4-yl]-acetamide (200 mg, 71%).

$^1$H-NMR (CDCl$_3$) δ: 1.1 (d, 3H), 1.1 (m, 1H), 2.0 (d, 3H), 2.3 (m, 1H), 4.7 (m, 1H), 5.6 (m, 1H), 6.5 (d, 1H), 6.7-7.0 (m, 3H), 7.1-7.4 (m, 8H).

MS m/z: 436 (M+1).

(2S,4R)-4-(4-{4-[Acetyl-(4-chloro-phenyl)-amino]-2-methyl-3,4-dihydro-2H-quinoline-1-carbonyl}-phenyl)-piperazine-1-carboxylic acid ethyl ester (G-1)

(2S,4R)-4-(4-{4-[Acetyl-(4-chloro-phenyl)-amino]-2-methyl-3,4-dihydro-2H-quinoline-1-carbonyl}-phenyl)-piperazine-1-carboxylic acid ethyl ester was made following general procedure G, substituting 4-(4-chlorocarbonyl-phenyl)-piperazine-1-carboxylic acid ethyl ester for 4-fluorobenzoyl chloride. The rest of the procedure is followed as indicated in general procedure G to yield (2S,4R)-4-(4-{4-[acetyl-(4-chloro-phenyl)-amino]-2-methyl-3,4-dihydro-2H-quinoline-1-carbonyl}-phenyl) -piperazine-1-carboxylic acid ethyl ester.

4-(4-Chlorocarbonyl-phenyl)-piperazine-1-carboxylic acid ethyl ester was prepared by the following procedure. Piperdine and 4-fluoro-benzoic acid methyl ester were heated at 65° C. in DMSO for 48 h (U.S. Pat. No. 6,069,143). The reaction was quenched with NaHCO$_3$ and extracted 3x ethyl acetate was dried over MgSO$_4$, filtered and concentrated down. The ester was used directly. 4-Piperazin-1-yl-benzoic acid methyl ester was acetylated with ethyl chloroformate and DIEA in CH$_2$Cl$_2$ to give 4-(4-methoxycarbonyl-phenyl)-piperazine-1-carboxylic acid ethyl ester. The methyl ester was hydrolyzed with to the acid by dissolving in tetrahydrofuran and ethanol and sodium hydroxide (1N) was added. The mixture was stirred at room temperature 2 hours. The mixture was cooled to 0° C., acidified to form a white precipitate. The solid was filtered to give 4-(4-methoxycarbonyl-phenyl)-piperazine-1-carboxylic acid. The acid was converted to the acid chloride by reaction with oxalyl chloride.

$^1$H-NMR (CDCl$_3$) δ: 1.10 (d, 3H), 1.24 (m, 4H), 2.00 (s, 3H), 2.27 (m, 1H), 3.13 (t, 4H), 3.55 (t, 4H), 4.12 (q, 2H), 4.70 (m, 1H), 5.56 (brs, 1H), 6.54 (d, 1H), 6.62 (d, 2H), 6.91 t, 1H), 7.09 (d, 2H), 7.14 (d, 2H), 7.27 (m, 2H), 7.36 (d, 2H).

MS m/z: 575.16 (M+1).

N-{3-[(glycoloylamino)methyl]phenyl}-N-[(2S,4R)-1-(4-methoxybenzoyl)-2-methyl-1,2,3,4-tetrahydro-quinolin-4-yl]acetamide (G-2)

N-{3-[(glycoloylamino)methyl]phenyl}-N-[(2S,4R)-1-(4-methoxybenzoyl)-2-methyl-1,2,3,4-tetrahydroquinolin-4-yl]acetamide was prepared following general procedure G, substituting 4-methoxybenzoyl chloride for 4-fluorobenzoyl chloride, and (3-cyanophenyl)boronic acid for 4-chlorophenylboronic acid. The rest of the procedures were followed as indicated in general procedure A to afford N-(3-cyanophenyl)-N-[(2S,4R)-1-(4-methoxybenzoyl)-2-methyl-1,2,3,4-tetrahydroquinolin-4-yl]acetamide.

N-(3-cyanophenyl)-N-[(2S,4R)-1-(4-methoxybenzoyl)-2-methyl-1,2,3,4-tetrahydroquinolin-4-yl]acetamide was further treated with cobalt(II)chloride and sodium borohydride (1 eq, 3 eq) to afford N-[3-(aminomethyl)phenyl]-N-[(2S,4R)-1-(4-methoxybenzoyl)-2-methyl-1,2,3,4-tetrahydroquinolin-4-yl]acetamide.

N-[3-(aminomethyl)phenyl]-N-[(2S,4R)-1-(4-methoxybenzoyl)-2-methyl-1,2,3,4-tetrahydroquinolin-4-yl]acetamide was then further coupled with glycolic acid using coupling reagent such as EDCI with HOBt to afford N-{3-[(glycoloylamino)methyl]phenyl}-N-[(2S,4R)-1-(4-methoxybenzoyl)-2-methyl-1,2,3,4-tetrahydroquinolin-4-yl]acetamide $^1$H-NMR (CDCl3) δ: 1.1-1.2 (m, 4H), 2.0 (s, 3H), 2.3 (m, 1H), 3.8 (s, 3H), 4.2 (m, 1H), 4.5 (m, 2H), 4.7 (m, 2H), 5.6 (br, 1H), 6.5 (m, 1H), 6.6 (m, 2H), 6.9 (m, 1H), 7.1-7.4 (m, 8H).

MS m/z: 502 (M+1).

N-(4-chloro-2-fluorophenyl)-N-[(2S,4R)-1-(4-methoxybenzoyl)-2-methyl-1,2,3,4-tetrahydroquinolin-4-yl]acetamide (G-3)

N-(4-chloro-2-fluorophenyl)-N-[(2S,4R)-1-(4-methoxybenzoyl)-2-methyl-1,2,3,4-tetrahydroquinolin-4-yl]acetamide was made following general procedure G, substituting 4-methoxybenzoyl chloride for 4-fluorobenzoyl chloride. The amine-aryl coupling was performed differently to what is described in procedure G. Therefore (2S,4R)-1-(4-methoxybenzoyl)-2-methyl-1,2,3,4-tetrahydroquinolin-4-amine (obtained from the hydrogenation step, 200 mg, 0.6 mmol, 1 equ.) was dissolved in ethylene glycol dimethyl ether (1 mL) in a Schlenk tube. To this solution was added sequentially 1-bromo-4-chloro-2-fluorobenzene (105 uL, 0.84 mmol, 1.4 equ.), cesium carbonate (274 mg, 0.84 mmol, 1.4 equ.), palladium acetate (16 mg, 0.024 mmol, 0.04 equ.) and 2-(Dicyclohexylphosphino)-2',4',6'-tri-i-propyl-1,1'-biphenyl (23 mg, 0.048 mmol, 0.08 equ.). The reaction mixture was flushed with nitrogen and heated to 95° C. in the Schlenk tube for 48 h. Reaction mixture was concentrated to leave a residue which was partitioned between water and ethyl acetate and extracted. The aqueous layer was separated and the organic layer was washed with brine, dried over magnesium sulfate, filtered and concentrated to give a black oil. The crude product was purified by silica gel chromatography (methylene chloride/methanol: 100/0 to 99/1 gradient) to provide (2S,4R)-N-(4-chloro-2-fluorophenyl)-1-(4-methoxybenzoyl)-2-methyl-1,2,3,4-tetrahydroquinolin-4-amine (60 mg, 24%).

To a solution of (2S,4R)-N-(4-chloro-2-fluorophenyl)-1-(4-methoxybenzoyl)-2-methyl-1,2,3,4-tetrahydroquinolin-4-amine (60 mg, 0.14 mmol, 1 equ.) in acetyl chloride (0.5 mL) was added diisopropylethylamine (25 uL, 0.14 mmol, 1 equ.). The mixture was stirred at room temperature for 16 h. The mixture was concentrated under reduced pressure, dissolved in ethyl acetate, washed with sat. aqueous sodium bicarbonate, brine and dried over magnesium sulfate, filtered, and concentrated under reduced pressure. The residue was purified by silica gel chromatography (methylene chloride/methanol 99.5/0.5) to afford pure N-(4-chloro-2-fluorophenyl)-N-[(2S,4R)-1-(4-methoxybenzoyl)-2-methyl-1,2,3,4-tetrahydroquinolin-4-yl]acetamide (140 mg, 92%).

$^1$H-NMR (CDCl3) δ: 1.15 (d, 3H), 2.05 (s, 3H), 2.30 (m, 1H), 3.75 (s, 3H), 4.75 (m, 1H), 5.65 (m, 1H), 6.50 (d, 1H), 6.70 (d, 2H), 7.00 (t, 1H), 7.15-7.20 (m, 4H), 7.25-7.40 (m, 3H).

MS m/z: 467 (M+1).

4-{[(2S,4R)-4-[acetyl(4-chlorophenyl)amino]-2-methyl-3,4-dihydroquinolin-1(2H)-yl]carbonyl}benzamide (G-4)

N-(4-chlorophenyl)-N-[(2S,4R)-1-(4-cyanobenzoyl)-2-methyl-1,2,3,4-tetrahydroquinolin-4-yl]acetamide (143 mg, 0.33 mmol) and potassium hydroxide (55 mg, 1.00 mmol)) were dissolved in water (150 mL), ethanol (3 mL) and heated to 70° C. for 4 h. The slurry was portioned between 1N HCl (until acidic) and methylene chloride. The organic layer was collected, concentrated and subjected to flash chromatography (EtOAc to 20% MeOH, EtOAc) to afford the title compound as a white solid.

$^1$H-NMR (CDCl$_3$) δ: 1.15-1.25 (m, 1H), 1.17 (d, 3H), 2.11 (s, 3H), 2.20-2.34 (m, 1H), 4.70-4.84 (m, 1H), 5.50-5.80 (m, 1H), 5.80-6.00 (m, 1H), 6.40-6.60 (m, 1H), 6.40 (d, 1H), 6.83 (t, 1H), 7.08-7.30 (m, 8H), 7.60 (d, 2H).

MS m/z: 462 (M+1)

(2S,4R)-4-(4-{4-[Acetyl-(4-chloro-phenyl)-amino]-2-methyl-3,4-dihydro-2H-quinoline-1-carbonyl}-2-fluoro-phenoxy)-2,2-dimethyl-butyric acid methyl ester (G-5)

To a solution of (2S,4R)-(2-methyl-1,2,3,4-tetrahydroquinolin-4-yl)-carbamic acid benzyl ester in methylene chloride at room temperature was added diisopropylethylamine followed by 3-fluoro-4-methoxy-benzoyl chloride. The reaction was stirred over night at room temperature. The mixture was poured into water and extracted with ethyl acetate. The extracts were washed with 1 M (aq) NaOH and brine, dried over MgSO$_4$, filtered dried and concentrated. The crude residue was purified by silica gel chromatography (75% hexanes/25% ethyl acetate) to afford the pure amide.

(2S,4R)-[1(3-Fluoro-4-methoxy-benzoyl)-2-methyl-1,2,3,4-tetrahydro-quinolin-4-yl]-carbamic acid benzyl ester was dissolved in ethanol (30 mL). The vessel in which resided the resulting solution was evacuated and backfilled with argon. A catalytic amount of Palladium on Carbon (10%) was added. The vessel was once again evacuated and this time was backfilled with hydrogen and shaken in a Parr bottle at 40 psi hydrogen. Reaction was complete after 4 hours. The mixture was carefully filtered and concentrated to 10% volume. The resulting concentrated solution was filtered through an Celite® and concentrated to afford the crude amine.

To a solution of (2S,4R)-(4-Amino-2-methyl-3,4-dihydro-2H-quinolin-1-yl)-(3-fluoro-4-methoxy-phenyl)-methanonein in DMF (dry) was added 4-chlorophenylboronic acid, pyridine and copper(II)acetate. The heterogeneous green mixture was stirred open to air for 1 hour and then warmed to 60° C. and stirred over night (14 h). The mixture was then cooled to room temperature, poured into rapidly stirred ethyl acetate (150 mL); solids were removed by filtration through Celite®. The extracts were washed several times with water and then once with brine. The extracts were then dried over anhydrous MgSO$_4$, filtered, and concentrated under reduced pressure. The crude residue was purified by silica gel chromatography (95% methylene chloride/5% ethyl acetate) to afford the aniline product as a yellow oil.

To a solution of (2S,4R)-[4-(4-chloro-phenylamino)-2-methyl-3,4-dihydro-2H-quinolin-1-yl]-(3-fluoro-4-methoxy-phenyl)-methanone in methylene chloride was added diisopropylethylamine followed by acetyl chloride. The mixture was stirred at rt 4 h. The mixture was concentrated under reduced pressure, dissolved in ethyl acetate, washed with sat. aq. NaHCO$_3$, brine and dried over magnesium sulfate, filtered, and concentrated under reduced pressure. The residue was purified by silica gel chromatography (25/75 hexanes/ethyl acetate gradient) to afford pure the final product.

N-(4-Chloro-phenyl)-N-[1-(3-fluoro-4-hydroxy-benzoyl)-2-methyl-1,2,3,4-tetrahydro-quinolin-4-yl]-acetamide (115 mg, 0.256 mmol) was dissolved in DMF (5 mL) at room temperature. K$_2$CO$_3$ (175 mg, 1.28 mmol) and 5-bromo-2,2-dimethyl-pentanoic acid ethyl ester (100 mg, 0.511 mmol) was added and the reaction mixture was allowed to stir over night. The mixture was partitioned between methylene chloride and water; the methylene chloride layer was dried over MgSO$_4$, filtered and concentrated. The crude residue was purified by silica gel chromatography (2/1 hexanes/ethyl acetate-ethyl acetate gradient) to afford the product.

$^1$H-NMR (CDCl$_3$) δ: 1.1 (d, 3H), 1.2 (s, 6H), 1.2 (m, 1H), 2.0 (s, 3H), 2.0 (t, 1H), 2.3 (m, 1H), 3.8 (s, 3H), 4.0 (t, 2H), 4.7 (m, 2H), 5.6 (bs, 1H), 6.5 (d, 1H), 6.6 (t, 1H), 6.7 (d, 1H), 6.9 (t, 1H), 7.2 (m, 5H), 7.4 (d, 2H).

MS m/z: 581 (M+1).

(2S,4R)-N-(4-chloro-phenyl)-N-[1-(3,4-dihydro-2H-benzo[1,4]oxazine-6-carbonyl)-2-methyl-1,2,3,4-tetrahydro-quinolin-4-yl]-acetamide (G-6)

6-{4-[Acetyl-(4-chloro-phenyl)-amino]-2-methyl-3,4-dihydro-2H-quinoline-1-carbonyl}-2,3-dihydro-benzo[1,4]oxazine-4-carboxylic acid ethyl ester was dissolved in methylene chloride (3 mL) and iodotrimethylsilane (1 mL). After 4 days, the reaction was quenched with sat. aq. NaHCO$_3$. The residue was partitioned between methylene chloride and water, then extracted three times with methylene chloride, dried over MgSO$_4$, filtered and concentrated. The crude residue was purified by silica gel chromatography (ethyl acetate) to afford the product.

$^1$H-NMR (CDCl$_3$) δ: 1.1 (d, 3H), 1.2 (m, 1H), 2.0 (s, 3H), 2.3 (m, 1H), 3.3 (m, 2H), 4.2 (m, 2H), 4.7 (m, 1H), 5.5 (m, 1H), 6.4 (d, 1H), 6.5 (d, 1H), 6.6 (d, 2H), 6.96 (t, 1H), 7.2 (m, 5H), 7.4 (d, 2H).

MS m/z: 476 (M+1).

N-(4-chlorophenyl)-N-((2S,4R)-2-methyl-1-{4-[3-(trifluoromethyl)-1H-pyrazol-1-yl]benzoyl}-1,2,3,4-tetrahydroquinolin-4-yl)acetamide (G-7)

N-(4-chlorophenyl)-N-((2S,4R)-2-methyl-1-{4-[3-(trifluoromethyl)-1H-pyrazol-1-yl]benzoyl}-1,2,3,4-tetrahydroquinolin-4-yl)acetamide was prepared following general procedure A, substituting 4-[3-(trifluoromethyl)-1H-pyrazol-1-yl]benzoyl chloride for 4-fluorobenzoyl chloride. (4-[3-(trifluoromethyl)-1H-pyrazol-1-yl]benzoyl chloride was prepared in one step from 4-[3-(trifluoromethyl)-1H-pyrazol-1-yl]benzoic acid. 4-[3-(Trifluoromethyl)-1H-pyrazol-1-yl]benzoic acid was treated with oxalyl chloride in DCM and catalytic DMF to afford 4-[3-(trifluoromothyl)-1H-pyrazol-1-yl]benzoyl chloride in decent yield). The rest of the procedures were followed as indicated in general procedure A to afford N-(4-chlorophenyl)-N-((2S,4R)-2-methyl-1-{4-[3-(trifluoromethyl)-1H-pyrazol-1-yl]benzoyl}-1,2,3,4-tetrahydroquinolin-4-yl)acetamide.

$^1$H-NMR (CDCl3) δ: 1.20 (d, 3H; t, 1H), 2.03 (s, 3H), 2.33 (m, 1H), 4.80 (m, 1H), 5.62 (m, 1H), 6.47 (d, 1H), 6.77 (d, 1H), 6.90 (t, 1H), 7.00-7.40 (m, 10H)., 7.66 (d, 1H)

MS m/z: 553 (M+1).

(2S,4R)-N-(4-Chloro-phenyl)-N-[2-methyl-1-(4-methyl-3,4-dihydro-2H-benzo [1,4]oxazine-7-carbonyl)-1,2,3,4-tetrahydro-quinolin-4-yl]-acetamide (G-8)

To a solution of (2S,4R)-(2-methyl-1,2,3,4-tetrahydroquinolin-4-yl)-carbamic acid benzyl ester (400 mg, 1.36 mmol) in methylene chloride (4 mL) at room temperature was added triethylamine (0.320 mL, 2.3 mmol) followed by 4-methyl-3,4-dihydro-2H-benzo[1,4]oxazine-7-carbonyl chloride (1.5 mmol). The reaction was stirred over night at room temperature. The mixture was poured into water and extracted with ethyl acetate. The extracts were washed with 1 M (aq) NaOH and brine, dried over MgSO$_4$, filtered and concentrated. The crude residue was purified by silica gel chromatography (75% hexanes/25% ethyl acetate) to afford the pure amide.

(2S,4R)-[2-methyl-1-(4-methyl-3,4-dihydro-2H-benzo[1,4]oxazine-7-carbonyl)-1,2,3,4-tetrahydro-quinolin-4-yl]-carbamic acid benzyl ester (300 mg) was dissolved in ethanol. The vessel in which resided the resulting solution was evacuated and backfilled with argon. A catalytic amount of Palladium on Carbon (10%) was added. The vessel was once again evacuated and this time was backfilled with hydrogen and shaken in a Parr bottle at 40 psi hydrogen. Reaction was complete after 4 hours. The mixture was carefully filtered and concentrated to 10% volume. The resulting concentrated solution was filtered through an Celite® and concentrated to afford the crude amine.

To a solution of (2S,4R)-(4-amino-2-methyl-3,4-dihydro-2H-quinolin-1-yl)-(4-methyl-3,4-dihydro-2H-benzo[1,4]oxazin-7-yl)-methanone (662 mg, 1.87 mmol) in methylene chloride (8 mL) was added 4-chlorophenylboronic acid (583 mg, 3.74 mmol), triethylamine (1.81 ml, 13.09 mmol) and copper(II)acetate (681 mg, 3.74 mmol). The heterogeneous green mixture was stirred open to air for 1 hour and then warmed to 60° C. and stirred over night (14 h). The mixture was then cooled to room temperature, poured into rapidly stirred ethyl acetate (150 mL); solids were removed by filtration through Celite®. The extracts were washed several times with water and then once with brine. The extracts were then dried over anhydrous MgSO$_4$, filtered, and concentrated under reduced pressure. The crude residue was purified by silica gel chromatography (95% methylene chloride/5% ethyl acetate) to afford the aniline product as a yellow oil.

To a solution of (2S,4R)-[4-(4-Chloro-phenylamino)-2-methyl-3,4-dihydro-2H-quinolin-1-yl]-(4-methyl-3,4-dihydro-2H-benzo[1,4]oxazin-7-yl)-methanone (540 mg, 1.25 mmol) in methylene chloride (5 mL) was added diisopropylethylamine (0.240 mL, 1.37 mmol) followed by acetyl chloride (2 mL). The mixture was stirred at room temperature 4 hours. The mixture was concentrated under reduced pressure, dissolved in ethyl acetate, washed with sat. aq. NaHCO$_3$, brine and dried over magnesium sulfate, filtered, and concentrated under reduced pressure. The residue was purified by silica gel chromatography (25/75 hexanes/ethyl acetate gradient) to afford the final product.

$^1$H-NMR (CDCl$_3$) δ: 1.1 (d, 3H), 1.1 (m, 1H), 2.0 (d, 3H), 2.3 (m, 1H), 2.8 (s, 3H), 3.2 (t, 2H), 4.2 (t, 2H), 4.7 (m, 1H), 5.6 (m, 1H), 6.3 (d, 1H), 6.5 (d, 1H), 6.6 (d, 1H), 6.8 (s, 1H), 6.9 (t, 1H), 7.2 (m, 5H), 7.4 (d, 2H).

MS m/z: 490 (M+1).

(2S,4R)-N-(4-Chloro-phenyl)-N-[1-(2,2-difluoro-benzo[1,3]dioxole-5-carbonyl)-2-methyl-1,2,3,4-tetrahydro-quinolin-4-yl]-acetamide (G-9)

(2S,4R)-N-(4-Chloro-phenyl)-N-[1-(2,2-difluoro-benzo[1,3]dioxole-5-carbonyl)-2-methyl-1,2,3,4-tetrahydro-quinolin-4-yl]-acetamide was prepared following general procedure G, substituting 2,2-difluoro-1,3-benzodioxole-5-carbonyl chloride for 4-fluorobenzoyl chloride. The rest of the procedures were followed as indicated in general procedure G to afford (2S,4R)-N-(4-Chloro-phenyl)-N-[1-(2,2-difluoro-benzo[1,3]dioxole-5-carbonyl)-2-methyl-1,2,3,4-tetrahydro-quinolin-4-yl]-acetamide.

$^1$H-NMR (CDCl3) δ: 1.15 (3H, d; overlapping 1H, t), 2.02 (3H, s), 2.33 (1H, m), 4.78 (1H, m), 5.60 (1H, m), 6.44 (1H, d), 6.68 (1H, d), 6.95 (1H, t), 7.00-7.40 (8H, complex.

MS m/z: 499 (M+1).

5-(4-{[(2S,4R)-4-[acetyl(4-chlorophenyl)amino]-2-methyl-3,4-dihydroquinolin-1(2H)-yl]carbonyl}phenyl)pentanamide (G-10)

Benzyl [(2S,4R)-1-(4-iodobenzoyl)-2-methyl-1,2,3,4-tetrahydroquinolin-4-yl]carbamate was prepared following general procedure G, substituting 4-iodo-benzoyl chloride for 4-fluorobenzoyl chloride.

To a solution of benzyl [(2S,4R)-1-(4-iodobenzoyl)-2-methyl-1,2,3,4-tetrahydroquinolin-4-yl]carbamate (0.6 g, 1.14 mmol) in DMF (15 mL) at room temperature was added pent-4-enoic acid ethyl ester (0.292 g, 2.28 mmol), potassium acetate (0.67 g, 6.84 mmol), palladium acetate (0.05 g, 0.228 mmol), tetrabutylammonium chloride (0.32 g, 1.14 mmol), and triphenylphosphine (0.06 g, 0.228 mmol). The mixture was stirred at room temperature for 1 hour and then heated to 70° C. for 3 hours. The mixture was concentrated and ethyl acetate was added. The solution was washed with water, dried and concentrated. The residue was purified by silica gel chromatography (70% $CH_2Cl_2$/30% EtOAc) to afford ethyl (4E)-5-(4-{[(2S,4R)-4-{[(benzyloxy)carbonyl]amino}-2-methyl-3,4-dihydroquinolin-1(2H)-yl]carbonyl}phenyl)pent-4-enoate (0.5 g, 83%), which was further converted into ethyl 5-(4-{[(2S,4R)-4-[acetyl(4-chlorophenyl)amino]-2-methyl-3,4-dihydroquinolin-1(2H)-yl]carbonyl}phenyl)pentanoate following general procedure G.

Ethyl 5-(4-{[(2S,4R)-4-[acetyl(4-chlorophenyl)amino]-2-methyl-3,4-dihydroquinolin-1(2H)-yl]carbonyl}phenyl) pentanoate (0.135 g, 0.25 mmol) was hydrolyzed to the acid by dissolving in 6 ml methanol and potassium carbonate (0.2 g in 4 ml water) was added. The mixture was heated to 40° C. for 24 hours and methanol was removed in vacuo. The mixture was acidified to form a white precipitate. The solid was filtered to give the acid. To a solution of the acid in DMF (10 mL) at room temperature was added HATU (0.143 g, 0.375 mmol), DIEA (0.18 mL, 1 mmol), HOBt (0.057 g, 0.375 mmol), and ammonium chloride (0.027 g, 0.5 mmol) was added. The mixture was stirred for 18 hours and concentrated. The residue was dissolved in $CH_2Cl_2$ and washed with water. The organic layer was concentrated and purified by silica gel chromatography (87% $CH_2Cl_2$/13% methanol) to afford 5-(4-{[(2S,4R)-4-[acetyl(4-chlorophenyl)amino]-2-methyl-3,4-dihydroquinolin-1(2H)-yl]carbonyl}phenyl)pentanamide.

$^1$H-NMR (CDCl$_3$) δ: 1.16 (d, 3H), 1.18 (m, 1H), 1.56 (m, 3H), 1.98 (s, 3H), 2.05 (m, 1H), 2.14 (m, 2H), 2.26 (m, 1H), 2.53 (m, 2H), 4.74 (m, 1H), 5.59 (br, 2H), 5.76 (m, 1H), 6.48 (d, 1H), 6.88 (t, 1H), 6.94 (m, 2H), 7.19 (m, 6H), 7.32 (d, 2H).

MS m/z: 519 (M+1)

(2S,4R)-N-(4-Chloro-phenyl)-N-[1-(2,3-dihydro-benzofuran-5-carbonyl)-2-methyl-1,2,3,4-tetrahydro-quinolin-4-yl]-acetamide (G-11)

(2S,4R)-N-(4-Chloro-phenyl)-N-[1-(2,3-dihydro-benzofuran-5-carbonyl)-2-methyl-1,2,3,4-tetrahydro-quinolin-4-yl]-acetamide was made following general procedure G, substituting 2,3-dihydro-benzofuran-5-carbonyl chloride for 4-fluorobenzoyl chloride. The rest of the procedure is followed as indicated in general procedure G to yield (2S,4R)-N-(4-chloro-phenyl)-N-[1-(2,3-dihydro-benzofuran-5-carbonyl)-2-methyl-1,2,3,4-tetrahydro-quinolin-4-yl]-acetamide.

$^1$H-NMR (CDCl$_3$) δ: 1.09 (d, 3H), 1.22 (t, 1H), 1.99 (s, 3H), 2.25 (s, 1H), 3.04 (m, 2H), 4.49 (t, 2H), 4.70 (m, 1H), 5.61 (bs, 1H), 6.50 (m, 2H), 6.88 (m, 2H), 7.10 (d, 2H), 7.18 (d, 2H), 7.26 (d, 1H), 7.34 (d, 2H).

MS m/z: 461.2 (M+1).

N-(4-chlorophenyl)-N-[(2S,4R)-2-methyl-1-(pyridin-3-ylcarbonyl)-1,2,3,4-tetrahydroquinolin-4-yl]acetamide (G-12)

N-(4-chlorophenyl)-N-[(2S,4R)-2-methyl-1-(pyridin-3-ylcarbonyl)-1,2,3,4-tetrahydroquinolin-4-yl]acetamide was prepared following general procedure G, substituting nicotinoyl chloride hydrochloride for 4-fluorobenzoyl chloride. The rest of the procedures were followed as indicated in general procedure G to afford N-(4-chlorophenyl)-N-[(2S,4R)-2-methyl-1-(pyridin-3-ylcarbonyl)-1,2,3,4-tetrahydroquinolin-4-yl]acetamide in decent yield.

$^1$H-NMR (CDCl$_3$, 300 MHz) δ: 1.07-1.09 (d, 3H), 2.01 (s, 3H), 2.21-2.33 (m, 2H), 4.05-4.12 (q, 1H), 4.76-4.81 (m, 1H), 6.54-6.74 (d, 1H), 6.93-7.38 (m, 9H), 8.49-8.56 (d, 2H).

MS m/z: 420 (M+1).

N-[(2S,4R)-1-(4-methoxybenzoyl)-2-methyl-1,2,3,4-tetrahydroquinolin-4-yl]-N-phenylacetamide (G-13)

N-(4-chlorophenyl)-N-[(2S,4R)-1-(4-methoxybenzoyl)-2-methyl-1,2,3,4-tetrahydroquinolin-4-yl]acetamide was prepared following general procedure G, substituting 4-methoxybenzoyl chloride for 4-fluorobenzoyl chloride. The rest of the procedures were followed as indicated in general procedure G to afford (2S,4R)-N-(4-Chloro-phenyl)-N-[1-(4-methoxy-benzoyl)-2-methyl-1,2,3,4-tetrahydro-quinolin-4-yl]-acetamide was obtained in decent yield.

(2S,4R)-N-(4-Chloro-phenyl)-N-[1-(4-methoxy-benzoyl)-2-methyl-1,2,3,4-tetrahydro-quinolin-4-yl]-acetamide (200 mg, 0.36 mmol) was dissolved in MeOH and a catalytic amount of Palladium on Carbon (10%) was added. The round bottom flask in which resided the resulting solution was evacuated and backfilled with hydrogen. The reaction was stirred under the hydrogen atmosphere overnight. The mixture was carefully filtered through a Celite® plug and concentrated to afford crude product. The crude product was purified by silica gel chromatography (hexanes/ethyl acetate system) to afford N-[(2S,4R)-1-(4-methoxybenzoyl)-2-methyl-1,2,3,4-tetrahydroquinolin-4-yl]-N-phenylacetamide (142 mg, 95%).

$^1$H-NMR (CDCl$_3$) δ: 1.10 (d, 3H), 1.60 (s, 1H), 2.02 (s, 3H), 2.30 (m, 1H), 3.74 (s, 3H), 4.75 (m, 1H), 5.45 (b, 1H), 6.50 (d, 1H), 6.67 (d, 2H), 6.92 (t, 1H) 7.13-7.18 (m, 3H), 7.28 (d, 1H), 7.32-7.40 (m, 5H).

MS m/z: 415 (M+1)

(2S,4R)-4-(4-{4-[Acetyl-(4-chloro-phenyl)-amino]-2-methyl-3,4-dihydro-2H-quinoline-1-carbonyl}-2-fluoro-phenoxy)-2,2-dimethyl-butyric acid (G-14)

(2S,4R)-4-(4-{4-[Acetyl-(4-chloro-phenyl)-amino]-2-methyl-3,4-dihydro-2H-quinoline-1-carbonyl}-2-fluoro-phenoxy)-2,2-dimethyl-butyric acid methyl ester (100 mg) was dissolved in methanol/THF (1:1, 5 mL), and lithium hydroxide (1.0N, 1 mL) was added. After 1 hour, the reaction was acidified (HCl) and extracted from with methylene chloride. The organic layer was dried, filtered, and concentrated. The crude residue was purified by silica gel chromatography ethyl acetate-5% MeOH/ethylacetate gradient) to afford the product.

$^1$H-NMR (CDCl$_3$) δ: 1.1 (d, 3H), 1.2 (s, 6H), 1.2 (m, 1H), 2.0 (s, 3H), 2.0 (t, 1H), 2.3 (m, 1H), 4.0 (t, 2H), 4.7 (m, 2H), 5.6 (bs, 1H), 6.5 (d, 1H), 6.6 (t, 1H), 6.7 (d, 1H), 6.9 (t, 1H), 7.2 (m, 5H), 7.4 (d, 2H), 11.1 (bs, 1H).

MS m/z: 567 (M+1).

(2S,4R)-N-(4-Chloro-phenyl)-N-[1-(1-isopropyl-1H-indazole-5-carbonyl)-2-methyl-1,2,3,4-tetrahydro-quinolin-4-yl]-acetamide (G-15)

(2S,4R)-N-(4-Chloro-phenyl)-N-[1-(1-isopropyl-1H-indazole-5-carbonyl)-2-methyl-1,2,3,4-tetrahydro-quinolin-4- yl]-acetamide was prepared following general procedure G, substituting 1-Isopropyl-1H-indazole-5-carbonyl chloride for 4-fluorobenzoyl chloride. (1-Isopropyl-1H-indazole-5-carbonyl chloride was prepared in three steps from 1H-Indazole-5-carboxylic acid ethyl ester. 1H-Indazole-5-carboxylic acid ethyl ester was alkylated using 2-bromopropane in presence of sodium hydride in DMF at room temperature to yield the desired 1-isopropyl-1H-indazole-5-carboxylic acid ethyl ester. Ester hydrolysis using 1N sodium hydroxide in ethanol at 80° C. gave 1-Isopropyl-1H-indazole-5-carboxylic acid and subsequent treatment of this carboxylic acid with oxalyl chloride and catalytic DMF afforded 1-isopropyl-1H-indazole-5-carbonyl chloride in decent yield). The rest of the procedures were followed as indicated in general procedure G to afford (2S,4R)-N-(4-Chloro-phenyl)-N-[1-(1-isopropyl-1H-indazole-5-carbonyl)-2-methyl-1,2,3,4-tetrahydro-quinolin-4-yl]-acetamide. (The first exception being in the deprotection of the benzyloxycarbonyl group by treatment with 30% HBr in AcOH substituting for palladium on carbon (10%) and the other in the step of N-arylation of (2S,4R)-(4-amino-2-methyl-3,4-dihydro-2H-quinolin-1-yl)-(1-isopropyl-1H-indazol-5-yl)-methanone with 4-chlorophenylboronic acid, in presence of copper acetate, triethylamine was substituted for pyridine, and the reaction was carried out in dichloromethane at room temperature to afford the (2S,4R)-N-(4-chloro-phenyl)-N-[1-(1-isopropyl-1H-indazole-5-carbonyl)-2-methyl-1,2,3,4-tetrahydro-quinolin-4-yl]-acetamide).

$^1$H-NMR (CDCl$_3$) δ: 1.15 (3H, d; overlapping 1H, t), 1.60 (2×3H, d), 2.02 (3H, s), 2.33 (1H, m), 4.78 (2×1H, m, overlapping), 5.60 (1H, m), 6.44 (1H, d), 6.95 (1H, t), 7.00-7.40 (9H, complex).

ESI-MS m/z: 501 (M+1).

N-(4-Chlorophenyl)-N-[(2S,4R)-1-(4-methoxybenzoyl)-2-methyl-1,2,3,4-tetrahydroquinolin-4-yl]-2-methylpropanamide (G-16)

N-(4-Chlorophenyl)-N-[(2S,4R)-1-(4-methoxybenzoyl)-2-methyl-1,2,3,4-tetrahydroquinolin-4-yl]-2-methylpropanamide was synthesized according to general procedure G by replacing 4-fluorobenzoyl chloride with 4-methoxybenzoyl chloride and by substituting acetyl chloride with 2-methyl propanoyl chloride. The rest of the procedure was followed as indicated in general procedure G to yield N-(4-chlorophenyl)-N-[(2S,4R)-1-(4-methoxybenzoyl)-2-methyl-1,2,3,4-tetrahydroquinolin-4-yl]-2-methylpropanamide.

$^1$H-NMR (CDCl$_3$) δ: 1.12-1.26 (m, 10H), 2.20-2.28 (m, 1H), 2.61 (sp, 1H), 3.72 (s, 3H), 4.69-4.79 (m, 1H), 5.61 (br s, 1H), 6.52 (d, 1H), 6.67 (d, 2H), 6.92 (t, 1H), 7.11-7.41 (m, 8H).

MS m/z: 477 (M+1).

N-(4-Chlorophenyl)-N-{(2S,4R)-1-[(1,3-dimethyl-1H-thieno[2,3-c]pyrazol-5-yl)carbonyl]-2-methyl-1,2,3,4-tetrahydroquinolin-4-yl}acetamide (G-17)

N-(4-Chlorophenyl)-N-{(2S,4R)-1-[(1,3-dimethyl-1H-thieno[2,3-c]pyrazol-5-yl)carbonyl]-2-methyl-1,2,3,4-tetrahydroquinolin-4-yl}acetamide was prepared following the procedure for N-(4-chlorophenyl)-N-{(2S,4R)-1-[(1-isopropyl-1H-pyrazol-4-yl)carbonyl]-2-methyl-1,2,3,4-tetrahydroquinolin-4-yl}acetamide substituting 1,3-dimethyl-1H-thieno[2,3-c]pyrazole-5-carbonyl chloride for 1-isopropyl-1H-pyrazole-4-carbonyl chloride. (1,3-Dimethyl-1H-thieno[2,3-c]pyrazol-5-carbonyl chloride was prepared from commercially available 1,3-dimethyl-1H-thieno[2,3-c]pyrazole-5-carboxylic acid by treatment with oxalyl chloride and catalytic DMF in dichloromethane).

$^1$H-NMR (CDCl$_3$) δ: 1.15 (d, 3H), 1.17 (t, 1H), 2.02 (s, 3H), 2.25 (s, 3H), 2.25 (m, 1H), 3.80 (s, 3H), 4.62-4.74 (m, 1H), 5.48-5.60 (m, 1H), 6.55 (s, 1H), 7.00-7.40 (m, 8H).

MS m/z: 493 (M+1).

N-(4-chlorophenyl)-N-{(2S,4R)-1-[(1-isopropyl-1H-pyrazol-4-yl)carbonyl]-2-methyl-1,2,3,4-tetrahydroquinolin-4-yl}acetamide (G-18)

N-(4-Chlorophenyl)-N-{(2S,4R)-1-[(1-isopropyl-1H-pyrazol-4-yl)carbonyl]-2-methyl-1,2,3,4-tetrahydroquinolin-4-yl}acetamide was prepared following general procedure G, substituting 1-isopropyl-1H-pyrazole-4-carbonyl chloride for 4-fluorobenzoyl chloride. (1-Isopropyl-1H-pyrazole-4-carbonyl chloride was prepared from commercially available 1-isopropyl-1H-pyrazole-4-carboxylic acid by treatment with oxalyl chloride and catalytic DMF in dichloromethane). Other modifications to general procedure A were inclusive of the deprotection of the benzyloxycarbonyl group via treatment with 30% HBr in acetic acid instead of palladium on carbon (10%) and the use of triethylamine instead of pyridine using dichloromethane as solvent at room temperature during the N-arylation sequence.

$^1$H-NMR (CDCl$_3$) δ: 1.11 (d, 3H), 1.13 (t, 1H), 1.36 (d, 6H), 2.00 (s, 3H), 2.21-2.28 (m, 1H), 4.25-4.34 (m, 1H), 4.65-4.76 (m, 1H), 5.36-5.56 (br, 1H), 6.95 (d, 1H), 7.00-7.40 (m, 9H).

MS m/z: 451 (M+1).

N-1H-indol-4-yl-N-[(2S,4R)-1-(4-methoxybenzoyl)-2-methyl-1,2,3,4-tetrahydroquinolin-4-yl]acetamide (G-19)

N-1H-indol-4-yl-N-[(2S,4R)-1-(4-methoxybenzoyl)-2-methyl-1,2,3,4-tetrahydroquinolin-4-yl]acetamide was made following general procedure G, substituting 4-methoxybenzoyl chloride for 4-fluorobenzoyl chloride.

A mixture of (2S,4R)-1-(4-methoxybenzoyl)-2-methyl-1,2,3,4-tetrahydroquinolin-4-amine (0.12 g, 0.4 mmol) (obtained after the hydrogenation step), tert-butyl 4-bromo-1H-indole-1-carboxylate (0.099 g, 0.39 mmol), palladium dba (0.018 g, 0.02 mmol), biphenyl-2-yl(di-tert-butyl)phosphine (0.006 g, 0.02 mmol) and cesium carbonate (0.13 g, 0.4 mmol) in dimethoxy ethane (3 mL) was stirred at 80 C under nitrogen for 15 h. The reaction mixture was filtered. The filtrate was evaporated to yield the crude product (0.222 g) which was then cleaned by silica gel chromatography (10% ethyl acetate:hexane) to give desired tert-Butyl 4-{[(2S,4R)-1-(4-methoxybenzoyl)-2-methyl-1,2,3,4-tetrahydroquinolin-4-yl]amino}-1H-indole-1-carboxylate (0.054 g, 32%).

$^1$H-NMR (CDCl$_3$) δ: 1.32 (d, 3H), 1.47-1.57 (m, 1H), 1.71 (s, 9H), 2.87-2.96 (m, 1H), 3.81 (s, 3H), 4.63-4.69 (m, 1H), 4.88-5.01 (m, 1H), 6.46 (d, 1H), 6.56-6.63 (m, 2H), 6.75-6.78 (m, 2H), 6.94-7.09 (m, 2H), 7.2-7.36 (m, 4H), 7.59-7.66 (m, 2H).

MS m/z: 512 (M+1).

A mixture of methyl tert-butyl 4-{[(2S,4R)-1-(4-methoxybenzoyl)-2-methyl-1,2,3,4-tetrahydroquinolin-4-yl]amino}-1H-indole-1-carboxylate (0.054 g, 0.1 mmol), freshly distilled acetyl chloride (0.5 mL), diisopropylethylamine (0.015 g, 0.12 mmol) and 4-N,N-dimethylaminopyridine (catalytic amount) was stirred at room temperature for 43 h. Ice was added to the reaction mixture and stirred for 1 h. The reaction mixture was neutralized with solid sodium bicarbonate and extracted with ethyl acetate. The ethyl acetate extract was washed twice with water, brine, dried over sodium sulphate and evaporated. The crude product (0.055 g) thus obtained was cleaned by silica gel chromatography (ethyl acetate: hexane) to give clean tert-butyl 4-{acetyl[(2S,4R)-1-(4-methoxybenzoyl)-2-methyl-1,2,3,4-tetrahydroquinolin-4-yl]amino}-1H-indole-1-carboxylate (0.035 g, 60%).

$^1$H-NMR (CDCl$_3$) δ: 1.04 (d, 3H), 1.47-1.57 (m, 1H), 1.69 (s, 9H), 1.97 (s, 3H), 2.87-2.96 (m, 1H), 3.75 (s, 3H), 4.64-4.77 (m, 1H), 4.88-5.01 (m, 1H), 6.53 (d, 1H), 6.66 (d, 1H), 6.69 (d, 2H), 6.92-6.97 (m, 1H), 7.14-7.29 (m, 5H), 7.45 (d, 1H), 7.73 (d, 1H), 8.21 (d, 1H).

MS m/z: 411, 280.

tert-Butyl 4-{acetyl[(2S,4R)-1-(4-methoxybenzoyl)-2-methyl-1,2,3,4-tetrahydroquinolin-4-yl]amino}-1H-indole-1-carboxylate (0.035 g, 0.068 mmol) was stirred in 4 N HCl in dioxane (1 mL) for 24 h and then evaporated to dryness. The residue was dissolved in ethyl acetate, washed with 1N NaOH, water, brine, dried over sodium sulphate and evaporated to dryness to give the crude product (0.023 g). The crude was cleaned by silica gel chromatography to give clean N-1H-indol-4-yl-N-[(2S,4R)-1-(4-methoxybenzoyl)-2-methyl-1,2,3,4-tetrahydroquinolin-4-yl]acetamide (0.008 g, 28%).

$^1$H-NMR (CDCl$_3$) δ: 1.03 (d, 3H), 2.01 (s, 3H), 3.75 (s, 3H), 4.08-4.16 (m, 1H), 4.61-4.79 (m, 1H), 6.52-6.55 (m, 2H), 6.67-6.7 (m, 2H), 6.92-7.51 (m, 9H), 8.62 (bs, 1H).

MS m/z: 454 (M+1).

4-[(4-{[(2S,4R)-4-[Acetyl-(4-chlorophenyl)amino]-2-methyl-3,4-dihydroquinolin-1(2H)-yl]carbonyl}phenyl)(methyl)amino]-2,2-dimethylbutanoic acid (G-20)

Methyl 4-[(4-{[(2S,4R)-4-[acetyl(4-chlorophenyl)amino]-2-methyl-3,4-dihydroquinolin-1(2H)-yl]carbonyl}phenyl)(methyl)amino]-2,2-dimethylbutanoate was dissolved in methanol/tetrahydrofuran/water (2/1/1) then sodium hydroxide (3 equivalents) was added and reaction mixture heated to 40° C. for 2 h. The mixture was concentrated, the residue acidified with a 1N HCl aqueous solution and extracted with ethyl acetate. The organic layer was washed with brine, dried over magnesium sulfate, filtered and concentrated to give 4-[(4-{[(2S,4R)-4-[Acetyl-(4-chlorophenyl)amino]-2-methyl-3,4-dihydroquinolin-1(2H)-yl]carbonyl}phenyl)(methyl)amino]-2,2-dimethylbutanoic acid.

$^1$H-NMR (CDCl$_3$) δ: 1.09-1.12 (m, 1H), 1.11 (d, 3H), 1.22 (d, 6H), 1.69-1.74 (m, 2H), 2.01 (s, 3H), 2.24-2.31 (m, 1H), 2.83 (s, 3H), 3.27 (t, 2H), 4.65-4.76 (m, 1H), 5.60 (br s, 1H), 6.39 (d, 2H), 6.62 (d, 1H), 6.95 (t, 1H), 7.07-7.16 (m, 3H), 7.18-7.28 (m, 3H), 7.37 (d, 2H).

MS m/z: 562 (M+1).

N-(4-chlorophenyl)-2-hydroxy-N-[(2S,4R)-1-(4-methoxybenzoyl)-2-methyl-1,2,3,4-tetrahydroquinolin-4-yl]acetamide (G-21)

N-(4-chlorophenyl)-2-hydroxy-N-[(2S,4R)-1-(4-methoxybenzoyl)-2-methyl-1,2,3,4-tetrahydroquinolin-4-yl]acetamide was made following general procedure G, substituting 4-methoxybenzoyl chloride for 4-fluorobenzoyl chloride. Procedure A was followed further substituting acetoxyacetyl-chloride for acetyl chloride in the last step to yield 2-{(4-chlorophenyl)[(2S,4R)-1-(4-methoxybenzoyl)-2-methyl-1,2,3,4-tetrahydroquinolin-4-yl]amino}-2-oxoethyl acetate.

2-{(4-Chlorophenyl)[(2S,4R)-1-(4-methoxybenzoyl)-2-methyl-1,2,3,4-tetrahydroquinolin-4-yl]amino}-2-oxoethyl acetate (496 mg, 0.98 mmol, 1 eq.) was dissolved in methanol (12 ml). A solution of potassium carbonate (1.08 g, 7.84 mmol, 8 eq.) in water (5 ml) was added and reaction mixture was stirred at room temperature for 4 h. The mixture was concentrated and the residue dissolved in ethyl acetate and washed with water, brine, and then dried over magnesium sulfate, filtered and concentrated. The crude residue was purified by silica gel chromatography (methylene chloride/methanol: 98/2) to afford N-(4-chlorophenyl)-2-hydroxy-N-[(2S,4R)-1-(4-methoxybenzoyl)-2-methyl-1,2,3,4-tetrahydroquinolin-4-yl]acetamide (380 mg, 84%).

$^1$H-NMR (DMSO) δ: 1.05 (d, 3H), 2.45 (m, 1H), 3.70 (s, 3H), 3.80-3.95 (dd, 2H), 4.60 (m, 1H), 4.80 (m, 1H), 5.40 (m, 1H), 6.55 (d, 1H), 6.75 (d, 2H), 6.95 (t, 1H), 7.10 (d, 2H), 7.20 (t, 1H), 7.40-7.60 (m, 5H).

MS m/z: 465 (M+1).

(2S,4R)-6-{4-[Acetyl-(4-chloro-phenyl)-amino]-2-methyl-3,4-dihydro-2H-quinoline-1-carbonyl}-2,3-dihydro-benzo[1,4]oxazine-4-carboxylic acid ethyl ester (G-22)

To a solution of (2S,4R)-(2-methyl-1,2,3,4-tetrahydroquinolin-4-yl)-carbamic acid benzyl ester (990 mg, 3.49 mmol) in methylene chloride at room temperature was added triethylamine (1.21 mL, 8.71 mmol) followed by 6-chlorocarbonyl-2,3-dihydro-benzo[1,4]oxazine-4-carboxylic acid ethyl ester (3.49 mmol). The reaction was stirred over night at room temperature. The mixture was poured into water and extracted with ethyl acetate. The extracts were washed with 1 M (aq) NaOH and brine, dried over MgSO$_4$, filtered dried and concentrated. The crude residue was purified by silica gel chromatography (75% hexanes/25% ethyl acetate) to afford the pure amide.

(2S,4R)-6-(4-Benzyloxycarbonylamino-2-methyl-3,4-dihydro-2H-quinoline-1-carbonyl)-2,3-dihydro-benzo[1,4]oxazine-4-carboxylic acid ethyl ester (697 mmol) was dissolved in ethanol (30 mL). The vessel in which resided the resulting solution was evacuated and backfilled with argon. A catalytic amount of Palladium on Carbon (10%) was added. The vessel was once again evacuated and this time was backfilled with hydrogen and shaken in a Parr bottle at 40 psi hydrogen. Reaction was complete after 4 hours. The mixture was carefully filtered and concentrated to 10% volume. The resulting concentrated solution was filtered through an Celite® and concentrated to afford the crude amine.

To a solution of (2S,4R)-6-(4-Amino-2-methyl-3,4-dihydro-2H-quinoline-1-carbonyl)-2,3-dihydro-benzo[1,4]oxazine-4-carboxylic acid ethyl ester (470 mg, 1.18 mmol) in methylene chloride was added 4-chlorophenylboronic acid (368 mg, 2.36 mmol), triethylamine (1.31 mL, 9.42 mmol) and copper(II)acetate (429 mg, 2.36 mmol). The heterogeneous green mixture was stirred open to air for 1 hour and then warmed to 60° C. and stirred over night (14 hours). The mixture was then cooled to room temperature, poured into rapidly stirred ethyl acetate (150 mL); solids were removed by filtration through Celite®. The extracts were washed several times with water and then once with brine. The extracts were then dried over anhydrous MgSO$_4$, filtered, and concentrated under reduced pressure. The crude residue was purified by silica gel chromatography (95% methylene chloride/5% ethyl acetate) to afford the aniline product as a yellow oil.

To a solution of (2S,4R)-6-[4-(4-Chloro-phenylamino)-2-methyl-3,4-dihydro-2H-quinoline-1-carbonyl]-2,3-dihydro-benzo[1,4]oxazine-4-carboxylic acid ethyl ester (343 mg, 0.673 mmol) in methylene chloride (2 mL) was added diisopropylethylamine (0.129 mL, 0.739 mmol) followed by acetyl chloride (2 mL). The mixture was stirred at room temperature 4 hours. The mixture was concentrated under reduced pressure, dissolved in ethyl acetate, washed with sat. aq. sodium NaHCO$_3$, brine and dried over MgSO$_4$, filtered, and concentrated under reduced pressure. The residue was purified by silica gel chromatography (25/75 hexanes/ethyl acetate gradient) to afford pure product.

$^1$H-NMR (CDCl$_3$) δ: 1.1 (d, 3H), 1.2 (m, 1H), 1.3 (t, 3H), 2.0 (s, 3H), 2.3 (m, 1H), 3.3 (m, 2H), 4.0 (m, 2H), 4.3 (m, 2H), 4.7 (m, 1H), 5.5 (m, 1H), 6.4 (d, 1H), 6.5 (d, 1H), 6.6 (d, 2H), 6.96 (t, 1H), 7.2 (m, 4H), 7.4 (d, 2H).

MS m/z: 548 (M+1).

N-[(2S,4R)-6-chloro-1-(4-methoxybenzoyl)-2-methyl-1,2,3,4-tetrahydroquinolin-4-yl]-N-(4-chlorophenyl)acetamide (G-23)

N-[(2S,4R)-6-chloro-1-(4-methoxybenzoyl)-2-methyl-1,2,3,4-tetrahydroquinolin-4-yl]-N-(4-chlorophenyl)acetamide was synthesized as described for (2S,4R)-(2-methyl-1,2,3,4-tetrahydroquinolin-4-yl)-carbamic acid benzyl ester, substituting 4-chloroaniline for aniline. Further elaboration following general procedure A, substituting 4-methoxy-benzoyl chloride for 4-fluorobenzoyl chloride, yielded N-[(2S,4R)-6-chloro-1-(4-methoxybenzoyl)-2-methyl-1,2,3,4-tetrahydroquinolin-4-yl]-N-(4-chlorophenyl)acetamide.

$^1$H-NMR (CDCl$_3$) δ: 1.13 (d, 3H), 1.15 (t, 1H), 2.03 (s, 3H), 2.27 (m, 1), 3.76 (s, 3H), 4.72 (sextet, 1), 5.58 (bs, 1H), 6.43 (d, 1H), 6.71 (d, 2H), 6.93 (d, 1H), 7.14-7.29 (m, 5H), 7.41 (d, 2H).

MS m/z: 483 (M+1)

[(5-{[(2S,4R)-4-[acetyl(4-chlorophenyl)amino]-2-methyl-3,4-dihydroquinolin-1(2H)-yl]carbonyl}isoxazol-3-yl)oxy]acetic acid (G-24)

Ethyl [(5-{[(2S,4R)-4-[acetyl(4-chlorophenyl)amino]-2-methyl-3,4-dihydroquinolin-1(2H)-yl]carbonyl}isoxazol-3-yl)oxy]acetate was prepared following the procedure for N-(4-chlorophenyl)-N-{(2S,4R)-1-[(1-isopropyl-1H-pyrazol-4-yl)carbonyl]-2-methyl-1,2,3,4-tetrahydroquinolin-4-yl}acetamide substituting ethyl {[5-(chlorocarbonyl)isoxazol-3-yl]oxy}acetate for 1-isopropyl-1H-pyrazole-4-carbonyl chloride. (Ethyl {[15-chlorocarbonyl)isoxazol-3-yl]oxy}acetate was prepared in 4 steps from methyl 3-hydroxy 5-isoxazole carboxylate. Methyl 3-hydroxy 5-isoxazole carboxylate (1.00 g, 6.95 mmol) was alkylated using ethyl bromoacetate (0.850 mL, 7.64 mmol) in presence of potassium carbonate (1.05 g, 7.64 mmol) and catalytic potassium iodide in DMF (3.00 mL) at room temperature overnight. Water was added to the reaction mixture and extracted with ethyl acetate. The organics were washed with brine, dried over anhydrous sodium sulfate, filtered and concentrated in vacuo to yield the desired methyl 3-(2-ethoxy-2-oxoethoxy)isoxazole-5-carboxylate (60%). (Ref: WO 03/063800 PCT/US03/03224). Methyl 3-(2-ethoxy-2-oxoethoxy)isoxazole-5-carboxylate was further treated with aqueous 5% sodium hydroxide in methanol to yield 3-(carboxymethoxy)isoxazole-5-carboxylic acid (86%). This diacid (0.700 g, 3.76 mmol) was selectively esterified in the presence of catalytic p-toluenesulfonic acid monohydrate (100 mg) in ethanol at room temperature. Water was added to the reaction and the mixture was extracted with ethyl acetate. The organics were washed with brine, dried over anhydrous sodium sulfate, filtered and concentrated in vacuo to give the desired 3-(2-ethoxy-2-oxoethoxy)isoxazole-5-carboxylic acid (90%). 3-(2-Ethoxy-2-oxoethoxy)isoxazole-5-carboxylic acid was treated with oxalyl chloride and catalytic DMF in dichloromethane to yield the desired ethyl {[5-(chlorocarbonyl)isoxazol-3-yl]oxy}acetate). Ethyl [(5-{[(2S,4R)-4-[acetyl(4-chlorophenyl)amino]-2-methyl-3,4-dihydroquinolin-1(2H)-yl]carbonyl}isoxazol-3-yl)oxy]acetate was treated with a solution of lithium hydroxide monohydrate (aq) in methanol at room temperature overnight to afford [(5-{[(2S,4R)-4-[acetyl(4-chlorophenyl)amino]-2-methyl-3,4-dihydroquinolin-1(2H)-yl]carbonyl}isoxazol-3-yl)oxy]acetic acid in 60% yield.

$^1$H-NMR (CDCl$_3$) δ: 1.15 (d, 3H), 1.17 (t, 1H), 2.02 (s, 3H), 2.42-2.68 (m, 1H), 4.69 (s, 1H) 4.72-4.78 (m, 1H), 5.44-5.58 (br, 1H), 6.80 (d, 1H), 7.00-7.40 (m, 8H).

MS m/z: 484 (M+1).

N-(4-chlorophenyl)-N-[(2S,4R)-1-(4-cyanobenzoyl)-2-methyl-1,2,3,4-tetrahydroquinolin-4-yl]acetamide (G-25)

N-(4-chlorophenyl)-N-[(2S,4R)-1-(4-cyanobenzoyl)-2-methyl-1,2,3,4-tetrahydroquinolin-4-yl]acetamide was made following general procedure G, substituting 4-cyanobenzoyl chloride for 4-fluorobenzoyl chloride. The rest of the procedure is followed as indicated in general procedure G to yield N-(4-chlorophenyl)-N-[(2S,4R)-1-(4-cyanobenzoyl)-2-methyl-1,2,3,4-tetrahydroquinolin-4-yl]acetamide.

$^1$H-NMR (CDCl$_3$) δ: 1.10-1.20 (m, 1H), 1.16 (d, 3H), 2.03 (s, 3H), 2.20-2.36 (m, 1H), 4.70-4.84 (m, 1H), 5.48-5.70 (m, 1H), 6.40 (d, 1H), 6.91 (t, 1H), 7.16-7.32 (m, 6H), 7.38 (d, 2H), 7.47 (d, 2H).

MS m/z: 444 (M+1).

Ethyl 4-[(5-{[(2S,4R)-4-[acetyl(4-chlorophenyl)amino]-2-methyl-3,4-dihydroquinolin-1(2H)-yl]carbonyl}isoxazol-3-yl)oxy]-2,2-dimethylbutanoate (G-26)

Ethyl 4-[(5-{[(2S,4R)-4-[acetyl(4-chlorophenyl)amino]-2-methyl-3,4-dihydroquinolin-1(2H)-yl]carbonyl}isoxazol-3-yl)oxy]-2,2-dimethylbutanoate was prepared following the procedure for N-(4-chlorophenyl)-N-{(2S,4R)-1-[(1-isopropyl-1H-pyrazol-4-yl)carbonyl]-2-methyl-1,2,3,4-tetrahydroquinolin-4-yl}acetamide, substituting ethyl 4-{[5-(chlorocarbonyl)isoxazol-3-yl]oxy}-2,2-dimethylbutanoate for 1-isopropyl-1H-pyrazole-4-carbonyl chloride. (Ethyl 4-{[5-(chlorocarbonyl)isoxazol-3-yl]oxy}-2,2-dimethylbutanoate was prepared in three steps from methyl 3-hydroxy 5-isoxazole carboxylate. Methyl 3-hydroxy 5-isoxazole carboxylate (1.00 g, 6.94 mmol) was alkylated using ethyl 4-bromo-2,2-dimethylbutanoate (1.59 g, 7.63 mmol) in the presence of potassium carbonate (1.05 g, 7.64 mmol) and catalytic potassium iodide in DMF (5.00 mL) at room temperature overnight. Water was added to the reaction mixture and the mixture was extracted with ethyl acetate. The organics were washed with brine, dried over anhydrous sodium sulfate, filtered, concentrated in vacuo and purified on silica gel by flash chromatography using hexane/ethyl acetate (10-50% gradient) to afford methyl 3-(4-ethoxy-3,3-dimethyl-4-oxobutoxy)isoxazole-5-carboxylate in 35% yield. Selective hydrolysis of the methyl ester by subsequent treatment with lithium hydroxide (aq) (1.50 equiv.) in methanol at room temperature afforded 3-(4-ethoxy-3,3-dimethyl-4-oxobutoxy)isoxazole-5-carboxylic acid which was then treated with oxalyl chloride and catalytic DMF in dichloromethane to yield the desired ethyl 4-{[5-(chlorocarbonyl)isoxazol-3-yl]oxy}-2,2-dimethylbutanoate).

¹H-NMR (CDCl₃) δ: 1.18 (d, 3H), 1.18 (t, 1H), 1.19 (s, 6H), 1.20 (t, 3H), 1.99-2.02 (s, 3H; m, 1H), 2.24-2.36 (m, 1H), 4.15 (q, 2H), 4.17-4.22 (m, 2H), 4.64-4.74 (m, 1H), 5.60-5.68 (br, 1H), 6.80 (d, 1H), 7.00-7.40 (m, 8H).

MS m/z: 568 (M+1).

4-{[(2S,4R)-4-[acetyl(4-chlorophenyl)amino]-2-methyl-3,4-dihydroquinolin-1(2H)-yl]carbonyl}benzoic acid (G-27)

Methyl 4-((2S,4R)-4-(N-(4-chlorophenyl)acetamido)-2-methyl-1,2,3,4-tetrahydroquinoline-1-carbonyl)benzoate was made following general procedure G, substituting methyl 4-(chlorocarbonyl)benzoate for 4-fluorobenzoyl chloride. The rest of the procedure is followed as indicated in general procedure A to yield Methyl 4-((2S,4R)-4-(N-(4-chlorophenyl)acetamido)-2-methyl-1,2,3,4-tetrahydroquinoline-1-carbonyl)benzoate, which was saponified with excess lithium hydroxide in MeOH/THF/H₂O (2:1:2). The slurry was acidified with 1N HCl and the crude product was extracted using methylene chloride. The organic portion was concentrated, and the resulting slurry was subjected to preparatory HPLC to afford the title compound as a white solid. ¹H-NMR (CDCl₃ δ: 1.15-1.22 (m, 1H), 1.16 (d, 3H), 2.06 (s, 3H), 2.20-2.36 (m, 1H), 3.50-4.05 (bs, 1H), 4.72-4.88 (m, 1H), 5.50-5.75 (m, 1H), 6.45 (d, 1H), 6.85 (t, 1H), 7.08-7.30 (m, 6H), 7.40 (d, 2H), 7.87 (d, 2H).

MS m/z: 463 (M+1).

N-(4-chlorophenyl)-N-[(2S,4R)-1-(4-methoxybenzoyl)-2-methyl-1,2,3,4-tetrahydroquinolin-4-yl]cyclopropanecarboxamide (G-28)

N-(4-chlorophenyl)-N-[(2S,4R)-1-(4-methoxybenzoyl)-2-methyl-1,2,3,4-tetrahydroquinolin-4-yl]cyclopropanecarboxamide was made following general procedure G, substituting 4-methoxybenzoyl chloride for 4-fluorobenzoyl chloride. Procedure G was followed further substituting cyclopropane carbonyl chloride for acetyl chloride in the last step to yield N-(4-chlorophenyl)-N-[(2S,4R)-1-(4-methoxybenzoyl)-2-methyl-1,2,3,4-tetrahydroquinolin-4-yl]cyclopropanecarboxamide.

¹H-NMR (CDCl₃) δ: 0.75 (m, 2H), 1.00-1.20 (m, 5H), 1.45 (m, 1H), 2.30 (m, 1H), 3.75 (s, 3H), 4.75 (m, 1H), 5.60 (m, 1H), 6.50 (d, 1H), 6.60 (d, 2H), 6.90 (t, 1H), 7.10-7.45 (m, 8H).

MS m/z: 475 (M+1).

N-[(2S,4R)-1-(4-methoxybenzoyl)-2-methyl-1,2,3,4-tetrahydroquinolin-4-yl]-N-[4-(1H-pyrrol-1-yl)phenyl]acetamide (G-29)

N-(4-amino-phenyl)-N-[(2S,4R)-1-(4-methoxy-benzoyl)-2-methyl-1,2,3,4-tetrahydro-quinolin-4-yl]-acetamide was prepared similarly to General Procedure G: To a solution of (2S,4R)-(2-methyl-1,2,3,4-tetrahydro-quinolin-4-yl)-carbamic acid benzyl ester (1.00 equiv.) in methylene chloride at room temperature was added diisopropylethylamine (1.50 equiv.) followed by 4-anisoyl chloride (1.15 equiv). The reaction was stirred over night at room temperature. The mixture was poured into water and extracted with ethyl acetate. The extracts were washed with 1 M (aq) NaOH and brine, dried over magnesium sulfate, filtered, dried and concentrated. The crude residue was purified by silica gel chromatography (75% hexanes/25% ethyl acetate) to afford 2S,4R)-[1-(4-methoxybenzoyl)-2-methyl-1,2,3,4-tetrahydro-quinolin-4-yl]-carbamic acid benzyl ester.

(2S,4R)-[1-(4-methoxybenzoyl)-2-methyl-1,2,3,4-tetrahydro-quinolin-4-yl]-carbamic acid benzyl ester (1.00 equiv.) was dissolved in ethanol (30 mL). The vessel in which resided the resulting solution was evacuated and backfilled with argon. A catalytic amount of Palladium on Carbon (10%, 0.10 equiv. by wt.) was added. The vessel was once again evacuated and this time was backfilled with hydrogen and shaken in a Parr bottle at 40 psi hydrogen. Reaction was complete after 4 h. The mixture was carefully filtered and concentrated to 10% volume. The resulting concentrated solution was filtered through a Celite® and concentrated to afford the crude amine, (2S,4R)-(4-amino-2-methyl-3,4-dihydro-2H-quinolin-1-yl)-(4-methoxy-phenyl)-methanone.

To a solution of (2S,4R)-(4-amino-2-methyl-3,4-dihydro-2H-quinolin-1-yl)-(4-methoxy-phenyl)-methanone (1.00 equiv.) in DMF was added 4-nitrophenylboronic acid (2.00 equiv.), pyridine (2.50 equiv.) and copper(II)acetate (2.00 equiv.). The heterogeneous green mixture was stirred open to air for 1 h and then warmed to 60° C. and stirred over night (14 h). The mixture was then cooled to rt, poured into rapidly stirred ethyl acetate (150 mL); solids were removed by filtration through Celite®. The extracts were washed several times with water and then once with brine. The extracts were then dried over anhydrous magnesium sulfate, filtered, and concentrated under reduced pressure. The crude residue was purified by silica gel chromatography (95% methylene chloride/5% ethyl acetate) to afford (4-methoxy-phenyl)-[(2S,4R)-2-methyl-4-(4-nitro-phenylamino)-3,4-dihydro-2H-quinolin-1-yl]-methanone as a yellow solid.

To a solution of (2S,4R)-[4-(4-nitro-phenylamino)-2-methyl-3,4-dihydro-2H-quinolin-1-yl]-(4-methoxy-phenyl)-methanone (1.00 equiv.) in methylene chloride was added diisopropylethylamine (1.05 equiv) followed by acetyl chloride (1.00 equiv). The mixture was stirred at rt 48 h. The mixture was concentrated under reduced pressure, dissolved in ethyl acetate, washed with sat. aqueous sodium bicarbonate, brine and dried over magnesium sulfate, filtered, and concentrated under reduced pressure. The residue was purified by silica gel chromatography (25/75 hexanes/ethyl acetate gradient) to afford pure N-(4-nitro-phenyl)-N-[1-(4-methoxy-benzoyl)-2-methyl-1,2,3,4-tetrahydro-quinolin-4-yl]-acetamide; which was reduced to N-(4-amino-phenyl)-N-[1-(4-methoxy-benzoyl)-2-methyl-1,2,3,4-tetrahydro-quinolin-4-yl]-acetamide using excess NH₄CO₂H, catalyic Pt(sulfided), in ethanol at reflux for 30 m., followed by filtration and concentration. The amine was used without further purification due to inherent chemical instability.

N-(4-amino-phenyl)-N-[1-(4-methoxy-benzoyl)-2-methyl-1,2,3,4-tetrahydro-quinolin-4-yl]-acetamide (22 mg, 0.05 mmol) was dissolved in MeOH:THF (1 mL each) and cooled to 10° C. 2,5-dimethoxy-tetrahydrofuran (1.25 equiv.) was dissolved in THF and catalytic H₂SO₄, and added drop wise to the aniline mixture. The mixture was poured into sat. NaHCO₃ and extracted with ethyl acetate. The organic layer was dried, filtered and concentrated, and the crude residue was purified by preparative HPLC to afford the title compound as an off-white solid.

¹H-NMR (CDCl₃) δ: 1.00-1.22 (m, 1H), 1.12 (s, 3H), 2.04 (s, 3H), 2.22-2.42 (m, 1H), 3.72 (s, 3H), 4.64-4.84 (m, 1H), 5.50-5.80 (m, 1H), 6.38 (s, 2H), 6.53 (d, 1H), 6.67 (d, 2H), 6.94 (t, 1H), 7.05-7.48 (m, 10H).

MS m/z: 480 (M+1)

Methyl 4-[(4-{[(2S,4R)-4-[acetyl(4-chlorophenyl) amino]-2-methyl-3,4-dihydroquinolin-1(2N)-yl] carbonyl}phenyl)(methyl)amino]-2,2-dimethylbutanoate (G-30)

Methyl 4-[(4-{[(2S,4R)-4-[acetyl(4-chlorophenyl) amino]-2-methyl-3,4-dihydroquinolin-1(2H)-yl] carbonyl}phenyl)(methyl)amino]-2,2-dimethylbutanoate was prepared according to procedure G substituting 4-nitrobenzoyl chloride for 4-fluorobenzoyl chloride in the first step and, to avoid complications, the CBZ protecting group was cleaved by treatment of a solution of the protected amine, benzyl [(2S,4R)-2-methyl-1-(4-nitrobenzoyl)-1,2,3,4-tetrahydroquinolin-4-yl]carbamate, in dichloromethane with hydrogen bromide in acetic acid (30 wt %) followed by precipitation of the product from the reaction mixture by the addition of hexanes. The rest of general procedure A was followed as indicated to yield N-(4-chlorophenyl)-N-[(2S, 4R)-2-methyl-1-(4-nitrobenzoyl)-1,2,3,4-tetrahydroquinolin-4-yl]acetamide.

This material was reduced by exposure to sulfided platinum (10 wt %) and ammonium formate (4.0 equivalents) in ethanol at 70° C. until all starting material was consumed to afford N-[(2S,4R)-1-(4-aminobenzoyl)-2-methyl-1,2,3,4-tetrahydro-quinolin-4-yl]-N-(4-chlorophenyl)acetamide.

This material underwent reductive alkylation first with methyl 2,2-dimethyl-4-oxobutanoate then formaldehyde. (Methyl 2,2-dimethyl-4-oxobutanoate was prepared in 3 steps from methyl 4,4-dimethoxybutanoate. Methyl 4,4-dimethoxybutanoate underwent lithium enolate formation with lithium diisopropyl amide (1.1 equivalents) in THF at −78° C. followed by quenching with methyl iodide (2.0 equivalents) and aqueous work up; repeating the same protocol yielded, after standard chromatography (5% ethyl acetate/hexanes), methyl 4,4-dimethoxy-2,2-dimethylbutanoate. Subsequent treatment of this material with aqueous 6 normal hydrochloric acid in acetone afforded, after standard aqueous work up, methyl 2,2-dimethyl-4-oxobutanoate). A solution of methyl 2,2-dimethyl-4-oxobutanoate (1.0 equivalents), sodium triacetoxyborohydride (1.2 equivalents) and aniline in THF with acetic acid (1.0 equivalent) was stirred until all starting material had been consumed. The reaction was then diluted with methanol, acidified with concentrated hydrochloric acid (3 drops) and an excess formaldehyde (37 weight % in H$_2$O) and sodium cyanoborohydride (5 equivalents) were added. The reaction mixture stirred at room temperature until all starting material had been consumed, then standard aqueous work up followed by chromatography (50% ethyl acetate/hexanes) afforded methyl 4-[(4-{[(2S,4R)-4-[acetyl (4-chlorophenyl)amino]-2-methyl-3,4-dihydroquinolin-1 (2H)-yl]carbonyl}phenyl)(methyl)amino]-2,2-dimethylbutanoate.

$^1$H-NMR (CDCl$_3$) δ: 1.09-1.14 (m, 1H), 1.13 (d, 3H), 1.20 (d, 6H), 1.71-1.79 (m, 2H), 1.98 (s, 3H), 2.24-2.28 (m, 1H), 3.02 (s, 3H), 3.30 (t, 2H), 3.57 (s, 3H), 4.69-4.76 (m, 1H), 5.51 (br s, 1H), 6.39 (d, 1H), 6.84 (t, 1H), 7.16 (d, 2H), 7.24-7.29 (m, 4H), 7.34 (d, 2H), 7.54 (d, 2H).

MS m/z: 576 (M+1).

N-[3-(acetylamino)phenyl]-N-[(2S,4R)-1-(4-methoxybenzoyl)-2-methyl-1,2,3,4-tetrahydroquinolin-4-yl]acetamide (G-31)

N-[3-(acetylamino)phenyl]-N-[(2S,4R)-1-(4-methoxybenzoyl)-2-methyl-1,2,3,4-tetrahydroquinolin-4-yl]acetamide was prepared following general procedure G, substituting 4-methoxybenzoyl chloride for 4-fluorobenzoyl chloride, and 3-acetamidophenylboronic acid for 4-chlorophenylboronic acid. The rest of the procedures were followed as indicated in general procedure G to afford N-[3-(acetylamino) phenyl]-N-[(2S,4R)-1-(4-methoxybenzoyl)-2-methyl-1,2,3, 4-tetrahydroquinolin-4-yl]acetamide $^1$H-NMR (CDCl$_3$) δ: 1.1-1.2 (m, 4H), 2.0 (s, 3H), 2.3 (m, 4H), 3.7 (s, 3H), 4.8 (m, 1H), 5.6 (br, 1H), 6.5 (d, 1H), 6.7 (m, 2H,), 6.9 (m, 1H,), 7.1-7.4 (m, 7H,), 7.5 (m, 1H)

MS m/z: 472 (M+1).

N-[(2S,4R)-1-(4-methoxybenzoyl)-2-methyl-1,2,3,4-tetrahydroquinolin-4-yl]-N-{4-[(methylsulfonyl) amino]phenyl}acetamide (G-32)

N-(4-amino-phenyl)-N-[1-(4-methoxy-benzoyl)-2-methyl-1,2,3,4-tetrahydro-quinolin-4-yl]-acetamide (32 mg, 0.075 mmol) was dissolved in methylene chloride (1 mL) and triethylamine (10 equiv.), then cooled to −30° C. Methanesulfonyl chloride (5 equiv.) was added; after 30 min, TLC showed complete consumption of the starting aniline. The mixture was poured into water and extracted with EtOAc. The organic layer was dried, filtered and concentrated to afford the corresponding bis-methanesulfonated adduct.

The crude residue was dissolved in MeOH and 20 equiv. of Cs$_2$CO$_3$ was added. After stirring for 5 min, the mixture was poured into sat. NaHCO$_3$ and EtOAc. The organic layer was dried, filtered and concentrated. The resulting crude material was subjected to flash chromatography (EtOAc) to afford the title compounds as a white solid.

$^1$H-NMR (CDCl$_3$) δ: 1.00-1.22 (m, 1H), 1.11 (s, 3H), 1.20-1.28 (m, 1H), 2.01 (s, 3H), 2.20-2.40 (m, 1H), 3.01 (s, 3H) 3.72 (s, 3H), 4.64-4.82 (m, 1H), 5.45-5.75 (m, 1H), 6.51 (d, 1H), 6.63 (d, 2H), 6.91 (t, 1H), 7.10-7.35 (m, 7H), 7.38-7.44 (m, 1H).

MS m/z: 508 (M+1)

N-[(2S,4R)-1-(4-methoxybenzoyl)-2-methyl-1,2,3,4-tetrahydroquiolin-4-yl]-N-pyridin-4-ylacetamide (G-33)

N-[(2S,4R)-1-(4-methoxybenzoyl)-2-methyl-1,2,3,4-tetrahydroquinolin-4-yl]-N-pyridin-4-ylacetamide was made following general procedure G, substituting 4-methoxybenzoyl chloride for 4-fluorobenzoyl chloride. The amine-aryl coupling was performed differently to what is described in procedure G. Therefore (2S,4R)-1-(4-methoxybenzoyl)-2-methyl-1,2,3,4-tetrahydroquinolin-4-amine (obtained from the hydrogenation step, 356 mg, 1.2 mmol, 1 equ.) was dissolved in ethylene glycol dimethyl ether (4 mL) in a Schlenk tube. To this solution was added sequentially 4-bromopyridine hydrochloride (280 mg, 1.44 mmol, 1.2 equ.), cesium carbonate (940 mg, 2.88 mmol, 2.4 equ.), palladium acetate (32 mg, 0.048 mmol, 0.04 equ.) and 2-(Dicyclohexylphosphino)-2',4',6'-tri-1-propyl-1,1'-biphenyl (48 mg, 0.096 mmol, 0.08 equ.). The reaction mixture was flushed with nitrogen and heated to 100° C. in the Schlenk tube for 48 h. Reaction mixture was concentrated to leave a residue which was partitioned between water and ethyl acetate and extracted. The aqueous layer was separated and the organic layer was washed with brine, dried over magnesium sulfate, filtered and concentrated to give a brown oil. The crude product was purified by silica gel chromatography (methylene chloride/methanol: 99/1 to 90/10 gradient) to provide (2S, 4R)-1-(4-methoxybenzoyl)-2-methyl-N-pyridin-4-yl-1,2,3, 4-tetrahydroquinolin-4-amine (125 mg, 28%).

To a solution of (2S,4R)-1-(4-methoxybenzoyl)-2-methyl-N-pyridin-4-yl-1,2,3,4-tetrahydroquinolin-4-amine (90 mg, 0.24 mmol, 1 equ.) in methylene chloride (0.8 mL) was added diisopropylethylamine (84 uL, 0.48 mmol, 2 equ.) followed by acetyl chloride (340 uL, 4.80 mmol, 20 equ.). The mixture was stirred at room temperature for 2 h. The mixture was concentrated under reduced pressure, dissolved in ethyl acetate, washed with sat. aqueous sodium bicarbonate, brine and dried over magnesium sulfate, filtered, and concentrated under reduced pressure. The residue was purified by silica gel chromatography (methylene chloride/methanol 97/3) to afford pure N-[(2S,4R)-1-(4-methoxybenzoyl)-2-methyl-1,2,3,4-tetrahydroquinolin-4-yl]-N-pyridin-4-ylacetamide (60 mg, 61%).

$^1$H-NMR (CDCl$_3$) δ: 1.20 (d, 3H), 2.20 (s, 3H), 2.30 (m, 1H), 3.75 (s, 3H), 4.80 (m, 1H), 5.65 (m, 1H), 6.60 (d, 1H), 6.70 (d, 2H), 7.05 (t, 1H), 7.10-7.20 (m, 4H), 7.25-7.40 (m, 2H), 8.70 (d, 2H).

MS m/z: 416 (M+1).

N-(4-chloro-2-methylphenyl)-N-[(2S,4R)-1-(4-methoxybenzoyl)-2-methyl-1,2,3,4-tetrahydroquinolin-4-yl]acetamide (G-34)

N-(4-chloro-2-methylphenyl)-N-[(2S,4R)-1-(4-methoxybenzoyl)-2-methyl-1,2,3,4-tetrahydroquinolin-4-yl]acetamide was made following general procedure G, substituting 4-methoxybenzoyl chloride for 4-fluorobenzoyl chloride. The amine-aryl coupling was performed differently to what is described in procedure G. Therefore (2S,4R)-1-(4-methoxybenzoyl)-2-methyl-1,2,3,4-tetrahydroquinolin-4-amine (obtained from the hydrogenation step, 500 mg, 1.5 mmol, 1 equ.) was dissolved in ethylene glycol dimethyl ether (5 mL) in a Schlenk tube. To this solution was added sequentially 2-bromo-5-chlorotoluene (400 mg, 1.95 mmol, 1.3 equ.), cesium carbonate (684 mg, 2.10 mmol, 1.4 equ.), palladium acetate (40 mg, 0.06 mmol, 0.04 equ.) and 2-(Dicyclohexylphosphino)-2',4',6'-tri-1-propyl-1,1'-biphenyl (60 mg, 0.12 mmol, 0.08 equ.). The reaction mixture was flushed with nitrogen and heated to 90° C. in the Schlenk tube for 48 h. Reaction mixture was concentrated to leave a residue which was partitioned between water and ethyl acetate and extracted. The aqueous layer was separated and the organic layer was washed with brine, dried over magnesium sulfate, filtered and concentrated to give a black oil. The crude product was purified by silica gel chromatography (methylene chloride/methanol: 99/1) to provide (2S,4R)-N-(4-chloro-2-methylphenyl)-1-(4-methoxybenzoyl)-2-methyl-1,2,3,4-tetrahydroquinolin-4-amine (200 mg, 32%).

To a solution of (2S,4R)-N-(4-chloro-2-methylphenyl)-1-(4-methoxybenzoyl)-2-methyl-1,2,3,4-tetrahydroquinolin-4-amine (140 mg, 0.33 mmol, 1 equ.) in acetyl chloride (1.0 mL) was added diisopropylethylamine (58 uL, 0.33 mmol, 1 equ.). The mixture was stirred at room temperature for 5 h. The mixture was concentrated under reduced pressure, dissolved in ethyl acetate, washed with sat. aqueous sodium bicarbonate, brine and dried over magnesium sulfate, filtered, and concentrated under reduced pressure. The residue was purified by silica gel chromatography (methylene chloride/methanol 99/1) to afford pure N-(4-chloro-2-methylphenyl)-N-[(2S,4R)-1-(4-methoxybenzoyl)-2-methyl-1,2,3,4-tetrahydroquinolin-4-yl]acetamide (140 mg, 92%).

$^1$H-NMR (CDCl$_3$) δ: 1.10 (d, 3H), 1.95 (s, 3H), 2.15 (m, 1H), 2.35 (s, 3H), 3.70 (s, 3H), 4.75 (m, 1H), 5.60 (m, 1H), 6.50 (d, 1H), 6.65 (d, 2H), 6.95 (t, 1H), 7.15-7.30 (m, 6H), 7.40 (s, 1H).

MS m/z: 463 (M+1).

TABLE 7

Exemplary Compounds:

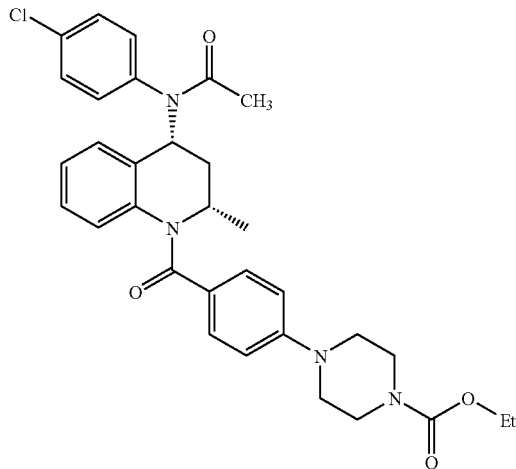

G-1

G-2

G-3

TABLE 7-continued
Exemplary Compounds:
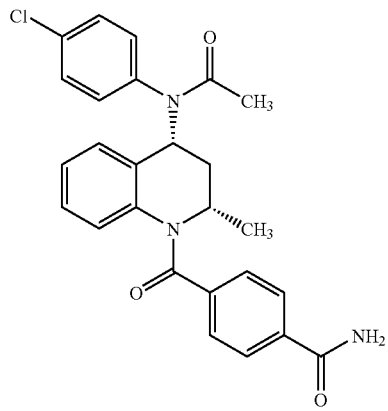
G-4
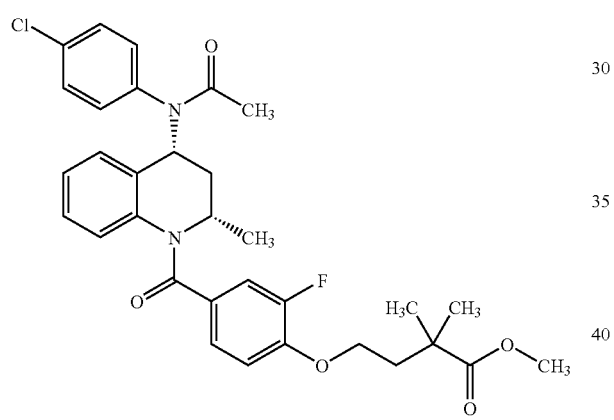
G-5
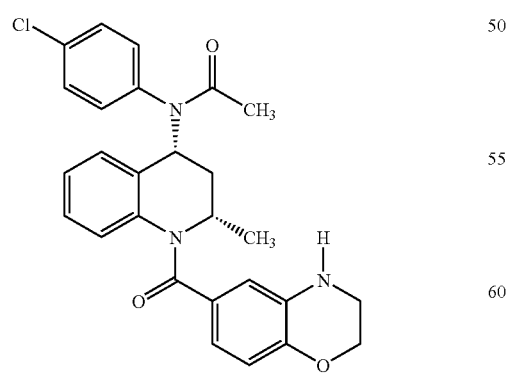
G-6
TABLE 7-continued
Exemplary Compounds:
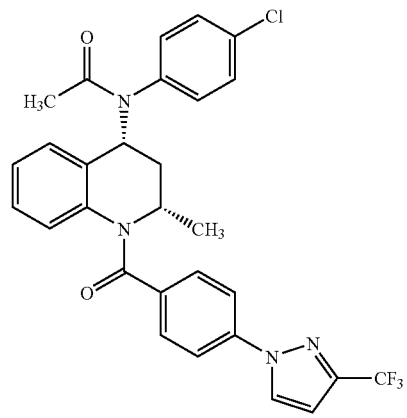
G-7
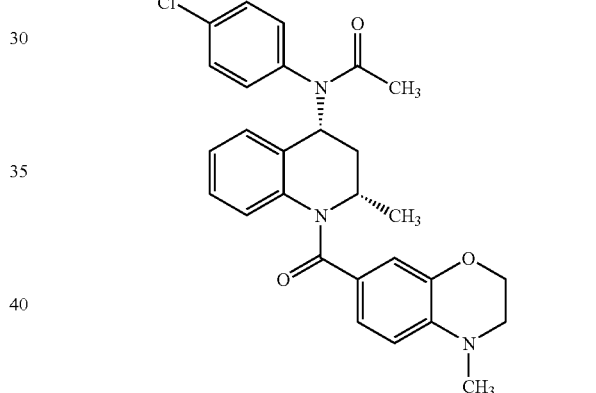
G-8
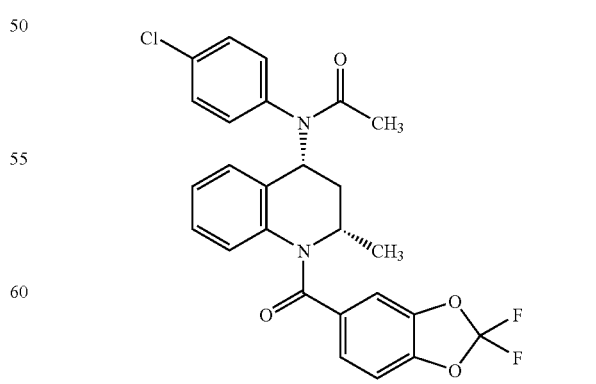
G-9

TABLE 7-continued
Exemplary Compounds:
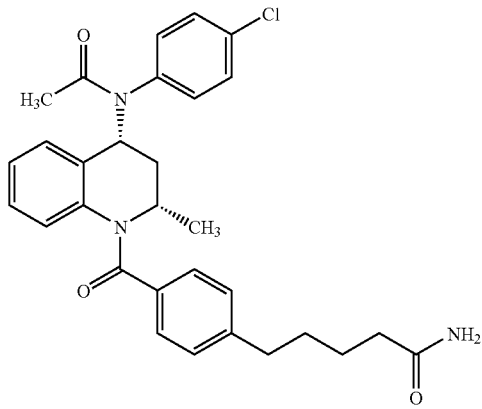
G-10
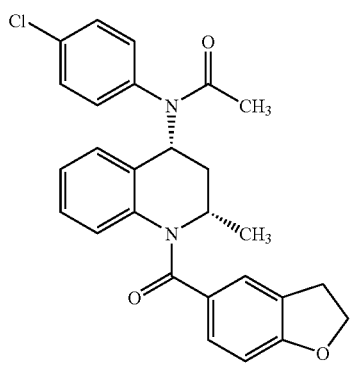
G-11
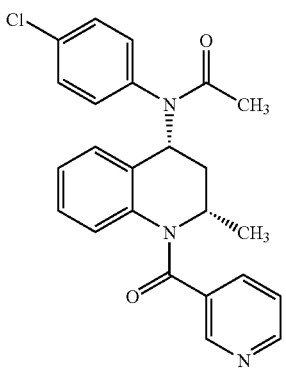
G-12
TABLE 7-continued
Exemplary Compounds:
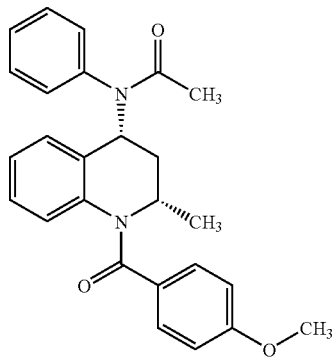
G-13
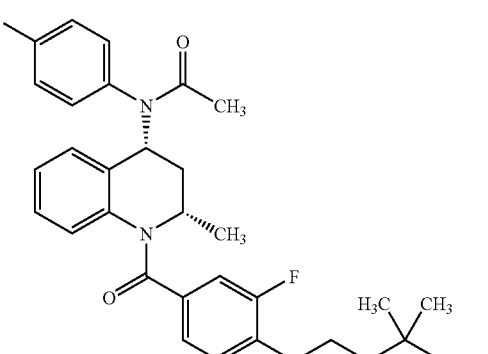
G-14
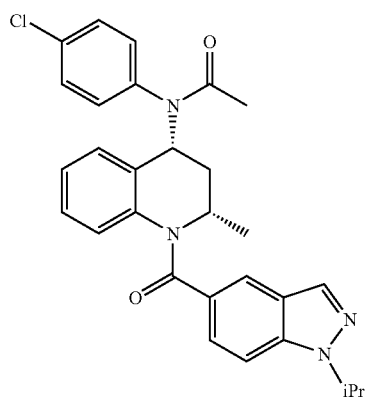
G-15

TABLE 7-continued
Exemplary Compounds:
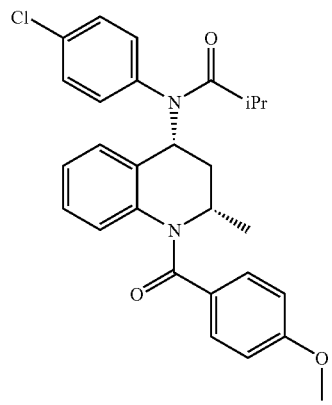
G-16
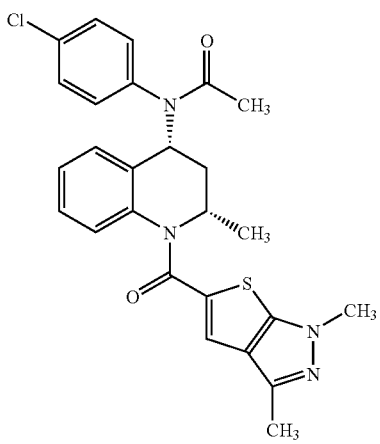
G-17
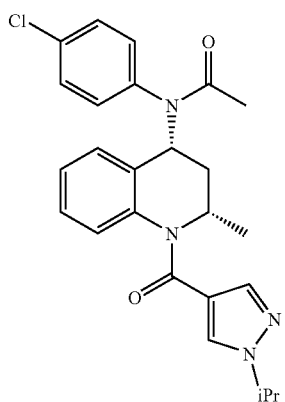
G-18
TABLE 7-continued
Exemplary Compounds:
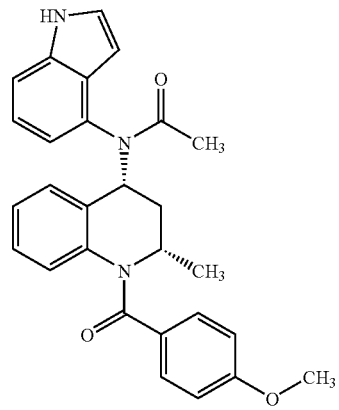
G-19
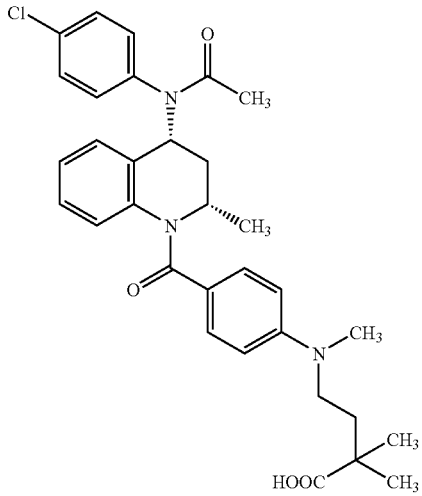
G-20
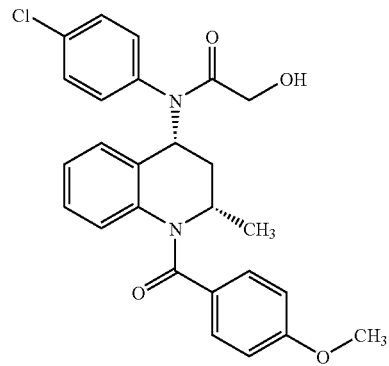
G-21

TABLE 7-continued
Exemplary Compounds:
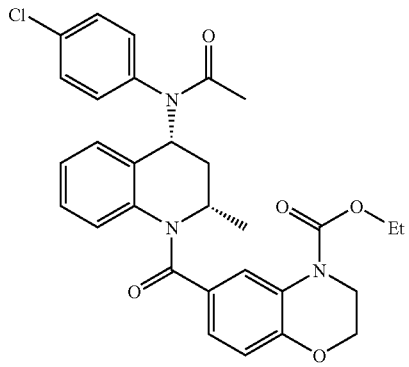
G-22
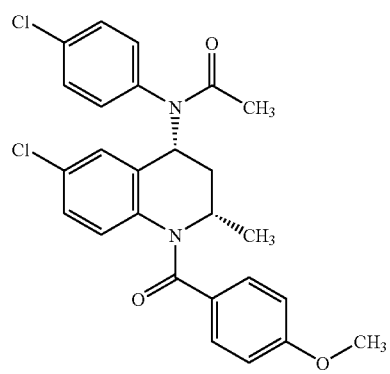
G-23
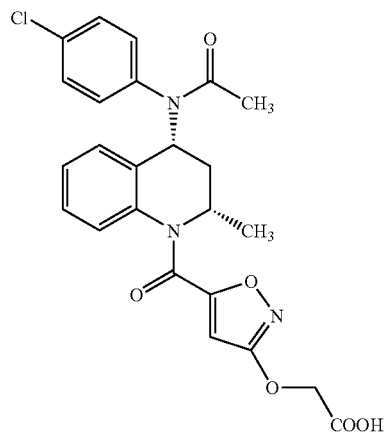
G-24
TABLE 7-continued
Exemplary Compounds:
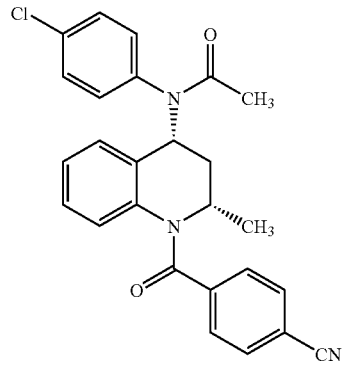
G-25
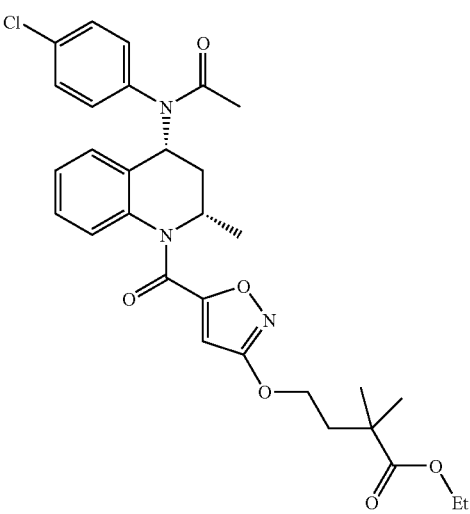
G-26
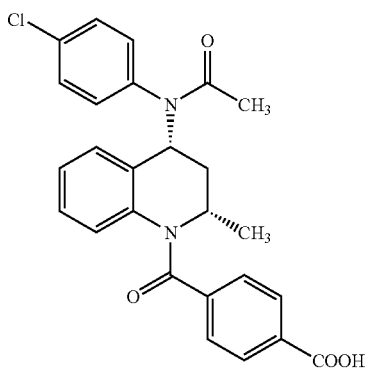
G-27

TABLE 7-continued
Exemplary Compounds:
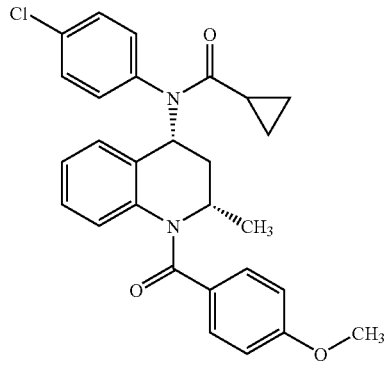
G-28
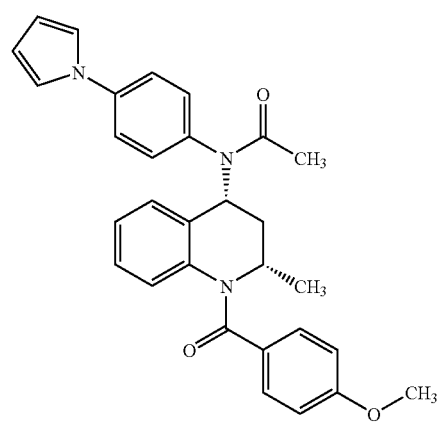
G-29
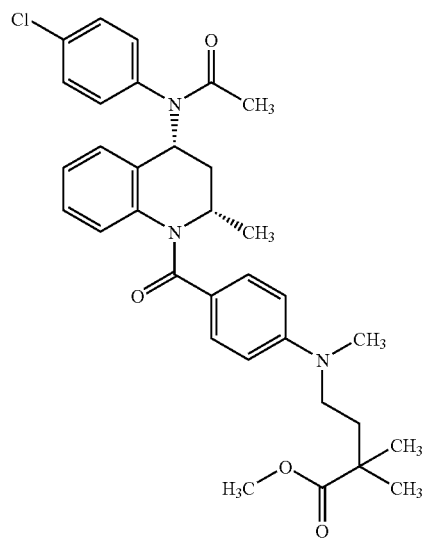
G-30
TABLE 7-continued
Exemplary Compounds:
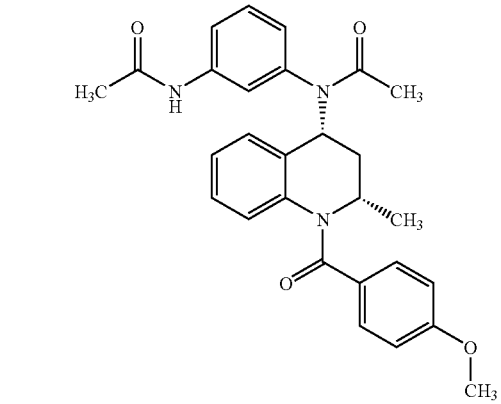
G-31
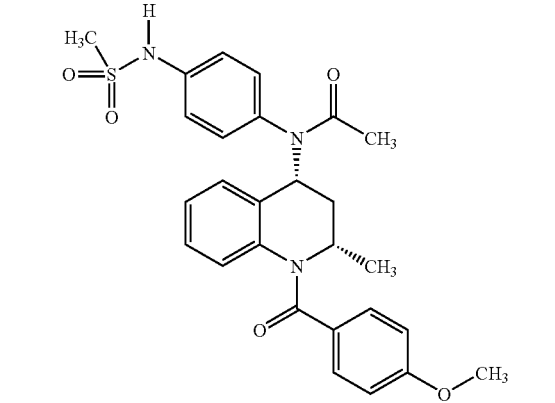
G-32
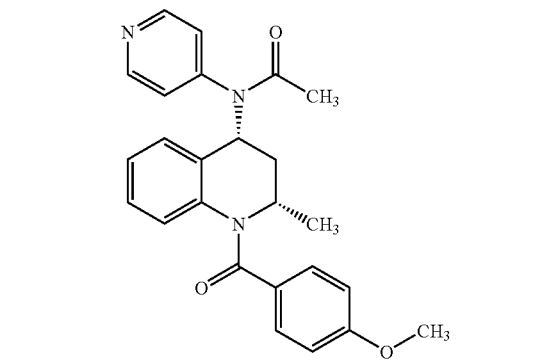
G-33

TABLE 7-continued

Exemplary Compounds:

[Structure of G-34]

TABLE 8

Names of Compounds Exemplified in Table 7:

G-1 Ethyl 4-(4-{[(2S,4R)-4-[acetyl(4-chlorophenyl)amino]-2-methyl-3,4-dihydroquinolin-1(2H)-yl]carbonyl}phenyl)piperazine-1-carboxylate
G-2 N-{3-[(Glycoloylamino)methyl]phenyl}-N-[(2S,4R)-1-(4-methoxybenzoyl)-2-methyl-1,2,3,4-tetrahydroquinolin-4-yl]acetamide
G-3 N-(4-Chloro-2-fluorophenyl)-N-[(2S,4R)-1-(4-methoxybenzoyl)-2-methyl-1,2,3,4-tetrahydroquinolin-4-yl]acetamide
G-4 4-{[(2S,4R)-4-[Acetyl(4-chlorophenyl)amino]-2-methyl-3,4-dihydroquinolin-1(2H)-yl]carbonyl}benzamide
G-5 Methyl 4-(4-{[(2S,4R)-4-[acetyl(4-chlorophenyl)amino]-2-methyl-3,4-dihydroquinolin-1(2H)-yl]carbonyl}-2-fluorophenoxy)-2,2-dimethylbutanoate
G-6 N-(4-Chlorophenyl)-N-[(2S,4R)-1-(3,4-dihydro-2H-1,4-benzoxazin-6-ylcarbonyl)-2-methyl-1,2,3,4-tetrahydroquinolin-4-yl]acetamide
G-7 N-(4-Chlorophenyl)-N-((2S,4R)-2-methyl-1-{4-[3-(trifluoromethyl)-1H-pyrazol-1-yl]benzoyl}-1,2,3,4-tetrahydroquinolin-4-yl)acetamide
G-8 N-(4-Chlorophenyl)-N-{(2S,4R)-2-methyl-1-[(4-methyl-3,4-dihydro-2H-1,4-benzoxazin-7-yl)carbonyl]-1,2,3,4-tetrahydroquinolin-4-yl}acetamide
G-9 N-(4-Chlorophenyl)-N-{(2S,4R)-1-[(2,2-difluoro-1,3-benzodioxol-5-yl)carbonyl]-2-methyl-1,2,3,4-tetrahydroquinolin-4-yl}acetamide
G-10 5-(4-{[(2S,4R)-4-[Acetyl(4-chlorophenyl)amino]-2-methyl-3,4-dihydroquinolin-1(2H)-yl]carbonyl}phenyl)pentanamide
G-11 N-(4-Chlorophenyl)-N-[(2S,4R)-1-(2,3-dihydro-1-benzofuran-5-ylcarbonyl)-2-methyl-1,2,3,4-tetrahydroquinolin-4-yl]acetamide
G-12 N-(4-Chlorophenyl)-N-[(2S,4R)-2-methyl-1-(pyridin-3-ylcarbonyl)-1,2,3,4-tetrahydroquinolin-4-yl]acetamide
G-13 N-[(2S,4R)-1-(4-Methoxybenzoyl)-2-methyl-1,2,3,4-tetrahydroquinolin-4-yl]-N-phenylacetamide
G-14 4-(4-{[(2S,4R)-4-[Acetyl(4-chlorophenyl)amino]-2-methyl-3,4-dihydroquinolin-1(2H)-yl]carbonyl}-2-fluorophenoxy)-2,2-dimethylbutanoic acid
G-15 N-(4-Chlorophenyl)-N-{(2S,4R)-1-[(1-isopropyl-1H-indazol-5-yl)carbonyl]-2-methyl-1,2,3,4-tetrahydroquinolin-4-yl}acetamide
G-16 N-(4-Chlorophenyl)-N-[(2S,4R)-1-(4-methoxybenzoyl)-2-methyl-1,2,3,4-tetrahydroquinolin-4-yl]-2-methylpropanamide
G-17 N-(4-Chlorophenyl)-N-{(2S,4R)-1-[(1,3-dimethyl-1H-thieno[2,3-c]pyrazol-5-yl)carbonyl]-2-methyl-1,2,3,4-tetrahydroquinolin-4-yl}acetamide
G-18 N-(4-Chlorophenyl)-N-{(2S,4R)-1-[(1-isopropyl-1H-pyrazol-4-yl)carbonyl]-2-methyl-1,2,3,4-tetrahydroquinolin-4-yl}acetamide
G-19 N-1H-Indol-4-yl-N-[(2S,4R)-1-(4-methoxybenzoyl)-2-methyl-1,2,3,4-tetrahydroquinolin-4-yl]acetamide
G-20 4-[(4-{[(2S,4R)-4-[Acetyl(4-chlorophenyl)amino]-2-methyl-3,4-dihydroquinolin-1(2H)-yl]carbonyl}phenyl)(methyl)amino]-2,2-dimethylbutanoic acid

TABLE 8-continued

Names of Compounds Exemplified in Table 7:

G-21  N-(4-Chlorophenyl)-2-hydroxy-N-[(2S,4R)-1-(4-methoxybenzoyl)-2-methyl-1,2,3,4-tetrahydroquinolin-4-yl]acetamide G-22  Ethyl 6-{[(2S,4R)-4-[acetyl(4-chlorophenyl)amino]-2-methyl-3,4-dihydroquinolin-1(2H)-yl]carbonyl}-2,3-dihydro-4H-1,4-benzoxazine-4-carboxylate G-23  N-[(2S,4R)-6-Chloro-1-(4-methoxybenzoyl)-2-methyl-1,2,3,4-tetrahydroquinolin-4-yl]-N-(4-chlorophenyl)acetamide G-24  [(5-{[(2S,4R)-4-[Acetyl(4-chlorophenyl)amino]-2-methyl-3,4-dihydroquinolin-1(2H)-yl]carbonyl}isoxazol-3-yl)oxy]acetic acid G-25  N-(4-Chlorophenyl)-N-[(2S,4R)-1-(4-cyanobenzoyl)-2-methyl-1,2,3,4-tetrahydroquinolin-4-yl]acetamide G-26  Ethyl 4-[(5-{[(2S,4R)-4-[acetyl(4-chlorophenyl)amino]-2-methyl-3,4-dihydroquinolin-1(2H)-yl]carbonyl}isoxazol-3-yl)oxy]-2,2-dimethylbutanoate G-27  4-{[(2S,4R)-4-[Acetyl(4-chlorophenyl)amino]-2-methyl-3,4-dihydroquinolin-1(2H)-yl]carbonyl}benzoic acid G-28  N-(4-Chlorophenyl)-N-[(2S,4R)-1-(4-methoxybenzoyl)-2-methyl-1,2,3,4-tetrahydroquinolin-4-yl]cyclopropanecarboxamide G-29  N-[(2S,4R)-1-(4-Methoxybenzoyl)-2-methyl-1,2,3,4-tetrahydroquinolin-4-yl]-N-[4-(1H-pyrrol-1-yl)phenyl]acetamide G-30  Methyl 4-[(4-{[(2S,4R)-4-[acetyl(4-chlorophenyl)amino]-2-methyl-3,4-dihydroquinolin-1(2H)-yl]carbonyl}phenyl)(methyl)amino]-2,2-dimethylbutanoate G-31  N-[3-(Acetylamino)phenyl]-N-[(2S,4R)-1-(4-methoxybenzoyl)-2-methyl-1,2,3,4-tetrahydroquinolin-4-yl]acetamide G-32  N-[(2S,4R)-1-(4-Methoxybenzoyl)-2-methyl-1,2,3,4-tetrahydroquinolin-4-yl]-N-{4-[(methylsulfonyl)amino]phenyl}acetamide G-33  N-[(2S,4R)-1-(4-Methoxybenzoyl)-2-methyl-1,2,3,4-tetrahydroquinolin-4-yl]-N-pyridin-4-ylacetamide G-34  N-(4-Chloro-2-methylphenyl)-N-[(2S,4R)-1-(4-methoxybenzoyl)-2-methyl-1,2,3,4-tetrahydroquinolin-4-yl]acetamide

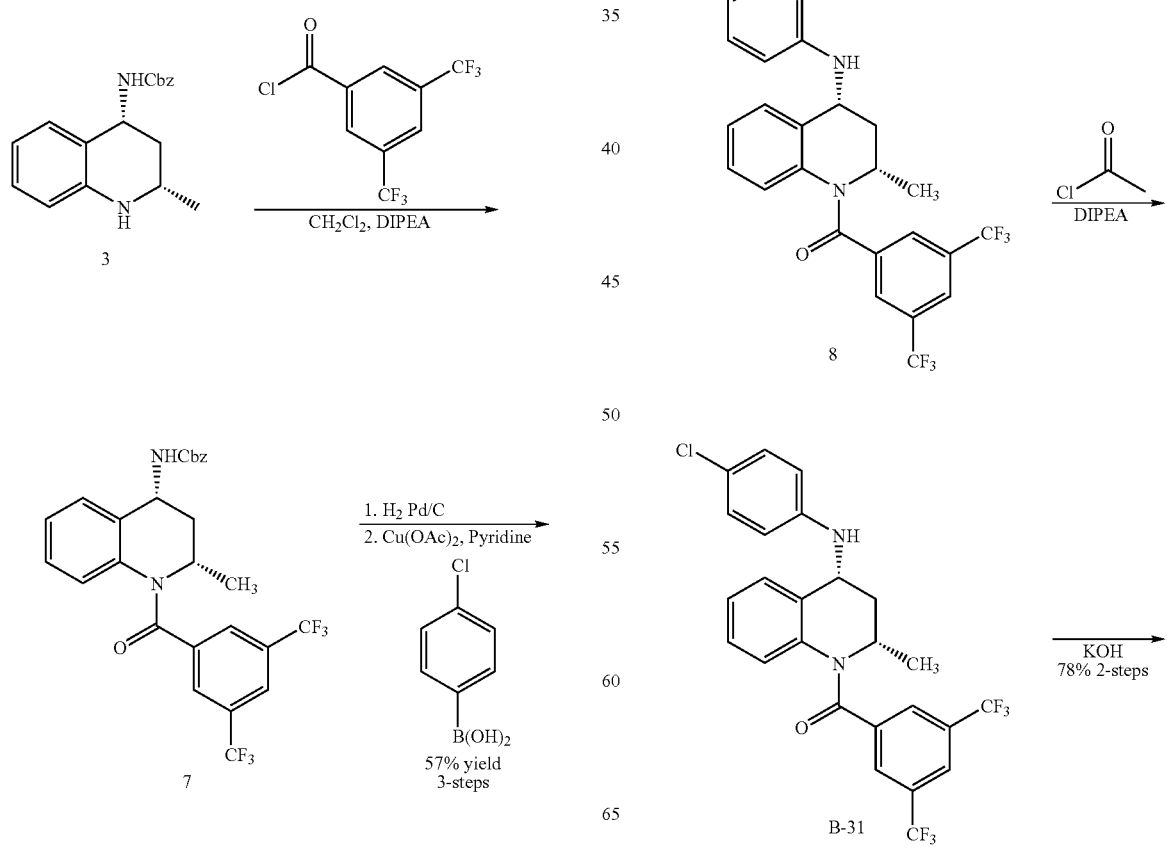

Scheme 22

-continued

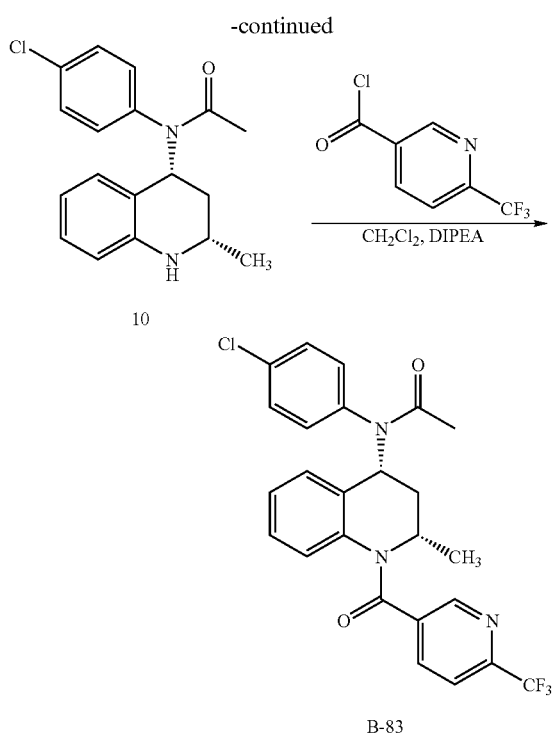

B-83

General Procedure H:

N-(4-chlorophenyl)-N-((2S,4R)-2-methyl-1-{[6-(trifluoromethyl)pyridin-3-yl]carbonyl}-1,2,3,4-tetrahydroquinolin-4-yl)acetamide (H-83)

To a solution of (2S,4R)-(2-methyl-1,2,3,4-tetrahydroquinolin-4-yl)-carbamic acid benzyl ester (20.0 g, 0.067 mol) in methylene chloride (150 mL) at room temperature was added diisopropylethylamine (40.2 mL, 0.288 mol) at 0° C. followed by addition of 3,5-bis(trifluoromethyl)benzylchloride (24.2 g, 15.8 mL, 0.087 mol). A catalytic amount of 4-dimethylaminopyridine was added and the reaction turned a dark brown and was allowed stir overnight at room temperature. The mixture was partitioned between sodium bicarbonate (saturated) and methylene chloride. The organic layer was separated and dried over sodium sulfate, filtered and concentrated to a brown solid. The crude material was taken up in 150 mL of methanol and stirred with 15 g of cesium carbonate for 20 min. 160 mL of methylene chloride and 150 mL of water was added to the solution and separated. The aqueous layer was extracted 2 additional times with methylene chloride. The organics were collected together and dried over sodium sulfate, filtered and concentrated down to give a light orange solid (36 g, quant.).

Benzyl (2S,4R)-1-(3,5-bis(trifluoromethyl)benzoyl)-2-methyl-1,2,3,4-tetrahydroquinolin-4-ylcarbamate (36 g, 0.067 mol) was dissolved in ethanol (135 mL). The vessel in which resided the resulting solution was evacuated and backfilled with argon. A catalytic amount of Palladium on Carbon (10%) was added. The vessel was once again evacuated and this time was backfilled with hydrogen and shaken in a Parr bottle at 10 psi hydrogen. Reaction was allowed to shake until no starting material remained (1 day). The mixture was carefully filtered through a Celite® pad and concentrated to afford the crude amine (26.6 g, 99%).

(3,5-bis(trifluoromethyl)phenyl)((2S,4R)-4-amino-2-methyl-3,4-dihydroquinolin-1(2H)-yl)methanone (26.6 g, 0.066 mol) was dissolved in 1.0 L of dry methylene chloride. To the solution was also added 4-chlorophenylboronic acid (20.7 g, 0.132 mol, 2 equ.), triethylamine (71.2 mL, 0.496 mol, 7.5 equ) and copper(II)acetate (24 g, 0.132 mol, 2 equ.). Finally 20 gm of molecular sieves was added. The heterogeneous green mixture was stirred open to air for 1 h, an additional 2 equivalent of 4-chlorophenylboronic acid (20.7 gm, 0.132 mol) was added. The mixture was allowed to stir at room temperature overnight and was then filtered through Celite®. The filtrate was diluted with ethyl acetate to precipitate the copper salts, the mixture was filtered a second time through Celite® to give a brown solution which was concentrated down. The residue was purified by flash chromatography (95% methylene chloride/5% ethyl acetate) to afford 19.54 g of the product in 57% yield as a white solid.

A solution of (3,5-bis(trifluoromethyl)phenyl)((2S,4R)-4-(4-chlorophenylamino)-2-methyl-3,4-dihydroquinolin-1(2H)-yl)methanone (19.44 g, 0.037 mol) in acetyl chloride (5 mL) was cooled to 0° C. and triethylamine (6.59 mL, 0.037 mol) was added dropwise over 30 min, a precipitate forms during this time. An additional 250 mL of methylene chloride was added to completely dissolve all the precipitate. The reaction was allowed to stir overnight at room temperature. The mixture was concentrated under reduced pressure, partitioned between ethyl acetate and 1N sodium hydroxide while cooled to 0° C. The aqueous layer was extracted 3 times with ethyl acetate washed with sat. aqueous sodium bicarbonate, brine and dried over magnesium sulfate, filtered, and concentrated under reduced pressure. The residue was purified by silica gel chromatography (25/75 hexanes/ethyl acetate gradient) to afford pure N-((2S,4R)-1-(3,5-bis(trifluoromethyl)benzoyl)-2-methyl-1,2,3,4-tetrahydroquinolin-4-yl)-N-(4-chlorophenyl)acetamide (H-31) (18.2 g, 86%).

$^1$H-NMR (CDCl$_3$) δ: 1.20 (d, 3H), 1.10-1.20 (m, 1H), 2.03 (s, 3H), 2.24-2.40 (m, 1H), 4.72-4.86 (m, 1H), 5.40-5.70 (m, 1H), 6.41 (d, 1H), 6.94 (t, 1H), 7.18-7.28 (m, 4H), 7.37 (t, 2H), 7.59 (s, 2H), 7.76 (s, 1H).

MS m/z: 555 (M+1).

To a solution of N-((2S,4R)-1-(3,5-bis(trifluoromethyl)benzoyl)-2-methyl-1,2,3,4-tetrahydroquinolin-4-yl)-N-(4-chlorophenyl)acetamide (5.5 g, 9.9 mmol) in ethanol (60 mL) and water (10 mL) was added potassium hydroxide (3.00 g, 53.5 mmol). The mixture was heated to 70° C. After 1 hour, an additional portion of potassium hydroxide (3.00 g, 53.5 mmol) was added and the reaction was stirred for an additional 30 m. The mixture was partitioned between ethyl acetate and sodium bicarbonate (sat. aq.). The organic layer was separated, washed twice with brine, dried over sodium sulfate, filtered and concentrated. The crude matarial was subjected to flash chromatography (2/1 hexanes/ethyl acetate gradient), resulting in pure N-(4-chlorophenyl)-N-((2S,4R)-2-methyl-1,2,3,4-tetrahydroquinolin-4-yl)acetamide as a white solid (2.85 g, 91%).

$^1$H-NMR (CDCl$_3$) δ: 1.10 (d, 3H), 1.30 (m, 1H), 1.80 (m, 1H), 1.90 (s, 3H), 3.50 (m, 1H), 3.60 (m, 1H), 6.30 (s broad, 1H), 6.45 (d, 1H), 6.70 (t, 1H), 6.90 (d, 2H), 7.00 (t, 1H), 7.15-7.25 (m, 3H). MS m/z: 315 (M+1).

To a solution of N-(4-chlorophenyl)-N-((2S,4R)-2-methyl-1,2,3,4-tetrahydroquinolin-4-yl)acetamide (104 mg, 0.33 mmol, 1 equ.) in methylene chloride (2.0 mL) at room temperature was added diisopropylethylamine (86 uL, 0.49 mmol, 1.50 equ.) followed by 6-trifluoromethyl nicotinyl chloride (104 mg, 0.49 mmol, 1.50 equ.). The reaction was stirred over night at room temperature. The mixture was concentrated, then poured into water and extracted with ethyl acetate. The extracts were washed with 1 M (aq) NaOH and brine, dried over magnesium sulfate, filtered, dried and concentrated. The crude residue was purified by silica gel chromatography (ethyl acetate/hexane 1:1) to afford the pure N-(4-chlorophenyl)-N-((2S,4R)-2-methyl-1-{[6-(trifluoromethyl)pyridin-3-yl]carbonyl}-1,2,3,4-tetrahydroquinolin-4-yl)acetamide (140 mg, 87%).

$^1$H-NMR (CDCl$_3$) δ: 1.16-1.18 (m, 1H), 1.17 (d, 3H), 1.99 (s, 3H), 2.20-2.28 (m, 1H), 4.77 (sextet, 1H), 5.50 (bs, 1H), 6.44 (d, 1H), 6.93 (t, 1H), 7.16-7.22 (m, 3H), 7.45-7.30 (m, 5H), 8.65 (s, 1H).

MS m/z=465 (M+1).

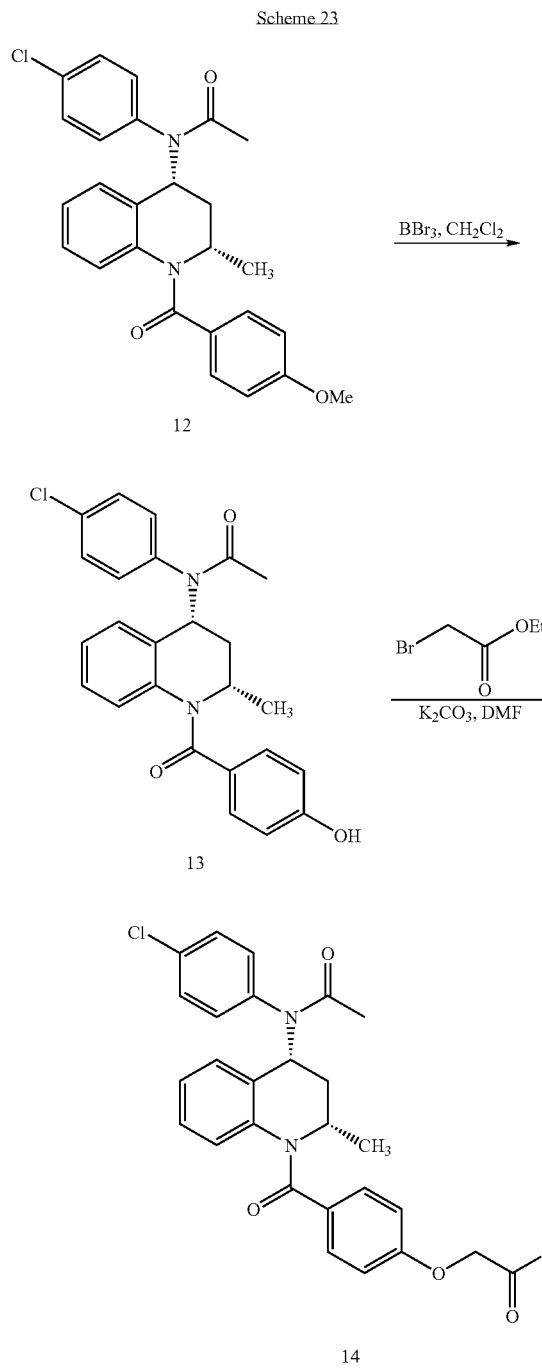

General Procedure I:

(2S,4R)-N-(4-Chloro-phenyl)-N-[1-(4-hydroxy-benzoyl)-2-methyl-1,2,3,4-tetrahydro-quinolin-4-yl]-acetamide (13)

(2S,4R)-N-(4-Chloro-phenyl)-N-[1-(4-methoxy-benzoyl)-2-methyl-1,2,3,4-tetrahydro-quinolin-4-yl]-acetamide was prepared following general procedure G, substituting 4-methoxybenzoyl chloride for 4-fluorobenzoyl chloride. (2S,4R)-N-(4-chloro-phenyl)-N-[1-(4-methoxy-benzoyl)-2-methyl-1,2,3,4-tetrahydro-quinolin-4-yl]-acetamide was dissolved in dichloromethane and a solution of BBr$_3$ (1.0 M in dichloromethane, 10 mL) was added; the reaction was allowed to stir at room temperature for until no starting material remained. The reaction was washed with sat NaHCO$_3$ carefully and brine. The organics were dried over MgSO$_4$, filtered and concentrated down. The residue was purified by Biotage flash chromatography using 100% EtOAc to give (2S,4R)-N-(4-chloro-phenyl)-N-[1-(4-hydroxy-benzoyl)-2-methyl-1,2,3,4-tetrahydro-quinolin-4-yl]-acetamide (2S,4R)-(4-{4-[Acetyl-(4-chloro-phenyl)-amino]-2-methyl-3,4-dihydro-2H-quinoline-1-carbonyl}-phenoxy)-acetic acid ethyl ester (14)

(2S,4R)-N-(4-Chloro-phenyl)-N-[1-(4-hydroxy-benzoyl)-2-methyl-1,2,3,4-tetrahydro-quinolin-4-yl]-acetamide (0.147 g) was dissolved in DMF at room temperature and K$_2$CO$_3$ was added. Ethyl 4-bromoacetate (0.065 g) was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (80/20 hexanes/ethyl acetate-50/50 hexanes ethyl acetate gradient) to afford the product in 130 mg, 73%.

(2S,4R)-3-(4-{4-[Acetyl-(4-chloro-phenyl)-amino]-2-methyl-3,4-dihydro-2H-quinoline-1-carbonyl}-phenylamino)-propionamide (H-1)

(2S,4R)-3-(4-{4-[Acetyl-(4-chloro-phenyl)-amino]-2-methyl-3,4-dihydro-2H-quinoline-1-carbonyl}-phenylamino)-propionamide was prepared from (2S,4R)-3-(4-{4-[acetyl(4-chloro-phenyl)-amino]-2-methyl-3,4-dihydro-2H-quinoline-1-carbonyl}-phenylamino)-propionic acid. The acid (0.060 g, 0.118 mmol) was dissolved in DMF (1.5 mL) at room temperature and HOBt (0.024 g, 0.177 mmol), HATU (0.068 g, 0.177 mol), and diisopropylethylamine (0.082 mL, 0.472 mmol) was added followed by ammonium chloride (0.014 g, 0.236 mmol) and stirred at room temperature for 18 h. The reaction was diluted with ethyl acetate, washed with 1N NaOH, 1N HCl and brine. The organics were dried over MgSO$_4$, filtered and concentrated down. The crude residue was purified HPLC purification.

$^1$H-NMR (CDCl$_3$) δ: 1.10 (d, 3H), 1.23 (m, 1H), 1.64 (br, 1H), 2.01 (s, 3H), 2.27 (m, 1H), 2.44 (t, 2H), 3.37 (t, 2H), 4.69 (m, 1H), 5.40 (br, 1H), 5.61 (brs, 1H), 5.80 (br, 1H), 6.31 (d, 2H), 6.59 (d, 1H), 6.94 (t, 1H), 7.02 (d, 1H), 7.10-7.23 (m, 4H), 7.36 (d, 2H).

MS m/z: 505.3 (M+1).

4-(4-{[(2S,4R)-4-[acetyl(4-chlorophenyl)amino]-2-methyl-3,4-dihydroquinolin-1(2H)-yl]carbonyl}-2-fluorophenoxy)-2,2-dimethylbutanoic acid (H-2)

To the solution of methyl 4-(4-{[(2S,4R)-4-[acetyl(4-chlorophenyl)amino]-2-methyl-3,4-dihydroquinolin-1(2H)-yl]carbonyl}-2-fluorophenoxy)-2,2-dimethylbutanoate (176 mg, 0.30 mmol) in MeOH/THF (1 mL/1 mL) was added excessive LiOH (1N aqueous solution). The reaction mixture was stirred at r.t. overnight. The reaction was quenched by adding 6N HCl to PH 2. The mixture was concentrated under reduced pressure to remove MeOH and THF. DCM (30 mL) was added. The reaction mixture was washed with brine (30 mL). The organic layer was dried over magnesium sulfate, filtered, and concentrated under reduced pressure. The crude residue was purified by silica gel chromatography (hexanes-ethyl acetate system) to afford slightly yellow solid product (120 mg, 70%).

$^1$H-NMR (CDCl$_3$, 300MHz) δ: 1.11-1.13 (d, 3H), 1.25 (s, 6H), 2.02-2.08 (m, 5H), 2.22-2.40 (m, 2H), 3.99-4.04 (t, 2H), 4.71-4.76 (q, 1H), 5.46 (b, 1H), 6.51-6.75 (m, 3H), 6.92-7.06 (m, 2H), 7.16-7.38 (m, 5H).

MS m/z: 567 (M+1).

(2S,4R)-(4-{4-[Acetyl-(4-chloro-phenyl)-amino]-2-methyl-3,4-dihydro-2H-quinoline-1-carbonyl}-phenoxy)-fluoro-acetic acid ethyl ester (H-3)

(2S,4R)-N-(4-Chloro-phenyl)-N-[1-(4-hydroxy-benzoyl)-2-methyl-1,2,3,4-tetrahydro-quinolin-4-yl]-acetamide (202 mg, 0.46 mmol) was dissolved in DMF (2 mL) at room temperature. Cs$_2$CO$_3$ (760 mg, 2.33 mmol) was added followed by bromo-fluoro-acetic acid ethyl ester (0.070 mL, 0.583 mmol) and the reaction was allowed to stir overnight. The mixture was partitioned between methylene chloride and water; the organic layer was dried over Na$_2$SO$_4$, filtered and concentrated. The crude residue was purified by silica gel chromatography (2/1 hexanes/ethyl acetate) to afford the product.

$^1$H-NMR (CDCl$_3$) δ: 1.1 (d, 3H), 1.2 (m, 1H), 1.3 (t, 3H), 2.0 (s, 3H), 2.3 (m, 1H), 4.3 (q, 2H), 4.8 (m, 1H), 5.6 (bs, 1H), 5.9 (d, 1H), 6.5 (d, 1H), 6.9 (m, 3H), 7.2 (m, 6H), 7.4 (d, 2H).

MS m/z: 539 (M+1).

(2S,4R)-2-[4-(4-{4-[Acetyl-(4-chloro-phenyl)-amino]-2-methyl-3,4-dihydro-2H-quinoline-1-carbonyl}-phenyl)-piperazin-1-yl]-acetamide (H-4)

(2S,4R)-2-[4-(4-{4-[Acetyl-(4-chloro-phenyl)-amino]-2-methyl-3,4-dihydro-2H-quinoline-1-carbonyl}-phenyl)-piperazin-1-yl]-acetamide was made from (2S,4R)-[4-(4-{4-[Acetyl-(4-chloro-phenyl)-amino]-2-methyl-3,4-dihydro-2H-quinoline-1-carbonyl}-phenyl)-piperazin-1-yl]-acetic acid. The acid (0.120 g, 0.21 mmol) was dissolved in DMF (2 mL) at room temperature and HOBt (0.043 g, 0.32 mmol), HATU (0.122 g, 0.32 mol), and diisopropylethylamine (0.15 mL, 0.64 mmol) was added followed by ammonium chloride (0.023 g, 0.42 mmol) and stirred at room temperature for 18 h. The reaction was diluted with ethyl acetate, washed with 1N NaOH, 1N HCl and brine. The organics were dried over MgSO$_4$, filtered and concentrated down. The crude residue was purified HPLC purification.

$^1$H-NMR (CDCl$_3$) δ: 1.10 (d, 3H), 1.20 (m, 1H), 2.00 (s, 3H), 2.24 (m, 1H), 3.04 (t, 4H), 3.50 (m, 6H), 4.70 (m, 1H), 5.40 (br, 1H), 5.56 (brs, 1H), 5.80 (br, 1H), 6.51 (d, 1H), 6.63 (d, 2H), 6.89 (t, 1H), 7.07-7.25 (m, 6H), 7.35 (d, 2H).

MS m/z: 560 (M+1)

4-(4-{[(2S,4R)-4-[(4-Chlorophenyl)(isobutryl)amino]-2-methyl-3,4-dihydro-quinolin-1(2H)-yl]carbonyl}phenoxy)-2,2-dimethylbutanoic acid (H-5)

Methyl 4-(4-{[(2S,4R)-4-[(4-chlorophenyl)(isobutyryl)amino]-2-methyl-3,4-dihydroquinolin-1(2H)-yl]carbonyl}phenoxy)-2,2-dimethylbutanoate was dissolved in methanol/tetrahydrofuran/water (2/1/1) then sodium hydroxide (3 equivalents) was added and reaction mixture stirred at 40° C. overnight. The mixture was concentrated, the residue acidified with a 1N HCl aqueous solution and extracted with ethyl acetate. The organic layer was washed with brine, dried over magnesium sulfate, filtered and concentrated to give 4-(4-{[(2S,4R)-4-[(4-Chlorophenyl)(isobutyryl)amino]-2-methyl-3,4-dihydroquinolin-1(2H)-yl]carbonyl}phenoxy)-2,2-dimethylbutanoic acid.

$^1$H-NMR (CDCl$_3$) δ: 1.11-1.21 (m, 10H), 1.25 (s, 6H), 2.03 (t, 2H), 2.21-2.29 (m, 1H), 2.61 (sp, 1H), 3.95 (t, 2H), 4.69-4.76 (m, 1H), 5.60 (br s, 1H), 6.51 (d, 1H), 6.62 (d, 2H), 6.91 (t, 1H), 7.11-7.43 (m, 8H).

MS m/z: 577 (M+1).

{[3-(4-{[(2S,4R)-4-[acetyl(4-chlorophenyl)amino]-2-methyl-3,4-dihydroquinolin-1(2H)-yl]carbonyl}phenoxy)propyl]amino}acetic acid (H-6)

{[3-(4-{[(2S,4R)-4-[acetyl(4-chlorophenyl)amino]-2-methyl-3,4-dihydroquinolin-1(2H)-yl]carbonyl}phenoxy)propyl]amino}acetic acid was prepared from (2S,4R)-N-{1-[4-(3-amino-propoxy)-benzoyl]-2-methyl-1,2,3,4-tetrahydro-quinolin-4-yl}-N-(4-chloro-phenyl)-acetamide. (2S,4R)-N-{1-[4-(3-amino-propoxy)-benzoyl]-2-methyl-1,2,3,4-tetrahydro-quinolin-4-yl}-N-(4-chloro-phenyl)-acetamide (0.032 g, 0.065 mmol) was dissolved in dimethylformamide, ethyl bromoisobutyrate (0.05 mL, 0.26 mmol) and potassium carbonate (0.018 g, 0.13 mmol) were added. The reaction was heated to 50° C. for 17 h. The reaction was concentrated down and purified using 50% ethyl acetate/50% hexane to 100% ethyl acetate to give 0.007 g, 12% yield of {[3-(4-{[(2S,4R)-4-[acetyl(4-chlorophenyl)amino]-2-methyl-3,4-dihydroquinolin-1(2H)-yl]carbonyl}phenoxy)propyl]amino}acetic ethyl ester.

$^1$H-NMR (CDCl$_3$) δ: 1.13 (d, 3H), 1.17 (t, 3H), 1.23 (m, 1H), 1.55 (s, 6H), 2.02 (s, 3H), 2.06-2.12 (m, 1H), 2.28 (m, 1H), 3.63 (q, 2H), 3.70-3.77 (m, 2H), 3.91-3.95 (m, 1H), 4.13 (q, 2H), 4.74 (sextet, 1H), 5.58 (bs, 1H), 6.49-6.68 (m, 3H), 6.92 (t, 1H), 7.05-7.28 (m, 6H), 7.37 (d, 1H). MS m/z=606.1 (M+1).

{[3-(4-{[(2S,4R)-4-[acetyl(4-chlorophenyl)amino]-2-methyl-3,4-dihydroquinolin-1(2H)-yl]carbonyl}phenoxy)propyl]amino}acetic ethyl ester was hydrolyzed to the acid by dissolving in tetrahydrofuran and ethanol and sodium hydroxide (1N) was added. The mixture was stirred at room temperature overnight. The mixture was cooled to rt, acidified to form a white precipitate. The solid was filtered to give {[3-(4-{[(2S,4R)-4-[acetyl(4-chlorophenyl)amino]-2-methyl-3,4-dihydroquinolin-1(2H)-yl]carbonyl}phenoxy)propyl]amino}acetic acid 0.005 g, 75% yield.

MS m/z: 578.3 (M+1).

N-[(2S,4R)-1-(4-tert-butylbenzoyl)-2-methyl-1,2,3,4-tetrahydroquinolin-4-yl]-N-(4-chlorophenyl)acetamide (H-7)

N-[(2S,4R)-1-(4-tert-Butylbenzoyl)-2-methyl-1,2,3,4-tetrahydroquinolin-4-yl]-N-(4-chlorophenyl)acetamide was synthesized according to general procedure H substituting 4-tert-butylbenzoyl chloride for 6-trifluoromethyl nicotinyl chloride. The rest of the procedure was followed as indicated in general procedure H to yield N-[(2S,4R)-1-(4-tert-butyl-benzoyl)-2-methyl-1,2,3,4-tetrahydroquinolin-4-yl]-N-(4-chlorophenyl)acetamide.

$^1$H-NMR (CDCl$_3$) δ: 1.13-1.22 (m, 1H), 1.14 (d, 3H), 1.22 (s, 9H), 2.03 (s, 3H), 2.24-2.35 (m, 1H), 4.72-4.80 (m, 1H), 5.61 (br s, 1H), 6.52 (d, 1H), 6.89 (t, 1H), 7.10-7.29 (m, 8H), 7.37 (d, 2H).

MS m/z: 475 (M+1).

(2S,4R)-N-(4-Chloro-phenyl)-N-{1-[4-(3-hydroxy-3-methyl-butoxy)-benzoyl]-2-methyl-1,2,3,4-tetrahydro-quinolin-4-yl}-acetamide (H-8)

(2S,4R)-N-(4-Chloro-phenyl)-N-[1-(4-hydroxy-benzoyl)-2-methyl-1,2,3,4-tetrahydro-quinolin-4-yl]-acetamide was dissolved in DMF (5 mL) at room temperature. K$_2$CO$_3$ was added followed by 4-bromo-2-methyl-butan-2-ol and the reaction was allowed to stir at 90° C. over night. The reaction mixture was concentrated in vacuo. The residue was partitioned between ethyl acetate and water, then extracted three times with ethyl acetate, dried over MgSO$_4$, filtered and concentrated down. The crude residue was purified by HPLC to afford the product.

4-bromo-2-methyl-butan-2-ol was prepared from 3-bromo-propionic acid ethyl ester. 3-Bromo-propionic acid ethyl ester (1.0 g, 5.5 mmol) was dissolved in 10 mL of ether and 3.7 mL of methyl magnesium bromide (3.0 M in ether) was added at 0° C. The raction was stirred at 0° C. until no starting material remained. The reaction was quenched with a sat'd ammonium chloride solution and extracted 3× with ether. The organic were collected together and dried over MgSO$_4$, filtered and concentrated down to give 4-bromo-2-methyl-butan-2-ol.

$^1$H-NMR (CDCl$_3$) δ: 1.12 (d, 3H), 1.24 (s+m, 7H), 1.90 (t, 2H), 2.01 (s, 3H), 2.22 (m, 2H), 4.07 (t, 2H), 4.72 (m, 1H), 5.60 (brs, 1H), 6.50 (d, 1H), 6.65 (d, 2H), 6.90 (t, 1H), 7.10-7.20 (m, 5H), 7.25 (t, 1H), 7.35 (d, 2H).

MS m/z: 521 (M+1).

N-(4-chlorophenyl)-N-[(2S,4R)-1-(4-iodobenzoyl)-2-methyl-1,2,3,4-tetrahydro-quinolin-4-yl]acetamide (H-9)

Purification of crude material in the last step of the synthesis of 5-(4-{(2S,4R)-4-[acetyl(4-chloro-phenyl)-amino]-2-methyl-3,4-dihydro-2H-quinoline-1-carbonyl}-phenyl)-2,2-dimethyl-pentanoic acid also allowed to isolate N-(4-chlorophenyl)-N-[(2S,4R)-1-(4-iodobenzoyl)-2-methyl-1,2,3,4-tetrahydroquinolin-4-yl]acetamide as a by-product in the synthesis (45 mg).

$^1$H-NMR (MeOD) δ: 1.15 (d, 3H), 2.05 (s, 3H), 2.45 (m, 1H), 4.75 (m, 1H), 5.55 (m, 1H), 6.55 (d, 1H), 6.95 (t, 1H), 7.25 (m, 5H), 7.30-7.55 (m, 5H).

MS m/z: 545 (M+1).

(2S,4R)-N-{1-[4-(3-Acetylamino-propoxy)-benzoyl]-2-methyl-1,2,3,4-tetrahydro-quinolin-4-yl}-N-(4-chloro-phenyl)-acetamide (H-10)

(2S,4R)-N-{1-[4-(3-Amino-propoxy)-benzoyl]-2-methyl-1,2,3,4-tetrahydro-quinolin-4-yl}-N-(4-chloro-phenyl)-acetamide (99 mg, 0.202 mmol) was dissolved in methylene chloride (2 mL) and triethylamine (0.056 mL, 0.404 mmol) and cooled to 40° C. Acetyl chloride (15 drops via pipet) was added and the mixture was warmed to 0° C. for 30 minutes. The mixture was partitioned between methylene chloride and water; the methylene chloride layer was dried over MgSO$_4$, filtered and concentrated. The crude residue was purified by silica gel chromatography (1/1 hexanes/ethyl acetate-ethyl acetate gradient) to afford the product.

$^1$H-NMR (CDCl$_3$) δ: 1.1 (s, 3H), 1.2 (m, 1H), 1.9 (s, 3H), 2.0 (m, 2H), 2.0 (s, 3H), 2.3 (m, 1H), 3.4 (q, 2H), 4.0 (t, 2H), 4.7 (m, 1H), 5.6 (bs, 1H), 5.7 (bs, 1H), 6.5 (d, 1H), 6.6 (d, 2H), 6.9 (t, 1H), 7.2 (m, 6H), 7.4 (d, 2H).

MS m/z: 534 (M+1).

(2S,4R)-N-(4-Chloro-phenyl)-N-{2-methyl-1-[4-(4,4,4-trifluoro-3-hydroxy-3-trifluoromethyl-butoxy)-benzoyl]-1,2,3,4-tetrahydro-quinolin-4-yl}-acetamide (H-11)

(2S,4R)-N-(4-Chloro-phenyl)-N-[1-(4-hydroxy-benzoyl)-2-methyl-1,2,3,4-tetrahydro-quinolin-4-yl]-acetamide was dissolved in DMF (5 mL) at room temperature. K$_2$CO$_3$ was added followed by toluene-4-sulfonic acid 4,4,4-trifluoro-3-hydroxy-3-trifluoromethyl-butyl ester and the reaction was allowed to stir at 90° C. over night. The reaction mixture was concentrated in vacuo. The residue was partitioned between ethyl acetate and water, then extracted three times with ethyl acetate, dried over MgSO$_4$, filtered and concentrated down. The crude residue was purified by HPLC to afford the product.

Toluene-4-sulfonic acid 4,4,4-trifluoro-3-hydroxy-3-trifluoromethyl-butyl ester was prepared from 4,4,4-trifluoro-3-hydroxy-3-trifluoromethyl-butyric acid. 4,4,4-trifluoro-3-hydroxy-3-trifluoromethyl-butyric acid (1.74 g, 7.0 mmol) was dissolved in THF (2 mL) at 0° C. and BH$_3$SMe$_3$ (2.6 mL, 26 mmol) was added dropwise (Ref: Tetrahedron, 2002, 9839). The reaction was allowed to warm to room temperature and stir for 16 h. The reaction was quenched with methanol and the solvent was removed to give the crude 4,4,4-trifluoro-3-trifluoromethyl-butane-1,3-diol. The alcohol was converted to the tosylate by addition of 4,4,4-trifluoro-3-trifluoromethyl-butane-1,3-diol dissolved in pyridine (2 mL) to tosyl chloride (1.39 mL) in 2 mL of CH$_2$Cl$_2$ and a catalytic amount of DMAP. The reaction was stirred at room temperature for 2 h and quenched.

$^1$H-NMR (CDCl$_3$) δ: 1.12 (m, 4H), 2.01 (s, 3H), 2.24 (m, 1H), 2.25 (t, 2H), 3.94 (t, 2H), 4.70 (m, 1H), 5.53 (brs, 2H), 6.48 (d, 1H), 6.61 (d, 2H), 6.93 (t, 1H), 7.09-7.27 (m, 6H), 7.37 (d, 2H).

MS m/z: 629 (M+1).

(2S,4R)-4-(4-{4-[Acetyl-(4-chloro-phenyl)-amino]-2-methyl-3,4-dihydro-2H-quinoline-1-carbonyl}-phenoxy)-cyclohexanecarboxylic acid amide (H-12)

(2S,4R)-4-(4-{4-[Acetyl-(4-chloro-phenyl)-amino]-2-methyl-3,4-dihydro-2H-quinoline-1-carbonyl}-phenoxy)-cyclohexanecarboxylic acid (0.070 g, 0.125 mmol) was converted to the amide by dissolving in THF (1 mL) at room temperature. HOBt (0.025 g), EDCI (0.035 g), and ammonium chloride (0.014 g, 0.25 mmol) was added along with 2 drops of DMF and stirred at room temperature for 11 h. The reaction was diluted with ethyl acetate, washed with 1N NaOH, 1N HCl and brine. The organics were dried over MgSO$_4$, filtered and concentrated down. The crude residue was purified by silica gel chromatography (50% ethyl acetate/50% methanol) to afford the product as a white powder in a 71% yield.

$^1$H-NMR (CDCl$_3$) δ: 1.13 (d, 4H), 1.19-1.60 (m, 7H), 2.01 (s, 4H), 2.20-2.39 (m, 2H), 4.72 (sextet, 1H), 5.60 (bs, 1H), 6.54 (d, 1H), 6.63 (d, 2H), 6.91 (t, 1H) 7.11-7.38 (m, 8H).

MS m/z: 560 (M+1).

(2S,4R)-N-(4-Chloro-phenyl)-N-(2-methyl-1-{4-[3-(1H-tetrazol-5-yl)-propoxy]-benzoyl}-1,2,3,4-tetrahydro-quinolin-4-yl)-acetamide (H-13)

The nitrile was prepared from (2S,4R)-N-(4-chloro-phenyl)-N-{1-[4-(3-cyano-propoxy)-benzoyl]-2-methyl-1,2,3,4-tetrahydro-quinolin-4-yl}-acetamide by dissolving in toluene, sodium azide and triethylammonium hydrochloride were added and the mixture was heated to 80° C. over night. Reaction was cooled to room temperature and water was added, followed by hydrochloric acid (1 N) until acidic. The aqueous solution was extracted three times with dichloromethane. The combined extracts were dried over magnesium sulfate, filtered, dried and concentrated. The crude product was triturated with ethyl ether/hexanes to yield a white solid in 63% yield.

$^1$H-NMR (CDCl$_3$) δ: 1.02 (d, 3H), 1.19 (m, 1H), 1.89 (s, 3H), 1.96 (m, 2H), 2.11 (m, 1H), 2.79 (m, 2H), 3.63 (m, 2H), 4.59 (sextet, 1H), 5.42 (bs, 1H), 6.35 (m, 3H), 6.77 (t, 1H), 6.91-7.08 (m, 7H), 7.22 (d, 1H).

MS m/z: 545 (M+1).

Methyl 4-(4-{[(2S,4R)-4-[(4-chlorophenyl)(cyclopropylcarbonyl)amino]-2-methyl-3,4-dihydroquinolin-1(2H)-yl]carbonyl}phenoxy)-2,2-dimethylbutanoate (H-14)

To a solution of N-(4-chlorophenyl)-N-[(2S,4R)-1-(4-methoxybenzoyl)-2-methyl-1,2,3,4-tetrahydroquinolin-4-yl]cyclopropanecarboxamide (200 mg, 0.42 mmol, 1 equ.) in methylene chloride (0.3 mL) was added a 1 M solution of boron tribromide in methylene chloride (1.2 mL, 1.26 mmol, 3 equ.). The reaction mixture was stirred at room temperature for 4 h, then the reaction was quenched with methanol and concentrated. The residue was partitioned between water and ethyl acetate and extracted. The aqueous layer was separated and the organic layer was washed with brine, dried over magnesium sulfate, filtered and concentrated to give N-(4-chlorophenyl)-N-[(2S,4R)-1-(4-hydroxybenzoyl)-2-methyl-1,2,3,4-tetrahydroquinolin-4-yl]cyclopropanecarboxamide as a beige powder (190 mg, 98%).

Methyl 4-(4-[{(2S,4R)-4-[(4-chlorophenyl)(cyclopropylcarbonyl)amino]-2-methyl-3,4-dihydro-quinolin-1(2H)-yl]carbonyl}phenoxy)-2,2-dimethylbutanoate was made from N-(4-chlorophenyl)-N-[(2S,4R)-1-(4-hydroxybenzoyl)-2-methyl-1,2,3,4-tetrahydroquinolin-4-yl]cyclopropanecarboxamide following general procedure I, substituting methyl 4-bromo-2,2-dimethylbutanoate for ethyl 4-bromoacetate to yield methyl 4-(4-{[(2S,4R)-4-[(4-chlorophenyl)(cyclopylcarbonyl)amino]-2-methyl-3,4-dihydroquinolin-1(2H)-yl]carbonyl}phenoxy)-2,2-dimethylbutanoate.

$^1$H-NMR (CDCl$_3$) δ: 0.75 (m, 2H), 1.10 (m, 2H), 1.20 (d, 3H), 1.25 (s, 6H), 1.45 (m, 1H), 2.05 (t, 2H), 2.30 (m, 1H), 3.65 (s, 3H), 3.95 (t, 2H), 4.75 (m, 1H), 5.60 (m, 1H), 6.50 (d, 1H), 6.60 (d, 2H), 6.90 (t, 1H), 7.10-7.45 (m, 8H).

MS m/z: 589 (M+1).

Methyl 5-(4-{[(2S,4R)-4-[acetyl(4-chlorophenyl)amino]-2-methyl-3,4-dihydroquinolin-1(2H)-yl]carbonyl}-2-fluorophenyl)-2,2-dimethylpentanoate (H-15)

Methyl 5-(4-{[(2S,4R)-4-[acetyl(4-chlorophenyl)amino]-2-methyl-3,4-dihydro1quinolin-1(2H)-yl]carbonyl}-2-fluorophenyl)-2,2-dimethylpentanoate was prepared following general procedure B, substituting methyl 5-[4-(chlorocarbonyl)-2-fluorophenyl]-2,2-dimethylpentanoate for 6-trifluoromethyl nicotinyl chloride. (Methyl 5-[4-(chlorocarbonyl)-2-fluorophenyl]-2,2-dimethylpentanoate was prepared in five steps from 4-bromo-3-fluorobenzoic acid. To a solution of 3-bromo-3-fluorobenzoic acid in toluene/methanol was added dropwise a 2M solution of trimethylsilyl diazomethane until slight yellow coloration persists indicating reaction had gone to completion. Reaction mixture was concentrated to give methyl-3-bromo-3-fluorobenzoate. To a solution of methyl-3-bromo-3-fluorobenzoate in dimethylformamide was added sequentially palladium acetate, triphenylphosphine, tetrabutylammonium chloride, potassium acetate and methyl 2,2-dimethylpent-4-enoate. Reaction mixture was heated under microwave irradiation at 130° C. for 10 m. to give methyl 3-fluoro-4-[(1E)-5-methoxy-4,4-dimethyl-5-oxopent-1-en-1-yl]benzoate. Hydrogenation of this diester gave methyl 3-fluoro-4-(5-methoxy-4,4-dimethyl-5-oxopentyl)benzoate which benzoic ester was selectively hydrolyzed using lithium hydroxide to give 3-fluoro-4-(5-methoxy-4,4-dimethyl-5-oxopentyl)benzoic acid. Subsequent treatment of this carboxylic acid with oxalyl chloride and catalytic DMF afforded methyl 5-[4-(chlorocarbonyl)-2-fluorophenyl]-2,2-dimethylpentanoate in decent yield). The rest of the procedures were followed as indicated in general procedure H to afford methyl 5-(4-{[(2S,4R)-4-[acetyl(4-chlorophenyl)amino]-2-methyl-3,4-dihydroquinolin-1(2H)-yl]carbonyl}-2-fluorophenyl)-2,2-dimethylpentanoate.

$^1$H-NMR (CDCl3) δ: 1.15 (d, 3H), 1.45 (m, 4H), 2.05 (s, 3H), 2.30 (m, 1H), 2.55 (m, 2H), 3.65 (s, 3H), 4.80 (m, 1H), 5.60 (m, 1H), 6.55 (d, 1H), 6.75 (d, 1H), 6.90-7.05 (m, 3H), 7.15-7.25 (m, 3H), 7.30-7.40 (m, 3H).

MS m/z: 579 (M+1).

(2S,4R)-N-3-(4-{4-[Acetyl-(4-chloro-phenyl)-amino]-2-methyl-3,4-dihydro-2H-quinoline-1-carbonyl}-phenoxy)-2,2-dimethyl-propionic acid (H-16)

(2S,4R)-N-(4-Chloro-phenyl)-N-[1-(4-hydroxy-benzoyl)-2-methyl-1,2,3,4-tetrahydro-quinolin-4-yl]-acetamide (0.32 g, 0.74 mmol) was dissolved in 10 ml DMF at room temperature and K$_2$CO$_3$ (0.51 g, 3.7 mmol) was added. 3-Chloro-2,2-dimethyl-propionic acid ethyl ester (0.25 g, 1.52 mmol) was added and the reaction was allowed to heat to 90° C. for 6 days. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (60% EtOAc/40% Hexane) to afford the (2S,4R)-3-(4-{4-[acetyl(4-chloro-phenyl)-amino]-2-methyl-3,4-dihydro-2H-quinoline-1-carbonyl}-phenoxy)-2,2-dimethyl-propionic acid ethyl ester (0.13 g, 32%).

The ester was hydrolyzed to the acid by dissolving in 8 ml tetrahydrofuran/methanol (1/1) and potassium hydroxide (0.052 g in 2.5 ml water) was added. The mixture was heated to 40° C. for 3 hours. The mixture was cooled to rt, acidified to form a white precipitate. The solid was filtered to give the product (0.098 g, 79%).

$^1$H-NMR (CDCl$_3$) δ: 1.13 (d, 3H), 1.15 (t, 1H), 1.31 (s, 6H), 2.03 (s, 3H), 2.27 (m, 1H), 3.88 (q, 2H), 4.72 (sextet, 1H), 5.58 (bs, 1H), 6.52 (d, 1H), 6.69 (d, 2H), 6.83 (t, 2H), 7.08-7.35 (m, 6H), 7.38 (d, 2H).

MS m/z: 535 (M+1)

(2S,4R)-3-(4-{4-[Acetyl-(4-chloro-phenyl)-amino]-2-methyl-3,4-dihydro-2H-quinoline-1-carbonyl}-phenoxy)-propane-1-sulfonic acid (H-17)

(2S,4R)-N-(4-Chloro-phenyl)-N-[1-(4-hydroxy-benzoyl)-2-methyl-1,2,3,4-tetrahydro-quinolin-4-yl]-acetamide (207 mg, 0.481 mmol) was dissolved in DMF (5 mL) at room temperature. NaH (58 mg, 2.40 mmol) was added followed by 3-chloro-propane-1-sulfonic acid (sodium salt, 135 mg, 0.60 mmol) and the reaction was allowed to stir over night. The mixture was partitioned between methylene chloride and HCl (1.0N/water), then extracted three times with methylene chloride, dried over $MgSO_4$, filtered and concentrated. The crude residue was purified by preparatory HPLC to afford the product.

$^1$H-NMR ($CDCl_3$) δ: 1.1 (d, 3H), 1.1 (m, 1H), 2.0 (s, 3H), 2.2 (m, 3H), 3.2 (t, 2H), 3.9 (t, 2H), 4.8 (d, 1H), 5.6 (bs, 1H), 6.5 (d, 1H), 6.6 (d, 2H), 6.9 (t, 1H), 7.2 (m, 6H), 7.4 (d, 2H), 10.6 (bs, 1H).

MS m/z: 557 (M+1).

Methyl 4-(5-{[(2S,4R)-4-[acetyl(4-chlorophenyl)amino]-2-methyl-3,4-dihydroquinolin-1(2H)-yl]carbonyl}-2-fluorophenoxy)-2,2-dimethylbutanoate (H-18)

N-(4-chlorophenyl)-N-[(2S,4R)-1-(4-fluoro-3-hydroxybenzoyl)-2-methyl-1,2,3,4-tetrahydroquinolin-4-yl]acetamide (476 mg, 1.05 mmol) was dissolved in DMF at room temperature and $Cs_2CO_3$ (854 mg, 2.63 mmol) was added. Methyl 4-bromo-2,2-dimethylbutanoate (702 mg, 1.58 mmol) was added and the reaction was stirred at r.t. overnight. The reaction mixture was concentrated under reduced pressure. The residue was partitioned between ethyl acetate and water, then extracted three times with ethyl acetate, dried over $MgSO_4$, filtered and concentrated down. The crude residue was purified by silica gel chromatography (hexanes-ethyl acetate system) to afford methyl 4-(5-{[(2S,4R)-4-[acetyl(4-chlorophenyl)amino]-2-methyl-3,4-dihydroquinolin-1(2H)-yl]carbonyl}-2-fluorophenoxy)-2,2-dimethylbutanoate (286 mg, 52%).

$^1$H-NMR ($CDCl_3$, 300MHz) δ: 1.11-1.14 (d, 3H), 1.18-1.19 (d, 6H), 2.00 (s, 3H), 2.22-2.27 (m, 1H), 3.64 (s, 3H), 3.88-3.95 (m, 1H), 4.69-4.77 (m, 1H), 5.57 (b, 1H), 6.48-6.50 (d, 1H), 6.72-6.84 (m, 3H), 6.91-6.96 (m, 1H), 7.12-7.37 (m, 6H).

MS m/z: 581 (M+1).

N-(4-chlorophenyl)-N-[(2S,4R)-1-(4-fluoro-3-hydroxybenzoyl)-2-methyl-1,2,3,4-tetrahydroquinolin-4-yl]acetamide (H-19)

N-[(2S,4R)-1-(3-{[tert-butyl-(dimethyl)silyl]oxy}-4-fluorobenzoyl)-2-methyl-1,2,3,4-tetrahydroquinolin-4-yl]-N-(4-chlorophenyl)acetamide (543 mg, 0.95 mmol) was dissolved in dichloromethane and a solution of TBAF (1.0 M in THF, 5.0 mL) was added; the reaction mixture was stirred at room temperature for until no starting material remained. The reaction was washed with sat. $NaHCO_3$ and brine carefully. The organic layer was dried over $MgSO_4$, filtered and concentrated. The residue was purified by flash chromatography using Hexanes-EtOAc system to give N-(4-chlorophenyl)-N-[(2S,4R)-1-(4-fluoro-3-hydroxybenzoyl)-2-methyl-1,2,3,4-tetrahydroquinolin-4-yl]acetamide (477 mg, 100%).

$^1$H-NMR ($CDCl_3$) δ: 1.15 (d, 3H), 1.25 (m, 2H), 2.07 (s, 3H), 2.30 (b, 1H), 4.75 (m, 1H), 6.55 (d, 1H), 6.68 (d, 1H), 6.62-6.70 (m, 3H) 7.15-7.25 (m, 4H), 7.35-7.42 (m, 2H).

MS m/z: 453 (M+1)

(2S,4R)-4-(4-{4-[Acetyl-(4-chloro-phenyl)-amino]-2-methyl-3,4-dihydro-2H-quinoline-1-carbonyl}-phenoxy)-N,N-diethyl-butyramide (H-20)

(2S,4R)-4-(4-{4-[Acetyl-(4-chloro-phenyl)-amino]-2-methyl-3,4-dihydro-2H-quinoline-1-carbonyl}-phenoxy)-N,N-diethyl-butyramide was prepared from (2S,4R)-4-(4-{4-[acetyl(4-chloro-phenyl)-amino]-2-methyl-3,4-dihydro-2H-quinoline-1-carbonyl}-phenoxy)-butyric acid ethyl ester. (2S,4R)-4-(4-{4-[acetyl(4-chloro-phenyl)-amino]-2-methyl-3,4-dihydro-2H-quinoline-1-carbonyl}-phenoxy)-butyric acid ethyl ester (0.511 g, 0.93 mmol) was hydrolyzed to the acid by dissolving in tetrahydrofuran and ethanol and sodium hydroxide (1N) was added. The mixture was stirred at room temperature 4 hours. The mixture was cooled to rt, acidified to form a white precipitate. The solid was filtered to give (2S,4R)-4-(4-{4-[acetyl(4-chloro-phenyl)-amino]-2-methyl-3,4-dihydro-2H-quinoline-1-carbonyl}-1-ethylidene-pentG-2,4-dienyloxy)-butyric acid in 74% yield. The acid (0.050 g, 0.09 mmol) was converted to the amide by dissolving in THF (2 mL) at room temperature. HOBt (0.019 g), EDCI (0.022 g), and diethylamine (0.010 mL) was added along with 2 drops of DMF and stirred at room temperature for 11 h. The reaction was diluted with ethyl acetate, washed with 1N NaOH, 1N HCl and brine. The organics were dried over $MgSO_4$, filtered and concentrated down. The crude residue was purified by silica gel chromatography (50% ethyl acetate/50% hexane to 100% ethyl acetate) to afford the product (0.023 mg, 54%).

$^1$H-NMR ($CDCl_3$) δ: 0.91 (d, 3H), 0.96 (t, 6H), 1.06 (m, 1H), 1.58 (m, 2H), 1.86 (s, 3H), 2.11 (m, 1H), 2.29 (m, 2H), 3.11-3.17 (m, 4H), 3.78 (m, 2H), 4.56 (sextet, 1H), 5.43 (bs, 1H), 6.34 (d, 1H), 6.48 (d, 2H), 6.76 (t, 1H), 6.59-7.19 (m, 8H).

MS m/z: 576 (M+1).

N-{(2S,4R)-6-chloro-2-methyl-1-[(3-methylisoxazol-5-yl)carbonyl]-1,2,3,4-tetrahydroquinolin-4-yl}-N-(4-chlorophenyl)acetamide (H-21)

N-{(2S,4R)-6-chloro-2-methyl-1-[(3-methylisoxazol-5-yl)carbonyl]-1,2,3,4-tetrahydroquinolin-4-yl}-N-(4-chlorophenyl)acetamide was prepared following the procedure described for N-{(2S,4R)-1-[3,5-bis(trifluoromethyl)benzoyl]-6-chloro-2-methyl-1,2,3,4-tetrahydroquinolin-4-yl}-N-(4-chlorophenyl)acetamide substituting 3-methylisoxazole-5-carbonyl chloride for 3,5-bistrifluoromethyl benzoyl chloride.

$^1$H-NMR ($CDCl_3$) δ: 1.10 (d, 3H), 1.10 (1H, m), 2.02 (s, 3H), 2.20 (s, 3H), 2.24-2.32 (m, 1H), 4.68-4.74 (m, 1H), 5.45-5.50 (m, 1H), 5.80 (s, 1H), 6.80 (d, 1H), 7.10-7.40 (m, 7H).

MS m/z: 458 (M+1).

(2S,4R)-4-(4-{4-[Acetyl-(4-chloro-phenyl)-amino]-2-methyl-3,4-dihydro-2H-quinoline-1-carbonyl}-phenoxy)-cyclohexanecarboxylic acid (H-22)

(2S,4R)-4-(4-{4-[Acetyl-(4-chloro-phenyl)-amino]-2-methyl-3,4-dihydro-2H-quinoline-1-carbonyl}-phenoxy)-cyclohexanecarboxylic acid ethyl ester (0.060, 0.10 mmol) was hydrolyzed to the acid by dissolving in tetrahydrofuran and ethanol and sodium hydroxide (1N) was added. The mixture was stirred at room temperature 10 hours. The mixture was cooled to room temperature, acidified to form a white precipitate. The solid was filtered to give (2S,4R)-4-(4-{4-[acetyl(4-chloro-phenyl)-amino]-2-methyl-3,4-dihydro-2H-quinoline-1-carbonyl}-phenoxy)-cyclohexanecarboxylic acid as a white powder in 62% yield.

$^1$H-NMR (CDCl$_3$) δ: 1.13 (d, 4H), 1.24-1.60 (m, 5H), 2.01 (s, 6H), 2.20-2.39 (m, 2H), 4.72 (sextet, 1H), 5.60 (bs, 1H), 6.53 (d, 1H), 6.64 (d, 2H), 6.91 (t, 1H) 7.11-7.38 (m, 8H).

MS m/z: 561 (M+1).

Methyl 5-(4-{[(2S,4R)-4-[[(acetyloxy)acetyl](4-chlorophenyl)amino]-2-methyl-3,4-dihydroquinolin-1(2H)-yl]carbonyl}phenyl)-2,2-dimethylpentanoate (H-23)

Methyl 5-(4-{[(2S,4R)-4-[[(acetyloxy)acetyl](4-chlorophenyl)amino]-2-methyl-3,4-dihydroquinolin-1(2H)-yl]carbonyl}phenyl)-2,2-dimethylpentanoate was prepared following general procedure B, substituting acetoxyacetylchloride for acetyl chloride in step 3 to provide 2-[{(2S,4R)-1-[3,5-bis(trifluoromethyl)benzoyl]-2-methyl-1,2,3,4-tetrahydroquinolin-4-yl}(4-chlorophenyl)amino]-2-1-oxoethyl acetate.

To a solution of 2-[{(2S,4R)-1-[3,5-bis(trifluoromethyl)benzoyl]-2-methyl-1,2,3,4-tetrahydroquinolin-4-yl}(4-chlorophenyl)amino]-2-oxoethyl acetate (500 mg, 0.82 mmol, 1 equ.) in ethanol (6 mL) and water (1 mL) was added potassium hydroxide (229 mg, 4.1 mmol, 5 equ.). The mixture was heated to 70° C. for 4 h. The mixture was neutralized with 1N aqueous HCl and extracted with ethyl acetate. The organic layer was separated, washed with a saturated aqueous solution of sodium bicarbonate and twice with brine, dried over sodium sulfate, filtered and concentrated to give crude N-(4-chlorophenyl)-2-hydroxy-N-[(2S,4R)-2-methyl-1,2,3,4-tetrahydroquinolin-4-yl]acetamide used as such in the next step.

N-(4-Chlorophenyl)-2-hydroxy-N-[(2S,4R)-2-methyl-1,2,3,4-tetrahydroquinolin-4-yl]acetamide (300 mg, 0.91 mmol, 1 equ.) was dissolved in methylene chloride (3 mL). To this solution was added EDC (464 mg, 2.7 mmol, 3 equ.) and acetic acid (164 mg, 2.7 mmol, 3 equ.) and the reaction mixture was stirred at room temperature for 20 h. Reaction mixture was concentrated and the residue dissolved in ethyl acetate and washed with water, brine, and then dried over magnesium sulfate, filtered and concentrated. The crude residue was purified by silica gel chromatography (methylene chloride/methanol: 99/1 to 98/2 gradient) to afford 2-{(4-chlorophenyl)[(2S,4R)-2-methyl-1,2,3,4-tetrahydroquinolin-4-yl]amino}-2-oxoethyl acetate (240 mg, 84%).

To a solution of 2-{(4-chlorophenyl)[(2S,4R)-2-methyl-1,2,3,4-tetrahydroquinolin-4-yl]amino}-2-oxoethyl acetate (170 mg, 0.45 mmol, 1 equ.) in methylene chloride (2.0 mL) at room temperature was added diisopropylethylamine (127 uL, 0.73 mmol, 1.60 equ.) followed by methyl 5-[4-(chlorocarbonyl)phenyl]-2,2-dimethylpentanoate (196 mg, 0.73 mmol, 1.60 equ.). The reaction was stirred over night at room temperature. The mixture was concentrated, then poured into water and extracted with ethyl acetate. The extracts were washed with brine, dried over magnesium sulfate, filtered dried and concentrated. The crude residue was purified by silica gel chromatography (ethyl acetate/hexane 25/75 to 1:1 gradient) to afford the pure methyl 5-(4-{[(2S,4R)-4-[[(acetyloxy)acetyl](4-chlorophenyl)amino]-2-methyl-3,4-dihydroquinolin-1(2H)-yl]carbonyl}phenyl)-2,2-dimethylpentanoate (110 mg, 40%).

$^1$H-NMR (CDCl3) δ: 1.10 (s, 6H), 1.15 (d, 3H), 1.45 (m, 4H), 2.15 (s, 3H), 2.35 (m, 1H), 2.50 (m, 2H), 3.65 (s, 3H), 4.40-4.55 (q, 2H), 4.80 (m, 1H), 5.55 (m, 1H), 6.55 (d, 1H), 6.90-7.0 (m, 3H), 7.05-7.20 (m, 3H), 7.30-7.55 (m, 5H).

MS m/z: 619 (M+1).

4-(4-{[(2S,4R)-4-[acetyl(4-chlorophenyl)amino]-2-methyl-3,4-dihydroquinolin-1(2H)-yl]carbonyl}phenoxy)-1-methylpyrrolidine-2-carboxylic acid (H-24)

4-Hydroxy-1-methyl-pyrrolidine-2-carboxylic acid (0.27 g, 1.85 mmol) was dissolved in 5 ml methanol at room temperature and (trimethylsilyl)diazomethane (2M solution in hexane) was added until solution become yellow. The mixture was concentrated down to afford crude 4-hydroxy-1-methylpyrrolidine-2-carboxylic acid methyl ester, which was converted to 4-(4-{[(2S,4R)-4-[acetyl(4-chlorophenyl)amino]-2-methyl-3,4-dihydroquinolin-1(2H)-yl]carbonyl}phenoxy)-1-methylpyrrolidine-2-carboxylic acid following the same procedure as for the preparation of (1R, 2R)-2-[(4-{[(2S,4R)-4-[acetyl(4-chlorophenyl)amino]-2-methyl-3,4-dihydroquinolin-1(2H)-yl]carbonyl}phenoxy)methyl]cyclopentanecarboxylic acid.

(2S,4R)-N-4-(4-{4-[Acetyl-(4-chloro-phenyl)-amino]-2-methyl-3,4-dihydro-2H-quinoline-1-carbonyl}-phenoxy)-2,2-dimethyl-butyramide (H-25)

(2S,4R)-N-4-(4-{4-[Acetyl-(4-chloro-phenyl)-amino]-2-methyl-3,4-dihydro-2H-quinoline-1-carbonyl}-phenoxy)-2,2-dimethyl-butyramide was prepared from (2S,4R)-N-4-(4-{4-[Acetyl-(4-chloro-phenyl)-amino]-2-methyl-3,4-dihydro-2H-quinoline-1-carbonyl}-phenoxy)-2,2-dimethyl-butyric acid by coupling NH$_4$Cl, HATU, DIEA, HOBt in DMF at room temperature to yield (2S,4R)-N-4-(4-{4-[Acetyl-(4-chloro-phenyl)-amino]-2-methyl-3,4-dihydro-2H-quinoline-1-carbonyl}-phenoxy)-butyramide. The reaction mixture was concentrated down and partitioned between ethyl acetate and water, then extracted three times with ethyl acetate, dried over magnesium sulfate, filtered and concentrated down. The residue was purified by silica gel chromatography (10% methanol/90% dichloromethane) to afford pure (2S,4R)-N-4-(4-{4-[acetyl(4-chloro-phenyl)-amino]-2-methyl-3,4-dihydro-2H-quinoline-1-carbonyl}-phenoxy)-butyramide (63%).

$^1$H-NMR (CDCl$_3$) δ: 1.13 (d, 3H), 1.15 (t, 1H), 1.25 (s, 6H), 1.98 (t, 2H), 2.04 (s, 3H), 2.27 (m, 1H), 3.96 (t, 2H), 4.72 (sextet, 1H), 5.52 (br, 2H), 5.58 (bs, 1H), 6.52 (d, 1H), 6.67 (d, 2H), 6.86 (t, 1H), 7.08-7.35 (m, 6H), 7.38 (d, 2H).

MS m/z: 548 (M+1)

(2S,4R)-N-(4-Chloro-phenyl)-N-{2-methyl-1-[4-(3-pyridin-3-yl-propoxy)-benzoyl]-1,2,3,4-tetrahydro-quinolin-4-yl}-acetamide (H-26)

(2S,4R)-N-(4-Chloro-phenyl)-N-[1-(4-hydroxy-benzoyl)-2-methyl-1,2,3,4-tetrahydro-quinolin-4-yl]-acetamide was dissolved in DMF (5 mL) at room temperature. K$_2$CO$_3$ was added followed by 3-(3-bromo-propyl)-pyridine and the reaction was allowed to stir at 90° C. over night. The reaction mixture was concentrated in vacuo. The residue was partitioned between ethyl acetate and water, then extracted three times with ethyl acetate, dried over MgSO$_4$, filtered and concentrated down. The crude residue was purified by HPLC to afford the product.

$^1$H-NMR (CDCl$_3$) δ: 1.12 (m, 4H), 1.83 (m, 2H), 2.01 (s, 3H), 2.24 (m, 1H), 2.76 (t, 2H), 3.89 (t, 2H), 4.73 (m, 1H), 5.60 (brs, 1H), 6.52 (d, 1H), 6.64 (d, 2H), 6.93 (t, 1H), 7.12-7.29 (m, 7H), 7.37 (d, 2H), 7.48 (d, 1H), 8.45 (m, 2H).

MS m/z: 554.36 (M+1).

(2S,4R)-5-(4-{4-[Acetyl-(4-chloro-phenyl)-amino]-2-methyl-3,4-dihydro-2H-quinoline-1-carbonyl}-phenoxymethyl)-furan-2-carboxylic acid amide (H-27)

(2S,4R)-5-(4-{4-[Acetyl-(4-chloro-phenyl)-amino]-2-methyl-3,4-dihydro-2H-quinoline-1-carbonyl}-phenoxymethyl)-furan-2-carboxylic acid (0.065 g, 0.12 mmol) was converted to the amide by dissolving in THF (1 mL) at room temperature. HOBt (0.024 g), EDCI (0.033 g), and ammonium chloride (0.013 g, 0.232 mmol) was added along with 2 drops of DMF and stirred at room temperature for 11 h. The reaction was diluted with ethyl acetate, washed with 1N NaOH, 1N HCl and brine. The organics were dried over $MgSO_4$, filtered and concentrated down. The crude residue was purified by silica gel chromatography (10 ethyl acetate:1 methanol) to afford the product as a white solid in 61% yield.

$^1$H-NMR (CDCl$_3$) δ: 1.13-1.20 (m, 4H), 2.01 (s, 3H), 2.23-2.29 (m, 1H), 4.72-4.74 (m, 1H), 4.99 (s, 2H), 5.59 (bs, 1H) 6.47-6.51 (m, 2H), 6.71 (d, 2H), 6.91 (t, 1H), 7.09-7.38 (m, 9H).

MS m/z: 558 (M+1).

(2S,4R)-N-(4-Chloro-phenyl)-N-{2-methyl-1-[4-(3-piperazin-1-yl-propoxy)-benzoyl]-1,2,3,4-tetrahydro-quinolin-4-yl}-acetamide (H-28)

(2S,4R)-N-(4-Chloro-phenyl)-N-{2-methyl-1-[4-(3-piperazin-1-yl-propoxy)-benzoyl]-1,2,3,4-tetrahydro-quinolin-4-yl}-acetamide was prepared from (2S,4R)-4-[3-(4-{4-[acetyl(4-chloro-phenyl)-amino]-2-methyl-3,4-dihydro-2H-quinoline-1-carbonyl}-phenoxy)-propyl]-piperazine-1-carboxylic acid tert-butyl ester. (2S,4R)-N-(4-Chloro-phenyl)-N-[1-(4-hydroxy-benzoyl)-2-methyl-1,2,3,4-tetrahydro-quinolin-4-yl]-acetamide (0.40 g, 0.92 mmol) was dissolved in DMF at room temperature and K$_2$CO$_3$ (0.127 g, 0.921 mmol) was added. 4-(3-Chloro-propyl)-piperazine-1-carboxylic acid tert-butyl ester (0.242 g, 0.921 mmol) was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography to afford the product as colorless oil in 50% yield. (2S,4R)-4-[3-(4-{4-[Acetyl-(4-chloro-phenyl)-amino]-2-methyl-3,4-dihydro-2H-quinoline-1-carbonyl}-phenoxy)-propyl]-piperazine-1-carboxylic acid tert-butyl ester (246 mg) was dissolved in 4M HCl in dioxane (2 mL). The mixture was stirred for 2 h at room temperature. After concentration, the white solid was washed with EtOAc to provide the title compound in 100% yield.

$^1$H-NMR (DMSO, 2HCl salt) δ: 1.00-1.02 (m, 4H), 1.88-1.94 (m, 3H), 2.10-2.15 (m, 1H), 3.15-3.80 (m, 12H), 4.02 (t, 2H), 4.56-4.59 (m, 1H), 5.49 (bs, 1H), 6.50 (d, 1H), 6.76 (d, 2H), 6.96 (t, 1H), 7.04 (d, 2H), 7.16 (t, 1H), 7.39-7.53 (m, 5H).

MS m/z: 561 (M+1).

Methyl 4-(4-{[(2S,4R)-4-[acetyl(4-chlorophenyl)amino]-2-methyl-3,4-dihydroquinolin-1(2H)-yl]carbonyl}-2,6-difluorophenoxy)-2,2-dimethylbutanoate (H-29)

N-(4-chlorophenyl)-N-[(2S,4R)-1-(3,5-difluoro-4-methoxybenzoyl)-2-methyl-1,2,3,4-tetrahydroquinolin-4-yl]acetamide was prepared following general procedure H, substituting 3,5-difluoro-4-methoxybenzoyl chloride for 6-trifluoromethyl nicotinyl chloride. The rest of the procedures were followed as indicated in general procedure H to afford N-(4-chlorophenyl)-N-[(2S,4R)-1-(3,5-difluoro-4-methoxybenzoyl)-2-methyl-1,2,3,4-tetrahydroquinolin-4-yl]acetamide was obtained in decent yield.

N-(4-chlorophenyl)-N-[(2S,4R)-1-(3,5-difluoro-4-methoxybenzoyl)-2-methyl-1,2,3,4-tetrahydroquinolin-4-yl]acetamide (200 mg, 0.41 mmol) was dissolved in dichloromethane and a solution of BBr$_3$ (1.0 M in dichloromethane, 10 mL) was added; the reaction was allowed to stir at room temperature for until no starting material remained. The reaction was washed with sat. NaHCO$_3$ and brine. The organic layer were dried over MgSO$_4$, filtered and concentrated down. The residue was purified by flash chromatography using hexanes-ethyl acetate system to give N-(4-chlorophenyl)-N-[(2S,4R)-1-(3,5-difluoro-4-hydroxybenzoyl)-2-methyl-1,2,3,4-tetrahydroquinolin-4-yl]acetamide (152 mg, 78%).

N-(4-chlorophenyl)-N-[(2S,4R)-1-(3,5-difluoro-4-hydroxybenzoyl)-2-methyl-1,2,3,4-tetrahydroquinolin-4-yl]acetamide (150 mg, 0.32 mmol) was dissolved in DMF at room temperature and Cs$_2$CO$_3$ (259 mg, 0.80 mmol) was added. Methyl 4-bromo-2,2-dimethylbutanoate (157 mg, 0.48 mmol) was added and the reaction was stirred at room temperature overnight. The reaction mixture was concentrated under reduced pressure. The residue was partitioned between ethyl acetate and water, then extracted three times with ethyl acetate, dried over MgSO$_4$, filtered and concentrated. The crude residue was purified by silica gel chromatography (hexanes-ethyl acetate system) to afford the product (118 mg, 61%).

$^1$H-NMR (CDCl$_3$, 300MHz) δ: 1.12-1.14 (d, 3H), 1.21-1.24 (m, 6H), 1.48-1.55 (m, 2H), 2.02 (s, 3H), 2.20-2.32 (m, 1H), 3.64 (s, 3H), 4.11-4.16 (m, 1H), 4.65-4.75 (m, 1H), 5:45-5.55 (m, 1H), 6.51-6.54 (d, 1H), 6.70-6.73 (m, 1H), 6.76-6.90 (m, 1H), 7.18-7.39 (m, 7H).

MS m/z: 599 (M+1).

(2S,4R)-1-(4-{4-[Acetyl-(4-chloro-phenyl)-amino]-2-methyl-3,4-dihydro-2H-quinoline-1-carbonyl}-phenyl)-piperidine-4-carboxylic acid amide (H-30)

(2S,4R)-1-(4-{4-[Acetyl-(4-chloro-phenyl)-amino]-2-methyl-3,4-dihydro-2H-quinoline-1-carbonyl}-phenyl)-piperidine-4-carboxylic acid amide was prepared from (2S,4R)-1-(4-{4-[acetyl(4-chloro-phenyl)-amino]-2-methyl-3,4-dihydro-2H-quinoline-1-carbonyl}-phenyl)-piperidine-4-carboxylic acid. The acid (0.120 g, 0.22 mmol) was dissolved in DMF (2.5 mL) at room temperature and HOBt (0.044 g, 0.33 mmol), HATU (0.125 g, 0.33 mol), and diisopropylethylamine (0.15 mL, 0.88 mmol) was added followed by ammonium chloride (0.024 g, 0.44 mmol) and stirred at room temperature for 16 h. The reaction was diluted with ethyl acetate, washed with 1N NaOH, 1N HCl and brine. The organics were dried over MgSO$_4$, filtered and concentrated down. The crude residue was purified HPLC purification.

$^1$H-NMR (CDCl$_3$) δ: 1.10 (d, 3H), 1.23 (m, 1H), 1.79 (m, 4H), 2.01 (m, 3H), 2.27 (m, 1H), 2.48 (m, 1H), 2.96 (m, 1H), 3.13 (m, 1H), 3.35 (m, 1H), 3.52 (m, 1H), 4.70 (m, 1H), 5.50 (br, 2H), 6.24 (br, 1H), 6.56 (d, 1H), 6.67 (d, 2H), 6.92 (t, 1H), 7.08-7.28 (m, 6H), 7.37 (d, 2H).

MS m/z: 545.4 (M+1).

2-{[3-(4-{[(2S,4R)-4-[acetyl(4-chlorophenyl) amino]-2-methyl-3,4-dihydroquinolin-1(2H)-yl] carbonyl}phenyl)propanoyl]amino}-2-methylpropanoic acid (H-32)

Methyl 3-(4-{[(2S,4R)-4-[acetyl(4-chlorophenyl)amino]-2-methyl-3,4-dihydroquinolin-1(2H)-yl]carbonyl}phenyl) propanoate (90 mg, 0.15 mmol, 1 equ.) was dissolved in methanol/tetrahydrofuran (2/1) (1 ml). A solution of sodium hydroxide (12 mg, 0.30 mmol, 2 eq.) in water (0.5 ml) was added and reaction mixture was stirred at room temperature for 20 h. The mixture was concentrated and the residue was acidified with a 1N HCl aqueous solution and extracted with ethyl acetate. The organic layer was washed with brine, dried over magnesium sulfate, filtered and concentrated to give 2-{[3-(4-{[(2S,4R)-4-[acetyl(4-chlorophenyl)amino]-2-methyl-3,4-dihydroquinolin-1(2H)-yl]carbonyl}phenyl)propanoyl]amino}-2-methylpropanoic acid (76 mg, 87%).

$^1$H-NMR (CDCl3) δ: 1.15 (d, 3H), 1.45 (d, 6H), 2.05 (s, 3H), 2.30 (m, 1H), 2.40 (t, 2H), 2.85 (t, 2H), 4.75 (m, 1H), 5.60 (m, 1H), 6.30 (s, 1H), 6.55 (d, 1H), 6.90 (t, 1H), 6.90-7.15 (m, 8H), 7.40 (d, 2H).

MS m/z: 576 (M+1).

Methyl 4-[5-{[(2S,4R)-4-[acetyl(4-chlorophenyl)amino]-2-methyl-3,4-dihydroquinolin-1(2H)-yl]carbonyl}-2-oxopyridin-1(2H)-yl]-2,2-dimethylbutanoate (H-33) and methyl 4-[(5-{[(2S,4R)-4-[acetyl(4-chlorophenyl)amino]-2-methyl-3,4-dihydroquinolin-1(2H)-yl]carbonyl}pyridin-2-yl)oxy]-2,2-dimethylbutanoate (H-143)

Methyl 4-[(5-{[(2S,4R)-4-[acetyl(4-chlorophenyl)amino]-2-methyl-3,4-dihydroquinolin-1(2H)-yl] carbonyl}pyridin-2-yl)oxy]-2,2-dimethylbutanoate was prepared from (2S,4R)-N-(4-chloro-phenyl)-N-[1-(6-methoxy-pyridine-3-carbonyl)-2-methyl-1,2,3,4-tetrahydro-quinolin-4-yl]-acetamide by deprotection of the methoxy and elaboration. (2S,4R)-N-(4-chloro-phenyl)-N-[1-(6-methoxy-pyridine-3-carbonyl)-2-methyl-1,2,3,4-tetrahydro-quinolin-4-yl]-acetamide (0.062 g, 0.13 mmol) was dissolved in methylene chloride and TMSI (0.020 mL, 0.13 mmol) was added and stirred at room temperature for 14 h. The reaction mixture was concentrated down and methanol was added and stirring was continued for 10 h, concentrated down and used directly. N-(4-chlorophenyl)-N-{(2S,4R)-1-[(6-hydroxypyridin-3-yl)carbonyl]-2-methyl-1,2,3,4-tetrahydroquinolin-4-yl}acetamide (0.060 g, 0.13 mmol) was dissolved in 2 mL of dimethylformamide, followed by 0.046 g of methyl 4-bromo-2,2-dimethylbutanoate (0.20 mmol) and 0.057 g of silver carbonate (0.20 mmol). The flask was covered with aluminum foil and the lights were turned off in the enclosure. The reaction was allowed to heat to 80° C. for 24 h. Additional methyl 4-bromo-2,2-dimethylbutanoate (0.046 g, 0.20 mmol) was added and continued stirring at 80° C. for 24 h. The reaction was concentrated down and partitioned between ethyl acetate and water. The organics were collected together and dried over MgSO$_4$, filtered and concentrated. The residue was purified with 2% methanol/98% methylene chloride to 5% methanol/95% methylene chloride to 10% methanol/90% methylene chloride. Two products were obtained the O- and N-alkylated product, methyl 4-[(5-{[(2S,4R)-4-[acetyl(4-chlorophenyl)amino]-2-methyl-3,4-dihydroquinolin-1(2H)-yl]carbonyl}pyridin-2-yl)oxy]-2,2-dimethylbutanoate (0.025 g, 32%) and methyl 4-[5-{[(2S,4R)-4-[acetyl(4-chlorophenyl)amino]-2-methyl-3,4-dihydroquinolin-1(2H)-yl]carbonyl}-2-oxopyridin-1(2H)-yl]-2,2-dimethylbutanoate (0.025 g, 32%).

O-alkylated $^1$H-NMR (CDCl$_3$) δ: 1.13 (m, 1H), 1.14 (d, 3H), 1.22 (s, 6H), 1.99 (t, 2H), 2.01 (s, 3H), 2.29 (m, 1H), 3.62 (s, 3H), 4.27 (t, 2H), 4.74 (sextet, 1H), 5.58 (bs, 1H), 6.37 (d, 1H), 6.56 (d, 1H), 7.00 (t, 1H), 7.28-7.16 (m, 5H), 7.37 (d, 2H), 8.14 (bs, 1H).

MS m/z=564 (M+1).

N-alkylated $^1$H-NMR (CDCl$_3$) δ: 1.11 (m, 1H), 1.12 (d, 3H), 1.22 (s, 6H), 1.72-1.90 (m, 2H), 2.01 (s, 3H), 2.25 (m, 1H), 3.67 (s, 3H), 3.71-3.88 (m, 2H), 4.64 (, sextet, 1H), 5.51 (bs, 1H), 6.15 (d, 1H), 6.74 (d, 2H), 7.09 (t, 1H), 7.15-7.33 (m, 4H), 7.37 (d, 2H), 7.57 (s, 1H).

MS m/z: 564 (M+1).

N-{(2S,4R)-1-[4-(aminomethyl)benzoyl]-2-methyl-1,2,3,4-tetrahydroquinolin-4-yl}-N-(4-chlorophenyl) acetamide (H-34)

N-{(2S,4R)-1-[4-(aminomethyl)benzoyl]-2-methyl-1,2,3,4-tetrahydroquinolin-4-yl}-N-(4-chlorophenyl)acetamide was made following general procedure H, substituting 4-cyanobenzoyl chloride for 6-trifluoromethyl nicotinyl chloride. The rest of the procedure is followed as indicated in general procedure H to yield the corresponding nitrile, N-(4-chlorophenyl)-N-[(2S,4R)-1-(4-cyano-benzoyl)-2-methyl-1,2,3,4-tetrahydro-quinolin-4-yl]-acetamide. N-(4-Chloro-phenyl)-N-[(2S,4R)-1-(4-cyano-benzoyl)-2-methyl-1,2,3,4-tetrahydro-quinolin-4-yl]-acetamide (225 mg, 0.51 mmol) was dissolved in ethanol (7 mL) and cobalt dichloride (0.079 g, 0.61 mmol) and NaBH$_4$ (0.059 g, 1.57 mmol) were added and the mixture was stirred at room temperature for 2 h. The slurry was filtered, concentrated, and subjected to flash chromatography (1% NH$_4$OH, 15% MeOH, EtOAc) to yield the title compound (188 mg, 83%) as a white solid. $^1$H-NMR (CDCl$_3$) δ: 1.00-1.20 (m, 1H), 1.14 (s, 3H), 1.48 (bs, 2H), 2.02 (s, 3H), 2.20-2.36 (m, 1H), 3.79 (s, 2H), 4.73-4.83 (m, 1H), 5.35-5.70 (m, 1H), 6.49 (d, 1H), 6.89 (t, 1H), 7.11-7.29 (m, 8H), 7.37 (d, 2H).

MS m/z: 448 (M+1)

(2S,4R)-N-[3-(4-{4-[Acetyl-(4-chloro-phenyl)-amino]-2-methyl-3,4-dihydro-2H-quinoline-1-carbonyl}-phenoxy)-propyl]-2,2-dimethyl-propionamide (H-35)

(2S,4R)-N-{1-[4-(3-Amino-propoxy)-benzoyl]-2-methyl-1,2,3,4-tetrahydro-quinolin-4-yl}-N-(4-chloro-phenyl)-acetamide (60 mg, 0.122 mmol) was dissolved in methylene chloride (2 mL) and triethylamine (0.034 mL, 0.243 mmol) and cooled to 40° C. Pivaloyl chloride (10 drops via pipet) was added and the mixture was warmed to 0° C. for 30 minutes. The mixture was partitioned between methylene chloride and water; the methylene chloride layer was dried over MgSO$_4$, filtered and concentrated. The crude residue was purified by silica gel chromatography (1/1 hexanes/ethyl acetate-ethyl acetate gradient) to afford the product.

$^1$H-NMR (CDCl$_3$) δ: 1.1 (s, 3H), 1.1 (s, 9H), 1.2 (m, 1H), 2.0 (m, 2H), 2.0 (s, 3H), 2.3 (m, 1H), 3.4 (q, 2H), 4.0 (t, 2H), 4.7 (m, 1H), 5.6 (bs, 1H), 6.0 (s, 1H), 6.5 (d, 1H), 6.6 (d, 2H), 6.9 (t, 1H), 7.2 (m, 6H), 7.4 (d, 2H).

MS m/z: 576 (M+1).

Methyl 4-(4-{[(2S,4R)-4-[acetyl(4-chlorophenyl)amino]-2-methyl-3,4-dihydroquinolin-1(2H)-yl]carbonyl}-2-fluorophenoxy)-2,2-dimethylbutanoate (H-36)

N-(4-chlorophenyl)-N-[(2S,4R)-1-(3-fluoro-4-methoxybenzoyl)-2-methyl-1,2,3,4-tetrahydroquinolin-4-yl]acetamide was prepared following general procedure H, substituting 3-fluoro-4-methoxybenzoyl chloride for 6-trifluoromethyl nicotinyl chloride. The rest of the procedures were followed as indicated in general procedure H to afford N-(4-chlorophenyl)-N-[(2S,4R)-1-(3-fluoro-4-methoxybenzoyl)-2-methyl-1,2,3,4-tetrahydro-quinolin-4-yl]acetamide.

N-(4-chlorophenyl)-N-[(2S,4R)-1-(3-fluoro-4-methoxybenzoyl)-2-methyl-1,2,3,4-tetrahydro-quinolin-4-yl]acetamide was dissolved in dichloromethane and a solution of $BBr_3$ (1.0 M in dichloromethane, 10 mL) was added; the reaction was allowed to stir at room temperature for until no starting material remained. The reaction was washed with sat. $NaHCO_3$ and brine. The organic layer were dried over $MgSO_4$, filtered and concentrated down. The residue was purified by flash chromatography using hexanes-ethyl acetate system to give N-(4-chlorophenyl)-N-[(2S,4R)-1-(3-fluoro-4-hydroxybenzoyl)-2-methyl-1,2,3,4-tetrahydro-quinolin-4-yl]acetamide in decent yield.

N-(4-chlorophenyl)-N-[(2S,4R)-1-(3-fluoro-4-hydroxybenzoyl)-2-methyl-1,2,3,4-tetrahydroquinolin-4-yl]acetamide (317 mg, 0.70 mmol) was dissolved in DMF at room temperature and $Cs_2CO_3$ (567 mg, 1.75 mmol) was added. Methyl 4-bromo-2,2-dimethylbutanoate (465 mg, 1.05 mmol) was added and the reaction was stirred at room temperature overnight. The reaction mixture was concentrated under reduced pressure. The residue was partitioned between ethyl acetate and water, then extracted three times with ethyl acetate, dried over $MgSO_4$, filtered and concentrated. The crude residue was purified by silica gel chromatography (hexanes/ethyl acetate system) to afford the product (176 mg, 43%).

$^1$H-NMR ($CDCl_3$, 300MHz) δ: 1.11-1.13 (d, 3H), 1.22-1.29 (m, 6H), 1.51-1.64 (m, 2H), 2.07-2.09 (m, 5H), 2.25-2.29 (m, 2H), 3.65 (s, 3H), 3.95-3.99 (m, 2H), 4.70-4.75 (q, 1H), 5.27 (b, 1H), 6.51-6.75 (m, 3H), 6.92-7.03 (m, 2H), 7.14-7.38 (m, 6H).

MS m/z: 581 (M+1).

(2S,4R)-N-(4-chloro-phenyl)-N-{2-methyl-1-[4-(2-oxo-imidazolidin-1-yl)-benzoyl]-1,2,3,4-tetrahydro-quinolin-4-yl}-acetamide (H-37)

N-[1-(4-Amino-benzoyl)-2-methyl-1,2,3,4-tetrahydro-quinolin-4-yl]-N-(4-chloro-phenyl)-acetamide (156 mg, 0.373 mmol) was dissolved in methylene chloride (3 mL) and was added triethylamine (0.078 mL, 0.559 mmol) and 1-chloro-2-isocyanato-ethane 0.038 mL, 0.448 mmol). The reaction was stirred at room temperature over night, and the reaction was quenched with sat. aq. $NaHCO_3$. The residue was partitioned between methylene chloride and water, then extracted three times with methylene chloride, dried over $MgSO_4$, filtered and concentrated down. The crude residue was purified by silica gel chromatography (ethyl acetate) to afford the product.

$^1$H-NMR ($CDCl_3$) δ: 1.2 (d, 3H), 1.2 (m, 1H), 2.0 (s, 3H), 2.3 (m, 1H), 4.0 (t, 2H), 4.4 (t, 2H), 4.8 (m, 1H), 5.6 (m, 1H), 6.5 (d, 1H), 6.9 (t, 1H), 7.2 (m, 9H), 7.4 (d, 2H).

MS m/z: 503 (M+1).

(2S,4R)-4-[(4-{4-[Acetyl-(4-chloro-phenyl)-amino]-2-methyl-3,4-dihydro-2H-quinoline-1-carbonyl}-phenyl)-methyl-amino]-butyric acid (H-38)

(2S,4R)-4-[(4-{4-[Acetyl-(4-chloro-phenyl)-amino]-2-methyl-3,4-dihydro-2H-quinoline-1-carbonyl}-phenyl)-methyl-amino]-butyric acid was prepared from (2S,4R)-4-[(4-{4-[acetyl(4-chloro-phenyl)-amino]-2-methyl-3,4-dihydro-2H-quinoline-1-carbonyl}-phenyl)-methyl-amino]-butyric acid methyl ester was hydrolyzed to the acid by dissolving in tetrahydrofuran and ethanol and lithium hydroxide (1N) was added and heated 50° C. for 2 h. The mixture was cooled to room temperature, acidified to form a white precipitate. The solid was filtered to give to afford the product after HPLC purification.

$^1$H-NMR ($CDCl_3$) δ: 1.10 (d, 3H), 1.18 (m, 1H), 1.81 (t, 2H), 2.02 (s, 3H), 2.28 (m, 3H), 2.86 (s, 3H), 3.28 (t, 2H), 4.70 (m, 1H), 5.58 (brs, 1H), 6.39 (d, 2H), 6.61 (d, 1H), 6.94 (t, 1H), 7.06-7.27 (m, 6H), 7.36 (d, 2H), 8.90 (br, 1H).

MS m/z: 534 (M+1).

(2S,4R)-N-(4-Chloro-phenyl)-N-{1-[4-(4-hydroxy-4-methyl-pentyloxy)-benzoyl]-2-methyl-1,2,3,4-tetrahydro-quinolin-4-yl}-acetamide (H-39)

(2S,4R)-N-(4-Chloro-phenyl)-N-[1-(4-hydroxy-benzoyl)-2-methyl-1,2,3,4-tetrahydro-quinolin-4-yl]-acetamide (0.1 g, 0.23 mmol) was dissolved in DMF (5 mL) at room temperature. $K_2CO_3$ (0.317 g, 2.3 mmol) was added. 5-Bromo-2-methyl-pentan-2-ol (0.092 g, 0.51 mmol) was added and the reaction was allowed to heat to 80° C. overnight. The reaction mixture was concentrated in vacuo. The residue was partitioned between ethyl acetate and water, then extracted three times with ethyl acetate, dried over $MgSO_4$, filtered and concentrated down. The crude residue was purified by silica gel chromatography (70% EtOAc/30% Hexane) to afford the product (0.097 g, 79%).

$^1$H-NMR ($CDCl_3$) δ: 1.13 (d, 3H), 1.15 (t, 1H), 1.26 (s, 6H), 1.52-1.90 (m, 5H), 2.04 (s, 3H), 2.27 (m, 1H), 3.91 (t, 2H), 4.72 (sextet, 1H), 5.48 (bs, 1H), 6.52 (d, 1H), 6.67 (d, 2H), 6.86 (t, 1H), 7.08-7.35 (m, 6H), 7.38 (d, 2H).

MS m/z: 535 (M+1)

(2S,4R)-1-[3-(4-{4-[Acetyl-(4-chloro-phenyl)-amino]-2-methyl-3,4-dihydro-2H-quinoline-1-carbonyl}-phenoxy)-propyl]-1H-imidazole-2-carboxylic acid amide (H-40)

(2S,4R)-1-[3-(4-{4-[Acetyl-(4-chloro-phenyl)-amino]-2-methyl-3,4-dihydro-2H-quinoline-1-carbonyl}phenoxy)-propyl]-1H-imidazole-2-carboxylic acid amide was prepared from (2S,4R)-1-[3-(4-{4-[Acetyl-(4-chloro-phenyl)-amino]-2-methyl-3,4-dihydro-2H-quinoline-1-carbonyl}-phenoxy)-propyl]-1H-imidazole-2-carboxylic acid ethyl ester. The ester (0.100 g, 0.16 mmol) was hydrolyzed to the acid by dissolving in tetrahydrofuran and ethanol and sodium hydroxide (1N) was added. The mixture was stirred at room temperature 4 hours. The mixture was cooled to rt, acidified to form a white precipitate. The solid was filtered to give (2S, 4R)-1-[3-(4-{4-[Acetyl-(4-chloro-phenyl)-amino]-2-methyl-3,4-dihydro-2H-quinoline-1-carbonyl}-phenoxy)-propyl]-1H-imidazole-2-carboxylic acid in 65% yield. The acid (0.066 g, 0.09 mmol) was converted to the amide by dissolving in DMF (2 mL) at room temperature. HATU (0.061 g, 0.16 mmol), HOBt (0.021 g, 0.15 mmol), and diisopropylethylamine (0.074 mL, 0.43 mmol) were added and stirred for 5 min. followed by ammonium chloride (0.011 g, 0.20 mmol). The reaction was stirred at room temperature for 12 h and concentrated down the residue was diluted with ethyl acetate and washed with 1N HCl and dried over MgSO$_4$, filtered and concentrated down. The crude residue was purified by silica gel chromatography (5% MeOH/95% CH$_2$Cl$_2$/NH$_4$OH to 10% MeOH/90% CH$_2$Cl$_2$/NH$_4$OH to 15% MeOH/85% CH$_2$Cl$_2$/NH$_4$OH) to afford the product (0.050 mg, 81%).

$^1$H-NMR (CDCl$_3$) δ: 1.11 (d, 3H), 1.37 (m, 1H), 2.00 (s, 3H), 2.22 (m, 3H), 3.82 (t, 2H), 4.57 (t, 2H), 4.72 (sextet, 1H), 5.56 (bs, 1H), 6.49 (d, 1H), 6.60 (d, 2H), 6.90 (t, 1H), 6.89 (t, 1H), 6.93 (d, 2H), 7.11 (d, 2H), 7.15-7.27 (m, 5H), 7.34 (d, 1H).

MS m/z: 586 (M+1).

(2S,4R)-N-(4-Chloro-phenyl)-N-{2-methyl-1-[4-(2-oxo-oxazolidin-5-ylmethoxy)-benzoyl]-1,2,3,4-tetrahydro-quinolin-4-yl}-acetamide (H-41)

(2S,4R)-N-(4-Chloro-phenyl)-N-[1-(4-hydroxy-benzoyl)-2-methyl-1,2,3,4-tetrahydro-quinolin-4-yl]-acetamide (0.5 g, 1.14 mmol) was dissolved in DMF at room temperature and K$_2$CO$_3$ (1.26 g, 9.13 mmol) was added. 2-Chloromethyl-oxirane (0.42 g, 4.57 mmol) was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (50% EtOAc/50% Hexane) to afford (2S,4R)-N-(4-chloro-phenyl)-N-[2-methyl-1-(4-oxiranylmethoxy-benzoyl)-1,2,3,4-tetrahydro-quinolin-4-yl]-acetamide (0.55 g, 77%), which was further elaborated to the product following ref. (*Tetrahedron Lett* 2002, 43(46), 8327).

$^1$H-NMR (CDCl$_3$) δ: 1.13 (d, 3H), 1.15 (t, 1H), 2.03 (s, 3H), 2.27 (m, 1H), 3.57 (m, 1H), 3.68 (m, 1H), 4.05 (m, 2H), 4.73 (m, 1H), 4.86 (m, 1H), 5.58 (bs, 1H), 6.52 (d, 1H), 6.67 (d, 2H), 6.86 (t, 1H), 7.08-7.35 (m, 6H), 7.38 (d, 2H).

MS m/z: 535 (M+1)

5-(4-{[(2S,4R)-4-[acetyl(4-chlorophenyl)amino]-2-methyl-3,4-dihydroquinolin-1(2H)-yl]carbonyl}phenyl)-2,2-dimethylpentanoic acid (H-42)

5-(4-{(2S,4R)-4-[acetyl(4-chloro-phenyl)-amino]-2-methyl-3,4-dihydro-2H-quinoline-1-carbonyl}-phenyl)-2,2-dimethyl-pentanoic acid methyl ester (500 mg, 0.89 mmol, 1 eq.) was dissolved in methanol/tetrahydrofuran (2/1) (4 ml). A solution of sodium hydroxide (71 mg, 1.8 mmol, 2 eq.) in water (1 ml) was added and reaction mixture heated to 60° C. for 20 h. The mixture was concentrated and the residue was acidified with a 1N HCl aqueous solution and extracted with ethyl acetate. The organic layer was washed with brine, dried over magnesium sulfate, filtered and concentrated to give the crude acid. Purification by silica gel chromatography gave pure 5-(4-{(2S,4R)-4-[acetyl(4-chloro-phenyl)-amino]-2-methyl-3,4-dihydro-2H-quinoline-1-carbonyl}-phenyl)-2,2-dimethyl-pentanoic acid (292 mg, 60%).

$^1$H-NMR (MeOD) δ: 1.10 (d, 3H), 1.13 (s, 6H), 1.50 (m, 4H), 2.05 (s, 3H), 2.45 (m, 1H), 2.55 (t, 2H), 4.75 (m, 1H), 5.55 (m, 1H), 6.55 (d, 1H), 6.95 (t, 1H), 7.05-7.20 (dd, 4H), 7.25 (t, 1H), 7.40-7.55 (m, 5H).

MS m/z: 547 (M+1).

Methyl 4-(4-{[(2S,4R)-4-[acetyl(4-chlorophenyl)amino]-2-methyl-3,4-dihydroquinolin-1(2H)-yl]carbonyl}phenyl)-2,2-dimethylbutanoate (H-43)

Methyl 4-(4-{[(2S,4R)-4-[acetyl(4-chlorophenyl)amino]-2-methyl-3,4-dihydroquinolin-1(2H)-yl]carbonyl}phenyl)-2,2-dimethylbutanoate was prepared according to general procedure B, substituting methyl 4-[4-(chlorocarbonyl)phenyl]-2,2-dimethylbutanoate for 6-trifluoromethyl nicotinyl chloride. (Methyl 4-[4-(chlorocarbonyl)phenyl]-2,2-dimethylbutanoate was prepared in 5 steps from 4-(4-iodophenyl) butanoic acid. 4-(4-iodophenyl)butanoic acid was converted to methyl 4-(4-iodophenyl)butanoate by treatment with trimethylsilyl diazomethane (1.5 equivalents) in benzene/methanol (4/1) at room temperature. Lithium enolate formation with lithium diisopropyl amide (1.1 equivalents) in THF at −78° C. followed by quenching with methyl iodide (2.0 equivalents) and aqueous work up then repeating the same protocol afforded, after standard chromatography (10% ethyl acetate/hexanes) methyl 4-(4-iodophenyl)-2,2-dimethylbutanoate. Subsequent treatment of this material with catalytic palladium(II)acetate (0.05 equivalents) and 1,3-bis(diphenylphosphino)propane (0.05 equivalents) in the presence of water (5.0 equivalents) and triethylamine (2.0 equivalents) in DMF at 80° C. under a carbon monoxide atmosphere afforded, after aqueous work up, 4-(4-methoxy-3,3-dimethyl-4-oxobutyl)benzoic acid. This material was directly converted to methyl 4-[4-(chlorocarbonyl)phenyl]-2,2-dimethylbutanoate by treatment with excess thionyl chloride in dichloromethane at room temperature for 2 hours then removal of the volatiles in vaccuo). The rest of the procedures were followed as indicated in general procedure B to afford methyl 4-(4-{[(2S,4R)-4-[acetyl(4-chlorophenyl)amino]-2-methyl-3,4-dihydroquinolin-1(2H)-yl]carbonyl}phenyl)-2,2-dimethylbutanoate.

$^1$H-NMR (CDCl$_3$) δ: 1.12-1.21 (m, 1H), 1.13 (d, 3H), 1.18 (s, 6H), 1.73 (ddd, 2H), 2.01 (s, 3H), 2.23-2:30 (m, 1H), 2.43 (ddd, 2H), 3.64 (s, 3H), 4.71-4.79 (m, 1H), 5.60 (br s, 1H), 6.49 (d, 1H), 6.89 (t, 1H), 6.95 (d, 2H), 7.08-7.29 (m, 6H), 7.37 (d, 2H).

MS m/z: 547 (M+1).

3-(4-{[(2S,4R)-4-[acetyl(4-chlorophenyl)amino]-6-chloro-2-methyl-3,4-dihydroquinolin-1(2H)-yl]carbonyl}phenoxy)-2,2-dimethylpropanoic acid (H-44)

3-(4-{[(2S,4R)-4-[acetyl(4-chlorophenyl)amino]-6-chloro-2-methyl-3,4-dihydroquinolin-1(2H)-yl]carbonyl}phenoxy)-2,2-dimethylpropanoic acid was synthesized from (2S,4R)-N-3-(4-{4-[Acetyl-(4-chloro-phenyl)-amino]-2-methyl-3,4-dihydro-2H-quinoline-1-carbonyl}-phenoxy)-2,2-dimethyl-propionic acid (0.030 g, 0.057 mmol) by addition of 1 mL of dimethylformamide and TCCA (0.0044 g, 0.018 mmol, 0.33 equ.) and stirred at room temperature for 40 min. The reaction mixture was diluted with water and acidified with 1N HCl to form a white precipitate. The solid was dried on the lyophilizer and purified with 5% methanoldichloromethane to 10% methanol/90% dichloromethane to yield 0.400 g, 87% of 4-(4-{[(2S,4R)-4-[acetyl(4-chlorophenyl)amino]chloro-2-methyl-3,4-dihydroquinolin-1(2H)-yl]carbonyl}phenoxy)-2,2-dimethylbutanoic acid.

$^1$H-NMR (CDCl$_3$) δ: 1.10 (d, 3H), 1.13 (m, 1H), 1.29 (s, 6H), 2.03 (s, 3H), 2.27 (m, 1H), 3.92-3.85 (m, 2H), 4.72 (sextet, 1H), 5.51 (bs, 1H), 6.43 (d, 1H), 6.67 (d, 2H), 6.90 (d, 1H), 7.11 (s, 1H), 7.13 (d, 2H), 7.19 (d, 2H), 7.38 (d, 2H).

MS m/z: 569 (M+1).

N-(4-aminophenyl)-N-[(2S,4R)-1-(4-methoxybenzoyl)-2-methyl-1,2,3,4-tetrahydroquinolin-4-yl]acetamide (H-45)

Benzyl (4-{acetyl[(2S,4R)-1-(4-methoxybenzoyl)-2-methyl-1,2,3,4-tetrahydroquinolin-4-yl]amino}phenyl)carbamate was dissolved in MeOH and was added a catalytic amount of Palladium on Carbon (10%). The system was purged by Hydrogen gas, the subjected to 1 atm of $H_2$ for 2 h. The reaction was quenched with air and filtered to give the title compound as a white solid.

$^1$H-NMR (CDCl$_3$) δ: 1.10-1.60 (m, 1H), 1.10 (d, 3H), 2.01 (s, 3H), 2.22-2.38 (m, 1H), 3.70-3.95 (bs, 2H), 3.72 (s, 3H), 4.64-4.80 (m, 1H), 5.45-5.72 (m, 1H), 6.49 (d, 1H), 6.54-6.70 (m, 2H), 6.64 (d, 2H), 6.89 (t, 1H), 6.99 (d, 2H), 7.08-7.20 (m, 3H), 7.30 (d, 1H).

MS m/z: 430 (M+1)

(2S,4R)-N-(4-Chloro-phenyl)-N-{1-[4-(4-methanesulfonylamino-3,3-dimethyl-4-oxo-butoxy)-benzoyl]-2-methyl-1,2,3,4-tetrahydro-quinolin-4-yl}-acetamide (H-46)

(2S,4R)-4-(4-{4-[Acetyl-(4-chloro-phenyl)-amino]-2-methyl-3,4-dihydro-2H-quinoline-1-carbonyl}-phenoxy)-2,2-dimethyl-butyric acid (200 mg, 0.37 mmol) was dissolved in methylene chloride (5 mL) and oxalyl chloride (2 mL). A single drop of DMF was added, and the mixture was stirred at room temperature until gas evolution ceased. All volatiles were removed. The slurry was dissolved in methylene chloride (10 mL) and triethylamine (2 mL). Methanesulfonamide (200 mg, 2.10 mmol) was added and the reaction mixture was stirred for 3 hours. The mixture was partitioned between methylene chloride and water; the organic layer was dried over $Na_2SO_4$, filtered and concentrated. The crude residue was purified by preparatory HPLC.

$^1$H-NMR (CDCl$_3$) δ: 1.1 (d, 3H), 1.2 (m, 1H), 1.2 (s, 3H), 1.3 (s, 3H), 2.0 (s, 3H), 2.1 (t, 1H), 2.3 (m, 1H), 3.4 (m, 4H), 3.9 (m, 2H), 4.7 (m, 1H), 5.6 (bs, 1H), 5.9 (d, 1H), 6.5 (d, 1H), 6.4 (d, 2H), 6.9 (t, 1H), 7.2 (m, 6H), 7.4 (d, 2H).

MS m/z: 626 (M+1).

(2S,4R)-1-(4-{4-[Acetyl-(4-chloro-phenyl)-amino]-2-methyl-3,4-dihydro-2H-quinoline-1-carbonyl}-phenyl)-piperidine-3-carboxylic acid (H-47)

(2S,4R)-1-(4-{4-[Acetyl-4-chloro-phenyl)-amino]-2-methyl-3,4-dihydro-2H-quinoline-1-carbonyl}-phenyl)-piperidine-3-carboxylic acid was prepared from (2S,4R)-1-(4-{4-[acetyl(4-chloro-phenyl)-amino]-2-methyl-3,4-dihydro-2H-quinoline-1-carbonyl}-phenyl)-piperidine-3-carboxylic acid ethyl ester (0.300 g, 0.522 mol) was hydrolyzed to the acid by dissolving in tetrahydrofuran and ethanol and lithium hydroxide (1N) was added and heated 50° C. for 2 h. The mixture was cooled to room temperature, acidified to form a white precipitate. The solid was filtered to give to afford the product after HPLC purification.

$^1$H-NMR (CDCl$_3$) δ: 1.11 (d, 3H), 1.23 (m, 1H), 1.77 (m, 2H), 1.94 (m, 2H), 2.02 (s, 3H), 2.27 (m, 1H), 2.43 (m, 1H), 2.78 (t, 2H), 3.60 (m, 2H), 4.71 (m, 1H), 5.58 (brs, 1H), 6.57 (d, 1H), 6.63 (d, 2H), 6.93 (t, 1H), 7.07-7.28 (m, 6H), 7.37 (d, 2H), 9.30 (br, 1H).

MS m/z: 546.3 (M+1).

N-{(2S,4R)-6-Chloro-1-[(6-ethylpyridin-3-yl)carbonyl]-2-methyl-1,2,3,4-tetrahydroquinolin-4-yl}-N-(4-chlorophenyl)acetamide (H-48)

N-{(2S,4R)-6-Chloro-1-[(6-ethylpyridin-3-yl)carbonyl]-2-methyl-1,2,3,4-tetrahydroquinolin-4-yl}-N-(4-chlorophenyl)acetamide was prepared following the procedure described for N-{(2S,4R)-1-[3,5-bis(trifluoromethyl)benzoyl]-6-chloro-2-methyl-1,2,3,4-tetrahydroquinolin-4-yl}-N-(4-chlorophenyl)acetamide substituting 6-ethyl nicotinyl chloride for 3,5-bistrifluoromethyl benzoyl chloride. (6-Ethyl nicotinyl chloride was prepared in two steps from methyl 6-chloronicotinate as described in the procedure for N-(4-chlorophenyl)-N-{(2S,4R)-1-[(6-ethylpyridin-3-yl)carbonyl]-2-methyl-1,2,3,4-tetrahydroquinolin-4-yl}acetamide).

$^1$H-NMR (CDCl$_3$) δ: 1.26 (d, 3H); 1.28 (t, 3H), 1.28-1.31 (m, 1H), 2.02 (s, 3H), 2.22-2.36 (m, 1H), 2.81 (q, 2H), 4.70-4.80 (m, 1H), 5.42-5.56 (br, 1H), 6.50 (d, 1H), 6.90-7.00 (m, 2H), 7.20-7.40 (m, 7H), 8.50 (br s, 1H).

MS m/z: 482 (M+1).

4-(4-{[(2S,4R)-4-[(4-chlorophenyl)(cyclopropylcarbonyl)amino]-2-methyl-3,4-dihydroquinolin-1(2H)-yl]carbonyl}phenoxy)-2,2-dimethylbutanoic acid (H-49)

Methyl 4-(4-{[(2S,4R)-4-[(4-chlorophenyl)(cyclopropylcarbonyl)amino]-2-methyl-3,4-dihydroquinolin-1(2H)-yl]carbonyl}phenoxy)-2,2-dimethylbutanoate (100 mg, 0.17 mmol, 1 equ.) was dissolved in methanol/tetrahydrofuran (2/1) (1 ml). A solution of sodium hydroxide (21 mg, 0.51 mmol, 3 eq.) in water (0.5 ml) was added and reaction mixture heated to 40° C. for 2 h. The mixture was concentrated and the residue was acidified with a 1N HCl aqueous solution and extracted with ethyl acetate. The organic layer was washed with brine, dried over magnesium sulfate, filtered and concentrated to give the crude acid. Purification by silica gel chromatography (methylene chloride/methanol 98/2) gave pure 4-(4-{[(2S,4R)-4-[(4-chlorophenyl)(cyclopropylcarbonyl)amino]-2-methyl-3,4-dihydroquinolin-1(2H)-yl]carbonyl}phenoxy)-2,2-dimethylbutanoic acid (85 mg, 87%).

$^1$H-NMR (CDCl$_3$) δ: 0.75 (m, 2H), 1.10 (m, 2H), 1.20 (d, 3H), 1.25 (s, 6H), 1.45 (m, 1H), 2.05 (t, 2H), 2.30 (m, 1H), 3.95 (t, 2H), 4.75 (m, 1H), 5.60 (m, 1H), 6.50 (d, 1H), 6.60 (d, 2H), 6.90 (t, 1H), 7.10-7.45 (m, 8H).

MS m/z: 575 (M+1).

N-(4-Chlorophenyl)-N-[(2S,4R)-1-(3-ethyl-4-fluorobenzoyl)-2-methyl-1,2,3,4-tetrahydroquinolin-4-yl]acetamide (H-50)

N-(4-Chlorophenyl)-N-[(2S,4R)-1-(3-ethyl-4-fluorobenzoyl)-2-methyl-1,2,3,4-tetrahydroquinolin-4-yl]acetamide was prepared following general procedure B, substituting 4-fluoro-3-ethylbenzoyl chloride for 6-trifluoromethyl nicotinyl chloride.

(4-fluoro-3-ethylbenzoyl chloride was prepared in 5 steps from 3-bromo-4-fluorobenzoic acid. 3-bromo-4-fluorobenzoic acid was converted to methyl 3-bromo-4-fluorobenzoate by treatment with trimethylsilyl diazomethane (1.5 equivalents) in benzene/methanol (4/1) at room temperature. Subsequent reaction with tributyl(vinyl) tin (1.2 equivalents) in DMF in the presence of catalytic dichlororbis(triphenylphosphine)palladium(II) (0.1 equivalents) at 80° C. under an argon atmosphere, followed by aqueous work up and standard chromatography (10% ethyl acetate/hexanes), yielded methyl 4-fluoro-3-vinylbenzoate. Hydrogenation of the vinyl group by treatment of this material with palladium on carbon (10% palladium on carbon, 10% by mass) in methanol under an hydrogen atmosphere then afforded methyl 3-ethyl-4-fluorobenzoate. This material was dissolved in methanol/tetrahydrofuran/water (2/1/1) then lithium hydroxide (5.0 equivalents) was added and reaction mixture stirred at room temperature for 2 hours. The mixture was concentrated, the residue acidified with a 1N HCl aqueous solution and extracted with ethyl acetate. The organic layer was washed with brine, dried over magnesium sulfate, filtered and concentrated to give 4-fluoro-3-ethylbenzoic acid. This material was directly converted to 4-fluoro-3-ethylbenzoyl chloride by treatment with thionyl chloride (2.2 equivalents) in dichloromethane at room temperature for 2 hours followed by removal of the volatiles in vaccuo). The rest of the procedures were followed as indicated in general procedure B to afford N-(4-chlorophenyl)-N-[(2S,4R)-1-(3-ethyl-4-fluorobenzoyl)-2-methyl-1,2,3,4-tetrahydroquinolin-4-yl]acetamide.

$^1$H-NMR (CDCl$_3$) δ: 1.03 (t, 3H), 1.15 (d, 3H), 1.22-1.26 (m, 1H), 2.03 (s, 3H), 2.24-2.32 (m, 1H), 2.42-2.58 (m, 2H), 4.70-4.82 (m, 1H), 5.61 (br s, 1H), 6.48 (d, 1H), 6.78 (t, 1H), 6.92 (t, 1H), 6.97-7.02 (m, 1H), 7.07 (d, 1H), 7.13-7.30 (m, 4H), 7.38 (d, 2H).

MS m/z: 465 (M+1).

(2S,4R)-N-(4-Chloro-phenyl)-N-{1-[4-(3-imidazol-1-yl-3-methyl-butoxy)-benzoyl]-2-methyl-1,2,3,4-tetrahydro-quinolin-4-yl}-acetamide (H-51)

3-Imidazol-1-yl-3-methyl-butan-1-ol was dissolved in benzene at room temperature with PPh$_3$ (0.088 g, 0.33 mmol) added (2S,4R)-N-(4-chloro-phenyl)-N-[1-(4-hydroxy-benzoyl)-2-methyl-1,2,3,4-tetrahydro-quinolin-4-yl]-acetamide (0.133 g, 0.30 mmol) and stirred for 5 min. DEAD (0.058 g, 0.33 mmol) was added and the reaction was stirred for 18 h at room temperature. The reaction was concentrated and purified by silica gel chromatography (4% MeOH/96% CH$_2$Cl$_2$ to 5% MeOH/95% CH$_2$Cl$_2$ to 6% MeOH/94% CH$_2$Cl$_2$) to afford the product in 46% yield Preparation of 3-Imidazol-1-yl-3-methyl-butan-1-ol 3-Imidazol-1-yl-3-methyl-butan-1-ol was prepared from ethyl-2,2-dimethylacrylate. Ethyl-2,2-dimethylacrylate (2.04 mL, 14.7 mmol) and imidazole (0.500 g, 7.34 mmol) were mixed and heated to 90° C. for 48 h and cooled to room temperature. The reaction mixture was diluted with CH$_2$Cl$_2$ and water. The aqueous layer was extracted 3×CH$_2$Cl$_2$ and dried over MgSO$_4$, filtered and concentrated down. The crude residue was purified by silica gel chromatography (10% MeOH/90% CH$_2$Cl$_2$) to give 35% yield of 3-imidazol-1-yl-3-methyl-butyric acid ethyl ester. The ester was reduced to the alcohol (US Patent application WO03047586). 3-imidazol-1-yl-3-methyl-butyric acid ethyl ester (0.500 g, 2.5 mmol) was dissolved in THF (40 mL) and cooled to 0° C. and 2.55 mL of LiAlH$_4$ (1.0 M in ether) was added dropwise over 15 min. The reaction was allowed to warm up to room temperature over 1 h and quenched with dropwise addition of a sat'd Na$_2$SO$_4$ solution. The resulting slurry was dried over solid Na$_2$SO$_4$ and diluted with ethyl acetate, filtered through a plug of Celite and concentrated down.

$^1$H-NMR (CDCl$_3$) δ: 1.09 (d, 3H), 1.11 (m, 1H), 1.56 (s, 6H), 1.97 (s, 3H), 2.08 (m, 1H), 2.16 (t, 2H), 3.67 (m, 2H), 4.67 (sextet, 1H), 5.51 (bs, 1H), 6.49 (d, 1H), 6.87 (t, 1H), 6.96-7.61 (m, 10H), 7.64 (m, 1H).

MS m/z: 568 (M+1).

(2S,4R)-N-(4-Chloro-phenyl)-N-{1-[4-(1-ethyl-piperidin-4-ylmethoxy)-benzoyl]-2-methyl-1,2,3,4-tetrahydro-quinolin-4-yl}-acetamide (H-52)

(2S,4R)-N-4-(4-{4-[Acetyl-(4-chloro-phenyl)-amino]-2-methyl-3,4-dihydro-2H-quinoline-1-carbonyl}-phenoxymethyl)-piperidine-1-carboxylic acid benzyl ester (0.25 g) was converted to the piperdine by hydrogenation with Pd/C (0.075 g) under hydrogen in ethanol (17 ml). The reaction mixture was filtered through Celite and concentrated down to give (2S,4R)-N-(4-Chloro-phenyl)-N-{2-methyl-1-[4-(piperidin-4-ylmethoxy)-benzoyl]-1,2,3,4-tetrahydro-quinolin-4-yl}-acetamide (0.17 g, 85%).

The piperdine was reacted with acetaldehyde, Na(OAc)$_3$BH in dichloromethane at room temperature overnight. Then washed with 1N NaOH, dried over MgSO$_4$, filtered and concentrated down. The crude residue was purified by silica gel chromatography (10% methanol/90% dichloromethane) to afford the product (55%).

$^1$H-NMR (CDCl$_3$) δ: 0.98-1.18 (m, 7H), 1.37 (m, 2H), 1.72-1.93 (m, 5H), 2.04 (s, 3H), 2.27 (m, 1H), 2.37 (q, 2H), 2.95 (m, 2H), 3.73 (d, 2H), 4.72 (sextet, 1H), 5.58 (bs, 1H), 6.52 (d, 1H), 6.67 (d, 2H), 6.86 (t, 1H), 7.08-7.35 (m, 6H), 7.38 (d, 2H).

MS m/z: 560 (M+1)

(2S,4R)-4-[(4-{4-[Acetyl-(4-chloro-phenyl)-amino]-2-methyl-3,4-dihydro-2H-quinoline-1-carbonyl}-phenyl)-methyl-amino]-butyramide (H-53)

(2S,4R)-4-[(4-{4-[Acetyl-(4-chloro-phenyl)-amino]-2-methyl-3,4-dihydro-2H-quinoline-1-carbonyl}-phenyl)-methyl-amino]-butyramide was made from (2S,4R)-4-(4-{4-[Acetyl-(4-chloro-phenyl)-amino]-2-methyl-3,4-dihydro-2H-quinoline-1-carbonyl}-phenyl)-piperazine-1-carboxylic acid. The acid (0.050 g, 0.096 mmol) was dissolved in DMF (1 mL) at room temperature and HOBt (0.020 g, 0.144 mmol), HATU (0.055 g, 0.144 mol), and diisopropylethylamine (0.067 mL, 0.384 mmol) was added followed by ammonium chloride (0.011 g, 0.192 mmol) and stirred at room temperature for 16 h. The reaction was diluted with ethyl acetate, washed with 1N NaOH, 1N HCl and brine. The organics were dried over MgSO$_4$, filtered and concentrated down. The crude residue was purified HPLC purification.

$^1$H-NMR (CDCl$_3$) δ: 1.10 (d, 3H), 1.18 (m, 1H), 1.80 (t, 2H), 2.00 (s, 3H), 2.13 (t, 2H), 2.27 (m, 1H), 2.85 (s, 3H), 3.27 (t, 2H), 4.70 (m, 1H), 5.65 (br, 2H), 5.85 (brs, 1H), 6.39 (d, 2H), 6.59 (d, 1H), 6.93 (t, 1H), 7.03-7.34 (m, 6H), 7.36 (d, 2H).

MS m/z: 533 (M+1).

(2S,4R)-4-(4-{4-[Acetyl-(4-chloro-phenyl)-amino]-2-methyl-3,4-dihydro-2H-quinoline-1-carbonyl}-phenoxy)-3-(S)-hydroxy-butyric acid (H-54)

(2S,4R)-N-(4-chloro-phenyl)-N-[1-(4-hydroxy-benzoyl)-2-methyl-1,2,3,4-tetrahydro-quinolin-4-yl]-acetamide (200 mg, 0.46 mmol) was dissolved in DMF (5 mL) at room temperature. Cs$_2$CO$_3$ (374 mg, 1.15 mmol) was added followed by 4-bromo-3-(S)-(tert-butyl-dimethyl-silanyloxy)-butyric acid methyl ester (214 mg, 0.69 mmol) and the reaction was stirred at room temperature for 18 hours. The mixture was concentrated under reduced pressure and dissolved in ethyl acetate (15 mL). The reaction mixture was washed with sat. aq. NaHCO$_3$ (15 mL), water (15 mL) and brine (15 mL). The organic phase was dried over MgSO$_4$, filtered, and concentrated under reduced pressure. The crude residue was purified by silica gel chromatography (5/95 ethyl acetate/hexane-50/50 ethyl acetate/hexane gradient) to afford slightly yellow solid product (74 mg, 37%).

(2S,4R)-4-(4-{4-[Acetyl-(4-chloro-phenyl)-amino]-2-methyl-3,4-dihydro-2H-quinoline-carbonyl}-phenoxy)-3-(S)-(tert-butyl-dimethyl-silanyloxy)-butyric acid methyl ester (99 mg, 0.148 mmol) was dissolved in THF (4 mL). To this solution was added tetrabutyl ammonium fluoride (1.0 M in THF, 1 mL). The reaction mixture was stirred at room temperature for 3 hours. The mixture was concentrated under reduced pressure and dissolved in DCM (15 mL). The reaction mixture was washed with sat. aq. NaHCO₃ (15 mL), water (15 mL) and brine (15 mL). The organic phase was dried over MgSO₄, filtered, and concentrated under reduced pressure. The residue was purified by silica gel chromatography (2/98 methanol/dichloromethane-10/90 methanol/dichloromethane gradient) to afford white solid product (41 mg, 51%).

(2S,4R)-4-(4-{4-[Acetyl-(4-chloro-phenyl)-amino]-2-methyl-3,4-dihydro-2H-quinoline-carbonyl}-phenoxy)-3-(S)-hydroxy-butyric acid methyl ester (41.2 mg, 0.075 mmol) was dissolved in MeOH/THF (2:1, 3 mL). To this solution was added 2N LiOH (2 mL). The reaction was stirred at room temperature for 18 hours. The reaction mixture was concentrated in vacuo to remove MeOH and THF. Then 6N HCl aqueous solution was added to acidify the reaction mixture to pH 2-3. The reaction mixture was extracted with DCM (5 mL×3). The extract was washed with brine (15 mL) and dried over MgSO₄, filtered and concentrated down. The crude residue was purified by preparatory HPLC to afford the product (35 mg, 87%).

¹H-NMR (CDCl₃, 300MHz) δ: 1.05-1.14 (m, 4H), 2.0 (s, 3H), 2.25-2.27 (m, 1H), 2.60-2.62 (m, 2H), 3.87-3.88 (m, 2H), 4.28-4.34 (m, 1H), 4.70-4.77 (m, 1H), 5.58-5.62 (broad, 1H), 6.49-6.93 (m, 4H), 7.12-7.39 (m, 8H).

MS m/z: 538 (M+1).

(2S,4R)-N-3-(4-{4-[Acetyl-(4-chloro-phenyl)-amino]-2-methyl-3,4-dihydro-2H-quinoline-1-carbonyl}-phenoxy)-2,2-dimethyl-propionamide (H-55)

(2S,4R)-N-3-(4-{4-[Acetyl-(4-chloro-phenyl)-amino]-2-methyl-3,4-dihydro-2H-quinoline-1-carbonyl}-phenoxy)-2,2-dimethyl-propionamide was prepared from (2S,4R)-N-3-(4-{4-[Acetyl-(4-chloro-phenyl)-amino]-2-methyl-3,4-dihydro-2H-quinoline-1-carbonyl}-phenoxy)-2,2-dimethyl-propionic acid by coupling NH₄Cl, HATU, DIEA, HOBt in DMF at room temperature to yield (2S,4R)-N-4-(4-{4-[Acetyl-(4-chloro-phenyl)-amino]-2-methyl-3,4-dihydro-2H-quinoline-1-carbonyl}-phenoxy)-butyramide. The reaction mixture was concentrated down and partitioned between ethyl acetate and water, then extracted three times with ethyl acetate, dried over magnesium sulfate, filtered and concentrated down. The residue was purified by silica gel chromatography (10% methanol/90% dichloromethane) to afford the product in a 88% yield.

¹H-NMR (CDCl₃) δ: 1.13 (d, 3H), 1.15 (t, 1H), 1.31 (s, 6H), 1.71 (bs, 1H), 2.03 (s, 3H), 2.27 (m, 1H), 3.83 (q, 2H), 4.72 (sextet, 1H), 5.58 (bs, 1H), 6.17 (br, 1H), 6.52 (d, 1H), 6.69 (d, 2H), 6.83 (t, 2H), 7.08-7.35 (m, 6H), 7.38 (d, 2H).

MS m/z: 534 (M+1)

(2S,4R)-N-(1-{4-[2-(1-Acetyl-piperidin-4-yl)-ethoxyl-benzoyl]-2-methyl-1,2,3,4-tetrahydro-quinolin-4-yl}-N-(4-chloro-phenyl)-acetamide (H-56)

(2S,4R)-N-(4-Chloro-phenyl)-N-{2-methyl-1-[4-(2-piperidin-4-yl-ethoxy)-benzoyl]-1,2,3,4-tetrahydro-quinolin-4-yl}-acetamide (0.085 g, 0.15 mmol) was dissolved in dichloromethane at room temperature and DIEA (0.1 g, 0.56 mmol) was added. Acetyl chloride (0.2 mL, 2.8 mmol) was added and the reaction was stirred at room temperature for 4 hours. The reaction mixture was concentrated in vacuo. The crude residue was purified by silica gel chromatography (10% methanol/90% dichloromethane) to afford the product (0.068 g, 75%).

¹H-NMR (CDCl₃) δ: 1.15 (d, 3H), 1.15 (t, 1H), 1.21 (m, 2H), 1.58-1.77 (m, 5H), 1.98 (s, 3H), 2.04 (s, 3H), 2.27 (m, 1H), 2.51 (t, 1H), 2.98 (t, 1H), 3.72 (m, 1H), 3.93 (t, 2H), 4.51 (m, 1H), 4.72 (sextet, 1H), 5.58 (bs, 1H), 6.52 (d, 1H), 6.69 (d, 2H), 6.83 (t, 2H), 7.08-7.35 (m, 6H), 7.38 (d, 2H).

MS m/z: 588 (M+1).

4-(5-{[(2S,4R)-4-[acetyl(4-chlorophenyl)amino]-2-methyl-3,4-dihydro-quinolin-1(2H)-yl]carbonyl}-2-fluorophenoxy)-2,2-dimethylbutanoic acid (H-57)

To the solution of Methyl 4-(5-{[(2S,4R)-4-[acetyl(4-chlorophenyl)amino]-2-methyl-3,4-dihydroquinolin-1(2H)-yl]carbonyl}-2-fluorophenoxy)-2,2-dimethylbutanoate in MeOH/THF (1 mL/1 mL) was added excessive LiOH (1N aqueous solution). The reaction mixture was stirred at r.t. for overnight. The reaction was quenched by adding 6N HCl to PH 2. The mixture was concentrated under reduced pressure to remove MeOH and THF. DCM was added. The reaction mixture was washed with brine. The organic phase was dried over magnesium sulfate, filtered, and concentrated under reduced pressure. The crude residue was purified by preparative HPLC to afford pure product.

¹H-NMR (CDCl₃, 300MHz) δ: 0.90-0.94 (m, 2H), 1.12-1.14 (d, 3H), 1.21-1.24 (m, 3H), 1.60-1.72 (m, 2H), 1.95-2.03 (m, 1H), 2.09 (s, 3H), 2.20-2.27 (m, 1H), 3.45-3.59 (m, 1H), 3.60-3.75 (m, 1H), 4.65-4.75 (m, 1H), 5.72-5.80 (m, 1H), 6.31-6.34 (m, 1H), 6.45-6.47 (m, 1H), 6.90-6.96 (m, 1H), 7.04-7.08 (m, 1H), 7.15-7.20 (m, 3H), 7.24-7.36 (m, 6H).

MS m/z: 567 (M+1).

N-(4-chlorophenyl)-N-((2S,4R)-2-methyl-1-{4-[(methylsulfonyl)amino]benzoyl}-1,2,3,4-tetrahydroquinolin-4-yl)acetamide (H-58)

To a solution of N-[(2S,4R)-1-(4-aminobenzoyl)-2-methyl-1,2,3,4-tetrahydroquinolin-4-yl]-N-(4-chlorophenyl) acetamide (208 mg, 0.48 mmol) in methylene chloride (4.0 mL) at 0° C. was added methanesulphonic anhydride (175 mg, 1.01 mmol) and N,N-diisopropylethylamine (0.460 mL, 2.63 mmol). The reaction was warmed to room temperature and stirred for 4 days. (Analysis by LCMS indicated a mixture of starting aniline, mono-sulfonamide, and bis-sulfonamide). Additional methanesulphonic anhydride (170 mg, 0.98 mmol) was added and the reaction was stirred an additional 2 days at room temperature. The resulting reaction was diluted with dichloromethane (25 mL) and poured into a 1:1 mixture of water and brine (25 mL). The organic layer was separated, dried over anhydrous magnesium sulfate, filtered, and concentrated under reduced pressure to afford crude N-((2S,4R)-1-{4-[bis(methylsulfonyl)amino]benzoyl}-2-methyl-1,2,3,4-tetrahydroquinolin-4-yl)-N-(4-chlorophenyl)acetamide (273 mg) as a yellow foam. The crude material was used directly in subsequent reactions.

To a solution of N-((2S,4R)-1-{4-[bis(methylsulfonyl)amino]benzoyl}-2-methyl-1,2,3,4-tetrahydroquinolin-4-yl)-N-(4-chlorophenyl)acetamide (259 mg, 0.44 mmol) in tetrahydrofuran (5.0 mL) at room temperature was added 1.0 M sodium hydroxide (0.880 mL, 0.88 mmol). The reaction was stirred at room temperature for 2 days. The resulting reaction mixture was poured into a 1:1 mixture of water and saturated sodium bicarbonate (25 mL) and extracted with ethyl acetate (1×25 mL). The aqueous layer was neutralized via addition of 1N HCl to pH ~8 and extracted with ethyl acetate (2×25 mL). The combined organic layers were washed once with brine, dried over anhydrous magnesium sulfate, filtered, and concentrated under reduced pressure to afford N-(4-chlorophenyl)-N-((2S,4R)-2-methyl-1-{4-[(methylsulfonyl)amino]benzoyl}-1,2,3,4-tetrahydroquinolin-4-yl)acetamide (190 mg, 76%) as a light-yellow, foamy solid.

$^1$H-NMR (CDCl$_3$) δ: 1.14 (d, 3H), 2.04 (s, 3H), 2.05-2.12 (m, 1H), 2.20-2.35 (m, 1H), 2.95 (s, 3H), 4.65-4.80 (m, 1H), 5.44-5.66 (m, 1H), 6.50 (d, 1H), 6.88-7.01 (m, 3H), 7.07-7.32 (m, 6H), 7.35-7.46 (m, 3H).

MS m/z: 512 (M+1).

(2S,4R)-1-Methyl-pyrrolidine-2-carboxylic acid [3-(4-{4-[acetyl(4-chloro-phenyl)-amino]-2-methyl-3,4-dihydro-2H-quinoline-1-carbonyl}-phenoxy)-propyl]-amide (H-59)

(2S,4R)-N-{1-[4-(3-Amino-propoxy)-benzoyl]-2-methyl-1,2,3,4-tetrahydro-quinolin-4-yl}-N-(4-chloro-phenyl)-acetamide (100 mg, 0.204 mmol) was dissolved in methylene chloride (2 mL) and pyridine (2 mL). N-methyl proline (33 mg, 0.255 mmol) and EDC (63 mg, 0.255 mmol) were added and the reaction was stirred for 1 hour. The mixture was partitioned between methylene chloride and water; the methylene chloride layer was dried over MgSO$_4$, filtered and concentrated. The crude residue was purified by silica gel chromatography (ethyl acetate) to afford the product.

$^1$H-NMR (CDCl$_3$) δ: 1.1 (s, 3H), 1.2 (m, 1H), 1.8 (m, 2H), 2.0 (m, 2H), 2.0 (s, 3H), 2.2 (m, 2H), 2.3 (m, 1H), 2.4 (s, 3H), 2.6 (m, 1H), 3.2 (m, 2H), 3.4 (q, 2H), 4.0 (t, 2H), 4.1 (m, 1H), 4.8 (m 1H), 5.6 (bs, 1H), 6.5 (d, 1H), 6.6 (d, 2H), 6.9 (t, 1H), 7.2 (m, 6H), 7.4 (d, 2H).

MS m/z: 603 (M+1).

4-(4-{[(2R,4S)-4-[acetyl(4-chlorophenyl)amino]-2-methyl-3,4-dihydroquinolin-1(2H)-yl]carbonyl}phenoxy)-2,2-dimethylbutanoic acid (H-60)

4-(4-{[(2R,4S)-4-[acetyl(4-chlorophenyl)amino]-2-methyl-3,4-dihydroquinolin-1(2H)-yl]carbonyl}phenoxy)-2,2-dimethylbutanoic acid was prepared following the procedure to prepare 4-(4-{[(2S,4R)-4-[acetyl(4-chlorophenyl)amino]-2-methyl-3,4-dihydro-quinolin-1(2H)-yl]carbonyl}phenoxy)-2,2-dimethylbutanoic acid, substituting N-(4-chlorophenyl)-N-[(2R,4S)-1-(4-methoxybenzoyl)-2-methyl-1,2,3,4-tetrahydro-quinolin-4-yl]acetamide for N-(4-chlorophenyl)-N-[(2S,4R)-1-(4-methoxybenzoyl)-2-methyl-1,2,3,4-tetrahydro-quinolin-4-yl]acetamide.

$^1$H-NMR (CDCl$_3$) δ: 1.14 (d, 3H), 1.15 (t, 1H), 1.25 (s, 6H), 2.02 (t, 2H), 2.05 (m, 2H), 2.27 (m, 1H), 3.96 (t, 2H), 4.72 (sextet, 1H), 5.52 (br, 2H), 5.58 (bs, 1H), 6.52 (d, 1H), 6.67 (d, 2H), 6.86 (t, 1H), 7.08-7.35 (m, 6H), 7.38 (d, 2H).

MS m/z: 549 (M+1).

(2S,4R)-N-(1-{4-[3-(Acetyl-ethyl-amino)-propoxy]-benzoyl}-2-methyl-1,2,3,4-tetrahydroquinolin-4-yl)-N-(4-chloro-phenyl)-acetamide (H-61)

(2S,4R)-N-{1-[4-(3-Acetylamino-propoxy)-benzoyl]-2-methyl-1,2,3,4-tetrahydro-quinolin-4-yl}-N-(4-chloro-phenyl)-acetamide (30 mg, 0.056 mmol) was dissolved in DMF (1 mL). Sodium hydride (20 mg, 0.833 mmol) and iodoethane (10 drops via pipet) were added and the reaction was stirred at room temperature over night. The mixture was partitioned between methylene chloride and water; the methylene chloride layer was dried over MgSO$_4$, filtered and concentrated. The crude residue was purified by preparatory HPLC.

$^1$H-NMR (CDCl$_3$) δ: 1.1 (m, 7H), 2.0 (m, 8H), 2.3 (m, 1H), 3.3 (q, 1H), 3.4 (q, 1H), 3.4 (t, 2H), 3.9 (t, 2H), 4.7 (m, 1H), 5.6 (bs, 1H), 6.5 (d, 1H), 6.7 (d, 2H), 6.9 (t, 1H), 7.2 (m, 6H), 7.4 (d, 2H).

MS m/z: 562 (M+1).

N-(4-chlorophenyl)-N-{(2S,4R)-1-[4-(4-hydroxy-4-methylpentyl)benzoyl]-2-methyl-1,2,3,4-tetrahydroquinolin-4-yl}acetamide (H-62)

N-(4-chlorophenyl)-N-{(2S,4R)-2-methyl-1-[4-(4-oxopentyl)benzoyl]-1,2,3,4-tetrahydroquinolin-4-yl}acetamide was prepared following general procedure H, substituting 4-(4-oxopentyl)benzoyl chloride for 6-trifluoromethyl nicotinyl chloride to afford N-(4-chlorophenyl)-N-{(2S,4R)-2-methyl-1-[4-(4-oxopentyl)benzoyl]-1,2,3,4-tetrahydroquinolin-4-yl}acetamide $^1$H-NMR (CDCl$_3$): 1.14 (d, 4H), 1.87 (q, 2H), 2.01 (s, 3H), 2.04 (m, 1H), 2.06 (s, 3H), 2.32 (t, 2H), 2.52 (t, 2H), 4.74 (q, 1H), 5.60 (br, 1H), 6.47 (d, 1H), 6.96 (m, 3H), 7.20 (m, 8H). MS m/z: 503 (M+1). (4-(4-oxopentyl)benzoyl chloride was prepared in six steps from pent-4-en-2-ol. (as follows: Pent-4-en-2-ol (4.0 g, 46.44 mmol) was dissolved in CH$_2$Cl$_2$ (30 mL). TBDMSCl (13.93 g, 92.88 mmol) and imidazole (6.31 g, 92.88 mmol) were added at 0° C. The reaction mixture was stirred at RT for overnight. The organic phase was washed with sat. NaHCO$_3$ and brine, dried over MgSO$_4$ and concentrated. The residue was purified by column chromatography (hexane) to give 5.14 g of desired product as a colorless oil (55% yield). $^1$H-NMR (CDCl$_3$) δ: 0.02 (s, 6H), 0.89 (s, 9H), 1.11 (d, 3H), 2.14 (q, 2H), 3.80 (q, 1H), 5.03 (m, 2H), 5.80 (m, 1H). MS m/z: 200 (M+1)

To a solution of ethyl 4-iodobenzoate (4.15 g, 15.03 mmol) in DMF (20 mL), was added tert-butyl-(dimethyl)[(1-methylbut-3-en-1-yl)oxy]silane (3.0 g, 15.03 mmol) and Pd(OAc)$_2$ (342 mg, 1.50 mmol), triethyl amine (2 mL, 30.06 mmol) and DPPP (1.05 g, 2.55 mmol) under Argon. The mixture was stirred at 80° C. for overnight. After concentrating, the residue was dissolved in EtOAc (20 mL). The organic phase was washed with Sat. NaHCO$_3$ and brine, dried over MgSO$_4$ and concentrated. The residue was purified by column chromatography (Hexane:EtOAc, 20:1) to give 3.15 g of desired product as a yellow oil (60% yield). $^1$H-NMR (CDCl$_3$) δ: 0.02 (s, 6H), 0.86 (s, 9H), 1.16 (d, 3H), 1.36 (t, 3H), 2.34 (q, 2H), 3.89 (q, 1H), 4.34 (q, 2H), 6.38 (m, 2H), 7.36 (d, 2H), 7.95 (d, 2H).

MS m/z: 348 (M+1).

To a solution of ethyl ethyl 4-(E-4-{[tert-butyl(dimethyl)silyl]oxy}pent-1-en-1-yl)benzoate (3.15 g, 9.07 mmol) in THF (10 mL), was added TBAF (18.15 mL, 18.15 mmol, 1M solution in THF) at RT. The reaction mixture was stirred at RT for 2 h. The organic phase was washed with Sat. NaHCO$_3$ and brine, dried over MgSO$_4$ and concentrated. The residue was purified by column chromatography (hexane: EtOAc, 4:1) to give 1.25 g of desired product as a yellow oil (58% yield). $^1$H-NMR (CDCl$_3$) δ: 1.19 (d, 3H), 1.25 (t, 3H), 2.34 (m, 2H), 3.91 (m, 1H), 4.34 (q, 2H), 6.38 (m, 2H), 7.36 (d, 2H), 7.93 (d, 2H).

MS m/z: 237 (M+1).

A solution of ethyl 4-[(1E)-4-hydroxypent-1-en-1-yl]benzoate (1.25 g, 5.29 mmol) and Pd/C (10% weight, 0.125 g) in EtOH (20 mL) was degassed and bubbled through H$_2$. The mixture was stirred at RT for overnight. After filtering through celite, the organic solution was concentrated to give a colorless oil which was used in the next step without purification (1.1 g, 88% yield). $^1$H-NMR (CDCl$_3$) δ: 1.15 (d, 3H), 1.35 (t, 3H), 2.70 (m, 2H), 2.66 (t, 2H), 3.80 (quan., 1H), 4.33 (q, 2H), 7.23 (d, 2H), 7.94 (d, 2H).

MS m/z: 239 (M+1).

To a solution of ethyl 4-(4-hydroxypentyl)benzoate (1.1 g, 4.62 mmol) and triethyl amine (1.9 mL, 13.86 mmol) in CH$_2$Cl$_2$ (20 mL), was added sulfur trioxide pyridine complex (2.2 g, 13.86 mmol) in DMSO (2 mL) at 0° C. The mixture was stirred at 0° C. for 2 h. The reaction mixture was washed with 1N HCl solution, dried over MgSO$_4$ and concentrated. The residue was purified by column chromatography (Hexane:EtOAc, 3:1) to give 0.5 g of desired product as a colorless oil (50% yield). $^1$H-NMR (CDCl$_3$) δ: 1.36 (t, 3H), 1.86 (q, 2H), 2.09 (s, 3H), 2.40 (t, 2H), 2.67 (t, 2H), 4.32 (q, 2H), 7.23 (d, 2H), 7.95 (d, 2H). MS m/z: 237 (M+1).

To a solution of ethyl 4-(4-oxopentyl)benzoate (500 mg, 2.11 mmol) in THF/EtOH/H$_2$O (5 mL, 10:1:1), was added NaOH (254 mg, 6.33 mmol). The mixture was reflux for overnight. After acidification, the mixture was extracted with EtOAc. The combined organic phases were dried over MgSO$_4$ and concentrated. The residue was purified by column chromatography (EtOAc) to give 0.31 g of desired product as a white solid (70% yield). $^1$H-NMR (CDCl$_3$) 1.87 (q, 2H), 2.10 (s, 3H), 2.50 (t, 2H), 2.70 (t, 2H), 7.24 (d, 2H), 8.01 (d, 2H). MS m/z: 207 (M−1, ES).

To a solution of N-(4-chlorophenyl)-N-((2S,4R)-2-methyl-1-(4-(4-oxopentyl)benzoyl)-1,2,3,4-tetrahydroquinolin-4-yl)acetamide (40 mg, 0.079 mmol) in THF (2 mL), was added MeMgBr (68 uL, 0.095 mmol, 1.4 M solution in THF) at 0° C. The mixture was stirred at 0° C. for 2 h. After quenching with sat. NH$_4$Cl solution, the mixture was extracted with EtOAc. The combined organic phases were dried over MgSO$_4$ and concentrated. The residue was purified by column chromatography (EtOAc) to give 16 mg of desired product as a white solid (40% yield).

$^1$H-NMR (CDCl$_3$): 1.14 (m, 10H), 1.37 (m, 2H), 1.61 (m, 2H), 2.01 (s, 3H), 2.22 (m, 1H), 2.49 (t, 2H), 4.74 (q, 1H), 5.60 (br, 1H), 6.49 (d, 1H), 6.97 (m, 3H), 7.20 (m, 8H).

MS m/z: 519 (M+1).

N-(4-chlorophenyl)-N-[(2S,4R)-1-(3,5-difluoro-4-hydroxybenzoyl)-2-methyl-1,2,3,4-tetrahydroquinolin-4-yl]acetamide (H-63)

N-(4-chlorophenyl)-N-[(2S,4R)-1-(3,5-difluoro-4-methoxybenzoyl)-2-methyl-1,2,3,4-tetrahydroquinolin-4-yl]acetamide (200 mg, 0.41 mmol) was dissolved in dichloromethane and a solution of BBr$_3$ (1.0 M in dichloromethane, 3.0 mL) was added; the reaction mixture was stirred at room temperature for until no starting material remained. The reaction mixture was washed with sat. NaHCO$_3$ and brine carefully. The organic layer was dried over MgSO$_4$, filtered and concentrated. The residue was purified by flash chromatography using Hexanes-EtOAc system to give N-(4-chlorophenyl)-N-[(2S,4R)-1-(3,5-difluoro-4-hydroxybenzoyl)-2-methyl-1,2,3,4-tetrahydroquinolin-4-yl]acetamide (152 mg, 78%).

$^1$H-NMR (CDCl$_3$) δ: 1.12 (d, 3H), 1.24 (m, 2H), 2.07 (s, 3H), 2.25 (b, 1H), 4.70 (m, 1H), 6.52 (d, 1H), 6.78 (d, 2H), 7.18 (t, 1H), 7.20-7.40 (m, 6H).

MS m/z: 471 (M+1)

(2S,4R)-[3-(4-{4-[Acetyl-(4-chloro-phenyl)-amino]-2-methyl-3,4-dihydro-2H-quinoline-1-carbonyl}-phenoxy)-propyl]-carbamic acid methyl ester (H-64)

(2S,4R)-N-{1-[4-(3-Amino-propoxy)-benzoyl]-2-methyl-1,2,3,4-tetrahydro-quinolin-4-yl}-N-(4-chloro-phenyl)-acetamide (150 mg, 0.30 mmol) was dissolved in DCM (1 mL). To this solution was added TEA (36.4 mg, 0.36 mmol) followed by methyl chloroformate (34 mg, 0.36 mmol). The reaction mixture was stirred at room temperature for 18 hours. The mixture was concentrated under reduced pressure and dissolved in DCM (15 mL). The reaction mixture was washed with sat. aq. NaHCO$_3$ (15 mL), water (15 mL) and brine (15 mL). The organic phase was dried over MgSO$_4$, filtered, and concentrated under reduced pressure. The residue was purified by silica gel chromatography (5/95 ethyl acetate/hexane-50/50 ethyl acetate/hexane gradient) to afford white solid product (71 mg, 52%).

$^1$H-NMR (CDCl$_3$, 300MHz) δ: 0.68-0.88 (m, 2H), 1.00-1.05 (m, 4H), 1.23 (s, 3H), 1.61-1.64 (broad, 1H) 2.02 (s, 3H), 2.22-2.33 (m, 1H), 3.31-3.37 (m, 1H), 3.62 (s, 3H), 3.93-3.97 (m, 1H), 4.73-4.75 (m, 1H) 5.28-5.31 (broad, 1H), 6.50-6.93 (m, 4H), 7.12-7.39 (m, 8H).

MS m/z: 551 (M+1).

Methyl 5-{[(2S,4R)-4-[acetyl(4-chlorophenyl)amino]-2-methyl-3,4-dihydroquinolin-1(2H)-yl]carbonyl}thiophene-2-carboxylate (H-65)

Methyl 5-{[(2S,4R)-4-[acetyl(4-chlorophenyl)amino]-2-methyl-3,4-dihydroquinolin-1(2H)-yl]carbonyl}thiophene-2-carboxylate was prepared following general procedure H, substituting methyl 5-(chlorocarbonyl)thiophene-2-carboxylate for 6-trifluoromethyl nicotinyl chloride. (methyl 5-(chlorocarbonyl)thiophene-2-carboxylate was prepared in one step from thiophene-2,5-dicarboxylic acid monomethyl ester. Treatment of this carboxylic acid with oxalyl chloride and catalytic DMF afforded methyl 5-(chlorocarbonyl)thiophene-2-carboxylate in decent yield). The rest of the procedures were followed as indicated in general procedure H to afford methyl 5-{[(2S,4R)-4-[acetyl(4-chlorophenyl)amino]-2-methyl-3,4-dihydroquinolin-1(2H)-yl]carbonyl}thiophene-2-carboxylate.

$^1$H-NMR (CDCl$_3$) δ: 1.10 (d, 3H), 2.05 (s, 3H), 2.20 (m, 1H), 3.80 (s, 3H), 4.65 (m, 1H), 5.50 (m, 1H), 6.45 (d, 1H), 6.80 (d, 1H), 7.00 (t, 1H), 7.15 (d, 2H), 7.20-7.40 (m, 5H).

MS m/z: 483 (M+1).

(2S,4R)-5-(4-{4-[Acetyl-(4-chloro-phenyl)-amino]-2-methyl-3,4-dihydro-2H-quinoline-1-carbonyl}-phenoxymethyl)-furan-2-carboxylic acid (H-66)

(2S,4R)-N-(4-Chloro-phenyl)-N-[1-(4-hydroxy-benzoyl)-2-methyl-1,2,3,4-tetrahydro-quinolin-4-yl]-acetamide (0.28 g, 0.64 mmol) was dissolved in DMF at room temperature and K$_2$CO$_3$ (0.125 g, 0.89 mmol) was added. 5-chloromethyl-furan-2-carboxylic acid methyl ester (0.130 g, 0.64 mmol) was added and the reaction was allowed to heat to 80° C. overnight. The reaction mixture was concentrated in vacuo. The residue was partitioned between ethyl acetate and water, then extracted three times with ethyl acetate, dried over MgSO₄, filtered and concentrated down. The crude residue was purified by silica gel chromatography to afford the product as colorless oil in 53% yield.

(2S,4R)-5-(4-{4-[Acetyl-(4-chloro-phenyl)-amino]-2-methyl-3,4-dihydro-2H-quinoline-1-carbonyl}-phenoxymethyl)-furan-2-carboxylic acid methyl ester (0.145 g, 0.25 mmol) was hydrolyzed to the acid by dissolving in tetrahydrofuran and ethanol and sodium hydroxide (1N) was added. The mixture was stirred at room temperature 4 hours. The mixture was cooled to rt, acidified to form a white precipitate. The solid was filtered to give (2S,4R)-5-(4-{4-[Acetyl-(4-chloro-phenyl)-amino]-2-methyl-3,4-dihydro-2H-quinoline-1-carbonyl}-phenoxymethyl)-furan-2-carboxylic acid as a white solid.

¹H-NMR (CDCl₃) δ: 1.12-1.19 (m, 4H), 2.03 (s, 3H), 2.23-2.29 (m, 1H), 4.73-4.75 (m, 1H), 4.95 (s, 2H), 5.59 (bs, 1H) 6.48-6.51 (m, 2H), 6.69 (d, 2H), 6.91 (t, 1H), 7.12-7.37 (m, 9H).

MS m/z: 559 (M+1).

(2S,4R)-N-5-(4-{4-[Acetyl-(4-chloro-phenyl)-amino]-2-methyl-3,4-dihydro-2H-quinoline-1-carbonyl}-phenoxy)-pentanoic acid amide (H-67)

(2S,4R)-N-(4-Chloro-phenyl)-N-[1-(4-hydroxy-benzoyl)-2-methyl-1,2,3,4-tetrahydro-quinolin-4-yl]-acetamide (0.146 g, 0.34 mmol) was dissolved in 5 ml DMF at room temperature and K₂CO₃ (0.186 g, 1.35 mmol) was added. 5-Bromo-pentanoic acid ethyl ester (0.14 g, 0.67 mmol) was added and the reaction was allowed to heat to 80° C. overnight. The reaction mixture was concentrated in vacuo. The residue was partitioned between ethyl acetate and water, then extracted three times with ethyl acetate, dried over MgSO₄, filtered and concentrated down. The crude residue was purified by silica gel chromatography (50% EtOAc/50% Hexane) to afford the (2S,4R)-N-5-(4-{4-[acetyl(4-chloro-phenyl)-amino]-2-methyl-3,4-dihydro-2H-quinoline-1-carbonyl}-phenoxy)-pentanoic acid ethyl ester (0.148 g, 78%).

The ester was hydrolyzed to the acid by dissolving in 10 ml tetrahydrofuran/methanol (1/1) and potassium hydroxide (0.182 g in 5 ml water) was added. The mixture was heated to 40° C. for 3 hours. The mixture was cooled to rt, acidified to form a white precipitate. The solid was filtered to give (2S,4R)-N-5-(4-{4-[acetyl(4-chloro-phenyl)-amino]-2-methyl-3,4-dihydro-2H-quinoline-1-carbonyl}-phenoxy)-pentanoic acid (0.128 g, 91%).

(2S,4R)-N-5-(4-{4-[acetyl(4-chloro-phenyl)-amino]-2-methyl-3,4-dihydro-2H-quinoline-1-carbonyl}-phenoxy)-pentanoic acid amide was prepared from the acid by coupling NI₂CI, HATU, DIEA, HOBt in DMF at room temperature to yield (2S,4R)-N-1-[2-(4-{4-[acetyl(4-chloro-phenyl)-amino]-2-methyl-3,4-dihydro-2H-quinoline-1-carbonyl}-phenoxy)-ethyl]-cyclobutanecarboxylic acid amide. The reaction mixture was concentrated down and partitioned between ethyl acetate and water, then extracted three times with ethyl acetate, dried over magnesium sulfate, filtered and concentrated down. The residue was purified by silica gel chromatography (10% methanol/90% dichloromethane) to afford pure product in 69% yield.

¹H-NMR (CDCl₃) δ: 1.13 (d, 3H), 1.15 (t, 1H), 1.68 (m, 4H), 1.95 (s, 3H), 2.16-2.37 (m, 3H), 3.86 (t, 2H), 4.72 (sextet, 1H), 5.58 (bs, 1H), 5.79 (bs, 1H), 6.52 (d, 1H), 6.67 (d, 2H), 6.86 (t, 1H), 7.08-7.35 (m, 6H), 7.38 (d, 2H).

MS m/z: 534 (M+1)

N-(4-chlorophenyl)-N-{(2S,4R)-2-methyl-1-[(2-methylpyrimidin-5-yl)carbonyl]-1,2,3,4-tetrahydroquinolin-4-yl}acetamide (H-68)

N-(4-chlorophenyl)-N-{(2S,4R)-2-methyl-1-[(2-methylpyrimidin-5-yl)carbonyl]-1,2,3,4-tetrahydroquinolin-4-yl}acetamide was prepared following general procedure H, substituting 2-methylpyrimidine-5-carbonyl chloride for 6-trifluoromethyl nicotinyl chloride. (2-methylpyrimidine-5-carbonyl chloride was prepared in four steps. To a solution of 3,3-dimethoxypropionate in ethylene glycol dimethyl ether was added sodium hydride at 0° C., then methyl formate. The reaction mixture was warmed up to 50° C. for 30 m. and then stirred at room temperature for 20 h. Anhydrous diethyl ether was added and the precipitate was filtered to give sodium 2-(dimethoxymethyl)-3-methoxy-3-oxoprop-1-en-1-olate.

To a solution of acetamide hydrochloride in dimethylformamide was added preformed sodium 2-(dimethoxymethyl)-3-methoxy-3-oxoprop-1-en-1-olate. Reaction mixture was heated to 100° C. for 1 h. to give methyl 2-methylpyrimidine-5-carboxylate. Hydrolysis of the ester with sodium hydroxide gave 2-methylpyrimidine-5-carboxylic acid. Subsequent treatment of this carboxylic acid with oxalyl chloride and catalytic DMF afforded 2-methylpyrimidine-5-carbonyl chloride in decent yield). The rest of the procedures were followed as indicated in general procedure H to afford N-(4-chlorophenyl)-N-{(2S,4R)-2-methyl-1-[(2-methylpyrimidin-5-yl)carbonyl]-1,2,3,4-tetrahydroquinolin-4-yl}acetamide.

¹H-NMR (CDCl₃) δ: 1.15 (d, 3H), 2.05 (s, 3H), 2.30 (m, 1H), 2.70 (s, 3H), 4.75 (m, 1H), 5.55 (m, 1H), 6.50 (d, 1H), 7.00 (t, 1H), 7.20-7.45 (m, 6H), 8.40 (s, 2H).

MS m/z: 435 (M+1).

N-(4-chlorophenyl)-N-{(2S,4R)-1-[4-(1,1-dioxidoisothiazolidin-2-yl)benzoyl]-2-methyl-1,2,3,4-tetrahydroquinolin-4-yl}acetamide (H-69)

To a solution of N-[(2S,4R)-1-(4-aminobenzoyl)-2-methyl-1,2,3,4-tetrahydroquinolin-4-yl]-N-(4-chlorophenyl)acetamide (321 mg, 0.74 mmol) in methylene chloride (7.0 mL) at 0° C. was added triethylamine (0.654 mL, 4.70 mmol) and 3-chloropropane-1-sulfonyl chloride (0.610 mL, 4.90 mmol). The reaction was warmed to room temperature and stirred for 2 days. To the resulting reaction was added potassium carbonate (496 mg, 3.59 mmol) and N,N-dimethylformamide (2.0 mL). The reaction was stirred overnight (14 h) at room temperature. Next, 1N sodium hydroxide (1.5 mL) was added and the reaction stirred an additional 3 days at room temperature. The resulting reaction was diluted with methylene chloride (15 mL) and poured into water (25 mL). The aqueous layer was extracted with methylene chloride (2×25 mL) and the combined organic layers were washed once with brine. The organics were then dried over anhydrous magnesium sulfate, filtered, and concentrated under reduced pressure. The crude residue was purified by silica gel chromatography (0-5% methanol/methylene chloride gradient) to afford 85% pure product (220 mg). A portion of this material (100 mg) was further purified via HPLC to afford pure N-(4-chlorophenyl)-N-{(2S,4R)-1-[4-(1,1-dioxidoisothiazolidin-2-yl)benzoyl]-2-methyl-1,2,3,4-tetrahydroquinolin-4-yl}acetamide (73 mg, 18%).

¹H-NMR (CDCl₃) δ: 1.10-1.14 (m, 1H), 1.14 (d, 3H), 2.02 (s, 3H), 2.22-2.34 (m, 1H), 2.45-2.56 (m, 2H), 3.30-3.40 (m, 2H), 3.66-3.76 (m, 2H), 4.67-4.82 (m, 1H), 5.54-5.64 (m, 1H), 6.52 (d, 1H), 6.93 (t, 1H), 6.98-7.05 (m, 2H), 7.12-7.31 (m, 5H), 7.34-7.42 (m, 3H).

MS m/z: 538 (M+1).

N-(4-chlorophenyl)-N-[(2S,4R)-1-(3,5-dichloro-4-ethylbenzoyl)-2-methyl-1,2,3,4-tetrahydroquinolin-4-yl]acetamide (H-70)

N-(4-chlorophenyl)-N-[(2S,4R)-1-(3,5-dichloro-4-ethylbenzoyl)-2-methyl-1,2,3,4-tetrahydroquinolin-4-yl]acetamide was prepared following general procedure H, substituting 4-ethyl-3,5-dichlorobenzoyl chloride for 6-trifluoromethyl nicotinyl chloride. (4-ethyl-3,5-dichlorobenzoyl chloride was prepared in two steps from 3,5-dichlorobenzoic acid. To a solution of 3,5-dichlorobenzoic acid in tetrahydrofuran was added lithium diisopropyl amide at −78° C. After the reaction mixture was stirred at −78° C. for 1 h. ethyl iodide was added and reaction mixture stirred at room temperature for 2 h. to give 4-ethyl-3,5-dichlorobenzoic acid. Subsequent treatment of this carboxylic acid with oxalyl chloride and catalytic DMF afforded 4-ethyl-3,5-dichlorobenzoyl chloride in decent yield). The rest of the procedures were followed as indicated in general procedure B to afford N-(4-chlorophenyl)-N-[(2S,4R)-1-(3,5-dichloro-4-ethylbenzoyl)-2-methyl-1,2,3,4-tetrahydroquinolin-4-yl]acetamide.

$^1$H-NMR (CDCl$_3$) δ: 1.00 (t, 3H), 1.10 (d, 3H), 2.05 (s, 3H), 2.20 (m, 1H), 2.80 (q, 2H), 4.65 (m, 1H), 5.50 (m, 1H), 6.50 (d, 1H), 6.95 (d, 1H), 7.00 (s, 2H), 7.2 (m, 3H), 7.25-7.40 (m, 3H).

MS m/z: 517 (M+1).

(2S,4R)-4-(4-{4-[Acetyl-(4-chloro-phenyl)-amino]-2-methyl-3,4-dihydro-2H-quinoline-1-carbonyl}-phenoxy)-butyric acid ethyl ester (H-71)

(2S,4R)-N-(4-Chloro-phenyl)-N-[1-(4-hydroxy-benzoyl)-2-methyl-1,2,3,4-tetrahydro-quinolin-4-yl]-acetamide was dissolved in DMF at room temperature and K$_2$CO$_3$ was added. Ethyl-4-bromobutyrate was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (50% EtOAc/50% Hexane) to afford the product.

$^1$H-NMR (CDCl$_3$) δ: 1.10 (d, 3H), 1.11 (m, 1H), 1.20 (t, 3H), 2.43 (t, 2H), 1.99 (s, 3H), 2.24 (m, 1H), 3.90 (t, 2H), 4.09 (q, 2H), 4.72 (sextet, 1H), 5.55 (bs, 1H), 6.49 (d, 1H)<6.62 (d, 2H), 6.90 (t, 1H), 7.11 (d, 2H), 7.16 (m, 1H), 7.18 (d, 2H), 7.26 (d, 1H), 7.34 (d, 2H).

MS m/z: 549 (M+1).

(2S,4R)-3-(4-{4-[Acetyl-(4-chloro-phenyl)-amino]-2-methyl-3,4-dihydro-2H-quinoline-1-carbonyl}-phenoxymethyl)-benzoic acid methyl ester (H-72)

(2S,4R)-N-(4-Chloro-phenyl)-N-[1-(4-hydroxy-benzoyl)-2-methyl-1,2,3,4-tetrahydro-quinolin-4-yl]-acetamide (150 mg, 0.35 mmol) was dissolved in DMF (5 mL) at room temperature. Cs$_2$CO$_3$ (283 mg, 0.87 mmol) was added followed by methyl 3-(bromomethyl)benzoate (119 mg, 0.52 mmol) and the reaction was stirred at room temperature for 18 hours. The mixture was concentrated under reduced pressure and dissolved in ethyl acetate (15 mL). The reaction mixture was washed with sat. aq. NaHCO$_3$ (15 mL), water (15 mL) and brine (15 mL). The organic phase was dried over MgSO$_4$, filtered, and concentrated under reduced pressure. The crude residue was purified by silica gel chromatography (5/95 ethyl acetate/hexane-50/50 ethyl acetate/hexane gradient) to afford slightly yellow solid product (111 mg, 54%).

$^1$H-NMR (CDCl$_3$, 300MHz) δ: 1.02-1.08 (d, 3H), 1.55 (s, 1H), 2.02 (s, 3H), 2.24-2.32 (m, 1H,), 3.88-3.91 (s, 3H), 4.70-4.78 (m, 1H), 5.02-5.05 (s, 2H), 5.58-5.61 (b, 1H), 6.51-6.53 (m, 3H), 6.89-7.29 (m, 8H), 7.36-7.46 (m, 2H), 7.56-7.58 (m, 1H), 7.97-8.04 (m, 2H).

MS m/z: 584 (M+1).

(2S,4R)-1-(4-{4-[Acetyl-(4-chloro-phenyl)-amino]-2-methyl-3,4-dihydro-2H-quinoline-1-carbonyl}-phenyl)-piperidine-4-carboxylic acid ethyl ester (H-73)

(2S,4R)-1-(4-{4-[Acetyl-(4-chloro-phenyl)-amino]-2-methyl-3,4-dihydro-2H-quinoline-1-carbonyl}-phenyl)-piperidine-4-carboxylic acid ethyl ester was prepared from (2S,4R)-trifluoro-methanesulfonic acid 4-{4-[acetyl(4-chlorophenyl)-amino]-2-methyl-3,4-dihydro-2H-quinoline-1-carbonyl}-phenyl ester by adding piperidine-4-carboxylic acid ethyl ester (4 eq.), Cs$_2$CO$_3$ (3 eq.), 10% Pd$_2$(dba)$_3$, BINAP (0.20 equ), and 10% 18-Crown-6 (0.10 eq.) in toluene at 110° C. over night. The reaction mixture was concentrated in vacuo. The residue was partitioned between ethyl acetate and water, then extracted three times with ethyl acetate, dried over MgSO$_4$, filtered and concentrated down. The crude residue was purified by HPLC to afford the product.

$^1$H-NMR (CDCl$_3$) δ: 1.10 (d, 3H), 1.24 (m, 4H), 1.54-1.74 (mm, 4H), 2.00 (s, 3H), 2.27 (m, 1H), 2:57 (m, 1H), 2,80 (m, 1H), 3.01 (m, 1H), 3.48 (m, 1H), 3.71 (m, 1H), 4.10 (q, 2H), 4.70 (m, 1H), 5.56 (brs, 1H), 6.56 (d, 1H), 6.64 (d, 2H), 6.92 (t, 1H), 7.07-7.28 (m, 6H), 7.35 (d, 2H).

MS m/z: 574.31 (M+1).

N-(4-Chlorophenyl)-N-{(2S,4R)-1-[(6-ethylpyridin-3-yl)carbonyl]-2-methyl-1,2,3,4-tetrahydroquinolin-4-yl}acetamide (H-74)

N-(4-Chlorophenyl)-N-{(2S,4R)-1-[(6-ethylpyridin-3-yl)carbonyl]-2-methyl-1,2,3,4-tetrahydroquinolin-4-yl}acetamide was prepared following general procedure H, substituting 6-ethyl nicotinyl chloride for 6-trifluoromethyl nicotinyl chloride. (6-Ethyl nicotinyl chloride was prepared in two steps from methyl 6-chloronicotinate. To a solution of methyl 6-chloronicotinate (2.50 g, 14.6 mmol) in tetrahydrofuran (80 mL) and N-methyl pyrrolidone (3 mL) was added iron(I)acetyl acetonate (500 mg), followed by dropwise addition of a solution of ethyl magnesium bromide in ether (9.80 mL, 17.5 mmol). The reaction was stirred at room temperature for 2 hours (*JACS* 2002, 124, 13856-13863). The resulting reaction was quenched using (saturated) aqueous ammonium chloride. The mixture was extracted with ethyl acetate, and the organics were separated and washed with brine, then dried over anhydrous sodium sulfate, filtered and concentrated in vacuo. The crude product was purified on silica gel by flash chromatography using hexanes/ethyl acetate (10-30%) to afford methyl 6-ethylnicotinate in 66% yield. The methyl ester was then hydrolysed in the presence of aqueous lithium hydroxide in methanol at room temperature overnight to give 6-ethylnicotinic acid. Further treatment of 6-ethyl nicotinic acid with oxalyl chloride and catalytic DMF in dichloromethane gave the desired 6-ethyl nicotinyl chloride).

$^1$H-NMR (CDCl$_3$) δ: 1.16 (d, 3H), 1.24 (t, 3H), 1.24-1.26 (m, 1H), 2.02 (s, 3H), 2.24-2.38 (m, 1H), 2.70-2.85 (q, 2H), 4.70-4.80 (m, 1H), 5.44-5.64 (m, 1H), 6.50 (d, 1H), 6.92-6.98 (t, 2H), 7.20-7.40 (m, 8H), 8.50 (br s, 1H).

MS m/z: 448 (M+1).

(2S,4R)-N-(4-Chloro-phenyl)-N-{2-methyl-1-[4-(3-trifluoromethanesulfonylamino-propoxy)-benzoyl]-1,2,3,4-tetrahydro-quinolin-4-yl}-acetamide (H-75)

(2S,4R)-N-{1-[4-(3-Amino-propoxy)-benzoyl]-2-methyl-1,2,3,4-tetrahydro-quinolin-4-yl}-N-(4-chloro-phenyl)-acetamide (34 mg, 0.069 mmol) was dissolved in methylene chloride (0.5 mL) and triethylamine (0.019 mL, 0.138 mmol) and cooled to −40° C. Trifluoromethanesulfonic anhydride (0.015 mL, 0.086 mmol) was added and the mixture was warmed to 0° C. for 30 minutes. The mixture was partitioned between methylene chloride and water; the methylene chloride layer was dried over $MgSO_4$, filtered and concentrated. The crude residue was purified by silica gel chromatography (1/1 hexanes/ethyl acetate-ethyl acetate gradient) to afford the product.

$^1$H-NMR (CDCl$_3$) δ: 1.1 (s, 3H), 1.2 (m, 1H), 1.9 (m, 2H), 2.0 (s, 3H), 2.3 (m, 1H), 3.6 (m, 2H), 4.0 (t, 2H), 4.7 (m, 1H), 5.6 (bs, 1H), 6.5 (d, 1H), 6.6 (t, 1H), 6.7 (d, 1H), 6.9 (t, 1H), 7.2 (m, 7H), 7.4 (d, 2H).

MS m/z: 624 (M+1).

(2S,4R)-N-(4-Chloro-phenyl)-N-(2-methyl-1-{4-[3-(2-oxo-oxazolidin-3-yl)-propoxy]-benzoyl}-1,2,3,4-tetrahydro-quinolin-4-yl)-acetamide (H-76)

(2S,4R)-N-{1-[4-(3-Amino-propoxy)-benzoyl]-2-methyl-1,2,3,4-tetrahydro-quinolin-4-yl}-N-(4-chloro-phenyl)-acetamide (50 mg, 0.102 mmol) was dissolved in methylene chloride (3 mL) and triethylamine (0.150 mL, 1.08 mmol) and cooled to −40° C. 2-Bromoethylchloroformate (0.016 mL, 0.153 mmol) was added and the reaction was allowed to warm to room temperature. After 1 hour at room temperature, DMF (2 mL) and $Cs_2CO_3$ (100 mg, 0.307 mmol) were added and the mixture was stirred over night. The mixture was partitioned between methylene chloride and water; the methylene chloride layer was dried over $MgSO_4$, filtered and concentrated. The crude residue was purified by silica gel chromatography (1/1 hexanes/ethyl acetate-ethyl acetate gradient) to afford the product.

$^1$H-NMR (CDCl$_3$) δ: 1.1 (s, 3H), 1.2 (m, 1H), 1.9 (m, 2H), 2.0 (s, 3H), 2.3 (m, 1H), 3.4 (t, 2H), 3.5 (t, 2H), 3.9 (t, 2H), 4.3 (t, 2H), 4.7 (m, 1H), 5.6 (bs, 1H), 6.5 (d, 1H), 6.6 (d, 2H), 6.9 (t, 1H), 7.2 (m, 6H), 7.4 (d, 2H).

MS m/z: 562 (M+1).

(2S,4R)-3-(4-{4-[Acetyl-(4-chloro-phenyl)-amino]-2-methyl-3,4-dihydro-2H-quinoline-1-carbonyl}-phenylamino)-propionic acid (H-77)

(2S,4R)-3-(4-{4-[Acetyl-(4-chloro-phenyl)-amino]-2-methyl-3,4-dihydro-2H-quinoline-1-carbonyl}-phenylamino)-propionic acid was prepared following the procedure for (2S,4R)-1-(4-{4-[Acetyl-(4-chloro-phenyl)-amino]-2-methyl-3,4-dihydro-2H-quinoline-1-carbonyl}-phenyl)-piperidine-4-carboxylic acid ethyl ester, substituting 3-aminopropionic acid methyl ester for piperidine-4-carboxylic acid ethyl ester to yield the (2S,4R)-3-(4-{4-[Acetyl-(4-chloro-phenyl)-amino]-2-methyl-3,4-dihydro-2H-quinoline-1-carbonyl}-phenylamino)-propionic acid methyl ester. The ester was hydrolyzed to the acid by dissolving in tetrahydrofuran and ethanol and lithium hydroxide (1N) was added and heated 50° C. for 2 h. The mixture was cooled to room temperature, acidified to form a white precipitate. The solid was filtered to give to afford the product after HPLC purification.

$^1$H-NMR (CDCl$_3$) δ: 1.10 (d, 3H), 1.23 (m, 1H), 2.03 (s, 3H), 2.27 (m, 1H), 2.51 (s, 2H), 3.30 (t, 2H), 4.71 (m, 1H), 5.61 (brs, 1H), 6.27 (d, 2H), 6.59 (d, 1H), 6.93 (t, 1H), 7.01 (d, 2H), 7.02-7.27 (m, 4H), 7.37 (d, 2H), 8.90 (br, 1H).

MS m/z: 506.3 (M+1).

N-(4-chlorophenyl)-N-[(2S,4R)-1-(3,5-difluoro-4-methoxybenzoyl)-2-methyl-2,4-tetrahydroquinolin-4-yl]acetamide (H-78)

N-(4-chlorophenyl)-N-[(2S,4R)-1-(3,5-difluoro-4-methoxybenzoyl)-2-methyl-1,2,3,4-tetrahydroquinolin-4-yl]acetamide was prepared following general procedure H, substituting 3,5-difluoro-4-methoxybenzoyl chloride for 6-trifluoromethyl nicotinyl chloride. (3,5-Difluoro-4-methoxybenzoyl chloride was prepared in one step from 3,5-difluoro-4-methoxybenzoic acid. 3,5-difluoro-4-methoxybenzoic acid was treated with oxalyl chloride and catalytic amount of DMF to afford 3,5-difluoro-4-methoxybenzoyl chloride in decent yield). The rest of the procedures were followed as indicated in general procedure H to afford N-(4-chlorophenyl)-N-[(2S,4R)-1-(3,5-difluoro-4-methoxybenzoyl)-2-methyl-1,2,3,4-tetrahydroquinolin-4-yl]acetamide in decent yield.

$^1$H-NMR (CDCl$_3$) δ: 1.13 (d, 3H), 1.24 (m, 2H), 2.02 (s, 3H), 2.28 (b, 1H), 3.94 (s, 3H), 4.70 (m, 1H), 6.52 (d, 1H), 6.72 (d, 2H), 6.90 (t, 1H), 7.17-7.23 (m, 3H), 7.28-7.38 (m, 3H).

MS m/z: 484 (M+1).

(2S,4R)-4-{4-[4-(Acetyl-phenyl-amino)-2-methyl-3,4-dihydro-2H-quinoline-1-carbonyl]-phenoxy}-2,2-dimethyl-butyric acid (H-79)

4-(4-{4-[Acetyl-(4-chloro-phenyl)-amino]-2-methyl-3,4-dihydro-2H-quinoline-1-carbonyl}-phenoxy)-2,2-dimethyl-butyric acid (300 mg, 0.545 mmol) was dissolved in ethanol. Pd/C (10% Palladium) was added, followed by $H_2$ gas (1 atm-balloon). After 3 hours, the reaction mixture was filtered and concentrated. The crude residue was purified by silica gel chromatography (100% ethyl acetate to 5% methanol/ethyl acetate gradient) to afford the product.

$^1$H-NMR (CDCl$_3$) δ: 1.1 (d, 3H), 1.2 (m, 1H), 1.2 (s, 3H), 1.3 (s, 3H), 2.0 (s, 3H), 2.1 (t, 1H), 2.3 (m, 1H), 3.9 (m, 2H), 4.7 (m, 1H), 5.6 (bs, 1H), 5.9 (d, 1H), 6.5 (d, 1H), 6.4 (d, 2H), 6.9 (t, 1H), 7.2 (m, 7H), 7.4 (d, 2H), 10.8 (bs, 1H).

MS m/z: 515 (M+1).

(2S,4R)-(4-{4-[Acetyl-(4-chloro-phenyl)-amino]-2-methyl-3,4-dihydro-2H-quinoline-1-carbonyl}-phenoxy)-fluoro-acetic acid (H-80)

(2S,4R)-(4-{4-[Acetyl-(4-chloro-phenyl)-amino]-2-methyl-3,4-dihydro-2H-quinoline-1-carbonyl}-phenoxy)-fluoro-acetic acid ethyl ester (100 mg) was dissolved in methanol/THF (1:1, 5 mL), and potassium hydroxide (1.0N, 1 mL) was added. After 1 hour, the reaction was acidified and extracted with methylene chloride. The organic layer was dried, filtered, and concentrated. The crude residue was purified by silica gel chromatography 100% ethyl acetate to 5% methanol/ethyl acetate gradient to afford the product.

$^1$H-NMR (CDCl$_3$) δ: 1.1 (d, 3H), 1.2 (m, 1H), 2.0 (s, 3H), 2.3 (m, 1H), 4.8 (m, 1H), 5.6 (bs, 1H), 5.9 (d, 1H), 6.5 (d, 1H), 6.9 (m, 3H), 7.2 (m, 6H), 7.4 (d, 2H), 11.1 (bs, 1H).

MS m/z: 511 (M+1)

(2S,4R)-4-(4-{4-[Acetyl-(4-chloro-phenyl)-amino]-2-methyl-3,4-dihydro-2H-quinoline-1-carbonyl}-phenoxy)-cyclohexanecarboxylic acid ethyl ester (H-81)

To a solution of diethyl azodicarboxylate (120 mg) in 5 ml THF at 0° C., was added PPh$_3$ (181 mg). The mixture was stirred for 10 min at 0° C. Then (2S,4R)-N-(4-Chloro-phenyl)-N-[1-(4-hydroxy-benzoyl)-2-methyl-1,2,3,4-tetrahydro-quinolin-4-yl]-acetamide (200 mg) was added. The mixture was stirred for 20 min at 0° C. 4-Hydroxy-cyclohexanecarboxylic acid ethyl ester (80 mg) was added. The final reaction mixture was stirred for overnight at RT. The mixture was concentrated under reduced pressure, dissolved in ethyl acetate, washed with sat. aqueous sodium bicarbonate, brine and dried over magnesium sulfate, filtered, and concentrated under reduced pressure. The residue was purified by silica gel chromatography (30/70 hexanes/ethyl acetate gradient) to afford pure (2S,4R)-4-(4-{4-[acetyl(4-chloro-phenyl)-amino]-2-methyl-3,4-dihydro-2H-quinoline-1-carbonyl}-phenoxy)-cyclohexanecarboxylic acid ethyl ester (100 mg, 37%).

$^1$H-NMR (CDCl$_3$) δ: 1.13 (d, 4H), 1.22 (t, 3H), 1.26-1.60 (m, 5H), 2.00-2.18 (m, 5H), 2.20-2.39 (m, 3H), 4.11 (q, 2H), 4.72 (sextet, 1H), 5.60 (bs, 1H), 6.53 (d, 1H), 6.64 (d, 2H), 6.91 (t, 1H) 7.11-7.38 (m, 8H).

MS m/z: 589 (M+1).

(1R,2R)-2-[(4-{[(2S,4R)-4-[acetyl(4-chlorophenyl)amino]-2-methyl-3,4-dihydroquinolin-1(2H)-yl]carbonyl}phenoxy)methyl]cyclopentanecarboxylic acid (H-82)

Trans-2-Hydroxymethyl-cyclopentanecarboxylic acid methyl ester (0.127 g, 0.81 mmol) was dissolved in 10 ml toluene at room temperature with PPh$_3$ (0.211 g, 0.81 mmol), then added N-(4-chlorophenyl)-N-[(2S,4R)-1-(4-hydroxy-benzoyl)-2-methyl-1,2,3,4-tetrahydro-quinolin-4-yl]acetamide (0.1 g, 0.23 mmol) and stirred for 5 min. DEAD (0.141 g, 0.81 mmol) was added and the reaction was stirred for 18 h at room temperature. The reaction was concentrated and purified by silica gel chromatography (45% dichloromethane/55% ethyl acetate) to afford methyl 2-[(4-{[(2S,4R)-4-[acetyl(4-chlorophenyl)amino]-2-methyl-3,4-dihydroquinolin-1(2H)-yl]carbonyl}phenoxy)methyl]cyclopentanecarboxylate (0.12 g, 90%).

2-[(4-{[(2S,4R)-4-[acetyl(4-chlorophenyl)amino]-2-methyl-3,4-dihydroquinolin-1(2H)-yl]carbonyl}phenoxy)methyl]cyclopentanecarboxylate was hydrolyzed to the acid by dissolving in 5 ml methanol and potassium carbonate (0.100 g in 4 ml water) was added. The mixture was stirred for 2 days. The mixture was cooled to room temperature and methanol was removed in vacuo. The mixture was acidified to form a white precipitate. The solid was filtered to give (1R,2R)-2-[(4-{[(2S,4R)-4-[acetyl(4-chlorophenyl)amino]-2-methyl-3,4-dihydroquinolin-1(2H)-yl]carbonyl}phenoxy)methyl]cyclopentanecarboxylic acid (0.012 g, 10%)

$^1$H-NMR (CDCl$_3$) δ: 1.12 (m, 1H), 1.18 (d, 3H), 1.51 (m, 1H), 1.74 (m, 2H), 1.96 (m, 3H), 2.02 (s, 3H), 2.28 (m, 1H), 2.65 (m, 2H), 3.89 (m, 2H), 4.77 (m, 1H), 5.60 (m, 1H), 6.48 (d, 1H), 6.61 (m, 2H), 6.88 (t, 1H), 7.19 (m, 6H), 7.37 (d, 2H).

MS m/z: 562 (M+1)

(2S,4R)-N-(4-Chloro-phenyl)-N-{2-methyl-1-[4-(3-ureido-propoxy)-benzoyl]-1,2,3,4-tetrahydro-quinolin-4-yl}-acetamide (H-84)

To a solution of (2S,4R)-N-{1-[4-(3-Amino-propoxy)-benzoyl]-2-methyl-1,2,3,4-tetrahydro-quinolin-4-yl}-N-(4-chloro-phenyl)-acetamide (50 mg, 0.10 mmol) in DCM (1 mL) was added trimethylsilyl isocyanate (23 mg, 0.20 mmol). The reaction mixture was stirred at room temperature for 18 hours. The reaction was quenched by adding 0.2 mL of water and concentrated under reduced pressure. The crude residue was purified by preparatory HPLC to afford the product (9 mg, 17%).

MS m/z: 536 (M+1).

(2S,4R)-N-(4-Chloro-phenyl)-N-{1-[4-(2-imidazol-1-yl-ethoxy)-benzoyl]-2-methyl-1,2,3,4-tetrahydro-quinolin-4-yl}-acetamide (H-85)

(2S,4R)-N-(4-Chloro-phenyl)-N-[1-(4-hydroxy-benzoyl)-2-methyl-1,2,3,4-tetrahydro-quinolin-4-yl]-acetamide (0.065 g, 0.15 mmol) was dissolved in DMF at room temperature and K$_2$CO$_3$ (0.12 g, 0.87 mmol) was added. 1-(2-Bromo-ethyl)-1H-imidazole (0.08 g, 0.45 mmol) was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (10% methanol/90% dichloromethane) to afford the product (0.06 g, 76%).

$^1$H-NMR (CDCl$_3$) δ: 1.13 (d, 3H), 1.15 (t, 1H), 1.98 (s, 3H), 2.27 (m, 1H), 4.13 (t, 2H), 4.28 (t, 2H), 4.72 (sextet, 1H), 5.58 (bs, 1H), 6.48 (d, 1H), 6.64 (d, 2H), 6.91 (t, 1H), 6.98 (s, 1H), 7.03 (s, 1H), 7.08-7.35 (m, 6H), 7.38 (d, 2H), 7.55 (s, 1H).

MS m/z: 529 (M+1)

(2S,4R)-1-[3-(4-{4-[Acetyl-(4-chloro-phenyl)-amino]-2-methyl-3,4-hydro-2H-quinoline-1-carbonyl}-phenoxy)-propyl]-1H-imidazole-2-carboxylic acid ethyl ester (H-86

(2S,4R)-N-(4-Chloro-phenyl)-N-[1-(4-hydroxy-benzoyl)-2-methyl-1,2,3,4-tetrahydro-quinolin-4-yl]-acetamide was dissolved in DMF at room temperature and K$_2$CO$_3$ was added. 1-(3-Bromo-propyl)-1H-imidazole-2-carboxylic acid ethyl ester (prepared from the dibromide and the corresponding imidazole with NaH in THF) was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (5% MeOH(95% CH$_2$Cl$_2$NH$_4$OH to 10% MeOH/90% CH$_2$Cl$_2$/NH$_4$OH) to afford the product.

$^1$H-NMR (CDCl$_3$) δ: 1.10 (d, 3H), 1.11 (m, 1H), 1.38 (t, 3H), 2.01 (s, 3H), 2.22 (m, 2H), 3.83 (m, 2H), 4.35 (q, 2H), 4.55 (m, 2H), 4.71 (sextet, 1H), 5.58 (bs, 1H), 6.49 (d, 1H), 6.63 (d, 2H), 6.90 (t, 1H), 7.08-7.28 (m, 9H), 7.36 (d, 1H).

(2S,4R)-N-4-(4-{4-[Acetyl-(4-chloro-phenyl)-amino]-2-methyl-3,4-dihydro-2H-quinoline-1-carbonyl}-phenoxy)-2,2-dimethyl-butyric acid (H-87)

(2S,4R)-N-(4-Chloro-phenyl)-N-[1-(4-hydroxy-benzoyl)-2-methyl-1,2,3,4-tetrahydro-quinolin-4-yl]-acetamide (0.126 g, 0.242 mmol) was dissolved in 3 ml DMF at room temperature and K$_2$CO$_3$ (0.267 g, 1.94 mmol) was added. 4-Bromo-2,2-dimethyl-butyric acid methyl ester (0.202 g, 0.969 mmol, prepared according to the procedure from *Tetrahedron* 1994, 50(32), 9825-30) was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (50% EtOAc/50% Hexane) to afford the (2S,4R)-4-(4-{4-[acetyl(4-chloro-phenyl)-amino]-2-methyl-3,4-dihydro-2H-quinoline-1-carbonyl}-phenoxy)-2,2-dimethyl-butyric acid methyl ester (0.105 g, 77%).

The ester was hydrolyzed to the acid by dissolving in 6 ml tetrahydrofuran/methanol (1/1) and potassium hydroxide (0.042 g in 2 ml water) was added. The mixture was heated to 40° C. for 3 hours. The mixture was cooled to rt, acidified to form a white precipitate. The solid was filtered to give (2S, 4R)-N-4-(4-{4-[acetyl(4-chloro-phenyl)-amino]-2-methyl-3,4-dihydro-2H-quinoline-1-carbonyl}-phenoxy)-2,2-dimethyl-butyric acid (0.085 g, 83%).

$^1$H-NMR (CDCl$_3$) δ: 1.14 (d, 3H), 1.15 (t, 1H), 1.25 (s, 6H), 2.02 (t, 2H), 2.05 (m, 2H), 2.27 (m, 1H), 3.96 (t, 2H), 4.72 (sextet, 1H), 5.52 (br, 2H), 5.58 (bs, 1H), 6.52 (d, 1H), 6.67 (d, 2H), 6.86 (t, 1H), 7.08-7.35 (m, 6H), 7.38 (d, 2H).

MS m/z: 549 (M+1).

N-(4-Chlorophenyl)-N-{(2S,4R)-1-[4-(1,1-difluoro-ethyl)benzoyl]-2-methyl-1,2,3,4-tetrahydroquinolin-4-yl}acetamide (H-88)

N-(4-Chlorophenyl)-N-{(2S,4R)-1-[4-(1,1-difluoroethyl)benzoyl]-2-methyl-1,2,3,4-tetrahydroquinolin-4-yl}acetamide was prepared following general procedure H, substituting 4-(1,1-difluoroethyl)benzoyl chloride for 6-trifluoromethyl nicotinyl chloride. (4-(1,1-difluoroethyl)benzoyl chloride was prepared in 3 steps from 14-iodophenyl) ethanone. Treatment of 1-(4-iodophenyl)ethanone with neat [Bis(2-methoxyethyl)amino]sulfur trifluoride (1.7 equivalents) at 85° C. under argon in the presence of ethanol (0.1 equivalents), then quenching with saturated aqueous sodium bicarbonate followed by standard aqueous work up and chromatography (hexanes) afforded 1-(1,1-difluoroethyl)-4-iodobenzene. Subsequent lithium-halogen exchange with n-butyl lithium (1.2 equivalents) in THF at −78° C. under argon and quenching of the resultant organolithium species by bubbling carbon dioxide through the reaction mixture afforded 4-(1,1-difluoroethyl)benzoic acid which was converted to 4-(1,1-difluoroethyl)benzoyl chloride by treatment with thionyl chloride (2.2 equivalents) in dichloromethane at room temperature for 2 hours followed by removal of the volatiles in vaccuo). The rest of the procedures were followed as indicated in general procedure H to afford N-(4-chlorophenyl)-N-{(2S,4R)-1-[4-(1,1-difluoroethyl)benzoyl]-2-methyl-1,2,3,4-tetrahydroquinolin-4-yl}acetamide.

$^1$H-NMR (CDCl$_3$) δ: 1.16 (d, 3H), 1.22-1.26 (m, 1H), 1.82 (t, 3H), 2.03 (s, 3H), 2.24-2.35 (m, 1H), 4.72-4.83 (m, 1H), 5.63 (br s, 1H), 6.47 (d, 1H), 6.90 (t, 1H), 7.16-7.46 (m, 10H).

MS m/z: 483 (M+1).

N-[(2S,4R)-1-(3-{[tert-butyl-(dimethyl)silyl]oxy}-4-fluorobenzoyl)-2-methyl-1,2,3,4-tetrahydroquinolin-4-yl]-N-(4-chlorophenyl)acetamide (H-89)

N-[(2S,4R)-1-(3-{[tert-butyl-(dimethyl)silyl]oxy}-4-fluorobenzoyl)-2-methyl-1,2,3,4-tetrahydroquinolin-4-yl]-N-(4-chlorophenyl)acetamide was prepared following general procedure H, substituting 3-{[tert-butyl-(dimethyl)silyl]oxy}-4-fluorobenzoyl chloride for 6-trifluoromethyl nicotinyl chloride. (3-{[tert-butyl-(dimethyl)silyl]oxy}-4-fluorobenzoyl chloride was prepared in one step from 3-{[tert-butyl-(dimethyl)silyl]oxy}-4-fluorobenzoic acid. 3-{[tert-butyl-(dimethyl)silyl]oxy}-4-fluorobenzoic acid was treated with oxalyl chloride and catalytic amount of DMF to afford 3,5-difluoro-4-methoxybenzoyl chloride in decent yield). The rest of the procedures were followed as indicated in general procedure H to afford N-[(2S,4R)-1-(3-{[tert-butyl-(dimethyl)silyl]oxy}-4-fluorobenzoyl)-2-methyl-1,2,3,4-tetrahydroquinolin-4-yl]-N-(4-chlorophenyl)acetamide $^1$H-NMR (CDCl$_3$) δ: 0.1 (s, 9H), 0.9 (s, 6H), 1.15 (d, 3H), 2.07 (s, 4H), 2.30 (b, 1H), 4.75 (m, 1H), 6.55 (d, 1H), 6.68 (d, 1H), 6.62-6.70 (m, 3H) 7.15-7.25 (m, 4H), 7.35-7.42 (m, 2H).

MS m/z: 568 (M+1)

(2S,4R)-1-(4-{4-[Acetyl-(4-chloro-phenyl)-amino]-2-methyl-3,4-dihydro-2H-quinoline-1-carbonyl}-phenyl)-piperidine-3-carboxylic acid amide (H-90)

(2S,4R)-1-(4-{4-[Acetyl-(4-chloro-phenyl)-amino]-2-methyl-3,4-dihydro-2H-quinoline-1-carbonyl}-phenyl)-piperidine-3-carboxylic acid amide was prepared from (2S,4R)-1-(4-{4-[Acetyl-(4-chloro-phenyl)-amino]-2-methyl-3,4-dihydro-2H-quinoline-1-carbonyl}-phenyl)-piperidine-3-carboxylic acid. The acid (0.2 g, 0.366 mmol) was dissolved in DMF (3 mL) at room temperature and HOBt (0.74 g, 0.55 mmol), HATU (0.209 g, 0.55 mol), and diisopropylethylamine (0.25 mL,) was added followed by ammonium chloride (0.040 g, 0.74 mmol) and stirred at room temperature for 16 h. The reaction was diluted with ethyl acetate, washed with 1N NaOH, 1N HCl and brine. The organics were dried over MgSO$_4$, filtered and concentrated down. The crude residue was purified HPLC purification.

$^1$H-NMR (CDCl$_3$) δ: 1.10 (d, 3H), 1.20 (m, 1H), 1.73 (m, 2H), 1.84 (m, 2H), 2.01 (s, 3H), 2.24 (m, 2H), 2.65 (m, 2H), 3.66 (m, 2H), 4.70 (m, 1H), 5.62 (br, 2H), 6.93 (br, 1H), 6.56 (d, 1H), 6.60 (d, 2H), 6.92 (t, 1H), 7.05-7.27 (m, 6H), 7.37 (d, 2H).

MS m/z: 545.3 (M+1).

(2S,4R)-N-{1-[4-(1-Acetyl-piperidin-4-ylmethoxy)-benzoyl]-2-methyl-1,2,3,4-tetrahydro-quinolin-4-yl}-N-(4-chloro-phenyl)-acetamide (H-91)

(2S,4R)-N-(4-Chloro-phenyl)-N-{2-methyl-1-[4-(piperidin-4-ylmethoxy)-benzoyl]-1,2,3,4-tetrahydro-quinolin-4-yl}-acetamide (0.075 g, 0.14 mmol) was dissolved in dichloromethane at room temperature. DIEA (0.1 mL, 0.56 mmol) and acetyl chloride (0.2 mL, 2.8 mmol) was added. The reaction was stirred at room temperature overnight. The reaction mixture was concentrated in vacuo. The crude residue was purified by silica gel chromatography (10% methanol/90% dichloromethane) to afford the product (0.049 g, 49%).

$^1$H-NMR (CDCl$_3$) δ: 1.13 (d, 3H), 1.15 (t, 1H), 1.24 (m, 2H), 1.81 (m, 2H), 1.93 (m, 1H), 2.04 (s, 3H), 2.09 (s, 3H), 2.27 (m, 1H), 2.55 (t, 1H), 3.09 (t, 1H), 3.73 (m, 2H), 3.85 (m, 1H), 4.63 (m, 1H), 4.72 (sextet, 1H), 5.58 (bs, 1H), 6.52 (d, 1H), 6.67 (d, 2H), 6.86 (t, 1H), 7.08-7.35 (m, 6H), 7.38 (d, 2H).

MS m/z: 574 (M+1)

(2S,4R)-N-5-(4-{4-[Acetyl-(4-chloro-phenyl)-amino]-2-methyl-3,4-dihydro-2H-quinoline-1-carbonyl}-phenoxy)-2,2-dimethyl-pentanoic acid (H-92)

(2S,4R)-N-(4-Chloro-phenyl)-N-[1-(4-hydroxy-benzoyl)-2-methyl-1,2,3,4-tetrahydro-quinolin-4-yl]-acetamide (0.12 g, 0.28 mmol) was dissolved in 5 ml DMF at room temperature and $K_2CO_3$ (0.155 g, 1.12 mmol) was added. 5-Bromo-2,2-dimethyl-pentanoic acid methyl ester (0.123 g, 0.56 mmol, prepared according to the procedure from *Tetrahedron* 1994, 50(32), 9825-30) was added and the reaction was allowed to heat to 80° C. overnight. The reaction mixture was concentrated in vacuo. The residue was partitioned between ethyl acetate and water, then extracted three times with ethyl acetate, dried over $MgSO_4$, filtered and concentrated down. The crude residue was purified by silica gel chromatography (50% EtOAc/50% Hexane) to afford (2S,4R)-N-5-(4-{4-[acetyl(4-chloro-phenyl)-amino]-2-methyl-3,4-dihydro-2H-quinoline-1-carbonyl}-phenoxy)-2,2-dimethyl-pentanoic acid methyl ester (0.076 g, 48%).

The ester was hydrolyzed to the acid by dissolving in 8 ml tetrahydrofuran/methanol (1/1) and potassium hydroxide (0.03 g in 2 ml water) was added. The mixture was heated to 40° C. for 3 hours. The mixture was cooled to rt, acidified to form a white precipitate. The solid was filtered to give the product (0.057 g, 79%).

$^1$H-NMR (CDCl$_3$) δ: 1.13 (d, 3H), 1.15 (t, 1H), 1.27 (s, 6H), 1.70 (m, 4H), 1.1.98 (s, 3H), 2.28 (m, 1H), 3.89 (t, 2H), 4.72 (sextet, 1H), 5.58 (bs, 1H), 6.52 (d, 1H), 6.67 (d, 2H), 6.86 (t, 1H), 7.08-7.35 (m, 6H), 7.38 (d, 2H).

MS m/z: 535 (M+1)

(2S,4R)-4-[(4-{4-[Acetyl-(4-chloro-phenyl)-amino]-2-methyl-3,4-dihydro-2H-quinoline-1-carbonyl}-phenyl)-methyl-amino]-butyric acid methyl ester (H-93)

(2S,4R)-4-[(4-{4-[Acetyl-(4-chloro-phenyl)-amino]-2-methyl-3,4-dihydro-2H-quinoline-1-carbonyl}-phenyl)-methyl-amino]-butyric acid methyl ester was prepared from (2S,4R)-(4-{4-[acetyl(4-chloro-phenyl)-amino]-2-methyl-3,4-dihydro-2H-quinoline-1-carbonyl}-phenyl)-methyl-carbamic acid ethyl ester. (2S,4R)-(4-{4-[acetyl(4-chloro-phenyl)-amino]-2-methyl-3,4-dihydro-2H-quinoline-1-carbonyl}-phenyl)-methyl-carbamic acid ethyl ester was dissolved in acetonitrile (2 mL). Iodotrimethylsilane was added and the reaction was allowed to stir at room temperature over night. Excess reagent was quenched by the addition of methanol (1 mL) and the mixture was concentrated under reduced pressure. The crude residue was partitioned between ethyl acetate and saturated aqueous sodium bicarbonate. The extracts were washed with 1 M sodium hydroxide, saturated aqueous sodium thiosulfate and brine, dried over sodium sulfate, filtered, concentrated and purified by silica gel chromatography to yield N-(4-chloro-phenyl)-N-[2-methyl-1-(4-methylamino-benzoyl)-1,2,3,4-tetrahydro-quinolin-4-yl]-acetamide.

(2S,4R)-(N-(4-chloro-phenyl)-N-[2-methyl-1-(4-methylamino-benzoyl)-1,2,3,4-tetrahydro-quinolin-4-yl]-acetamide (0.015 g, 0.033 mmol) was dissolved in $CH_2Cl_2$ (0.5 mL) at room temperature. Sodium borohydride (0.007 g, 1.5 eq.) was added followed by 4-oxo-butyric acid methyl ester (0.020 g, 4 eq.) and the reaction was allowed to stir over night. The reaction mixture was concentrated in vacuo. The residue was partitioned between ethyl acetate and water, then extracted three times with ethyl acetate, dried over $MgSO_4$, filtered and concentrated down. The crude residue was purified by silica gel chromatography (33% Hexane/EA gradient) to afford the product.

$^1$H-NMR (CDCl$_3$) δ: 1.09-1.24 (m, 4H), 1.84 (m, 2H), 2.00 (s, 3H), 2.27 (m, 3H), 2.86 (s, 3H), 3.29 (t, 2H), 3.62 (s, 3H), 4.70 (m, 1H), 5.58 (brs, 1H), 6.39 (d, 2H), 6.59 (d, 1H), 6.96 (t, 1H), 7.05-7.21 (m, 5H), 7.25 (d, 1H), 7.36 (d, 2H).

MS m/z: 548 (M+1).

(2S,4R)-N-4-(4-{4-[Acetyl-(4-chloro-phenyl)-amino]-2-methyl-3,4-dihydro-2H-quinoline-1-carbonyl}-phenoxy)-2,2-difluoro-butyric acid (H-94)

2,2-Difluoro-4-hydroxy-butyric acid methyl ester (0.27 g, 3.21 mmol, prepared according to U.S. Pat. No. 4,421,690 procedure) was dissolved in toluene at room temperature with PPh$_3$ (0.421 g, 3.21 mmol), then added (2S,4R)-N-(4-chloro-phenyl)-N-[1-(4-hydroxy-benzoyl)-2-methyl-1,2,3,4-tetrahydro-quinolin-4-yl]-acetamide (0.20 g, 0.46 mmol) and stirred for 5 min. DEAD (0.028 g, 3.21 mmol) was added and the reaction was stirred for 18 h at room temperature. The reaction was concentrated and purified by silica gel chromatography (45% $CH_2Cl_2$/55% EtOAc) to afford (2S,4R)-N-4-(4-{4-[acetyl(4-chloro-phenyl)-amino]-2-methyl-3,4-dihydro-2H-quinoline-1-carbonyl}-phenoxy)-2,2-difluoro-butyric acid methyl ester (0.23 g, 87%).

The ester was hydrolyzed to the acid by dissolving in 8 ml tetrahydrofuran/methanol (1/1) and potassium hydroxide (0.1 g in 4 ml water) was added. The mixture was heated to 40° C. overnight. The mixture was cooled to rt, acidified to form a white precipitate. The solid was filtered to give the product (0.038 g, 97%).

$^1$H-NMR (CDCl$_3$) δ: 1.13 (d, 3H), 1.15 (t, 1H), 2.04 (s, 3H), 2.18-2.44 (bs, 4H), 3.95 (t, 2H), 4.72 (sextet, 1H), 5.58 (bs, 1H), 6.52 (d, 1H), 6.67 (d, 2H), 6.86 (t, 1H), 7.08-7.35 (m, 6H), 7.38 (d, 2H).

MS m/z: 557 (M+1).

{[3-(4-{[(2S,4R)-4-[acetyl(4-chlorophenyl)amino]-2-methyl-3,4-dihydroquinolin-1(2H)-yl]carbonyl}phenoxy)propyl]amino}acetic acid (H-95)

{[3-(4-{[(2S,4R)-4-[acetyl(4-chlorophenyl)amino]-2-methyl-3,4-dihydroquinolin-1(2H)-yl]carbonyl}phenoxy)propyl]amino}acetic acid was prepared from (2S,4R)-N-{1-[4-(3-amino-propoxy)-benzoyl]-2-methyl-1,2,3,4-tetrahydro-quinolin-4-yl}-N-(4-chloro-phenyl)-acetamide. (2S,4R)-N-{1-[4-(3-amino-propoxy)-benzoyl]-2-methyl-1,2,3,4-tetrahydro-quinolin-4-yl}-N-(4-chloro-phenyl)-acetamide (0.036 g, 0.07 mmol) was dissolved in dimethylformamide, ethyl bromoacetate (0.008 mL, 0.07 mmol) and potassium carbonate (0.021 g, 0.14 mmol) were added. The reaction was heated to 50° C. for 17 h. The reaction was concentrated down and purified using 50% ethyl acetate/50% hexane to 100% ethyl acetate.

$^1$H-NMR (CDCl$_3$) δ: 0.91 (t, 1H), 1.12 (d, 3H), 1.24 (t, 3H), 2.02 (s, 3H), 2.04 (m, 2H), 2.28 (m, 1H), 3.47-3.53 (m, 2H), 3.94-4.02 (m, 3H), 4.06 (m, 1H), 4.10-4.22 (q, 2H), 4.54 (d, 2H), 4.72 (sextet, 1H), 5.61 (bs, 1H), 6.51 (d, 1H), 6.64 (d, 2H), 6.92 (t, 1H), 7.12 (d, 2H), 7.16-7.21 (m, 3H), 7.27 (d, 1H), 7.36 (d, 2H). MS n/z=577 (M+1).

{[3-(4-{[(2S,4R)-4-[acetyl(4-chlorophenyl)amino]-2-methyl-3,4-dihydroquinolin-1(2H)-yl]carbonyl}phenoxy)propyl]amino}acetic ethyl ester was hydrolyzed to the acid by dissolving in tetrahydrofuran and ethanol and sodium hydroxide (1N) was added. The mixture was stirred at room temperature overnight. The mixture was cooled to rt, acidified to form a white precipitate. The solid was filtered to give {[3-(4-{[(2S,4R)-4-[acetyl(4-chlorophenyl)amino]-2-methyl-3,4-dihydroquinolin-1(2H)-yl]carbonyl}phenoxy)propyl]amino}acetic acid (0.003 g, 60% yield).

MS m/z: 564 (M+1).

(2S,4R)-N-4-(4-{4-[Acetyl-(4-chloro-phenyl)-amino]-2-methyl-3,4-dihydro-2H-quinoline-1-carbonyl}-phenoxy)-N-ethyl-butyramide (H-96)

(2S,4R)-N-4-(4-{4-[acetyl(4-chloro-phenyl)-amino]-2-methyl-3,4-dihydro-2H-quinoline-1-carbonyl}-1-ethylidene-pentG-2,4-dienyloxy)-butyric acid (0.064 g, 0.123 mmol) was converted to the amide by dissolving in THF (2 mL) at room temperature. HOBt (0.025 g), EDCI (0.028 g), and ethylamine (0.36 mmol) was added along with 2 drops of DMF and stirred at room temperature for 11 h. The reaction was diluted with ethyl acetate, washed with 1N NaOH, 1N HCl and brine. The organics were dried over $MgSO_4$, filtered and concentrated down. The crude residue was purified by silica gel chromatography (50% ethyl acetate/50% hexane to 100% ethyl acetate) to afford the product (0.050 g, 74%).

$^1$H-NMR (CDCl$_3$) δ: 1.06 (t, 3H), 1.13 (d, 3H), 1.15 (t, 1H), 1.81 (s, 1H), 2.04 (s, 3H), 2.06 (m, 2H), 2.27 (m, 1H), 2.32 (t, 2H), 3.28 (q, 2H), 3.91 (t, 2H), 4.72 (sextet, 1H), 5.66 (bs, 1H), 6.52 (d, 1H), 6.67 (d, 2H), 6.88 (t, 1H), 7.08-7.35 (m, 6H), 7.38 (d, 2H).

MS m/z: 548 (M+1)

(2S,4R)-N-(4-Chloro-phenyl)-N-{2-methyl-1-[4-(3-pyrazol-1-yl-propoxy)-benzoyl]-1,2,3,4-tetrahydro-quinolin-4-yl}-acetamide (H-97)

(2S,4R)-N-(4-Chloro-phenyl)-N-[1-(4-hydroxy-benzoyl)-2-methyl-1,2,3,4-tetrahydro-quinolin-4-yl]-acetamide (75 mg, 0.17 mmol) was dissolved in DMF (1 mL) at room temperature. $K_2CO_3$ (47 mg, 0.34 mmol) was added followed by 1-(3-bromopropyl)-pyrazole (64 mg, 0.34 mmol) (prepared from the reaction of 1,3-dibromopropane and pyrazole with sodium hydride in tetrahydrofuran). The reaction was allowed to stir at 70° C. for 3 hrs. The reaction mixture was concentrated in vacuo. The residue was partitioned between ethyl acetate and water, then extracted three times with ethyl acetate. Organic layers were washed with brine, dried over $MgSO_4$, filtered and concentrated down. The crude residue was purified by silica gel chromatography (1/99 methanol/dichloromethane-3/97 methanol/dichloromethane gradient) to afford the product.

$^1$H-NMR (CDCl$_3$) δ: 1.1 (d, 3H), 1.2 (m, 1H), 2.0 (s, 3H), 2.3 (m, 1H), 2.3 (m, 2H), 3.8 (t, 2H), 4.3 (t, 2H), 4.7 (m, 1H), 5.6 (m, 1H), 6.2 (t, 1H), 6.5 (d, 1H), 6.65 (d, 2H), 6.9 (t, 1H), 7.1-7.4 (m, 9H), 7.5 (s, 1H).

MS m/z: 443/445 (M+1).

N-(4-chlorophenyl)-N-{(2S,4R)-1-[(2-ethylpyrimidin-5-yl)carbonyl]-2-methyl-1,2,3,4 tetrahydro-quinolin-4-yl}acetamide (H-98)

N-(4-chlorophenyl)-N-{(2S,4R)-1-[(2-ethylpyrimidin-5-yl)carbonyl]-2-methyl-1,2,3,4-tetrahydroquinolin-4-yl}acetamide was prepared following general procedure H, substituting 2-ethylpyrimidine-5-carbonyl chloride for 6-trifluoromethyl nicotinyl chloride. (2-ethylpyrimidine-5-carbonyl chloride was prepared in four steps. To a solution of 3,3-dimethoxypropionate in ethylene glycol dimethyl ether was added sodium hydride at 0° C., then methyl formate. The reaction mixture was warmed up to 50° C. for 30 m. and then stirred at room temperature for 20 h. Anhydrous diethyl ether was added and the precipitate was filtered to give sodium 2-(dimethoxymethyl)-3-methoxy-3-oxoprop-1-en-1-olate. To a solution of propionamide hydrochloride in dimethylformamide was added preformed sodium 2-(dimethoxymethyl)-3-methoxy-3-oxoprop-1-en-1-olate. Reaction mixture was heated to 100° C. for 1 h. to give methyl 2-ethylpyrimidine-5-carboxylate. Hydrolysis of the ester with sodium hydroxide gave 2-ethylpyrimidine-5-carboxylic acid. Subsequent treatment of this carboxylic acid with oxalyl chloride and catalytic DMF afforded 2-ethylpyrimidine-5-carbonyl chloride in decent yield). The rest of the procedures were followed as indicated in general procedure H to afford N-(4-chlorophenyl)-N-{(2S,4R)-2-methyl-1-[(2-ethylpyrimidin-5-yl)carbonyl]-1,2,3,4-tetrahydroquinolin-4-yl}acetamide.

$^1$H-NMR (CDCl$_3$) δ: 1.15 (d, 3H), 1.25 (t, 3H), 2.05 (s, 3H), 2.30 (m, 1H), 2.90 (q, 2H), 4.75 (m, 1H), 5.55 (m, 1H), 6.50 (d, 1H), 7.00 (t, 1H), 7.20-7.45 (m, 6H), 8.40 (s, 2H).

MS m/z: 449 (M+1).

(2S,4R)-3-[3-(4-{4-[Acetyl-(4-chloro-phenyl)-amino]-2-methyl-3,4-dihydro-2H-quinoline-1-carbonyl}-phenoxy)-propyl]-5-methyl-3H-imidazole-4-carboxylic acid (H-99)

(2S,4R)-N-(4-Chloro-phenyl)-N-[1-(4-hydroxy-benzoyl)-2-methyl-1,2,3,4-tetrahydro-quinolin-4-yl]-acetamide was dissolved in DMF at room temperature and $K_2CO_3$ was added. 3-(3-Bromo-propyl)-5-methyl-3H-imidazole-4-carboxylic acid ethyl ester (prepared from the dibromide and the corresponding imidazole with NaH in THF) was added and the reaction was allowed to heat to 80° C. overnight. The reaction mixture was concentrated in vacuo. The residue was partitioned between ethyl acetate and water, then extracted three times with ethyl acetate, dried over $MgSO_4$, filtered and concentrated down. The crude residue was purified by silica gel chromatography (2% MeOH/95% $CH_2Cl_2$ to 10% MeOH/90% $CH_2Cl_2$) to afford (2S,4R)-3-[3-(4-{4-[acetyl(4-chloro-phenyl)-amino]-2-methyl-3,4-dihydro-2H-quinoline-1-carbonyl}-phenoxy)-propyl]-5-methyl-3H-imidazole-4-carboxylic acid ethyl ester. The ester (0.080 g, 0.12 mmol) was hydrolyzed to the acid by dissolving in tetrahydrofuran and ethanol and sodium hydroxide (1N) was added. The mixture was stirred at room temperature 16 hours. The mixture was cooled to room temperature, acidified to form a white precipitate. The solid was filtered to give (2S,4R)-3-[3-(4-{4-[Acetyl-(4-chloro-phenyl)-amino]-2-methyl-3,4-dihydro-2H-quinoline-1-carbonyl}-phenoxy)-propyl]-5-methyl-3H-imidazole-4-carboxylic acid in 61% yield.

$^1$H-NMR (CDCl$_3$) δ: 1.13 (d, 3H), 1.29 (m, 1H), 2.05 (s, 3H), 2.34 (m, 2H), 2.45 (m, 1H), 2.61 (s, 3H), 4.08 (m, 2H), 4.43 (m, 2H), 4.73 (sextet, 1H), 5.53 (bs, 1H), 6.55 (d, 1H), 6.73 (d, 2H), 6.96 (t, 1H), 7.18 (m, 3H), 7.41 (m, 5H), 9.08 (s, 1H).

MS m/z: 601 (M+1).

5-{[(2S,4R)-4-[acetyl(4-chlorophenyl)amino]-2-methyl-3,4-dihydroquinolin-1(2H)-yl]carbonyl}thiophene-2-carboxylic acid (H-100)

Methyl 5-{[(2S,4R)-4-[acetyl(4-chlorophenyl)amino]-2-methyl-3,4-dihydroquinolin-1(2H)-yl]carbonyl}thiophene-2-carboxylate (80 mg, 0.17 mmol, 1 eq.) was dissolved in methanol (6 ml). A solution of potassium carbonate (200 mg, 1.4 mmol, 8 eq.) in water (2 ml) was added and reaction mixture was stirred at room temperature for 20 h. The mixture was concentrated and the residue was acidified with a 1N HCl aqueous solution and extracted with ethyl acetate. The organic layer was washed with brine, dried over magnesium sulfate, filtered and concentrated to give 5-{[(2S,4R)-4-[acetyl(4-chlorophenyl)amino]-2-methyl-3,4-dihydroquinolin-1(2H)-yl]carbonyl}thiophene-2-carboxylic acid (76 mg, 99%).

$^1$H-NMR (CDCl$_3$) δ: 1.10 (d, 3H), 2.05 (s, 3H), 2.25 (m, 1H), 4.70 (m, 1H), 5.55 (m, 1H), 6.55 (d, 1H), 6.85 (d, 1H), 7.05 (t, 1H), 7.15-7.45 (m, 7H).

MS m/z: 469 (M+1).

(2S,4R)-N-1-[2-(4-{4-[Acetyl-(4-chloro-phenyl)-amino]-2-methyl-3,4-dihydro-2H-quinoline-1-carbonyl}-phenoxy)-ethyl]-cyclobutanecarboxylic acid amide (H-101)

(2S,4R)-N-1-[2-(4-{4-[Acetyl-(4-chloro-phenyl)-amino]-2-methyl-3,4-dihydro-2H-quinoline-1-carbonyl}-phenoxy)-ethyl]-cyclobutanecarboxylic acid amide was prepared from (2S,4R)-N-1-[2-(4-{4-[acetyl(4-chloro-phenyl)-amino]-2-methyl-3,4-dihydro-2H-quinoline-1-carbonyl}-phenoxy)-ethyl]-cyclobutanecarboxylic acid by coupling NH$_4$Cl, HATU, DIEA, HOBt in DMF at room temperature to yield (2S,4R)-N-1-[2-(4-{4-[acetyl(4-chloro-phenyl)-amino]-2-methyl-3,4-dihydro-2H-quinoline-1-carbonyl}-phenoxy)-ethyl]-cyclobutanecarboxylic acid amide. The reaction mixture was concentrated down and partitioned between ethyl acetate and water, then extracted three times with ethyl acetate, dried over magnesium sulfate, filtered and concentrated down. The residue was purified by silica gel chromatography (10% methanol/90% dichloromethane) to afford pure product (63%).

$^1$H-NMR (CDCl$_3$) δ: 1.16 (d, 3H), 1.15 (t, 1H), 1.77-1.96 (m, 4H), 2.04 (s, 3H), 2.16-2.48 (m, 5H), 3.96 (t, 2H), 4.72 (sextet, 1H), 5.58 (bs, 1H), 6.52 (d, 1H), 6.67 (d, 2H), 6.86 (t, 1H), 7.08-7.35 (m, 6H), 7.38 (d, 2H).

MS m/z: 560 (M+1)

(2S,4R)-N-(4-Chloro-phenyl)-N-{2-methyl-[4-(2-oxo-oxazolidin-3-yl)-benzoyl]-1,2,3,4-tetrahydro-quinolin-4-yl}-acetamide (H-102)

N-[1-(4-Amino-benzoyl)-2-methyl-1,2,3,4-tetrahydro-quinolin-4-yl]-N-(4-chloro-phenyl)-acetamide (61 mg, 0.142 mmol) was dissolved in methylene chloride (2 mL) and was added triethylamine (0.100 mL, 0.700 mmol). 2-Bromoethylchloroformate (0.023 mL, 0.213 mmol) was added and the reaction was allowed to warm to room temperature. After 1 hour at room temperature, DMF (2 mL) and Cs$_2$CO$_3$ (100 mg, 0.307 mmol) were added and the mixture was stirred over night. The mixture was partitioned between methylene chloride and water; the methylene chloride layer was dried over MgSO$_4$, filtered and concentrated. The crude residue was purified by silica gel chromatography (1/1 hexanes/ethyl acetate to 100% ethyl acetate gradient) to afford the product.

$^1$H-NMR (CDCl$_3$) δ: 1.2 (d, 3H), 1.2 (m, 1H), 2.0 (s, 3H), 2.3 (m, 1H), 3.8 (t, 2H), 4.4 (t, 2H), 4.8 (m, 1H), 5.6 (m, 1H), 6.5 (d, 1H), 6.9 (t, 1H), 7.2 (m, 8H), 7.4 (d, 2H).

MS m/z: 504 (M+1).

4-(4-{[(2S,4R)-4-[acetyl(4-chlorophenyl)amino]-2-methyl-3,4-dihydroquinolin-1(2H)-yl]carbonyl}phenoxy)-2-(diethylamino)butanoic acid (H-103)

2-tert-Butoxycarbonylamino-4-hydroxy-butyric acid (0.79 g, 3.6 mmol) was dissolved in 15 ml methanol at room temperature and (trimethylsilyl)diazomethane (2M solution in hexane) was added till solution become yellow. The mixture was concentrated down to afford crude 2-tert-butoxycarbonylamino-4-hydroxy-butyric acid methyl ester.

The ester was dissolved in 20 ml toluene at room temperature with PPh$_3$ (0.94 g, 3.6 mmol), then added N-(4-chlorophenyl)-N-[(2S,4R)-1-(4-hydroxybenzoyl)-2-methyl-1,2,3,4-tetrahydroquinolin-4-yl]acetamide (0.31 g, 0.71 mmol) and stirred for 5 min. DEAD (0.626 g, 3.6 mmol) was added and the reaction was stirred for 18 h at room temperature. The reaction was concentrated and purified by silica gel chromatography (45% CH$_2$Cl$_2$/55% EtOAc) to afford crude methyl 4-(4-{[(2S,4R)-4-[acetyl(4-chlorophenyl)amino]-2-methyl-3,4-dihydroquinolin-1(2H)-yl]carbonyl}phenoxy)-2-[(tert-butoxycarbonyl)amino]butanoate (0.47 g).

Methyl 4-(4-{[(2S,4R)-4-[acetyl(4-chlorophenyl)amino]-2-methyl-3,4-dihydro-quinolin-1(2H)-yl]carbonyl}phenoxy)-2-[(tert-butoxycarbonyl)amino]butanoate was dissolved in 20 ml dichloromethane and 4 ml HCl in dioxane (4M) was added. The mixture was stirred 2 hours and concentrated down. The residue was washed with ether, then partition between 1M NaOH and dichloromethane. The dichloromethane layer was removed and dried with MgSO$_4$. Sodium triacetoxyborohydride (0.61 g, 2.9 mmol) and acetaldehyde (0.33 ml, 5.8 mmol) was added. The mixture was stirred 2 days and washed with 1M NaOH. The mixture was then concentrated and purified by silica gel chromatography (40% CH$_2$Cl$_2$/60% EtOAc) to afford methyl 4-(4-{[(2S,4R)-4-[acetyl(4-chlorophenyl)amino]-2-methyl-3,4-dihydroquinolin-1(2H)-yl]carbonyl}phenoxy)-2-(diethylamino)butanoate (0.075 g, 17%).

Methyl 4-(4-{[(2S,4R)-4-[acetyl(4-chlorophenyl)amino]-2-methyl-3,4-dihydro-quinolin-1(2H)-yl]carbonyl}phenoxy)-2-(diethylamino)butanoate was hydrolyzed to the acid by dissolving in 6 ml tetrahydrofuran/methanol (1/1) and potassium hydroxide (0.04 g in 2 ml water) was added. The mixture was heated to 50° C. for 18 hours. The mixture was cooled to room temperature and concentrated. Then neutralized with 1M HCl and extracted with dichloromethane. The dichloromethane solution was dried and concentrated. The residue was purified by silica gel chromatography (87% CH$_2$Cl$_2$/13% methanol) to afford 4-(4-{[(2S,4R)-4-[acetyl(4-chlorophenyl)amino]-2-methyl-3,4-dihydroquinolin-1(2H)-yl]carbonyl}phenoxy)-2-(diethylamino)butanoic acid (0.04 g, 55%).

$^1$H-NMR (CDCl$_3$) δ: 1.14 (m, 1H), 1.19 (d, 3H), 1.38 (m, 7H), 2.01 (m, 1H), 2.03 (s, 3H), 2.31 (m, 2H), 2.92 (m, 2H), 3.26 (m, 2H), 3.75 (m, 1H), 4.23 (m, 2H), 4.70 (m, 1H), 5.58 (br, 2H), 6.48 (d, 1H), 6.61 (d, 2H), 6.88 (t, 1H), 7.19 (m, 6H), 7.37 (d, 2H).

MS m/z: 593 (M+1)

3-(4-{(2S,4R)-4-[Acetyl-(4-chloro-phenyl)-amino]-2-methyl-3,4-dihydro-2H-quinoline-1-carbonyl}-benzylamino)-propionic acid tert-butyl ester (H-104)

N-{(2S,4R)-1-[4-(aminomethyl)benzoyl]-2-methyl-1,2,3,4-tetrahydroquinolin-4-yl}-N-(4-chlorophenyl)acetamide (145 mg, 0.32 mmol) was dissolved in methylene chloride (2.5 mL) and tert-butyl acrolate (0.052 mL, 0.36 mmol) and stirred at room temperature overnight. The mixture was concentrated then subjected to flash chromatography (50% hexanes/50% ethyl acetate) to afford the title compound (159 mg, 85%) as a white solid.

$^1$H-NMR (CDCl$_3$) δ: 1.13 (s, 3H), 1.15-1.20 (m, 1H), 1.41 (s, 9H), 1.73-2.05 (m, 1H), 2.02 (s, 3H), 2.20-2.37 (m, 1H), 2.40 (t, 2H), 2.77 (t, 2H), 3.72 (s, 2H), 4.69-4.82 (m, 1H), 5.42-5.76 (m, 1H), 6.48 (d, 1H), 6.87 (t, 1H), 7.08-7.31 (m, 8H), 7.37 (d, 2H).

MS m/z: 576 (M+1)

N-{(2S,4R)-1-[3,5-Bis(trifluoromethyl)benzoyl]-6-chloro-2-methyl-1,2,3,4-tetrahydroquinolin-4-yl}-N-(4-chlorophenyl)acetamide (H-105)

N-{(2S,4R)-1-[3,5-Bis(trifluoromethyl)benzoyl]-6-chloro-2-methyl-1,2,3,4-tetrahydroquinolin-4-yl}-N-(4-chlorophenyl)acetamide was prepared following general procedure H up to intermediate 4, substituting benzyl [(2S,4R)-6-chloro-2-methyl-1,2,3,4-tetrahydroquinolin-4-yl] carbamate for benzyl [(2S,4R)-2-methyl-1,2,3,4-tetrahydroquinolin-4-yl]carbamate.

$^1$H-NMR (CDCl$_3$) δ: 1.16 (3H, t), 1.20 (1H, m), 2.02 (s, 3H), 2.25-2.37 (m, 1H), 4.70-4.80 (m, 1H), 5.42-5.56 (m, 1H), 6.40 (d, 1H), 6.90 (dd, 1H), 7.20-7.40 (m, 5H), 7.60 (s, 2H), 7.80 (s, 1H).

MS m/z: 589 (M+1).

N-(4-Chloro-phenyl)-N-[(2S,4R)-2-methyl-(4-pyrrolidin-2-yl-benzoyl)-1,2,3,4-tetrahydro-quinolin-4-yl]-acetamide (H-106)

Benzyl 2-(4-{[(2S,4R)-4-[acetyl(4-chlorophenyl)amino]-2-methyl-3,4-dihydroquinolin-1(2H)-yl]carbonyl}phenyl) pyrrolidine-1-carboxylate (237 mg, 0.381 mmol) was dissolved in HBr/Acetic acid (5 mL) and stirred for 2 h. The reddish slurry was partitioned between Et$_2$O and 1N HCl. The HCl/water layer was washed 3× with Et$_2$O to rid the benzyl bromide. The water layer was neutralized with 1N NaOH, and washed 3× with methylene chloride. The organic layer was dried over MgSO$_4$, filtered and concentrated to afford the title compound (170 mg, 91%) as a white solid. $^1$H-NMR (CDCl$_3$) δ: 1.05-1.20 (m, 1H), 1.13 (s, 3H), 1.50-1.62 (m, 1H), 1.76-1.90 (m, 2H), 2.02 (s, 3H), 2.05-2.20 (m, 2H), 2.20-2.38 (m, 1H), 2.93-3.03 (m, 1H), 3.09-3.18 (m, 1H), 4.05 (t, 1H), 4.72-4.82 (m, 1H), 5.45-5.75 (m, 1H), 6.49 (d, 1H), 6.88 (t, 1H), 7.11-7.29 (m, 8H), 7.37 (d, 2H).

MS m/z: 488 (M+1)

(2S,4R)-N-(4-{4-[Acetyl-(4-chloro-phenyl)-amino]-2-methyl-3,4-dihydro-2H-quinoline-1-carbonyl}-phenyl)-N-methyl-succinamic acid methyl ester (H-107)

(2S,4R)-N-(4-{4-[Acetyl-(4-chloro-phenyl)-amino]-2-methyl-3,4-dihydro-2H-quinoline-1-carbonyl}-phenyl)-N-methyl-succinamic acid methyl ester was prepared from (2S,4R)-N-[1-(4-Amino-benzoyl)-2-methyl-1,2,3,4-tetrahydro-quinolin-4-yl]-N-(4-chloro-phenyl)-acetamide. To a solution of (2S,4R)-N-[1-(4-Amino-benzoyl)-2-methyl-1,2,3,4-tetrahydro-quinolin-4-yl]-N-(4-chloro-phenyl)-acetamide (115 mg, 0.265 mmoles) in dichloromethane (5.0 mL) was added diisopropylethylamine (50 uL, 0.265 mmoles) followed by the addition of methyl succinyl chloride (44 mg, 0.291 mmoles) and was stirred at room temperature overnight. Reaction mixture was diluted with dichloromethane and extracted with saturated aqueous sodium bicarbonate, brine, dried over sodium sulfate, filtered and concentrated under reduced pressure. Product was purified on silica gel by flash chromatography using hexane/ethyl acetate (1:1), ethyl acetate (100%) and ethyl acetate/methanol (10%) to afford (2S,4R)-N-(4-{4-[Acetyl-(4-chloro-phenyl)-amino]-2-methyl-3,4-dihydro-2H-quinoline-1-carbonyl}-phenyl)-succinamic acid methyl ester (55 mg, 35%). $^1$H-NMR (CDCl$_3$) δ: 1.11 (3H, s; overlapping 1H, t), 2.00 (3H, s), 2.30 (1H, m), 2.60-2.80 (2×2H, m), 3.70 (3H, s), 4.70 (1H, m), 5.55 (1H, m), 6.55 (1H, d), 6.90 (1H, dd), 7.10-7.40 (9H, complex), 7.80 (1H, br,s).

ESI-MS m/z: 548 (M+1).

To a solution of (2S,4R)-N-(4-{4-[Acetyl-(4-chloro-phenyl)-amino]-2-methyl-3,4-dihydro-2H-quinoline-1-carbonyl}-phenyl)-succinamic acid methyl ester (55 mg, 0.100 mmoles) in DMF was added sodium hydride (60% dispersion in oil). After 30 minutes, iodomethane (16 uL, 0.11 mmoles) was added to the reaction mixture and stirred at room temperature overnight. Reaction was quenched with water and extracted with ethyl acetate. Combined organics were washed with saturated aqueous sodium bicarbonate, brine, dried over sodium sulfate, filtered and concentrated under reduced pressure. Product was purified on silica gel by flash chromatography using 100% ethyl acetate and 90% ethyl acetate/10% methanol to afford (2S,4R)-N-(4-{4-[Acetyl-(4-chloro-phenyl)-amino]-2-methyl-3,4-dihydro-2H-quinoline-1-carbonyl}-phenyl)-N-methyl-succinamic acid methyl ester (16 mg, 26%).

$^1$H-NMR (CDCl$_3$) δ: 1.11 (3H, s; overlapping 1H, t), 2.00 (3H, s), 2.30 (1H, m, 2H, m), 2.60 (2H, m), 3.18 (3H, s), 3.65 (3H, s), 4.80 (1H, m), 5.60 (1H, m), 6.55 (1H, d), 6.90 (1H, dd), 7.00-7.40 (10H, complex).

ESI-MS m/z: 562 (M+1)

(2S,4R)-N-(4-Chloro-phenyl)-N-{2-methyl-1-[4-(3-pyrrol-1-yl-propoxy)-benzoyl]-1,2,3,4-tetrahydro-quinolin-4-yl}-acetamide (H-108)

(2S,4R)-N-(4-Chloro-phenyl)-N-[1-(4-(hydroxy-benzoyl)-2-methyl-1,2,3,4-tetrahydro-quinolin-4-yl]-acetamide (75 mg, 0.17 mmol) was dissolved in DMF (1 mL) at room temperature. K$_2$CO$_3$ (47 mg, 0.34 mmol) was added followed by 1-(3-bromopropyl)-pyrrole and the reaction was allowed to stir at 70° C. for 3 hrs. The reaction mixture was concentrated in vacuo. The residue was partitioned between ethyl acetate and water, then extracted three times with ethyl acetate. Organic layers were washed with brine, dried over MgSO$_4$, filtered and concentrated down. The crude residue was purified by silica gel chromatography (1/1 ethyl acetate/hexanes) to afford the product.

$^1$H-NMR (CDCl$_3$) δ: 1.1 (d, 3H), 1.2 (m, 1H), 2.0 (s, 3H), 2.1 (m, 2H), 2.3 (m, 1H), 3.8 (t, 2H), 4.1 (t, 2H), 4.8 (m, 1H), 5.6 (m, 1H), 6.1 (d, 2H), 6.5 (d, 1H), 6.6 (d, 2H), 6.65 (d, 2H), 6.9 (t, 1H), 7.1-7.3 (m, 6H), 7.4 (d, 2H).

MS m/z: 442/444 (M+1).

(2S,4R)-2-(4-{4-[Acetyl-(4-chloro-phenyl)-amino]-2-methyl-3,4-dihydro-2H-quinoline-1-carbonyl}-phenoxy)-N-isopropyl-acetamide (H-109)

(2S,4R)-2-(4-{4-[Acetyl-(4-chloro-phenyl)-amino]-2-methyl-3,4-dihydro-2H-quinoline-1-carbonyl}-phenoxy)-N-isopropyl-acetamide was made from (4-{4-[Acetyl-(4-chloro-phenyl)-amino]-2-methyl-3,4-dihydro-2H-quinoline-1-carbonyl}-phenoxy)-acetic acid ethyl este (0.050 g, 0.096 mmol) by addition of isopropylamine (0.680 mL, 8 mmol) with trace sodium cyanide in ethanol (1 mL) to give 43% Yield of (2S,4R)-2-(4-{4-[acetyl(4-chloro-phenyl)-amino]-2-methyl-3,4-dihydro-2H-quinoline-1-carbonyl}-phenoxy)-N-isopropyl-acetamide after HPLC purification.

$^1$H-NMR (CDCl$_3$) δ: 1.12-1.19 (m, 10H), 2.02 (s, 3H), 2.28 (m, 1H), 4.11 (m, 1H), 4.37 (s, 2H), 4.73 (m, 1H), 5.59

(brs, 1H), 6.24 (br, 1H), 6.48 (d, 1H), 6.70 (d, 2H), 6.90 (t, 1H), 7.12-7.30 (m, 6H), 7.37 (d, 2H).
MS m/z: 534 (M+1).

(2S,4R)-4-(4-{4-[Acetyl-(4-chloro-phenyl)-amino]-2-methyl-3,4-dihydro-2H-quinoline-1-carbonyl}-phenyl)-piperazine-1-carboxylic acid tert-butyl ester (H-110)

(2S,4R)-4-(4-{4-[Acetyl-(4-chloro-phenyl)-amino]-2-methyl-3,4-dihydro-2H-quinoline-1-carbonyl}-phenyl)-piperazine-1-carboxylic acid tert-butyl ester was prepared following the procedure for (2S,4R)-1-(4-{4-[Acetyl-(4-chloro-phenyl)-amino]-2-methyl-3,4-dihydro-2H-quinoline-1-carbonyl}-phenyl)-piperidine-4-carboxylic acid ethyl ester, substituting piperazine-1-carboxylic acid tert-butyl ester for piperidine-4-carboxylic acid ethyl ester to yield the product.
$^1$H-NMR (CDCl$_3$) δ: 1.10 (d, 3H), 1.24 (m, 1H), 1.45 (s, 9H), 2.00 (s, 3H), 2.27 (m, 1H), 3.12 (t, 4H), 3.52 (t, 4H), 4.71 (m, 1H), 5.56 (brs, 1H), 6.54 (d, 1H), 6.62 (d, 2H), 6.92 (t, 1H), 7.09-7.28 (m, 6H), 7.36 (d, 2H).
MS m/z: 603.4 (M+1).

(2S,4R)-N-(4-Chloro-phenyl)-N-(1-{4-[2-(1-methanesulfonyl-piperidin-4-yl)-ethoxy]-benzoyl}-2-methyl-1,2,3,4-tetrahydro-quinolin-4-yl)-acetamide (H-111)

4-(2-Hydroxy-ethyl)-piperidine-1-carboxylic acid tert-butyl ester (0.119 g, 0.52 mmol) was dissolved in toluene at room temperature with PPh$_3$ (0.136 g, 0.52 mmol), then added (2S,4R)-N-(4-chloro-phenyl)-N-[1-(4-hydroxy-benzoyl)-2-methyl-1,2,3,4-tetrahydro-quinolin-4-yl]-acetamide (0.150 g, 0.35 mmol) and stirred for 5 min. DEAD (0.090 g, 0.52 mmol) was added and the reaction was stirred for 18 h at room temperature. The reaction was concentrated and purified by silica gel chromatography (45% CH$_2$Cl$_2$ /55% EtOAc) to afford (2S,4R)-4-[2-(4-{4-[acetyl(4-chloro-phenyl)-amino]-2-methyl-3,4-dihydro-2H-quinoline-1-carbonyl}-phenoxy)-ethyl]-piperidine-1-carboxylic acid tert-butyl ester (0.2 g, 90%)
The ester was convert to (2S,4R)-N-(4-chloro-phenyl)-N-{2-methyl-1-[4-(2-piperidin-4-yl-ethoxy)-benzoyl]-1,2,3,4-tetrahydro-quinolin-4-yl}-acetamide by reacting with HCl (4M in dioxane) in dichloromethane at room temperature for 3 hours. The piperidine was dissolved in dichloromethane at room temperature and DIEA was added. Methanesulfonyl chloride was added and the reaction was stirred at room temperature for 4 hours. The reaction mixture was concentrated in vacuo. The crude residue was purified by silica gel chromatography (10% methanol/90% dichloromethane) to afford the product in a 76% yield.
$^1$H-NMR (CDCl$_3$) δ: 1.13 (d, 3H), 1.15 (t, 1H), 1.22-1.38 (m, 2H), 1.68-1.87 (m, 5H), 2.04 (s, 3H), 2.27 (m, 1H), 2.67 (t, 2H), 2.76 (s, 3H), 3.77 (m, 2H), 3.94 (t, 2H), 4.72 (sextet, 1H), 5.58 (bs, 1H), 6.52 (d, 1H), 6.69 (d, 2H), 6.83 (t, 2H), 7.08-7.35 (m, 6H), 7.38 (d, 2H).
MS m/z: 624 (M+1)

4-(4-{[(2S,4R)-4-[(4-Chlorophenyl)(propionyl)amino]-2-methyl-3,4-dihydroquinolin-1(2H)-yl]carbonyl}phenoxy)-2,2-dimethylbutanoic acid (H-112)

Methyl 4-(4-{[(2S,4R)-4-[(4-chlorophenyl)(propionyl)amino]-2-methyl-3,4-dihydroquinolin-1(2H)-yl]carbonyl}phenoxy)-2,2-dimethylbutanoate was dissolved in methanol/tetrahydrofuran/water (2/1/1) then sodium hydroxide (3 equivalents) was added and reaction mixture stirred at 40° C. overnight. The mixture was concentrated, the residue acidified with a 1N HCl aqueous solution and extracted with ethyl acetate. The organic layer was washed with brine, dried over magnesium sulfate, filtered and concentrated to give 4-(4-{[(2S,4R)-4-[(4-chlorophenyl)(propionyl)amino]-2-methyl-3,4-dihydroquinolin-1(2H)-yl]carbonyl}phenoxy)-2,2-dimethylbutanoic acid.
$^1$H-NMR (CDCl$_3$) δ: 1.12-1.16 (m, 6H), 1.22-1.32 (m, 1H), 1.25 (s, 6H), 2.02 (t, 2H), 2.13-2.31 (m, 3H), 3.95 (t, 2H), 4.70-4.77 (m, 1H), 5.60 (br s, 1H), 6.52 (d, 1H), 6.62 (d, 2H), 6.91 (t, 1H), 7.11-7.24 (m, 6H), 7.37 (d, 2H).
MS m/z: 563 (M+1).

(2S,4R)-3-(4-{4-[Acetyl-(4-chloro-phenyl)-amino]-2-methyl-3,4-dihydro-2H-quinoline-1-carbonyl}-phenoxymethyl)-benzoic acid (H-113)

(2S,4R)-3-(4-{4-[Acetyl-(4-chloro-phenyl)-amino]-2-methyl-3,4-dihydro-2H-quinoline-1-carbonyl}-phenoxymethyl)-benzoic acid methyl ester (93 mg, 0.16 mmol) was dissolved in MeOH/THF (2:1, 3 mL). To this solution was added LiOH (2M in H$_2$O, 2 mL). The reaction was stirred at room temperature for 18 hours. The reaction mixture was concentrated in vacuo to remove MeOH and THF. Then 6N HCl aqueous solution was added to acidify the reaction mixture to pH 2-3. The reaction mixture was extracted with DCM (5 mL×3). The extract was washed with water (15 mL), brine (15 mL) and dried over MgSO$_4$, filtered and concentrated under reduced pressure. The crude residue was purified by preparatory HPLC to afford the product (90 mg, 100%).
$^1$H-NMR (CDCl$_3$, 300 MHz) δ: 1.08-1.09 (d, 3H), 1.21-1.26 (s, 1H), 2.03 (s, 3H), 2.24-2.32 (m, 1H), 4.70-4.78 (m, 1H), 5.02-5.05 (s, 2H), 5.58-5.61 (b, 1H), 6.51-6.53 (m, 3H), 6.89-7.29 (m, 8H), 7.36-7.46 (m, 2H), 7.56-7.58 (m, 1H), 7.97-8.04 (m, 2H).
MS m/z: 570 (M+1).

3-[(4-{[(2S,4R)-4-[acetyl(4-chlorophenyl)amino]-2-methyl-3,4-dihydroquinolin-1(2H)-yl]carbonyl}benzyl)amino]propanoic acid (H-114)

3-(4-{(2S,4R)-4-[acetyl(4-chloro-phenyl)-amino]-2-methyl-3,4-dihydro-2H-quinoline-1-carbonyl}-benzylamino)-propionic acid tert-butyl ester (10 mg, 0.017 mmol, 1 equ.) was stirred in a 1/1 mixture of methylene chloride/trifluoroacetic acid (0.8 mL) at room temperature for 2 h. Reaction mixture was concentrated to give 3-[(4-{[(2S,4R)-4-[acetyl(4-chlorophenyl)amino]-2-methyl-3,4-dihydroquinolin-1(2H)-yl]carbonyl}benzyl)amino]propanoic acid as the trifluoroacetic acid salt (12 mg, quant.).
$^1$H-NMR (MeOD) δ: 1.05 (d, 3H), 2.00 (s, 3H), 2.35 (m, 1H), 2.65 (t, 2H), 3.15 (t, 2H), 4.10 (s, 2H), 4.70 (m, 1H), 5.50 (m, 1H), 6.45 (d, 1H), 6.80 (t, 1H), 7.10 (t, 1H), 7.20-7.45 (m, 9H).
MS m/z: 575 (M+1).

(2S,4R)-N-(4-Chloro-phenyl)-N-{1-[4-(3-methanesulfonylamino-propoxy)-benzoyl]-2-methyl-1,2,3,4-tetrahydro-quinolin-4-yl}-acetamide (H-115)

(2S,4R)-N-{1-[4-(3-Amino-propoxy)-benzoyl]-2-methyl-1,2,3,4-tetrahydro-quinolin-4-yl}-N-(4-chloro-phenyl)-acetamide(29 mg, 0.059 mmol) was dissolved in methylene chloride (0.5 mL) and triethylamine (10 drops via pipet) and cooled to −40° C. Methanesulfonyl chloride (5 drops via pipet) was added and the mixture was warmed to 0° C. for 30 minutes. The mixture was partitioned between methylene chloride and water; the methylene chloride layer was dried over MgSO$_4$, filtered and concentrated. The crude residue was purified by silica gel chromatography (50% hexanes/ 50% ethyl acetate—100% ethyl acetate gradient) to afford the product.

$^1$H-NMR (CDCl$_3$) δ: 1.1 (d, 3H), 1.2 (m, 1H), 1.9 (m, 2H), 2.0 (s, 3H), 2.3 (m, 1H), 2.9 (s, 3H), 3.3 (q, 2H), 3.9 (t, 2H), 4.6 (t, 1H), 4.7 (m, 1H), 5.6 (bs, 1H), 6.5 (d, 1H), 6.7 (d, 2H), 6.9 (t, 1H), 7.2 (m, 6H), 7.4 (d, 2H).

MS m/z: 570 (M+1).

4-[5-{[(2S,4R)-4-[acetyl(4-chlorophenyl)amino]-2-methyl-3,4-dihydroquinolin-1(2H)-yl]carbonyl}-2-oxopyridin-1(2H)-yl]-2,2-dimethylbutanoic acid (H-116)

4-[5-{[(2S,4R)-4-[acetyl(4-chlorophenyl)amino]-2-methyl-3,4-dihydroquinolin-1(2H)-yl]carbonyl}-2-oxopyridin-1(2H)-yl]-2,2-dimethylbutanoic acid was prepared from methyl 4-[5-{[(2S,4R)-4-[acetyl(4-chlorophenyl)amino]-2-methyl-3,4-dihydroquinolin-1(2H)-yl]carbonyl}-2-oxopyridin-1(2H)-yl]-2,2-dimethylbutanoate. methyl 4-[5-{[(2S,4R)-4-[acetyl(4-chlorophenyl)amino]-2-methyl-3,4-dihydroquinolin-1(2H)-yl]carbonyl}-2-oxopyridin-1(2H)-yl]-2,2-dimethylbutanoate (0.010 g, 0.017 mmol) was hydrolyzed to the acid by dissolving in tetrahydrofuran and methanol and sodium hydroxide (1N) was added. The mixture was stirred at room temperature overnight. The mixture was cooled to rt, acidified to pH=5 with 1N HCl to form a white precipitate (0.006 g, 63%). The solid was filtered to give 4-[5-{[(2S,4R)-4-[acetyl(4-chlorophenyl)amino]-2-methyl-3,4-dihydroquinolin-1(2H)-yl]carbonyl}-2-oxopyridin-1(2H)-yl]-2,2-dimethylbutanoic acid.

MS m/z: 550 (M+1).

(2S,4R)-N-1-[2-(4-{4-[Acetyl-(4-chloro-phenyl)-amino]-2-methyl-3,4-dihydro-2H-quinoline-1-carbonyl}-phenoxy)-ethyl]-cyclobutanecarboxylic acid (H-117)

(2S,4R)-N-(4-Chloro-phenyl)-N-[1-(4-hydroxy-benzoyl)-2-methyl-1,2,3,4-tetrahydro-quinolin-4-yl]-acetamide (0.17 g, 0.39 mmol) was dissolved in 5 ml DMF at room temperature and K$_2$CO$_3$ (0.323 g, 2.34 mmol) was added. 1-(2-Bromo-ethyl)-cyclobutanecarboxylic acid ethyl ester (0.184 g, 0.78 mmol) prepared according to the procedure from *Tetrahedron* 1994, 50(32), 9825-30 was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (50% EtOAc/50% Hexane) to afford the 1-[2-(4-{4-[acetyl(4-chloro-phenyl)-amino]-2-methyl-3,4-dihydro-2H-quinoline-1-carbonyl}-phenoxy)-ethyl]-cyclobutanecarboxylic acid ethyl ester (0.155 g, 67%).

The ester was hydrolyzed to the acid by dissolving in 8 ml tetrahydrofuran/methanol (1/1) and potassium hydroxide (0.08 g in 3 ml water) was added. The mixture was heated to 40° C. for 3 hours. The mixture was cooled to rt, acidified to form a white precipitate. The solid was filtered to give the product (0.145 g, 98%).

$^1$H-NMR (CDCl$_3$) δ: 1.13 (d, 3H), 1.15 (t, 1H), 1.96 (m, 4H), 2.04 (s, 3H), 2.27 (m, 1H), 2.29 (t, 2H), 2.49 (m, 2H), 3.96 (t, 2H), 4.72 (sextet, 1H), 5.58 (bs, 1H), 6.52 (d, 1H), 6.67 (d, 2H), 6.86 (t, 1H), 7.08-7.35 (m, 6H), 7.38 (d, 2H).

MS m/z: 561 (M+1)

(2S,4R)-N-(4-Chloro-phenyl)-N-(2-methyl-1-{4-[3-(2-oxo-imidazolidin-1-yl)-propoxyl]-benzoyl}-1,2,3,4-tetrahydro-quinolin-4-yl)-acetamide (H-118)

(2S,4R)-N-{1-[4-(3-Amino-propoxy)-benzoyl]-2-methyl-1,2,3,4-tetrahydro-quinolin-4-yl}-N-(4-chloro-phenyl)-acetamide (120 mg, 0.24 mmol) was dissolved in DCM (3 mL) at room temperature. TEA (48 mg, 0.48 mmol) was added followed by 2-chloroethyl isocyanate (51 mg, 0.48 mmol) and the reaction was stirred at room temperature for 18 hours. The mixture was concentrated under reduced pressure and dissolved in ethyl acetate (15 mL). The reaction mixture was washed with sat. aq. NaHCO$_3$ (15 mL), water (15 mL) and brine (15 mL). The organic phase was dried over MgSO$_4$, filtered, and concentrated under reduced pressure. The crude residue was purified by silica gel chromatography (5/95 ethyl acetate/hexane—50/50 ethyl acetate/hexane gradient) to afford to afford slight yellow solid product (163 mg, 100%).

(2S,4R)-N-[1-(4-{3-[3-(2-Chloro-ethyl)-ureido]-propoxy}-benzoyl)-2-methyl-1,2,3,4-tetrahydro-quinolin-4-yl]-N-(4-chloro-phenyl)-acetamide (151 mg, 0.25 mmol) was dissolved in DMF (3 mL) at room temperature. Cs$_2$CO$_3$ (98 mg, 0.30 mmol) was added. The reaction was stirred at room temperature for 18 hours. The mixture was concentrated under reduced pressure and dissolved in ethyl acetate (15 mL). The reaction mixture was washed with sat. aq. NaHCO$_3$ (15 mL), water (15 mL) and brine (15 mL). The organic phase was dried over MgSO$_4$, filtered, and concentrated under reduced pressure. The crude residue was purified by preparatory HPLC to afford the product (0.009 g, 6.4%).

$^1$H-NMR (CDCl$_3$, 300 MHz) δ: 1.11-1.14 (d, 3H), 1.88-1.93 (m, 1H), 1.98-2.01 (m, 5H), 2.26-2.27 (m, 1H), 3.27-3.29 (m, 1H), 3.43-3.47 (1, 2H), 3.77-3.83 (m, 1H) 3.93-3.96 (m, 1H), 4.17-4.20 (m, 1H), 4.51-4.57 (m, 1H), 4.72-4.74 (m, 1H), 4.97-4.10 (broad, 1H), 5.52-5.65 (b, 1H), 6.50-6.93 (m, 4H), 7.12-7.39 (m, 8H).

MS m/z: 562 (M+1).

(2S,4R)-N-(4-Chloro-phenyl)-N-{2-methyl-1-[4-(2-morpholin-4-yl-2-oxo-ethoxy)-benzoyl]-1,2,3,4-tetrahydro-quinolin-4-yl}-acetamide (H-119)

(2S,4R)-N-(4-Chloro-phenyl)-N-{2-methyl-1-[4-(2-morpholin-4-yl-2-oxo-ethoxy)-benzoyl]-1,2,3,4-tetrahydro-quinolin-4-yl}-acetamide was made from (4-{4-[acetyl(4-chloro-phenyl)-amino]-2-methyl-3,4-dihydro-2H-quinoline-1-carbonyl}-phenoxy)-acetic acid ethyl ester (0.050 g, 0.096 mmol) by addition of morpholine (0.400 mL, 4.0 mmol) with trace sodium cyanide in ethanol (1 mL) to give 63% yield of (2S,4R)-N-(4-chloro-phenyl)-N-{2-methyl-1-[4-(2-morpholin-4-yl-2-oxo-ethoxy)-benzoyl]-1,2,3,4-tetrahydro-quinolin-4-yl}-acetamide after HPLC purification.

$^1$H-NMR (CDCl$_3$) δ: 1.13 (m, 4H), 2.01 (s, 3H), 2.27 (m, 1H), 3.52-3.63 (m, 8H), 4.67 (s, 2H), 4.76 (m, 1H), 5.57 (brs, 1H), 6.49 (d, 1H), 6.70 (d, 2H), 6.90 (t, 1H), 7.13-7.28 (m, 6H), 7.36 (d, 2H).

MS m/z: 562 (M+1).

N-(4-Chlorophenyl)-N-[(2S,4R)-1-(4-fluoro-3-vinyl-benzoyl)-2-methyl-1,2,3,4-tetrahydro-quinolin-4-yl]acetamide (H-120)

N-(4-Chlorophenyl)-N-[(2S,4R)-1-(4-fluoro-3-vinylbenzoyl)-2-methyl-1,2,3,4-tetrahydro-quinolin-4-yl]acetamide was prepared following general procedure H, substituting 4-fluoro-3-vinylbenzoyl chloride for 6-trifluoromethyl nicotinyl chloride. (4-fluoro-3-vinylbenzoyl chloride was prepared in 4 steps from 3-bromo-4-fluorobenzoic acid. 3-bromo-4-fluorobenzoic acid was converted to methyl 3-bromo-4-fluorobenzoate by treatment with trimethylsilyl diazomethane (1.5 equivalents) in benzene/methanol (4/1) at room temperature. Subsequent reaction with tributyl(vinyl) tin (1.2 equivalents) in DMF in the presence of catalytic dichlororbis(triphenylphosphine)palladium(II) (0.1 equivalents) at 80° C. under an argon atmosphere, followed by aqueous work up and standard chromatography (10% ethyl acetate/hexanes), yielded methyl 4-fluoro-3-vinylbenzoate. This material was dissolved in methanol/tetrahydrofuran/water (2/1/1) then lithium hydroxide (5.0 equivalents) was added and reaction mixture stirred at room temperature overnight. The mixture was concentrated, the residue acidified with a 1N HCl aqueous solution and extracted with ethyl acetate. The organic layer was washed with brine, dried over magnesium sulfate, filtered and concentrated to give 4-fluoro-3-vinylbenzoic acid. This material was directly converted to 4-fluoro-3-vinylbenzoyl chloride by treatment with thionyl chloride (2.5 equivalents) in dichloromethane at room temperature for 2 hours followed by removal of the volatiles in vaccuo). The rest of the procedures were followed as indicated in general procedure H to afford N-(4-chlorophenyl)-N-[(2S,4R)-1-(4-fluoro-3-vinylbenzoyl)-2-methyl-1,2,3,4-tetrahydroquinolin-4-yl]acetamide.

$^1$H-NMR (CDCl$_3$) δ: 1.16 (d, 3H), 1.22-1.26 (m, 1H), 2.03 (s, 3H), 2.24-2.31 (m, 1H), 4.72-4.82 (m, 1H), 5.31 (d, 1H) 5.61 (br s, 1H), 5.65 (d, 1H), 6.51 (d, 1H), 6.71 (dd, 1H), 6.80 (dd, 1H), 6.91-7.01 (m, 2H), 7.15-7.31 (m, 4H), 7.37-7.45 (m, 3H).

MS m/z: 463 (M+1).

N-(4-chlorophenyl)-N-[(2S,4R)-1-(4-ethoxybenzoyl)-2-methyl-1,2,3,4-tetrahydroquinolin-4-yl]acetamide (H-121)

N-(4-chlorophenyl)-N-[(2S,4R)-1-(4-ethoxybenzoyl)-2-methyl-1,2,3,4-tetrahydroquinolin-4-yl]acetamide was made following general procedure I, substituting bromo-ethane for ethyl 4-bromoacetate.

$^1$H-NMR (CDCl$_3$) δ: 1.14 (d, 3H), 1.17 (m, 1H), 1.33 (t, 3H), 2.02 (s, 3H), 2.25 (m, 1H), 3.93 (q, 2H), 4.69 (m, 1H), 5.58 (br, 1H), 6.52 (d, 1H), 6.64 (d, 2H), 6.93 (t, 1H), 7.18 (m, 6H), 7.36 (d, 2H).

MS m/z: 463 (M+1)

(2S,4R)-1-(4-{4-[Acetyl-(4-chloro-phenyl)-amino]-2-methyl-3,4-dihydro-2H-quinoline-1-carbonyl}-phenyl)-piperidine-4-carboxylic acid (H-122)

(2S,4R)-1-(4-{4-[Acetyl-(4-chloro-phenyl)-amino]-2-methyl-3,4-dihydro-2H-quinoline-1-carbonyl}-phenyl)-piperidine-4-carboxylic acid was made from (2S,4R)-1-(4-{4-[acetyl(4-chloro-phenyl)-amino]-2-methyl-3,4-dihydro-2H-quinoline-1-carbonyl}-phenyl)-piperidine-4-carboxylic acid ethyl ester was hydrolyzed to the acid by dissolving in tetrahydrofuran and ethanol and lithium hydroxide (1N) was added and heated 50° C. for 2 h. The mixture was cooled to room temperature, acidified to form a white precipitate. The solid was filtered to give to afford the product after HPLC purification.

$^1$H-NMR (CDCl$_3$) δ: 1.10 (d, 3H), 1.23 (m, 1H), 1.64 (m, 2H), 2.00 (m, 5H), 2.34 (m, 1H), 2.59 (m, 1H), 2.84 (m, 1H), 3.08 (m, 1H), 3.40 (m, 1H), 3.67 (m, 1H), 4.71 (m, 1H), 5.58 (brs, 1H), 6.57 (d, 1H), 6.66 (d, 2H), 6.93 (t, 1H), 7.07-7.28 (m, 6H), 7.37 (d, 2H), 9.30 (br, 1H).

MS m/z: 546.3 (M+1).

(2S,4R)-N-(4-Chloro-phenyl)-N-{2-methyl-1-[4-(3-sulfamoyl-propoxy)-benzoyl]-1,2,3,4-tetrahydro-quinolin-4-yl}-acetamide (H-123)

(2S,4R)-3-(4-{4-[Acetyl-(4-chloro-phenyl)-amino]-2-methyl-3,4-dihydro-2H-quinoline-1-carbonyl}-phenoxy)-propane-1-sulfonic acid (175 mg, 0.315 mmol) was dissolved in methylene chloride (3 mL) and cooled to 0° C. PCl$_5$ (78 mg, 0.378 mmol) was added and the reaction was stirred at room temperature over night. The mixture was partitioned between methylene chloride and water; the organic layer was dried over Na$_2$SO$_4$, filtered and concentrated. The crude sulfonyl chloride was dissolved in acetone (5 mL); concentrated ammonium hydroxide (3.5 mL) was added. After 15 minutes, the mixture was partitioned between methylene chloride and water; the organic layer was dried over Na$_2$SO$_4$, filtered and concentrated. The crude residue was purified by preparatory HPLC to afford the product.

$^1$H-NMR (CDCl$_3$) δ: 1.1 (d, 3H), 1.1 (m, 1H), 2.0 (s, 3H), 2.2 (m, 3H), 3.2 (t, 2H), 3.9 (t, 2H), 4.8 (d, 1H), 5.6 (bs, 1H), 6.5 (d, 1H), 6.6 (d, 2H), 6.9 (t, 1H), 7.2 (m, 8H), 7.4 (d, 2H).

MS m/z: 556 (M+1).

3-{[(2S,4R)-4-[acetyl(4-chlorophenyl)amino]-2-methyl-3,4-dihydroquinolin-1(2H)-yl]carbonyl}benzoic acid (H-124)

3-{[(2S,4R)-4-[acetyl(4-chlorophenyl)amino]-2-methyl-3,4-dihydroquinolin-1(2H)-yl]carbonyl}benzoic acid was prepared following general procedure H, substituting methyl 3-(chlorocarbonyl)benzoate for 6-trifluoromethyl nicotinyl chloride. (Methyl 3-(chlorocarbonyl)benzoate was prepared in one step from 3-(methoxycarbonyl)benzoic acid. Treatment of this carboxylic acid with oxalyl chloride and catalytic DMF afforded methyl 3-(chlorocarbonyl)benzoate in decent yield). Hydrolysis of methyl 3-{[(2S,4R)-4-[acetyl(4-chlorophenyl)amino]-2-methyl-3,4-dihydroquinolin-1(2H)-yl]carbonyl}benzoate with lithium hydroxide, water, methanol and tetrahydrofuran yielded 3-{[(2S,4R)-4-[acetyl(4-chlorophenyl)amino]-2-methyl-3,4-dihydroquinolin-1(2H)-yl]carbonyl}benzoic acid.

$^1$H-NMR (CDCl$_3$) δ: 1.18 (d, 3H), 1.18-1.26 (m, 1H), 2.05 (s, 3H), 2.27-2.39 (m, 1H), 4.74-4.86 (m, 1H), 5.53-5.70 (m, 1H), 6.48 (d, 1H), 6.88 (t, 1H), 7.13-7.24 (m, 5H), 7.32 (d, 1H), 7.40 (d, 2H), 7.97-8.02 (m, 1H), 8.12 (bs, 1H).

MS m/z: 463 (M+1).

(2S,4R)-N-(4-Chloro-phenyl)-N-{1-[4-(3-cyano-propoxy)-benzoyl]-2-methyl-1,2,3,4-tetrahydro-quinolin-4-yl}-acetamide (H-125)

(2S,4R)-N-(4-Chloro-phenyl)-N-[1-(4-hydroxy-benzoyl)-2-methyl-1,2,3,4-tetrahydro-quinolin-4-yl]-acetamide was dissolved in DMF at room temperature and K$_2$CO$_3$ was added. 4-Bromobutylnitrile was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (50% EtOAc/50% Hexane) to afford the product.

$^1$H-NMR (CDCl$_3$) δ: 1.13 (d, 3H), 1.15 (m, 1H), 1.90 (m, 1H), 2.02 (s, 3H), 2.09 (m, 1H), 2.30 (m, 1H), 2.54 (t, 2H), 3.99 (t, 2H), 4.72 (sextet, 1H), 5.6 (bs, 1H), 6.52 (d, 1H), 6.65 (d, 2H), 6.93 (t, 1H), 7.15 (m, 5H), 7.27 (t, 1H), 7.37 (d, 2H).

MS m/z: 502 (M+1).

(2S,4R)-N-(4-Chloro-phenyl)-N-(2-methyl-1-{4-[3-(3-methyl-[1,2,4]oxadiazol-5-yl)-propoxy]-benzoyl}-1,2,3,4-tetrahydro-quinolin-4-yl)-acetamide (H-126)

(2S,4R)-N-(4-Chloro-phenyl)-N-(2-methyl-1-{4-[3-(3-methyl-[1,2,4]oxadiazol-5-yl)-propoxy]-benzoyl}-1,2,3,4-tetrahydro-quinolin-4-yl)-acetamide was prepared from (2S,4R)-4-(4-{4-[acetyl(4-chloro-phenyl)-amino]-2-methyl-3,4-dihydro-2H-quinoline-1-carbonyl}-phenoxy)-butyric acid methyl ester. Acetamide oxime (0.043 g, 0.58 mmol) was suspended in THF under N$_2$ and NaH (60% dispersion in oil) (0.025 g, 1.0 mmol) was added followed by 4A° molecular sieves and heated to 60° C. for 1 h. (2S,4R)-4-(4-{4-[acetyl (4-chloro-phenyl)-amino]-2-methyl-3,4-dihydro-2H-quinoline-1-carbonyl}-phenoxy)-butyric acid methyl ester was added and heated to reflux for 4.5 h. The reaction was filtered and concentrated down and partitioned between CH$_2$Cl$_2$ and water. The aqueous layer was extracted 3×CH$_2$Cl$_2$ and dried over MgSO$_4$, filtered, concentrated and purified by silica gel chromatography (100% EtOAc) to afford (2S,4R)-N-(4-Chloro-phenyl)-N-(2-methyl-1-{4-[3-(3-methyl-[1,2,4]oxadiazol-5-yl)-propoxy]-benzoyl}-1,2,3,4-tetrahydro-quinolin-4-yl)-acetamide in 44% yield.

$^1$H-NMR (CDCl$_3$) δ: 1.12 (d, 3H), 1.13 (m, 1H), 2.00 (s, 3H), 2.23 (m, 2H), 2.38 (s, 3H), 3.00 (m, 2H), 3.96 (m, 2H), 4.72 (sextet, 1H), 5.58 (bs, 1H), 6.49 (d, 1H), 6.62 (d, 2H), 6.91 (t, 1H), 7.31-7.25 (m, 7H), 7.34 (d, 1H).

MS m/z: 559 (M+1).

N-(4-chlorophenyl)-N-{(2S,4R)-1-[4-(difluoromethoxy)benzoyl]-2-methyl-1,2,3,4-tetrahydroquinolin-4-yl}acetamide (H-127)

N-(4-chlorophenyl)-N-{(2S,4R)-1-[4-(difluoromethoxy)benzoyl]-2-methyl-1,2,3,4-tetrahydroquinolin-4-yl}acetamide was made following general procedure I, substituting methyl chlorodifluoroacetate for ethyl 4-bromoacetate.

$^1$H-NMR (CDCl$_3$) δ: 1.16 (d, 3H), 1.17 (m, 1H), 2.02 (s, 3H), 2.29 (m, 1H), 4.75 (m, 1H), 5.58 (br, 1H), 6.52 (d, 1H), 6.93 (m, 3H), 7.19 (m, 6H), 7.38 (m, 3H).

MS m/z: 485 (M+1)

(2S,4R)-N-1-[2-(4-{4-[Acetyl-(4-chloro-phenyl)-amino]-2-methyl-3,4-dihydro-2H-quinoline-1-carbonyl}-phenoxy)-ethyl]-1H-imidazole-2-carboxylic acid amide (H-128)

(2S,4R)-N-1-[2-(4-{4-[Acetyl-(4-chloro-phenyl)-amino]-2-methyl-3,4-dihydro-2H-quinoline-1-carbonyl}-phenoxy)-ethyl]-1H-imidazole-2-carboxylic acid amide was prepared from (2S,4R)-N-1-[2-(4-{4-[Acetyl-(4-chloro-phenyl)-amino]-2-methyl-3,4-dihydro-2H-quinoline-1-carbonyl}-phenoxy)-ethyl]-1H-imidazole-2-carboxylic acid by coupling NH$_4$Cl, HATU, DIEA, HOBt in DMF at room temperature to yield (2S,4R)-N-1-[2-(4-{4-[acetyl(4-chloro-phenyl)-amino]-2-methyl-3,4-dihydro-2H-quinoline-1-carbonyl}-phenoxy)-ethyl]-1H-imidazole-2-carboxylic acid amide. The reaction mixture was concentrated down and partitioned between ethyl acetate and water, then extracted three times with ethyl acetate, dried over magnesium sulfate, filtered and concentrated down. The residue was purified by silica gel chromatography (10% methanol/90% dichloromethane) to afford pure product in a 67% yield.

$^1$H-NMR (CDCl$_3$) δ: 1.15 (d, 3H), 1.17 (t, 1H), 2.03 (s, 3H), 2.27 (m, 1H), 4.26 (bs, 2H), 4.72 (sextet, 1H), 4.78 (bs, 2H), 5.58 (bs, 1H), 6.48 (d, 1H), 6.64 (d, 2H), 6.91 (t, 1H), 6.98 (s, 1H), 7.03 (s, 1H), 7.08-7.40 (m, 10H).

MS m/z: 572 (M+1).

(2S,4R)-N-(1-{4-[3-(4-Acetyl-piperazin-1-yl)-propoxy]-benzoyl}-2-methyl-1,2,3,4-tetrahydro-quinolin-4-yl)-N-(4-chloro-phenyl)-acetamide (H-129)

(2S,4R)-N-(4-Chloro-phenyl)-N-{2-methyl-1-[4-(3-piperazin-1-yl-propoxy)-benzoyl]-1,2,3,4-tetrahydro-quinolin-4-yl}-acetamide (168 mg) was dissolved in CH$_2$Cl$_2$ (2 mL). Acetic chloride (47 mg) and DIEA (52 uL) were added. The reaction mixture was stirred at room temperature overnight. The organic phase was washed with sat. NaHCO$_3$ (2×5 mL), dried over Na$_2$SO$_4$ and concentrated. The residue was purified by silica gel chromatography (EtOAc) to afford pure (2S,4R)-N-(1-{4-[3-(4-acetyl-piperazin-1-yl)-propoxy]-benzoyl}-2-methyl-1,2,3,4-tetrahydro-quinolin-4-yl)-N-(4-chloro-phenyl)-acetamide (100 mg, 57%).

$^1$H-NMR (CDCl$_3$) δ: 1.13 (d, 4H), 1.88-1.94 (m, 2H), 2.02 (s, 3H), 2.06 (s, 3H), 2.20-2.48 (m, 7H), 3.43 (bs, 2H), 3.59 (bs, 2H), 3.94 (t, 2H), 4.74 (sextet, 1H), 5.60 (bs, 1H), 6.53 (d, 1H), 6.66 (d, 2H), 6.91 (t, 1H) 7.11-7.38 (m, 8H).

MS m/z: 603 (M+1).

(2S,4R)-1-(4-{4-[Acetyl-(4-chloro-phenyl)-amino]-2-methyl-3,4-dihydro-2H-quinoline-1-carbonyl}-phenyl)-piperidine-3-carboxylic acid ethyl ester (H-130)

(2S,4R)-1-(4-{4-[Acetyl-(4-chloro-phenyl)-amino]-2-methyl-3,4-dihydro-2H-quinoline-1-carbonyl}-phenyl)-piperidine-3-carboxylic acid ethyl ester was prepared following the procedure for (2S,4R)-1-(4-{4-[Acetyl-(4-chloro-phenyl)-amino]-2-methyl-3,4-dihydro-2H-quinoline-1-carbonyl}-phenyl)-piperidine-4-carboxylic acid ethyl ester, substituting piperidine-3-carboxylic acid ethyl ester for piperidine-4-carboxylic acid ethyl ester to yield the product.

$^1$H-NMR (CDCl$_3$) δ: 1.10 (d, 3H), 1.23 (t, 3H), 1.23 (m, 1H), 1.77 (m, 2H), 1.94 (m, 2H), 2.01 (s, 3H), 2.28 (m, 1H), 2.40 (m, 1H), 2.77 (t, 2H), 3.62 (m, 2H), 4.11 (q, 2H), 4.70 (m, 1H), 5.58 (brs, 1H), 6.56 (d, 1H), 6.64 (d, 2H), 6.92 (t, 1H), 7.07-7.28 (m, 6H), 7.35 (d, 2H).

MS m/z: 574.4 (M+1).

5-(4-{[(2S,4R)-4-[acetyl(4-chlorophenyl)amino]-2-methyl-3,4-dihydroquinolin-1(2H)-yl]carbonyl}-2-fluorophenyl)-2,2-dimethylpentanoic acid (H-131)

Methyl 5-(4-{[(2S,4R)-4-[acetyl(4-chlorophenyl)amino]-2-methyl-3,4-dihydroquinolin-1(2H)-yl]carbonyl}-2-fluorophenyl)-2,2-dimethylpentanoate (70 mg, 0.12 mmol, 1 eq.) was dissolved in methanol/tetrahydrofuran (2/1) (3 ml). A solution of sodium hydroxide (8 mg, 0.20 mmol, 1.7 eq.) in water (1 ml) was added and reaction mixture heated to 40° C. for 8 h. The mixture was concentrated and the residue was acidified with a 1N HCl aqueous solution and extracted with ethyl acetate. The organic layer was washed with brine, dried over magnesium sulfate, filtered and concentrated to give the crude acid. Purification by silica gel chromatography (methylene chloride/methanol: 99/1 to 98/2 gradient) gave pure 5-(4-{[(2S,4R)-4-[acetyl(4-chlorophenyl)amino]-2-methyl-3,4-dihydroquinolin-1(2H)-yl]carbonyl}-2-fluorophenyl)-2,2-dimethylpentanoic acid (56 mg, 84%).

$^1$H-NMR (CDCl$_3$) δ: 1.15 (d, 3H), 1.50 (m, 4H), 2.05 (s, 3H), 2.30 (m, 1H), 2.55 (m, 2H), 4.80 (m, 1H), 5.60 (m, 1H), 6.55 (d, 1H), 6.75 (d, 1H), 6.90 (m, 3H), 7.20-7.40 (m, 6H).

MS m/z: 565 (M+1).

(2S,4R)-N-(4-Chloro-phenyl)-N-(2-methyl-1-{4-[3-(2-oxo-pyrrolidin-1-yl)-propoxy]-benzoyl}-1,2,3,4-tetrahydro-quinolin-4-yl)-acetamide (H-132)

N-(3-hydroxypropyl)-2-pyrrolidone was dissolved in benzene at room temperature with PPh$_3$ (0.044 g, 0.16 mmol) added (2S,4R)-N-(4-chloro-phenyl)-N-[1-(4-hydroxy-benzoyl)-2-methyl-1,2,3,4-tetrahydro-quinolin-4-yl]-acetamide (0.100 g, 0.22 mmol) and stirred for 5 min. DEAD (0.029 g, 0.16 mmol) was added and the reaction was stirred for 18 h at room temperature. The reaction was concentrated and purified by silica gel chromatography (4% MeOH/96% CH$_2$Cl$_2$ to 5% MeOH/95% CH$_2$Cl$_2$ to 6% MeOH/94% CH$_2$Cl$_2$) to afford the product in 45% yield.

$^1$H-NMR (CDCl$_3$) δ: 1.13 (d, 3H), 1.14 (m, 1H), 1.96 (m, 4H), 2.02 (s, 3H), 2.34 (t, 3H), 3.39 (q, 4H), 3.90 (m, 2H), 4.72 (sextet, 1H), 5.59 (bs, 1H), 6.52 (d, 1H), 6.63 (d, 2H), 7.18 (m, 6H), 7.37 (d, 2H).

MS m/z: 560 (M+1).

(2S,4R)-N-(4-Chloro-phenyl)-N-{1-[4-(3-ethyl-2-oxo-oxazolidin-5-ylmethoxy)-benzoyl]-2-methyl-1,2,3,4-tetrahydro-quinolin-4-yl}-acetamide (H-133)

(2S,4R)-N-(4-Chloro-phenyl)-N-{1-[4-(3-ethyl-2-oxo-oxazolidin-5-ylmethoxy)-benzoyl]-2-methyl-1,2,3,4-tetrahydro-quinolin-4-yl}-acetamide was prepared from (2S,4R)-N-(4-chloro-phenyl)-N-{2-methyl-1-[4-(2-oxo-oxazolidin-5-ylmethoxy)-benzoyl]-1,2,3,4-tetrahydro-quinolin-4-yl}-acetamide following ref. (*Tetrahedron Lett* 2002, 43(46), 8327)

$^1$H-NMR (CDCl$_3$) δ: 1.15 (m, 7H), 2.03 (s, 3H), 2.27 (m, 1H), 3.28 (q, 2H), 3.47 (m, 1H), 3.63 (t, 1H), 4.05 (d, 2H), 4.73 (m, 2H), 5.58 (bs, 1H), 6.47 (d, 1H), 6.67 (d, 2H), 6.86 (t, 1H), 7.08-7.35 (m, 6H), 7.38 (d, 2H).

MS m/z: 563 (M+1)

4-(4-{[(2S,4R)-4-[acetyl(4-chlorophenyl)amino]-6-chloro-2-methyl-3,4-dihydroquinolin-1(2H)-yl]carbonyl}phenoxy)-2,2-dimethylbutanoic acid (H-134)

N-[(2S,4R)-6-chloro-1-(4-methoxybenzoyl)-2-methyl-1,2,3,4-tetrahydroquinolin-4-yl]-N-(4-chlorophenyl)acetamide was elaborated to 4-(4-{[(2S,4R)-4-[acetyl(4-chlorophenyl)amino]-6-chloro-2-methyl-3,4-dihydroquinolin-1(2H)-yl]carbonyl}phenoxy)-2,2-dimethylbutanoic acid following procedures described for 4-(4-{[(2S,4R)-4-[acetyl(4-chlorophenyl)amino]-2-methyl-3,4-dihydroquinolin-1(2H)-yl]carbonyl}phenoxy)-2,2-dimethylbutanoic acid.

$^1$H-NMR (CDCl$_3$) δ: 1.10 (d, 3H), 1.13 (t, 1H), 1.24 (s, 6H), 2.01 (s, 3H), 2.03 (t, 2H), 2.27 (m, 1H), 3.96 (t, 2H), 4.71 (sextet, 1H), 5.54 (bs, 1H), 6.43 (d, 1H), 6.65 (d, 2H), 6.89 (d, 1H), 7.10-7.20 (m, 5H), 7.38 (d, 2H).

MS m/z: 583 (M+1).

(2S,4R)-4-[4-(4-{4-[Acetyl-(4-chloro-phenyl)-amino]-2-methyl-3,4-dihydro-2H-quinoline-1-carbonyl}-phenyl)-piperazin-1-yl]-2,2-dimethyl-butyric acid methyl ester (H-135)

(2S,4R)-4-[4-(4-{4-[Acetyl-(4-chloro-phenyl)-amino]-2-methyl-3,4-dihydro-2H-quinoline-1-carbonyl}-phenyl)-piperazin-1-yl]-2,2-dimethyl-butyric acid methyl ester was prepared from (2S,4R)-4-(4-{4-[acetyl(4-chloro-phenyl)-amino]-2-methyl-3,4-dihydro-2H-quinoline-1-carbonyl}-phenyl)-piperazine-1-carboxylic acid ethyl ester by removal of the carbamate. (2S,4R)-4-(4-{4-[acetyl(4-chloro-phenyl)-amino]-2-methyl-3,4-dihydro-2H-quinoline-1-carbonyl}-phenyl)-piperazine-1-carboxylic acid ethyl ester was dissolved in acetonitrile (2 mL). Iodotrimetylsilane was added and the reaction was allowed to stir at room temperature over night. Excess reagent was quenched by the addition of methanol (1 mL) and the mixture was concentrated under reduced pressure. The crude residue was partitioned between ethyl acetate and saturated aqueous sodium bicarbonate. The extracts were washed with 1 M sodium hydroxide, saturated aqueous sodium thiosulfate and brine, dried over sodium sulfate, filtered, concentrated and purified by silica gel chromatography to yield N-(4-chloro-phenyl)-N-[2-methyl-1-(4-piperazin-1-yl-benzoyl)-1,2,3,4-tetrahydro-quinolin-4-yl]-acetamide.

(2S,4R)-N-(4-chloro-phenyl)-N-[2-methyl-1-(4-piperazin-1-yl-benzoyl)-1,2,3,4-tetrahydro-quinolin-4-yl]-acetamide was dissolved in DMF at room temperature. K$_2$CO$_3$ was added followed by 4-Bromo-2,2-dimethyl-butyric acid methyl ester and the reaction was allowed to stir at 90° C. over night. The reaction mixture was concentrated in vacuo. The residue was partitioned between ethyl acetate and water, then extracted three times with ethyl acetate, dried over MgSO$_4$, filtered and concentrated down. The crude residue was purified by HPLC to afford the product.

$^1$H-NMR (CDCl$_3$) δ: 1.12 (d, 3H), 1.18 (s+m, 7H), 1.75 (m, 2H), 2.01 (s, 3H), 2.32 (m, 3H), 2.52 (m, 4H), 3.16 (m, 4H), 3.64 (s, 3H), 4.71 (m, 1H), 5.60 (brs, 1H), 6.56 (d, 1H), 6.62 (d, 2H), 6.93 (t, 1H), 7.08-7.29 (m, 6H), 7.36 (d, 2H).

MS m/z: 631 (M+1).

(2S,4R)-4-(4-{4-[Acetyl-(4-chloro-phenyl)-amino]-2-methyl-3,4-dihydro-2H-quinoline-1-carbonyl}-phenoxy)-2-methyl-butyric acid methyl ester (H-136)

(2S,4R)-N-(4-Chloro-phenyl)-N-[1-(4-hydroxy-benzoyl)-2-methyl-1,2,3,4-tetrahydro-quinolin-4-yl]-acetamide (230 mg, 0.531 mmol) was dissolved in DMF (5 mL) at room temperature. Cs$_2$CO$_3$ (433 mg, 1.33 mmol) was added followed by 4-chloro-2-methyl-butyric acid methyl ester (120 mg, 0.796 mmol) and the reaction was allowed to stir overnight. The mixture was partitioned between methylene chloride and water; the organic layer was dried over Na$_2$SO$_4$, filtered and concentrated. The crude residue was purified by silica gel chromatography (1/1 hexanes/ethyl acetate—ethyl acetate gradient) to afford the product.

$^1$H-NMR (CDCl$_3$) δ: 1.1 (d, 3H), 1.2 (d, 3H), 1.2 (m, 1H), 1.8 (m, 1H), 2.0 (s, 3H), 2.1 (m, 1H), 2.2 (m, 1H), 2.7 (m, 1H), 3.7 (s, 3H), 3.9 (t, 2H), 4.7 (m, 1H), 5.6 (bs, 1H), 6.5 (d, 1H), 6.6 (d, 2H), 6.9 (t, 1H), 7.2 (m, 6H), 7.4 (d, 2H).

MS m/z: 549 (M+1).

(2S,4R)-N-1-[2-(4-{4-[Acetyl-(4-chloro-phenyl)-amino]-2-methyl-3,4-dihydro-2H-quinoline-1-carbonyl}-phenoxy)-ethyl]-1H-imidazole-2-carboxylic acid (H-137)

(2S,4R)-N-(4-Chloro-phenyl)-N-[1-(4-hydroxy-benzoyl)-2-methyl-1,2,3,4-tetrahydro-quinolin-4-yl]-acetamide (0.165 g, 0.38 mmol) was dissolved in DMF at room temperature and $K_2CO_3$ (0.315 g, 2.28 mmol) was added. 1-(2-Bromo-ethyl)-1H-imidazole-2-carboxylic acid methyl ester (0.304 g, 1.14 mmol) was added and the reaction was allowed to heat to 80° C. overnight. The reaction mixture was concentrated in vacuo. The residue was partitioned between ethyl acetate and water, then extracted three times with ethyl acetate, dried over $MgSO_4$, filtered and concentrated down. The crude residue was purified by silica gel chromatography (50% EtOAc/50% Hexane) to afford (2S,4R)-N-1-[2-(4-{4-[acetyl(4-chloro-phenyl)-amino]-2-methyl-3,4-dihydro-2H-quinoline-1-carbonyl}-phenoxy)-ethyl]-1H-imidazole-2-carboxylic acid methyl ester (0.176 g, 83%).

The ester was hydrolyzed to the acid by dissolving in tetrahydrofuran and ethanol and sodium hydroxide (1N) was added. The mixture was stirred at room temperature 4 hours. The mixture was cooled to room temperature, acidified to form a white precipitate. The solid was filtered to give the product in a 74% yield.

$^1$H-NMR (CDCl$_3$) δ: 1.13 (d, 3H), 1.15 (t, 1H), 1.98 (s, 3H), 2.27 (m, 1H), 4.29 (bs, 2H), 4.72 (sextet, 1H), 5.09 (bs, 2H), 5.58 (bs, 1H), 6.48 (d, 1H), 6.64 (d, 2H), 6.91 (t, 1H), 6.98 (s, 1H), 7.03 (s, 1H), 7.08-7.40 (m, 10H), 8.65 (bs, 1H).

MS m/z: 573 (M+1)

4-(4-{[(2S,4R)-4-[Acetyl-(4-chlorophenyl)amino]-2-methyl-3,4-dihydroquinolin-1(2H)-yl]carbonyl}phenyl)-2,2-dimethylbutanoic acid (H-138)

Methyl 4-(4-{[(2S,4R)-4-[acetyl(4-chlorophenyl)amino]-2-methyl-3,4-dihydroquinolin-1(2H)-yl]carbonyl}phenyl)-2,2-dimethylbutanoate was dissolved in methanol/tetrahydrofuran/water (2/1/1) then sodium hydroxide (3 equivalents) was added and reaction mixture stirred at 40° C. overnight. The mixture was concentrated, the residue acidified with a 1N HCl aqueous solution and extracted with ethyl acetate. The organic layer was washed with brine, dried over magnesium sulfate, filtered and concentrated to give 4-(4-{[(2S,4R)-4-[Acetyl-(4-chlorophenyl)amino]-2-methyl-3,4-dihydroquinolin-1(2H)-yl]carbonyl}phenyl)-2,2-dimethylbutanoic acid.

$^1$H-NMR (CDCl$_3$) δ: 1.14 (d, 3H), 1.22 (s, 6H), 1.22-1.26 (m, 1H), 1.75 (ddd, 2H), 2.03 (s, 3H), 2.24-2.32 (m, 1H), 2.49 (ddd, 2H), 4.72-4.80 (m, 1H), 5.60 (br s, 1H), 6.49 (d, 1H), 6.89 (t, 1H), 6.97 (d, 2H), 7.08-7.29 (m, 6H), 7.37 (d, 2H).

MS m/z: 533 (M+1).

5-(4-{[(2S,4R)-4-[(4-chlorophenyl)(glycoloyl)amino]-2-methyl-3,4-dihydroquinolin-1(2H)-yl]carbonyl}phenyl)-2,2-dimethylpentanoic acid (H-139)

Methyl 5-(4-{[(2S,4R)-4-[[(acetyloxy)acetyl](4-chlorophenyl)amino]-2-methyl-3,4-dihydroquinolin-1(2H)-yl]carbonyl}phenyl)-2,2-dimethylpentanoate (100 mg, 0.16 mmol, 1 eq.) was dissolved in methanol/tetrahydrofuran (2/1) (2 ml). A solution of sodium hydroxide (32 mg, 0.81 mmol, 5 eq.) in water (1 ml) was added and reaction mixture heated to 45° C. for 8 h and at room temperature for 20 h. The mixture was concentrated and the residue was acidified with a 1N HCl aqueous solution and extracted with ethyl acetate. The organic layer was washed with brine, dried over magnesium sulfate, filtered and concentrated to give the crude acid. Purification by silica gel chromatography gave pure 5-(4-{[(2S,4R)-4-[(4-chlorophenyl)(glycoloyl)amino]-2-methyl-3,4-dihydroquinolin-1(2H)-yl]carbonyl}phenyl)-2,2-dimethylpentanoic acid (63 mg, 70%).

$^1$H-NMR (MeOD) δ: 1.10 (d, 3H), 1.15 (s, 6H), 1.45 (m, 4H), 2.45 (m, 1H), 2.50 (t, 2H), 3.90-4.10 (dd, 2H), 4.75 (m, 1H), 5.55 (m, 1H), 6.55 (d, 1H), 6.95 (t, 1H), 7.00-7.20 (m, 5H), 7.30-7.55 (m, 5H).

MS m/z: 563 (M+1).

(2S,4R)-[4-(4-{4-[Acetyl-(4-chloro-phenyl)-amino]-2-methyl-3,4-dihydro-2H-quinoline-1-carbonyl}-phenyl)-piperazin-1-yl]-acetic acid (H-140)

(2S,4R)-[4-(4-{4-[Acetyl-(4-chloro-phenyl)-amino]-2-methyl-3,4-dihydro-2H-quinoline-1-carbonyl}-phenyl)-piperazin-1-yl]-acetic acid was prepared following the procedure for (2S,4R)-1-(4-{4-[acetyl(4-chloro-phenyl)-amino]-2-methyl-3,4-dihydro-2H-quinoline-1-carbonyl}-phenyl)-piperidine-4-carboxylic acid ethyl ester, substituting piperazin-1-yl-acetic acid ethyl ester for piperidine-4-carboxylic acid ethyl ester to yield the (2S,4R)-[4-(4-{4-[Acetyl-(4-chloro-phenyl)-amino]-2-methyl-3,4-dihydro-2H-quinoline-1-carbonyl}-phenyl)-piperazin-1-yl]-acetic acid ethyl ester. The ester was hydrolyzed to the acid by dissolving in tetrahydrofuran and ethanol and lithium hydroxide (1N) was added and heated 50° C. for 2 h. The mixture was cooled to room temperature, acidified to form a white precipitate. The solid was filtered to give to afford the product after HPLC purification.

$^1$H-NMR (CDCl$_3$) δ: 1.10 (d, 3H), 1.20 (m, 1H), 2.00 (s, 3H), 2.24 (m, 1H), 3.04 (t, 4H), 3.50 (m, 6H), 4.70 (m, 1H), 5.56 (brs, 1H), 6.51 (d, 1H), 6.63 (d, 2H), 6.89 (t, 1H), 7.07-7.25 (m, 6H), 7.35 (d, 2H).

MS m/z: 561 (M+1).

(2S,4R)-N-4-(4-{4-[Acetyl-(4-chloro-phenyl)-amino]-2-methyl-3,4-dihydro-2H-quinoline-1-carbonyl}-phenoxymethyl)-piperidine-1-carboxylic acid benzyl ester (H-141)

(2S,4R)-N-(4-Chloro-phenyl)-N-[1-(4-hydroxy-benzoyl)-2-methyl-1,2,3,4-tetrahydro-quinolin-4-yl]-acetamide (0.31 g, 0.71 mmol) was dissolved in DMF at room temperature and $K_2CO_3$ (0.392 g, 2.84 mmol) was added. 4-Bromomethyl-piperidine-1-carboxylic acid benzyl ester (0.668 g, 2.14 mmol) was added and the reaction was allowed to heat to 80° C. overnight. The reaction mixture was concentrated in vacuo. The residue was partitioned between ethyl acetate and water, then extracted three times with ethyl acetate, dried over $MgSO_4$, filtered and concentrated down. The crude residue was purified by silica gel chromatography (60% EtOAc/40% Hexane) to afford the product (0.25 g, 53%).

$^1$H-NMR (CDCl$_3$) δ: 1.13 (d, 3H), 1.15 (t, 1H), 1.24 (m, 2H), 1.76 (m, 2H), 1.88 (m, 1H), 2.04 (s, 3H), 2.27 (m, 1H), 2.75 (m, 2H), 3.68 (d, 2H), 4.17 (bs, 2H), 4.72 (sextet, 1H), 5.12 (s, 2H), 5.58 (bs, 1H), 6.52 (d, 1H), 6.67 (d, 2H), 6.86 (t, 1H), 7.08-7.38 (m, 13H).

MS m/z: 666 (M+1)

(2S,4R)-2-(4-{4-[Acetyl-(4-chloro-phenyl)-amino]-2-methyl-3,4-dihydro-2H-quinoline-1-carbonyl}-phenoxy)-N-(2-hydroxy-ethyl)-acetamide (H-142)

(2S,4R)-2-(4-{4-[Acetyl-(4-chloro-phenyl)-amino]-2-methyl-3,4-dihydro-2H-quinoline-1-carbonyl}-phenoxy)-N-(2-hydroxy-ethyl)-acetamide was made from (4-{4-[acetyl(4-chloro-phenyl)-amino]-2-methyl-3,4-dihydro-2H-quinoline-1-carbonyl}-phenoxy)-acetic acid ethyl ester (0.050 g, 0.096 mmol) by addition of 2-amino-ethanol (0.145 mL, 2.4 mmol) with trace sodium cyanide in ethanol (1 mL) at room temperature to give a 50% yield of (2S,4R)-2-(4-{4-[acetyl(4-chloro-phenyl)-amino]-2-methyl-3,4-dihydro-2H-quinoline-1-carbonyl}-phenoxy)-N-(2-hydroxy-ethyl)-acetamide after HPLC purification.

$^1$H-NMR (CDCl$_3$) δ: 1.13 (m, 4H), 2.02 (s, 3H), 2.26 (m, 1H), 2.70 (br, 1H), 3.46 (t, 2H), 3.68 (t, 2H), 4.41 (t, 2H), 4.72 (m, 1H), 5.58 (brs, 1H), 6.50 (d, 1H), 6.67 (d, 2H), 6.90 (t, 1H), 7.02 (br, 1H), 7.13-7.28 (m, 6H), 7.36 (d, 2H).

MS m/z: 536.2 (M+1).

2-(4-{[(2S,4R)-4-[Acetyl-(4-chlorophenyl)amino]-2-methyl-3,4-dihydroquinolin-1(2H)-yl]carbonyl}phenoxy)-2-methylpropanoic acid (H-144)

2-(4-{[(2S,4R)-4-[Acetyl-(4-chlorophenyl)amino]-2-methyl-3,4-dihydroquinolin-1(2H)-yl]carbonyl}phenoxy)-2-methylpropanoic acid was prepared according to general procedure I, substituting ethyl 2-bromo-2-methylpropanoate for ethyl 4-bromoacetate to afford ethyl 2-(4-{[(2S,4R)-4-[acetyl(4-chlorophenyl)amino]-2-methyl-3,4-dihydroquinolin-1(2H)-yl]carbonyl}phenoxy)-2-methylpropanoate.

This material was dissolved in methanol/tetrahydrofuran/water (2/1/1) then sodium hydroxide (3 equivalents) was added and reaction mixture heated to 40° C. for 2 h. The mixture was concentrated, the residue acidified with a 1N HCl aqueous solution and extracted with ethyl acetate. The organic layer was washed with brine, dried over magnesium sulfate, filtered and concentrated to give 2-(4-{[(2S,4R)-4-[acetyl(4-chlorophenyl)amino]-2-methyl-3,4-dihydroquinolin-1(2H)-yl]carbonyl}phenoxy)-2-methylpropanoic acid.

$^1$H-NMR (CDCl$_3$) δ: 1.10-1.14 (m, 1H), 1.13 (d, 3H), 1.53 (d, 6H), 2.24 (s, 3H), 2.27-2.31 (m, 1H), 4.72-4.79 (m, 1H), 5.60 (br s, 1H), 6.49 (d, 1H), 6.68 (d, 2H), 6.87 (t, 1H), 7.11 (t, 2H), 7.08-7.18 (m, 4H), 7.37 (d, 2H).

MS m/z: 521 (M+1).

(2S,4R)-4-(4-{4-[Acetyl-(4-chloro-phenyl)-amino]-2-methyl-3,4-dihydro-2H-quinoline-1-carbonyl}-phenoxy)-2-methyl-butyric acid (H-145)

(2S,4R)-4-(4-{4-[Acetyl-(4-chloro-phenyl)-amino]-2-methyl-3,4-dihydro-2H-quinoline-1-carbonyl}-phenoxy)-2-methyl-butyric acid methyl ester (100 mg) was dissolved in methanol/THF, and lithium hydroxide (1.0N, 2 mL) was added. After 1 hour, the reaction was acidified and extracted with methylene chloride. The organic layer was dried, filtered, and concentrated. The crude residue was purified by silica gel chromatography ethyl acetate—5% MeOH/ethyl acetate gradient) to afford the product.

$^1$H-NMR (CDCl$_3$) δ: 1.1 (d, 3H), 1.2 (d, 3H), 1.2 (m, 1H), 1.8 (m, 1H), 2.0 (s, 3H), 2.1 (m, 1H), 2.2 (m, 1H), 2.7 (m, 1H), 3.9 (t, 2H), 4.7 (m, 1H), 5.6 (bs, 1H), 6.5 (d, 1H), 6.6 (d, 2H), 6.9 (t, 1H), 7.2 (m, 6H), 7.4 (d, 2H), 10.6 (bs, 1H).

MS m/z: 535 (M+1).

3-[1-(4-{[(2S,4R)-4-acetyl(4-chlorophenyl)amino]-2-methyl-3,4-dihydroquinolin-1(2H)-yl]carbonyl}phenyl)-1H-pyrrol-3-yl]propanoic acid (H-146)

N-[(2S,4R)-1-(4-Amino-benzoyl)-2-methyl-1,2,3,4-tetrahydro-quinolin-4-yl]-N-(4-chloro-phenyl)-acetamide was made following general procedure H, substituting 4-nitrocarbonyl chloride for 6-trifluoromethyl nicotinyl chloride, followed by reduction to using excess NH$_4$CO$_2$H, catalyic Pt(sulfided), in ethanol at reflux for 30 m, filtration and concentration.

N-[(2S,4R)-1-(4-Amino-benzoyl)-2-methyl-1,2,3,4-tetrahydro-quinolin-4-yl]-N-(4-chloro-phenyl)-acetamide (181 mg, 0.433 mmol) was dissolved in glacial acetic acid (6 mL) and heated to 90° C. 2,5-dimethoxy-tetrahydrofuran-3-carbaldehyde was dissolved in glacial acetic acid (2 mL) and added drop wise to the aniline mixture. After 15 m at 90° C., the reaction was quenched with water, and extracted 2× with methylene chloride. The organics were combined and concentrated, and the yellowish residue was subjected to flash chromatography (EtOAc) to afford the corresponding aldehyde (150 mg, 70%).

In a round bottom flask at 0° C. was added the aldehyde (87 mg, 0.175 mmol), triethylphosphonoacetate (40 mL, 0.201 mmol), methylene chloride (1.5 mL), NaOH/H$_2$O (50% v/v, 1.5 mL), and catalytic ammonium iodide. After 1 hour, the slurry was partitioned between methylene chloride and water. The organic layer was collected and concentrated, and the residue was subject to flash chromatography (EtOAc) to yield (E)-3-[1-(4-{(2S,4R)-4-[Acetyl-(4-chloro-phenyl)-amino]-2-methyl-3,4-dihydro-2H-quinoline-1-carbonyl}-phenyl)-1H-pyrrol-3-yl]-acrylic acid ethyl ester (97 mg, 96%) as a white solid.

This product (80 mg, 0.16 mmol) was dissolved in EtOAc (3 mL) and acetic acid (1 drop). The mixture was subjected to ZnBr$_2$ (7 mg, 0.032 mmol) and 1 atm H$_2$ gas for 4 h. The reaction mixture was filtered, concentrated and used without further purification. The crude residue was dissolved in MeOH (2 mL) and 1N NaOH (2 mL) and stirred overnight. The mixture was monitored by TLC, neutralized (1N HCl), and partitioned between EtOAc and water. The organic layer was concentrated and the crude residue was purified by preparative HPLC to afford the title compound as a white solid.

MS m/z: 556 (M+1)

(2S,4R)-N-(4-Chloro-phenyl)-N-{1-[4-(3-dibenzyl-sulfamoyl-propoxy)-benzoyl]-2-methyl-1,2,3,4-tetrahydro-quinolin-4-yl}-acetamide (H-147)

(2S,4R)-N-(4-Chloro-phenyl)-N-[1-(4-hydroxy-benzoyl)-2-methyl-1,2,3,4-tetrahydro-quinolin-4-yl]-acetamide (300 mg, 0.693 mmol) was dissolved in DMF (10 mL) at room temperature. Cs$_2$CO$_3$ (1.12 g, 3.46 mmol) was added followed by 3-chloro-propane-1-sulfonic acid dibenzylamide (350 mg, 1.03 mmol) and the reaction was allowed to stir overnight. The mixture was partitioned between methylene chloride and water; the organic layer was dried over Na$_2$SO$_4$, filtered and concentrated. The crude residue was purified by silica gel chromatography (2/1 hexanes/ethyl acetate) to afford the product.

$^1$H-NMR (CDCl$_3$) δ: 1.1 (d, 3H), 1.1 (m, 1H), 2.0 (s, 3H), 2.2 (m, 3H), 3.0 (t, 2H), 3.9 (t, 2H), 4.3 (s, 4H), 4.7 (d, 1H), 5.6 (bs, 1H), 6.5 (d, 1H), 6.6 (d, 2H), 6.9 (t, 1H), 7.2 (m, 18H).

MS m/z: 736 (M+1).

Methyl 4-(4-{[(2S,4R)-4-[(4-chlorophenyl)(isobutyryl)amino]-2-methyl-3,4-dihydroquinolin-1(2H)-yl]carbonyl}phenoxy)-2,2-dimethylbutanoate (H-148)

Methyl 4-(4-{[(2S,4R)-4-[(4-chlorophenyl)(isobutyryl)amino]-2-methyl-3,4-dihydroquinolin-1(2H)-yl]carbonyl}phenoxy)-2,2-dimethylbutanoate was synthesized according to general procedure C replacing N-(4-chlorophenyl)-N-[(2S,4R)-1-(4-methoxybenzoyl)-2-methyl-1,2,3,4-tetrahydroquinolin-4-yl]acetamide with N-(4-chlorophenyl)-N-[(2S,4R)-1-(4-methoxybenzoyl)-2-methyl-1,2,3,4-tetrahydroquinolin-4-yl]-2-methylpropanamide and substituting 4-bromo-2,2-dimethylbutanoate for ethyl 4-bromoacetate. The rest of general procedure I was followed as indicated to afford Methyl 4-(4-{[(2S,4R)-4-[(4-chlorophenyl)(isobutyryl)amino]-2-methyl-3,4-dihydroquinolin-1(2H)-yl]carbonyl}phenoxy)-2,2-dimethylbutanoate.

$^1$H-NMR (CDCl$_3$) δ: 1.12-1.26 (m, 16H), 2.00 (t, 2H), 2.20-2.27 (m, 1H), 2.61 (sp, 1H), 3.64 (s, 3H), 3.91 (t, 2H), 4.68-4.78 (m, 1H), 5.60 (br s, 1H), 6.51 (d, 1H), 6.61 (d, 2H), 6.92 (t, 1H), 7.07-7.31 (m, 6H), 7.39 (d, 2H).

MS m/z: 592 (M+1).

(2S,4R)-N-(4-Chloro-phenyl)-N-{2-methyl-1-[4-(3-pyrrolidin-1-yl-propoxy)-benzoyl]-1,2,3,4-tetrahydro-quinolin-4-yl}-acetamide (H-149)

(2S,4R)-N-(4-Chloro-phenyl)-N-[1-(4-hydroxy-benzoyl)-2-methyl-1,2,3,4-tetrahydro-quinolin-4-yl]-acetamide (0.1 g, 0.23 mmol) was dissolved in DMF (5 mL) at room temperature. K$_2$CO$_3$ (0.317 g, 2.3 mmol) was added. 1-(3-Bromo-propyl)-pyrrolidine (0.177 g, 0.92 mmol) was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (10% methanol/90% dichloromethane) to afford the product (0.01 g, 8%).

$^1$H-NMR (CDCl$_3$) δ: 1.13 (d, 3H), 1.15 (t, 1H), 1.58-1.76 (m, 2H), 2.04 (s, 3H), 2.05-2.18 (m, 2H), 2.27 (m, 1H), 2.38 (m, 2H), 3.28 (t, 2H), 3.33 (m, 4H), 3.96 (t, 2H), 4.72 (sextet, 1H), 5.54 (bs, 1H), 6.52 (d, 1H), 6.67 (d, 2H), 6.88 (t, 1H), 7.08-7.35 (m, 6H), 7.38 (d, 2H).

MS m/z: 546 (M+1)

(2S,4R)-N-(4-Chloro-phenyl)-N-{2-methyl-[4-(2-pyrrol-1-yl-ethoxy)-benzoyl]-1,2,3,4-tetrahydro-quinolin-4-yl}-acetamide (H-150)

(2S,4R)-N-(4-Chloro-phenyl)-N-[1-(4-hydroxy-benzoyl)-2-methyl-1,2,3,4-tetrahydro-quinolin-4-yl]-acetamide (0.11 g, 0.25 mmol) was dissolved in DMF at room temperature and K$_2$CO$_3$ (0.207 g, 1.5 mmol) was added. 1-(2-Bromoethyl)-1H-pyrrole (0.088 g, 0.5 mmol) was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (70% EtOAc/30% Hexane) to afford the product (0.114 g, 85%).

$^1$H-NMR (CDCl$_3$) δ: 1.13 (d, 3H), 1.15 (t, 1H), 1.98 (s, 3H), 2.27 (m, 1H), 4.11 (t, 2H), 4.17 (t, 2H), 4.72 (sextet, 1H), 5.58 (bs, 1H), 6.12 (t, 2H), 6.48 (d, 1H), 6.57 (d, 2H), 6.68 (t, 2H), 6.86 (t, 1H), 7.08-7.35 (m, 6H), 7.38 (d, 2H).

MS m/z: 528 (M+1)

Methyl 4-(4-{[(2S,4R)-4-[(4-chlorophenyl)(propionyl)amino]-2-methyl-3,4-dihydroquinolin-1(2H)-yl]carbonyl}phenoxy)-2,2-dimethylbutanoate (H-151)

Methyl 4-(4-{[(2S,4R)-4-[(4-chlorophenyl)(propionyl)amino]-2-methyl-3,4-dihydroquinolin-1(2H)-yl]carbonyl}phenoxy)-2,2-dimethylbutanoate was synthesized according to general procedure C replacing N-(4-chlorophenyl)-N-[(2S,4R)-1-(4-methoxybenzoyl)-2-methyl-1,2,3,4-tetrahydroquinolin-4-yl]acetamide with N-(4-chlorophenyl)-N-[(2S,4R)-1-(4-methoxybenzoyl)-2-methyl-1,2,3,4-tetrahydroquinolin-4-yl]propanamide and substituting 4-bromo-2,2-dimethylbutanoate for ethyl 4-bromoacetate. (N-(4-chlorophenyl)-N-[(2S,4R)-1-(4-methoxybenzoyl)-2-methyl-1,2,3,4-tetrahydroquinolin-4-yl]propanamide was prepared following general procedure A by replacing 4-fluorobenzoyl chloride with 4-methoxybenzoyl chloride and by substituting acetyl chloride with propanoyl chloride; the rest of the procedure was followed as indicated to afford N-(4-chlorophenyl)-N-[(2S,4R)-1-(4-methoxybenzoyl)-2-methyl-1,2,3,4-tetrahydroquinolin-4-yl]propanamide). The rest of general procedure C was followed as indicated to afford Methyl 4-(4-{[(2S,4R)-4-[(4-chlorophenyl)(propionyl)amino]-2-methyl-3,4-dihydroquinolin-1(2H)-yl]carbonyl}phenoxy)-2,2-dimethylbutanoate.

$^1$H-NMR (CDCl$_3$) δ: 1.12-1.16 (m, 7H), 1.22 (s, 6H), 2.00 (t, 2H), 2.13-2.31 (m, 3H), 3.63 (s, 3H), 3.91 (t, 2H), 4.69-4.77 (m, 1H), 5.60 (br s, 1H), 6.51 (d, 1H), 6.61 (d, 2H), 6.92 (t, 1H), 7.11-7.24 (m, 6H), 7.37 (d, 2H).

MS m/z: 577 (M+1).

3-{[(2S,4R)-4-[acetyl(4-chlorophenyl)amino]-2-methyl-3,4-dihydroquinolin-1(2H)-yl]carbonyl}benzamide (H-152)

To a solution of 3-{[(2S,4R)-4-[acetyl(4-chlorophenyl)amino]-2-methyl-3,4-dihydroquinolin-1(2H)-yl]carbonyl}benzoic acid (90.2 mg, 0.195 mmol) in dimethylformamide (5 mL) at room temperature was added diisopropylethylamine (136 uL, 0.780 mmol) followed by addition of O-(7-Azabenzotriazol-1-yl)-N,N,N',N'-tetramethyluronium hexafluorophosphate (HATU) (110.9 mg, 0.292 mmol) and 1-Hydroxybenzotriazole hydrate (HOBT) (39.4 mg, 0.292 mmol). The reaction was allowed to stir overnight at room temperature. The mixture was partitioned between sodium bicarbonate (saturated) (20 ml) and ethyl acetate (20 ml). The aqueous layer was extracted 2 additional times with ethyl acetate (20 ml). The organics were collected together and washed with a brine solution (15 ml). The organics were dried over sodium sulfate, filtered and concentrated down to give a light white solid (40 mg, quant.) of 3-{[(2S,4R)-4-[acetyl(4-chlorophenyl)amino]-2-methyl-3,4-dihydroquinolin-1(2H)-yl]carbonyl}benzoic acid.

$^1$H-NMR (CDCl$_3$) δ: 1.17 (d, 3H), 1.22 (m 1H), 1.89 (bs, 2H), 2.03 (s, 3H), 2.25-2.36 (m, 1H), 4.78-4.93 (m, 1H), 5.56-5.67 (m, 1H), 6.52 (d, 1H), 6.62-6.68 (m, 1H), 6.93 (m, 1H), 7.15-7.27 (m, 4H), 7.36-7.41 (in, 3H), 7.63 (d, 1H), 7.97 (d, 1H).

MS m/z: 462 (M+1).

5-(4-{[(2S,4R)-4-[acetyl(4-chlorophenyl)amino]-2-methyl-3,4-dihydroquinolin-1(2H)-yl]carbonyl}phenyl)-2,2-dimethylpent-3-enoic acid (H-153)

Purification of crude material in the last step of the synthesis of 5-(4-{(2S,4R)-4-[acetyl(4-chloro-phenyl)-amino]-2-methyl-3,4-dihydro-2H-quinoline-1-carbonyl}-phenyl)-2,2-dimethyl-pentanoic acid also allowed to isolate 5-(4-{[(2S,4R)-4-[acetyl(4-chlorophenyl)amino]-2-methyl-3,4-dihydroquinolin-1(2H)-yl]carbonyl}phenyl)-2,2-dimethylpent-3-enoic acid as a by-product in the synthesis (5 mg).
$^1$H-NMR (MeOD) δ: 1.10 (d, 3H), 1.20 (s, 6H), 2.05 (s, 3H), 2.45 (m, 1H), 3.20 (d, 2H), 4.75 (m, 1H), 5.55 (m, 1H), 5.55-5.60 (m, 2H), 6.55 (d, 1H), 6.95 (t, 1H), 6.90-7.05 (dd, 2H), 7.05-7.20 (m, 4H), 7.25-7.45 (m, 4H).
MS m/z: 545 (M+1).

Methyl 2-{[3-(4-{[(2S,4R)-4-[acetyl(4-chlorophenyl)amino]-2-methyl-3,4-dihydroquinolin-1(2H)-yl]carbonyl}phenyl)propanoyl]amino}-2-methylpropanoate (H-154)

Methyl 3-(4-{[(2S,4R)-4-[acetyl(4-chlorophenyl)amino]-2-methyl-3,4-dihydroquinolin-1(2H)-yl]carbonyl}phenyl)propanoate was prepared following general procedure B, substituting methyl 3-[4-(chlorocarbonyl)phenyl]propanoate for 6-trifluoromethyl nicotinyl chloride. (methyl 3-[4-(chlorocarbonyl)phenyl]propanoate was prepared in three steps from 4-iodobenzoic acid. To a solution of 4-iodobenzoic acid in dimethylformamide were added methyl acrylate, palladium acetate and triethylamine. Reaction mixture was heated to 100° C. for 5 h. to give 4-(3-methoxy-3-oxoprop-1-en-1-yl)benzoic acid. Hydrogenation of this intermediate afforded 4-(3-methoxy-3-oxopropyl)benzoic acid. Subsequent treatment of this carboxylic acid with oxalyl chloride and catalytic DMF afforded methyl 3-[4-(chlorocarbonyl)phenyl]propanoate in decent yield).
Methyl 3-(4-{[(2S,4R)-4-[acetyl(4-chlorophenyl)amino]-2-methyl-3,4-dihydroquinolin-1(2H)-yl]carbonyl}phenyl)propanoate (200 mg, 0.4 mmol, 1 equ.) was dissolved in methanol/tetrahydrofuran (2/1) (1.5 ml). A solution of sodium hydroxide (32 mg, 0.8 mmol, 2 eq.) in water (0.5 ml) was added and reaction mixture stirred at room temperature for 20 h. The mixture was concentrated and the residue was acidified with a 1N HCl aqueous solution and extracted with ethyl acetate. The organic layer was washed with brine, dried over magnesium sulfate, filtered and concentrated to give 3-(4-{[(2S,4R)-4-[acetyl(4-chlorophenyl)amino]-2-methyl-3,4-dihydroquinolin-1(2H)-yl]carbonyl}phenyl)propanoic acid (190 mg, 97%).
To a suspension of 3-(4-{[(2S,4R)-4-[acetyl(4-chlorophenyl)amino]-2-methyl-3,4-dihydroquinolin-1(2H)-yl]carbonyl}phenyl)propanoic acid (50 mg, 0.10 mmol, 1 equ.) in methylene chloride (0.5 mL) was added a 2M solution of oxalyl chloride in methylene chloride (82 uL, 0.16 mmol, 1.6 equ.). Reaction mixture was stirred at room temperature for 30 m., and then concentrated to give 3-(4-{[(2S,4R)-4-[acetyl(4-chlorophenyl)amino]-2-methyl-3,4-dihydroquinolin-1(2H)-yl]carbonyl}phenyl)propanoyl chloride. To a solution of the preformed acid chloride in methylene chloride (0.5 mL) was added methyl-alfG-amino-isobutyrate hydrochloride (31 mg, 0.20 mmol, 2 equ.) and diisopropylethylamine (52 uL, 0.30 mmol, 3 equ.). Reaction mixture was stirred at room temperature for 20 h. and concentrated. The residue was dissolved in ethyl acetate and washed with water, brine, and then dried over magnesium sulfate, filtered and concentrated. The crude residue was purified by silica gel chromatography (ethyl acetate/hexane: 4/1 to 10/0 gradient) to afford methyl 2-{[3-(4-{[(2S,4R)-4-[acetyl(4-chlorophenyl)amino]-2-methyl-3,4-dihydroquinolin-1(2H)-yl]carbonyl}phenyl)propanoyl]amino}-2-methylpropanoate (105 mg, 46%).
$^1$H-NMR (CDCl$_3$) δ: 1.15 (d, 3H), 1.45 (d, 6H), 2.05 (s, 3H), 2.30 (m, 1H), 2.40 (t, 2H), 2.90 (t, 2H), 3.70 (s, 3H), 4.80 (m, 1H), 5.60 (m, 1H), 5.90 (s, 1H), 6.55 (d, 1H), 6.90 (t, 1H), 6.90-7.15 (m, 8H), 7.40 (d, 2H).
MS m/z: 590 (M+1).

(2S,4R)-[3-(4-{4-[Acetyl-(4-chloro-phenyl)-amino]-2-methyl-3,4-dihydro-2H-quinoline-1-carbonyl}-phenoxy)-propyl]-ethyl-carbamic acid methyl ester (H-155)

(2S,4R)-[3-(4-{4-[Acetyl-(4-chloro-phenyl)-amino]-2-methyl-3,4-dihydro-2H-quinoline-1-carbonyl}-phenoxy)-propyl]-carbamic acid methyl ester (41 mg, 0.074 mmol) was dissolved in THF/DMF (10:1, 3 mL). To this solution was added Sodium Hydride (2 mg, 0.089 mmol), followed by ethyl iodide (14 mg, 0.089 mmol). The reaction was stirred at room temperature for 7 hours and was quenched by adding 1 mL of water. The mixture was concentrated under reduced pressure and dissolved in DCM (15 mL). The reaction mixture was washed with sat. aq. NaHCO$_3$ (15 mL), water (15 mL) and brine (15 mL). The organic phase was dried over MgSO$_4$, filtered, and concentrated under reduced pressure. The residue was purified by silica gel chromatography (5/95 ethyl acetate/hexane—50/50 ethyl acetate/hexane gradient) to afford slightly yellow solid product (15 mg, 35%).
$^1$H-NMR (CDCl$_3$, 300 MHz) δ: 0.68-0.83 (m, 2H), 1.00-1.14 (m, 2H), 1.18-1.26 (m, 3H), 1.23 (t, 3H), 1.59-1.67 (broad, 1H), 1.61-1.64 (broad, 1H), 1.96-2.02 (m, 5H) 2.26-2.31 (m, 1H), 3.25-3.37 (m, 4H), 3.62-3.64 (m, 3H), 3.89-3.91 (m, 2H), 4.73-4.77 (m, 1H) 5.5-5.65 (broad, 1H), 6.50-6.93 (m, 4H), 7.12-7.39 (m, 8H).
MS m/z: 579 (M+1).

(2S,4R)-N-(4-Chloro-phenyl)-N-{1-[4-(3-diethylamino-2-hydroxy-propoxy)-benzoyl]-2-methyl-1,2,3,4-tetrahydro-quinolin-4-yl}-acetamide (H-156)

(2S,4R)-N-(4-Chloro-phenyl)-N-[2-methyl-1-(4-oxiranylmethoxy-benzoyl)-1,2,3,4-tetrahydro-quinolin-4-yl]-acetamide was further elaborated to (2S,4R)-N-{1-[4-(3-amino-2-hydroxy-propoxy)-benzoyl]-2-methyl-1,2,3,4-tetrahydro-quinolin-4-yl}-N-(4-chloro-phenyl)-acetamide following ref. (*Tetrahedron Lett* 2002, 43(46), 8327). The amine was reacted with acetaldehyde, Na(OAc)$_3$BH in dichloromethane at room temperature overnight. Then washed with 1N NaOH, dried over MgSO$_4$, filtered and concentrated down. The crude residue was purified by HPLC to afford the product in 38% yield.
$^1$H-NMR (CDCl$_3$) δ: 1.05-1.23 (m, 10H), 2.03 (s, 3H), 2.27 (m, 1H), 2.69-2.95 (m, 6H), 3.85 (m, 1H), 3.98 (m, 1H), 4.18 (m, 1H), 4.72 (sextet, 1H), 5.58 (bs, 1H), 6.58 (d, 1H), 6.67 (d, 2H), 6.86 (t, 1H), 7.08-7.35 (m, 6H), 7.38 (d, 2H).
MS m/z: 564 (M+1)

(2S,4R)-1-[3-(4-{4-[Acetyl-(4-chloro-phenyl)-amino]-2-methyl-3,4-dihydro-2H-quinoline-1-carbonyl}-phenoxy)-propyl]-1H-imidazole-2-carboxylic acid (H-157)

(2S,4R)-1-[3-(4-{4-[Acetyl-(4-chloro-phenyl)-amino]-2-methyl-3,4-dihydro-2H-quinoline-1-carbonyl}-phenoxy)-propyl]-1H-imidazole-2-carboxylic acid was prepared from (2S,4R)-1-[3-(4-{4-[Acetyl-(4-chloro-phenyl)-amino]-2-methyl-3,4-dihydro-2H-quinoline-1-carbonyl}-phenoxy)-propyl]-1H-imidazole-2-carboxylic acid ethyl ester. The ester (0.100 g, 0.16 mmol) was hydrolyzed to the acid by dissolving in tetrahydrofuran and ethanol and sodium hydroxide (1N) was added. The mixture was stirred at room temperature 4 hours. The mixture was cooled to room temperature, acidified to form a white precipitate. The solid was filtered to give (2S,4R)-1-[3-(4-{4-[acetyl(4-chloro-phenyl)-amino]-2-methyl-3,4-dihydro-2H-quinoline-1-carbonyl}-phenoxy)-propyl]-1H-imidazole-2-carboxylic acid in 65% yield.

MS m/z: 587 (M+1).

[4-(4-{[(2S,4R)-4-[acetyl(4-chlorophenyl)amino]-2-methyl-3,4-dihydroquinolin-1(2H)-yl]carbonyl}phenyl)piperidin-1-yl]acetic acid (H-158)

[4-(4-{[(2S,4R)-4-[acetyl(4-chlorophenyl)amino]-2-methyl-3,4-dihydroquinolin-1(2H)-yl]carbonyl}phenyl)piperidin-1-yl]acetic acid was prepared following general procedure H, substituting tert-butyl 4-(4-(chlorocarbonyl)phenyl)piperidine-1-carboxylate for 6-trifluoromethyl nicotinyl chloride (tert-butyl 4-(4-(chlorocarbonyl)phenyl)piperidine-1-carboxylate was prepared by treatment of 4-(1-(tert-butoxycarbonyl)piperidin-4-yl)benzoic acid with oxalyl chloride and catalytic DMF followed by removal of volatiles). The rest of the procedures were followed as indicated in general procedure B to afford the corresponding BOC-protected amine.

The tert-butyl carboxylate was removed by stirring the compound in 4N HCl/dioxane for 3 h, followed by concentration. The resulting hydrochloride salt (40 mg, 0.079 mmol) was heated in acetonitrile (3 mL), ethyl bromoacetate (88 uL, 0.79 mmol), and potassium carbonate (110 mg, 0.79 mmol) at 65° C. for 2 h. The crude slurry was subjected to flash chromatography (5% MeOH, EtOAc) to yield the corresponding ethyl ester. The ester was saponified with NaOH in MeOH/THF, then subjected to preparative HPLC to afford the title product as a white solid.

$^1$H-NMR (CDCl$_3$) δ: 1.02-1.22 (m, 1H), 1.13 (s, 3H), 1.92 (d, 2H), 2.02 (s, 3H), 2.10-2.38 (m, 3H), 2.57-2.70 (m, 1H), 2.79 (t, 2H), 3.49 (s, 2H), 3.65-3.80 (m, 2H), 4.55 (bs, 1H), 4.70-4.82 (m, 1H), 5.40-5.75 (m, 1H), 6.48 (d, 1H), 6.88 (t, 1H), 7.00-7.30 (m, 8H), 7.37 (d, 2H)

MS m/z: 560 (M+1).

(2S,4R)-N-4-(4-{4-[Acetyl-(4-chloro-phenyl)-amino]-2-methyl-3,4-dihydro-2H-quinoline-1-carbonyl}-phenoxy)-butyramide (H-159)

(2S,4R)-N-4-(4-{4-[Acetyl-(4-chloro-phenyl)-amino]-2-methyl-3,4-dihydro-2H-quinoline-1-carbonyl}-phenoxy)-butyramide was prepared from (2S,4R)-4-(4-{4-[acetyl(4-chloro-phenyl)-amino]-2-methyl-3,4-dihydro-2H-quinoline-1-carbonyl}-1-ethylidene-pentG-2,4-dienyloxy)-butyric acid by coupling NH$_4$Cl, HATU, DIEA, HOBt in DMF at room temperature to yield (2S,4R)-N-4-(4-{4-[acetyl-(4-chloro-phenyl)-amino]-2-methyl-3,4-dihydro-2H-quinoline-1-carbonyl}-phenoxy)-butyramide. The reaction mixture was concentrated down and partitioned between ethyl acetate and water, then extracted three times with ethyl acetate, dried over magnesium sulfate, filtered and concentrated down. The residue was purified by silica gel chromatography (10% methanol/90% dichloromethane) to afford pure (2S,4R)-N-4-(4-{4-[acetyl-(4-chloro-phenyl)-amino]-2-methyl-3,4-dihydro-2H-quinoline-1-carbonyl}-phenoxy)-butyramide in 46% yield.

$^1$H-NMR (CDCl$_3$) δ: 1.13 (d, 3H), 1.15 (t, 1H), 1.68 (bs, 2H), 2.04 (s, 3H), 2.08 (m, 2H), 2.27 (m, 1H), 2.38 (t, 2H), 3.97 (t, 2H), 4.72 (sextet, 1H), 5.48 (bs, 1H), 6.52 (d, 1H), 6.67 (d, 2H), 6.86 (t, 1H), 7.08-7.35 (m, 6H), 7.38 (d, 2H).

MS m/z: 520 (M+1)

Methyl 4-(4-{[(2S,4R)-4-[acetyl(4-chloro-2-methylphenyl)amino]-2-methyl-3,4-dihydroquinolin-1(2H)-yl]carbonyl}phenoxy)-2,2-dimethylbutanoate (H-160)

Methyl 4-(4-{[(2S,4R)-4-[acetyl(4-chloro-2-methylphenyl)amino]-2-methyl-3,4-dihydroquinolin-1(2H)-yl]carbonyl}phenoxy)-2,2-dimethylbutanoate was made from N-(4-chloro-2-methylphenyl)-N-[(2S,4R)-1-(4-methoxybenzoyl)-2-methyl-1,2,3,4-tetrahydroquinolin-4-yl]acetamide following general procedure C, substituting 4-bromo-2,2-dimethylbutanoate for ethyl 4-bromoacetate to yield methyl 4-(4-{[(2S,4R)-4-[acetyl(4-chloro-2-methylphenyl)amino]-2-methyl-3,4-dihydroquinolin-1(2H)-yl]carbonyl}phenoxy)-2,2-dimethylbutanoate.

$^1$H-NMR (CDCl$_3$) δ: 1.10 (d, 3H), 1.25 (s, 6H), 1.95 (s, 3H), 2.05 (t, 2H), 2.20 (m, 1H), 2.30 (s, 3H), 3.70 (s, 3H), 3.95 (t, 2H), 4.75 (m, 1H), 5.60 (m, 1H), 6.50 (d, 1H), 6.60 (d, 2H), 6.95 (t, 1H), 7.15-7.30 (m, 6H), 7.40 (s, 1H).

MS m/z: 577 (M+1).

4-(4-{[(2S,4R)-4-[acetyl(4-chloro-2-methylphenyl)amino]-2-methyl-3,4-dihydroquinolin-1(2H)-yl]carbonyl}phenoxy)-2,2-dimethylbutanoic acid (H-161)

Methyl 4-(4-{[(2S,4R)-4-[acetyl(4-chloro-2-methylphenyl)amino]-2-methyl-3,4-dihydroquinolin-1(2H)-yl]carbonyl}phenoxy)-2,2-dimethylbutanoate (60 mg, 0.10 mmol, 1 equ.) was dissolved in methanol/tetrahydrofuran (2/1) (0.8 ml). A solution of sodium hydroxide (12 mg, 0.30 mmol, 3 eq.) in water (0.3 ml) was added and reaction mixture heated to 40° C. for 2 h. The mixture was concentrated and the residue was acidified with a 1N HCl aqueous solution and extracted with ethyl acetate. The organic layer was washed with brine, dried over magnesium sulfate, filtered and concentrated to give 4-(4-{[(2S,4R)-4-[acetyl(4-chloro-2-methylphenyl)amino]-2-methyl-3,4-dihydroquinolin-1(2H)-yl]carbonyl}phenoxy)-2,2-dimethylbutanoic acid (50 mg, 89%).

$^1$H-NMR (CDCl$_3$) δ: 1.10 (d, 3H), 1.25 (s, 6H), 1.90 (s, 3H), 2.05 (m, 3H), 2.30 (s, 3H), 3.95 (t, 2H), 4.75 (m, 1H), 5.60 (m, 1H), 6.50 (d, 1H), 6.60 (d, 2H), 6.90 (t, 1H), 7.10-7.35 (m, 6H), 7.40 (s, 1H).

MS m/z: 563 (M+1).

Benzyl 2-(4-{[(2S,4R)-4-[acetyl(4-chlorophenyl)amino]-2-methyl-3,4-dihydroquinolin-1(2H)-yl]carbonyl}phenyl)pyrrolidine-1-carboxylate (H-162)

Benzyl 2-(4-{[(2S,4R)-4-[acetyl(4-chlorophenyl)amino]-2-methyl-3,4-dihydroquinolin-1(2H)-yl]carbonyl}phenyl)

pyrrolidine-1-carboxylate was prepared following general procedure H, substituting benzyl 2-(4-(chlorocarbonyl)phenyl)pyrrolidine-1-carboxylate for 6-trifluoromethyl nicotinyl chloride. (Benzyl 2-(4-(chlorocarbonyl)phenyl)pyrrolidine-1-carboxylate was prepared by treatment of 4-(1-(benzyloxycarbonyl)pyrrolidin-2-yl)benzoic acid with oxalyl chloride and catalytic DMF followed by removal of volatiles). The rest of the procedures were followed as indicated in general procedure B to afford benzyl 2-(4-{[(2S,4R)-4-[acetyl(4-chlorophenyl)amino]-2-methyl-3,4-dihydroquinolin-1(2H)-yl]carbonyl}phenyl)pyrrolidine-1-carboxylate.

$^1$H-NMR (CDCl$_3$) δ: 1.00-1.20 (m, 1H), 1.12 (s, 3H), 1.68-1.90 (m, 3H), 2.02 (s, 3H), 2.15-2.40 (m, 2H), 3.48-3.70 (m, 2H), 4.70-5.20 (m, 4H), 5.42-5.75 (m, 1H), 6.40-6.75 (m, 2H), 6.90-7.42 (m, 15H).

MS m/z: 622 (M+1)

N-(4-chlorophenyl)-N-[(2S,4R)-1-(4-ethyl-3-fluorobenzoyl)-2-methyl-1,2,3,4-tetrahydroquinolin-4-yl]acetamide (H-163)

N-(4-chlorophenyl)-N-[(2S,4R)-1-(4-ethyl-3-fluorobenzoyl)-2-methyl-1,2,3,4-tetrahydroquinolin-4-yl]acetamide was prepared following general procedure B, substituting 4-ethyl-3-fluorobenzoyl chloride for 6-trifluoromethyl nicotinyl chloride. (4-ethyl-3-fluorobenzoyl chloride was prepared in five steps from commercially available 4-bromo-3-fluorobenzoic acid. 4-Bromo-3-fluorobenzoic acid (0.828 g, 3.8 mmol) was dissolved in 20 mL of benzene/methanol (5:1) mixture. To the above mixture was added trimethylsilyldiazomethane until the reaction showed a light yellow color. Let stir for 30 minutes and concentrate down to yield methyl 4-bromo-3-fluorobenzoate. Methyl 4-bromo-3-fluorobenzoate was dissolved in 2 mL of DMF and vinyl tributyl tin (0.431 mL, 1.5 mmol), and degassed for 5 min with nitrogen gas. To the above mixture was added Pd(PPh$_3$)$_2$Cl$_2$ (0.086 g, 0.12 mmol) and heated at 80° C. with a condenser for 16 h. Cool to room temperature and dilute with ethyl acetate and wash with a 10% solution of KF in water. The mixture was allowed to stir for ~30 min at room temperature, then filter and extract the aqueous with ethyl acetate (3×). Dry over MgSO$_4$, filter and concentrate down. The residue was concentrated down and purified with 100% hexane to 10% ethyl acetate/90% hexane to yield 0.140 g, 63% of methyl 3-fluoro-4-vinylbenzoate. Methyl 3-fluoro-4-vinylbenzoate (0.750 g, 4.1 mmol) was reduced in the presence of Pd on carbon (10%) in ethanol to provide methyl 4-ethyl-3-fluorobenzoate (0.450 g, 59%). Methyl 4-ethyl-3-fluorobenzoate was hydrolyzed to the acid by dissolving in tetrahydrofuran and methanol and sodium hydroxide (1N) was added. The mixture was stirred at room temperature overnight. The mixture was cooled to rt, acidified to pH=5 with 1N HCl to form a white precipitate (0.270 g, 65%). The solid was filtered to give 4-ethyl-3-fluorobenzoic acid. The acid was converted to the acid chloride as described in general procedure B).

$^1$H-NMR (CDCl$_3$) δ: 1.12 (m, 1H), 1.13 (d, 3H), 1.18 (t, 3H), 2.02 (s, 3H), 2.27 (m, 1H), 3.58 (q, 2H), 4.75 (sextet, 1H), 5.59 (bs, 1H), 6.52 (d, 1H), 6.72 (d, 1H), 6.89-7.00 (m, 3H), 7.14-7.21 (m, 3H), 7.28 (d, 1H), 7.36 (d, 2H).

MS m/z: 465 (M+1).

N-(4-chlorophenyl)-N-[(2S,4R)-1-(4-ethyl-3,5-difluorobenzoyl)-2-methyl-1,2,3,4-tetrahydroquinolin-4-yl]acetamide (H-164)

N-(4-chlorophenyl)-N-[(2S,4R)-1-(4-ethyl-3,5-difluorobenzoyl)-2-methyl-1,2,3,4-tetrahydroquinolin-4-yl]acetamide was prepared following general procedure B, substituting 4-ethyl-3,5-difluorobenzoyl chloride for 6-trifluoromethyl nicotinyl chloride. (4-ethyl-3,5-difluorobenzoyl chloride was prepared in two steps from 3,5-difluorobenzoic acid. To a solution of 3,5-difluorobenzoic acid in tetrahydrofuran was added lithium diisopropyl amide at −78° C. After the reaction mixture was stirred at −78° C. for 1 h. ethyl iodide was added and reaction mixture stirred at room temperature for 2 h. to give 4-ethyl-3,5-difluorobenzoic acid. Subsequent treatment of this carboxylic acid with oxalyl chloride and catalytic DMF afforded 4-ethyl-3,5-difluorobenzoyl chloride in decent yield). The rest of the procedures were followed as indicated in general procedure B to afford N-(4-chlorophenyl)-N-[(2S,4R)-1-(4-ethyl-3,5-difluorobenzoyl)-2-methyl-1,2,3,4-tetrahydroquinolin-4-yl]acetamide.

$^1$H-NMR (CDCl$_3$) δ: 1.05 (t, 3H), 1.15 (d, 3H), 2.05 (s, 3H), 2.30 (m, 1H), 2.60 (q, 2H), 4.75 (m, 1H), 5.55 (m, 1H), 6.50 (d, 1H), 6.85 (d, 2H), 7.00 (t, 1H), 7.2 (m, 3H), 7.25-7.45 (m, 3H).

MS m/z: 483 (M+1).

4-[(5-{[(2S,4R)-4-[acetyl(4-chlorophenyl)amino]-2-methyl-3,4-dihydroquinolin-1(2H)-yl]carbonyl}pyridin-2-yl)oxy]-2,2-dimethylbutanoic acid (H-165)

4-[(5-{[(2S,4R)-4-[acetyl(4-chlorophenyl)amino]-2-methyl-3,4-dihydroquinolin-1(2H)-yl]carbonyl}pyridin-2-yl)oxy]-2,2-dimethylbutanoic acid was prepared from methyl 4-[(5-{[(2S,4R)-4-[acetyl(4-chlorophenyl)amino]-2-methyl-3,4-dihydroquinolin-1(2H)-yl]carbonyl}pyridin-2-yl)oxy]-2,2-dimethylbutanoate. methyl 4-[(5-{[(2S,4R)-4-[acetyl(4-chlorophenyl)amino]-2-methyl-3,4-dihydroquinolin-1(2H)-yl]carbonyl}pyridin-2-yl)oxy]-2,2-dimethylbutanoate (0.005 g, 0.0086 mmol) was hydrolyzed to the acid by dissolving in tetrahydrofuran and methanol and sodium hydroxide (1N) was added. The mixture was stirred at room temperature overnight. The mixture was cooled to rt, acidified to pH=5 with 1N HCl to form a white precipitate (0.002 g, 42%). The solid was filtered to give 4-[(5-{[(2S,4R)-4-[acetyl(4-chlorophenyl)amino]-2-methyl-3,4-dihydroquinolin-1(2H)-yl]carbonyl}pyridin-2-yl)oxy]-2,2-dimethylbutanoic acid.

$^1$H-NMR (CDCl$_3$) δ: 0.86 (m, 1H), 1.14 (d, 3H), 1.25 (s, 6H), 2.01 (s, 3H), 2.04 (t, 2H), 2.29 (s, 1H), 4.32 (t, 2H), 4.74 (sextet, 1H), 5.53 (bs, 1H), 6.40 (d, 1H), 6.56 (d, 1H), 6.98 (t, 1H), 7.16-7.31 (m, 5H), 7.37 (d, 2H), 8.12 (s, 1H).

MS m/z: 552 (M+1).

5-(4-{(2S,4R)-4-[acetyl(4-chloro-phenyl)-amino]-2-methyl-3,4-dihydro-2H-quinoline-1-carbonyl}-phenyl)-2,2-dimethyl-pentanoic acid methyl ester (H-166)

5-(4-{(2S,4R)-4-[acetyl(4-chloro-phenyl)-amino]-2-methyl-3,4-dihydro-2H-quinoline-1-carbonyl}-phenyl)-2,2-dimethyl-pentanoic acid methyl ester was prepared following general procedure B, substituting methyl 5-[4-(chlorocarbonyl)phenyl]-2,2-dimethylpentanoate for 6-trifluoromethyl nicotinyl chloride.(Methyl 5-[4-(chlorocarbonyl)phenyl]-2,2-dimethylpentanoate was prepared in four steps from 2,2-dimethyl-4-pentanoic acid. 2,2-dimethyl-4-pentanoic acid (2 g, 15.6 mmol, 1.0 eq.) was dissolved in anhydrous methanol (40 ml). The solution was cooled down to 0° C.; a 2 M solution of trimethylsilyl diazomethane in hexanes (11 ml, 21.8 mmol, 1.4 eq.) was added slowly until the reaction mixture turned slight yellow indicating the reaction was complete. Reaction mixture was concentrated down to give methyl-2,2-dimethyl-4-pentanoate as a colorless oil (2 g, 91%). Methyl-2,2-dimethyl-4-pentanoate (1.0 g, 7.0 mmol, 1 eq.) was dissolved in anhydrous dimethylformamide. The solution was purged with nitrogen, and 4-iodobenzoic acid (1.7 g, 7.0 mmol, 1 eq.), triethylamine (1.1 ml, 7.7 mmol, 1.1 eq.) and palladium acetate (79 mg, 0.35 mmol, 0.05 eq.) were sequentially added. Reaction was then heated to 80° C. under nitrogen for 18 h. Reaction mixture was concentrated under vacuo to leave a black oil which was partitioned between water and ethyl acetate and extracted. The aqueous layer was separated and the organic layer was washed with brine, dried over magnesium sulfate, filtered and concentrated to give a dark brown solid. The crude product was purified by silica gel chromatography (methylene chloride/methanol: 98/2 to 96/4 gradient) to provide 4-(4-methoxycarbonyl-4-methyl-pent-1-enyl)-benzoic acid as a light brown solid (915 mg, 50%). 4-(4-methoxycarbonyl-4-methyl-pent-1-enyl)-benzoic acid (900 mg, 3.4 mmol, 1 eq.) was dissolved in ethanol (13 ml) and triethylamine (568 ?ul, 4.1 mmol, 1.2 eq.) and palladium on carbon (90 mg, 10% Pd/C) were then added. The mixture was stirred under hydrogen atmosphere for 20 h. Reaction mixture was filtered over celite and washed with ethanol. The filtrate was evaporated to yield a yellow oil. This oil was dissolved in ethyl acetate and washed with a 1N aqueous hydrochloric acid solution. The aqueous layer was removed and the organic layer was washed with water, and brine, then dried over magnesium sulfate, filtered and concentrated to give 4-(4-methoxycarbonyl-4-methyl-pentyl)-benzoic acid (763 mg, 85%). 4-(4-methoxycarbonyl-4-methyl-pentyl)-benzoic acid (763 mg, 2.9 mmol, 1 eq.) was dissolved in methylene chloride (9 ml) and the solution was cooled down to 0° C. A 2 M solution of oxalyl chloride in methylene chloride (2.9 ml, 5.8 mmol, 2.0 eq.) was added followed by a catalytic amount of dimethylformamide. The reaction mixture was stirred at rt for 1 h, then concentrated to give methyl 5-[4-(chlorocarbonyl)phenyl]-2,2-dimethylpentanoate as an oil).

To the prepared methyl 5-[4-(chlorocarbonyl)phenyl]-2,2-dimethylpentanoate (2.9 mmol, 1.0 eq.) was added a solution of N-(4-chlorophenyl)-N-((2S,4R)-2-methyl-1,2,3,4-tetrahydroquinolin-4-yl)acetamide (754 mg, 2.4 mmol, 0.83 eq.) in methylene chloride (8 ml) followed by diisopropylethylamine (505 ul, 2.9 mmol, 1.0 eq.) and reaction mixture was stirred at room temperature for 20 h. The mixture was concentrated and the residue dissolved in ethyl acetate and washed with water, brine, and then dried over magnesium sulfate, filtered and concentrated. The crude residue was purified by silica gel chromatography (ethyl acetate/hexane: ⅓ to ½ gradient) to afford 5-(4-{(2S,4R)-4-[acetyl-(4-chloro-phenyl)-amino]-2-methyl-3,4-dihydro-2H-quinoline-1-carbonyl}-phenyl)-2,2-dimethyl-pentanoic acid methyl ester (675 mg, 50%).

$^1$H-NMR (CDCl$_3$) δ: 1.10 (s, 6H), 1.15 (d, 3H), 1.45 (m, 4H), 2.05 (s, 3H), 2.45 (m, 1H), 2.55 (t, 2H), 3.58 (s, 3H), 4.75 (m, 1H), 5.55 (m, 1H), 6.45 (d, 1H), 6.85 (t, 1H), 6.95 (d, 2H), 7.05-7.35 (m, 8H).

MS m/z: 561 (M+1).

(2S,4R)-N-(4-Chloro-phenyl)-N-{1-[4-(3-imidazol-1-yl-propoxy)-benzoyl]-2-methyl-1,2,3,4-tetrahydro-quinolin-4-yl}-acetamide (H-167)

(2S,4R)-N-(4-Chloro-phenyl)-N-[1-(4-hydroxy-benzoyl)-2-methyl-1,2,3,4-tetrahydro-quinolin-4-yl]-acetamide (0.1 g, 0.23 mmol) was dissolved in DMF (5 mL) at room temperature. K$_2$CO$_3$ (0.317 g, 2.3 mmol) was added. 1-(3-Bromo-propyl)-1H-imidazole (0.174 g, 0.92 mmol) was added and the reaction was allowed to heat to 80° C. overnight. The reaction mixture was concentrated in vacuo. The residue was partitioned between ethyl acetate and water, then extracted three times with ethyl acetate, dried over MgSO$_4$, filtered and concentrated down. The crude residue was purified by silica gel chromatography (60% EtOAc/40% Hexane) to afford the product (0.020 g, 16%).

$^1$H-NMR (CDCl$_3$) δ: 1.16 (d, 3H), 1.15 (t, 1H), 2.02 (s, 3H), 2.18 (m, 2H), 2.28 (m, 1H), 3.85 (t, 2H), 4.17 (t, 2H), 4.72 (sextet, 1H), 5.58 (bs, 1H), 6.52 (d, 1H), 6.67 (d, 2H), 6.84 (s, 1H), 6.88 (t, 1H), 7.03 (s, 1H), 7.08-7.35 (m, 6H), 7.38 (d, 2H), 7.43 (s, 1H).

MS m/z: 543 (M+1)

TABLE 9

Exemplary Compounds:

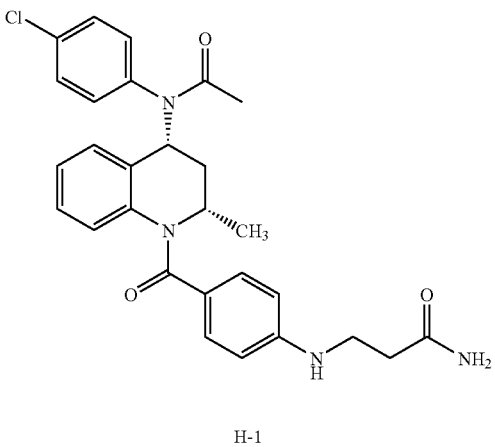

H-1

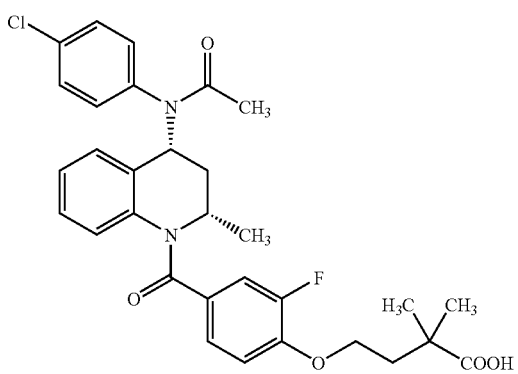

H-2

TABLE 9-continued
Exemplary Compounds:
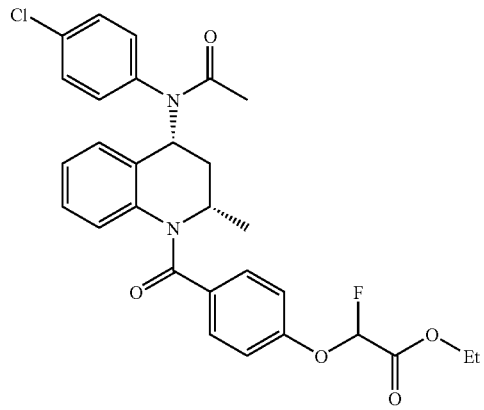
H-3
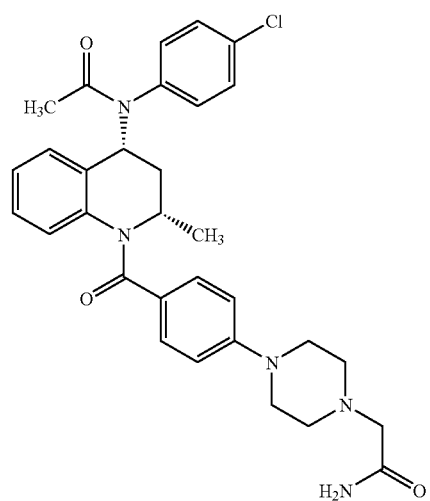
H-4
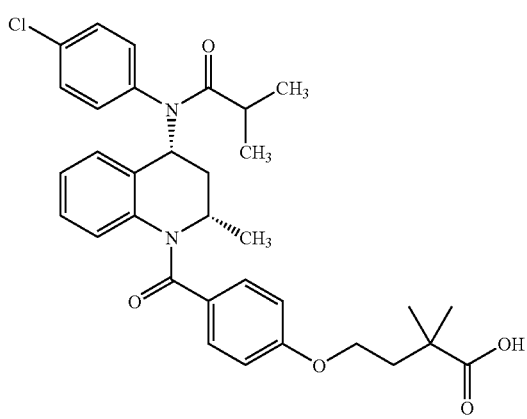
H-5
TABLE 9-continued
Exemplary Compounds:
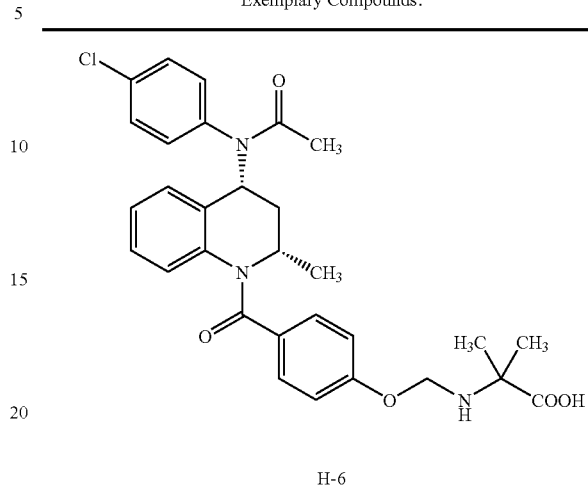
H-6
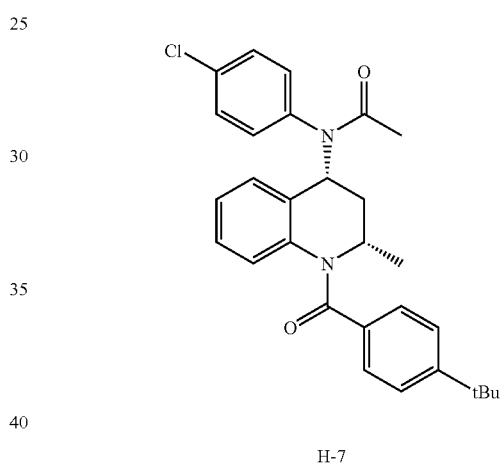
H-7
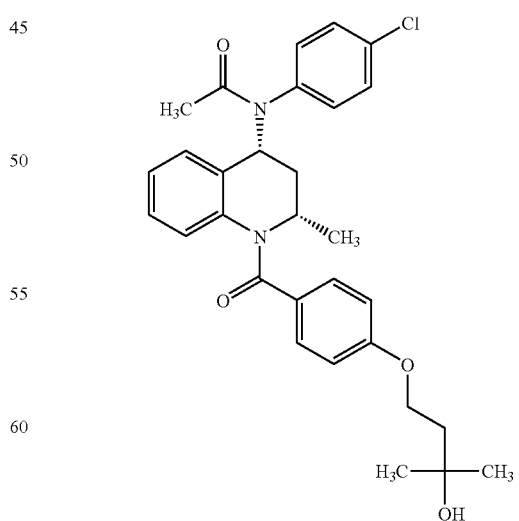
H-8

TABLE 9-continued
Exemplary Compounds:
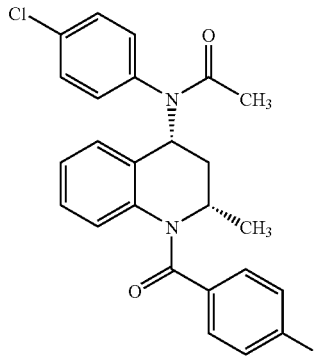
H-9
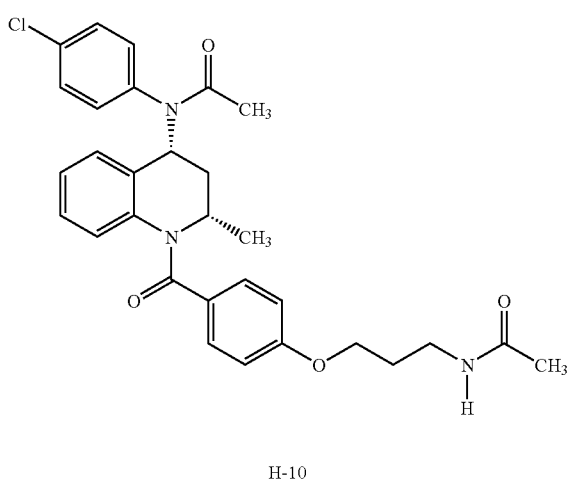
H-10
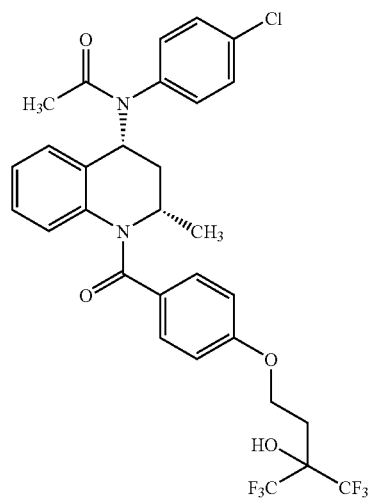
H-11
TABLE 9-continued
Exemplary Compounds:
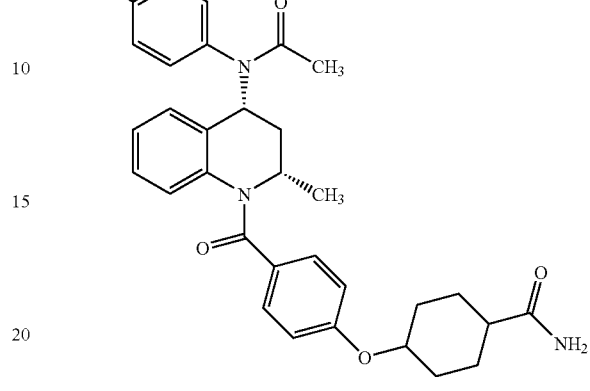
H-12
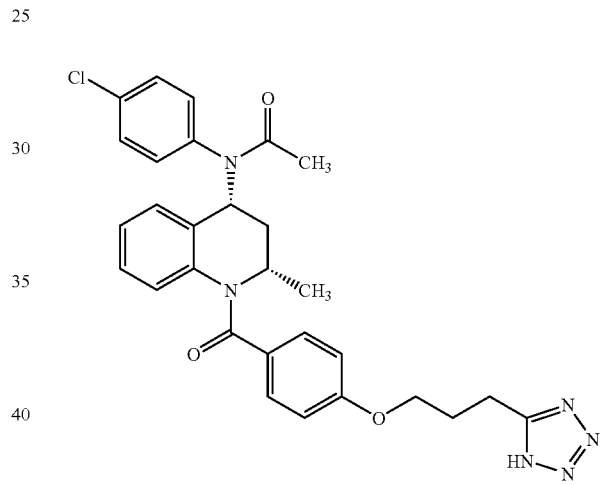
H-13
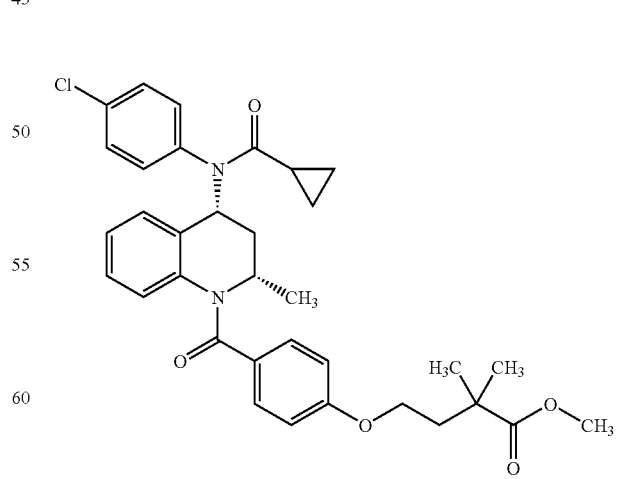
H-14

TABLE 9-continued
Exemplary Compounds:
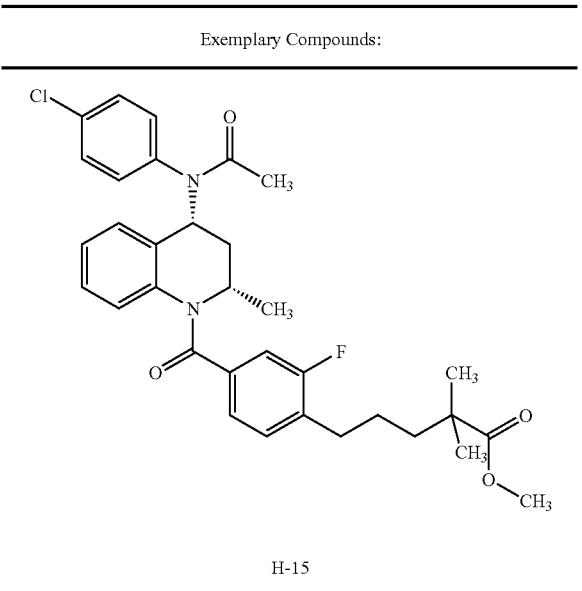
H-15
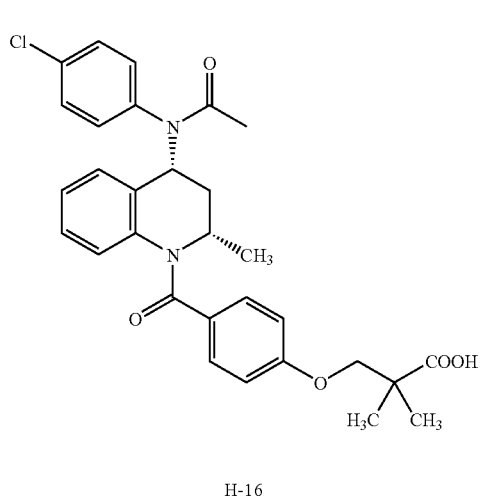
H-16
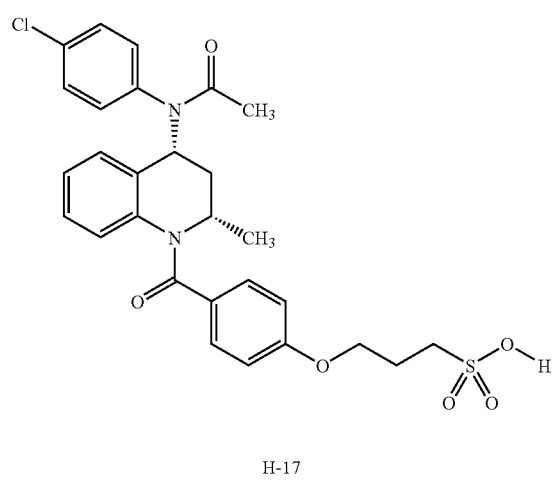
H-17
TABLE 9-continued
Exemplary Compounds:
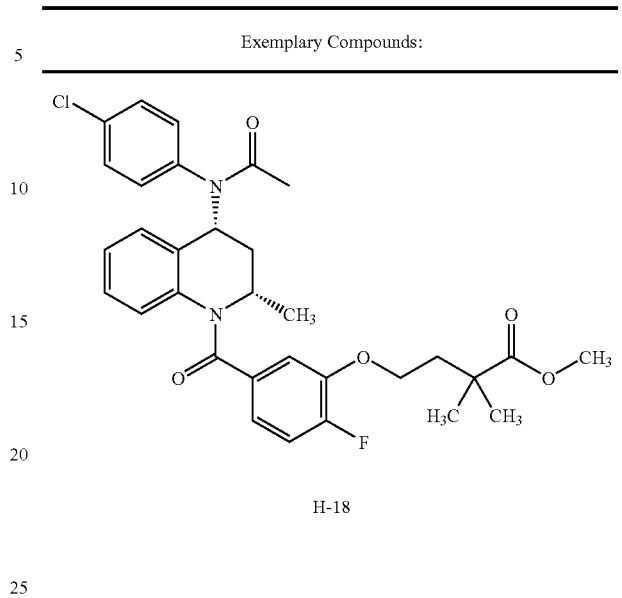
H-18
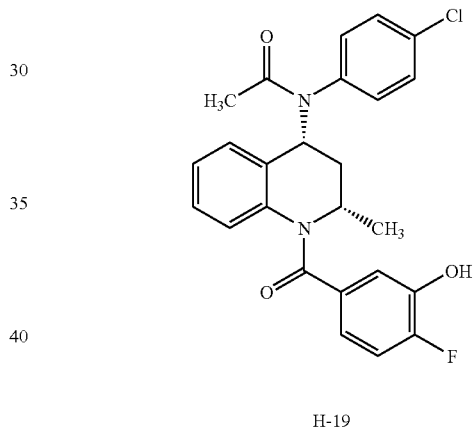
H-19
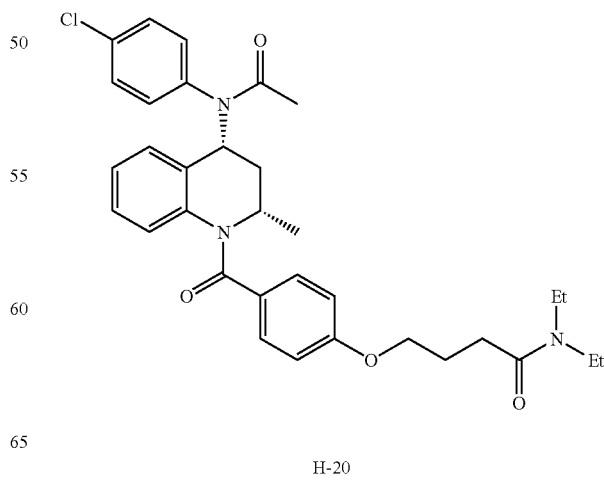
H-20

TABLE 9-continued
Exemplary Compounds:
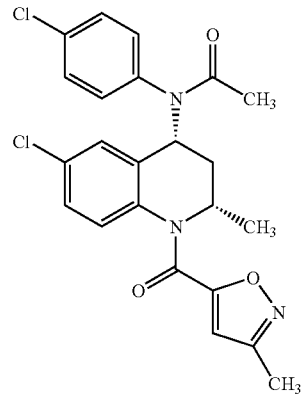
H-21
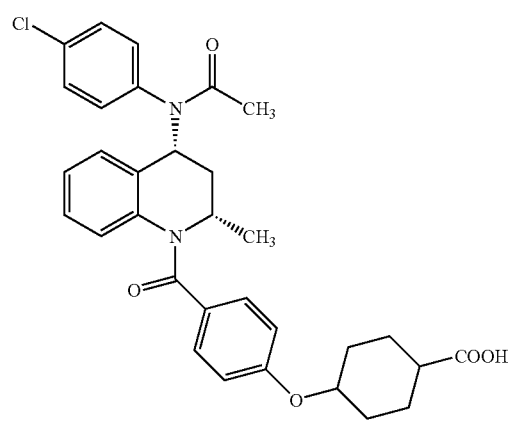
H-22
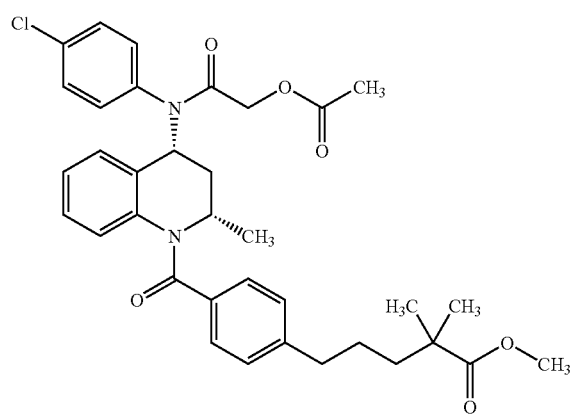
H-23
TABLE 9-continued
Exemplary Compounds:
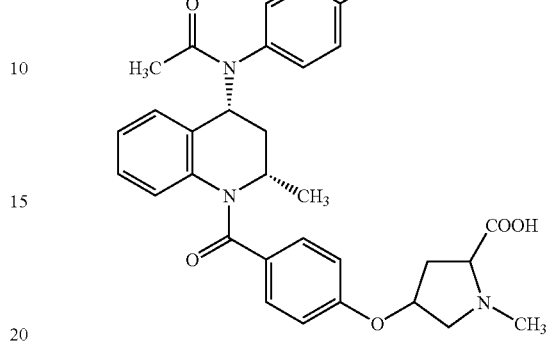
H-24
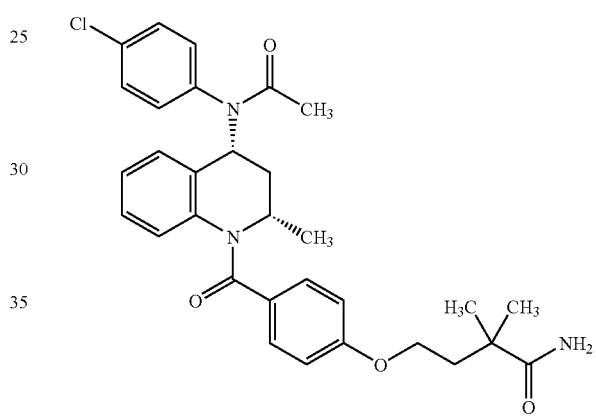
H-25
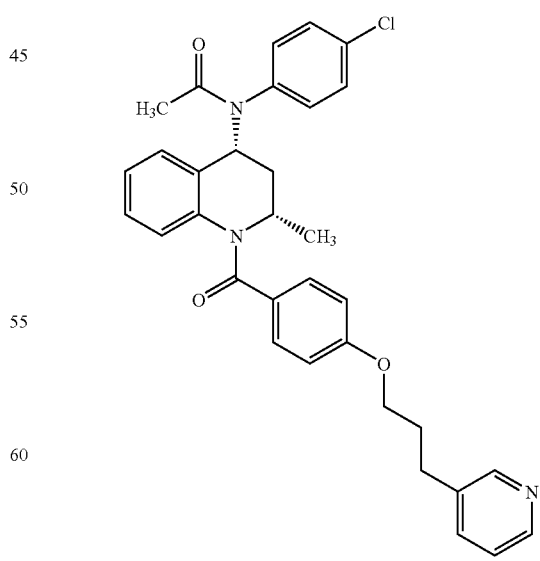
H-26

TABLE 9-continued
Exemplary Compounds:
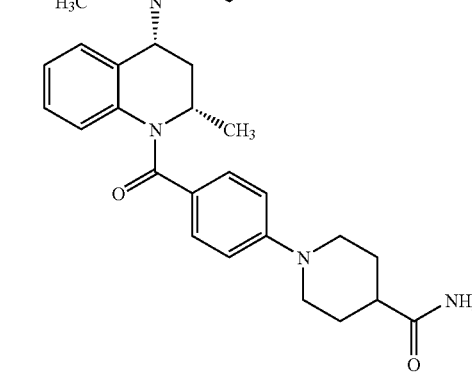
H-27
H-28
H-29
TABLE 9-continued
Exemplary Compounds:
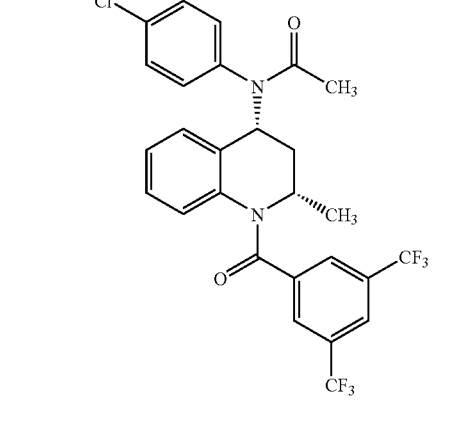
H-30
H-31
H-32

TABLE 9-continued
Exemplary Compounds:
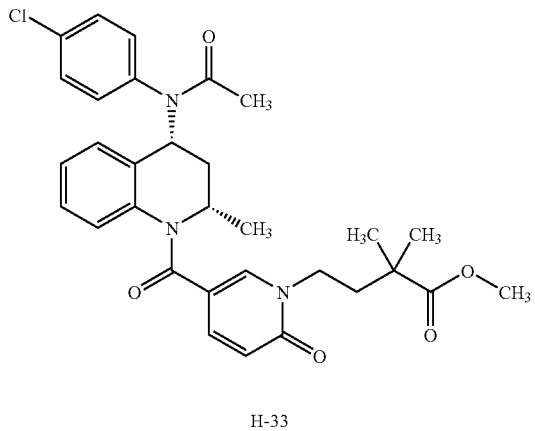
H-33
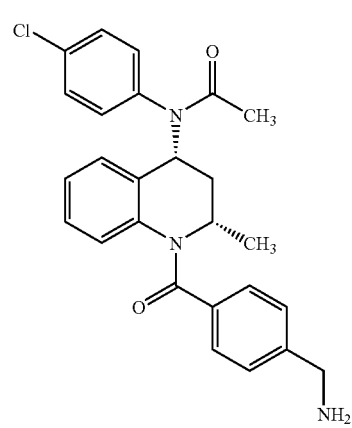
H-34
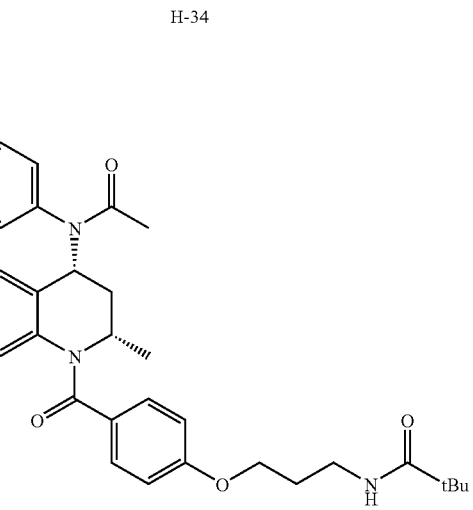
H-35
TABLE 9-continued
Exemplary Compounds:
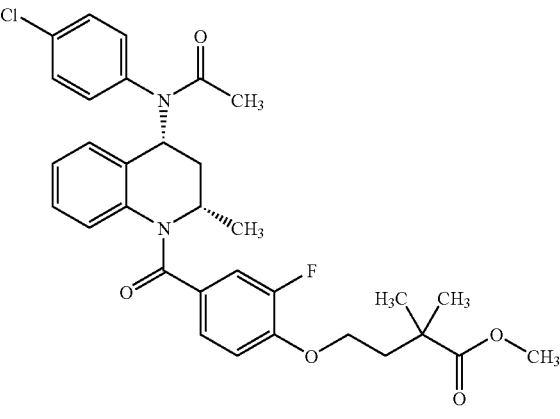
H-36
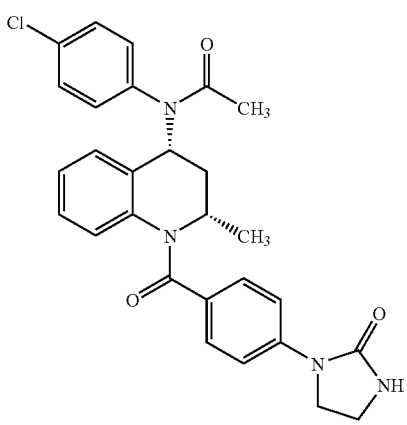
H-37
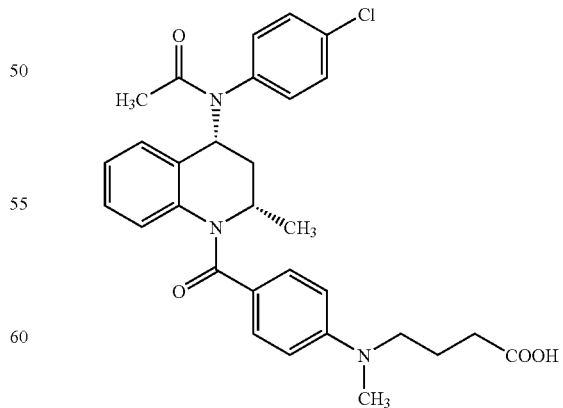
H-38

TABLE 9-continued
Exemplary Compounds:
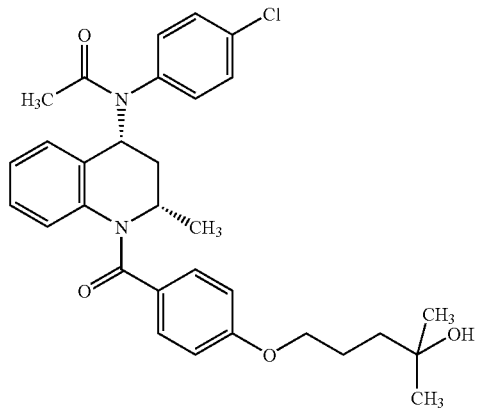
H-39
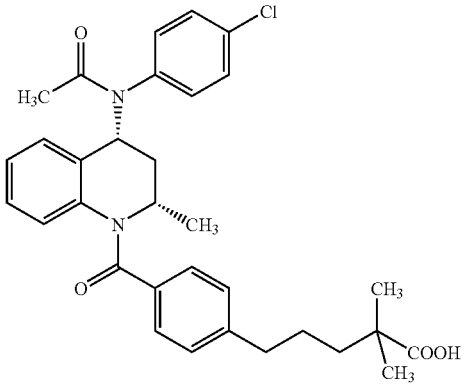
H-42
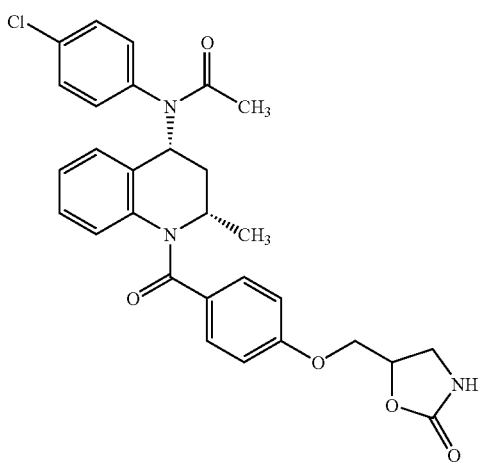
H-40
H-41
H-43
H-44

TABLE 9-continued
Exemplary Compounds:
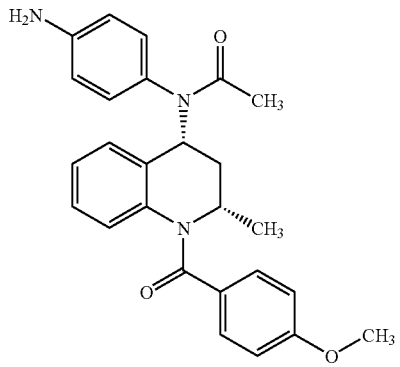
H-45
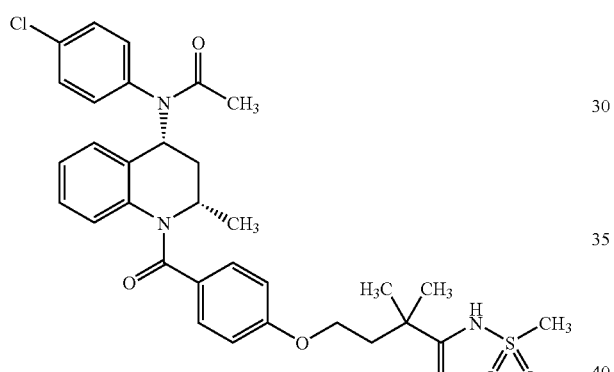
H-46
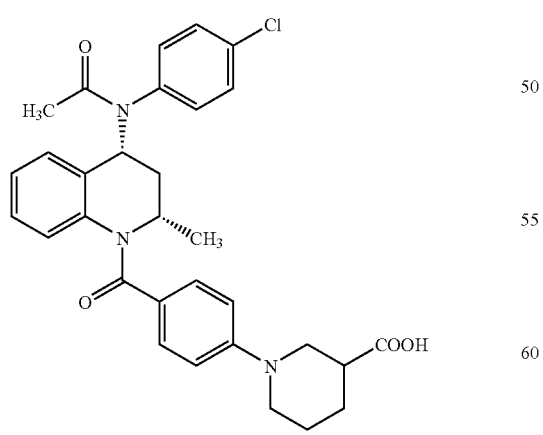
H-47
TABLE 9-continued
Exemplary Compounds:
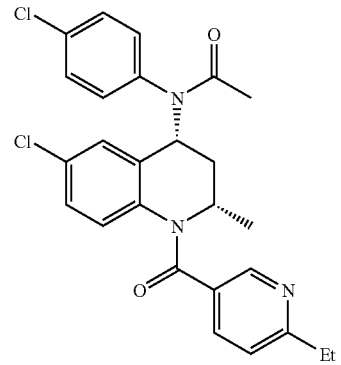
H-48
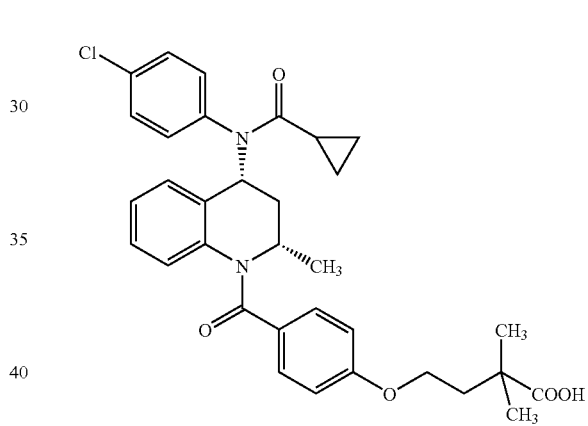
H-49
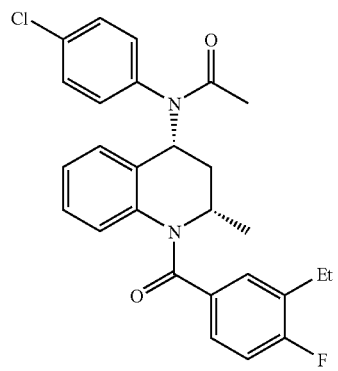
H-50

TABLE 9-continued
Exemplary Compounds:
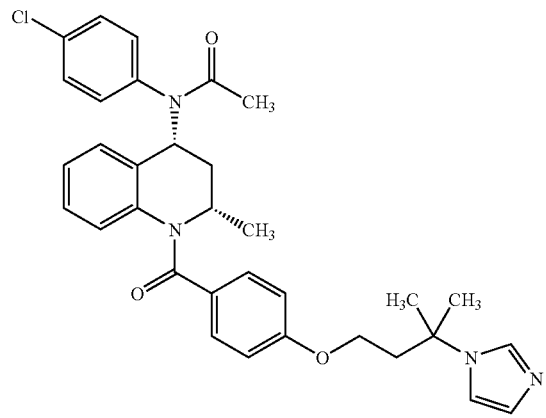
H-51
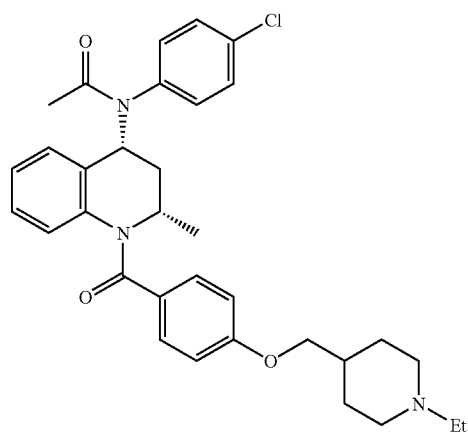
H-52
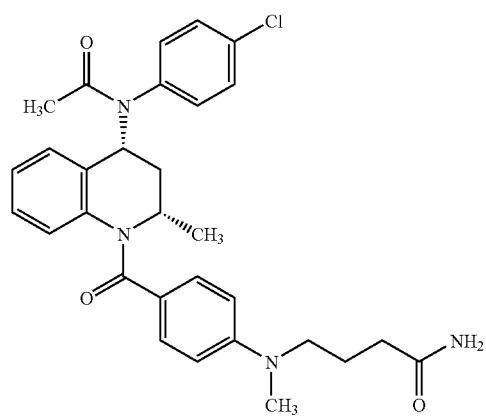
H-53
TABLE 9-continued
Exemplary Compounds:
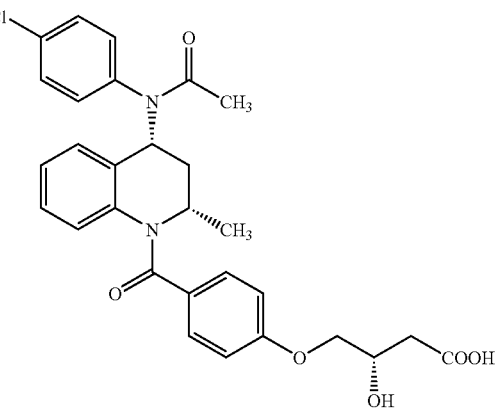
H-54
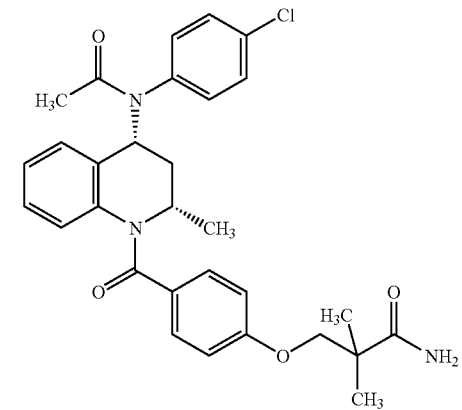
H-55
H-56

TABLE 9-continued
Exemplary Compounds:
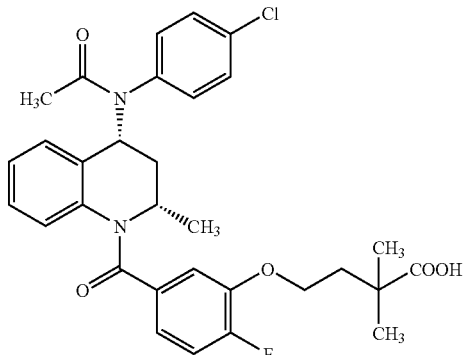
H-57
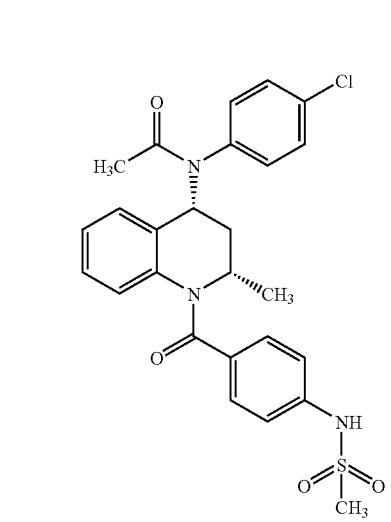
H-58
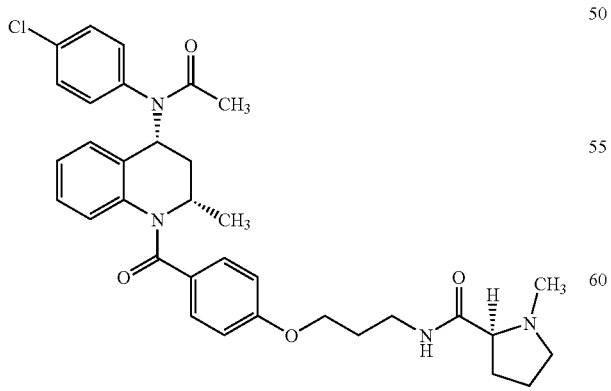
H-59
TABLE 9-continued
Exemplary Compounds:
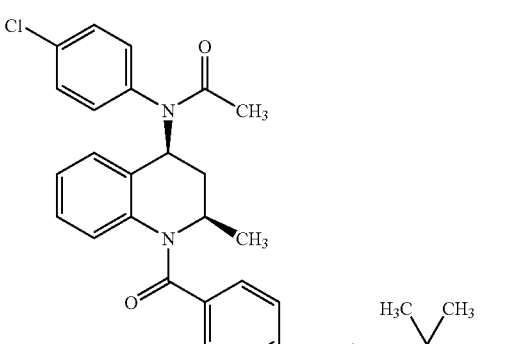
H-60
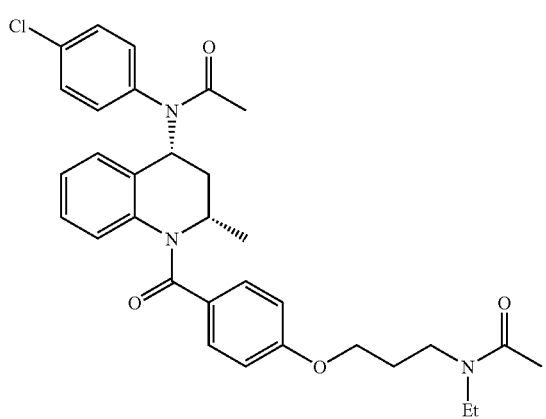
H-61
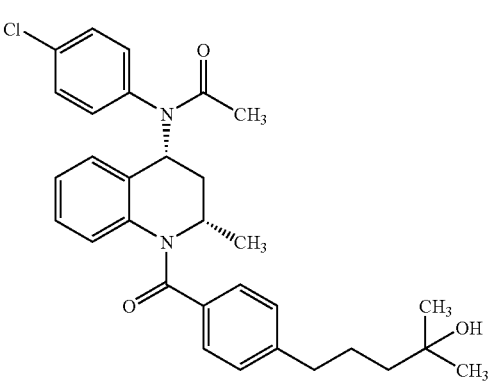
H-62

TABLE 9-continued
Exemplary Compounds:
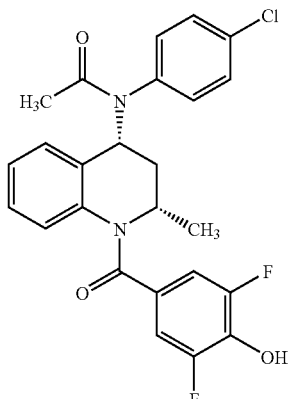
H-63
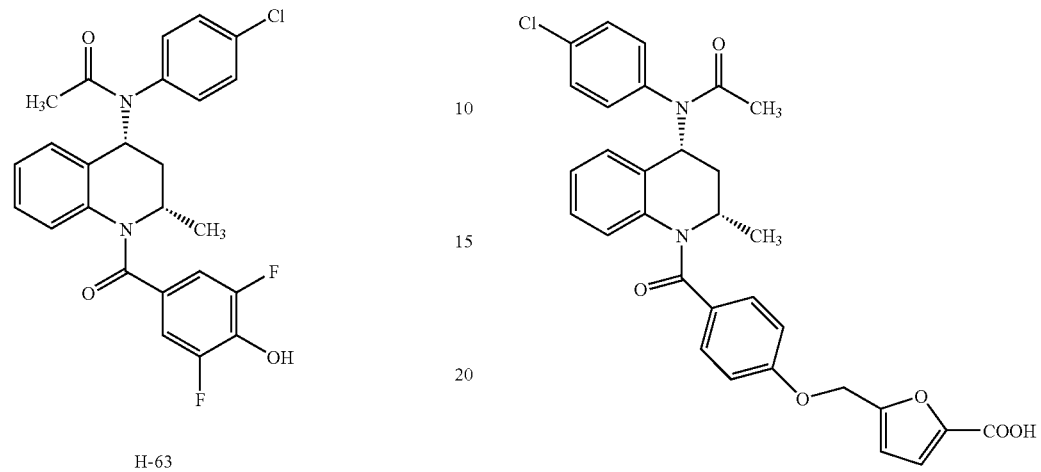
H-66
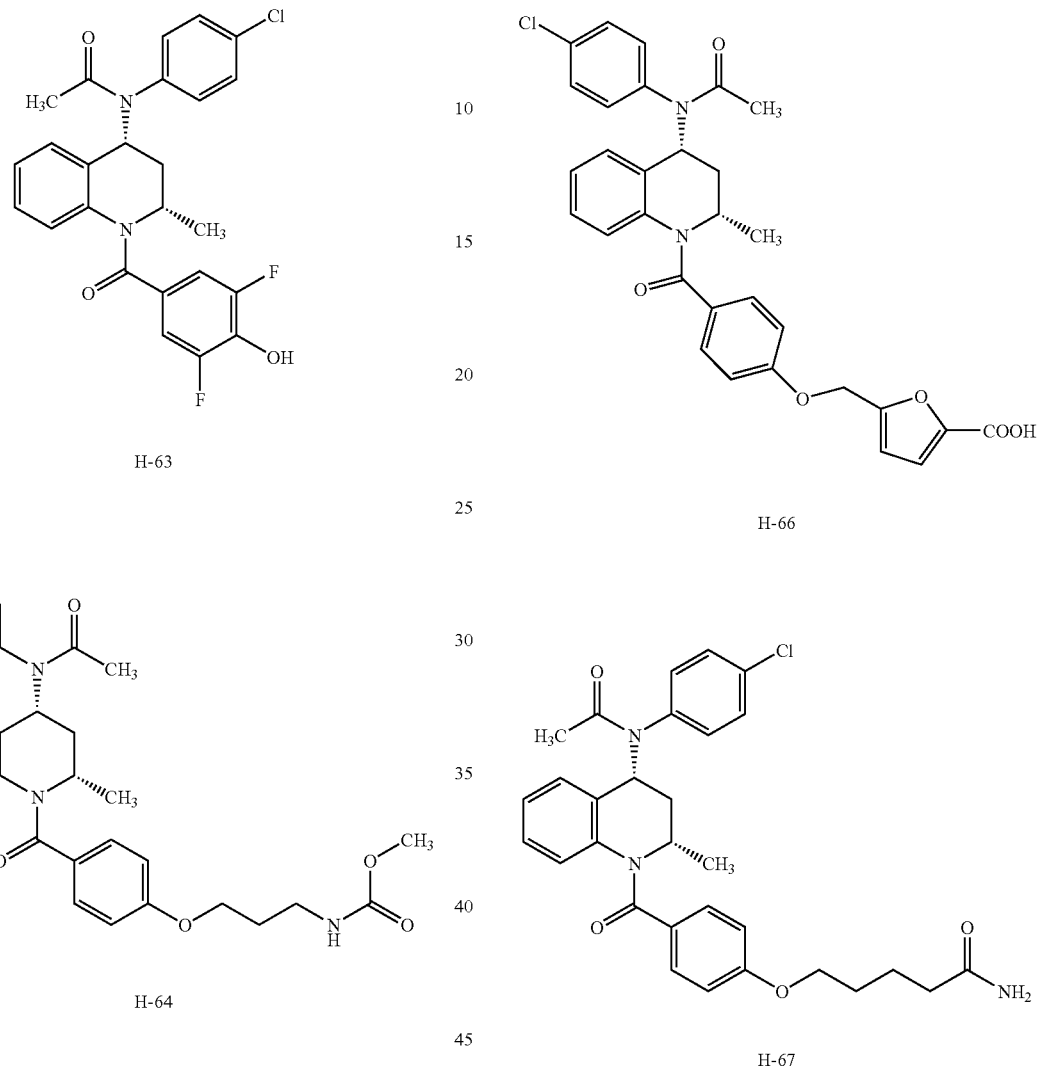
H-64
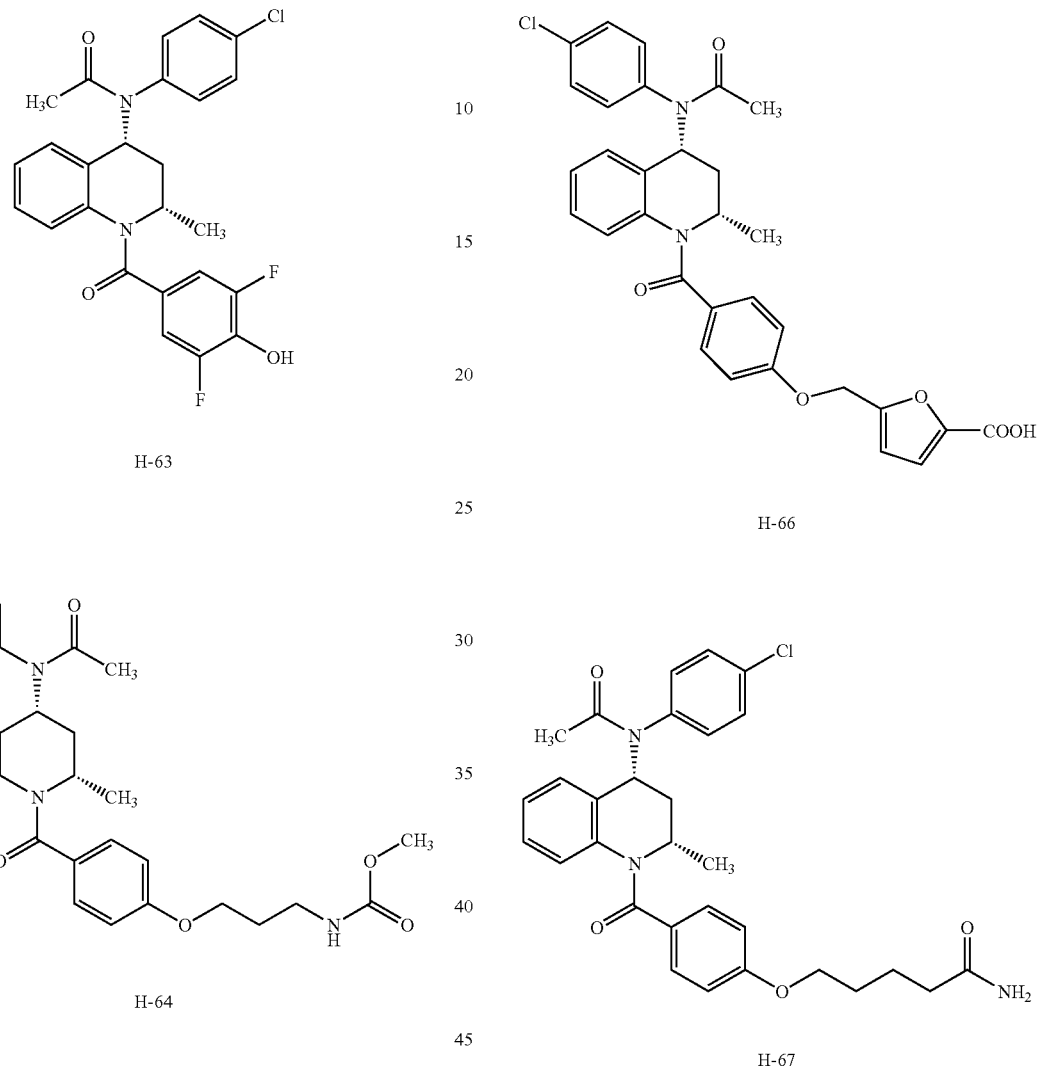
H-67
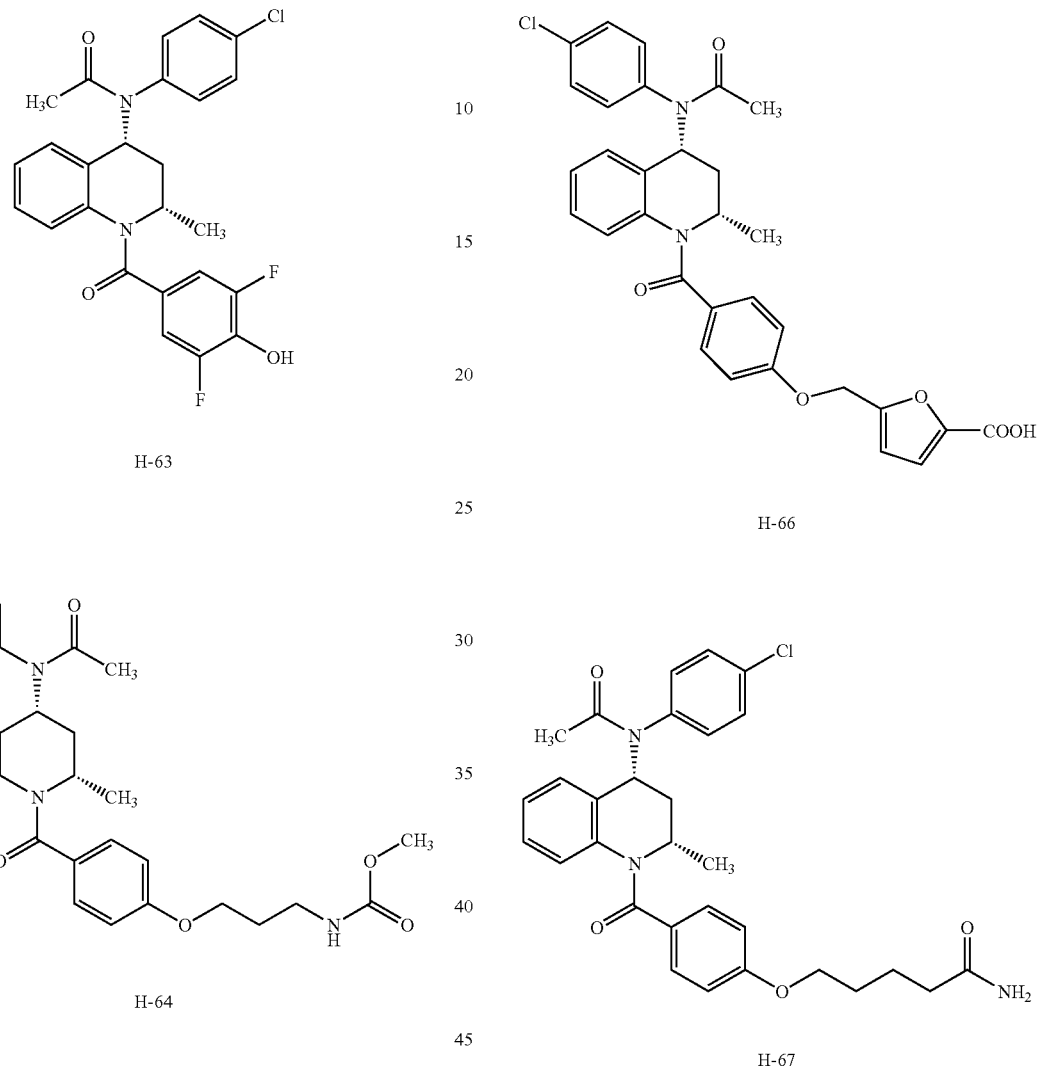
H-65
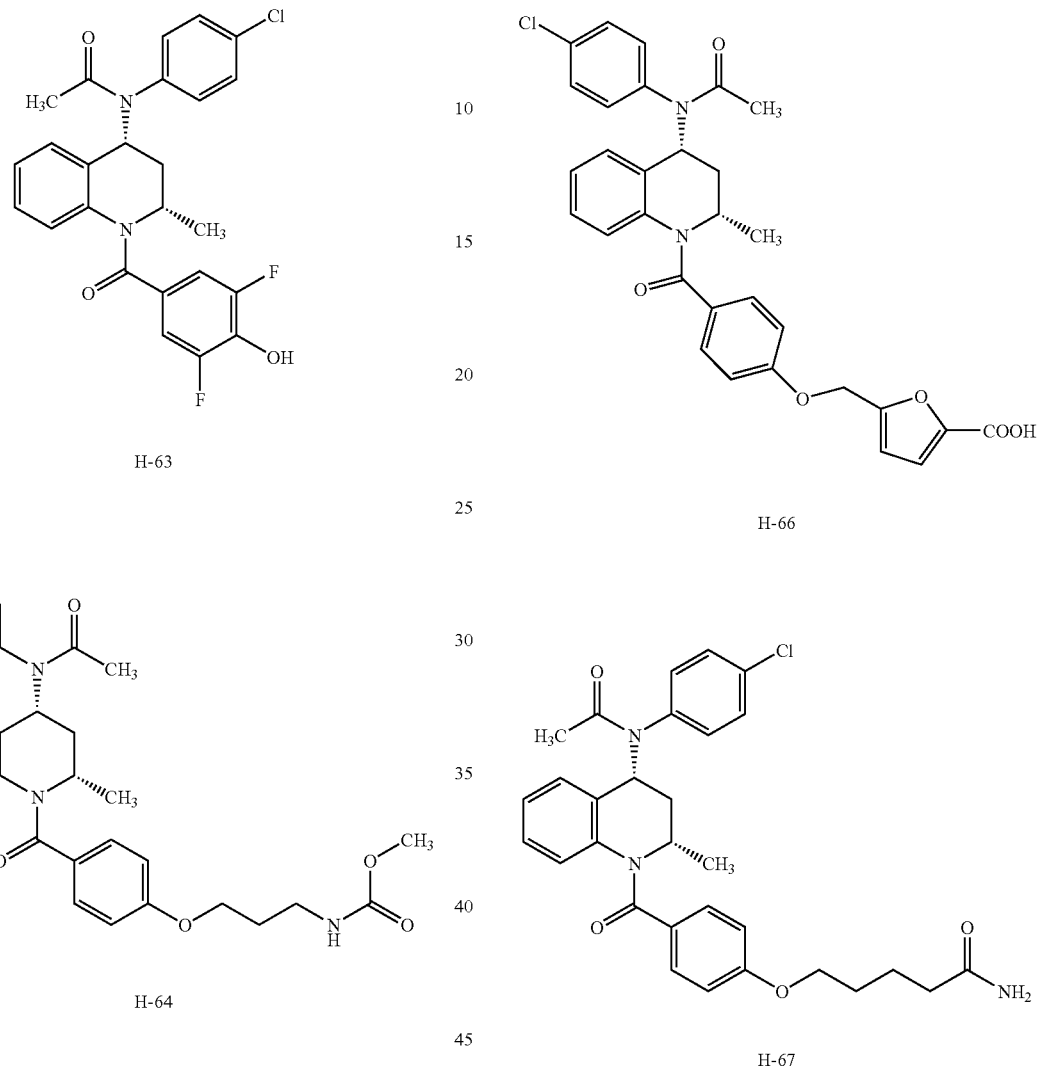
H-68

TABLE 9-continued
Exemplary Compounds:
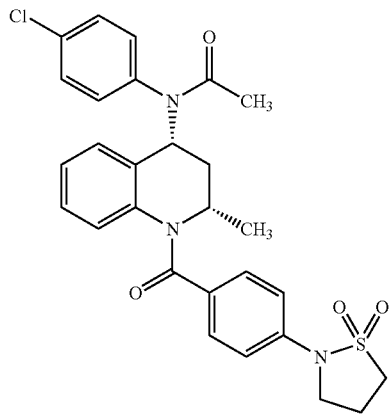
H-69
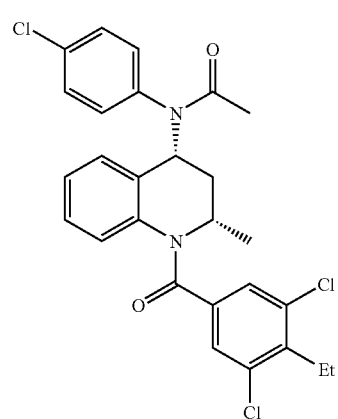
H-70
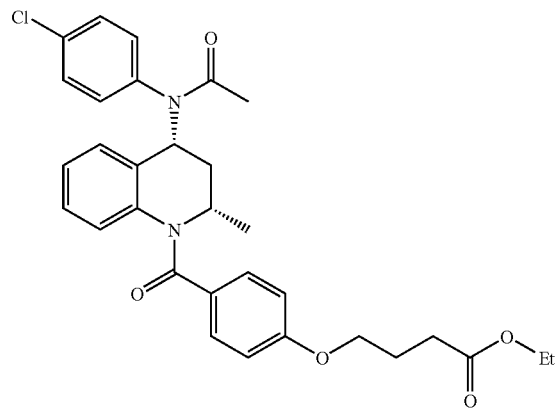
H-71
TABLE 9-continued
Exemplary Compounds:
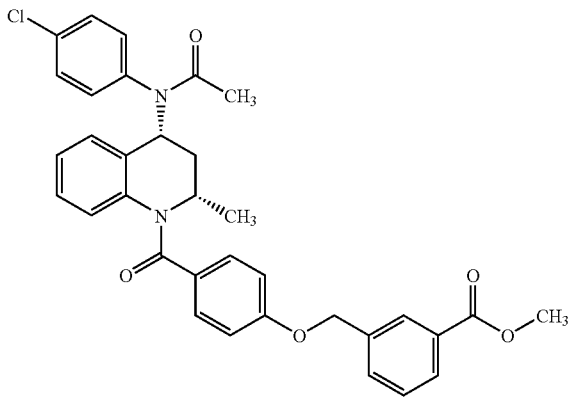
H-72
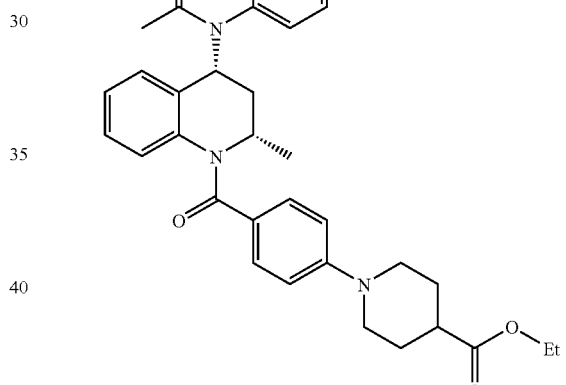
H-73
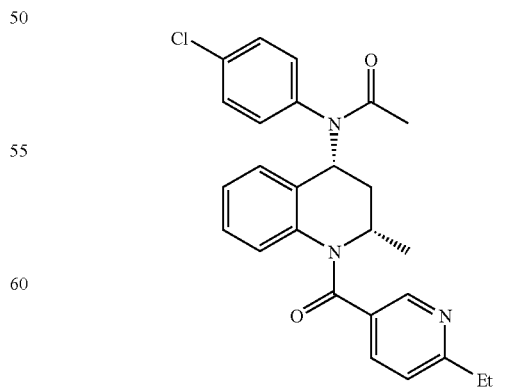
H-74

TABLE 9-continued
Exemplary Compounds:
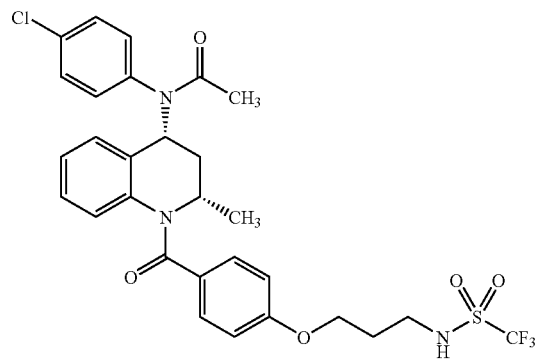
H-75
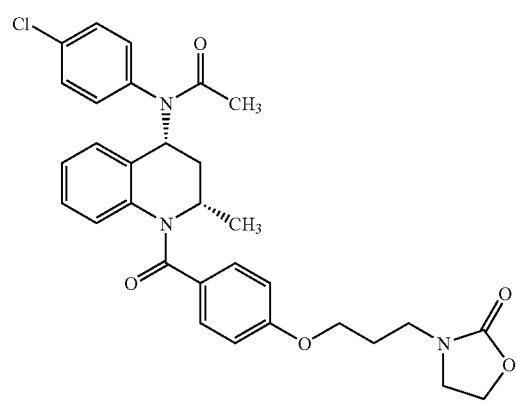
H-76
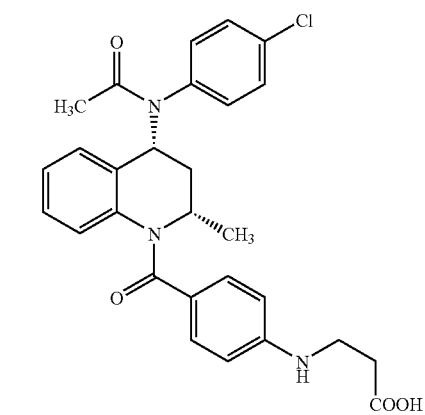
H-77
TABLE 9-continued
Exemplary Compounds:
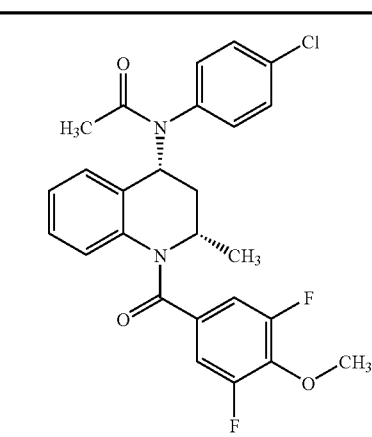
H-78
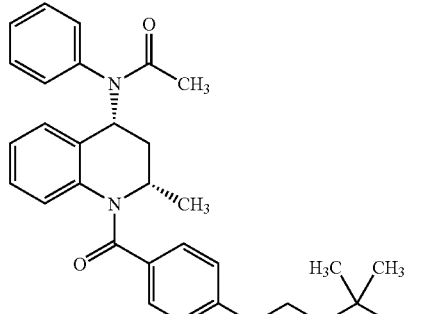
H-79
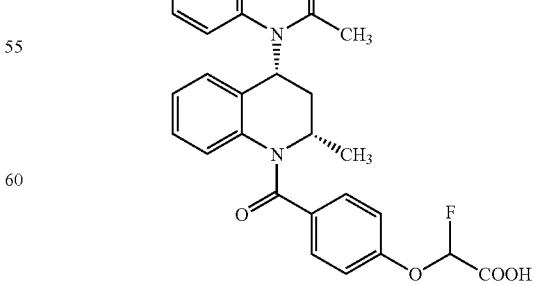
H-80

TABLE 9-continued
Exemplary Compounds:
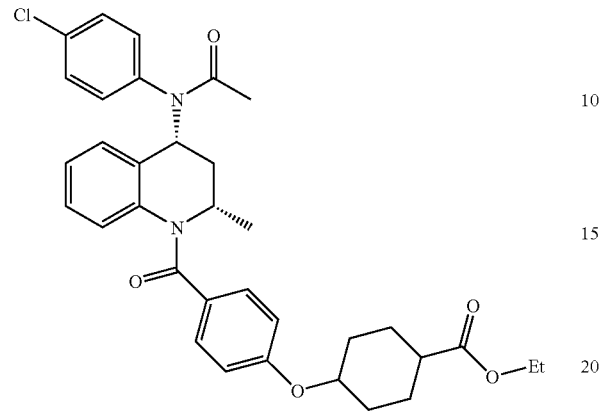
H-81
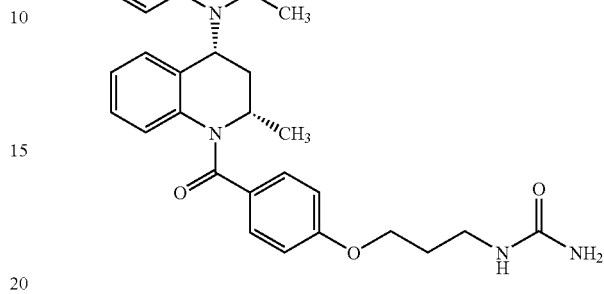
H-84
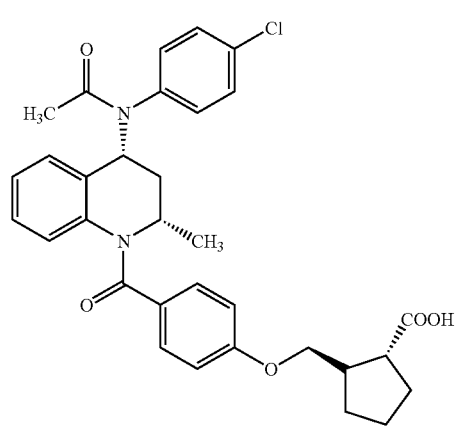
H-82
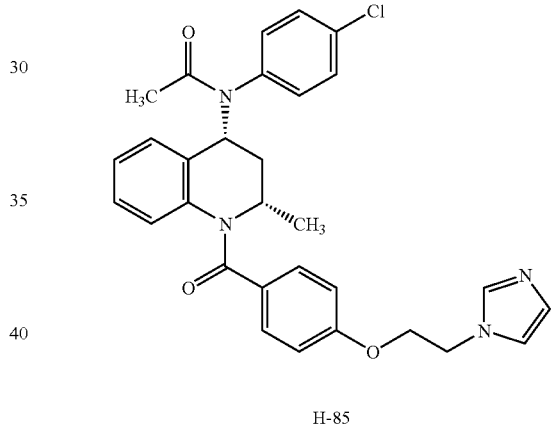
H-85
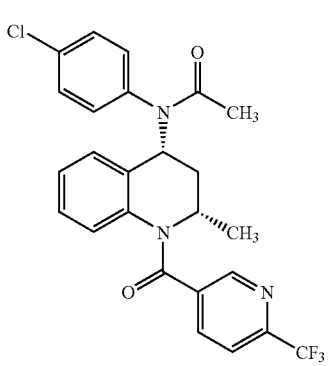
H-83
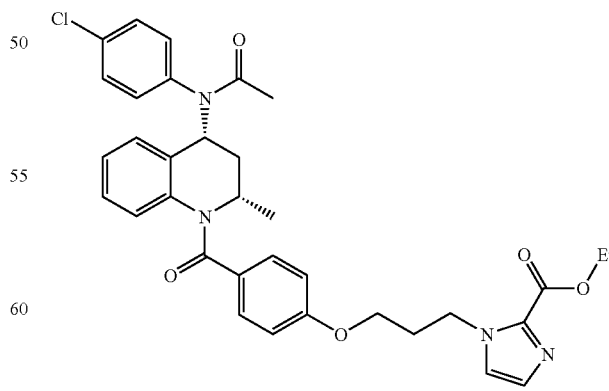
H-86

TABLE 9-continued
Exemplary Compounds:
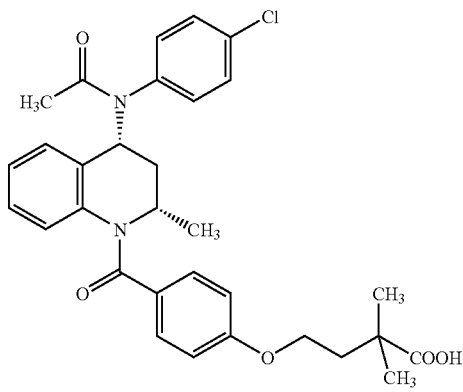
H-87
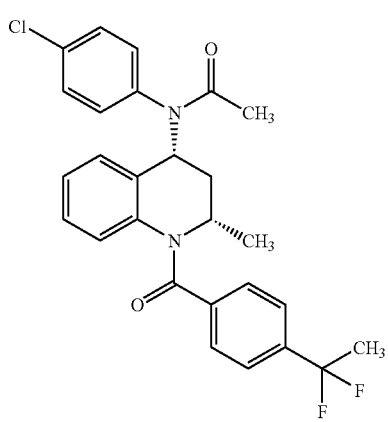
H-88
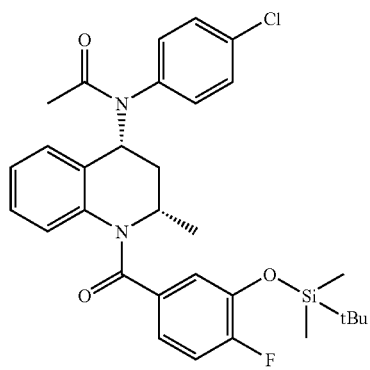
H-89
TABLE 9-continued
Exemplary Compounds:
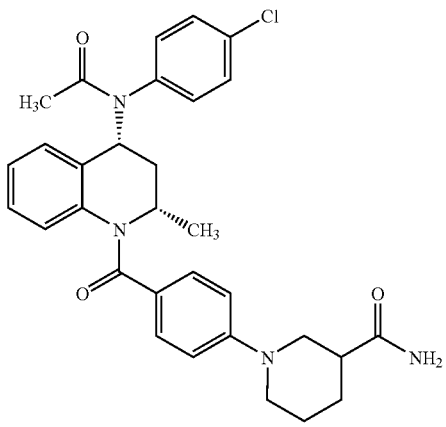
H-90
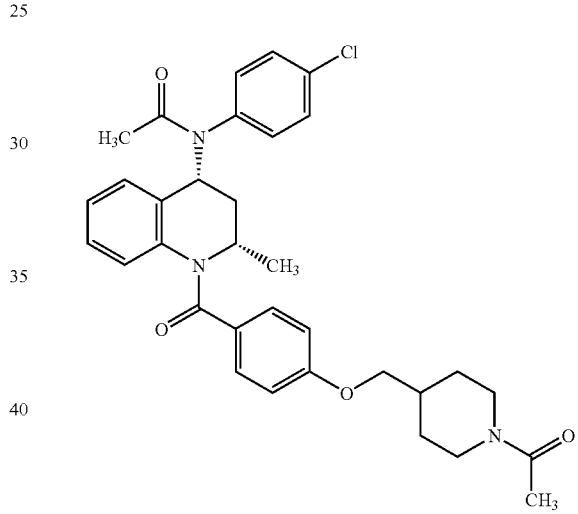
H-91
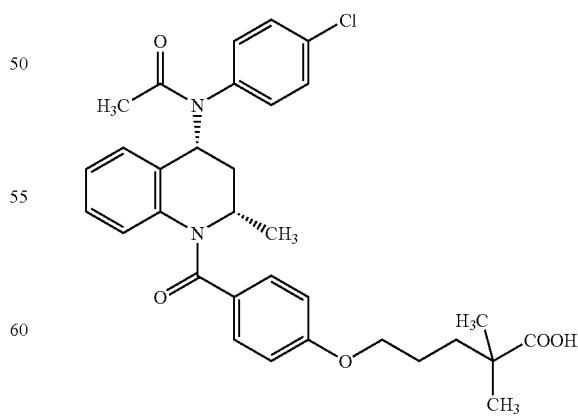
H-92

TABLE 9-continued
Exemplary Compounds:
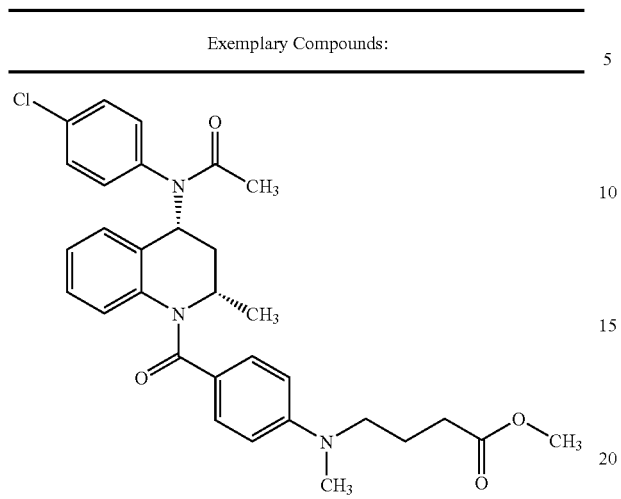
H-93
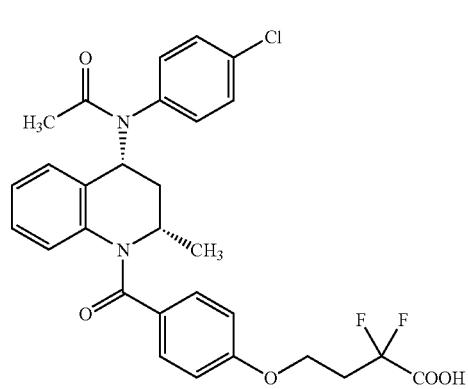
H-94
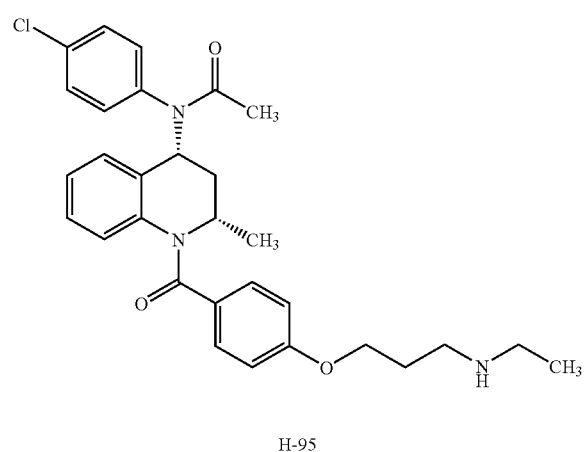
H-95
TABLE 9-continued
Exemplary Compounds:
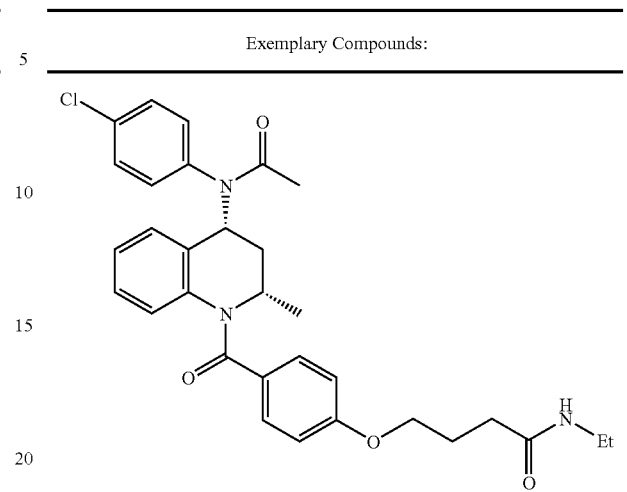
H-96
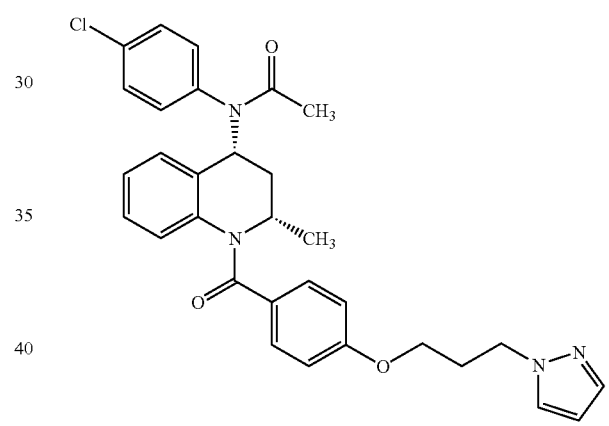
H-97
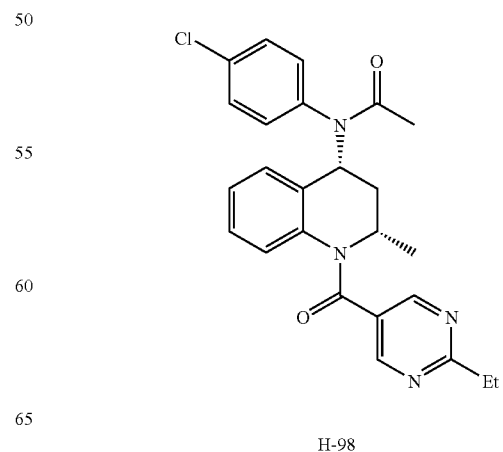
H-98

TABLE 9-continued
Exemplary Compounds:
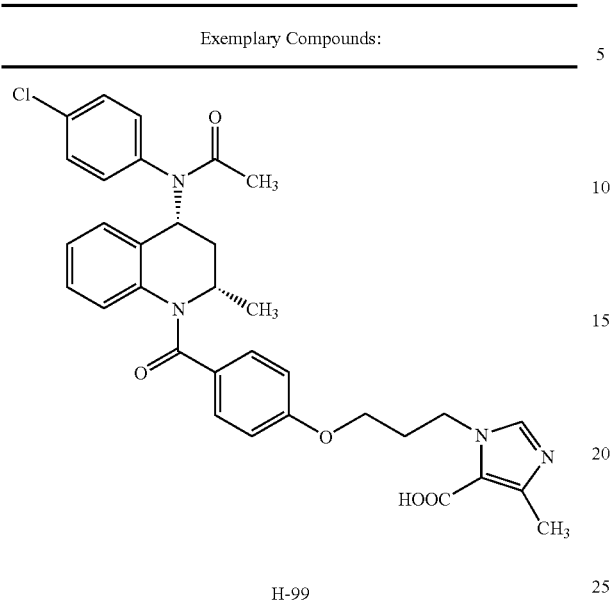
H-99
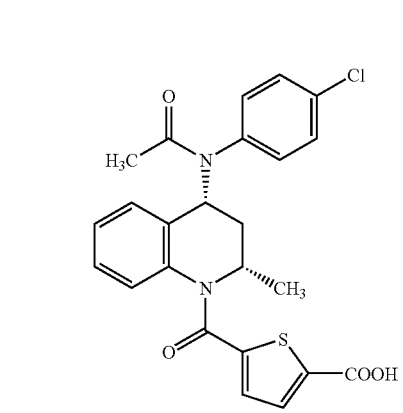
H-100
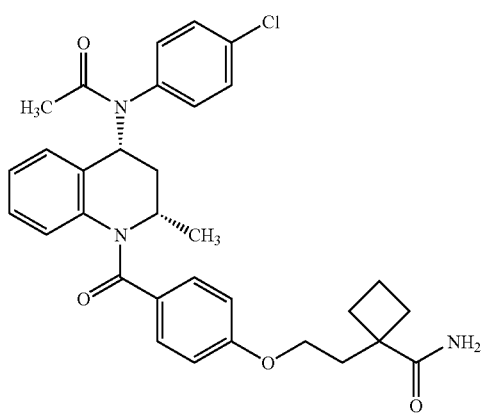
H-101
TABLE 9-continued
Exemplary Compounds:
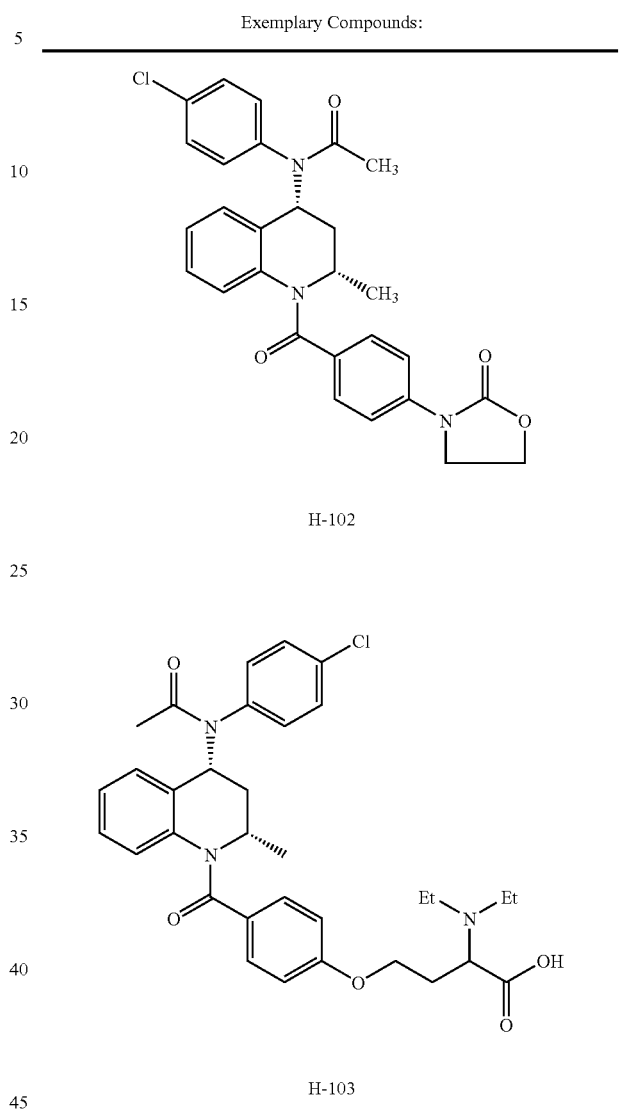
H-102
H-103
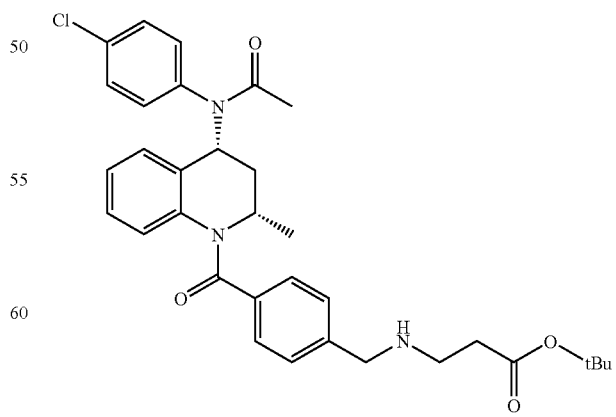
H-104

TABLE 9-continued
Exemplary Compounds:
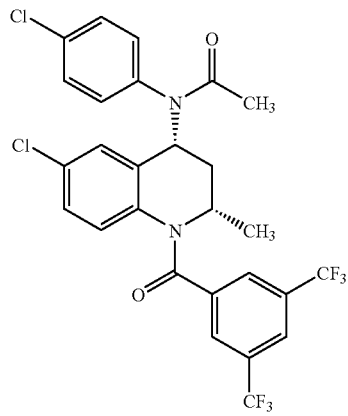
H-105
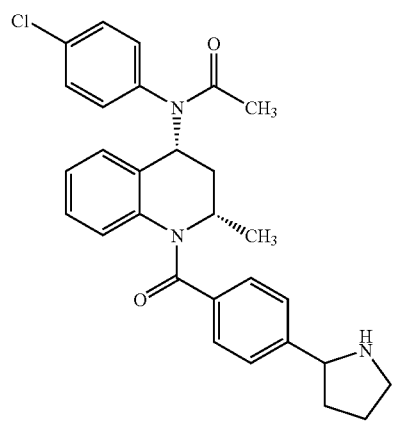
H-106
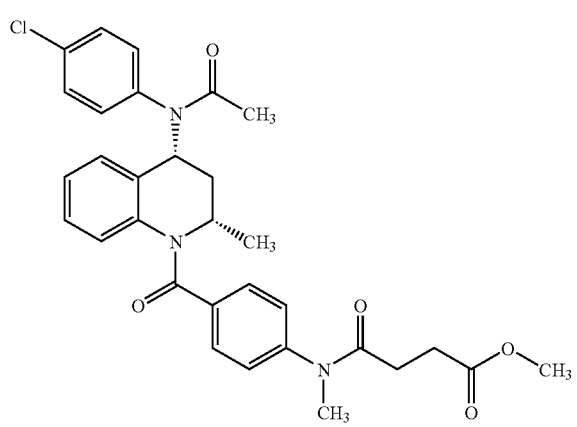
H-107
TABLE 9-continued
Exemplary Compounds:
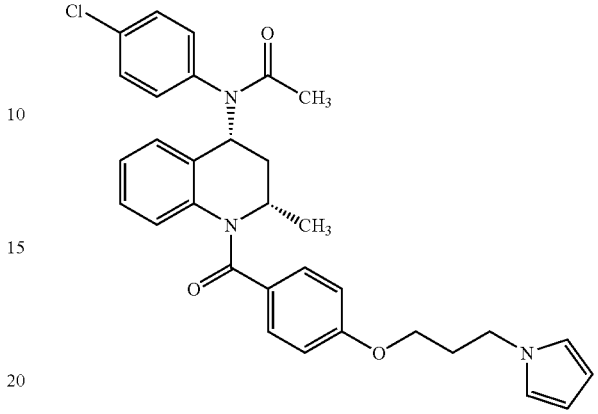
H-108
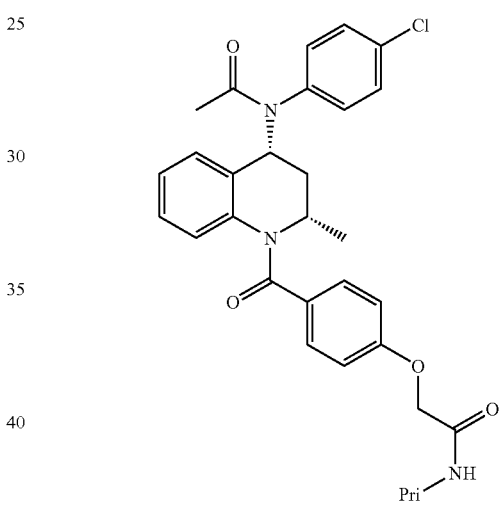
H-109
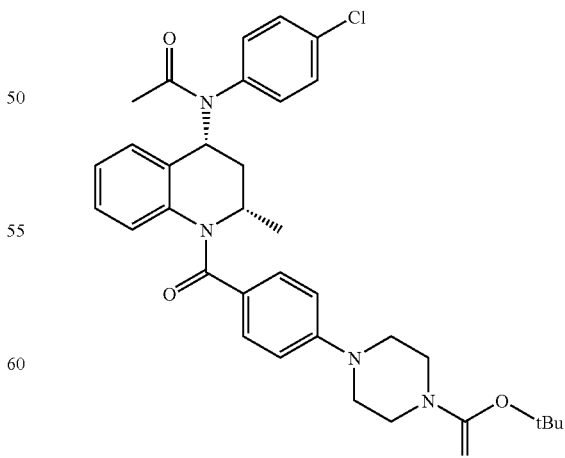
H-110

TABLE 9-continued
Exemplary Compounds:
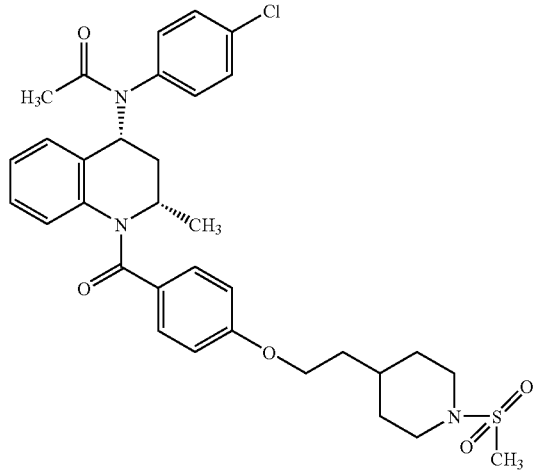
H-111
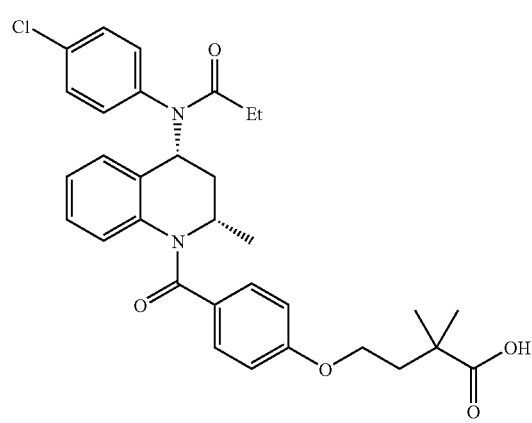
H-112
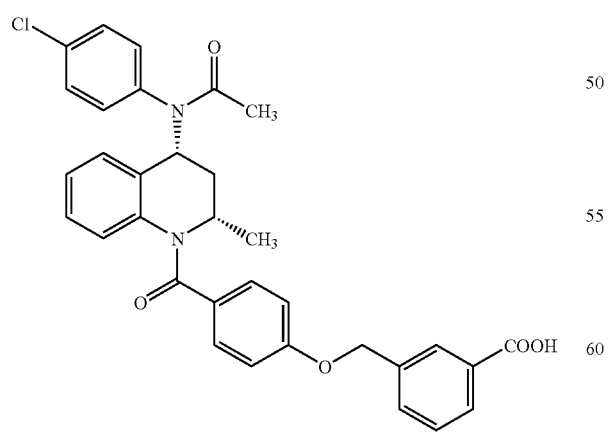
H-113
TABLE 9-continued
Exemplary Compounds:
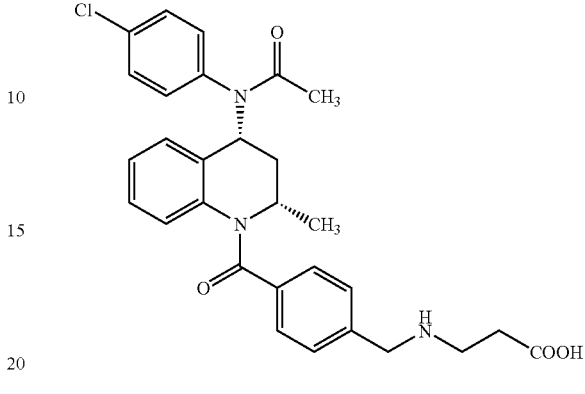
H-114
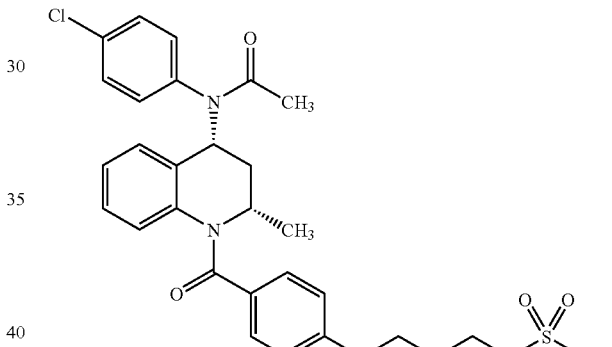
H-115
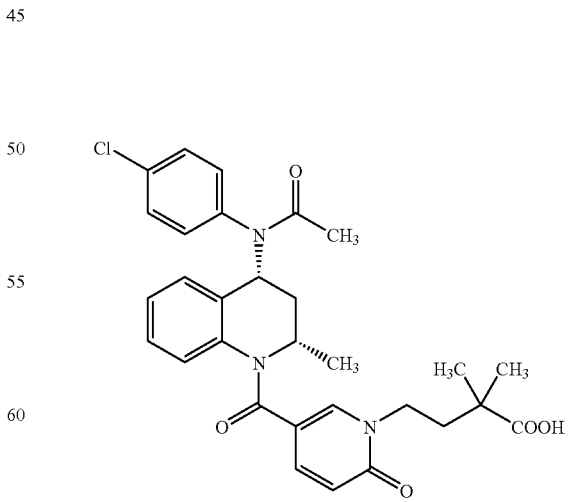
H-116

TABLE 9-continued
Exemplary Compounds:
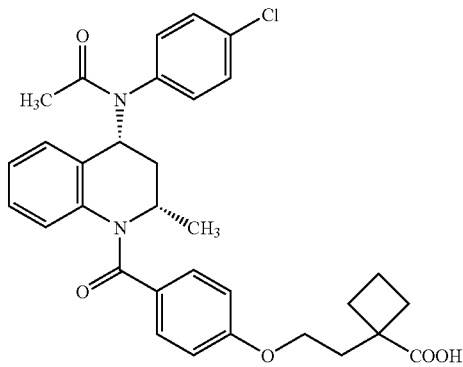
H-117
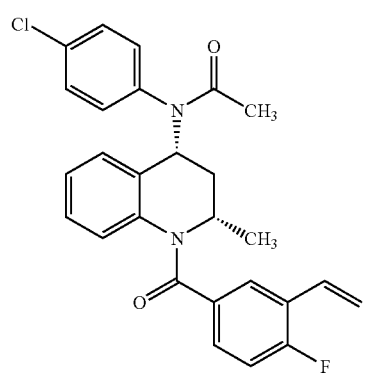
H-120
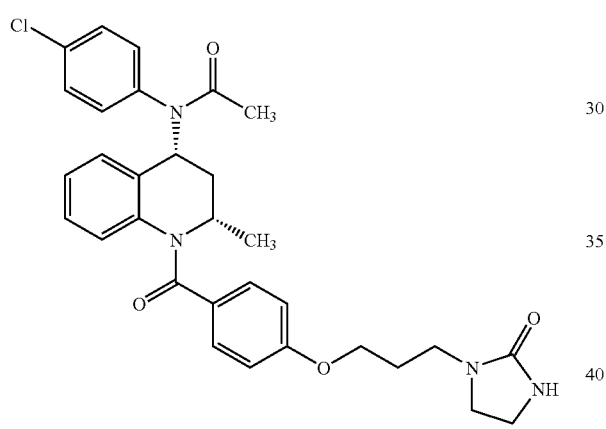
H-118
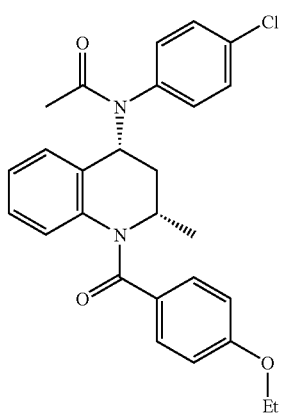
H-121
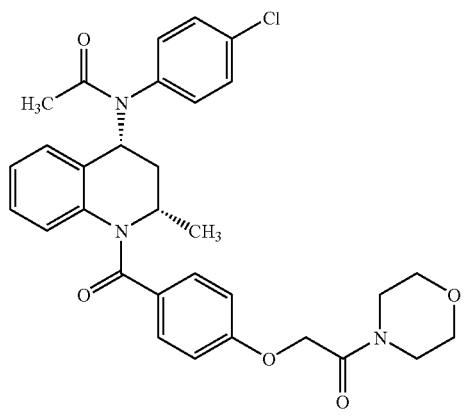
H-119
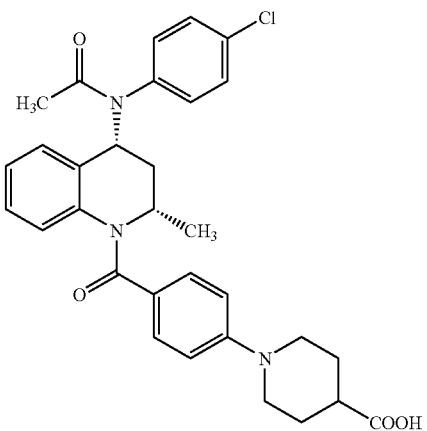
H-122

TABLE 9-continued
Exemplary Compounds:
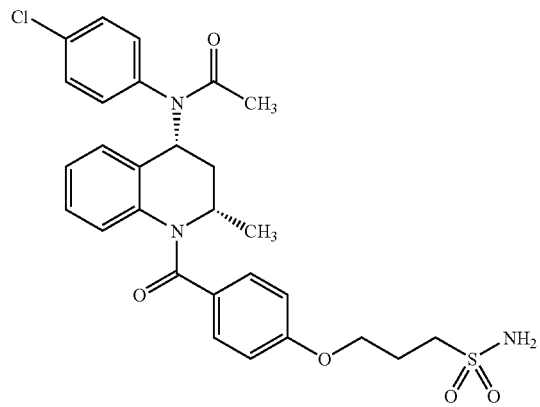
H-123
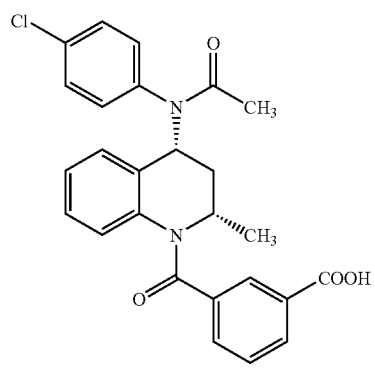
H-124
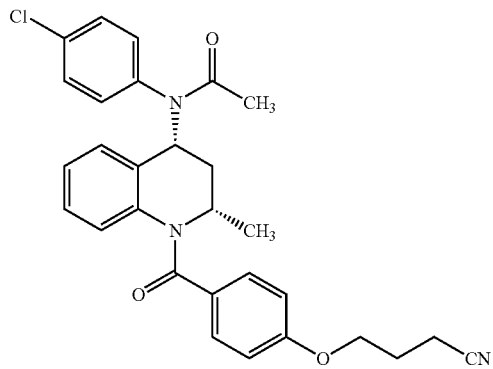
H-125
TABLE 9-continued
Exemplary Compounds:
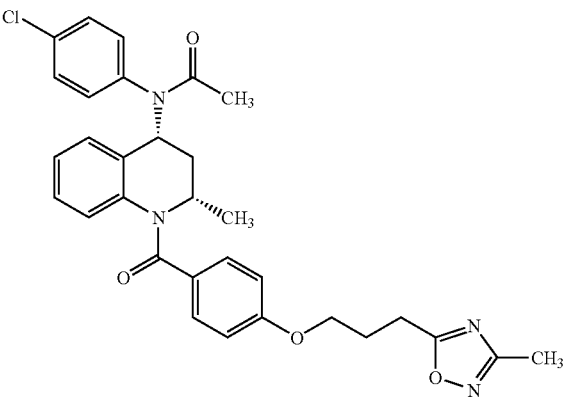
H-126
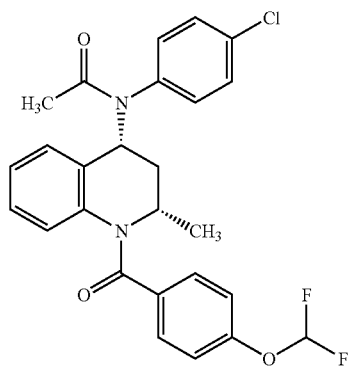
H-127
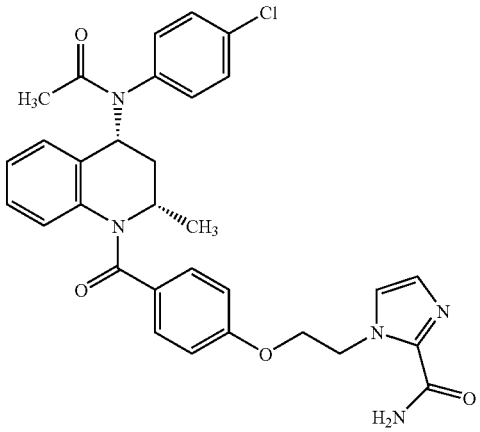
H-128

TABLE 9-continued
Exemplary Compounds:
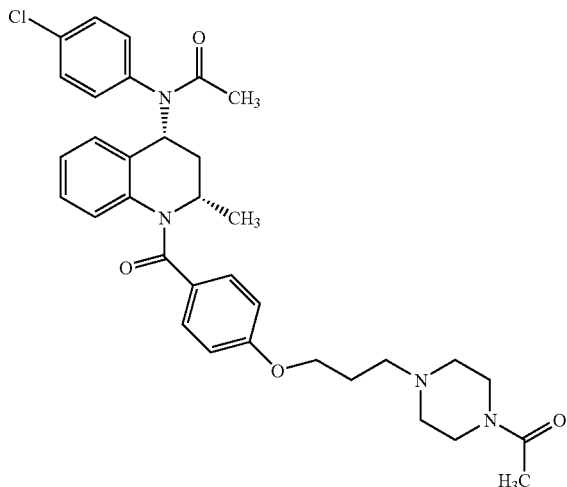
H-129
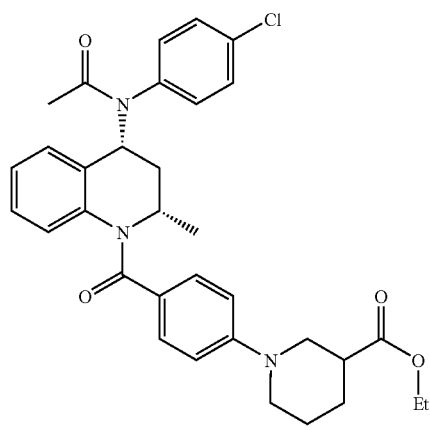
H-130
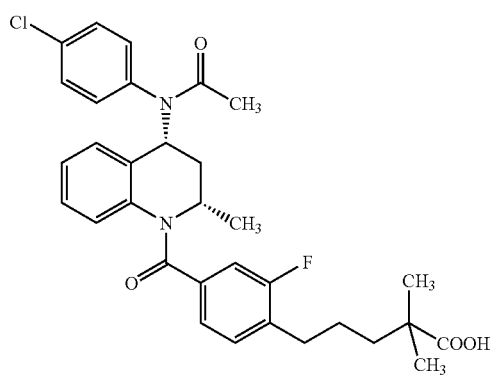
H-131
TABLE 9-continued
Exemplary Compounds:
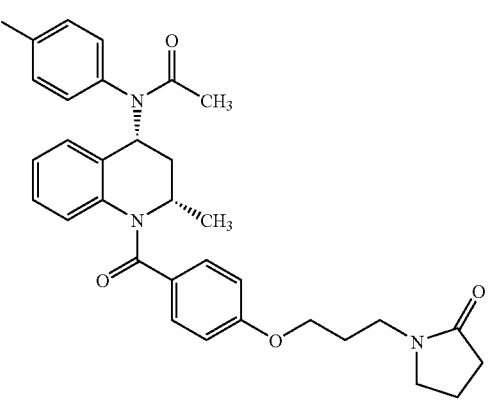
H-132
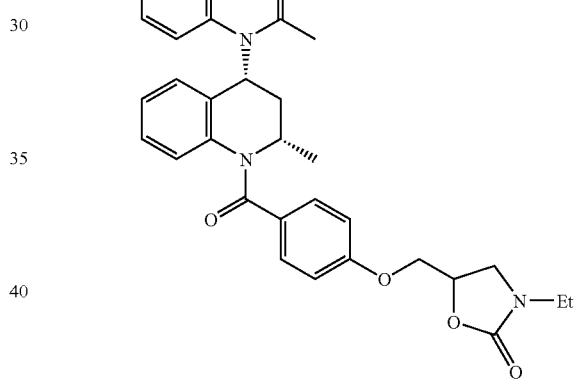
H-133
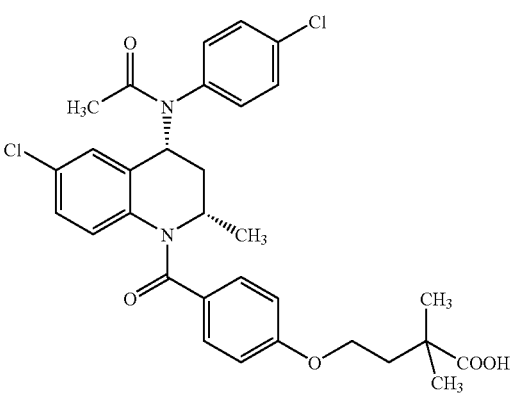
H-134

TABLE 9-continued
Exemplary Compounds:
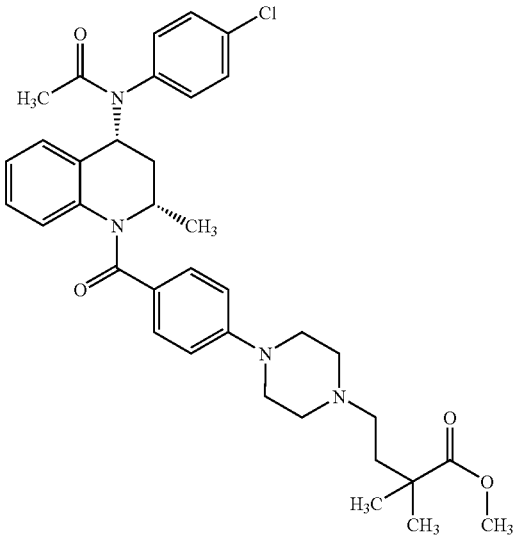
H-135
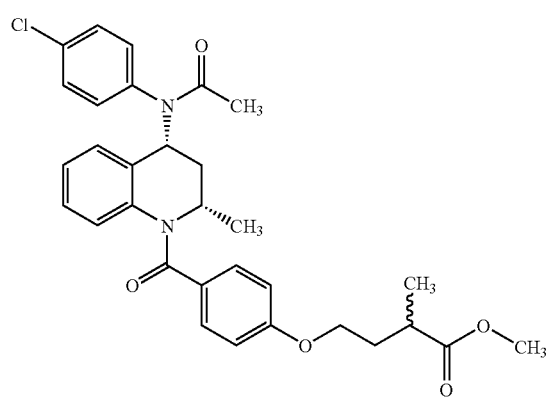
H-136
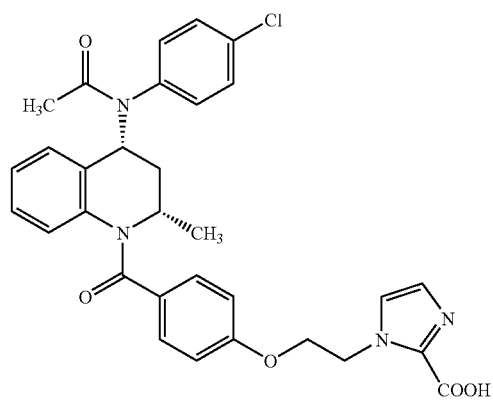
H-137
TABLE 9-continued
Exemplary Compounds:
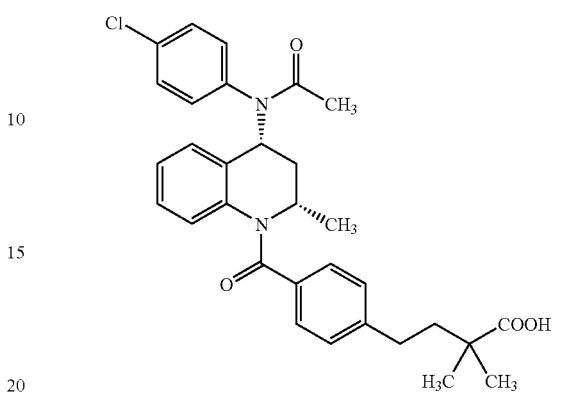
H-138
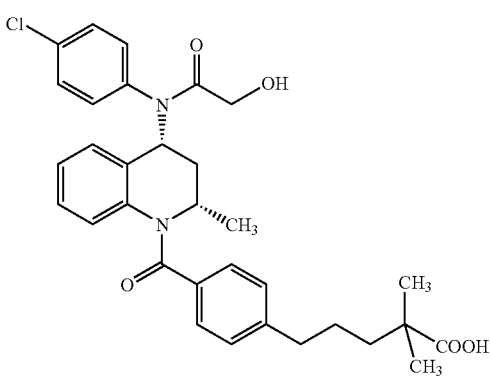
H-139
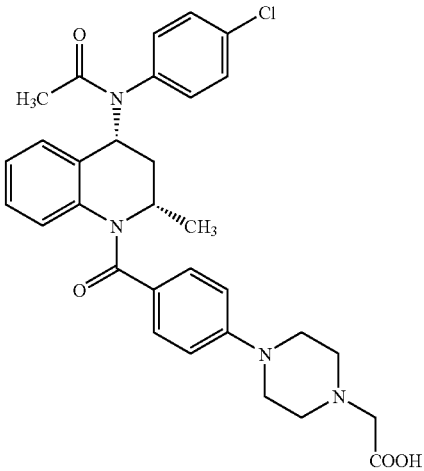
H-140

TABLE 9-continued
Exemplary Compounds:
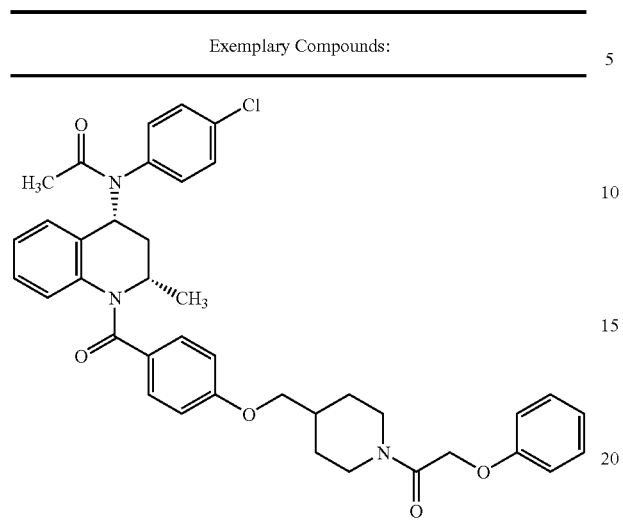
H-141
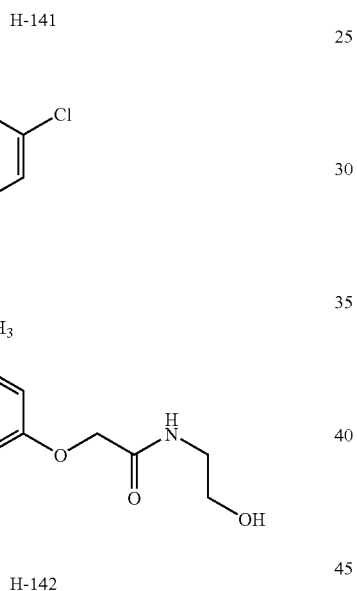
H-142
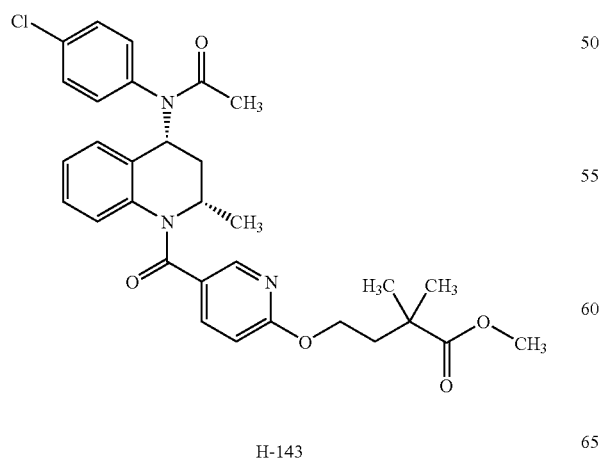
H-143
TABLE 9-continued
Exemplary Compounds:
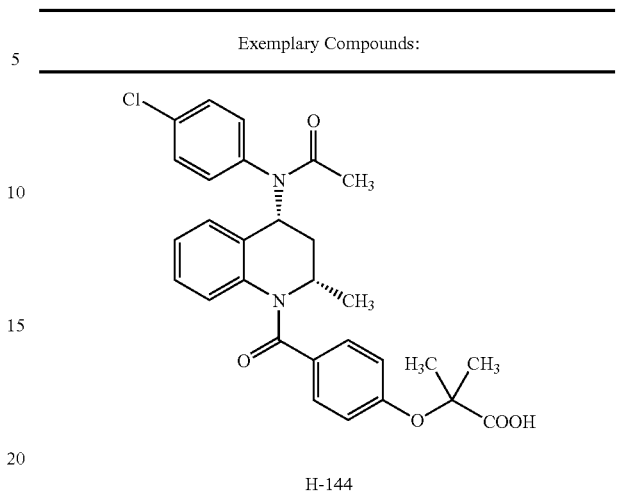
H-144
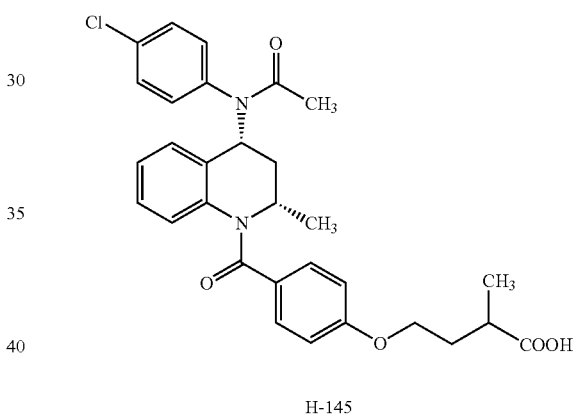
H-145
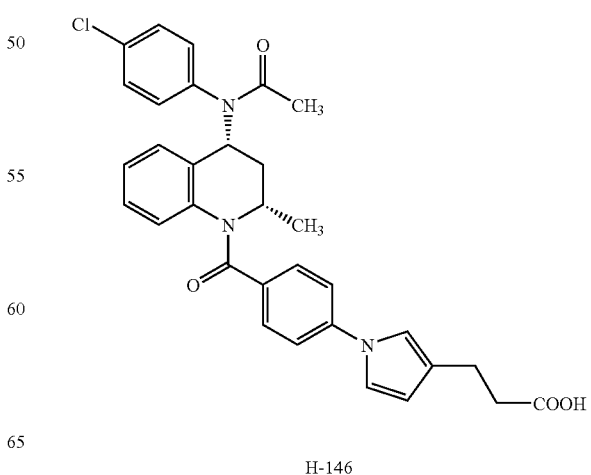
H-146

TABLE 9-continued
Exemplary Compounds:
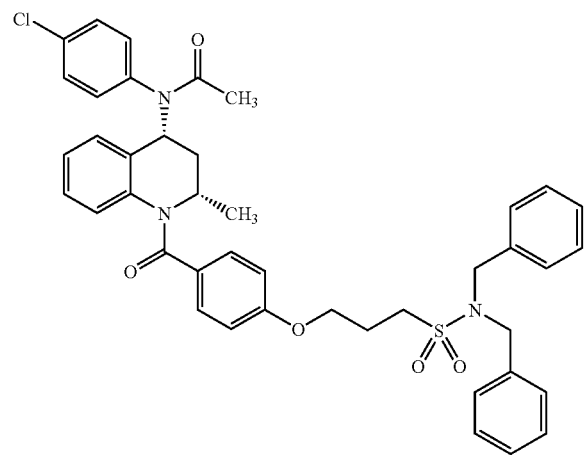
H-147
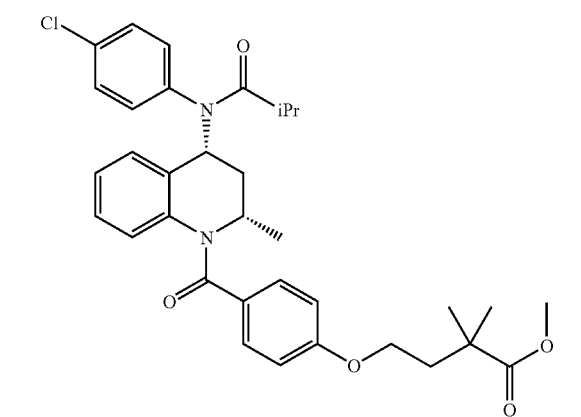
H-148
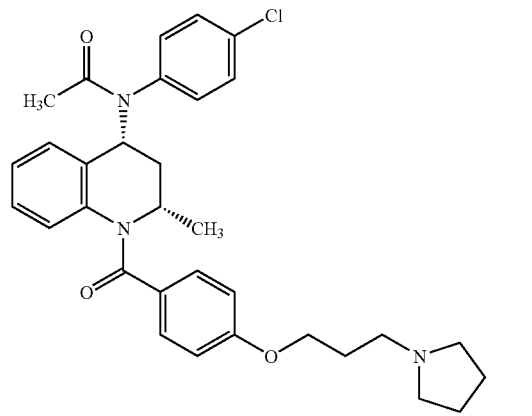
H-149
TABLE 9-continued
Exemplary Compounds:
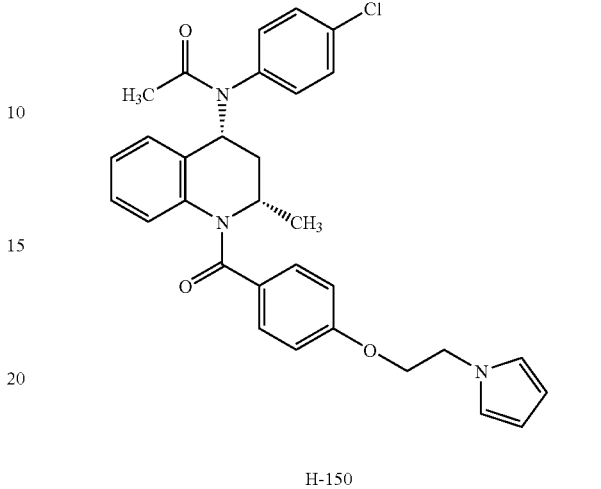
H-150
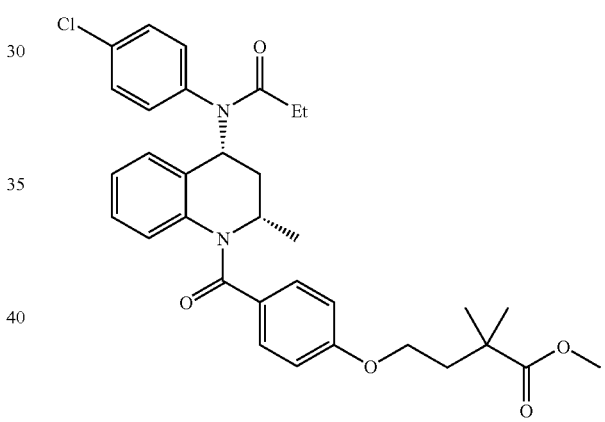
H-151
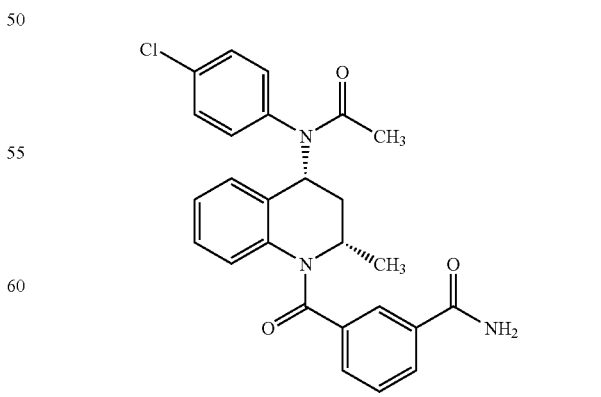
H-152

TABLE 9-continued
Exemplary Compounds:
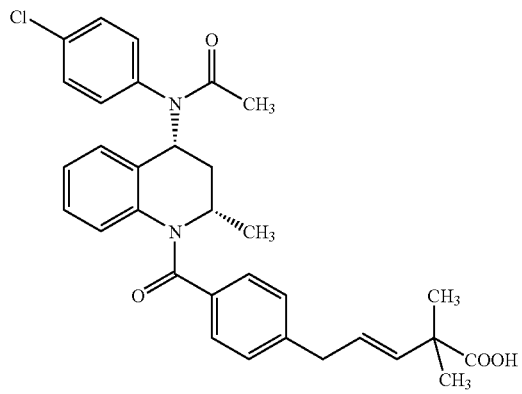
H-153
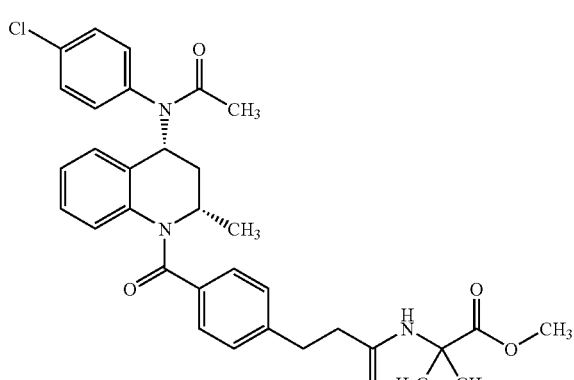
H-154
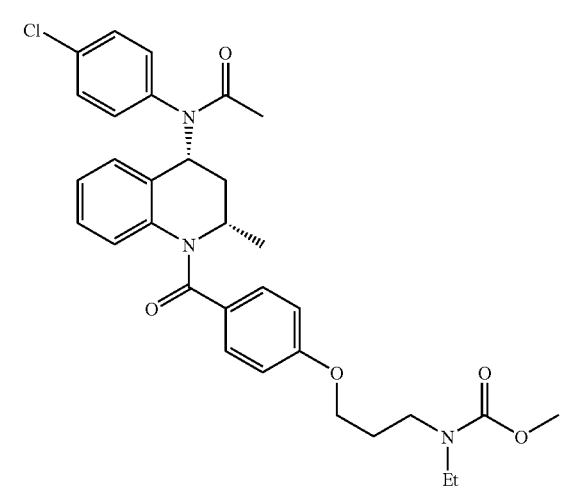
H-155
TABLE 9-continued
Exemplary Compounds:
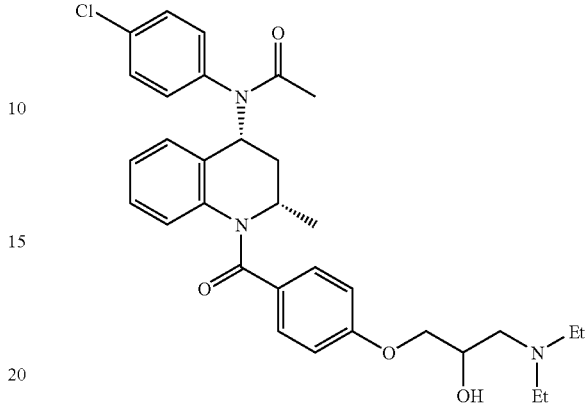
H-156
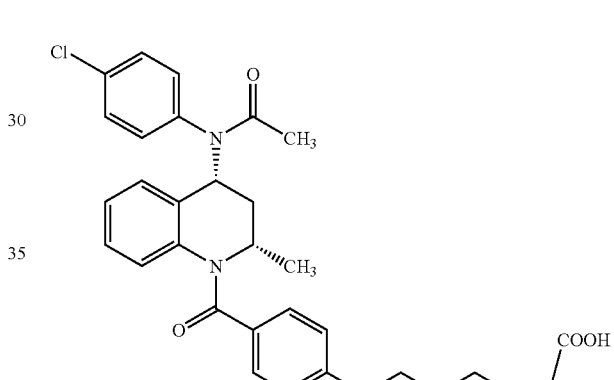
H-157
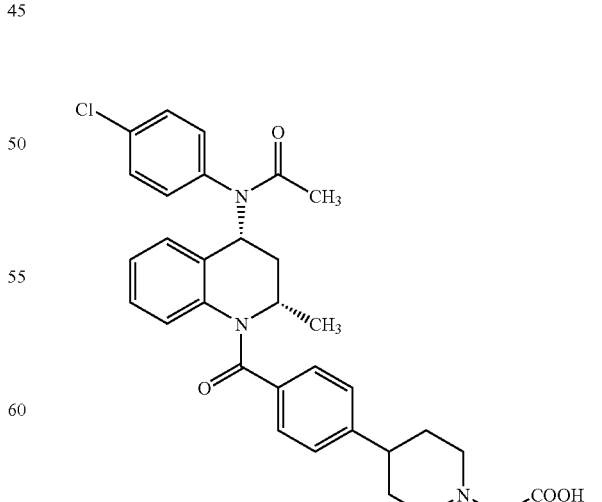
H-158

TABLE 9-continued
Exemplary Compounds:
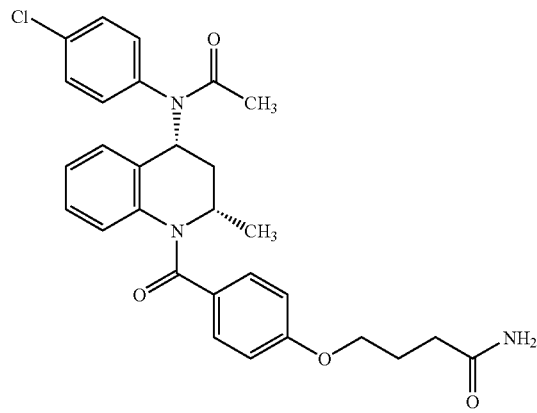
H-159
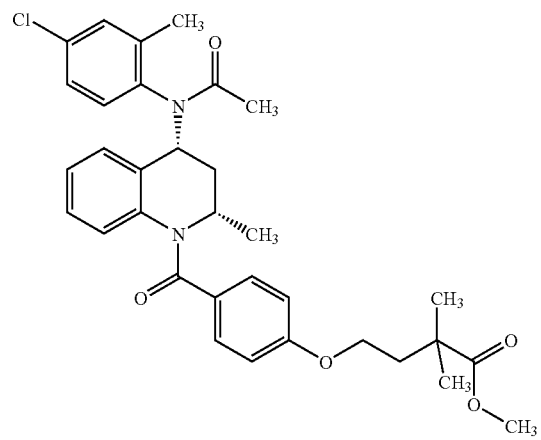
H-160
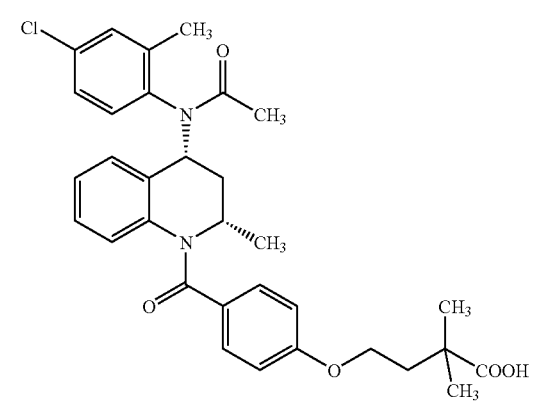
H-161
TABLE 9-continued
Exemplary Compounds:
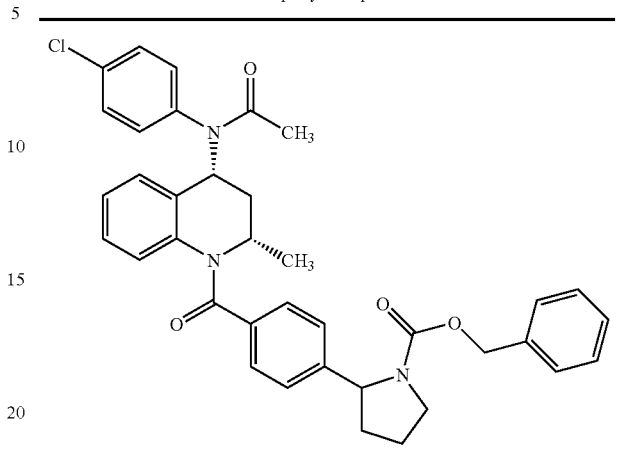
H-162
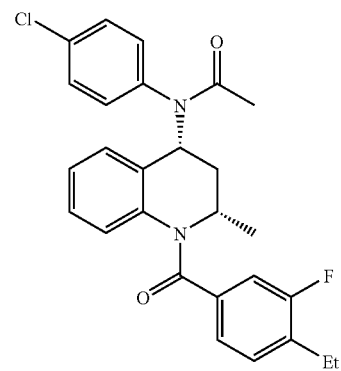
H-163
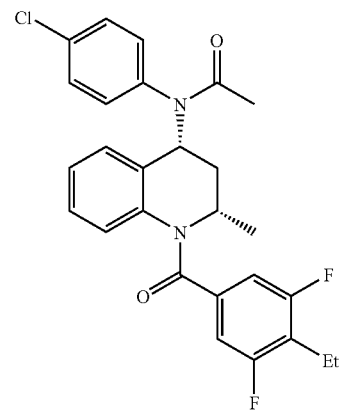
H-164

TABLE 9-continued

Exemplary Compounds:

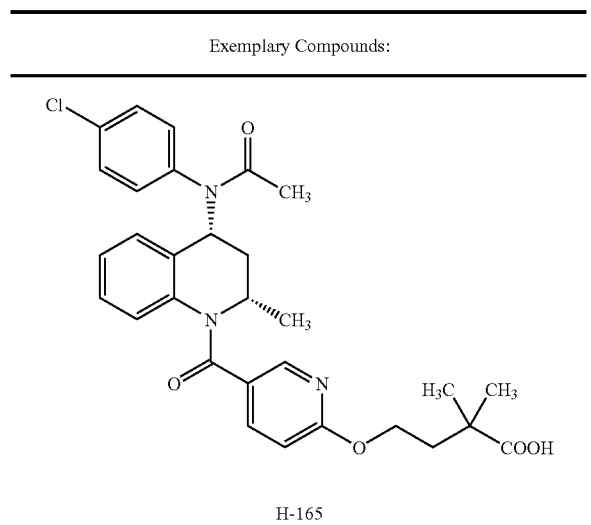

H-165

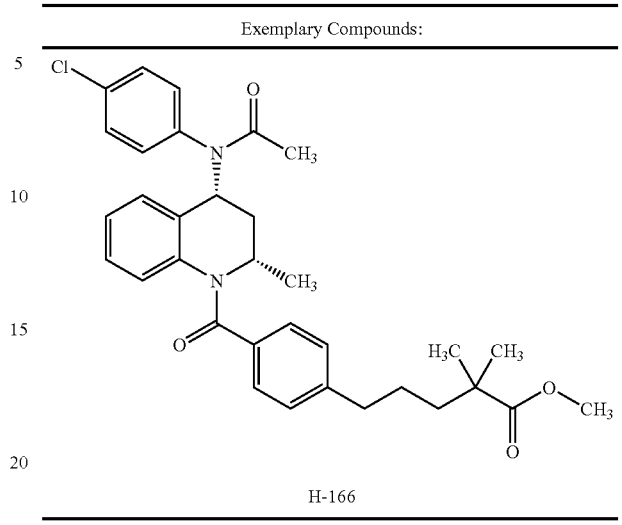

H-166

TABLE 10

Chemical Names of Compounds Represented in Table 9:

| | |
|---|---|
| H-1 | 3-[(4-{[(2S,4R)-4-[Acetyl(4-chlorophenyl)amino]-2-methyl-3,4-dihydroquinolin-1(2H)-yl]carbonyl}phenyl)amino]propanamide |
| H-2 | 4-(4-{[(2S,4R)-4-[Acetyl(4-chlorophenyl)amino]-2-methyl-3,4-dihydroquinolin-1(2H)-yl]carbonyl}-2-fluorophenoxy)-2,2-dimethylbutanoic acid |
| H-3 | Ethyl (4-{[(2S,4R)-4-[acetyl(4-chlorophenyl)amino]-2-methyl-3,4-dihydroquinolin-1(2H)-yl]carbonyl}phenoxy)(fluoro)acetate |
| H-4 | N-((2S,4R)-1-{4-[4-(2-Amino-2-oxoethyl)piperazin-1-yl]benzoyl}-2-methyl-1,2,3,4-tetrahydroquinolin-4-yl)-N-(4-chlorophenyl)acetamide |
| H-5 | 4-(4-{[(2S,4R)-4-[(4-Chlorophenyl)(isobutyryl)amino]-2-methyl-3,4-dihydroquinolin-1(2H)-yl]carbonyl}phenoxy)-2,2-dimethylbutanoic acid |
| H-6 | 2-{[3-(4-{[(2S,4R)-4-[Acetyl(4-chlorophenyl)amino]-2-methyl-3,4-dihydroquinolin-1(2H)-yl]carbonyl}phenoxy)propyl]amino}-2-methylpropanoic acid |
| H-7 | N-[(2S,4R)-1-(4-tert-Butylbenzoyl)-2-methyl-1,2,3,4-tetrahydroquinolin-4-yl]-N-(4-chlorophenyl)acetamide |
| H-8 | N-(4-Chlorophenyl)-N-{(2S,4R)-1-[4-(3-hydroxy-3-methylbutoxy)benzoyl]-2-methyl-1,2,3,4-tetrahydroquinolin-4-yl}acetamide |
| H-9 | N-(4-Chlorophenyl)-N-[(2S,4R)-1-(4-iodobenzoyl)-2-methyl-1,2,3,4-tetrahydroquinolin-4-yl]acetamide |
| H-10 | N-((2S,4R)-1-{4-[3-(Acetylamino)propoxy]benzoyl}-2-methyl-1,2,3,4-tetrahydroquinolin-4-yl)-N-(4-chlorophenyl)acetamide |
| H-11 | N-(4-Chlorophenyl)-N-((2S,4R)-2-methyl-1-{4-[4,4,4-trifluoro-3-hydroxy-3-(trifluoromethyl)butoxy]benzoyl}-1,2,3,4-tetrahydroquinolin-4-yl)acetamide |
| H-12 | 4-(4-{[(2S,4R)-4-[Acetyl(4-chlorophenyl)amino]-2-methyl-3,4-dihydroquinolin-1(2H)-yl]carbonyl}phenoxy)cyclohexanecarboxamide |
| H-13 | N-(4-Chlorophenyl)-N-((2S,4R)-2-methyl-1-{4-[3-(1H-tetrazol-5-yl)propoxy]benzoyl}-1,2,3,4-tetrahydroquinolin-4-yl)acetamide |
| H-14 | Methyl 4-(4-{[(2S,4R)-4-[(4-chlorophenyl)(cyclopropylcarbonyl)amino]-2-methyl-3,4-dihydroquinolin-1(2H)-yl]carbonyl}phenoxy)-2,2-dimethylbutanoate |
| H-15 | Methyl 5-(4-{[(2S,4R)-4-[acetyl(4-chlorophenyl)amino]-2-methyl-3,4-dihydroquinolin-1(2H)-yl]carbonyl}-2-fluorophenoxy)-2,2-dimethylpentanoate |
| H-16 | 3-(4-{[(2S,4R)-4-[Acetyl(4-chlorophenyl)amino]-2-methyl-3,4-dihydroquinolin-1(2H)-yl]carbonyl}phenoxy)-2,2-dimethylpropanoic acid |
| H-17 | 3-(4-{[(2S,4R)-4-[Acetyl(4-chlorophenyl)amino]-2-methyl-3,4-dihydroquinolin-1(2H)-yl]carbonyl}phenoxy)propane-1-sulfonic acid |
| H-18 | Methyl 4-(5-{[(2S,4R)-4-[acetyl(4-chlorophenyl)amino]-2-methyl-3,4-dihydroquinolin-1(2H)-yl]carbonyl}-2-fluorophenoxy)-2,2-dimethylbutanoate |
| H-19 | N-(4-Chlorophenyl)-N-[(2S,4R)-1-(4-fluoro-3-hydroxybenzoyl)-2-methyl-1,2,3,4-tetrahydroquinolin-4-yl]acetamide |
| H-20 | 4-(4-{[(2S,4R)-4-[Acetyl(4-chlorophenyl)amino]-2-methyl-3,4-dihydroquinolin-1(2H)-yl]carbonyl}phenoxy)-N,N-diethylbutanamide |
| H-21 | N-{(2S,4R)-6-Chloro-2-methyl-1-[(3-methylisoxazol-5-yl)carbonyl]-1,2,3,4-tetrahydroquinolin-4-yl}-N-(4-chlorophenyl)acetamide |
| H-22 | 4-(4-{[(2S,4R)-4-[Acetyl(4-chlorophenyl)amino]-2-methyl-3,4-dihydroquinolin-1(2H)-yl]carbonyl}phenoxy)cyclohexanecarboxylic acid |
| H-23 | Methyl 5-(4-{[(2S,4R)-4-[[(acetyloxy)acetyl](4-chlorophenyl)amino]-2-methyl-3,4-dihydroquinolin-1(2H)-yl]carbonyl}phenyl)-2,2-dimethylpentanoate |

TABLE 10-continued

Chemical Names of Compounds Represented in Table 9:

| | |
|---|---|
| H-24 | 4-(4-{[(2S,4R)-4-[Acetyl(4-chlorophenyl)amino]-2-methyl-3,4-dihydroquinolin-1(2H)-yl]carbonyl}phenoxy)-1-methylpyrrolidine-2-carboxylic acid |
| H-25 | 4-(4-{[(2S,4R)-4-[Acetyl(4-chlorophenyl)amino]-2-methyl-3,4-dihydroquinolin-1(2H)-yl]carbonyl}phenoxy)-2,2-dimethylbutanamide |
| H-26 | N-(4-Chlorophenyl)-N-{(2S,4R)-2-methyl-1-[4-(3-pyridin-3-ylpropoxy)benzoyl]-1,2,3,4-tetrahydroquinolin-4-yl}acetamide |
| H-27 | 5-[(4-{[(2S,4R)-4-[Acetyl(4-chlorophenyl)amino]-2-methyl-3,4-dihydroquinolin-1(2H)-yl]carbonyl}phenoxy)methyl]-2-furamide |
| H-28 | N-(4-Chlorophenyl)-N-{(2S,4R)-2-methyl-1-[4-(3-piperazin-1-ylpropoxy)benzoyl]-1,2,3,4-tetrahydroquinolin-4-yl}acetamide |
| H-29 | Methyl 4-(4-{[(2S,4R)-4-[acetyl(4-chlorophenyl)amino]-2-methyl-3,4-dihydroquinolin-1(2H)-yl]carbonyl}-2,6-difluorophenoxy)-2,2-dimethylbutanoate |
| H-30 | 1-(4-{[(2S,4R)-4-[Acetyl(4-chlorophenyl)amino]-2-methyl-3,4-dihydroquinolin-1(2H)-yl]carbonyl}phenyl)piperidine-4-carboxamide |
| H-31 | N-{(2S,4R)-1-[3,5-Bis(trifluoromethyl)benzoyl]-2-methyl-1,2,3,4-tetrahydroquinolin-4-yl}-N-(4-chlorophenyl)acetamide |
| H-32 | 2-{[3-(4-{[(2S,4R)-4-[Acetyl(4-chlorophenyl)amino]-2-methyl-3,4-dihydroquinolin-1(2H)-yl]carbonyl}phenyl)propanoyl]amino}-2-methylpropanoic acid |
| H-33 | Methyl 4-[5-{[(2S,4R)-4-[acetyl(4-chlorophenyl)amino]-2-methyl-3,4-dihydroquinolin-1(2H)-yl]carbonyl}-2-oxopyridin-1(2H)-yl]-2,2-dimethylbutanoate |
| H-34 | N-{(2S,4R)-1-[4-(Aminomethyl)benzoyl]-2-methyl-1,2,3,4-tetrahydroquinolin-4-yl}-N-(4-chlorophenyl)acetamide |
| H-35 | N-[3-(4-{[(2S,4R)-4-[Acetyl(4-chlorophenyl)amino]-2-methyl-3,4-dihydroquinolin-1(2H)-yl]carbonyl}phenoxy)propyl]-2,2-dimethylpropanamide |
| H-36 | Methyl 4-(4-{[(2S,4R)-4-[acetyl(4-chlorophenyl)amino]-2-methyl-3,4-dihydroquinolin-1(2H)-yl]carbonyl}-2-fluorophenoxy)-2,2-dimethylbutanoate |
| H-37 | N-(4-Chlorophenyl)-N-{(2S,4R)-2-methyl-1-[4-(2-oxoimidazolidin-1-yl)benzoyl]-1,2,3,4-tetrahydroquinolin-4-yl}acetamide |
| H-38 | 4-[(4-{[(2S,4R)-4-[Acetyl(4-chlorophenyl)amino]-2-methyl-3,4-dihydroquinolin-1(2H)-yl]carbonyl}phenyl)(methyl)amino]butanoic acid |
| H-39 | N-(4-Chlorophenyl)-N-((2S,4R)-1-{4-[(4-hydroxy-4-methylpentyl)oxy]benzoyl}-2-methyl-1,2,3,4-tetrahydroquinolin-4-yl)acetamide |
| H-40 | 1-[3-(4-{[(2S,4R)-4-[Acetyl(4-chlorophenyl)amino]-2-methyl-3,4-dihydroquinolin-1(2H)-yl]carbonyl}phenoxy)propyl]-1H-imidazole-2-carboxamide |
| H-41 | N-(4-Chlorophenyl)-N-((2S,4R)-2-methyl-1-{4-[(2-oxo-1,3-oxazolidin-5-yl)methoxy]benzoyl}-1,2,3,4-tetrahydroquinolin-4-yl)acetamide |
| H-42 | 5-(4-{[(2S,4R)-4-[Acetyl(4-chlorophenyl)amino]-2-methyl-3,4-dihydroquinolin-1(2H)-yl]carbonyl}phenyl)-2,2-dimethylpentanoic acid |
| H-43 | Methyl 4-(4-{[(2S,4R)-4-[acetyl(4-chlorophenyl)amino]-2-methyl-3,4-dihydroquinolin-1(2H)-yl]carbonyl}phenyl)-2,2-dimethylbutanoate |
| H-44 | 3-(4-{[(2S,4R)-4-[Acetyl(4-chlorophenyl)amino]-6-chloro-2-methyl-3,4-dihydroquinolin-1(2H)-yl]carbonyl}phenoxy)-2,2-dimethylpropanoic acid |
| H-45 | N-(4-Aminophenyl)-N-[(2S,4R)-1-(4-methoxybenzoyl)-2-methyl-1,2,3,4-tetrahydroquinolin-4-yl]acetamide |
| H-46 | 4-(4-{[(2S,4R)-4-[Acetyl(4-chlorophenyl)amino]-2-methyl-3,4-dihydroquinolin-1(2H)-yl]carbonyl}phenoxy)-2,2-dimethyl-N-(methylsulfonyl)butanamide |
| H-47 | 1-(4-{[(2S,4R)-4-[Acetyl(4-chlorophenyl)amino]-2-methyl-3,4-dihydroquinolin-1(2H)-yl]carbonyl}phenyl)piperidine-3-carboxylic acid |
| H-48 | N-{[(2S,4R)-6-Chloro-1-[(6-ethylpyridin-3-yl)carbonyl]-2-methyl-1,2,3,4-tetrahydroquinolin-4-yl}-N-(4-chlorophenyl)acetamide |
| H-49 | 4-(4-{[(2S,4R)-4-[(4-Chlorophenyl)(cyclopropylcarbonyl)amino]-2-methyl-3,4-dihydroquinolin-1(2H)-yl]carbonyl}phenoxy)-2,2-dimethylbutanoic acid |
| H-50 | N-(4-Chlorophenyl)-N-[(2S,4R)-1-(3-ethyl-4-fluorobenzoyl)-2-methyl-1,2,3,4-tetrahydroquinolin-4-yl]acetamide |
| H-51 | N-(4-Chlorophenyl)-N-((2S,4R)-1-{4-[3-(1H-imidazol-1-yl)-3-methylbutoxy]benzoyl}-2-methyl-1,2,3,4-tetrahydroquinolin-4-yl)acetamide |
| H-52 | N-(4-Chlorophenyl)-N-((2S,4R)-1-{4[(1-ethylpiperidin-4-yl)methoxy[benzoyl}-2-methyl-1,2,3,4-tetrahydroquinolin-4-yl)acetamide |
| H-53 | 4-[(4-{[(2S,4R)-4-[Acetyl(4-chlorophenyl)amino]-2-methyl-3,4-dihydroquinolin-1(2H)-yl]carbonyl}phenyl)(methyl)amino]butanamide |
| H-54 | (3S)-4-(4-{[(2S,4R)-4-[Aacetyl(4-chlorophenyl)amino]-2-methyl-3,4-dihydroquinolin-1(2H)-yl]carbonyl}phenoxy)-3-hydroxybutanoic acid |
| H-55 | 3-(4-{[(2S,4R)-4-[Acetyl(4-chlorophenyl)amino]-2-methyl-3,4-dihydroquinolin-1(2H)-yl]carbonyl}phenoxy)-2,2-dimethylpropanamide |
| H-56 | N-((2S,4R)-1-{4-[2-(1-Acetylpiperidin-4-yl)ethoxy]benzoy}-2-methyl-1,2,3,4-tetrahydroquinolin-4-yl)-N-(4-chlorophenyl)acetamide |
| H-57 | 4-(5-{[(2S,4R)-4-[Acetyl(4-chlorophenyl)amino]-2-methyl-3,4-dihydroquinolin-1(2H)-yl]carbonyl}-2-fluorophenoxy)-2,2-dimethylbutanoic acid |
| H-58 | N-(4-Chlorophenyl)-N-((2S,4R)-2-methyl-1-{4-[(methylsulfonyl)amino]benzoyl}-1,2,3,4-tetrahydroquinolin-4-yl)acetamide |
| H-59 | (2S)-N-[3-(4-{[(2S,4R)-4-[Acetyl(4-chlorophenyl)amino]-2-methyl-3,4-dihydroquinolin-1(2H-yl]carbonyl}phenoxy)propyl]-1-methylpyrrolidine-2-carboxamide |
| H-60 | 4-(4-{[(2R,4S)-4-[Acetyl(4-chlorophenyl)amino]-2-methyl-3,4-dihydroquinolin-1(2H)-yl]carbonyl}phenoxy)-2,2-dimethylbutanoic acid |
| H-61 | N-[3-(4-{[(2S,4R)-4-[Acetyl(4-chlorophenyl)amino]-2-methyl-3,4-dihydroquinolin-1(2H)-yl]carbonyl}phenoxy)propyl]-N-ethylacetamide |

TABLE 10-continued

Chemical Names of Compounds Represented in Table 9:

| | |
|---|---|
| H-62 | N-(4-Chlorophenyl)-N-{(2S,4R)-1-[4-(4-hydroxy-4-methylpentyl)benzoyl]-2-methyl-1,2,3,4-tetrahydroquinolin-4-yl}acetamide |
| H-63 | N-(4-Chlorophenyl)-N-[(2S,4R)-1-(3,5-difluoro-4-hydroxybenzoyl)-2-methyl-1,2,3,4-tetrahydroquinolin-4-yl]acetamide |
| H-64 | Methyl [3-(4-{[(2S,4R)-4-[acetyl(4-chlorophenyl)amino]-2-methyl-3,4-dihydroquinolin-1(2H)-yl]carbonyl}phenoxy)propyl]carbamate |
| H-65 | Methyl 5-{[(2S,4R)-4-[acetyl(4-chlorophenyl)amino]-2-methyl-3,4-dihydroquinolin-1(2H)-yl]carbonyl}thiophene-2-carboxylate |
| H-66 | 5-[(4-{[(2S,4R)-4-[Acetyl(4-chlorophenyl)amino]-2-methyl-3,4-dihydroquinolin-1(2H)-yl]carbonyl}phenoxy)methyl]-2-furoic acid |
| H-67 | 5-(4-{[(2S,4R)-4-[Acetyl(4-chlorophenyl)amino]-2-methyl-3,4-dihydroquinolin-1(2H)-yl]carbonyl}phenoxy)pentanamide |
| H-68 | N-(4-Chlorophenyl)-N-{(2S,4R)-2-methyl-1-[(2-methylpyrimidin-5-yl)carbonyl]-1,2,3,4-tetrahydroquinolin-4-yl}acetamide |
| H-69 | N-(4-Chlorophenyl)-N-{(2S,4R)-1-[4-(1,1-dioxidoisothiazolidin-2-yl)benzoyl]-2-methyl-1,2,3,4-tetrahydroquinolin-4-yl}acetamide |
| H-70 | N-(4-Chlorophenyl)-N-[(2S,4R)-1-(3,5-dichloro-4-ethylbenzoyl)-2-methyl-1,2,3,4-tetrahydroquinolin-4-yl]acetamide |
| H-71 | Ethyl 4-(4-{[(2S,4R)-4-[acetyl(4-chlorophenyl)amino]-2-methyl-3,4-dihydroquinolin-1(2H)-yl]carbonyl}phenoxy)butanoate |
| H-72 | Methyl 3-[(4-{[(2S,4R)-4-[acetyl(4-chlorophenyl)amino]-2-methyl-3,4-dihydroquinolin-1(2H)-yl]carbonyl}phenoxy)methyl]benzoate |
| H-73 | Ethyl 1-(4-{[(2S,4R)-4-[acetyl(4-chlorophenyl)amino]-2-methyl-3,4-dihydroquinolin-1(2H)-yl]carbonyl}phenyl)piperidine-4-carboxylate |
| H-74 | N-(4-Chlorophenyl)-N-{(2S,4R)-1-[(6-ethylpyridin-3-yl)carbonyl]-2-methyl-1,2,3,4-tetrahydroquinolin-4-yl}acetamide |
| H-75 | N-(4-Chlorophenyl)-N-{(2S,4R)-2-methyl-1-[4-(3-{[(trifluoromethyl)sulfonyl]amino}propoxy)benzoyl]-1,2,3,4-tetrahydroquinolin-4-yl}acetamide |
| H-76 | N-(4-Chlorophenyl)-N-((2S,4R)-2-methyl-1-{4-[3-(2-oxo-1,3-oxazolidin-3-yl)propoxy]benzoyl}-1,2,3,4-tetrahydroquinolin-4-yl)acetamide |
| H-77 | 3-[(4-{[(2S,4R)-4-[Acetyl(4-chlorophenyl)amino]-2-methyl-3,4-dihydroquinolin-1(2H)-yl]carbonyl}phenyl)amino]propanoic acid |
| H-78 | N-(4-Chlorophenyl)-N-[(2S,4R)-1-(3,5-difluoro-4-methoxybenzoyl)-2-methyl-1,2,3,4-tetrahydroquinolin-4-yl]acetamide |
| H-79 | 4-(4-{[(2S,4R)-4-[Acetyl(phenyl)amino]-2-methyl-3,4-dihydroquinolin-1(2H)-yl]carbonyl}phenoxy)-2,2-dimethylbutanoic acid |
| H-80 | (4-{[(2S,4R)-4-[Acetyl(4-chlorophenyl)amino]-2-methyl-3,4-dihydroquinolin-1(2H)-yl]carbonyl}phenoxy)(fluoro)acetic acid |
| H-81 | Ethyl 4-(4-{[(2S,4R)-4-[acetyl(4-chlorophenyl)amino]-2-methyl-3,4-dihydroquinolin-1(2H)-yl]carbonyl}phenoxy)cyclohexanecarboxylate |
| H-82 | (1R,2R)-2-[(4-{[(2S,4R)-4-[Acetyl(4-chlorophenyl)amino]-2-methyl-3,4-dihydroquinolin-1(2H)-yl]carbonyl}phenoxy)methyl]cyclopentanecarboxylic acid |
| H-83 | N-(4-Chlorophenyl)-N-((2S,4R)-2-methyl-1-{[6-(trifluoromethyl)pyridin-3-yl]carbonyl}-1,2,3,4-tetrahydroquinolin-4-yl)acetamide |
| H-84 | N-[(2S,4R)-1-(4-{3-[(Aminocarbonyl)amino]propoxy}benzoyl)-2-methyl-1,2,3,4-tetrahydroquinolin-4-yl]-N-(4-chlorophenyl)acetamide |
| H-85 | N-(4-Chlorophenyl)-N-((2S,4R)-1-{4-[2-(1H-imidazol-1-yl)ethoxy]benzoyl}-2-methyl-1,2,3,4-tetrahydroquinolin-4-yl)acetamide |
| H-86 | Ethyl 1-[3-(4-{[(2S,4R)-4-[acetyl(4-chlorophenyl)amino]-2-methyl-3,4-dihydroquinolin-1(2H)-yl]carbonyl}phenoxy)propyl]-1H-imidazole-2-carboxylate |
| H-87 | 4-(4-{[(2S,4R)-4-[Acetyl(4-chlorophenyl)amino]-2-methyl-3,4-dihydroquinolin-1(2H)-yl]carbonyl}phenoxy)-2,2-dimethylbutanoic acid |
| H-88 | N-(4-Chlorophenyl)-N-{(2S,4R)-1-[4-(1,1-difluoroethyl)benzoyl]-2-methyl-1,2,3,4-tetrahydroquinolin-4-yl}acetamide |
| H-89 | N-[(2S,4R)-1-(3-{[tert-Butyl(dimethyl)silyl]oxy}-4-fluorobenzoyl)-2-methyl-1,2,3,4-tetrahydroquinolin-4-yl]-N-(4-chlorophenyl)acetamide |
| H-90 | 1-(4-{[(2S,4R)-4-[Acetyl(4-chlorophenyl)amino]-2-methyl-3,4-dihydroquinolin-1(2H)-yl]carbonyl}phenyl)piperidine-3-carboxamide |
| H-91 | N-((2S,4R)-1-{4-[(1-Acetylpiperidin-4-yl)methoxy]benzoyl}-2-methyl-1,2,3,4-tetrahydroquinolin-4-yl)-N-(4-chlorophenyl)acetamide |
| H-92 | 5-(4-{[(2S,4R)-4-[Acetyl(4-chlorophenyl)amino]-2-methyl-3,4-dihydroquinolin-1(2H)-yl]carbonyl}phenoxy)-2,2-dimethylpentanoic acid |
| H-93 | Methyl 4-[(4-{[(2S,4R)-4-[acetyl(4-chlorophenyl)amino]-2-methyl-3,4-dihydroquinolin-1(2H)-yl]carbonyl}phenyl)(methyl)amino]butanoate |
| H-94 | 4-(4-{[(2S,4R)-4-[Acetyl(4-chlorophenyl)amino]-2-methyl-3,4-dihydroquinolin-1(2H)-yl]carbonyl}phenoxy)-2,2-difluorobutanoic acid |
| H-95 | {[3-(4-{[(2S,4R)-4-[Acetyl(4-chlorophenyl)amino]-2-methyl-3,4-dihydroquinolin-1(2H)-yl]carbonyl}phenoxy)propyl]amino}acetic acid |
| H-96 | 4-(4-{[(2S,4R)-4-[Acetyl(4-chlorophenyl)amino]-2-methyl-3,4-dihydroquinolin-1(2H)-yl]carbonyl}phenoxy)-N-ethylbutanamide |
| H-97 | N-(4-Chlorophenyl)-N-((2S,4R)-2-methyl-1-{4-[3-(1H-pyrazol-1-yl)propoxy]benzoyl}-1,2,3,4-tetrahydroquinolin-4-yl)acetamide |
| H-98 | N-(4-Chlorophenyl)-N-{(2S,4R)-1-[(2-ethylpyrimidin-5-yl)carbonyl]-2-methyl-1,2,3,4-tetrahydroquinolin-4-yl}acetamide |
| H-99 | 1-[3-(4-{[(2S,4R)-4-[Acetyl(4-chlorophenyl)amino]-2-methyl-3,4-dihydroquinolin-1(2H)-yl]carbonyl}phenoxy)propyl]-4-methyl-1H-imidazole-5-carboxylic acid |

TABLE 10-continued

Chemical Names of Compounds Represented in Table 9:

| | |
|---|---|
| H-100 | 5-{[(2S,4R)-4-[Acetyl(4-chlorophenyl)amino]-2-methyl-3,4-dihydroquinolin-1(2H)-yl]carbonyl}thiophene-2-carboxylic acid |
| H-101 | 1-[2-(4-{[(2S,4R)-4-[Acetyl(4-chlorophenyl)amino]-2-methyl-3,4-dihydroquinolin-1(2H)-yl]carbonyl}phenoxy)ethyl]cyclobutanecarboxamide |
| H-102 | N-(4-Chlorophenyl)-N-{(2S,4R)-2-methyl-1-[4-(2-oxo-1,3-oxazolidin-3-yl)benzoyl]-1,2,3,4-tetrahydroquinolin-4-yl}acetamide |
| H-103 | 4-(4-{[(2S,4R)-4-[Acetyl(4-chlorophenyl)amino]-2-methyl-3,4-dihydroquinolin-1(2H)-yl]carbonyl}phenoxy)-2-(diethylamino)butanoic acid |
| H-104 | tert-Butyl 3-[(4-{[(2S,4R)-4-[acetyl(4-chlorophenyl)amino]-2-methyl-3,4-dihydroquinolin-1(2H)-yl]carbonyl}benzyl)amino]propanoate |
| H-105 | N-{(2S,4R)-1-[3,5-bis(Trifluoromethyl)benzoyl]-6-chloro-2-methyl-1,2,3,4-tetrahydroquinolin-4-yl}-N-(4-chlorophenyl)acetamide |
| H-106 | N-(4-Chlorophenyl)-N-[(2S,4R)-2-methyl-1-(4-pyrrolidin-2-ylbenzoyl)-1,2,3,4-tetrahydroquinolin-4-yl]acetamide |
| H-107 | Methyl 4-[(4-{[(2S,4R)-4-[acetyl(4-chlorophenyl)amino]-2-methyl-3,4-dihydroquinolin-1(2H)-yl]carbonyl}phenyl)(methyl)amino]-4-oxobutanoate |
| H-108 | N-(4-Chlorophenyl)-N-((2S,4R)-2-methyl-1-{4-[3-(1H-pyrrol-1-yl)propoxy]benzoyl}-1,2,3,4-tetrahydroquinolin-4-yl)acetamide |
| H-109 | N-(4-Chlorophenyl)-N-((2S,4R)-1-{4-[2-(isopropylamino)-2-oxoethoxy]benzoyl}-2-methyl-1,2,3,4-tetrahydroquinolin-4-yl)acetamide |
| H-110 | tert-Butyl 4-(4-{[(2S,4R)-4-[acetyl(4-chlorophenyl)amino]-2-methyl-3,4-dihydroquinolin-1(2H)-yl]carbonyl}phenyl)piperazine-1-carboxylate |
| H-111 | N-(4-Chlorophenyl)-N-[(2S,4R)-2-methyl-1-(4-{2-[1-(methylsulfonyl)piperidin-4-yl]ethoxy}benzoyl)-1,2,3,4-tetrahydroquinolin-4-yl]acetamide |
| H-112 | 4-(4-{[(2S,4R)-4-[(4-Chlorophenyl)(propionyl)amino]-2-methyl-3,4-dihydroquinolin-1(2H)-yl]carbonyl}phenoxy)-2,2-dimethylbutanoic acid |
| H-113 | 3-[(4-{[(2S,4R)-4-[Acetyl(4-chlorophenyl)amino]-2-methyl-3,4-dihydroquinolin-1(2H)-yl]carbonyl}phenoxy)methyl]benzoic acid |
| H-114 | 3-[(4-{[(2S,4R)-4-[Acetyl(4-chlorophenyl)amino]-2-methyl-3,4-dihydroquinolin-1(2H)-yl]carbonyl}benzyl)amino]propanoic acid |
| H-115 | N-(4-Chlorophenyl)-N-[(2S,4R)-2-methyl-1-(4-{3-[(methylsulfonyl)amino]propoxy}benzoyl)-1,2,3,4-tetrahydroquinolin-4-yl]acetamide |
| H-116 | 4-[5-{[(2S,4R)-4-[Acetyl(4-chlorophenyl)amino]-2-methyl-3,4-dihydroquinolin-1(2H)-yl]carbonyl}-2-oxopyridin-1(2H)-yl]-2,2-dimethylbutanoic acid |
| H-117 | 1-[2-(4-{[(2S,4R)-4-[Acetyl(4-chlorophenyl)amino]-2-methyl-3,4-dihydroquinolin-1(2H)-yl]carbonyl}phenoxy)ethyl]cyclobutanecarboxylic acid |
| H-118 | N-(4-Chlorophenyl)-N-((2S,4R)-2-methyl-1-{4-[3-(2-oxoimidazolidin-1-yl)propoxy]benzoyl}-1,2,3,4-tetrahydroquinolin-4-yl)acetamide |
| H-119 | N-(4-Chlorophenyl)-N-{(2S,4R)-2-methyl-1-[4-(2-morpholin-4-yl-2-oxoethoxy)benzoyl]-1,2,3,4-tetrahydroquinolin-4-yl}acetamide |
| H-120 | N-(4-Chlorophenyl)-N-[(2S,4R)-1-(4-fluoro-3-vinylbenzoyl)-2-methyl-1,2,3,4-tetrahydroquinolin-4-yl]acetamide |
| H-121 | N-(4-Chlorophenyl)-N-[(2S,4R)-1-(4-ethoxybenzoyl)-2-methyl-1,2,3,4-tetrahydroquinolin-4-yl]acetamide |
| H-122 | 1-(4-{[(2S,4R)-4-[Acetyl(4-chlorophenyl)amino]-2-methyl-3,4-dihydroquinolin-1(2H)-yl]carbonyl}phenyl)piperidine-4-carboxylic acid |
| H-123 | N-((2S,4R)-1-{4-[3-(Aminosulfonyl)propoxy]benzoyl}-2-methyl-1,2,3,4-tetrahydroquinolin-4-yl)-N-(4-chlorophenyl)acetamide |
| H-124 | 3-{[(2S,4R)-4-[Acetyl(4-chlorophenyl)amino]-2-methyl-3,4-dihydroquinolin-1(2H)-yl]carbonyl}benzoic acid |
| H-125 | N-(4-Chlorophenyl)-N-{(2S,4R)-1-[4-(3-cyanopropoxy)benzoyl]-2-methyl-1,2,3,4-tetrahydroquinolin-4-yl}acetamide |
| H-126 | N-(4-Chlorophenyl)-N-((2S,4R)-2-methyl-1-{4-[3-(3-methyl-1,2,4-oxadiazol-5-yl)propoxy]benzoyl}-1,2,3,4-tetrahydroquinolin-4-yl)acetamide |
| H-127 | N-(4-Chlorophenyl)-N-{(2S,4R)-1-[4-(difluoromethoxy)benzoyl]-2-methyl-1,2,3,4-tetrahydroquinolin-4-yl}acetamide |
| H-128 | 1-[2-(4-{[(2S,4R)-4-[Acetyl(4-chlorophenyl)amino]-2-methyl-3,4-dihydroquinolin-1(2H)-yl]carbonyl}phenoxy)ethyl]-1H-imidazole-2-carboxamide |
| H-129 | N-((2S,4R)-1-{4-[3-(4-Acetylpiperazin-1-yl)propoxy]benzoyl}-2-methyl-1,2,3,4-tetrahydroquinolin-4-yl)-N-(4-chlorophenyl)acetamide |
| H-130 | Ethyl 1-(4-{[(2S,4R)-4-[acetyl(4-chlorophenyl)amino]-2-methyl-3,4-dihydroquinolin-1(2H)-yl]carbonyl}phenyl)piperidine-3-carboxylate |
| H-131 | 5-(4-{[(2S,4R)-4-[Acetyl(4-chlorophenyl)amino]-2-methyl-3,4-dihydroquinolin-1(2H)-yl]carbonyl}-2-fluorophenyl)-2,2-dimethylpentanoic acid |
| H-132 | N-(4-Chlorophenyl)-N-((2S,4R)-2-methyl-1-{4-[3-(2-oxopyrrolidin-1-yl)propoxy]benzoyl}-1,2,3,4-tetrahydroquinolin-4-yl)acetamide |
| H-133 | N-(4-Chlorophenyl)-N-((2S,4R)-1-{4-[(3-ethyl-2-oxo-1,3-oxazolidin-5-yl)methoxy]benzoyl}-2-methyl-1,2,3,4-tetrahydroquinolin-4-yl)acetamide |
| H-134 | 4-(4-{[(2S,4R)-4-[Acetyl(4-chlorophenyl)amino]-6-chloro-2-methyl-3,4-dihydroquinolin-1(2H)-yl]carbonyl}phenoxy)-2,2-dimethylbutanoic acid |
| H-135 | Methyl 4-[4-(4-{[(2S,4R)-4-[acetyl(4-chlorophenyl)amino]-2-methyl-3,4-dihydroquinolin-1(2H)-yl]carbonyl}phenyl)piperazin-1-yl]-2,2-dimethylbutanoate |
| H-136 | Methyl 4-(4-{[(2S,4R)-4-[acetyl(4-chlorophenyl)amino]-2-methyl-3,4-dihydroquinolin-1(2H)-yl]carbonyl}phenoxy)-2-methylbutanoate |
| H-137 | 1-[2-(4-{[(2S,4R)-4-[Acetyl(4-chlorophenyl)amino]-2-methyl-3,4-dihydroquinolin-1(2H)-yl]carbonyl}phenoxy)ethyl]-1H-imidazole-2-carboxylic acid |

TABLE 10-continued

Chemical Names of Compounds Represented in Table 9:

| | |
|---|---|
| H-138 | 4-(4-{[(2S,4R)-4-[Acetyl(4-chlorophenyl)amino]-2-methyl-3,4-dihydroquinolin-1(2H)-yl]carbonyl}phenyl)-2,2-dimethylbutanoic acid |
| H-139 | 5-(4-{[(2S,4R)-4-[(4-Chlorophenyl)(glycoloyl)amino]-2-methyl-3,4-dihydroquinolin-1(2H)-yl]carbonyl}phenyl)-2,2-dimethylpentanoic acid |
| H-140 | [4-(4-{[(2S,4R)-4-[Acetyl(4-chlorophenyl)amino]-2-methyl-3,4-dihydroquinolin-1(2H)-yl]carbonyl}phenyl)piperazin-1-yl]acetic acid |
| H-141 | Benzyl 4-[(4-{[(2S,4R)-4-[acetyl(4-chlorophenyl)amino]-2-methyl-3,4-dihydroquinolin-1(2H)-yl]carbonyl}phenoxy)methyl]piperidine-1-carboxylate |
| H-142 | N-(4-Chlorophenyl)-N-[(2S,4R)-1-(4-{2-[(2-hydroxyethyl)amino]-2-oxoethoxy}benzoyl)-2-methyl-1,2,3,4-tetrahydroquinolin-4-yl]acetamide |
| H-143 | Methyl 4-[(5-{[(2S,4R)-4-[acetyl(4-chlorophenyl)amino]-2-methyl-3,4-dihydroquinolin-1(2H)-yl]carbonyl}pyridin-2-yl)oxy]-2,2-dimethylbutanoate |
| H-144 | 2-(4-{[(2S,4R)-4-[Acetyl(4-chlorophenyl)amino]-2-methyl-3,4-dihydroquinolin-1(2H)-yl]carbonyl}phenoxy)-2-methylpropanoic acid |
| H-145 | 4-(4-{[(2S,4R)-4-[Acetyl(4-chlorophenyl)amino]-2-methyl-3,4-dihydroquinolin-1(2H)-yl]carbonyl}phenoxy)-2-methylbutanoic acid |
| H-146 | 3-[1-(4-{[(2S,4R)-4-Acetyl(4-chlorophenyl)amino]-2-methyl-3,4-dihydroquinolin-1(2H)-yl]carbonyl}phenyl)-1H-pyrrol-3-yl]propanoic acid |
| H-147 | N-(4-Chlorophenyl)-N-[(2S,4R)-1-(4-{3-[(dibenzylamino)sulfonyl]propoxy}benzoyl)-2-methyl-1,2,3,4-tetrahydroquinolin-4-yl]acetamide |
| H-148 | Methyl 4-(4-{[(2S,4R)-4-[(4-chlorophenyl)(isobutyryl)amino]-2-methyl-3,4-dihydroquinolin-1(2H)-yl]carbonyl}phenoxy)-2,2-dimethylbutanoate |
| H-149 | N-(4-Chlorophenyl)-N-{(2S,4R)-2-methyl-1-[4-(3-pyrrolidin-1-ylpropoxy)benzoyl]-1,2,3,4-tetrahydroquinolin-4-yl}acetamide |
| H-150 | N-(4-Chlorophenyl)-N-((2S,4R)-2-methyl-1-{4-[2-(1H-pyrrol-1-yl)ethoxy]benzoyl}-1,2,3,4-tetrahydroquinolin-4-yl)acetamide |
| H-151 | Methyl 4-(4-{[(2S,4R)-4-[(4-chlorophenyl)(propionyl)amino]-2-methyl-3,4-dihydroquinolin-1(2H)-yl]carbonyl}phenoxy)-2,2-dimethylbutanoate |
| H-152 | 3-{[(2S,4R)-4-[Acetyl(4-chlorophenyl)amino]-2-methyl-3,4-dihydroquinolin-1(2H)-yl]carbonyl}benzamide |
| H-153 | (3E)-5-(4-{[(2S,4R)-4-[Acetyl(4-chlorophenyl)amino]-2-methyl-3,4-dihydroquinolin-1(2H)-yl]carbonyl}phenyl)-2,2-dimethylpent-3-enoic acid |
| H-154 | Methyl 2-{[3-(4-{[(2S,4R)-4-[acetyl(4-chlorophenyl)amino]-2-methyl-3,4-dihydroquinolin-1(2H)-yl]carbonyl}phenyl)propanoyl]amino}-2-methylpropanoate |
| H-155 | Methyl [3-(4-{[(2S,4R)-4-[acetyl(4-chlorophenyl)amino]-2-methyl-3,4-dihydroquinolin-1(2H)-yl]carbonyl}phenoxy)propyl]ethylcarbamate |
| H-156 | N-(4-Chlorophenyl)-N-((2S,4R)-1-{4-[3-(diethylamino)-2-hydroxypropoxy]benzoyl}-2-methyl-1,2,3,4-tetrahydroquinolin-4-yl)acetamide |
| H-157 | 1-[3-(4-{[(2S,4R)-4-[Acetyl(4-chlorophenyl)amino]-2-methyl-3,4-dihydroquinolin-1(2H)-yl]carbonyl}phenoxy)propyl]-1H-imidazole-2-carboxylic acid |
| H-158 | [4-(4-{[(2S,4R)-4-[Acetyl(4-chlorophenyl)amino]-2-methyl-3,4-dihydroquinolin-1(2H)-yl]carbonyl}phenyl)piperidin-1-yl]acetic acid |
| H-159 | 4-(4-{[(2S,4R)-4-[Acetyl(4-chlorophenyl)amino]-2-methyl-3,4-dihydroquinolin-1(2H)-yl]carbonyl}phenoxy)butanamide |
| H-160 | Methyl 4-(4-{[(2S,4R)-4-[acetyl(4-chloro-2-methylphenyl)amino]-2-methyl-3,4-dihydroquinolin-1(2H)-yl]carbonyl}phenoxy)-2,2-dimethylbutanoate |
| H-161 | 4-(4-{[(2S,4R)-4-[Acetyl(4-chloro-2-methylphenyl)amino]-2-methyl-3,4-dihydroquinolin-1(2H)-yl]carbonyl}phenoxy)-2,2-dimethylbutanoic acid |
| H-162 | Benzyl 2-(4-{[(2S,4R)-4-[acetyl(4-chlorophenyl)amino]-2-methyl-3,4-dihydroquinolin-1(2H)-yl]carbonyl}phenyl)pyrrolidine-1-carboxylate |
| H-163 | N-(4-Chlorophenyl)-N-[(2S,4R)-1-(4-ethyl-3-fluorobenzoyl)-2-methyl-1,2,3,4-tetrahydroquinolin-4-yl]acetamide |
| H-164 | N-(4-Chlorophenyl)-N-[(2S,4R)-1-(4-ethyl-3,5-difluorobenzoyl)-2-methyl-1,2,3,4-tetrahydroquinolin-4-yl]acetamide |
| H-165 | 4-[(5-{[(2S,4R)-4-Acetyl(4-chlorophenyl)amino]-2-methyl-3,4-dihydroquinolin-1(2H)-yl]carbonyl}pyridin-2-yl)oxy]-2,2-dimethylbutanoic acid |
| H-166 | Methyl 5-(4-{[(2S,4R)-4-[acetyl(4-chlorophenyl)amino]-2-methyl-3,4-dihydroquinolin-1(2H)-yl]carbonyl}phenyl)-2,2-dimethylpentanoate |
| H-167 | N-(4-Chlorophenyl)-N-((2S,4R)-1-{4-[3-(1H-imidazol-1-yl)propoxy]benzoyl}-2-methyl-1,2,3,4-tetrahydroquinolin-4-yl)acetamide |

General Procedure J:

N-cyclopentyl-N-[(2S,4R)-1-(4-methoxybenzoyl)-2-methyl-1,2,3,4-tetrahydroquinolin-4-yl]acetamide (2S,4R)-1 4-methoxybenzoyl)-2-methyl-1,2,3,4-tetrahydroquinolin-4-amine was obtained following procedure G, substituting 4-methoxybenzoyl chloride for 4-fluorobenzoyl chloride. The rest of the procedures were followed as indicated in general procedure G to afford (2S,4R)-1-(4-methoxybenzoyl)-2-methyl-1,2,3,4-tetrahydroquinolin-4-amine in decent yield.

To (2S,4R)-1-(4-methoxybenzoyl)-2-methyl-1,2,3,4-tetrahydroquinolin-4-amine (200 mg, 0.67 mmol) in MeOH was added cyclopentanone (0.073 mL, 0.74 mmol) followed Na(OAc)$_3$BH (284 mg, 1.34 mmol) and catalytic amount of HOAc. The reaction mixture was stirred at room temperature over night. The reaction wash quenched by adding water. And the mixture was extracted with EtOAc 3 times. The organic layers were combined then dried over anhydrous magnesium sulfate, filtered, and concentrated under reduced pressure. The crude residue was purified by silica gel chromatography (hexanes-ethyl acetate system) to afford (2S,4R)-N-cyclopentyl-1-(4-methoxybenzoyl)-2-methyl-1,2,3,4-tetrahydroquinolin-4-amine in decent yield.

To a solution (2S,4R)-N-cyclopentyl-1-(4-methoxybenzoyl)-2-methyl-1,2,3,4-tetrahydroquinolin-4-amine (100 mg, 02.7 mmol) in methylene chloride (5 mL) was added diisopropylethylamine (120 uL, 0.70 mmol) followed by acetyl chloride (90 uL, 1.27 mmol). The mixture was stirred at r.t. for 4 h. The reaction mixture was concentrated under reduced pressure, dissolved in ethyl acetate, washed with sat. aqueous sodium bicarbonate, brine and dried over magnesium sulfate, filtered, and concentrated under reduced pressure. The residue was purified by silica gel chromatography (hexanes-ethyl acetate system) to afford pure N-cyclopentyl-N-[(2S,4R)-1-(4-methoxybenzoyl)-2-methyl-1,2,3,4-tetrahydroquinolin-4-yl]acetamide (100 mg, 91%).

$^1$H-NMR (CDCl$_3$, 300 MHz) δ: 1.24-1.34 (m, 3H), 1.48-1.56 (m, 2H), 1.90-2.07 (m, 2H), 2.26-2.30 (s, 3H), 2.30-2.42 (m, 1H), 2.70-2.77 (m, 2H), 3.35-3.45 (m, 1H), 3.75 (s, 3H), 4.05-4.09 (m, 1H), 4.32-4.37 (m, 1H), 4.82-4.88 (m, 1H), 6.50-6.58 (m, 1H), 6.65-6.68 (m, 2H), 6.86-6.89 (m, 1H), 6.95-7.15 (m, 5H), 7.24-7.28 (m, 2H).

MS m/z: 407 (M+1).

N-cyclopropyl-N-[2-methyl-1-(pyridin-3-ylcarbonyl)-1,2,3,4-tetrahydroquinolin-4-yl]acetamide At −5° C. to a solution of benzyl 2-methyl-4-oxo-3,4-dihydroquinoline-1(2H)-carboxylate (1 g, 3.39 mmol) in DCM was added TEA (3.76 mL, 27.09 mmol), followed by cyclopropyl amine (0.24 mL, 3.39 mmol). Then TiCl$_4$ (2.4 mL, 3.39 mmol) was added. The reaction mixture was allowed to warm to room temperature and was stirred overnight. The reaction mixture was conentrated under reduced pressure. The by-product percipiated out. After filtration the filtrate was concentrated. Without purification it was directly used in next step.

The crude product (895.1 mg, 3.48 mmol) from the previous step was dissolved in acetic acid (10 mL). NaBH(OAc)$_3$ (2.27 g, 10.7 mmol) was added. The reaction was stirred at r.t. overnight. The reaction mixture was washed with brine. The organic layer was dried over magnesium sulfate, filtered, and concentrated under reduced pressure. The crude residue was purified by silica gel chromatography (hexanes-ethyl acetate system) to afford benzyl 4-(cyclopropylamino)-2-methyl-3,4-dihydroquinoline-1(2H)-carboxylate.

At to 0° C. to a solution of benzyl 4-(cyclopropylamino)-2-methyl-3,4-dihydroquinoline-1(2H)-carboxylate (492.1 mg, 1.32 mmol) in methylene chloride (5 mL) was added acetyl chloride (0.11 mL, 1.57 mmol). Triethylamine (0.27 mL, 1.57 mmol) was added drop-wise over 30 min. A precipitate formed during this time. An additional DCM was added to completely dissolve all the precipitate. The reaction was stirred at r.t. overnight. The mixture was concentrated under reduced pressure, partitioned between ethyl acetate and 1N sodium hydroxide while cooled to 0° C. The aqueous layer was extracted 3 times with ethyl acetate washed with sat. sodium bicarbonate, brine and dried over magnesium sulfate, filtered, and concentrated under reduced pressure. The crude product was directly used in the following step.

Benzyl-4-[acetyl(cyclopropyl)amino]-2-methyl-3,4-dihydroquinoline-1(2H)-carboxylate was dissolved in MeOH and a catalytic amount of Palladium on Carbon (10%) was added. The round bottom flask in which resided the resulting solution was evacuated and backfilled with hydrogen. The reaction was stirred under the hydrogen atomosphere overnight. The mixture was carefully filtered through a Celite® plug and concentrated to afford crude product. The crude residue was purified by silica gel chromatography (hexanes/ethyl acetate system) to afford N-cyclopropyl-N-(2-methyl-1,2,3,4-tetrahydroquinolin-4-yl)acetamide.

To the solution of N-cyclopropyl-N-(2-methyl-1,2,3,4-tetrahydro-quinolin-4-yl)-acetamide (82 mg, 0.34 mmol) in DCM (5 mL) was added nicotinoyl chloride hydrochloride (71 mg, 0.40 mmol), followed by DIPEA (104 mg, 0.80 mmol). The reaction mixture was stirred at r.t. for overnight. The mixture was concentrated under reduced pressure and dissolved in ethyl acetate (15 mL). The reaction mixture was washed with sat. sodium bicarbonate and brine. The organic layer was dried over magnesium sulfate, filtered, and concentrated under reduced pressure. The crude residue was purified by silica gel chromatography (hexanes-ethyl acetate system) to afford slightly yellow solid product (81 mg, 68%).

$^1$H-NMR (CDCl$_3$, 300 MHz) δ: 0.70-0.81 (m, 4H), 1.24-1.26 (m, 3H), 1.31-1.37 (m, 1H), 1.75-2.05 (m, 1H), 2.34 (s, 3H), 2.67-2.89 (m, 1H), 4.84-4.86 (m, 1H), 5.50 (b, 1H), 6.42-6.46 (d, 1H), 6.82 (b, 1H), 6.84-6.87 (t, 1H), 7.00-7.06 (t, 1H), 7.24-7.27 (m, 1H), 8.47-8.49 (m, 1H), 8.65 (b, 1H).

MS m/z: 350 (M+1).

N-cyclopropyl-N-[1-(4-methoxybenzoyl)-2-methyl-1,2,3,4-tetrahydroquinolin-4-yl]acetamide At −5° C. to a solution of benzyl 2-methyl-4-oxo-3,4-dihydroquinoline-1(2H)-carboxylate (1 g, 3.39 mmol) in DCM was added TEA (3.76 mL, 27.09 mmol), followed by cyclopropyl amine (0.24 mL, 3.39 mmol). Then TiCl$_4$ (2.4 mL, 3.39 mmol) was added. The reaction mixture was allowed to warm to r.t. and was stirred overnight. The reaction mixture was conentrated under reduced pressure. The by-product percipiated out. After filtration the filtrate was concentrated. Without purification it was directly used in next step.

The crude product (895.1 mg, 3.48 mmol) from the previous step was dissolved in acetic acid (10 mL). NaBH(OAc)$_3$ (2.27 g, 10.7 mmol) was added. The reation was stirred at room temperature overnight. The reaction mixture was washed with brine. The organic layer was dried over magnesium sulfate, filtered, and concentrated under reduced pressure. The crude residue was purified by silica gel chromatography (hexanes-ethyl acetate system) to afford benzyl 4-(cyclopropylamino)-2-methyl-3,4-dihydroquinoline-1 (2H)-carboxylate.

At 0° C. to a solution benzyl 4-(cyclopropylamino)-2-methyl-3,4-dihydroquinoline-1(2H)-carboxylate (492.1 mg, 1.32 mmol) in methylene chloride (5 mL) was added acetyl chloride (0.11 mL, 1.57 mmol). Triethylamine (0.27 mL, 1.57 mmol) was added dropwise over ~30 min. A precipitate formed during this time. An additional methylene chloride was added to completely dissolve all the precipitate. The reaction was stirred at r.t. overnight. The mixture was concentrated under reduced pressure, partitioned between ethyl acetate and 1N sodium hydroxide while cooled to 0° C. The aqueous layer was extracted 3 times with ethyl acetate washed with sat. aqueous sodium bicarbonate, brine and dried over magnesium sulfate, filtered, and concentrated under reduced pressure. The crude product was directly used in the following step.

Benzyl-4-[acetyl(cyclopropyl)amino]-2-methyl-3,4-dihydroquinoline-1(2H)-carboxylate was dissolved in MeOH and a catalytic amount of Palladium on Carbon (10%) was added. The round bottom flask in which resided the resulting solution was evacuated and backfilled with hydrogen. The reaction was stirred under the hydrogen atmosphere overnight. The mixture was carefully filtered through a Celite® plug and concentrated to afford crude product. The crude residue was purified by silica gel chromatography (hexanes-ethyl acetate system) to afford N-cyclopropyl-N-(2-methyl-1,2,3,4-tetrahydroquinolin-4-yl)acetamide.

To the solution of N-cyclopropyl-N-(2-methyl-1,2,3,4-tetrahydroquinolin-4-yl)-acetamide (82 mg, 0.34 mmol) in DCM (5 mL) was added 4-methoxybenzoyl chloride (68 mg, 0.40 mmol), followed by DIPEA (104 mg, 0.80 mmol). The reaction mixture was stirred at r.t. overnight. The mixture was concentrated under reduced pressure and dissolved in ethyl acetate. The reaction mixture was washed with sat. sodium bicarbonate and brine. The organic phase was dried over magnesium sulfate, filtered, and concentrated under reduced pressure. The crude residue was purified by silica gel chromatography (hexanes-ethyl acetate) to afford only the cis isomer as a slightly yellow solid product (81 mg, 68%). The mixture of two enantiomers was purified by chiral HPLC using the OD column and the two enatiomers were obtained:

N-cyclopropyl-N-[(2S,4R)-1-(4-methoxybenzoyl)-2-methyl-1,2,3,4-tetrahydroquinolin-4-yl]acetamide $^1$H-NMR (CDCl$_3$, 300 MHz) δ: 0.75-0.86 (m, 2H), 1.24-1.36 (m, 2H), 1.56 (s, 3H), 2.03-2.07 (m, 1H), 2.39 (s, 1H), 2.68-2.69 (m, 1H), 3.72 (s, 3H), 4.78-4.86 (m, 1H), 5.50 (b, 1H), 6.47-6.50 (d, 1H), 6.63-6.73 (d, 2H), 6.82-6.89 (m, 1H), 6.96-7.01 (m, 1H), 7.09-7.12 (m, 2H), 7.24-7.27 (m, 1H).

MS m/z: 379 (M+1).

N-cyclopropyl-N-[(2R,4S)-1-(4-methoxybenzoyl)-2-methyl-1,2,3,4-tetrahydroquinolin-4-yl]acetamide $^1$H-NMR (CDCl$_3$, 300 MHz) δ: 0.75-0.86 (m, 2H), 1.24-1.36 (m, 2H), 1.56 (s, 3H), 2.03-2.07 (m, 1H), 2.39 (s, 1H), 2.68-2.69 (m, 1H), 3.72 (s, 3H), 4.78-4.86 (m, 1H), 5.50 (b, 1H), 6.47-6.50 (d, 1H), 6.63-6.73 (d, 2H), 6.82-6.89 (m, 1H), 6.96-7.01 (m, 1H), 7.09-7.12 (m, 2H), 7.24-7.27 (m, 1H).

MS m/z: 379 (M+1).

4-(4-{[(2S,4R)-4-[Acetyl-(cyclopropyl)amino]-2-methyl-3,4-dihydroquinolin-1(2H)-yl] carbonyl}phenoxy)-2,2-dimethylbutanoic acid 4-(4-{[(2S,4R)-4-[Acetyl-(cyclopropyl)amino]-2-methyl-3,4-dihydroquinolin-1(2H)-yl]carbonyl}phenoxy)-2,2-dimethylbutanoic acid was synthesized according to general procedure I replacing N-(4-chlorophenyl)-N-[(2S,4R)-1-(4-methoxybenzoyl)-2-methyl-1,2,3,4-tetrahydroquinolin-4-yl]acetamide with N-cyclopropyl-N-[1-(4-methoxybenzoyl)-2-methyl-1,2,3,4-tetrahydroquinolin-4-yl]acetamide and substituting 4-bromo-2,2-dimethylbutanoate for ethyl 4-bromoacetate. The rest of general procedure I was followed as indicated to afford methyl 4-(4-{[(2S,4R)-4-[acetyl(cyclopropyl)amino]-2-methyl-3,4-dihydroquinolin-1(2H)-yl]carbonyl}phenoxy)-2,2-dimethylbutanoate.

This material was dissolved in methanol/tetrahydrofuran/water (2/1/1) then sodium hydroxide (3 equivalents) was added and reaction mixture stirred at 40° C. overnight. The mixture was concentrated, the residue acidified with a 1N HCl aqueous solution and extracted with ethyl acetate. The organic layer was washed with brine, dried over magnesium sulfate, filtered and concentrated to give 4-(4-{[(2S,4R)-4-[acetyl(cyclopropyl)amino]-2-methyl-3,4-dihydroquinolin-1(2H)-yl]carbonyl}phenoxy)-2,2-dimethylbutanoic acid.

$^1$H-NMR (DMSO) δ: 0.44-0.96 (br m, 4H), 1.01 (s, 6H), 1.14-1.22 (m, 1H), 1.26 (d, 3H), 1.76 (t, 2H), 2.02-2.05 (m, 1H), 2.29 (br s, 3H), 2.69-2.84 (m, 1H), 3.93 (t, 2H), 4.58-4.70 (m, 1H), 5.25-5.37 (m, 1H), 6.46 (d, 1H), 6.72 (d, 2H), 6.77-6.92 (m, 3H), 6.98 (d, 2H).

MS m/z: 479 (M+1).

TABLE 11

Additional Exemplary Compounds Prepared According to the General Methods Detailed Above:

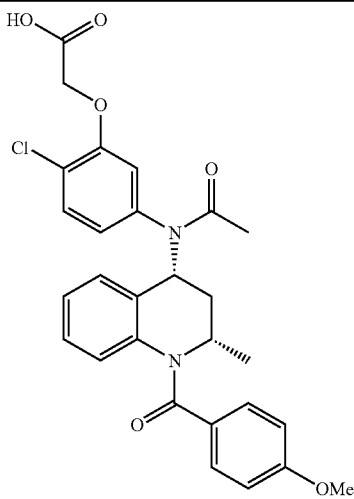

TABLE 11-continued

Additional Exemplary Compounds Prepared According to the General Methods Detailed Above:

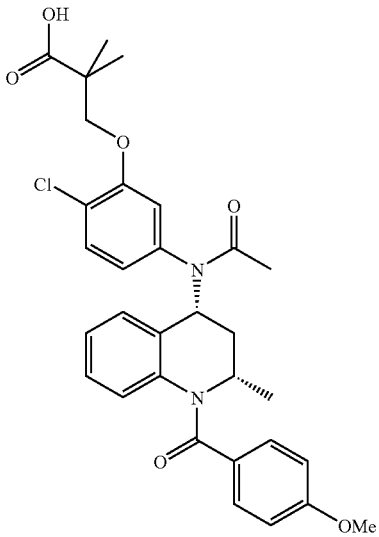

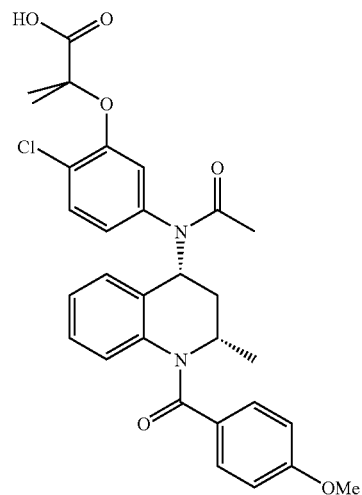

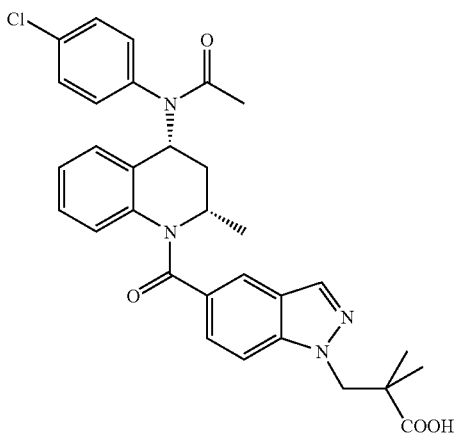

TABLE 11-continued

Additional Exemplary Compounds Prepared According to the General Methods Detailed Above:

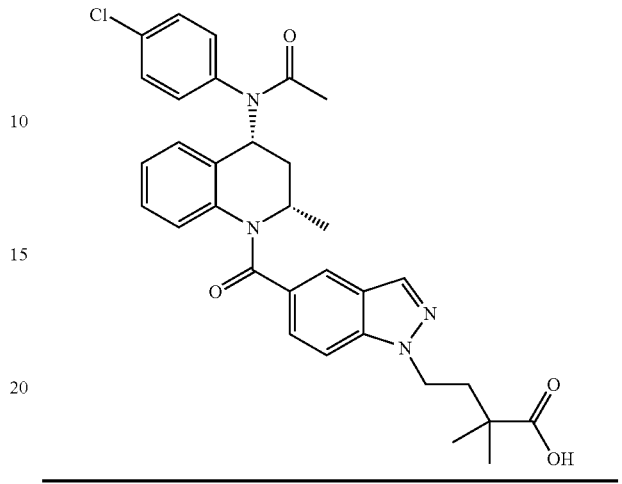

The Disclosed Compounds Inhibit Binding of PGD$_2$ to CRTH2

This radioligand membrane binding assay evaluates the ability of compounds to inhibit [$^3$H] Prostaglandin D$_2$ (PGD$_2$) binding to the cloned human CRTH2 receptor stably expressed in HEK-293 cells (expressing human CRTh2 receptor and α ?subunit or the heterotrimeric G protein 16 were prepared by Biosignal Company) using Scintillation Proximity Assay.

A binding buffer containing 50 mM Tris-HCl (pH 7.5), 5 mM MgCl$_2$ and 1 mM EDTA was prepared immediately prior to performing the assay. A bead/membrane solution at twice the final assay concentration comprising membranes (membranes bought from Biosignal) from the HEK-293 cells cloned to express CRTH2 receptor bound to and [3H] PGD$_2$ at twotimes the final assay concentration were prepared and stored on ice before adding to wells. Cold PGD$_2$ at twenty times the final assay concentration was prepared and stored on ice before adding to wells defining non-specific binding (NSB) coming plates #3653 were used for this assay.

10 mM stock concentrations of compounds in 100% DMSO were prepared and stored at room temperature. A 10 point concentration response curve was then constructed for each compound, starting at 10 μM (final assay concentration). The compounds were prepared at 40 times final assay concenrations with nine consequent-3-fold dilutions.

0.1 μl of each concentration of compound were added to the appropriate well of the 384 plate and 2 μl of cold PGD$_2$ was added into the wells defining NSB. 20 μl of [$^3$H] PGD$_2$ and then 20 μl of 2× of bead/membrane solution were then added to each well.

The plates were allowed to incubate at room temperature for approximately 2 hours and then counted on Packard Topcount using SPA tritium protocol for 1 minute/well.

The percent inhibition of PGD$_2$ binding (PGD$_2$ used at the K$_D$ value or lower) to the HEK-293 cell membranes was determined, the assay was always run as duplicate for n=1 for a total of n=2.

Compounds G-1 to G-34, H-1-H-22, H-24-35, H-37-H-63, H-65-H-89, H-91-H-106, H-105-H-167 have K$_i$<1 uM.

The invention claimed is:

1. A compound represented by the following structural formula:

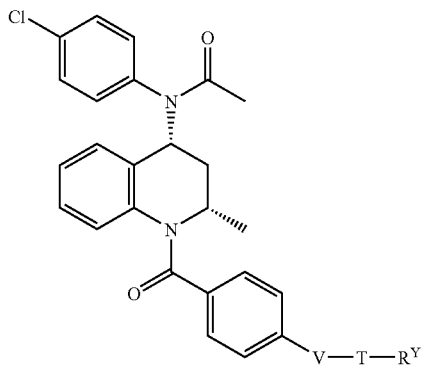

or a pharmaceutically acceptable salt thereof, wherein:

V is a covalent bond or —O—;

T is an straight chained $C_{1-10}$ alkylene substituted with alkyl, gem dialkyl, haloalkyl, spiro cycloalkyl, or an optionally N-substituted nitrogen containing spiro non-aromatic heterocyclic group;

$R^Y$ is $R^Y$ is —C(O)OR$^5$, —C(O)R$^5$, —OC(O)R$^5$, —C(O)N(R$^5$)$_2$, —NR$^5$C(O)R$^5$, —NR$^5$C(O)OR$^5$, —S(O)$_2$R$^5$, —S(O)$_2$COR$^5$, —S(O)$^2$N(R$^5$)$_2$, —NR$^5$S(O)$_2$, —NR$^5$S(O)$_2$R$^5$, S(O)$_2$OR$^5$, —S(O)OR$^5$, —SR$^5$, —C(O)NR$^5$S(O)$_2$R$^5$, —CN, —NR$^5$C(O)N(R$^5$)$_2$, —OC(O)N(R$^5$)$_2$, —N(R$^5$)$_2$, —OR$^5$, an optionally substituted non-aromatic heterocyclic group or an optionally substituted heteroaryl group; and each R$^5$ is independently —H, alkyl, haloalkyl, hydroxyalkyl, carboxyalkyl, —C(O)OCH$_2$C$_6$H$_5$, S(O)$_2$CH$_3$, —C(O)OH, —C(O)OMe, —C(O)OEt, C(O)NH$^2$, benzyl, pyrrolidinyl, morpholinyl, or —N(R$^5$)$_2$ is an optionally substituted nitrogen-containing non-aromatic heterocyclic group.

2. A compound represented by the following structural formula:

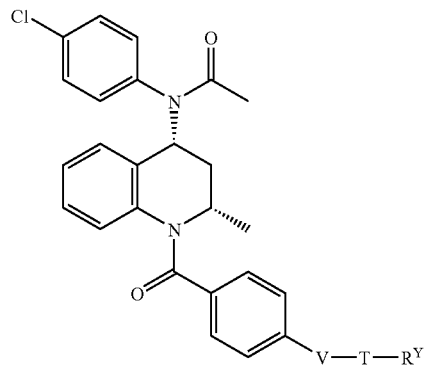

or a pharmaceutically acceptable salt thereof, wherein:

V is —O—;

T is an straight chained $C_{1-10}$ alkylene optionally substituted at any one or more substitutable carbon atoms with halide, alkyl, gem dialkyl, haloalkyl, gem dihalo, haloalkyl, alkoxy, haloalkoxy, spiro cycloalkyl, optionally N-substituted nitrogen containing spiro non-aromatic heterocyclic group, amine, alkylamine, dialkylamine, or hydroxyl;

$R^Y$ is —C(O)OR$^5$, —C(O)R$^5$, —OC(O)R$^5$, —C(O)N(R$^5$)$_2$, —NR$^5$C(O)R$^5$, —NR$^5$C(O)OR$^5$, —S(O)$_2$R$^5$, —S(O)$_2$COR$^5$, —S(O)$^2$N(R$^5$)$_2$, —NR$^5$S(O)$_2$, —NR$^5$S(O)$_2$R$^5$, S(O)$_2$OR$^5$, —S(O)OR$^5$, —SR$^5$, —C(O)NR$^5$S(O)$_2$R$^5$, —CN, —NR$^5$C(O)N(R$^5$)$_2$, —OC(O)N(R$^5$)$_2$, —N(R$^5$)$_2$, —OR$^5$, an optionally substituted non-aromatic heterocyclic each R$^5$ is independently —H, alkyl, haloalkyl, hydroxyalkyl, carboxyalkyl, —C(O)OCH$_2$C$_6$H$_5$, S(O)$_2$CH$_3$, —C(O)OH, —C(O)OMe, —C(O)OEt, C(O)NH$^2$, benzyl, pyrrolidinyl, morpholinyl, or —N(R$^5$)$_2$ is an optionally substituted nitrogen-containing non-aromatic heterocyclic group.

* * * * *

UNITED STATES PATENT AND TRADEMARK OFFICE
CERTIFICATE OF CORRECTION

PATENT NO. : 7,504,508 B2  
APPLICATION NO. : 11/101208  
DATED : March 17, 2009  
INVENTOR(S) : Shomir Ghosh et al.

It is certified that error appears in the above-identified patent and that said Letters Patent is hereby corrected as shown below:

In Claim 1, column 579, line 37, change "-S(O)$^2$ N(R$^5$)$_2$," to -- -S(O)$_2$ N(R$^5$)$_2$, --;

In Claim 1, column 579, line 45, change "C(O)NH$^2$," to -- C(O)NH$_2$, --;

In Claim 2, column 580, line 34, change "-S(O)$^2$ N(R$^5$)$_2$," to -- -S(O)$_2$ N(R$^5$)$_2$, --;

In Claim 2, column 580, line 38, change "an optionally substituted non-aromatic heterocyclic" to -- an optionally substituted non-aromatic heterocyclic group or an optionally substituted heteroaryl group and --;

In Claim 2, column 580, line 41, change "C(O)NH$^2$," to -- C(O)NH$_2$, --.

Signed and Sealed this

Ninth Day of June, 2009

JOHN DOLL  
*Acting Director of the United States Patent and Trademark Office*